United States Patent
Son et al.

(10) Patent No.: US 10,954,227 B2
(45) Date of Patent: Mar. 23, 2021

(54) NITROGEN-CONTAINING CYCLIC COMPOUND AND COLOR CONVERSION FILM COMPRISING SAME

(71) Applicant: LG CHEM, LTD., Seoul (KR)

(72) Inventors: Seonkyoung Son, Daejeon (KR); Milim Lee, Daejeon (KR); Cheol Jun Song, Daejeon (KR); Minju Kim, Daejeon (KR); Hoyong Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/640,448

(22) PCT Filed: Apr. 22, 2019

(86) PCT No.: PCT/KR2019/004826
§ 371 (c)(1),
(2) Date: Feb. 20, 2020

(87) PCT Pub. No.: WO2019/216573
PCT Pub. Date: Nov. 14, 2019

(65) Prior Publication Data
US 2020/0299290 A1    Sep. 24, 2020

(30) Foreign Application Priority Data
May 11, 2018 (KR) .................. 10-2018-0054489

(51) Int. Cl.
| C07D 417/10 | (2006.01) |
| C07F 7/08   | (2006.01) |
| H01L 51/00  | (2006.01) |
| H01L 51/50  | (2006.01) |
| F21V 8/00   | (2006.01) |

(52) U.S. Cl.
CPC .......... C07D 417/10 (2013.01); C07F 7/0812 (2013.01); G02B 6/005 (2013.01)

(58) Field of Classification Search
CPC .. C07D 285/14; C07D 417/10; C07D 417/14; C07F 7/0812; G02B 6/005; H01L 51/006; H01L 51/0072; H01L 51/0074; Y10S 428/917
See application file for complete search history.

(56) References Cited

U.S. PATENT DOCUMENTS

2006/0052612 A1* 3/2006 Stossel ................. C07D 417/14
                                                      548/126
2010/0133519 A1    6/2010 Chen et al.
(Continued)

FOREIGN PATENT DOCUMENTS

| CN | 103833507 A    | 6/2014 |
| JP | 2006-045398 A  | 2/2006 |

(Continued)

OTHER PUBLICATIONS

Search Report and Written Opinion issued for International Application No. PCT/KR2019/004826 dated Jul. 24, 2019, 7 pages.

*Primary Examiner* — Bijan Ahvazi
(74) *Attorney, Agent, or Firm* — Rothwell, Figg, Ernst & Manbeck, P.C.

(57) ABSTRACT

The present specification relates to a compound containing nitrogen, and a color conversion film, a backlight unit, and a display device, including the same.

14 Claims, 1 Drawing Sheet

(56) References Cited

U.S. PATENT DOCUMENTS

| | | |
|---|---|---|
| 2017/0062730 A1 | 3/2017 | Ahn et al. |
| 2018/0179439 A1 | 6/2018 | Umehara et al. |
| 2019/0131542 A1* | 5/2019 | Kim .................. H01L 51/0059 |

FOREIGN PATENT DOCUMENTS

| | | |
|---|---|---|
| KR | 10-2005-0042757 A | 5/2005 |
| KR | 10-2009-0097862 A | 9/2009 |
| KR | 10-2015-0127548 A | 11/2015 |
| KR | 10-2017-0119291 A | 10/2017 |
| KR | 10-2018-0006335 A | 1/2018 |
| KR | 10-2018-0007097 A | 1/2018 |
| KR | 10-2018-0022705 A | 3/2018 |

\* cited by examiner

[Figure 1]
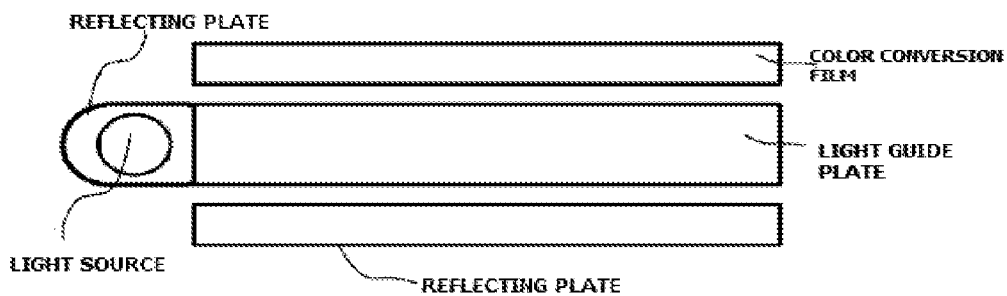
[Figure 2]
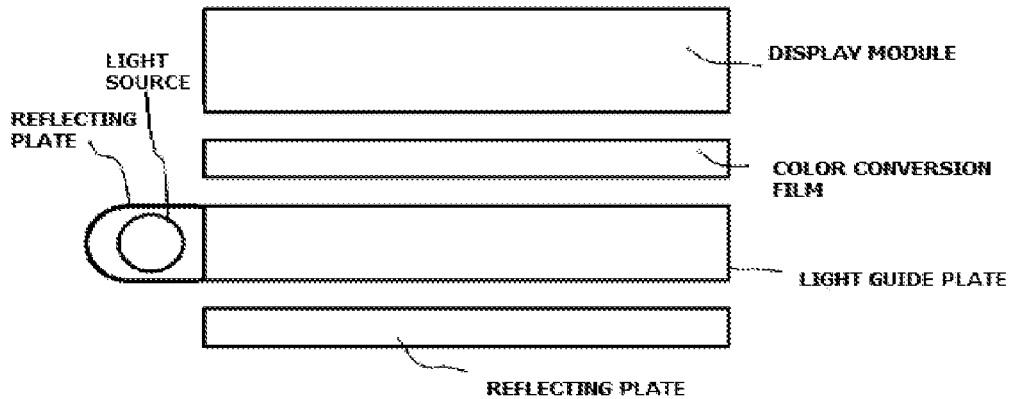

NITROGEN-CONTAINING CYCLIC COMPOUND AND COLOR CONVERSION FILM COMPRISING SAME

This application is a 35 U.S.C. 371 National Phase Entry Application from PCT/KR2019/004826, filed on Apr. 22, 2019, designating the United States and which claims priority to and the benefit of Korean Patent Application No. 10-2018-0054489 filed in the Korean Intellectual Property Office on May 11, 2018, the entire contents of which are incorporated herein by reference.

TECHNICAL FIELD

The present specification relates to a cyclic compound containing nitrogen, and a color conversion film, a backlight unit, and a display device, including the same.

BACKGROUND OF THE INVENTION

The existing light emitting diodes (LEDs) are obtained by mixing a green phosphor and a red phosphor with a blue light emitting diode or mixing a yellow phosphor and a blue-green phosphor with a UV light emission light emitting diode. However, in this method, it is difficult to control colors, and accordingly, the color rendition is not good. Therefore, the color gamut deteriorates.

In order to overcome the deterioration in the color gamut and reduce the production costs, methods of implementing green and red colors have been recently attempted by using a method of producing a quantum dot in the form of a film and combining the same with a blue LED. However, cadmium-based quantum dots have safety problems, and the other quantum dots have much lower efficiencies than those of the cadmium-based quantum dots. Further, quantum dots have low stability against oxygen and water, and have a disadvantage in that the performance thereof significantly deteriorates when the quantum dots are aggregated. In addition, when quantum dots are produced, it is difficult to constantly maintain the size thereof, and thus, the production cost is high.

BRIEF SUMMARY OF INVENTION

The present specification provides a cyclic compound containing nitrogen, and a color conversion film, a backlight unit, and a display device, including the same.

An exemplary embodiment of the present specification provides a compound represented by the following Formula 1.

[Formula 1]

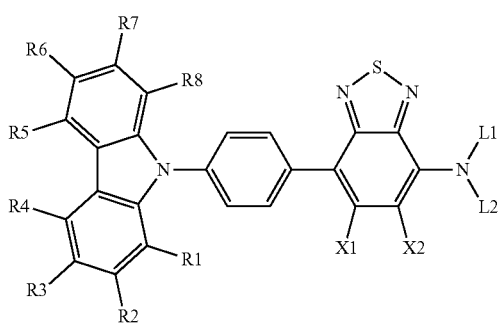

In Formula 1,

R1 to R8 are the same as or different from each other, and are each independently hydrogen; deuterium; a halogen group; a substituted or unsubstituted alkyl group; a substituted or unsubstituted aryl group; a substituted or unsubstituted silyl group; or a substituted or unsubstituted heteroaryl group, or adjacent groups may be bonded to each other to form one or more rings, X1 and X2 are the same as or different from each other, and are each independently hydrogen; deuterium; a halogen group; a substituted or unsubstituted alkyl group; a substituted or unsubstituted aryl group; or a substituted or unsubstituted heteroaryl group, and L1 and L2 are the same as or different from each other, and are each independently a substituted or unsubstituted aryl group.

Another exemplary embodiment of the present specification provides a color conversion film including: a resin matrix; and the compound represented by Formula 1, which is dispersed in the resin matrix.

Still another exemplary embodiment of the present specification provides a backlight unit including the color conversion film.

Yet another exemplary embodiment of the present specification provides a display device including the backlight unit.

Advantageous Effects

A compound according to an exemplary embodiment of the present specification has better processability and heat resistance than a compound having a BODIPY structure in the related art. Therefore, by using the compound described in the present specification as a fluorescent material of a color conversion film, it is possible to provide a color conversion film which has excellent brightness and color gamut and excellent heat resistance.

DESCRIPTION OF DRAWINGS

FIG. 1 is a schematic view in which a color conversion film according to an exemplary embodiment of the present specification is applied to a backlight unit.

FIG. 2 is a schematic view exemplifying a structure of a display device according to an exemplary embodiment of the present specification.

DETAILED DESCRIPTION OF INVENTION

Hereinafter, the present application will be described in more detail.

An exemplary embodiment of the present specification provides the compound represented by Formula 1.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; a substituted or unsubstituted alkyl group; a substituted or unsubstituted alkoxy group; a substituted or unsubstituted amine group; a substituted or unsubstituted fluoroalkyl group; a substituted or unsubstituted silyl group; a substituted or unsubstituted arylalkenyl group; a substituted or unsubstituted aryl group; and a substituted or unsubstituted heterocyclic group or being substituted with a substituent to which two or more substituents are linked among the substituents exemplified above, or having no substituent.

In the present specification, an example of a halogen group may be fluorine, chlorine, bromine or iodine.

In the present specification, the alkyl group may be straight-chained or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be straight-chained or branched, and the number of carbon atoms thereof is not particularly limited, but is preferably 2 to 30. Specific examples thereof include ethenyl, vinyl, 1-propenyl, isopropenyl, 1-butenyl, 2-butenyl, 3-butenyl, 1-pentenyl, 2-pentenyl, 3-pentenyl, 3-methyl-1-butenyl, 2,3-dimethylbutenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the alkoxy group may be straight-chained, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an amine group may be selected from the group consisting of —NH$_2$; a monoalkylamine group; a dialkylamine group; an N-alkylarylamine group; a monoarylamine group; a diarylamine group; an N-arylheteroarylamine group; an N-alkylheteroarylamine group, a monoheteroarylamine group, and a diheteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-biphenylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group; and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a tetraphenylsilyl group, a triphenylsilyl group, a diphenylsilyl group, a phenylsilyl group, and the like, but are not limited thereto.

In the present specification, an aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, tetraphenylethane, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted,
the substituent may be

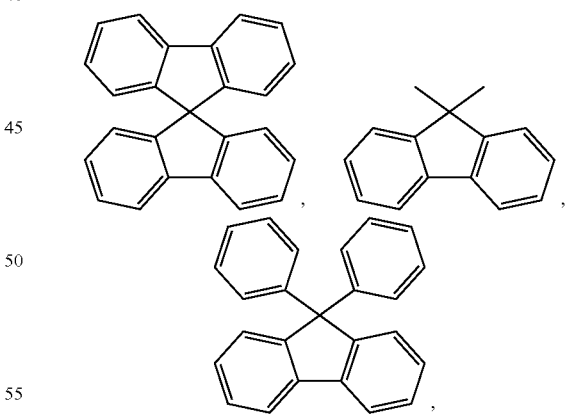

and the like. However, the substituent is not limited thereto.

In the present specification, a fluoroalkyl group is not limited thereto, but has preferably 1 to 10 carbon atoms, and specific examples thereof include a trifluoromethyl group, a perfluoroethyl group, and the like, but are not limited thereto.

In the present specification, a heteroaryl group includes one or more atoms other than carbon, that is, one or more heteroatoms, and specifically, the heteroatom may include one or more atoms selected from the group consisting of O, N, Se, S, and the like. The number of carbon atoms thereof is not particularly limited, but is preferably 2 to 30, and the heteroaryl group may be monocyclic or polycyclic. Examples of the heterocyclic group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, a thiazolyl group, an isoxazolyl group, an oxadiazolyl group, a thiadiazolyl group, a benzothiazolyl group, a phenothiazinyl group, a dibenzofuranyl group, a phenoxazine group,

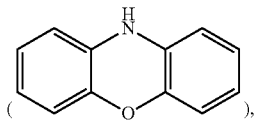 [SMILES: c1ccc2c(c1)Nc1ccccc1O2]

a phenothiazine group

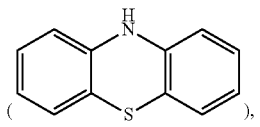 [SMILES: c1ccc2c(c1)Nc1ccccc1S2]

a dihydroacridine group

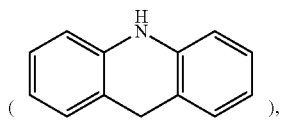

and the like, but are not limited thereto.

In the present specification, the heteroaryl group may be monocyclic or polycyclic, may be an aromatic ring, an aliphatic ring, or a fused ring of the aromatic ring and the aliphatic ring, and may be selected from the examples of the heteroaryl group.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the "adjacent groups are bonded to each other to form a ring" among the substituents means that a substituent is bonded to an adjacent group to form a substituted or unsubstituted hydrocarbon ring; or a substituted or unsubstituted hetero ring.

In the present specification, the above-described description on the aryl group and the alkenyl group may be applied to the aryl group and the alkenyl group in the arylalkenyl group.

In the present specification, the haloaryl group means an aryl group which is substituted with a halogen group, and the above-described description on the halogen group and the aryl group may be applied to the halogen group and the aryl group in the haloaryl group.

An exemplary embodiment of the present specification provides a compound represented by the following Formula 1.

[Formula 1]

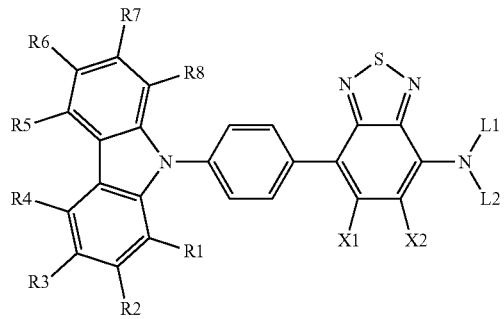

In Formula 1,

R1 to R8 are the same as or different from each other, and are each independently hydrogen; deuterium; a halogen group; a substituted or unsubstituted alkyl group; a substituted or unsubstituted aryl group; a substituted or unsubstituted silyl group; or a substituted or unsubstituted heteroaryl group, or adjacent groups may be bonded to each other to form one or more rings, X1 and X2 are the same as or different from each other, and are each independently hydrogen; deuterium; a halogen group; a substituted or unsubstituted alkyl group; a substituted or unsubstituted aryl group; or a substituted or unsubstituted heteroaryl group, and L1 and L2 are the same as or different from each other, and are each independently a substituted or unsubstituted aryl group.

In an exemplary embodiment of the present specification, R1 to R8 are the same as or different from each other, and are each independently hydrogen; deuterium; a halogen group; a substituted or unsubstituted alkyl group having 1 to 30 atoms; a substituted or unsubstituted aryl group having 6 to 30 carbon atoms; a substituted or unsubstituted silyl group; or a substituted or unsubstituted heteroaryl group having 2 to 30 carbon atoms, or adjacent group may be bonded to each other to form one or more rings.

In an exemplary embodiment of the present specification, R1 to R8 are the same as or different from each other, and are each independently hydrogen; deuterium; a halogen group; a substituted or unsubstituted alkyl group having 1 to 30 carbon atoms; an aryl group having 6 to 30 carbon atoms, which is unsubstituted or substituted with a halogen group, a substituted or unsubstituted alkyl group, a substituted or unsubstituted alkoxy group, a substituted or unsubstituted silyl group, a substituted or unsubstituted aryl group, or a substituted or unsubstituted heterocyclic group; a silyl group which is unsubstituted or substituted with an alkyl group; or a heteroaryl group having 2 to 30 carbon atoms, or adjacent groups may be bonded to each other to form one or more substituted or unsubstituted rings having 3 to 30 carbon atoms.

In an exemplary embodiment of the present specification, R1 to R8 are the same as or different from each other, and are each independently hydrogen; deuterium; a halogen group; an alkyl group having 1 to 30 carbon atoms; an aryl group having 6 to 30 carbon atoms, which is unsubstituted or substituted with one or more selected from the group consisting of a halogen group, a substituted or unsubstituted alkyl group having 1 to 30 carbon atoms, a substituted or unsubstituted alkoxy group having 1 to 30 atoms, a substituted or unsubstituted silyl group, a substituted or unsubstituted aryl group having 6 to 30 carbon atoms, and a substituted or unsubstituted heteroaryl group having 2 to 30 carbon atoms; a silyl group which is substituted with an alkyl group; a carbazolyl group; a substituted or unsubstituted dihydroacridine group; a phenothiazine group; a phenoxazine group; or a dibenzofuranyl group, or adjacent groups may be bonded to each other to form one or more substituted or unsubstituted rings having 3 to 30 carbon atoms.

In an exemplary embodiment of the present specification, R1 to R8 are the same as or different from each other, and are each independently hydrogen; deuterium; fluorine; an alkyl group having 1 to 30 carbon atoms; an aryl group having 6 to 30 carbon atoms, which is unsubstituted or substituted with one or more selected from the group consisting of a halogen group, an alkyl group having 1 to 30 carbon atoms, a fluoroalkyl group having 1 to 10 carbon atoms, an alkoxy group having 1 to 30 carbon atoms, a silyl group, an aryl group having 6 to 30 carbon atoms, and a heteroaryl group having 2 to 30 carbon atoms, which is unsubstituted or substituted with an aryl group; a silyl group which is substituted with an alkyl group; a carbazolyl group; a substituted or unsubstituted dihydroacridine group; a phenothiazine group; a phenoxazine group; or a dibenzofuranyl group, or adjacent groups may be bonded to each other to form one or more substituted or unsubstituted rings having 3 to 30 carbon atoms.

In an exemplary embodiment of the present specification, R1 to R8 are the same as or different from each other, and are each independently hydrogen; deuterium; fluorine; an alkyl group having 1 to 30 carbon atoms; an aryl group having 6 to 30 carbon atoms, which is unsubstituted or substituted with one or more selected from the group consisting of fluorine, an alkyl group having 1 to 30 carbon atoms, a trifluoromethyl group, a methoxy group, a triphenylsilyl group, a fluorenyl group, and a carbazole group which is unsubstituted or substituted with an aryl group; a silyl group which is substituted with a methyl group or an ethyl group; a carbazolyl group; a dihydroacridine group which is substituted with an alkyl group; a phenothiazine group; a phenoxazine group; or a dibenzofuranyl group, or adjacent groups may be bonded to each other to form one or more substituted or unsubstituted rings having 3 to 30 carbon atoms.

In an exemplary embodiment of the present specification, R1 to R8 are the same as or different from each other, and are each independently hydrogen; deuterium; fluorine; a methyl group; an ethyl group; a propyl group; a butyl group; an aryl group having 6 to 20 carbon atoms, which is unsubstituted or substituted with one or more selected from the group consisting of fluorine, a methyl group, an ethyl group, a propyl group, a butyl group, a trifluoromethyl group, a methoxy group, a triphenylsilyl group, a fluorenyl group, and a carbazole group which is unsubstituted or substituted with an aryl group; a silyl group which is substituted with a methyl group or an ethyl group; a carbazolyl group; a dihydroacridine group which is substituted with an alkyl group; a phenothiazine group; a phenoxazine group; or a dibenzofuranyl group, or adjacent groups may be bonded to each other to form one or more substituted or unsubstituted rings having 3 to 30 carbon atoms.

In an exemplary embodiment of the present specification, X1 and X2 are the same as or different from each other, and are each independently hydrogen; deuterium; a halogen group; a substituted or unsubstituted alkyl group; a substituted or unsubstituted aryl group; or a substituted or unsubstituted heteroaryl group.

In an exemplary embodiment of the present specification, X1 and X2 are the same as or different from each other, and are each independently hydrogen; deuterium; a halogen group; or a substituted or unsubstituted alkyl group.

In an exemplary embodiment of the present specification, X1 and X2 are the same as or different from each other, and are each independently hydrogen; deuterium; or a halogen group.

In an exemplary embodiment of the present specification, X1 and X2 are the same as or different from each other, and are each independently hydrogen; deuterium; or fluorine.

In an exemplary embodiment of the present specification, L1 and L2 are the same as or different from each other, and are each independently a substituted or unsubstituted aryl group having 6 to 30 carbon atoms.

In an exemplary embodiment of the present specification, L1 and L2 are the same as or different from each other, and are each independently an aryl group having 6 to 30 carbon atoms, which is unsubstituted or substituted with one or more selected from the group consisting of a halogen group, a cyano group, a substituted or unsubstituted amine group, a substituted or unsubstituted alkyl group, a substituted or unsubstituted alkenyl group, a substituted or unsubstituted alkoxy group, a substituted or unsubstituted silyl group, a substituted or unsubstituted arylalkenyl group, a substituted or unsubstituted aryl group, and a substituted or unsubstituted heteroaryl group.

In an exemplary embodiment of the present specification, L1 and L2 are the same as or different from each other, and are each independently an aryl group having 6 to 30 carbon atoms, which is unsubstituted or substituted with one or more selected from the group consisting of a halogen group, a cyano group, a substituted or unsubstituted amine group having 1 to 30 carbon atoms, a substituted or unsubstituted alkyl group having 1 to 30 carbon atoms, a substituted or unsubstituted alkenyl group having 2 to 30 carbon atoms, a substituted or unsubstituted alkoxy group having 1 to 30 carbon atoms, a substituted or unsubstituted silyl group, a substituted or unsubstituted arylalkenyl group, a substituted or unsubstituted aryl group having 6 to 30 carbon atoms, and a substituted or unsubstituted heteroaryl group having 2 to 30 carbon atoms.

In an exemplary embodiment of the present specification, L1 and L2 are the same as or different from each other, and are each independently an aryl group having 6 to 30 carbon atoms, which is unsubstituted or substituted with one or more selected from the group consisting of fluorine, a cyano group, an N-biphenylamine group which is substituted with an aryl group unsubstituted or substituted with an alkyl group, a methyl group, a propyl group, a butyl group, a neopentyl group which is substituted with an aryl group, a trifluoromethyl group, an ethenyl group which is substituted with a cyano group and an aryl group, an ethenyl group which is substituted with an aryl group, a methoxy group, a triphenylsilyl group, a fluorenyl group, a terphenyl group, a naphthyl group, a substituted or unsubstituted phenoxazine group, a phenothiazine group, a dibenzofuranyl group, a substituted or unsubstituted dihydroacridine group, and a substituted or unsubstituted carbazole group.

In an exemplary embodiment of the present specification, L1 and L2 are the same as or different from each other, and are each independently an aryl group having 6 to 30 carbon atoms, which is unsubstituted or substituted with one or more selected from the group consisting of fluorine, a cyano group, an N-biphenylamine group which is substituted with an aryl group unsubstituted or substituted with an alkyl group, a methyl group, a propyl group, a butyl group, a neopentyl group which is substituted with an aryl group, a trifluoromethyl group, an ethenyl group which is substituted with a cyano group and an aryl group, an ethenyl group which is substituted with an aryl group, a methoxy group, a triphenylsilyl group, a fluorenyl group, a terphenyl group, a naphthyl group, a phenoxazine group which is unsubstituted or substituted with an aryl group, a phenothiazine group, a dibenzofuranyl group, a dihydroacridine group which is substituted with an alkyl group, and a carbazole group which is unsubstituted or substituted with an aryl group unsubstituted or substituted with an alkyl group or a halogen group.

In an exemplary embodiment of the present specification, Formula 1 is represented by the following structural formulae.

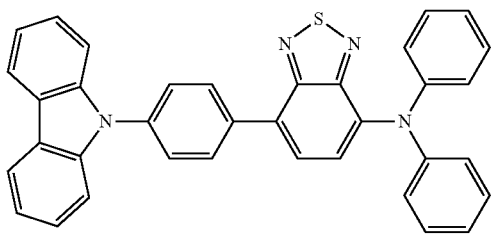
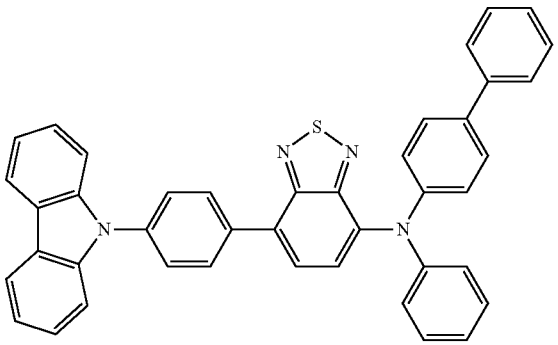
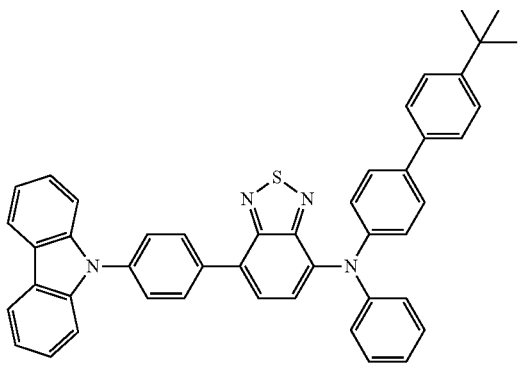
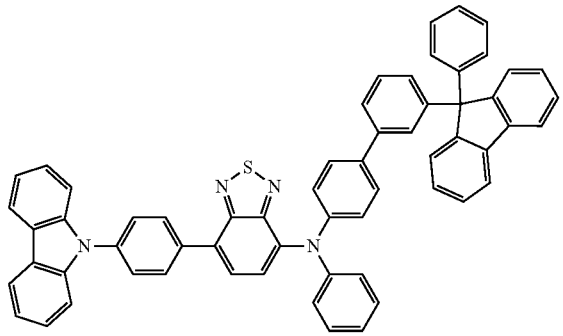
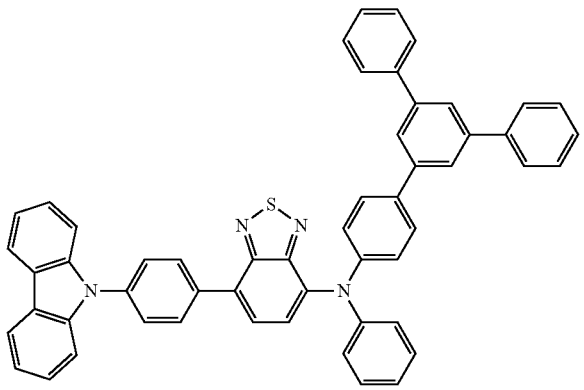
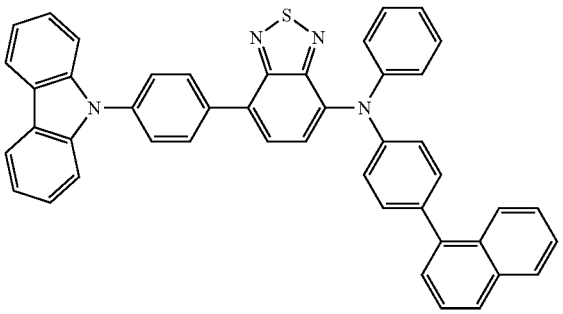

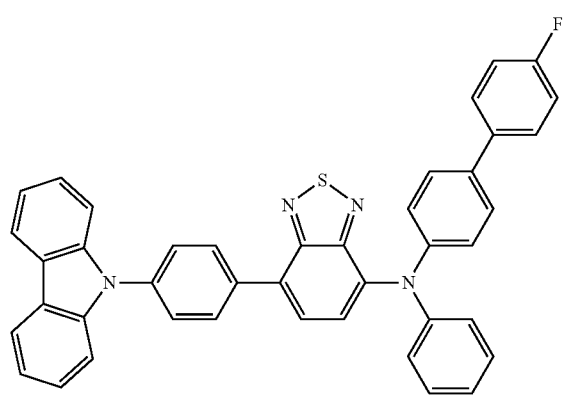
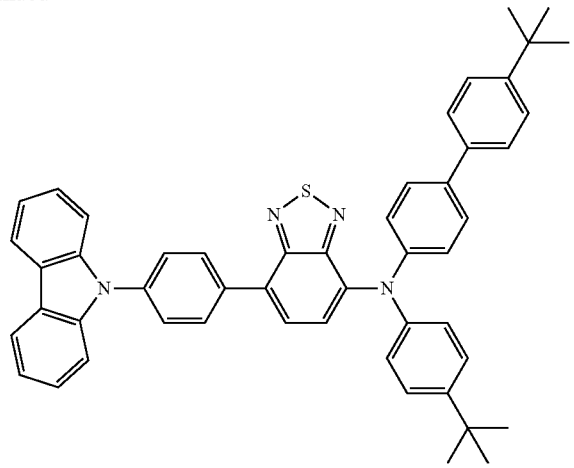
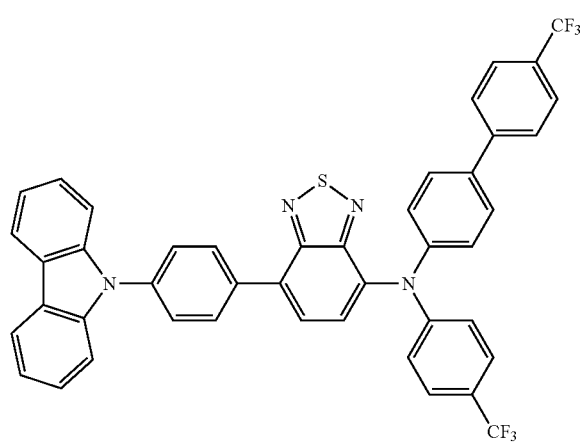
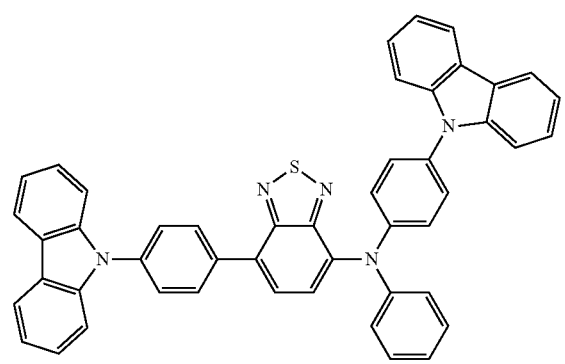
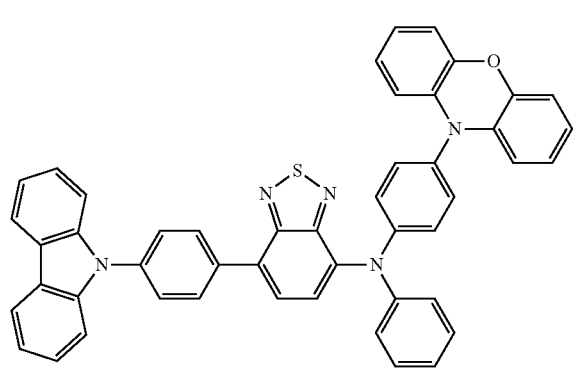
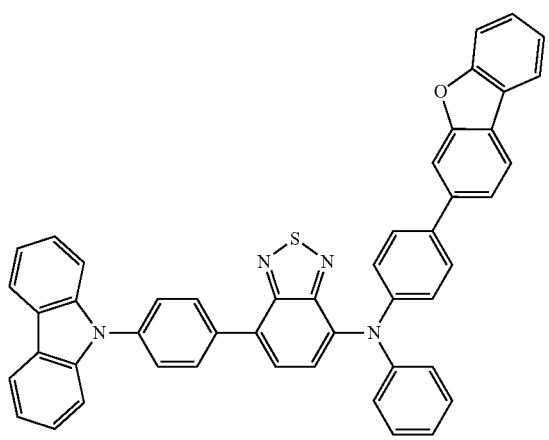

-continued
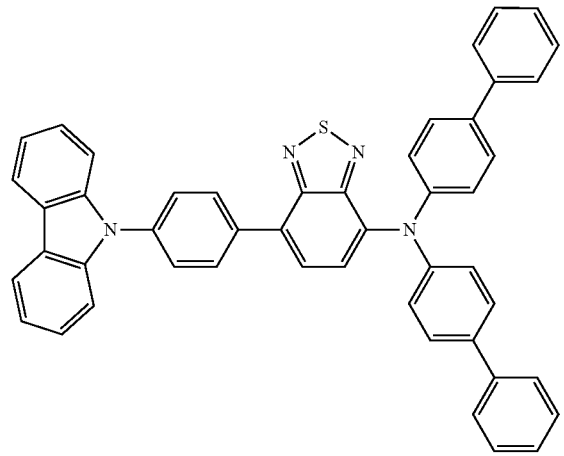
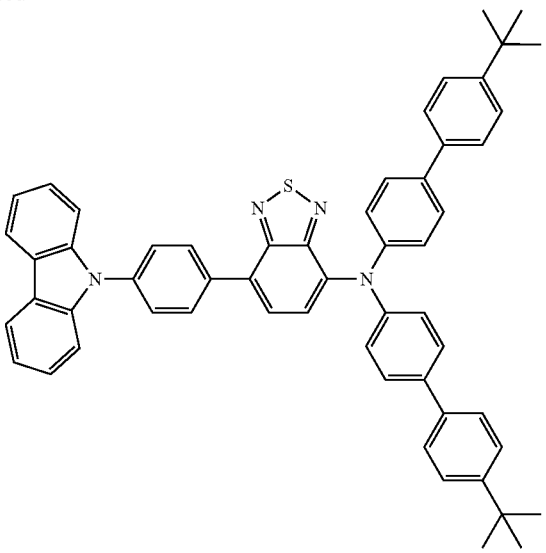
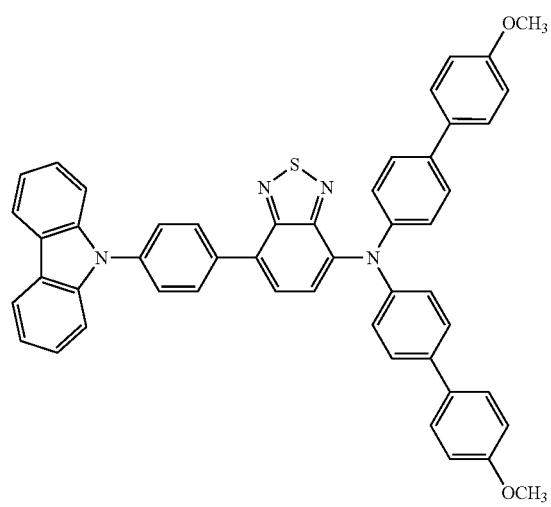
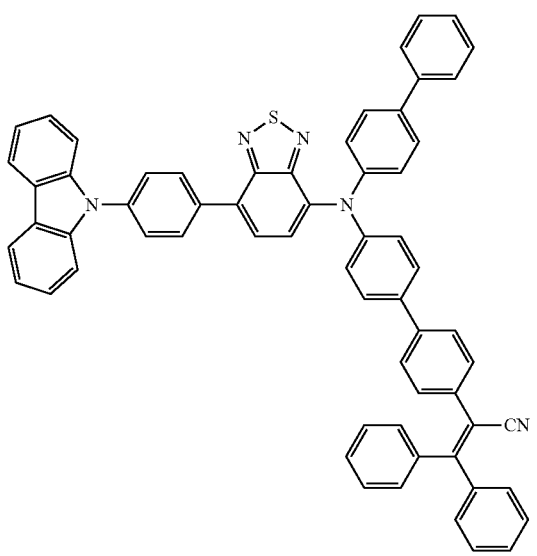
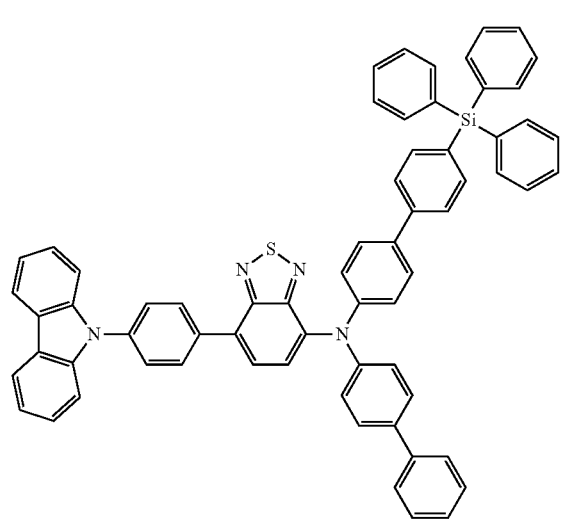
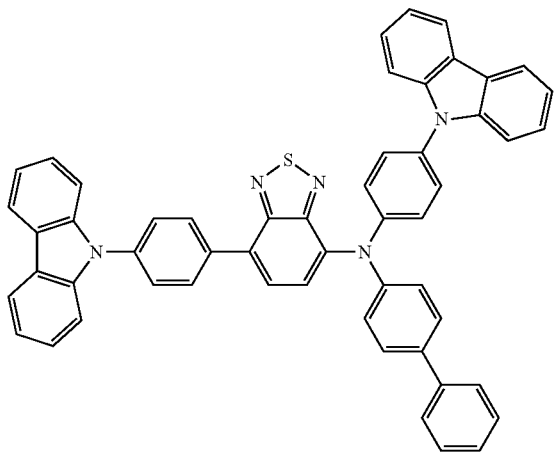

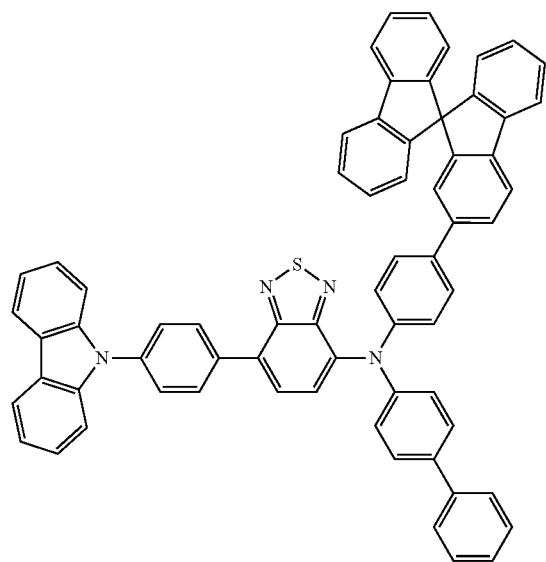
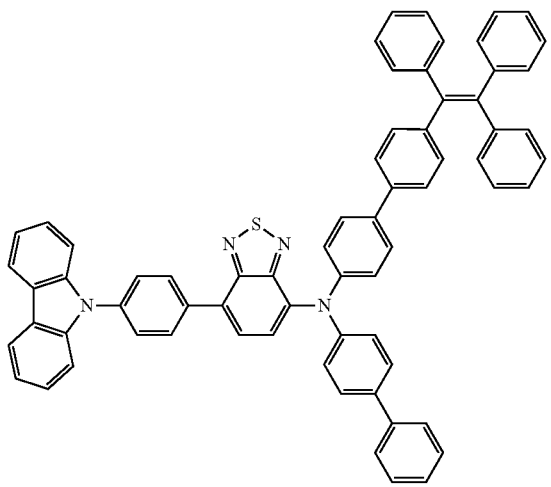
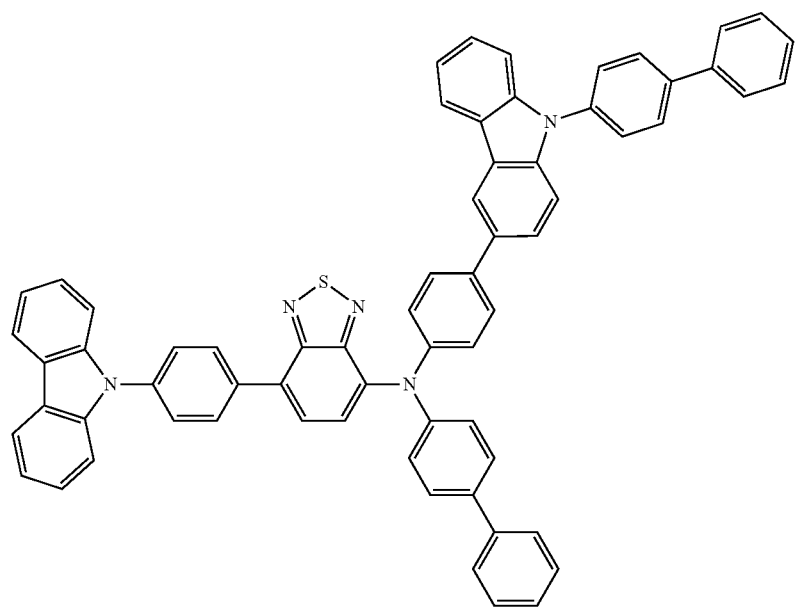

-continued
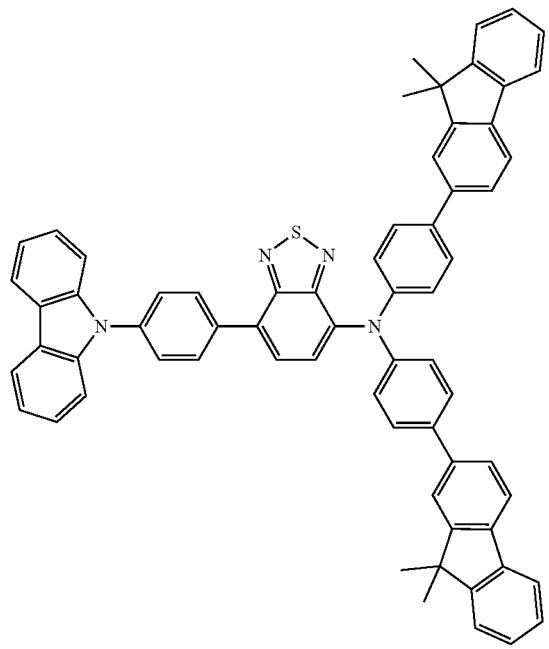
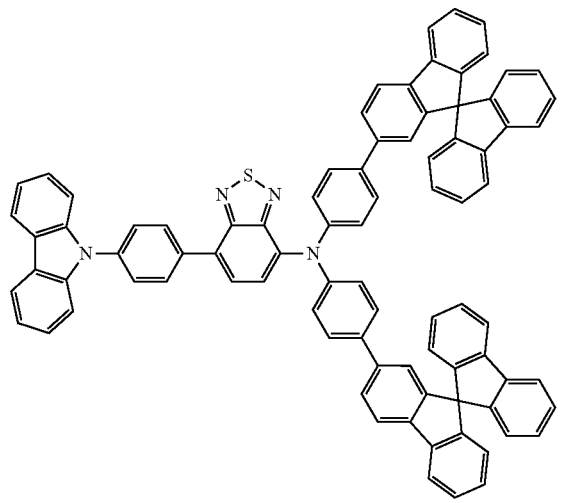
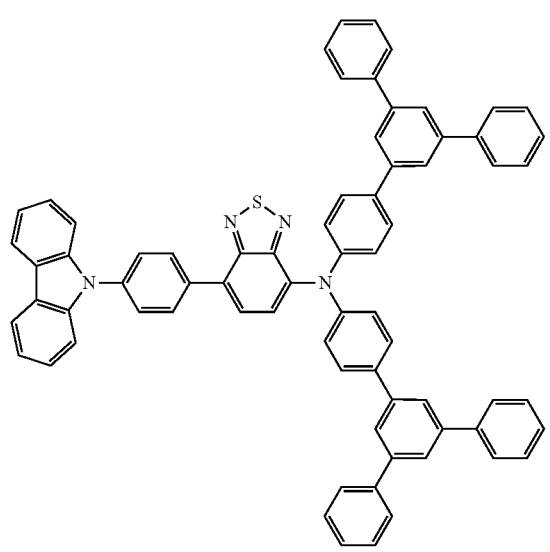
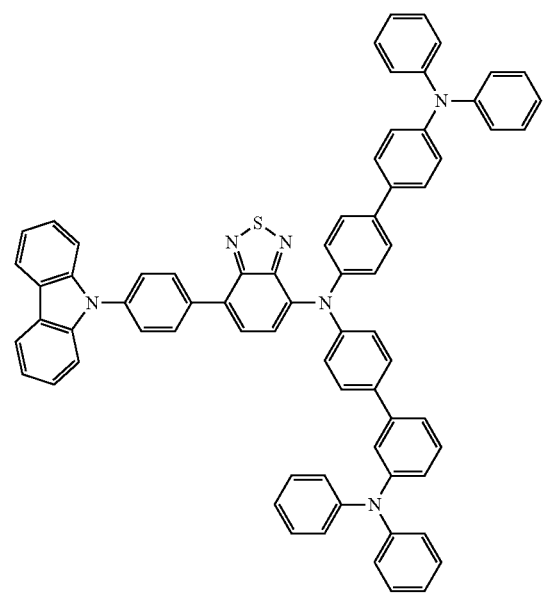

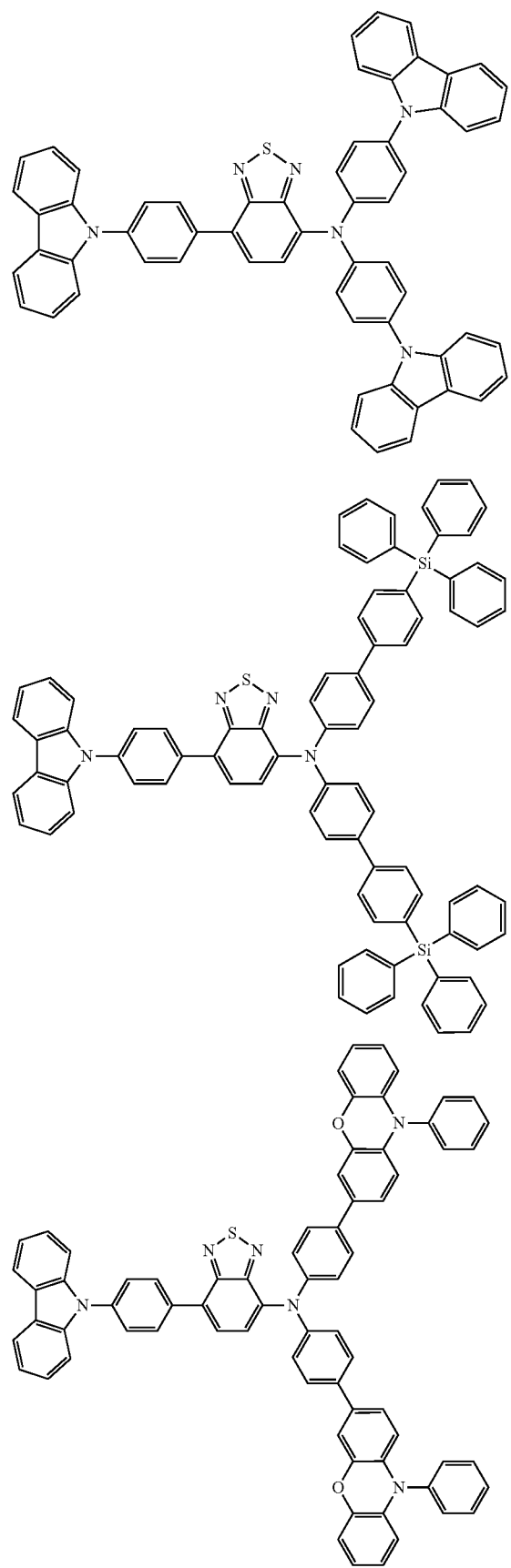
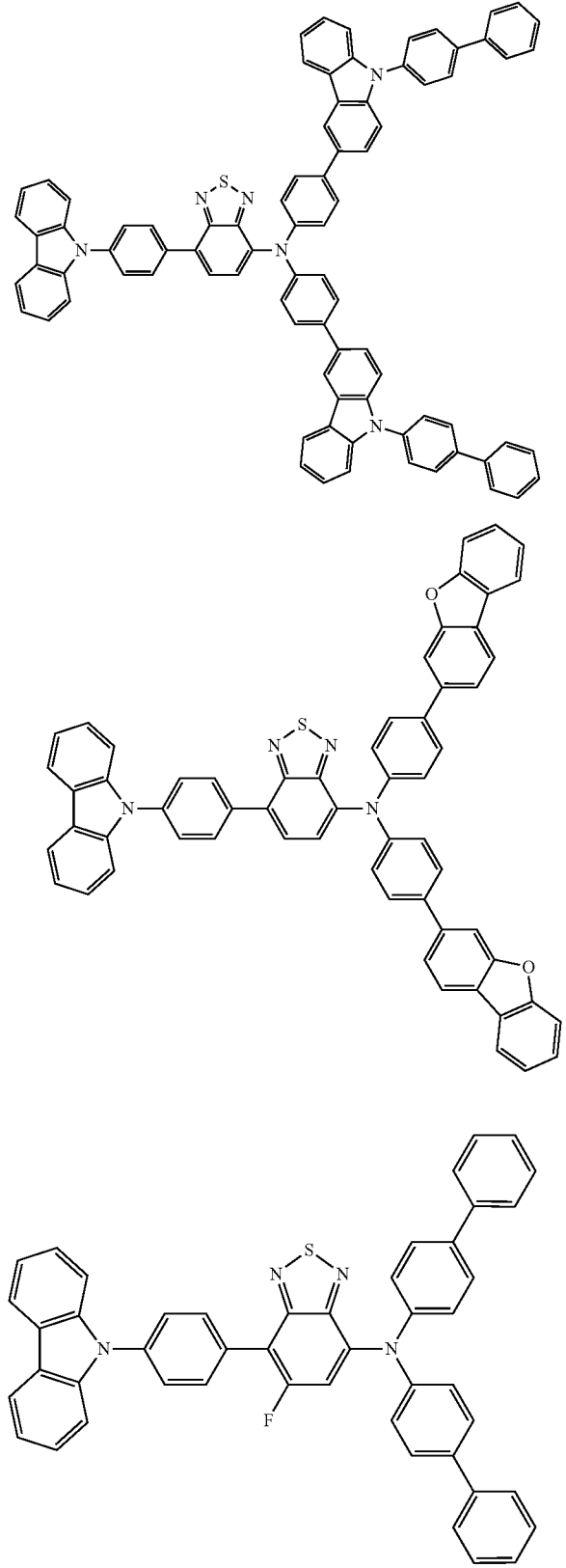

-continued
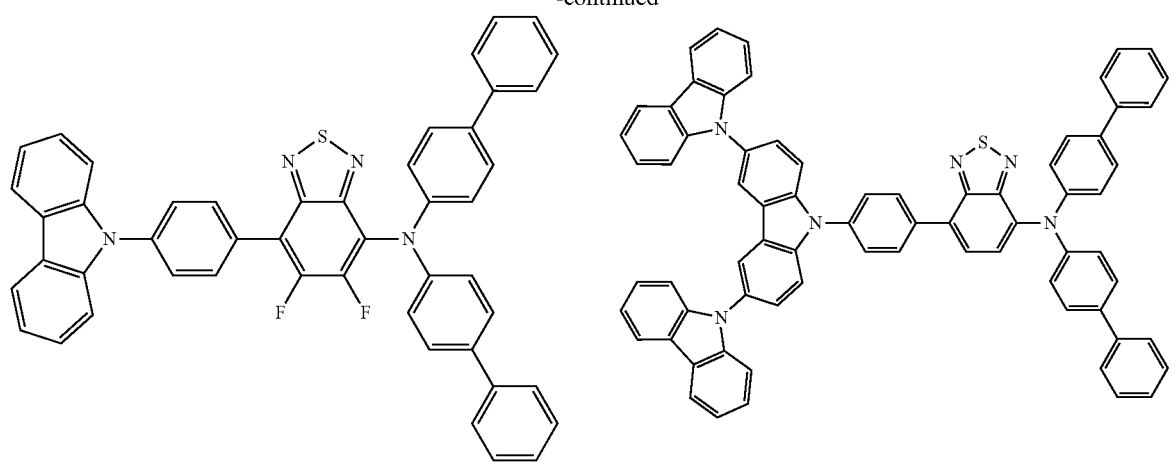
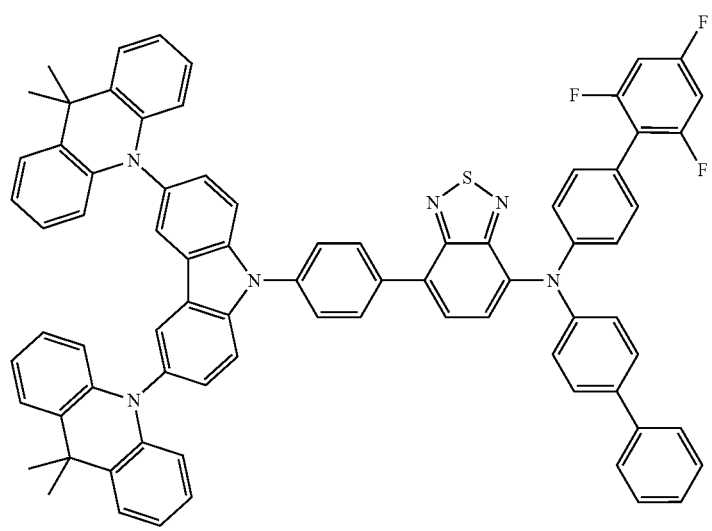
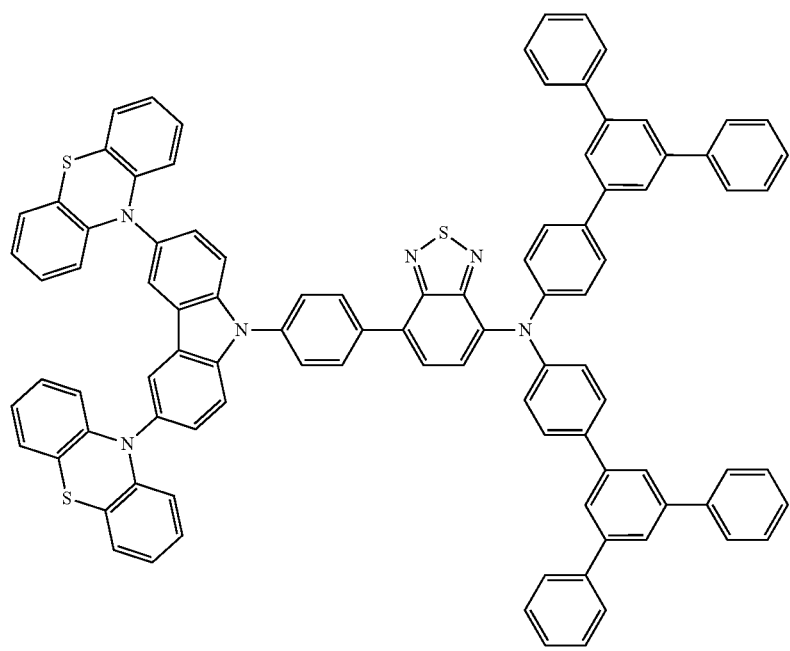

-continued
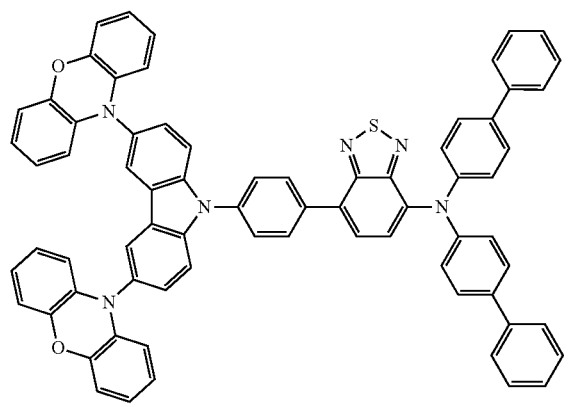
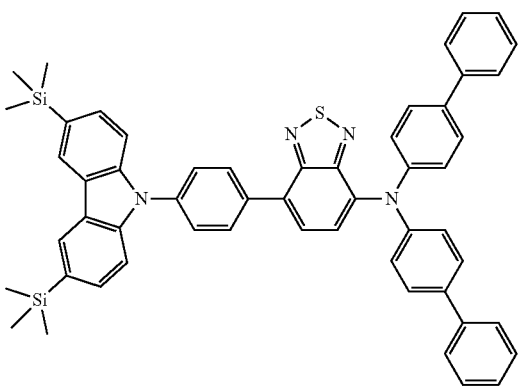
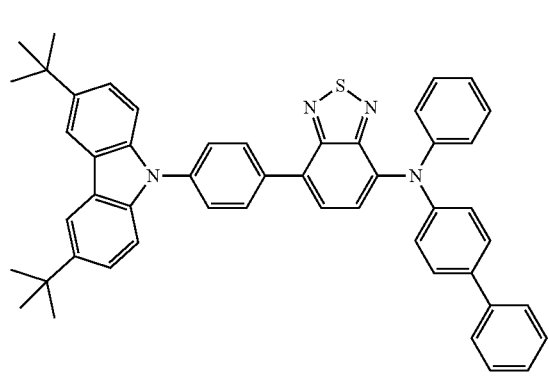
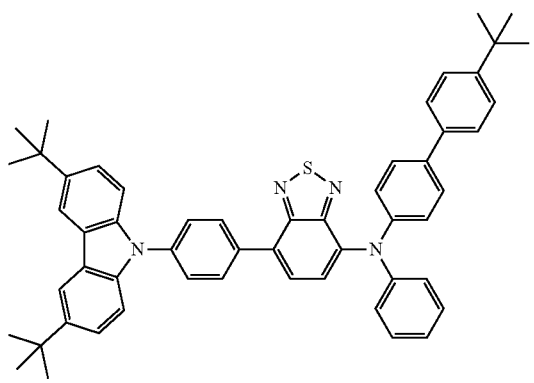
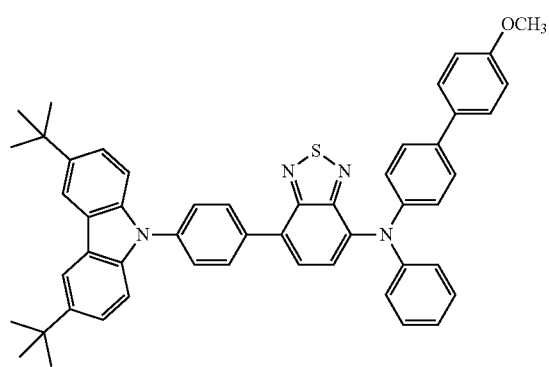
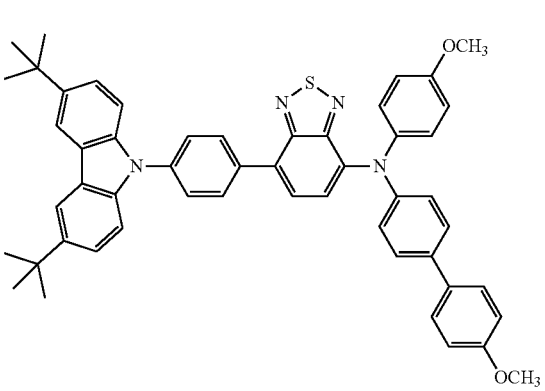
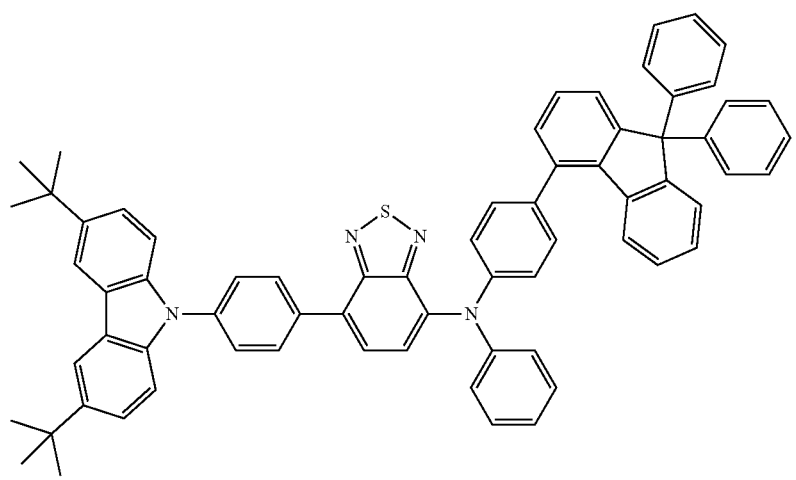

-continued
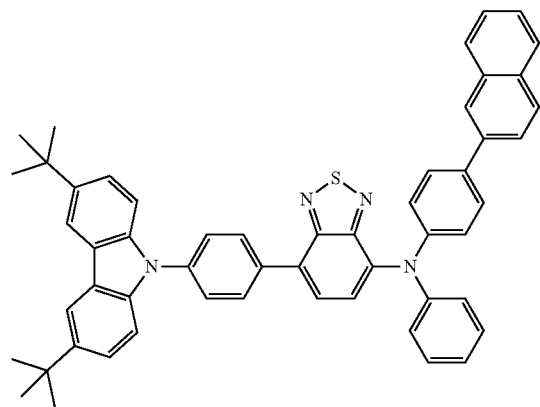
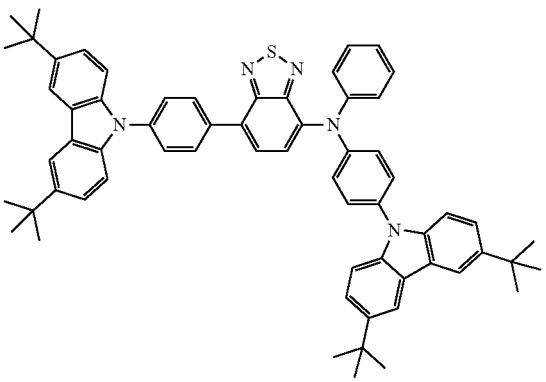
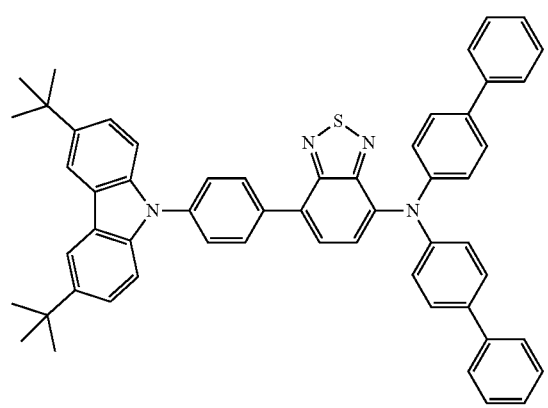
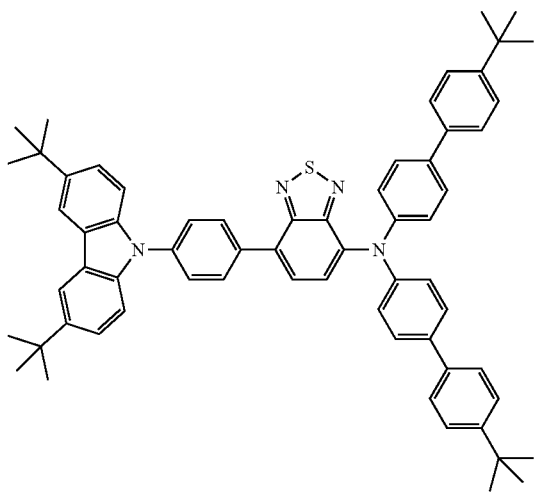
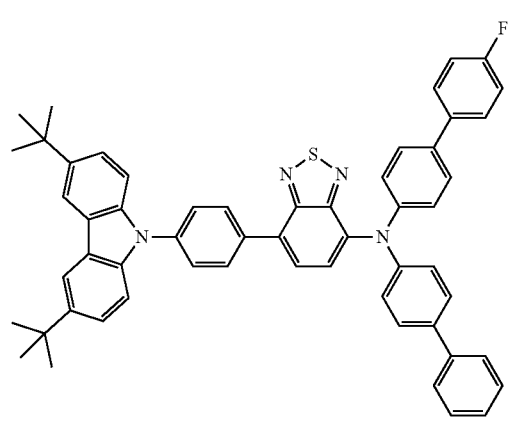
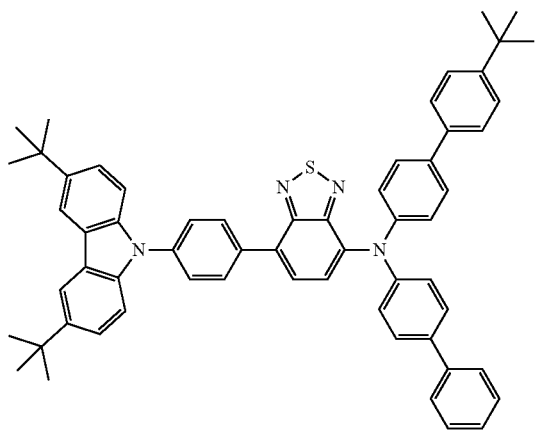

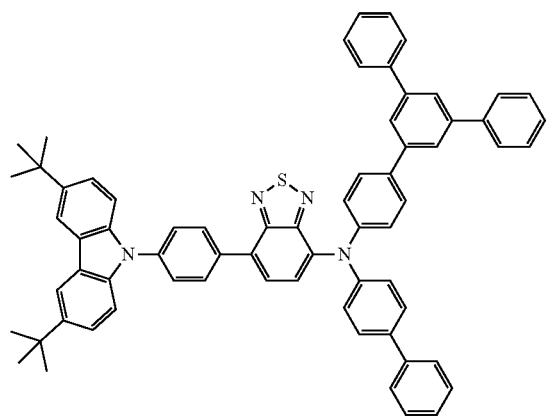
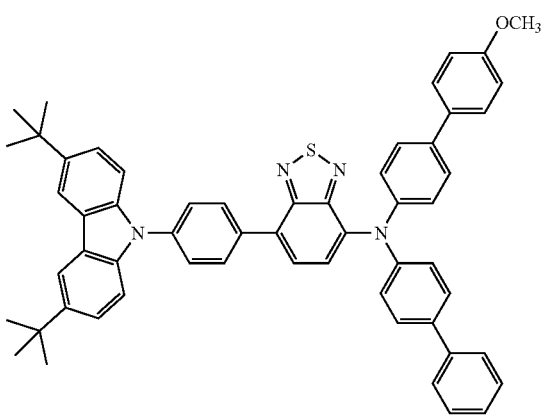
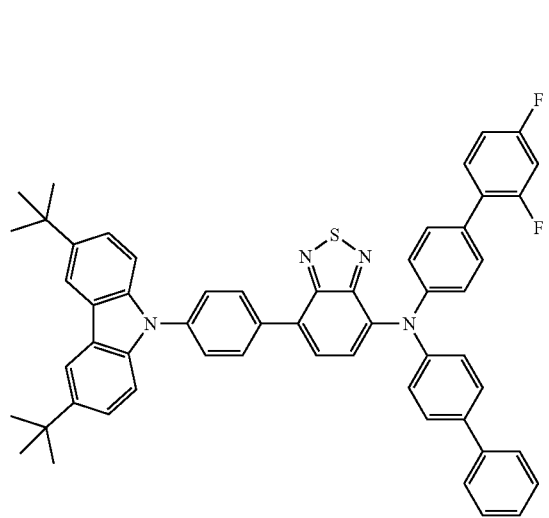
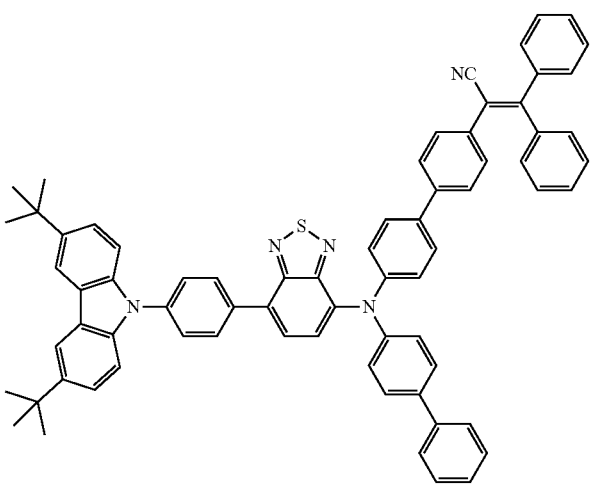
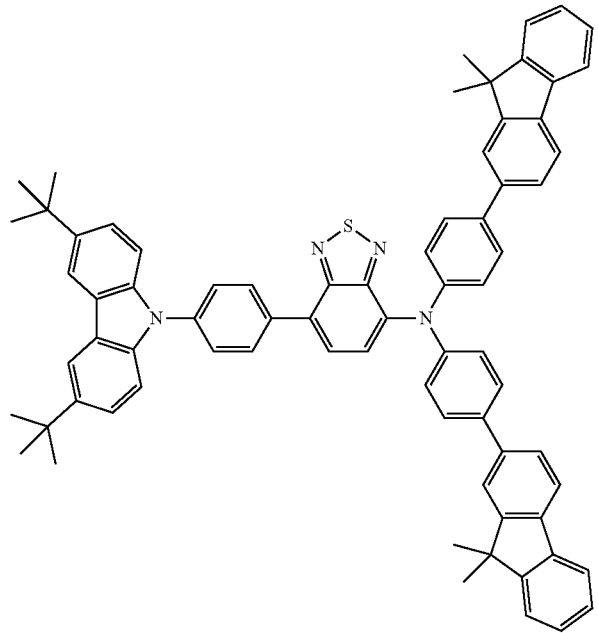

-continued
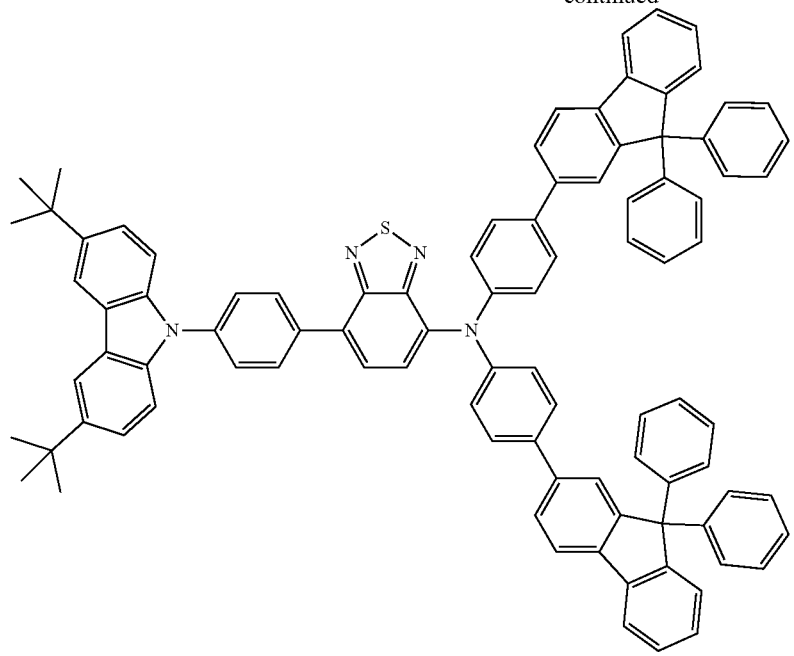
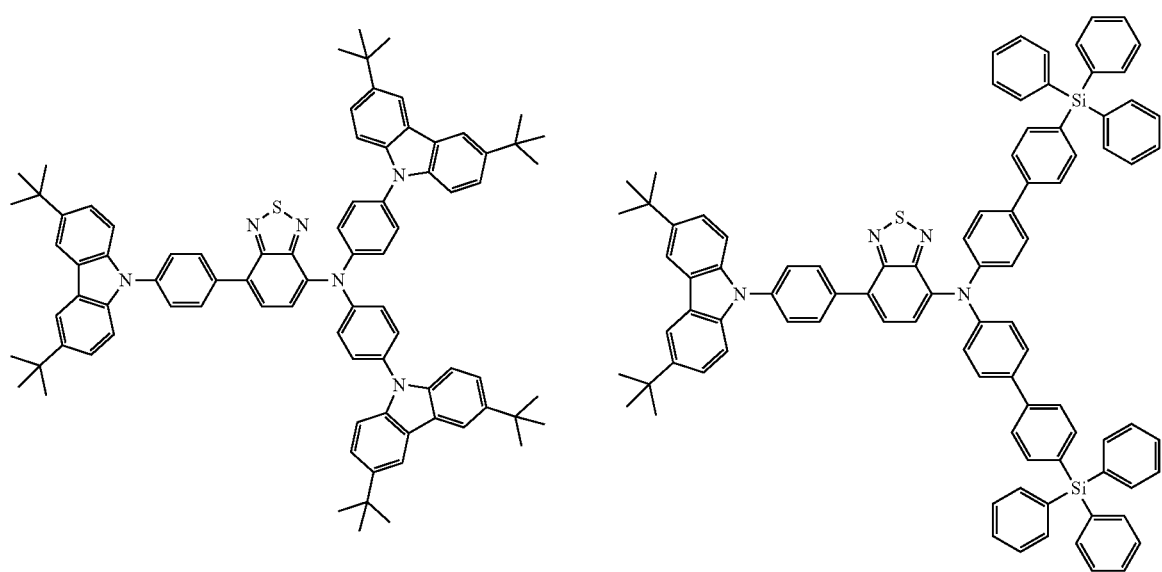

-continued
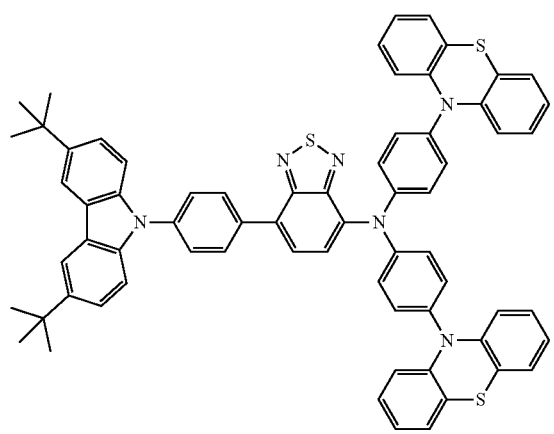
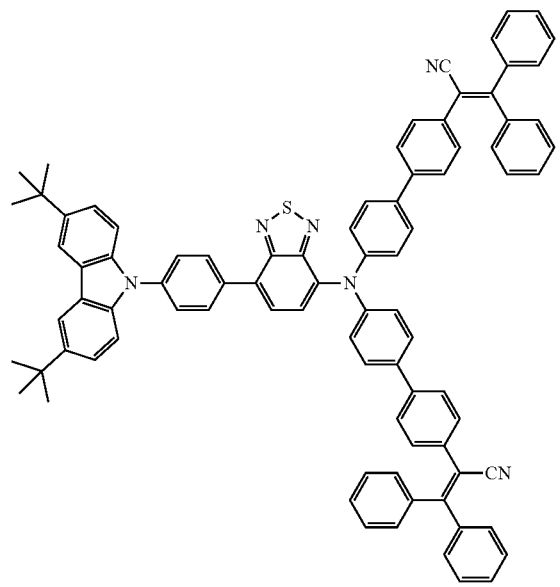
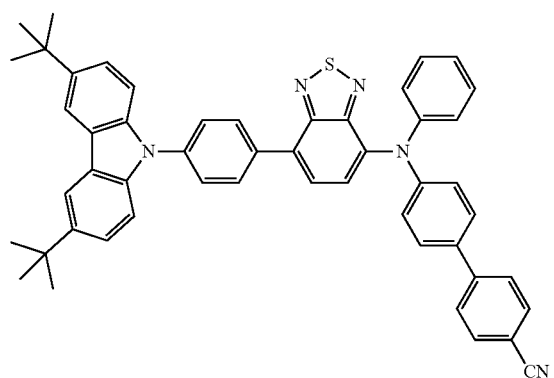
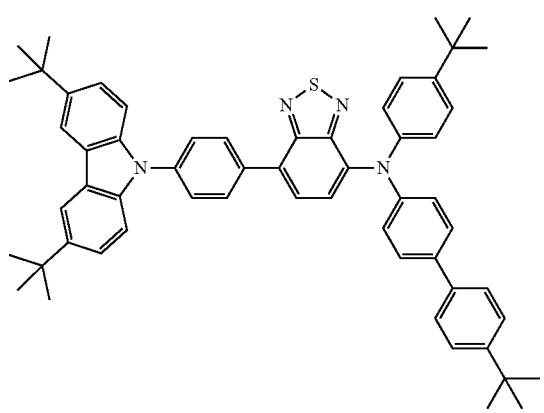
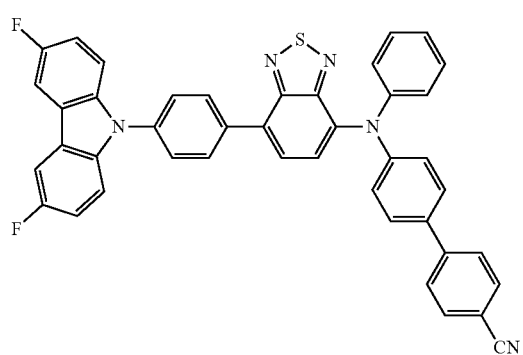
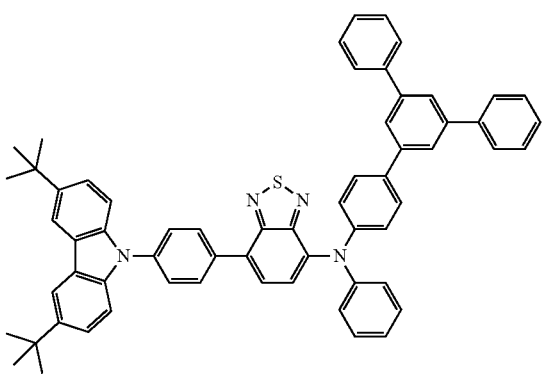

-continued
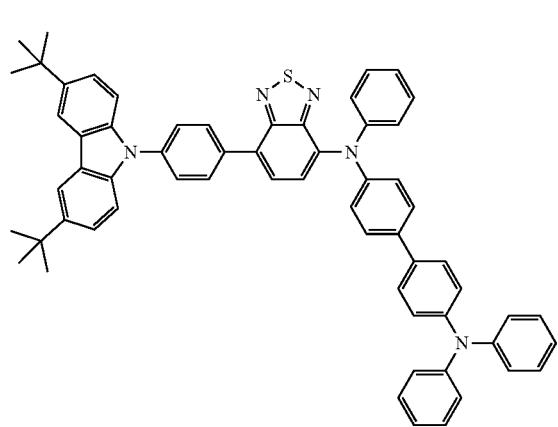
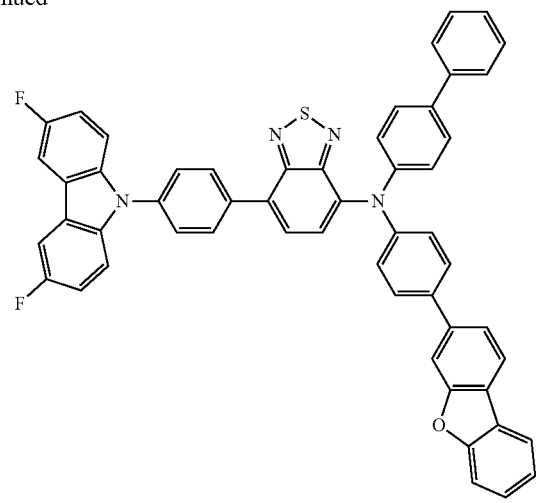
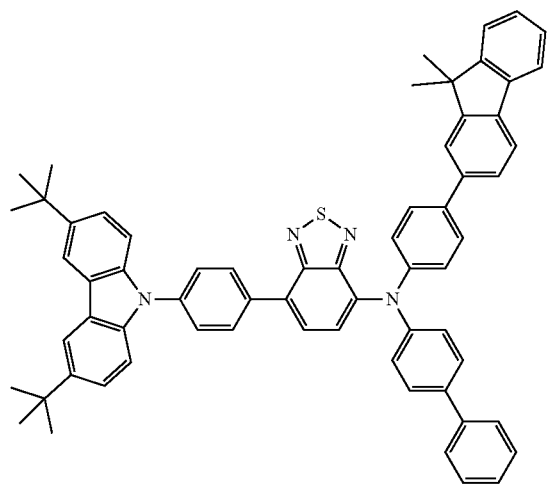
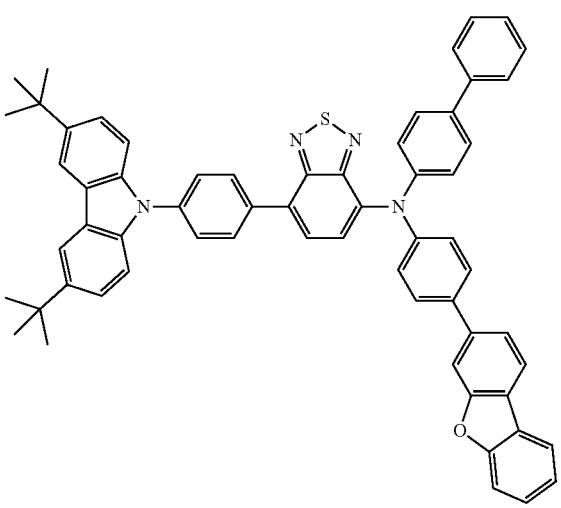
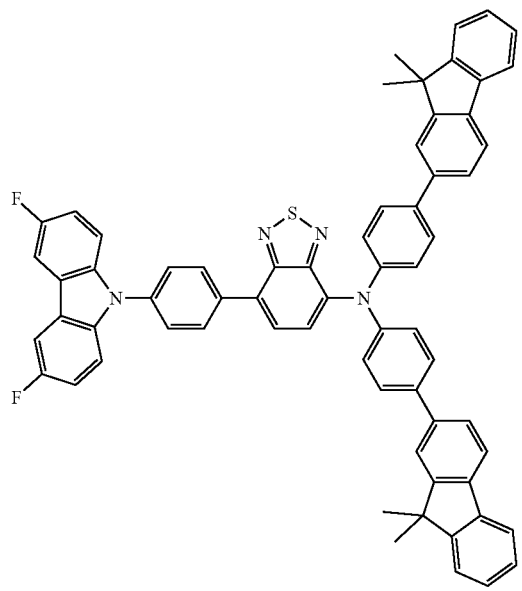
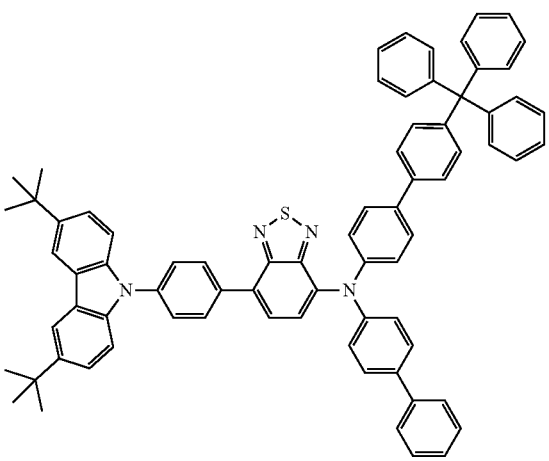

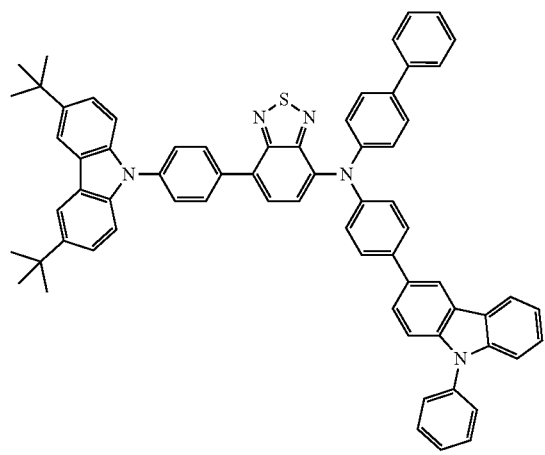
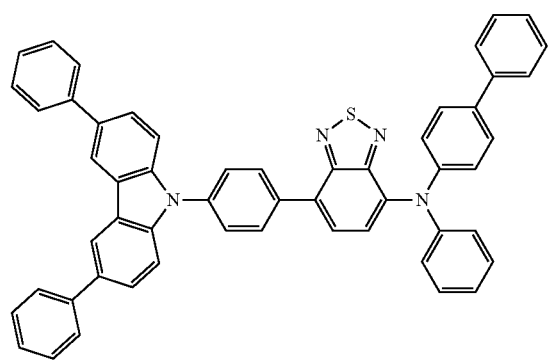
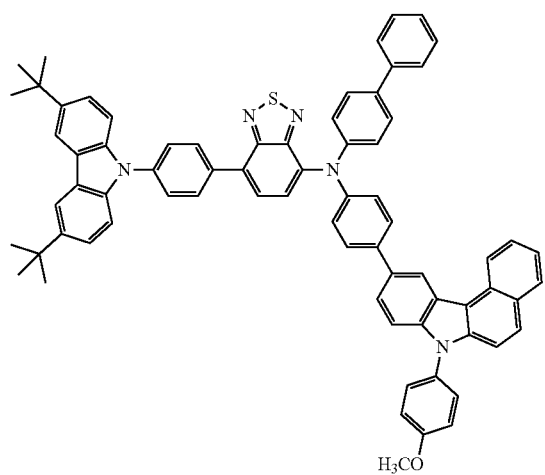
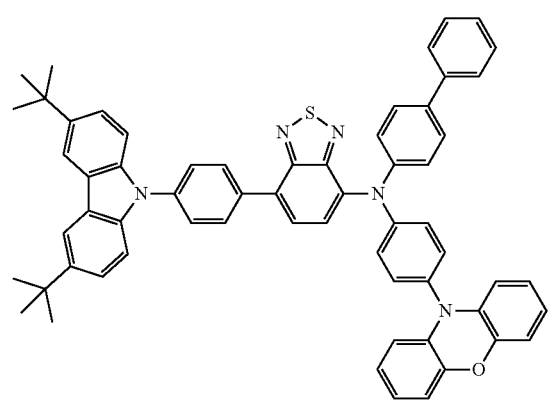
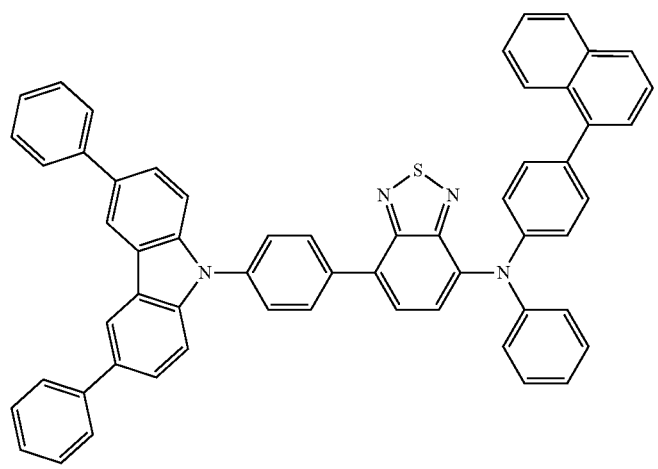

-continued
37
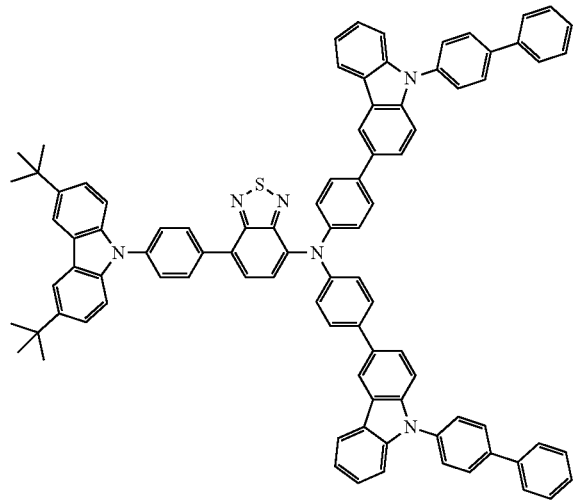
38
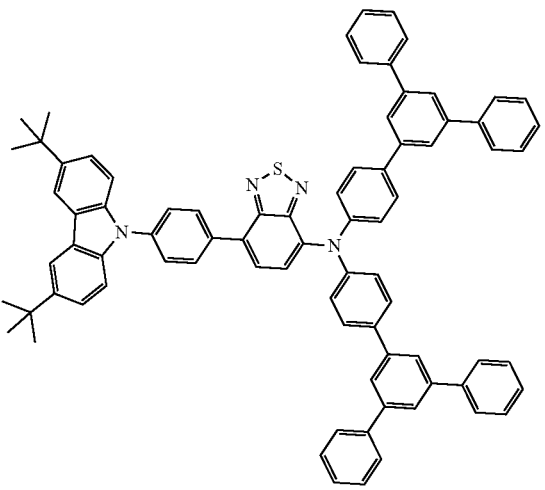
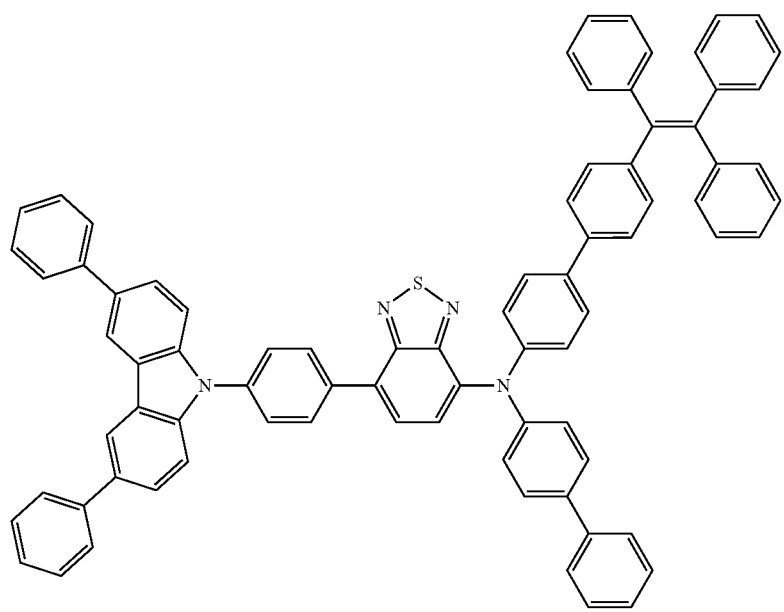
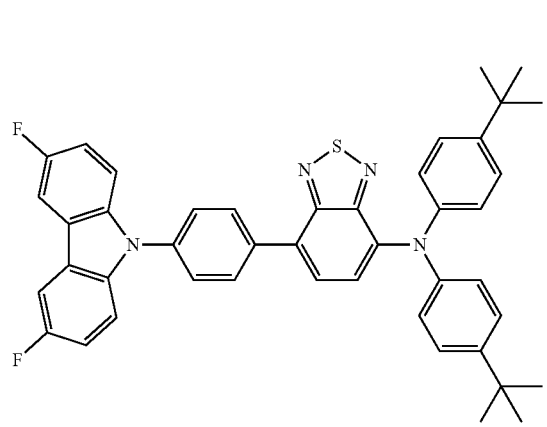
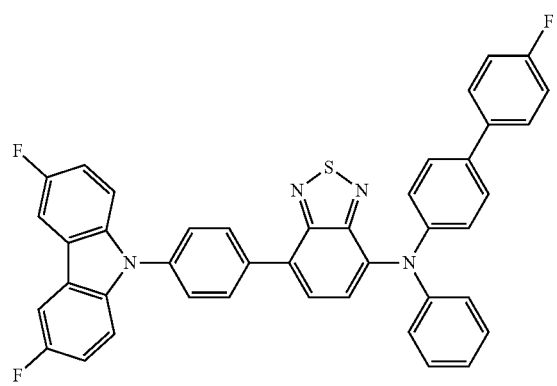

-continued
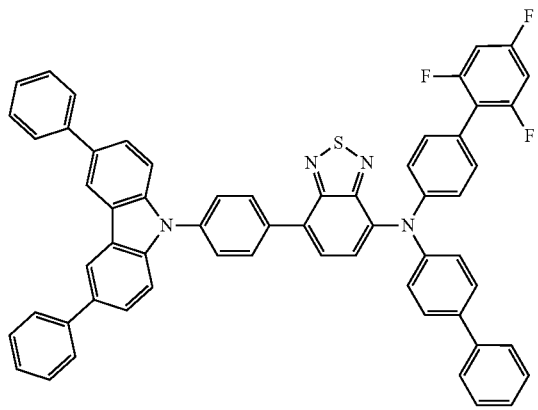
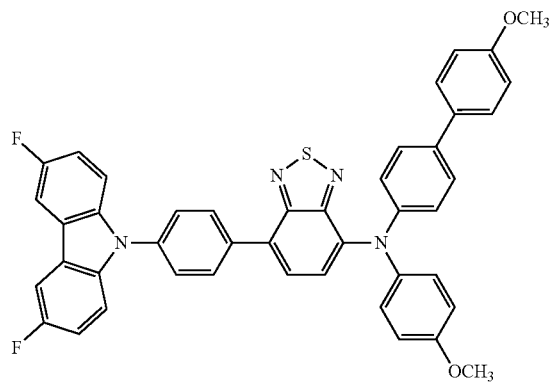
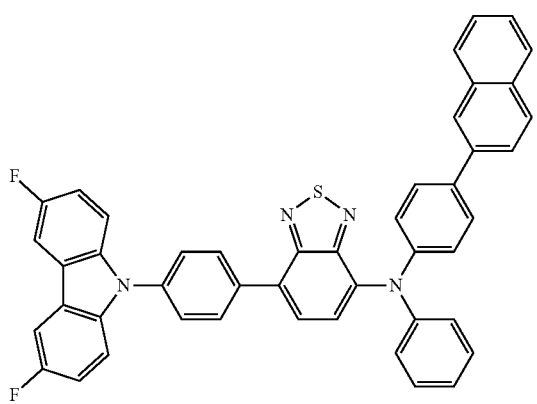
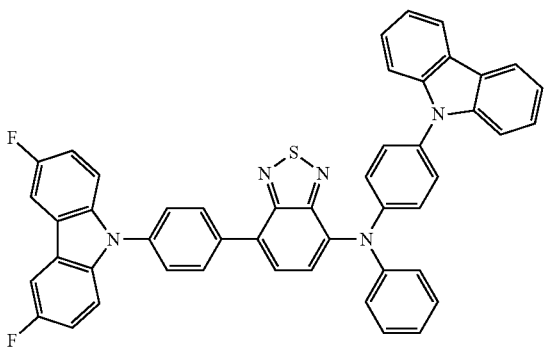
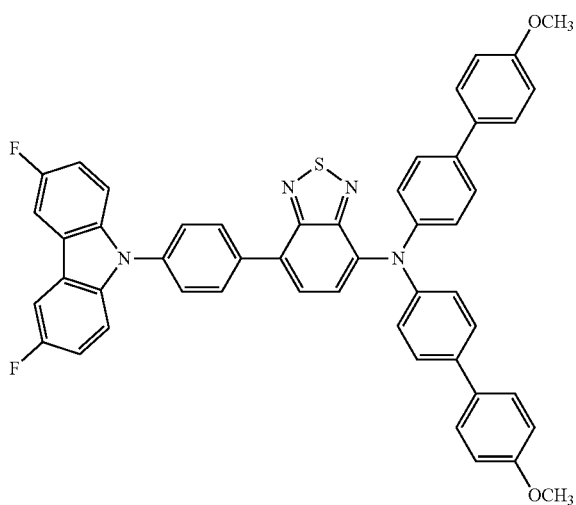
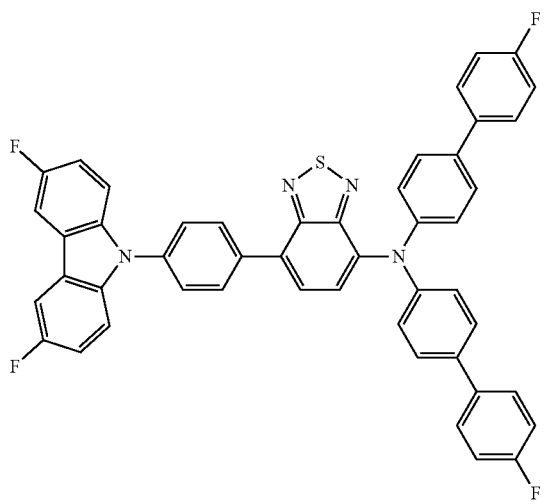

-continued
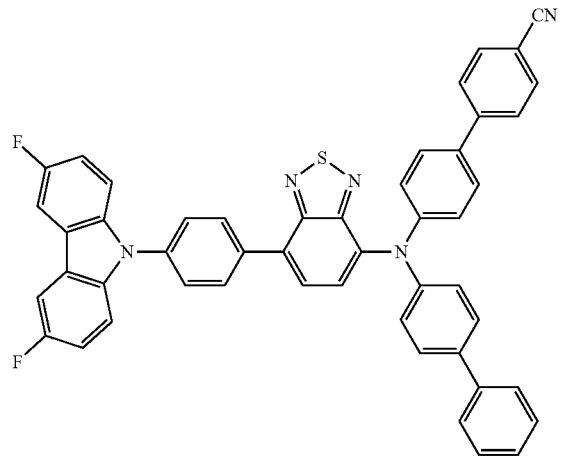
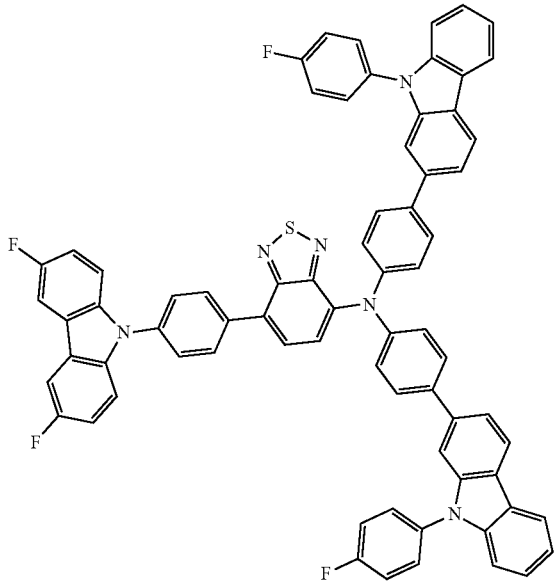
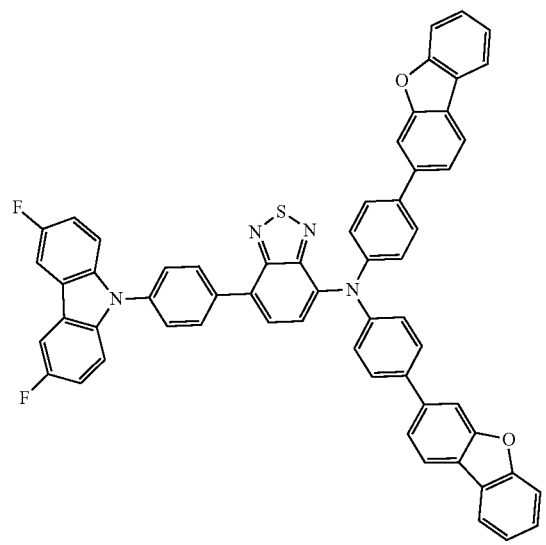
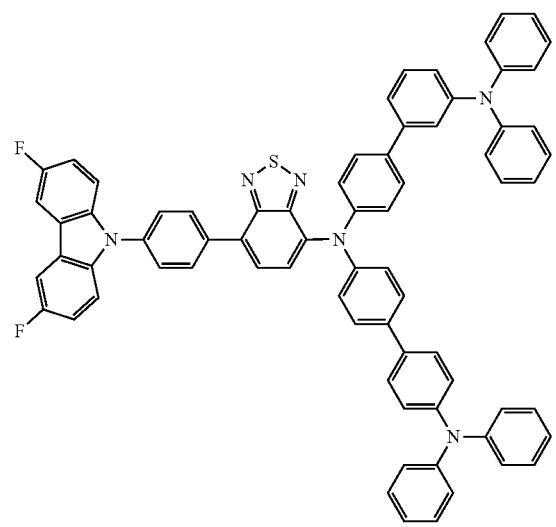
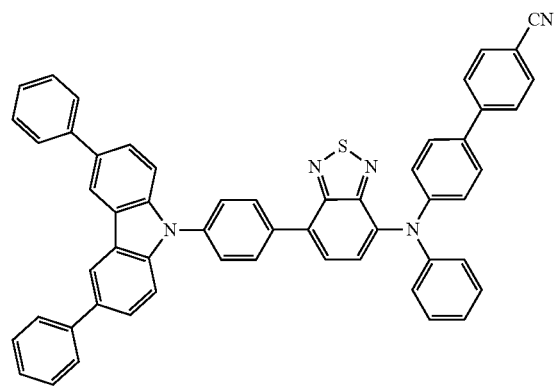
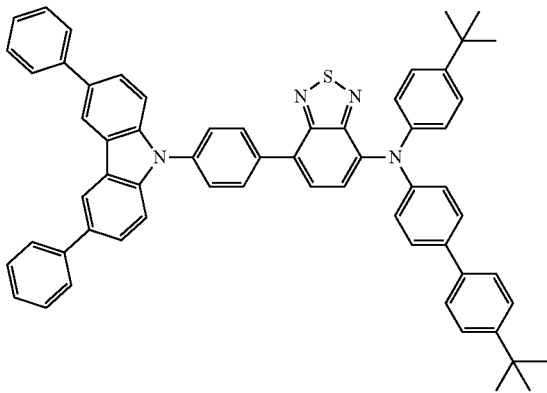

-continued
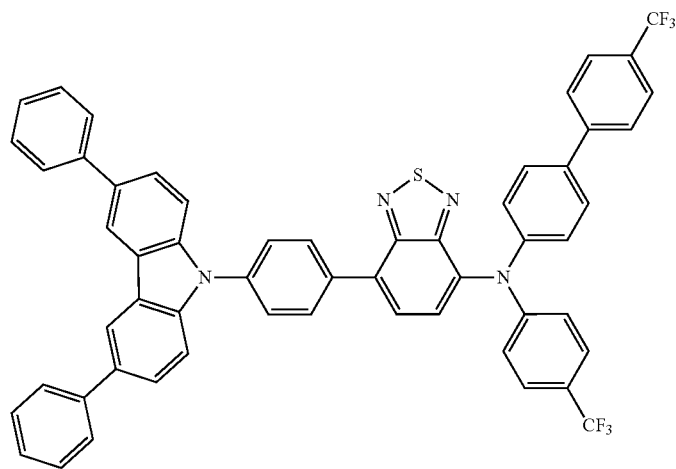
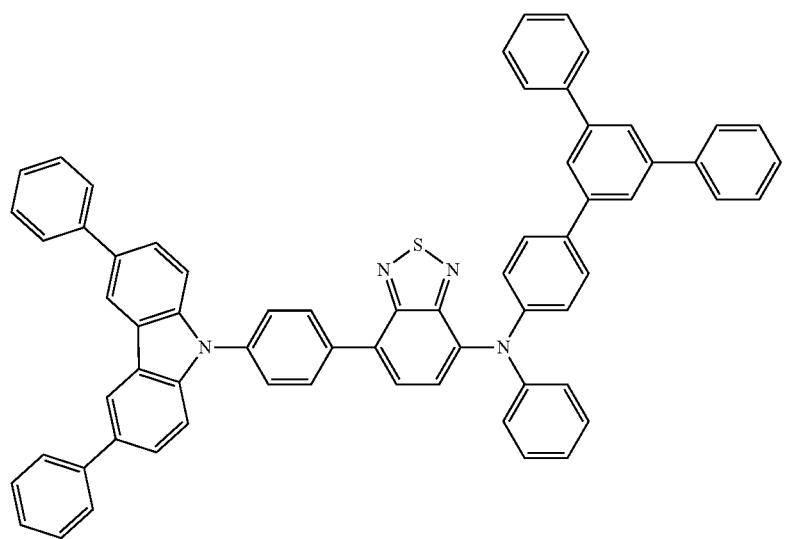
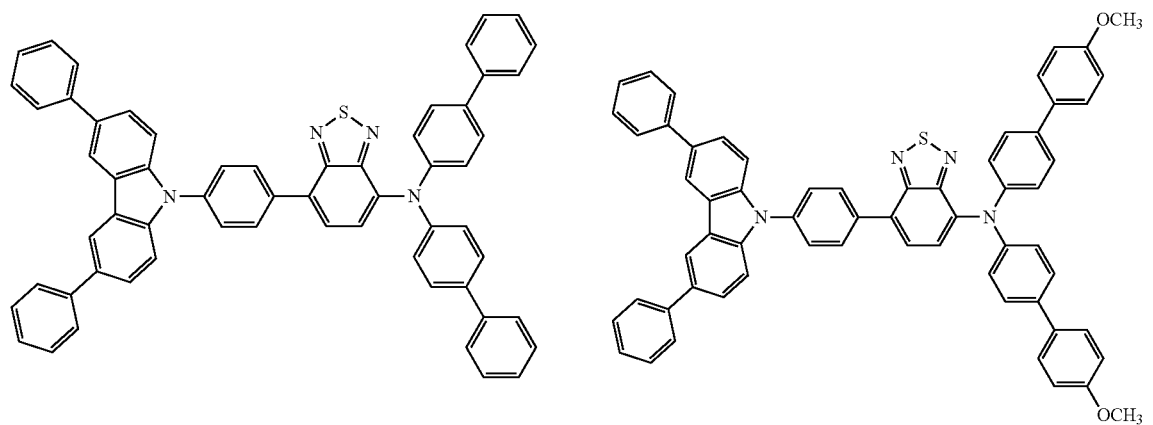

-continued
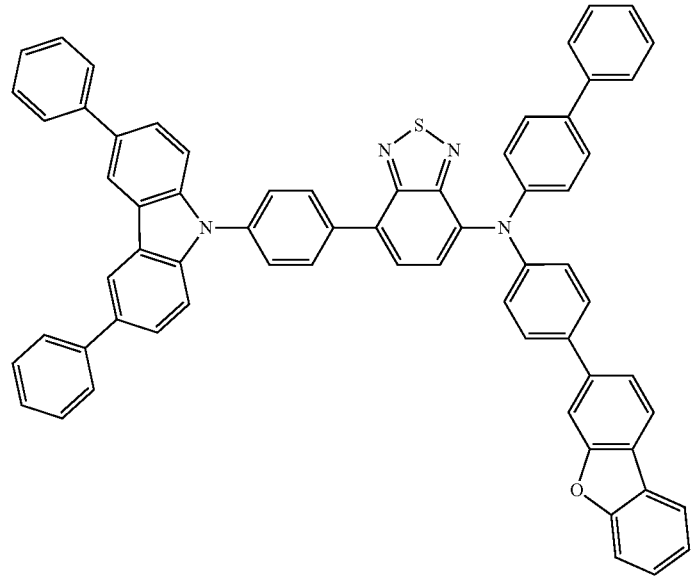
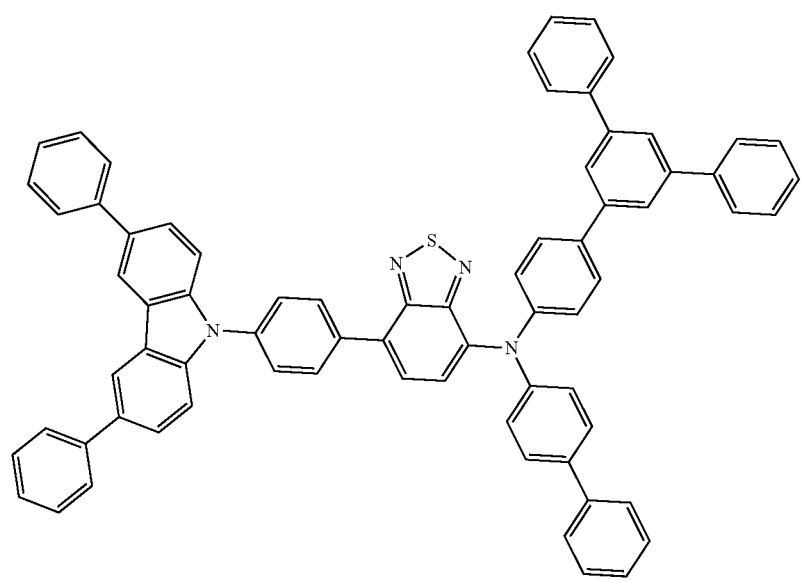

-continued
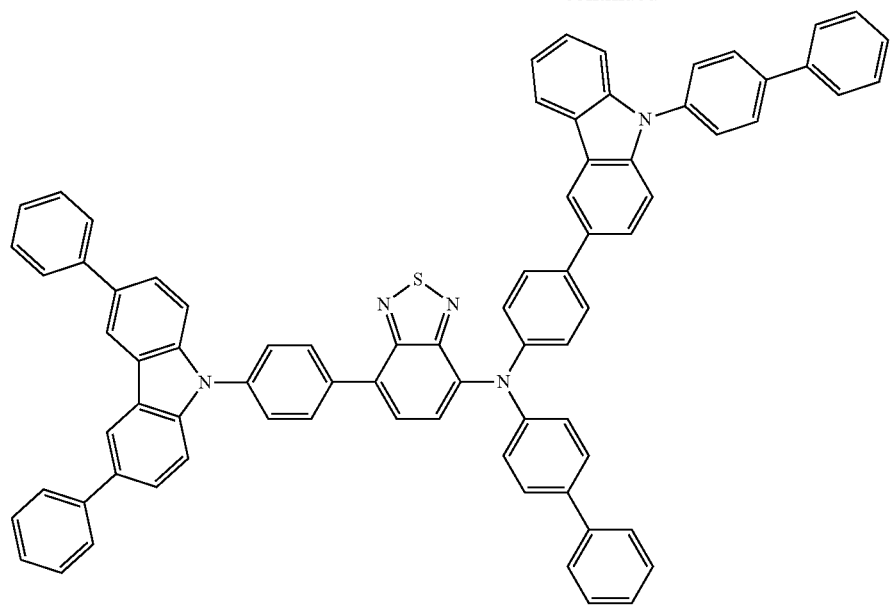
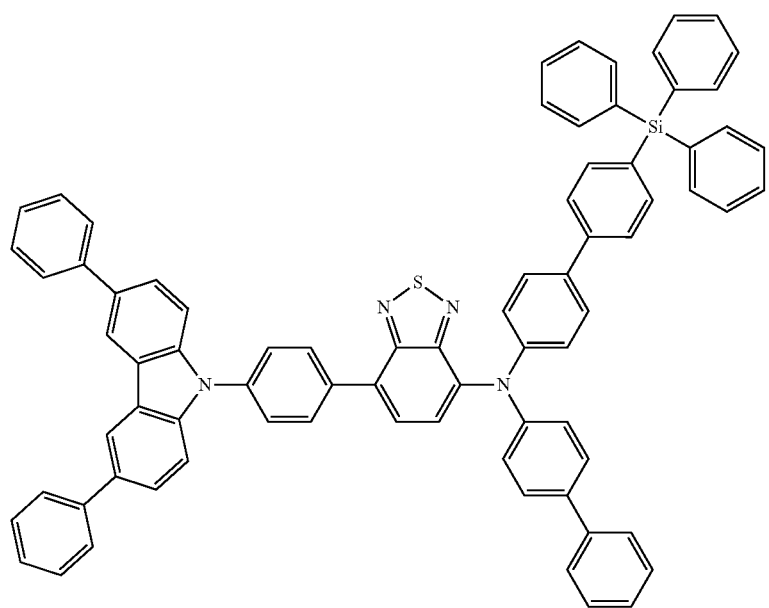

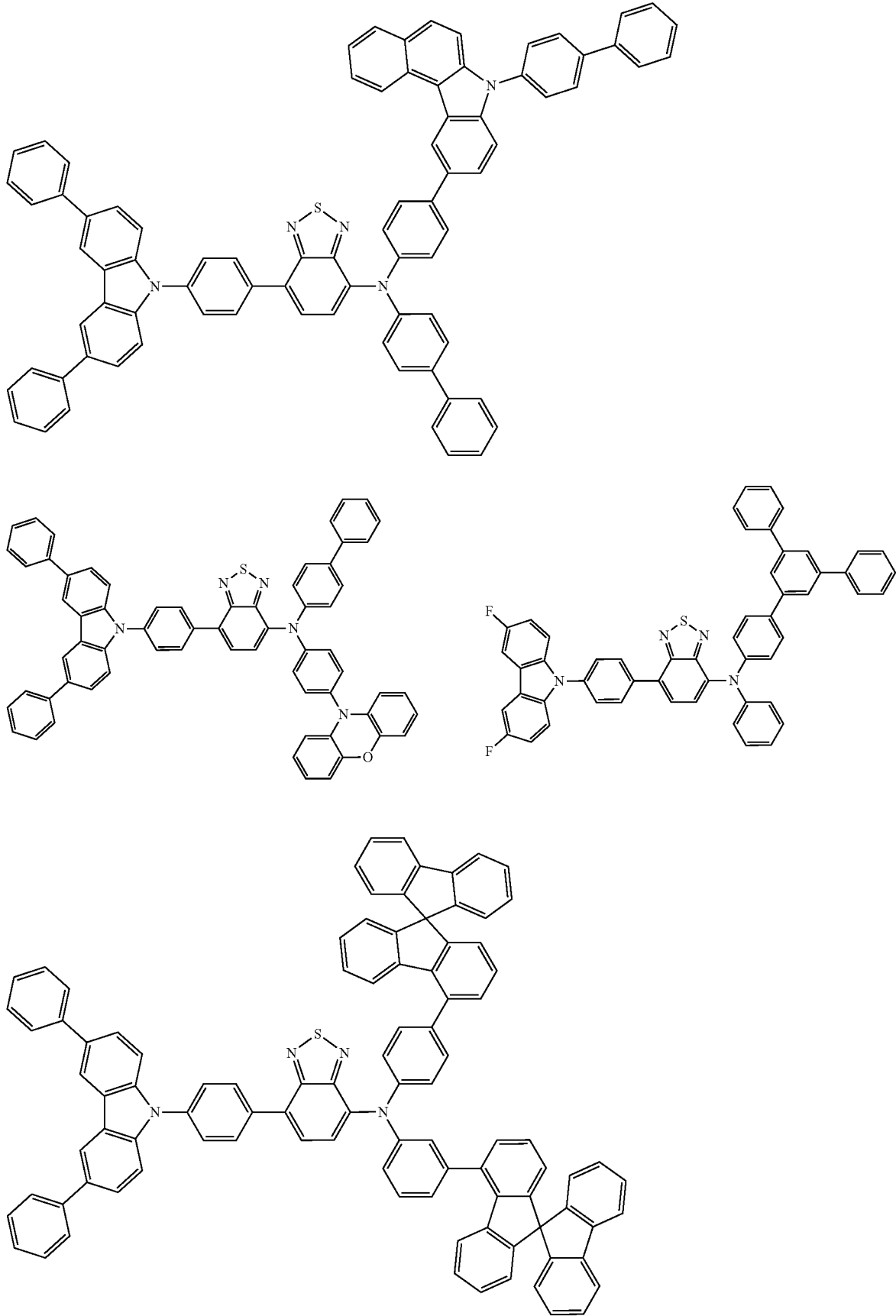

51
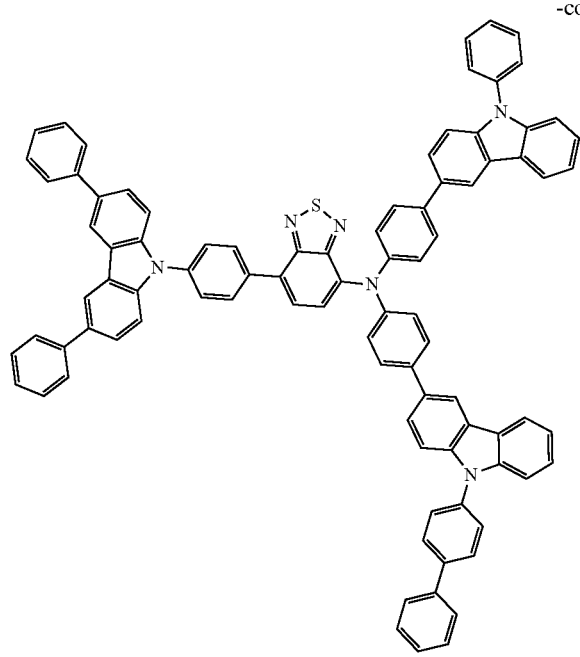
52
-continued
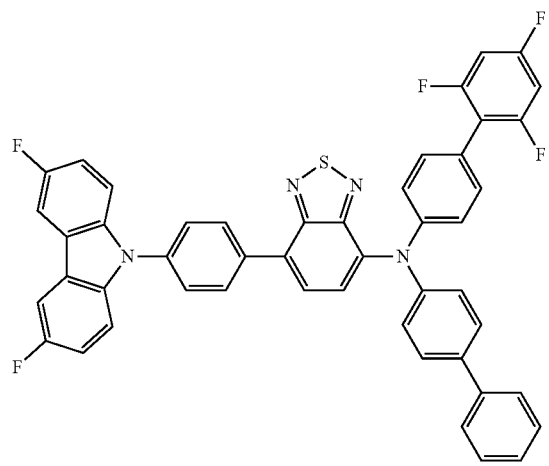
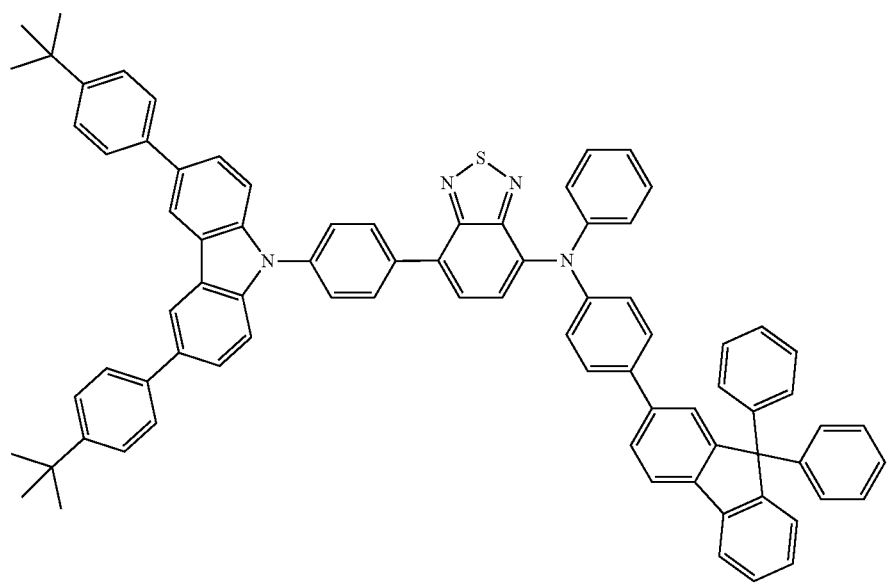

-continued
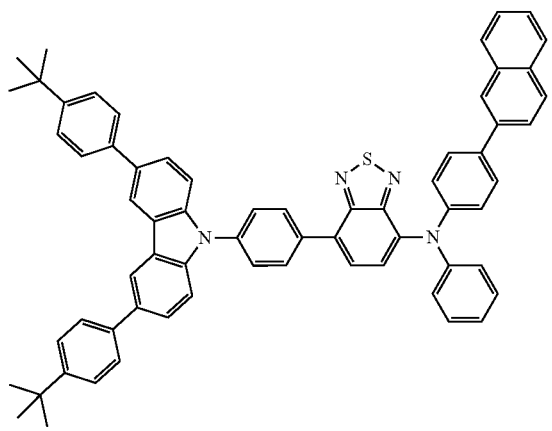
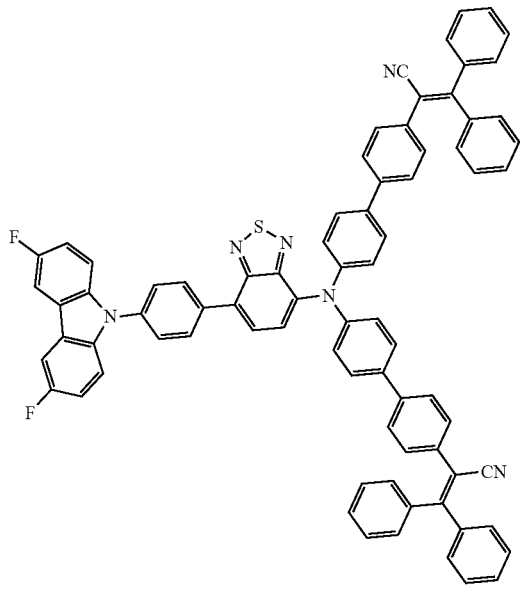
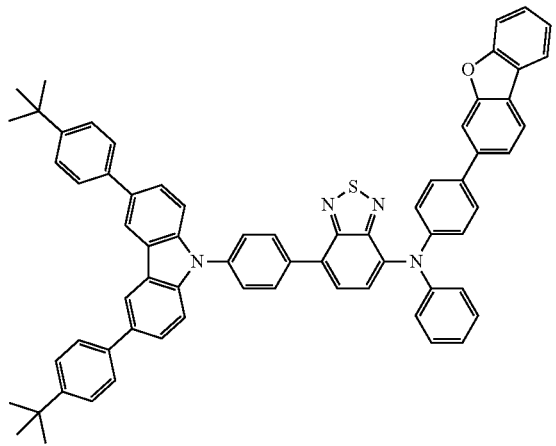
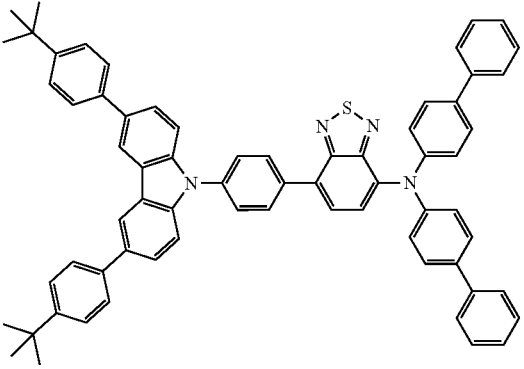
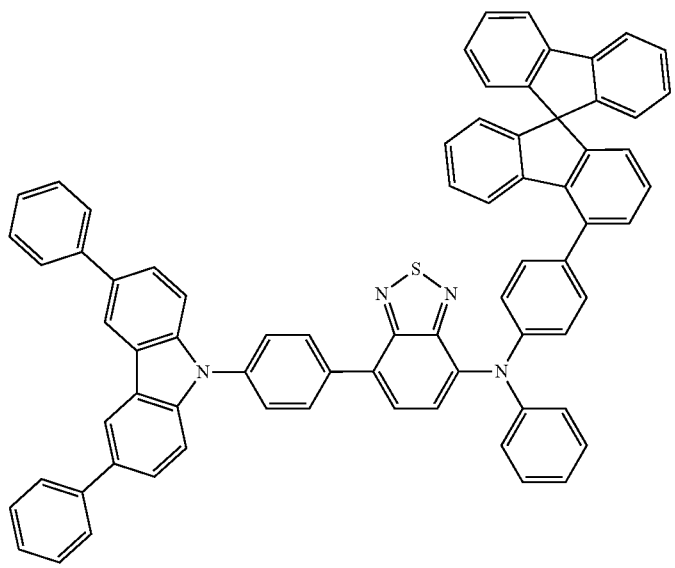

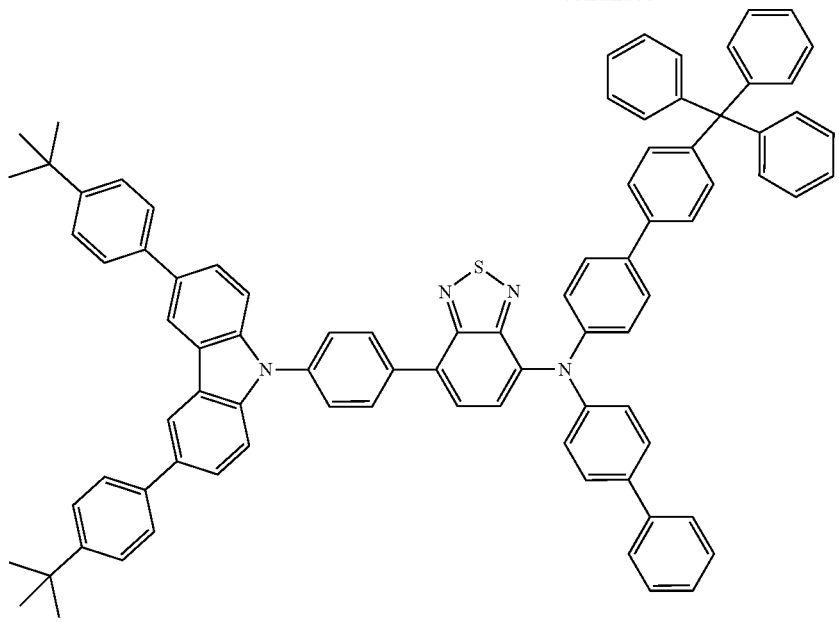
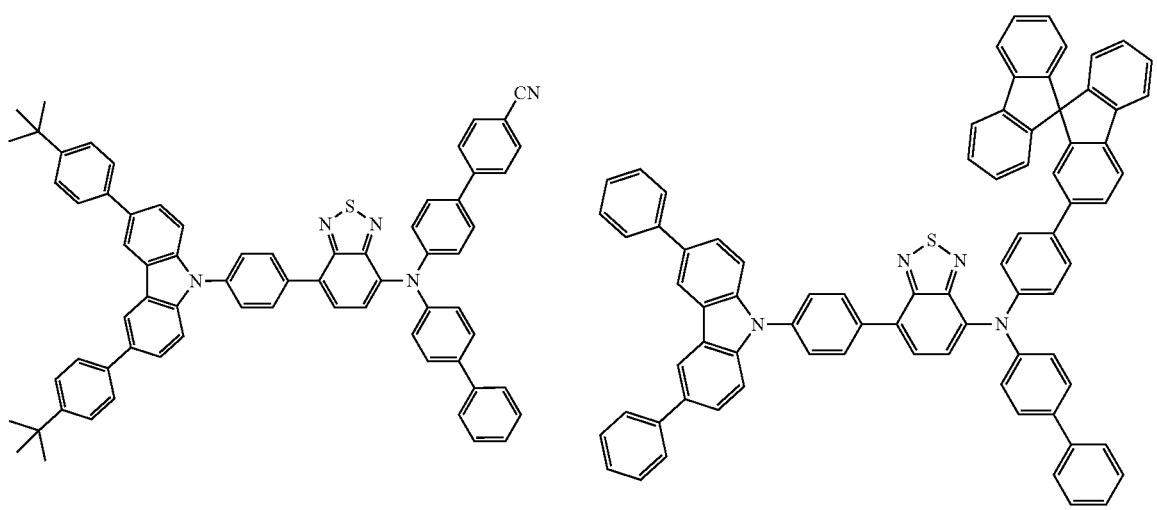

-continued
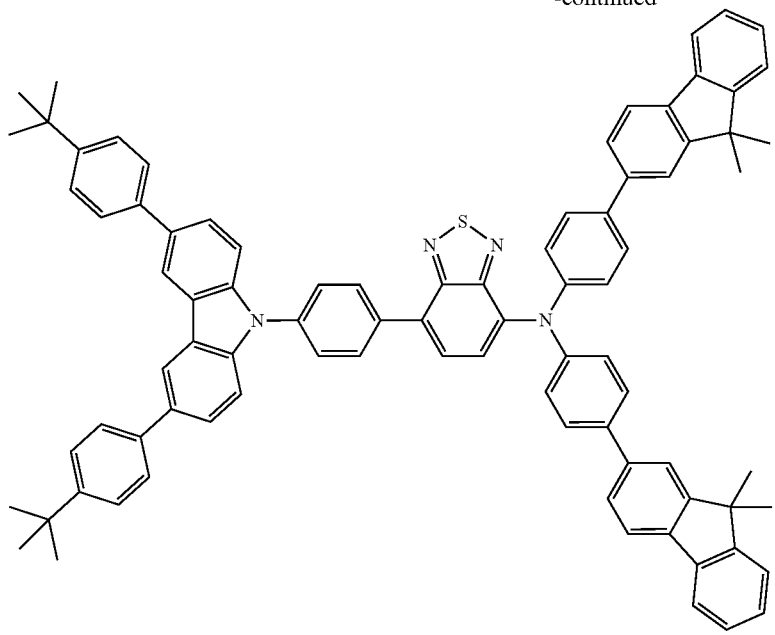
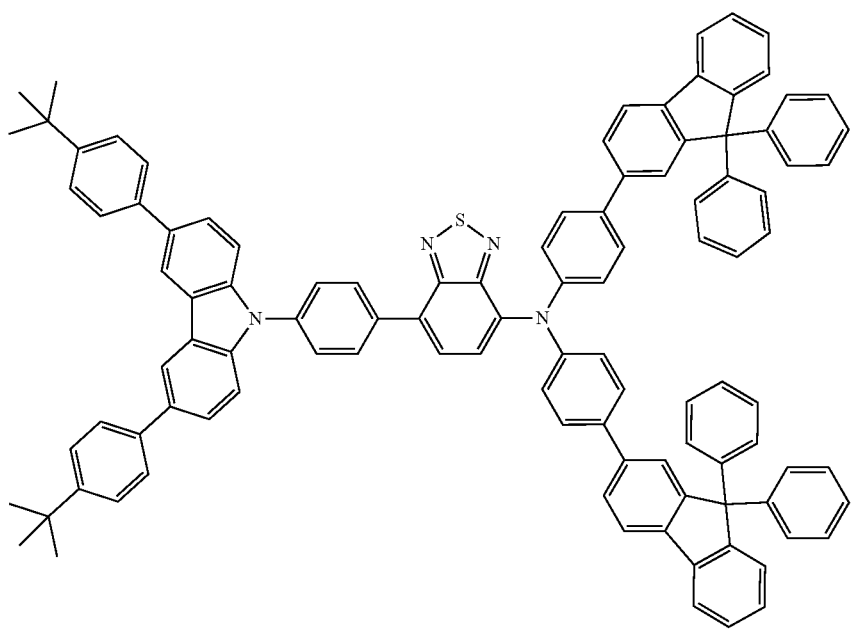

-continued
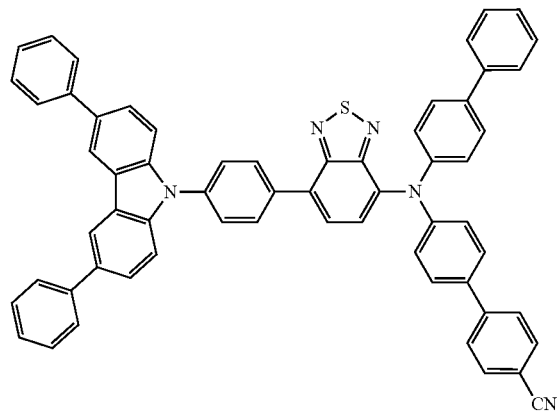
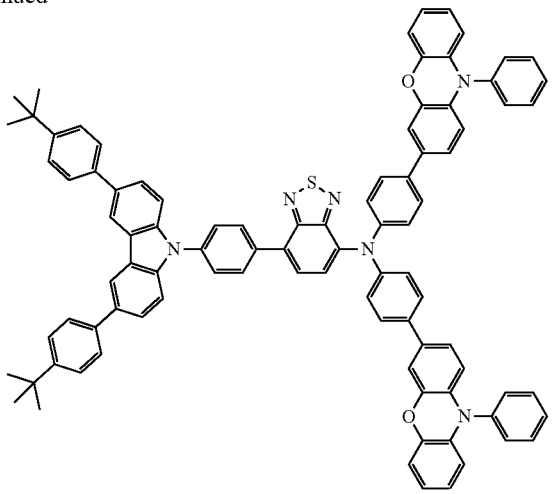
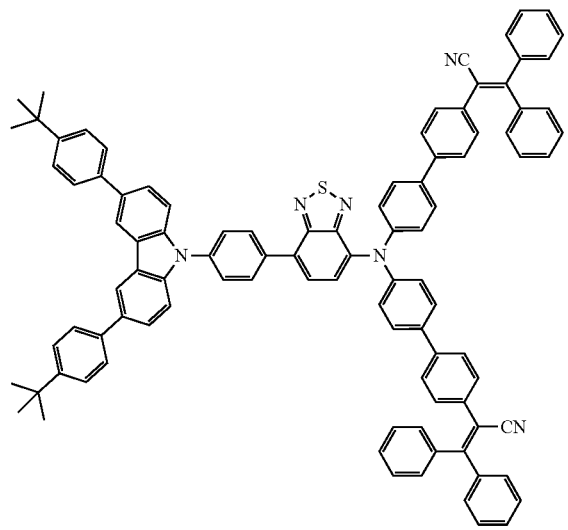
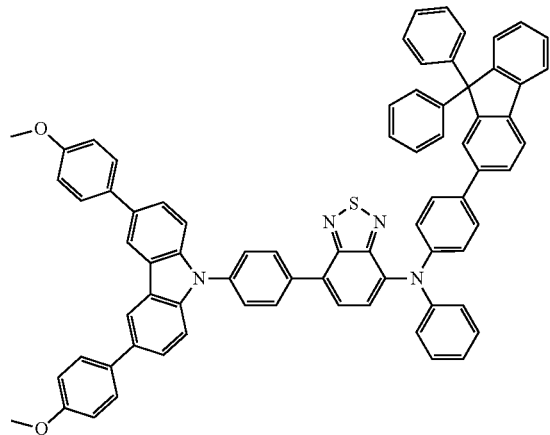
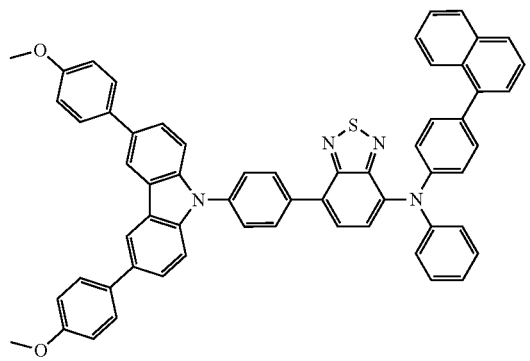

-continued
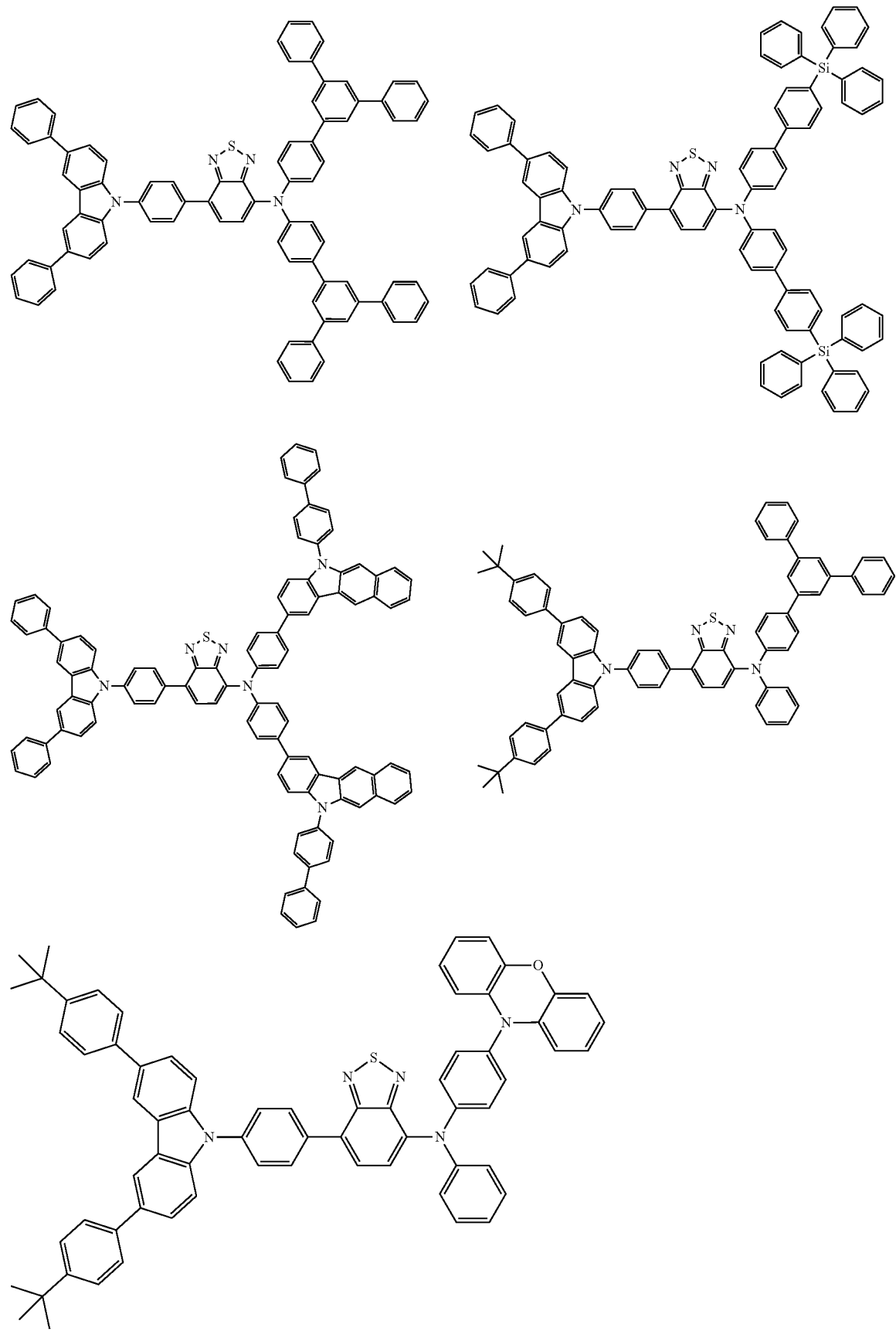

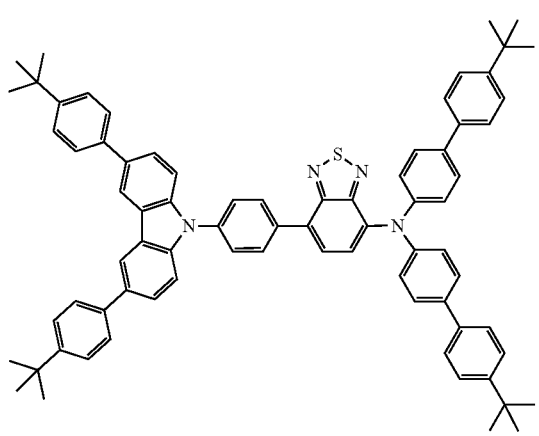
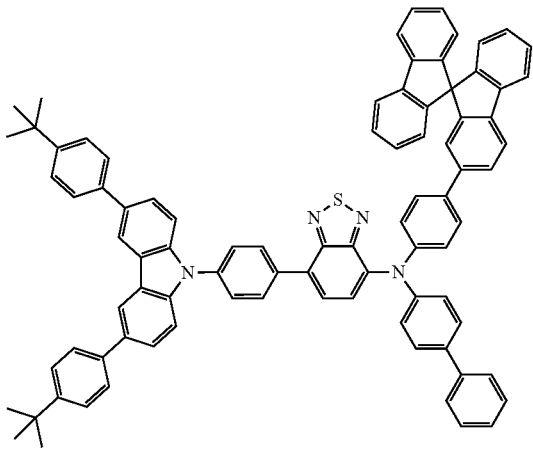
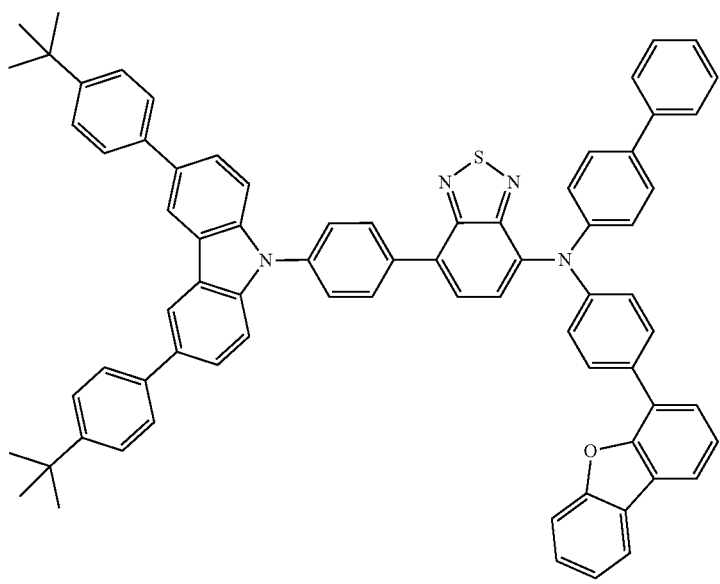
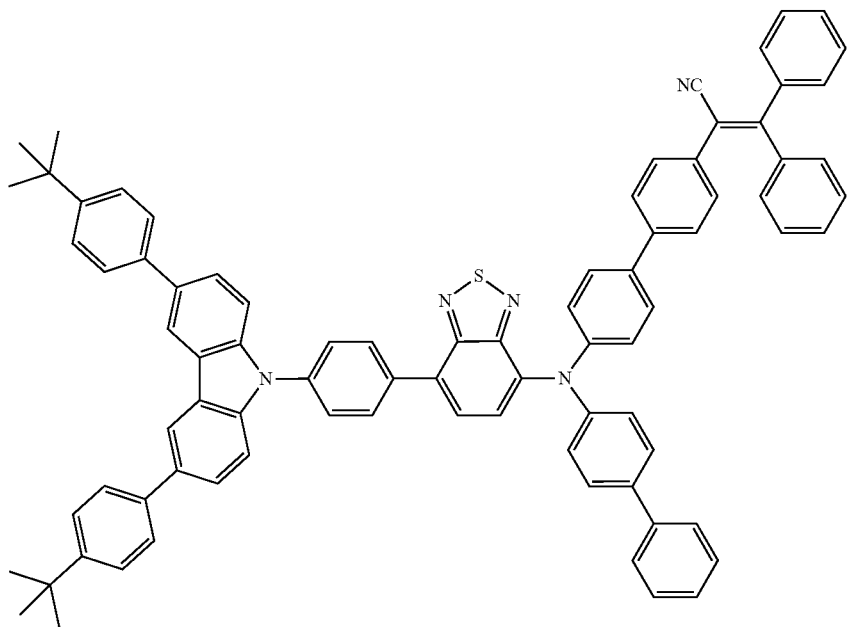

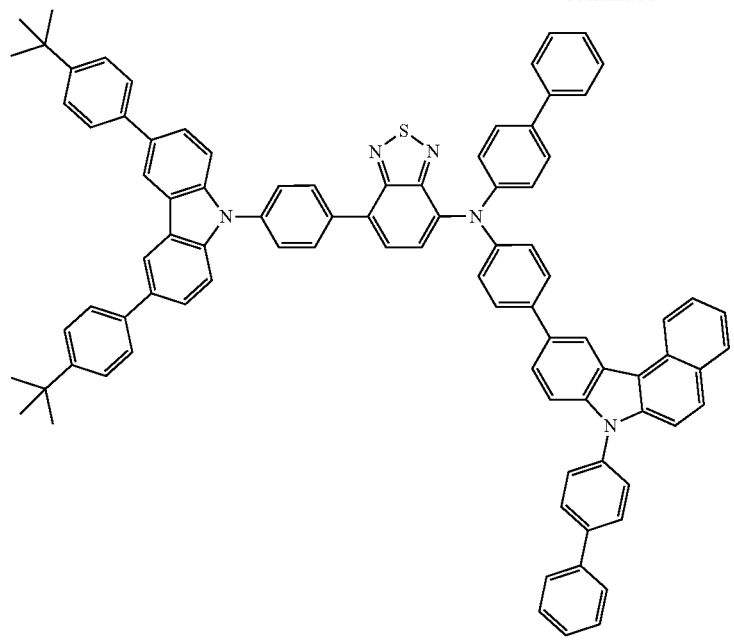
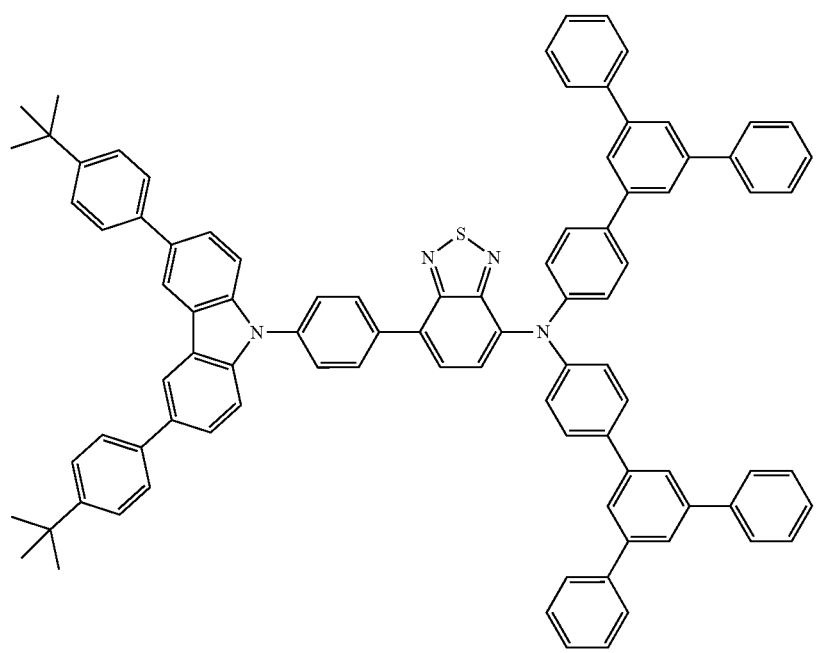

-continued
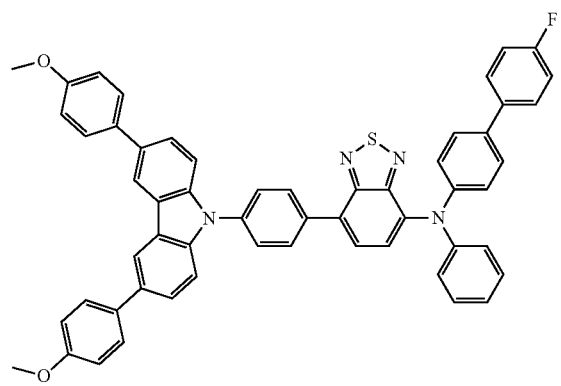
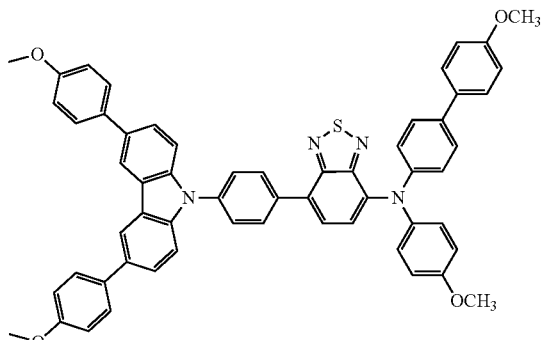
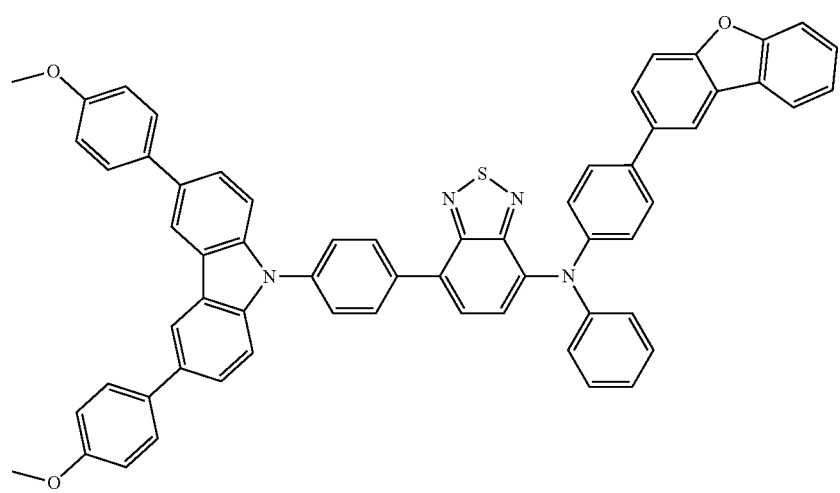
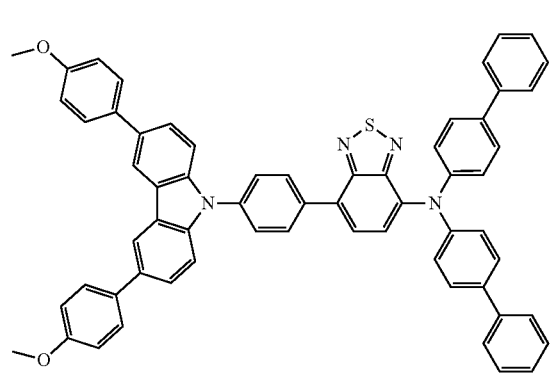

-continued
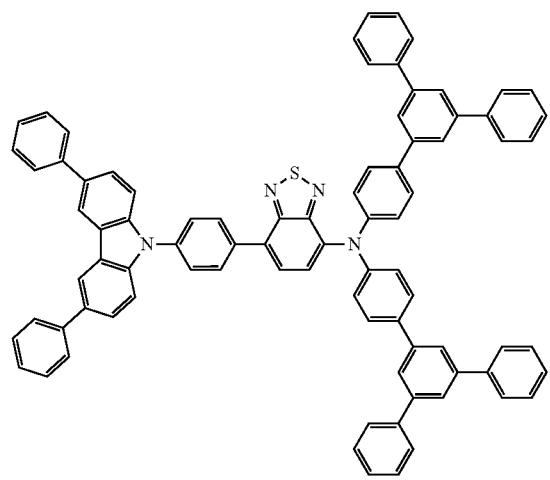
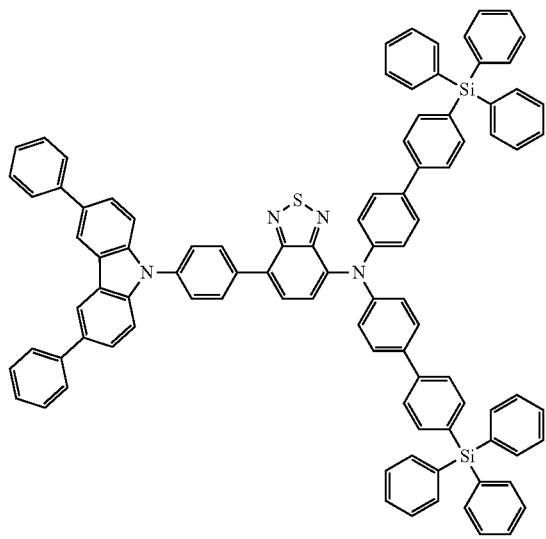
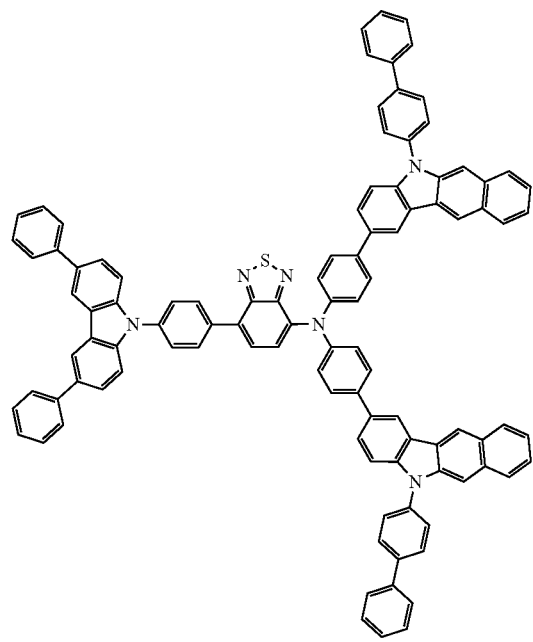
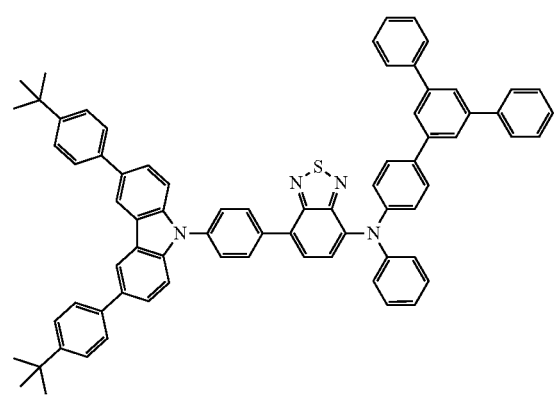
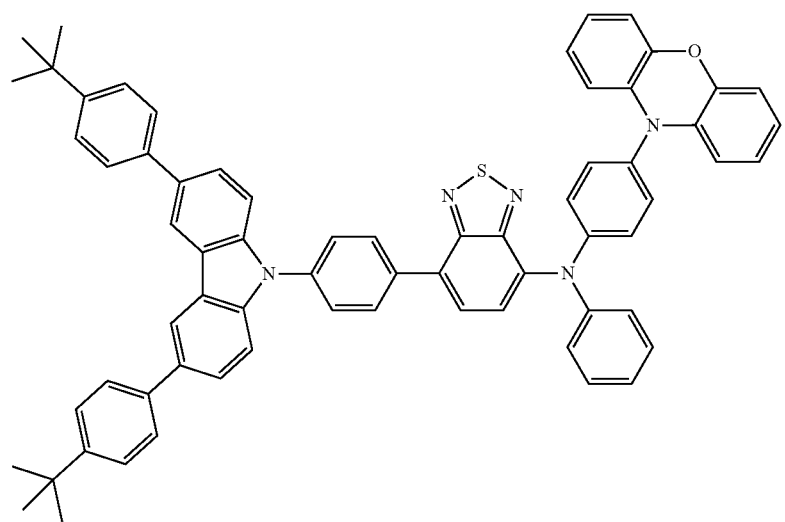

-continued
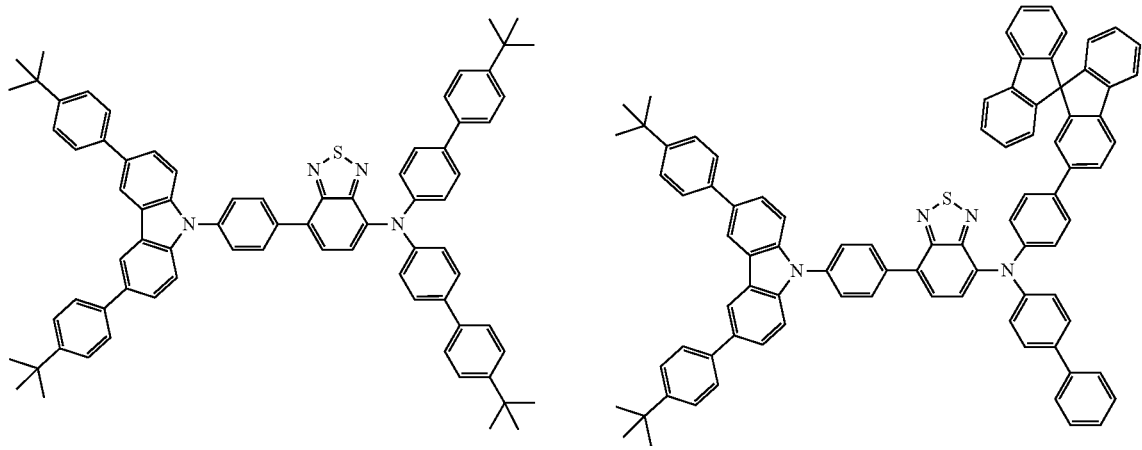
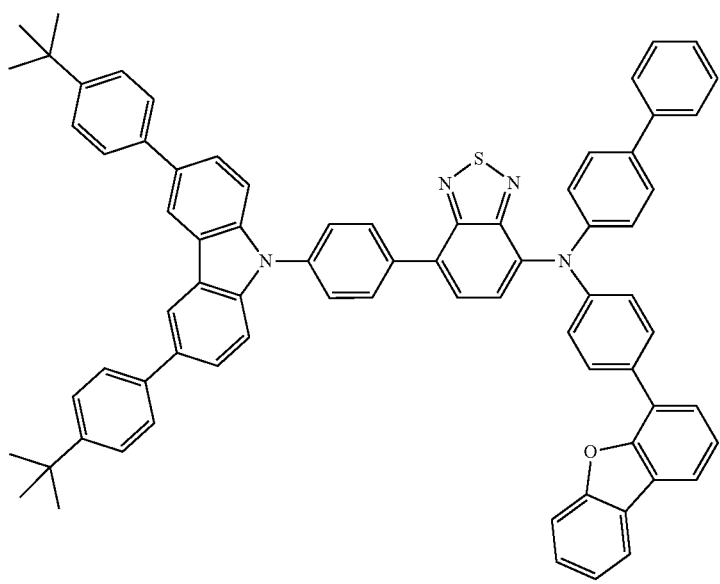
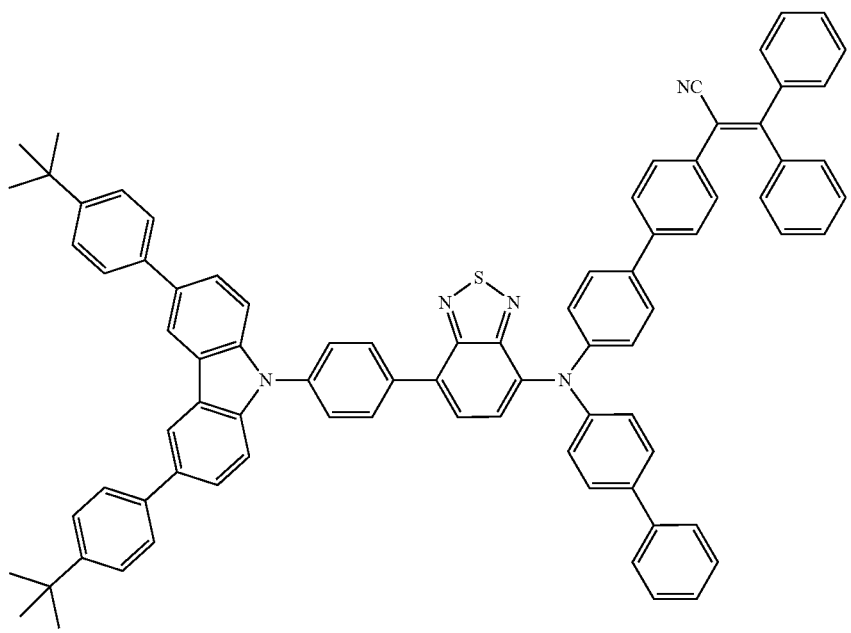

-continued
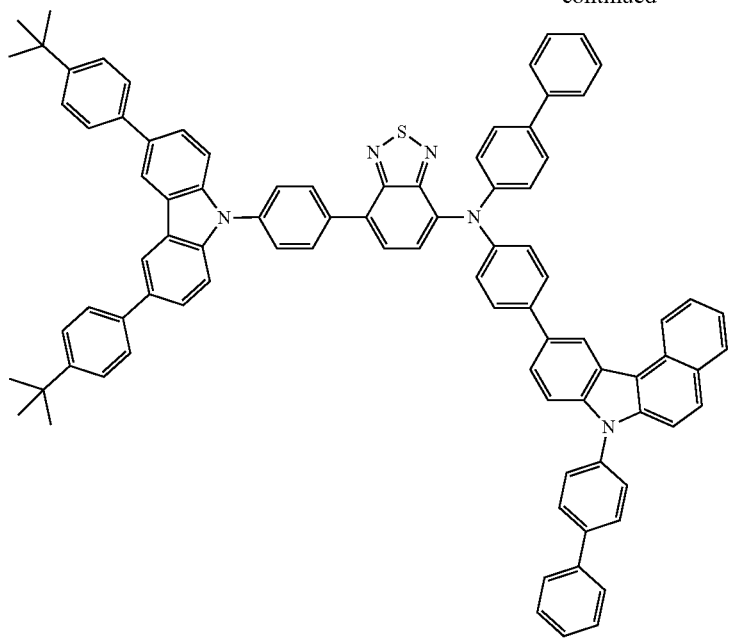
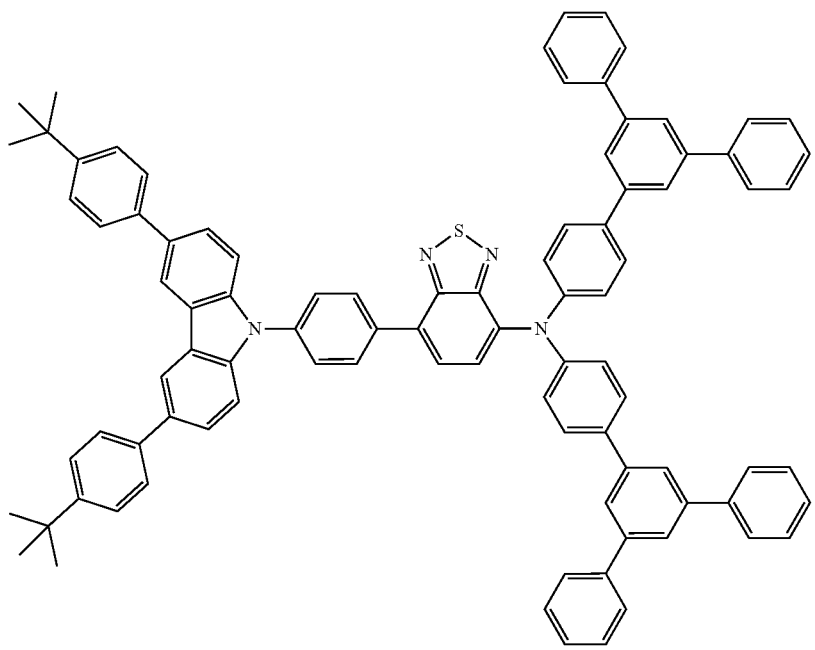
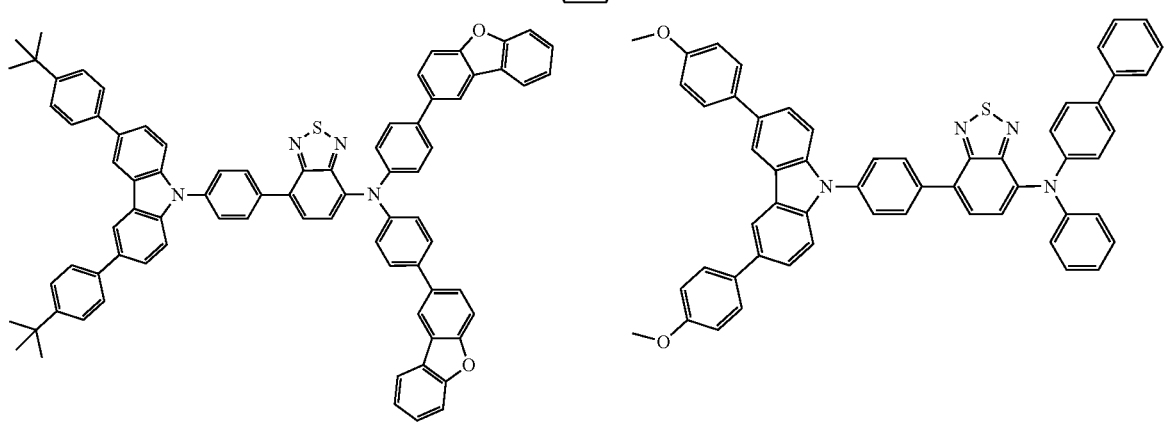

-continued
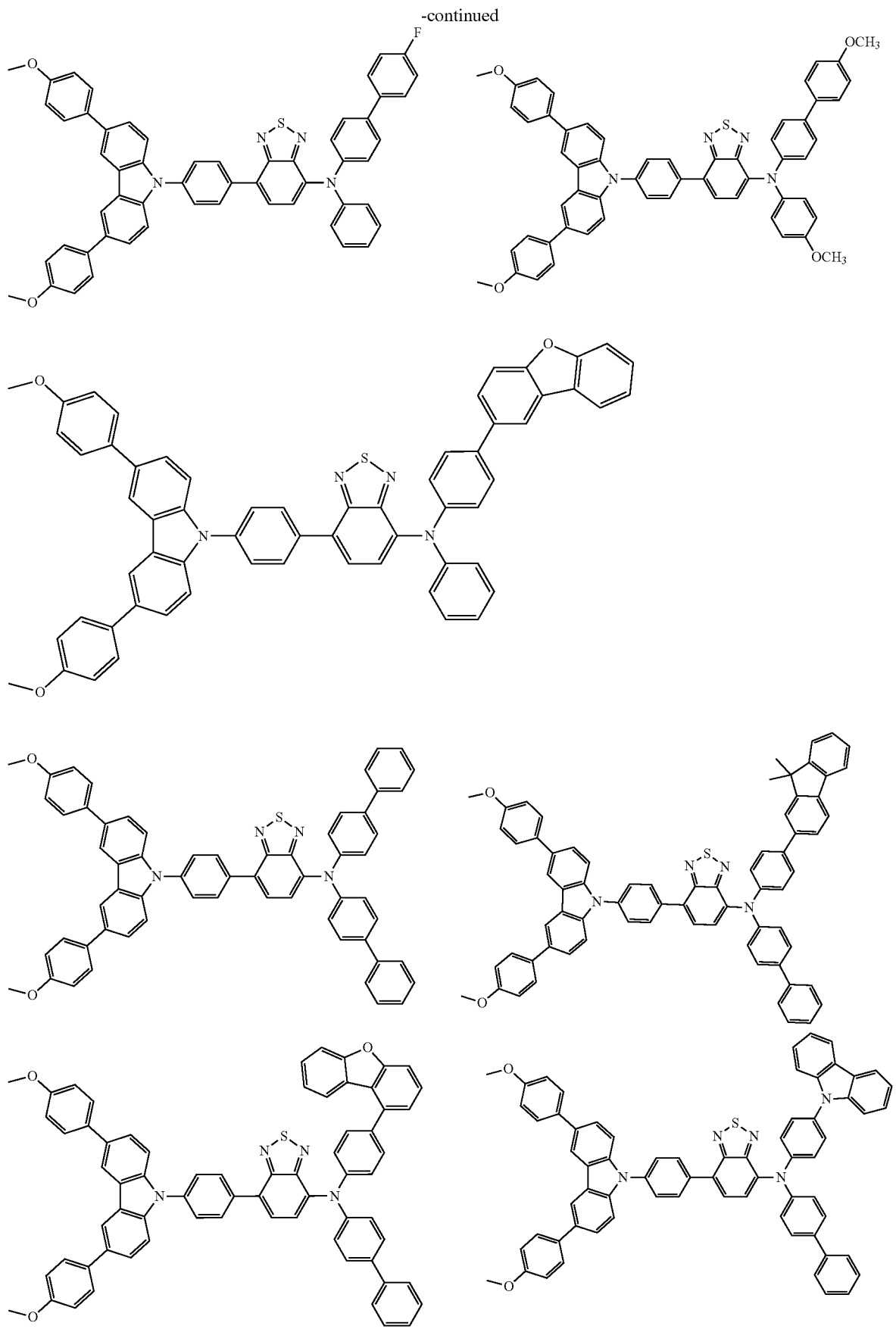

-continued
77
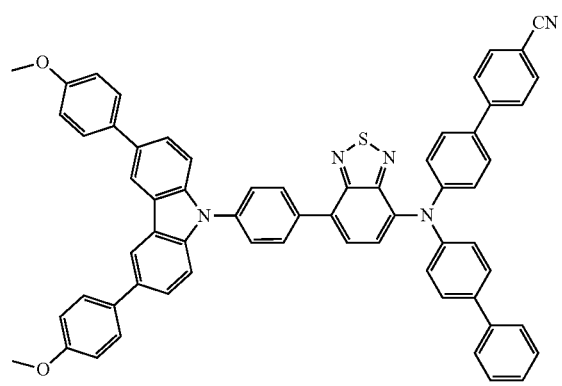
78
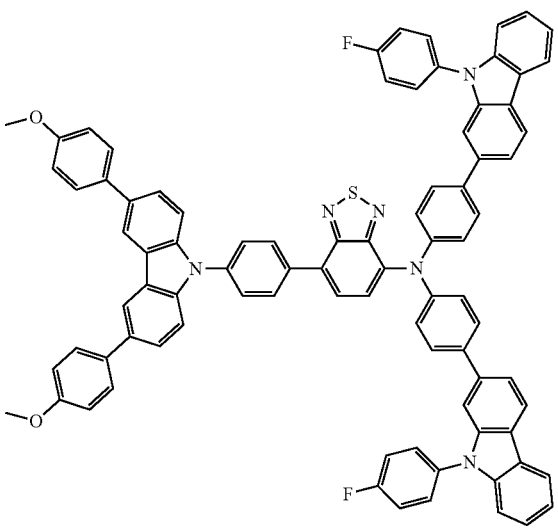
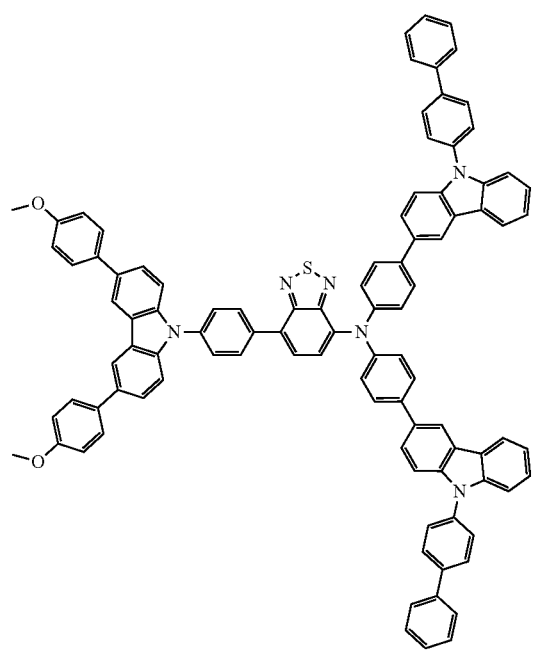

-continued
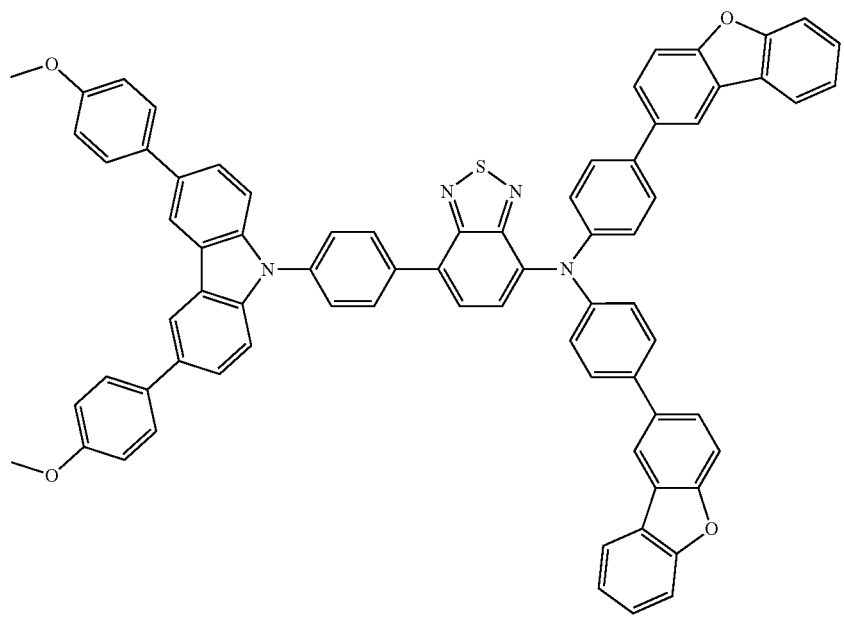
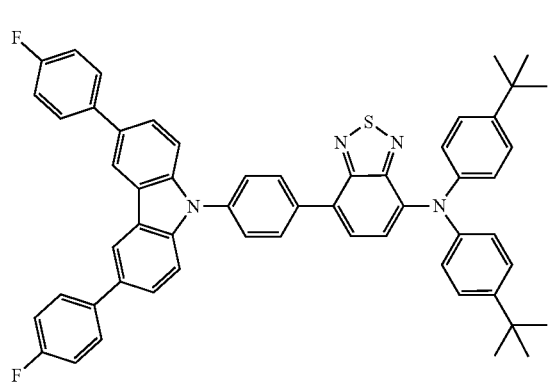
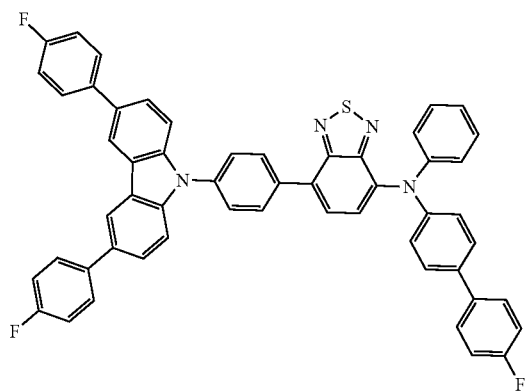
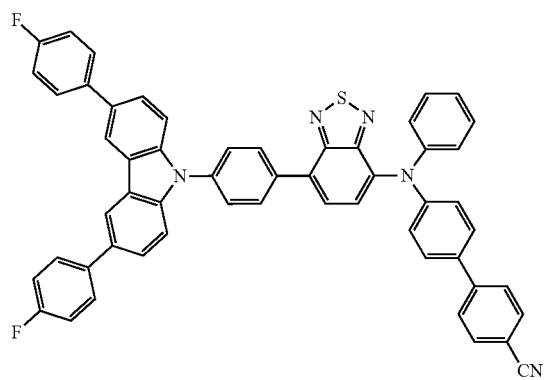
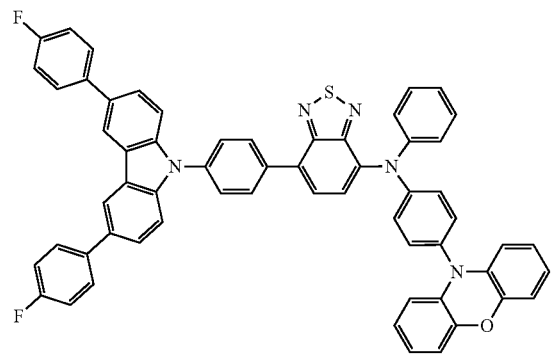

-continued
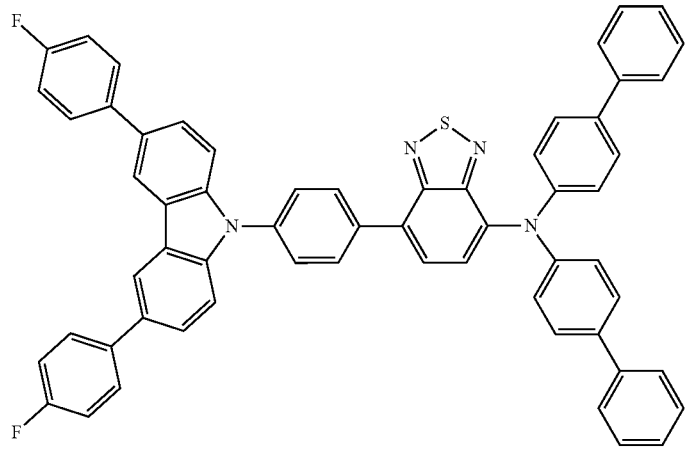
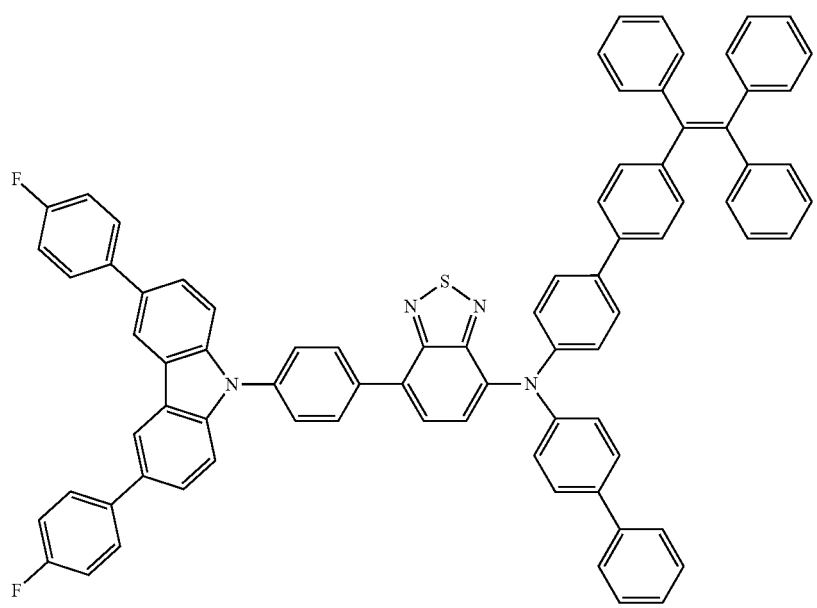
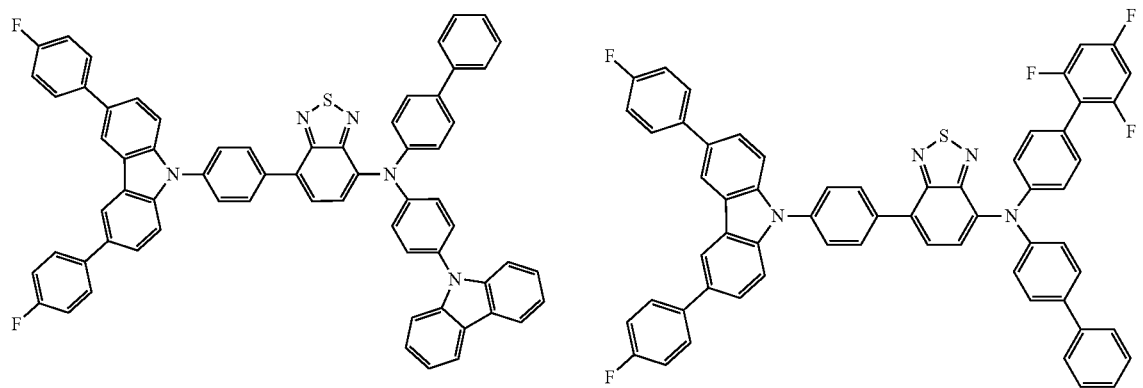

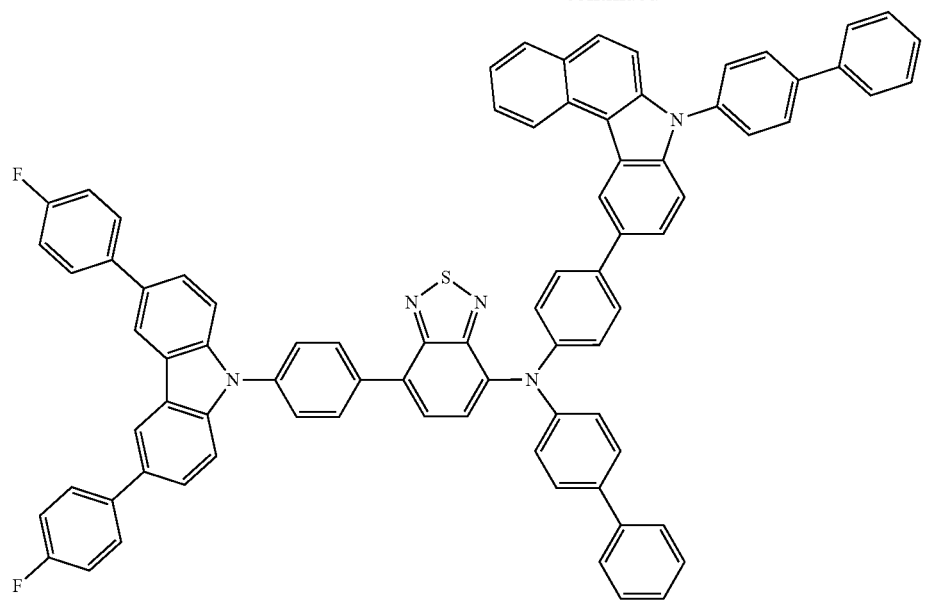
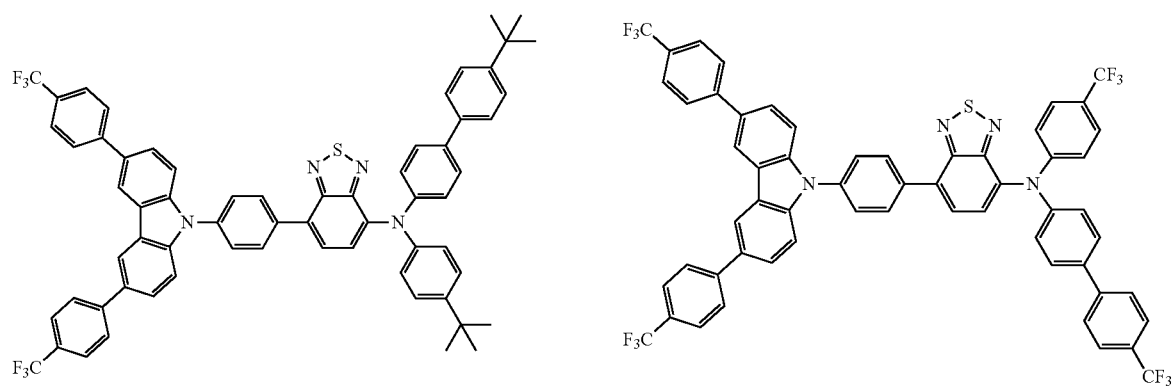
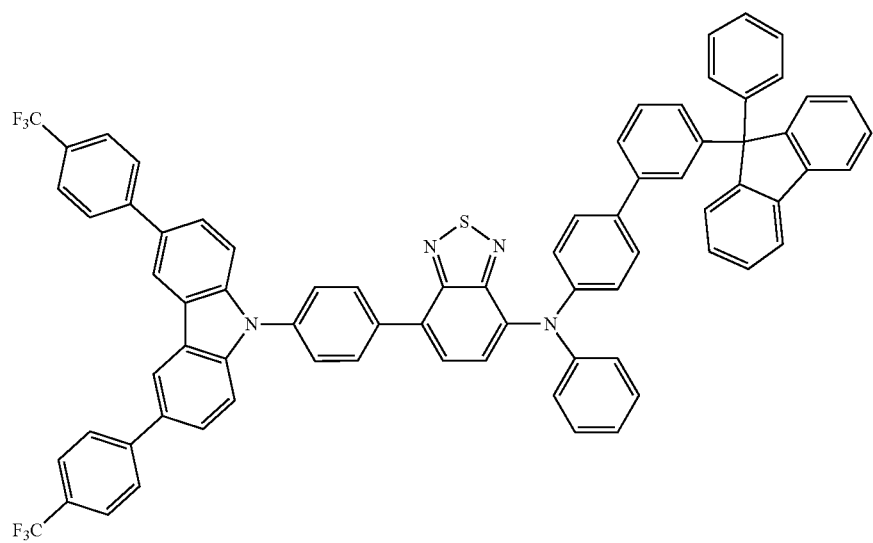

-continued
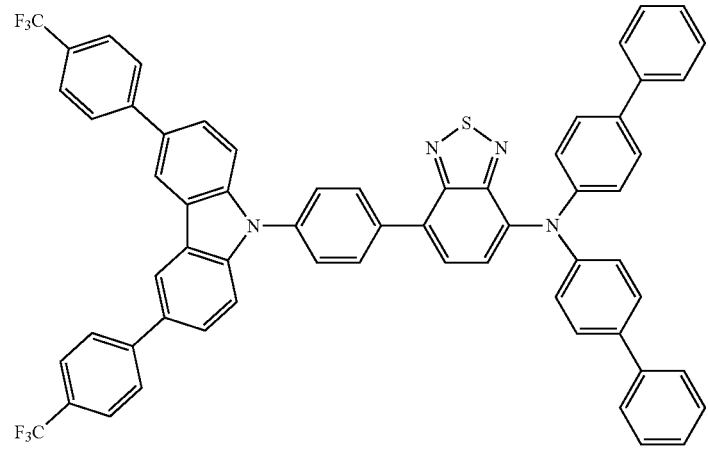
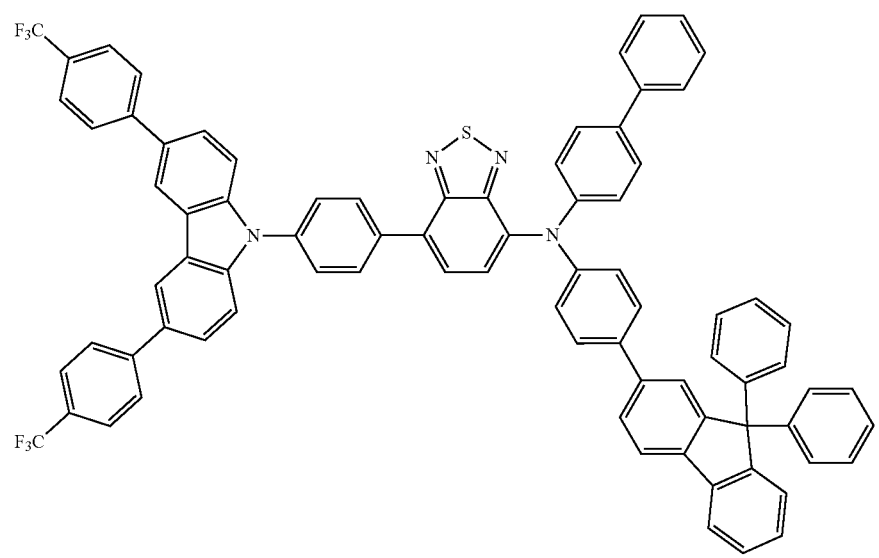
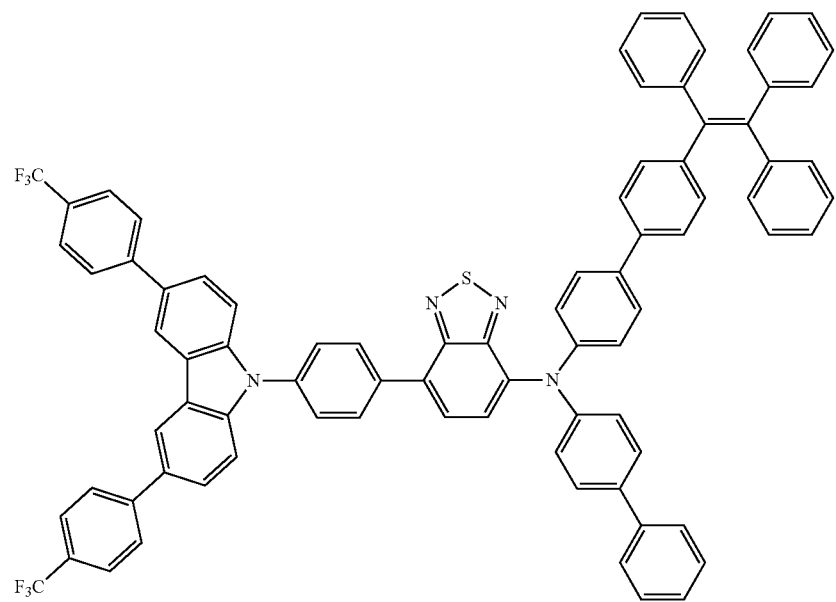

-continued
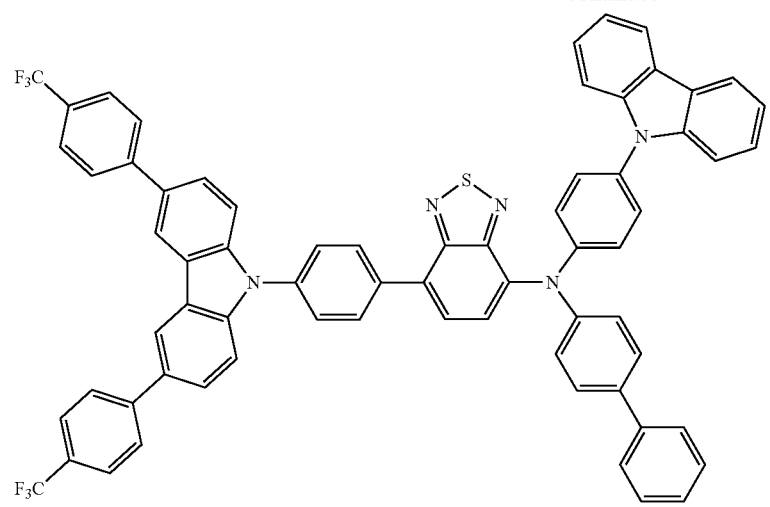
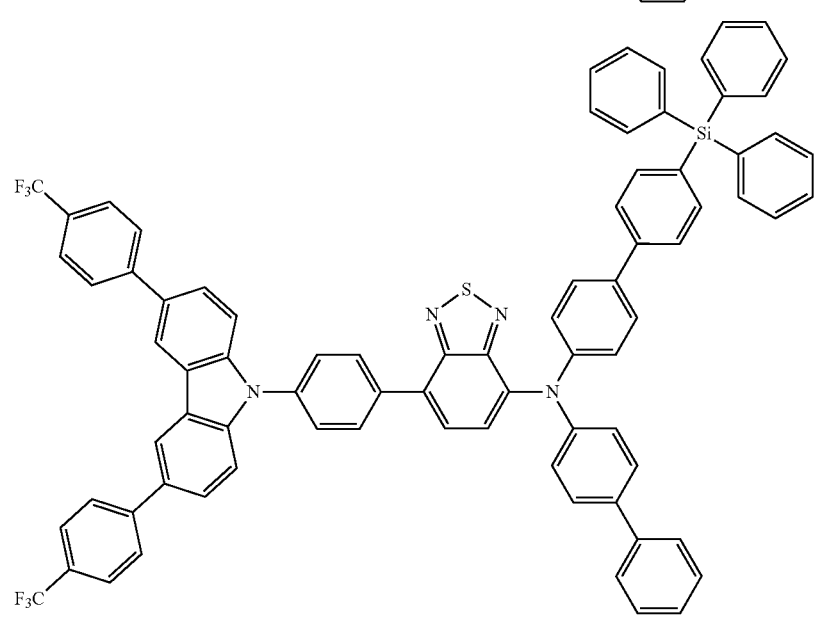
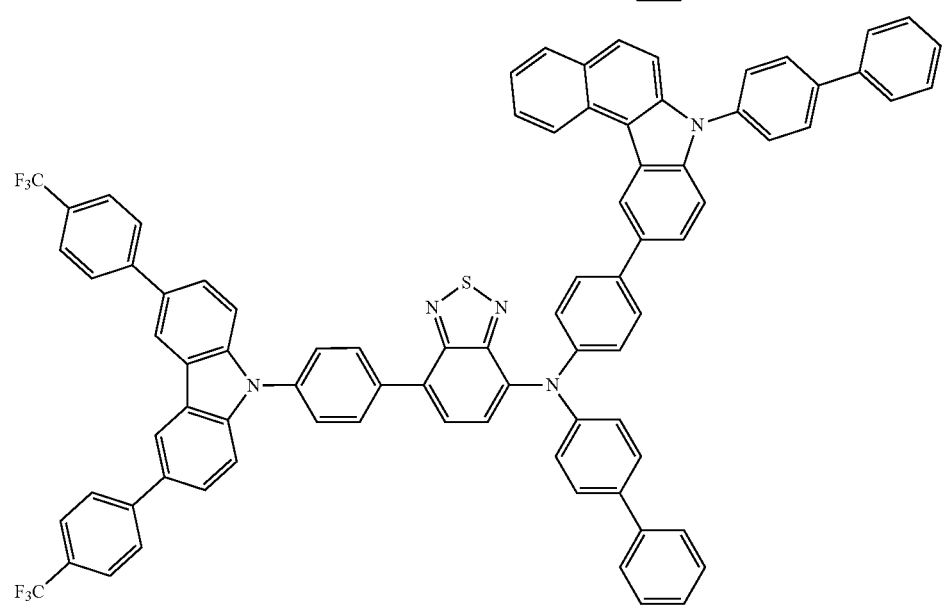

-continued
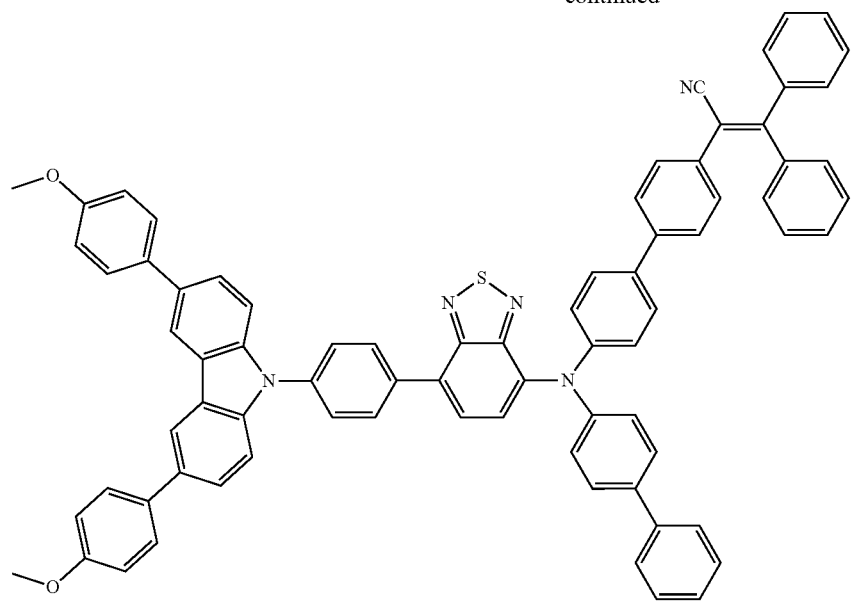
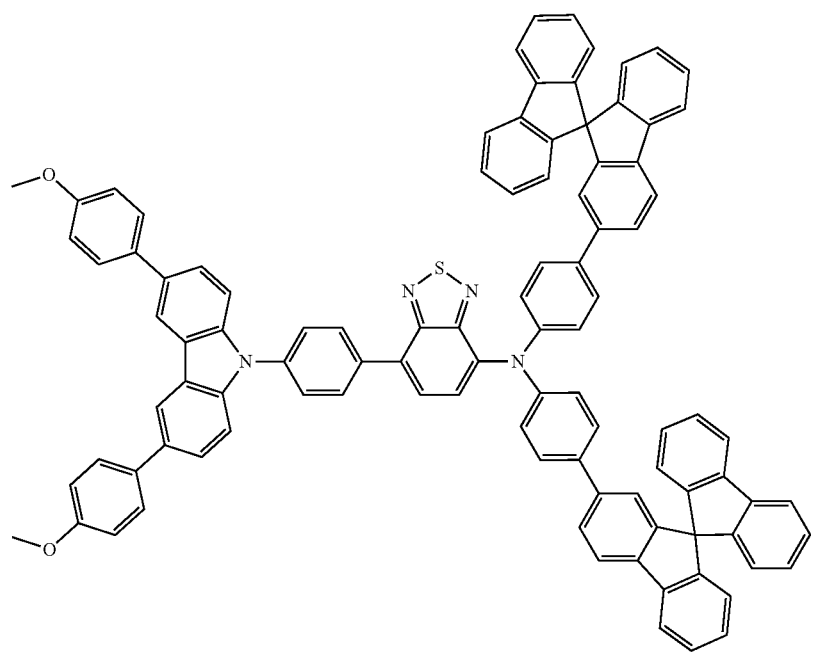

-continued
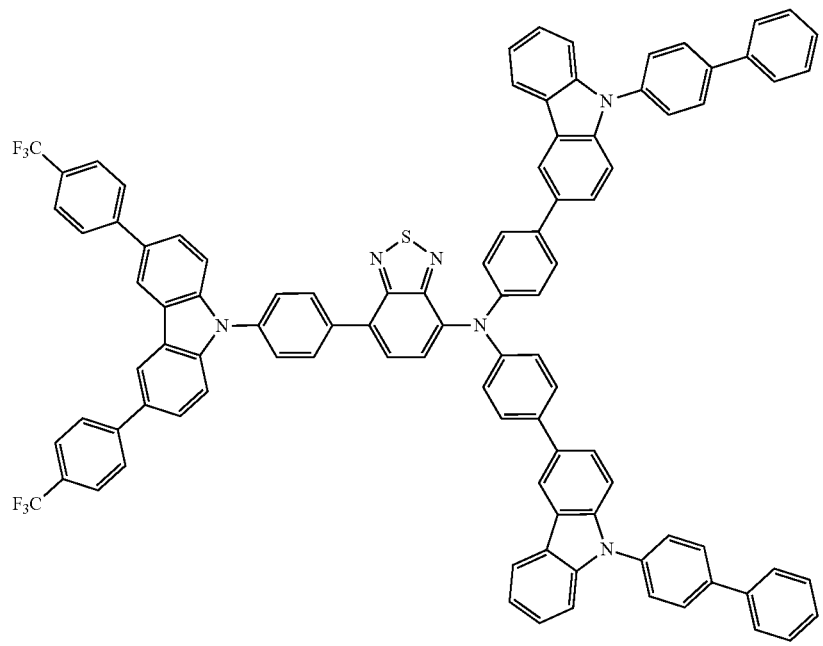
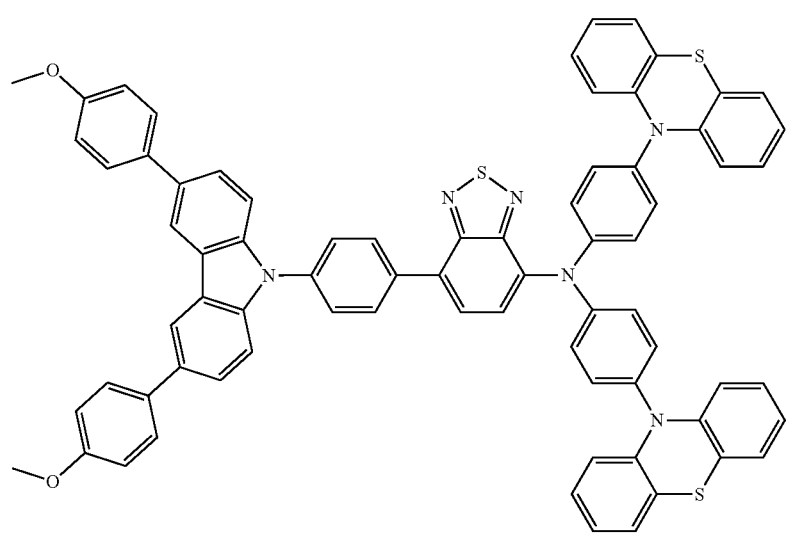
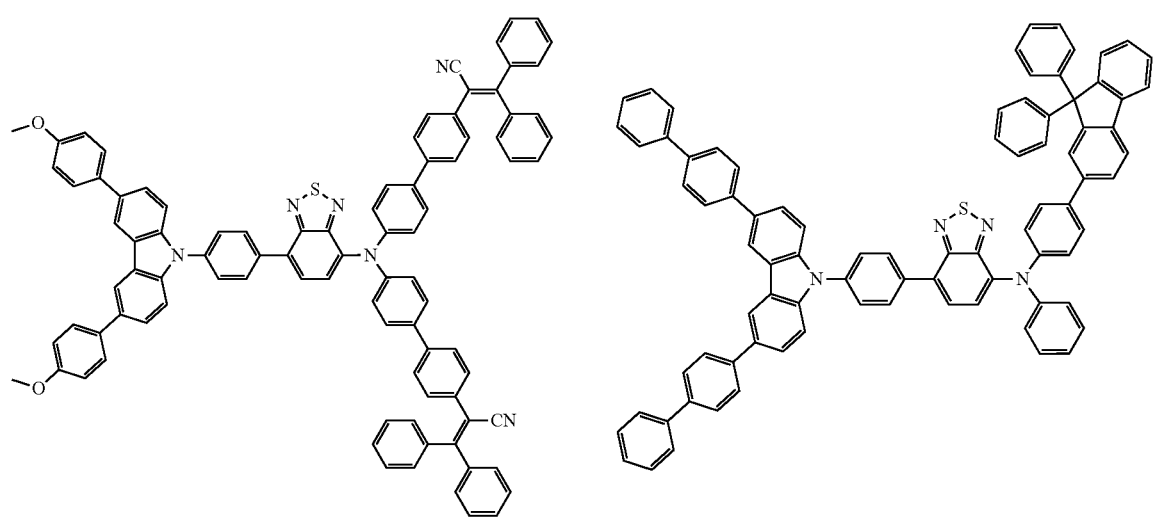

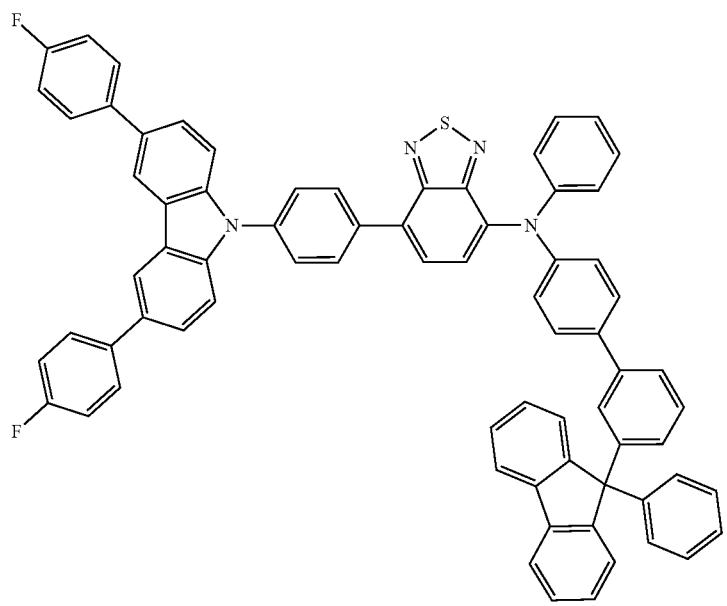
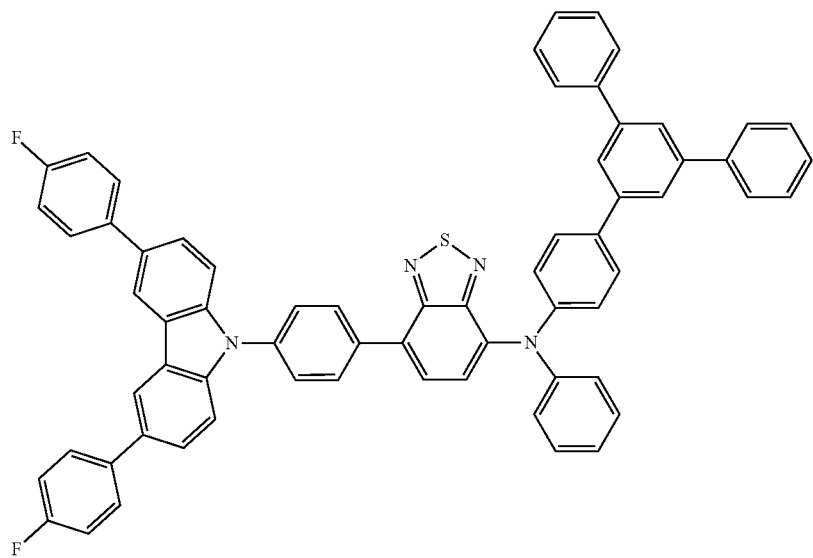
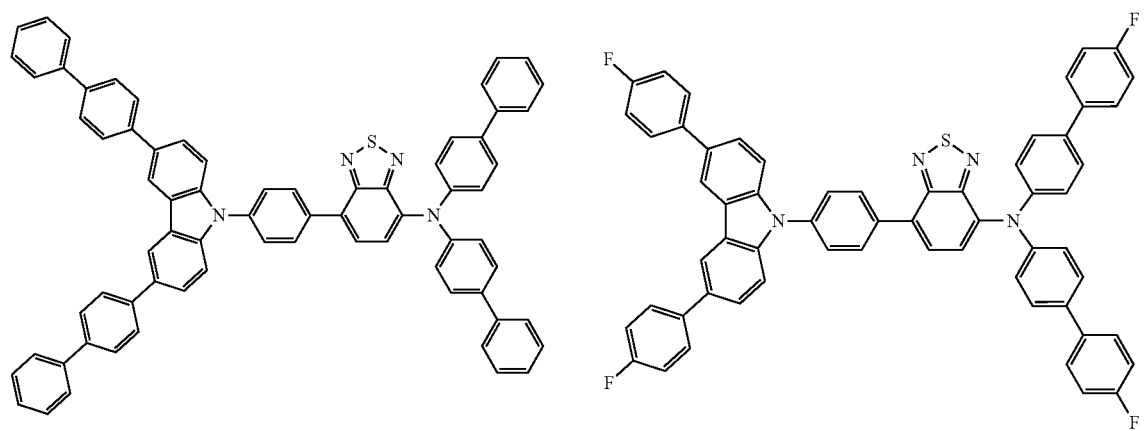

-continued
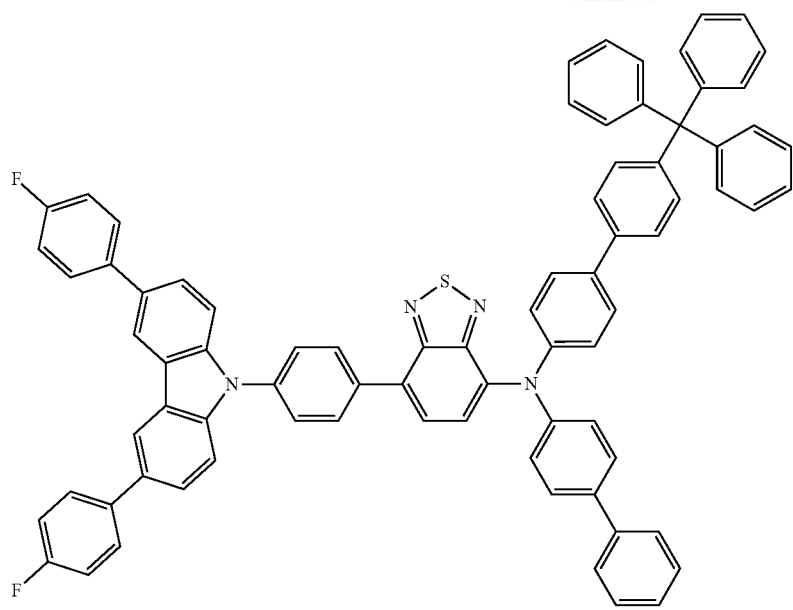
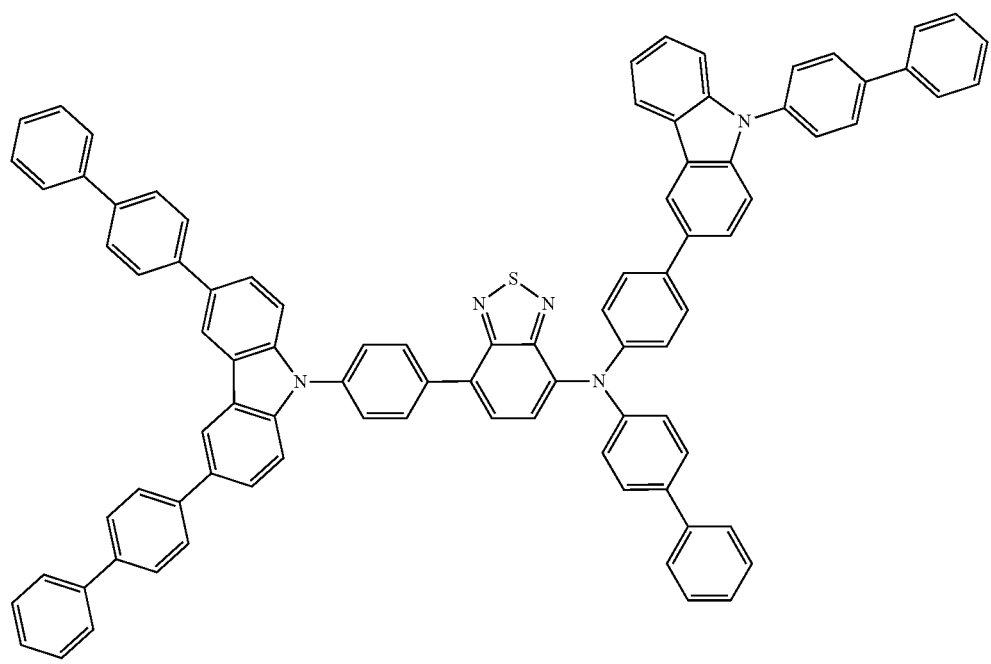

97
98
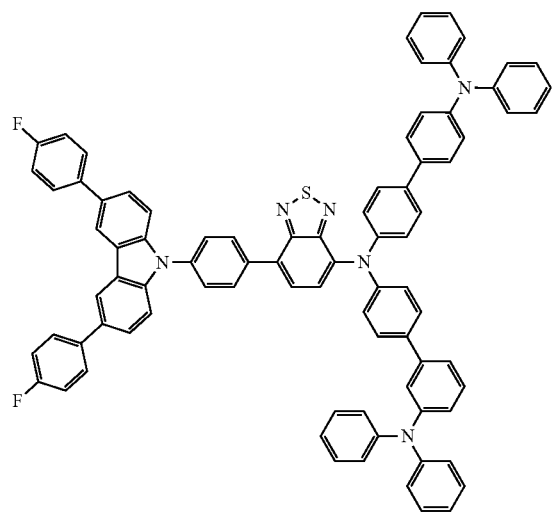
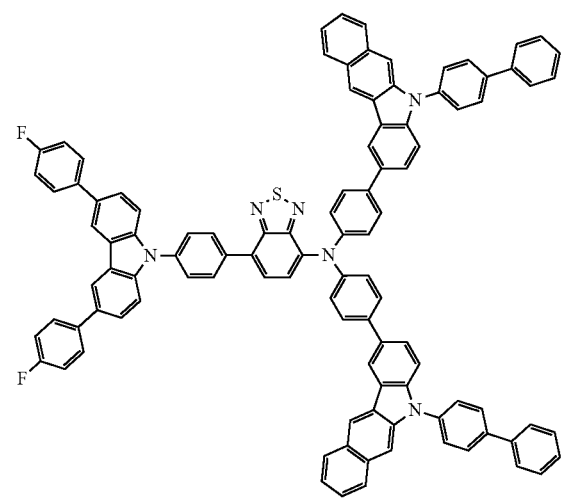
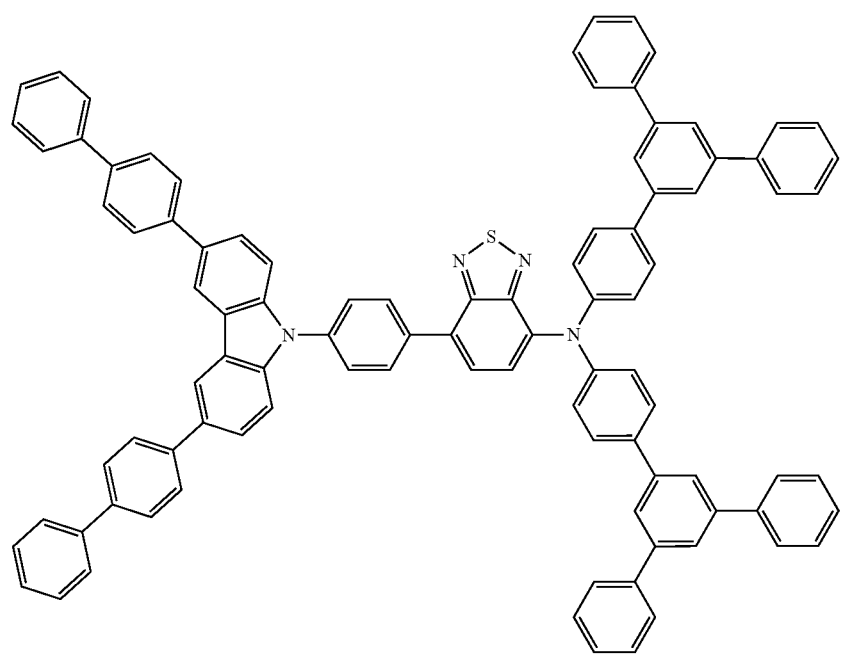
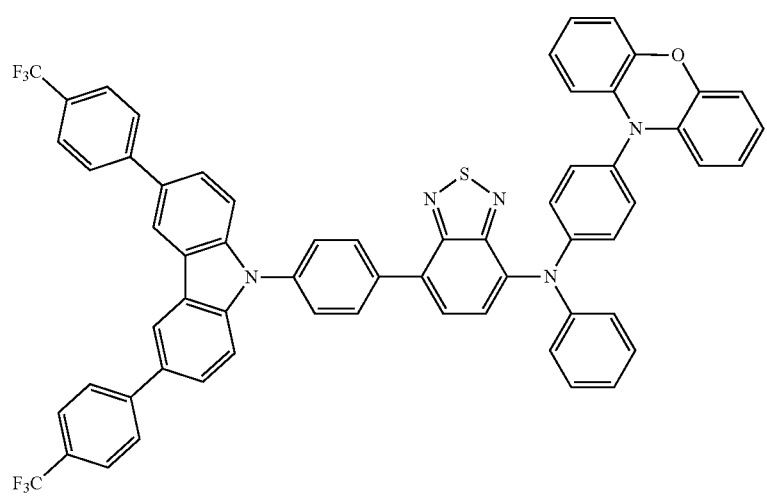

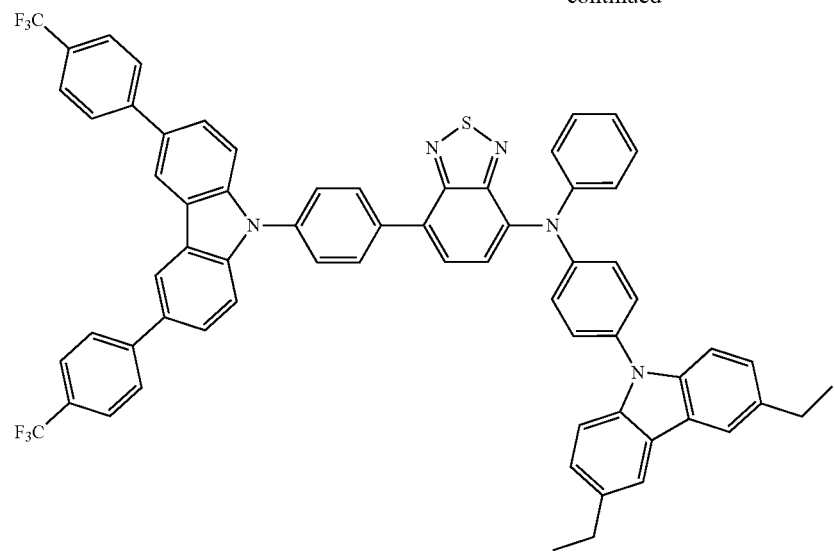
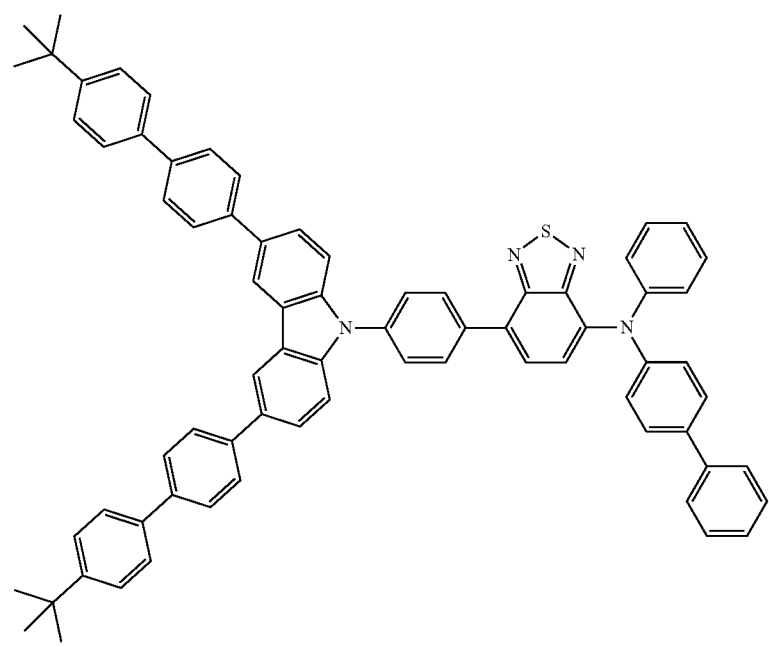
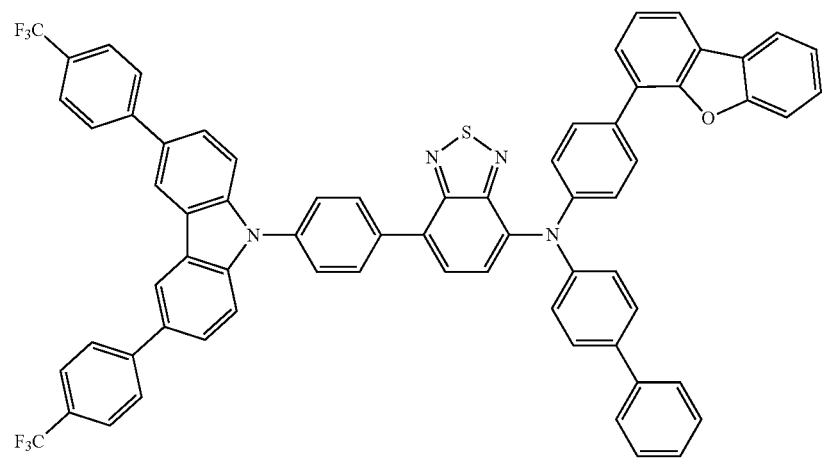

-continued
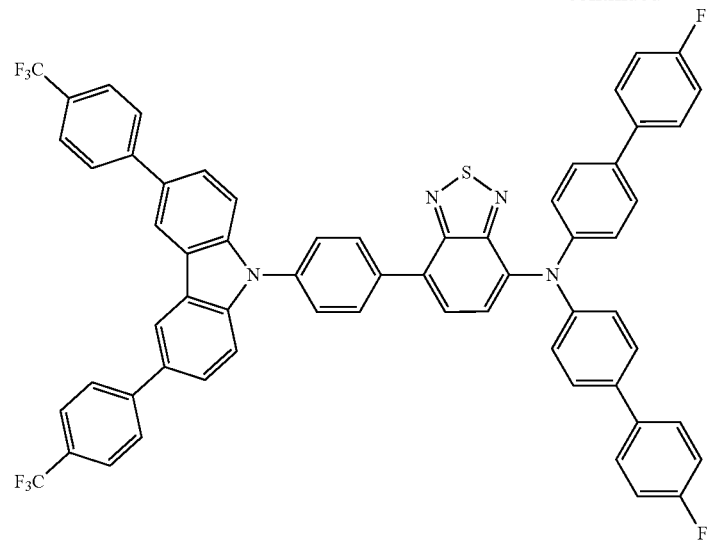
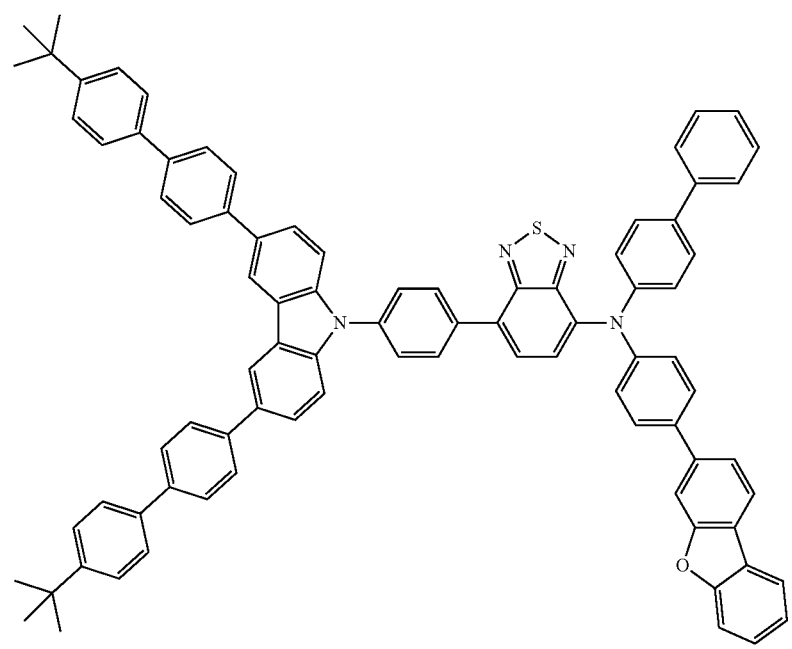

-continued
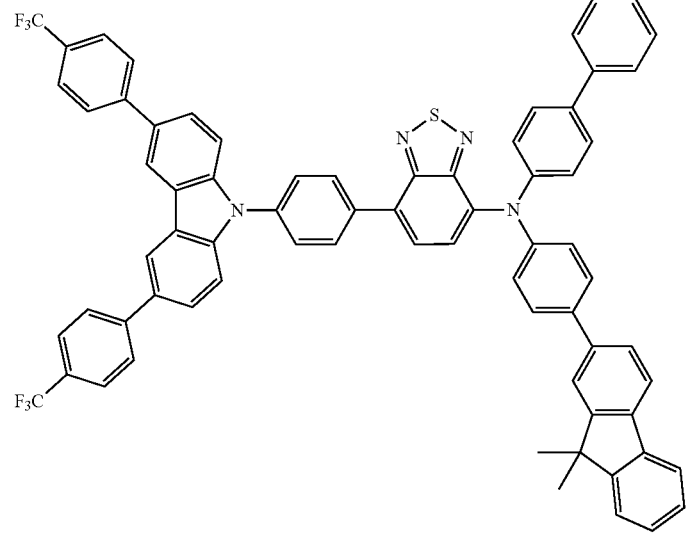
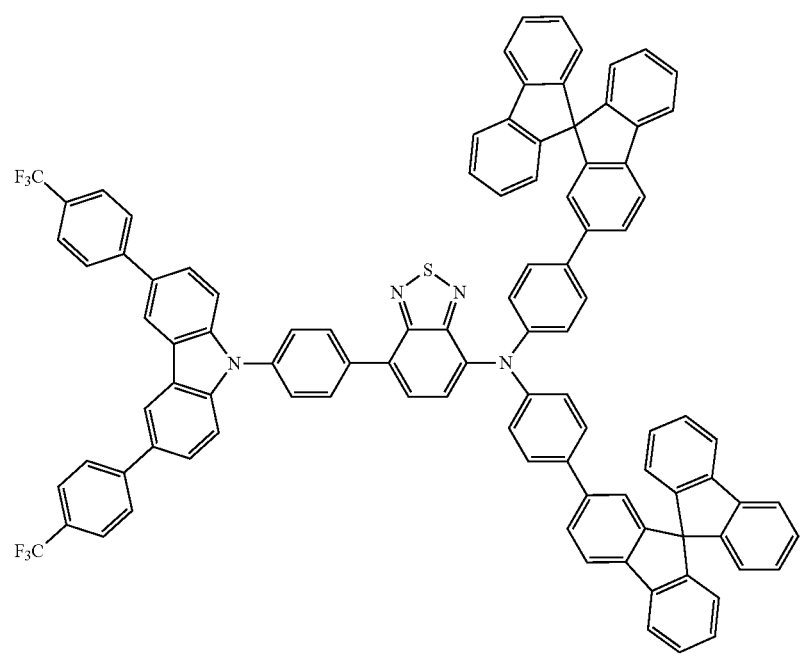

-continued
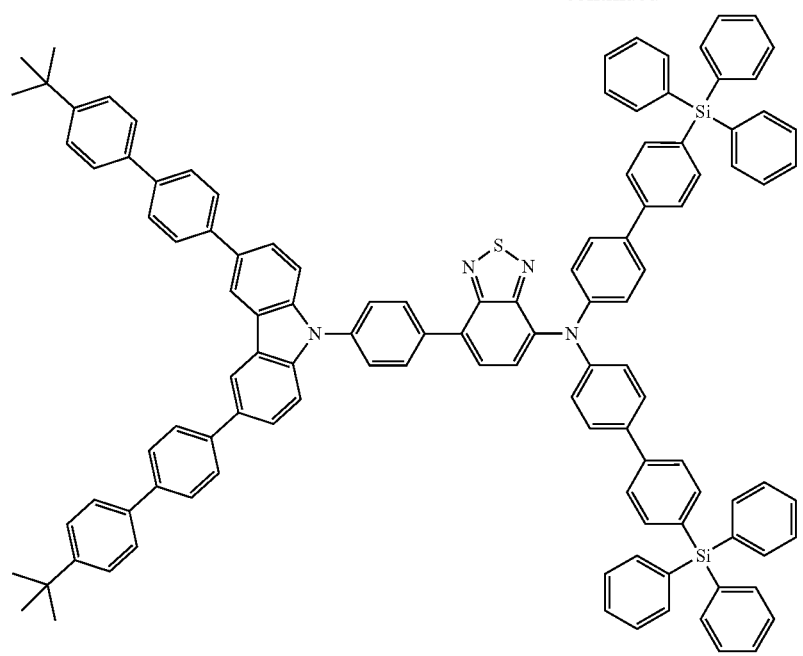
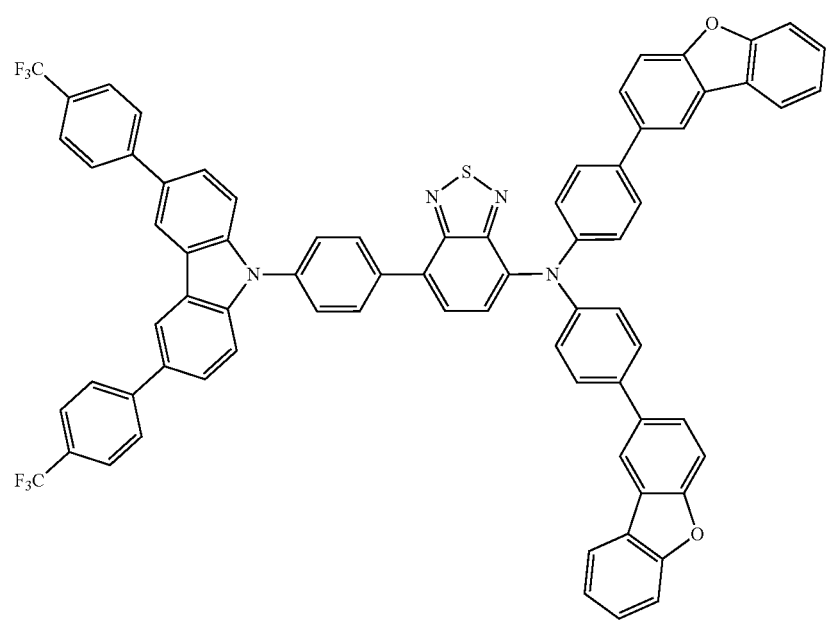

-continued
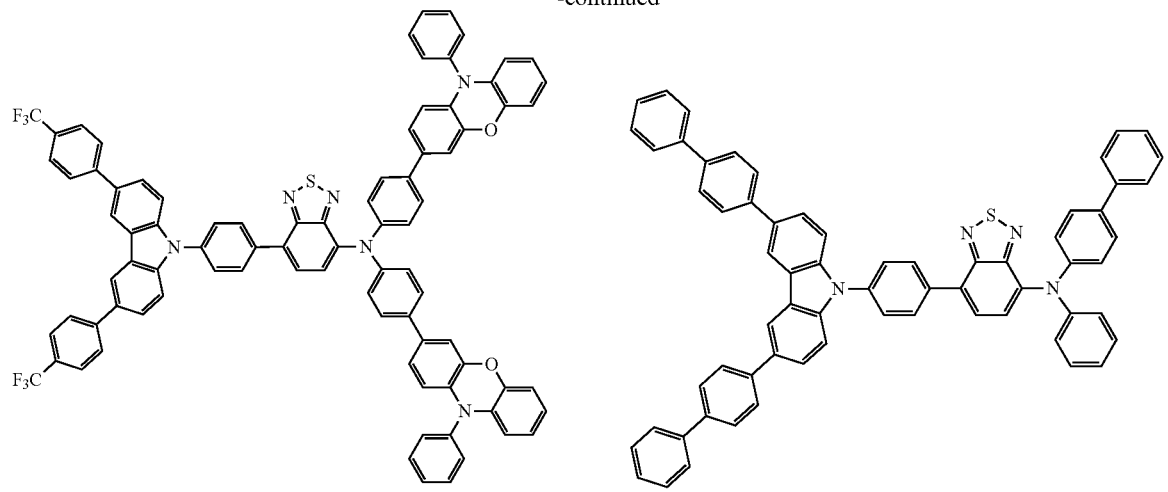
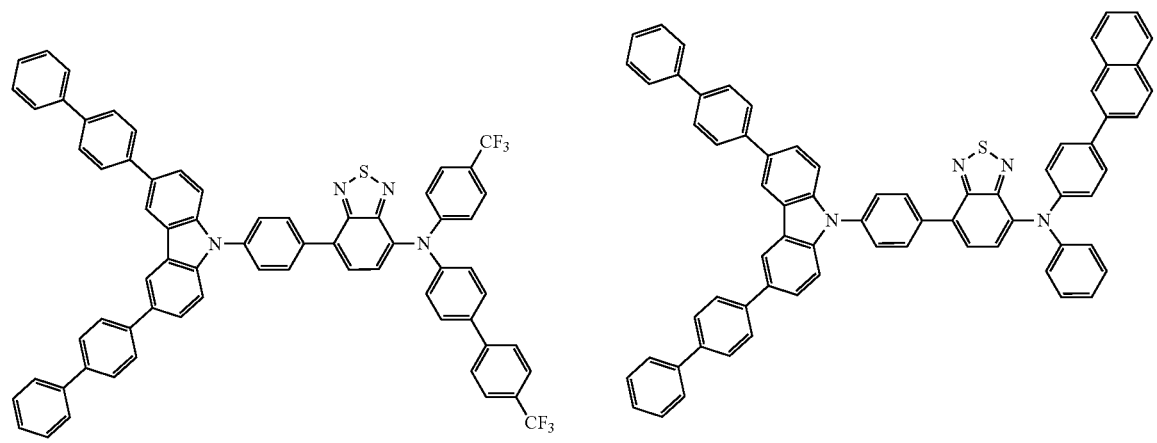
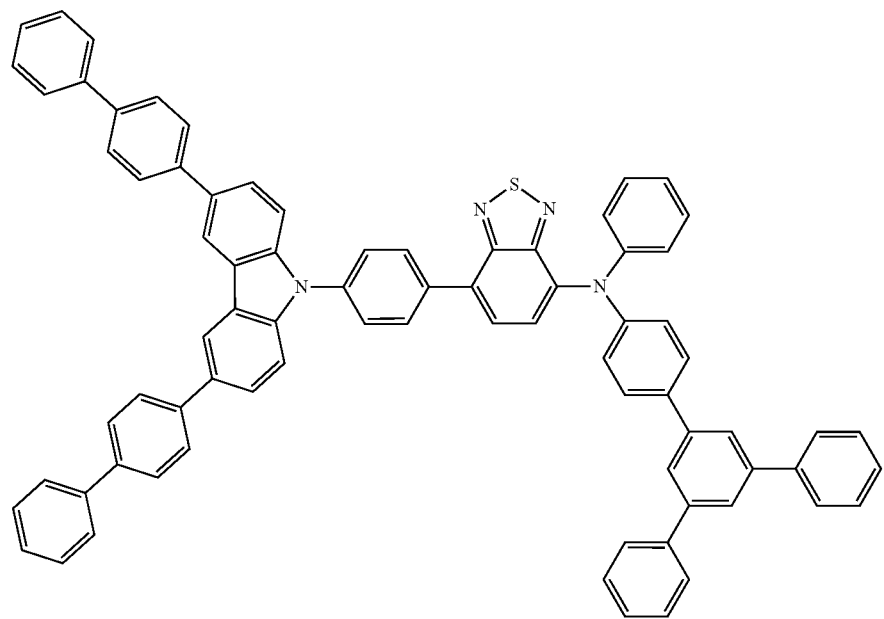

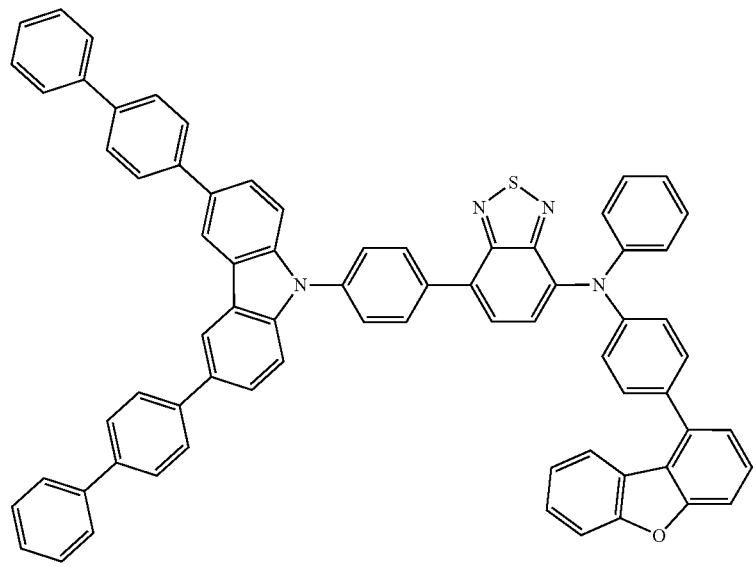
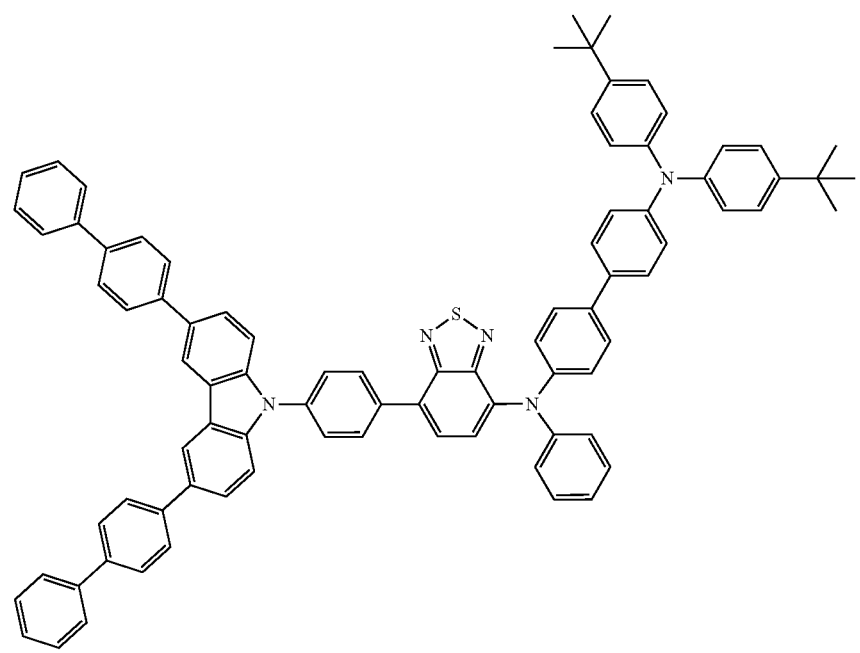

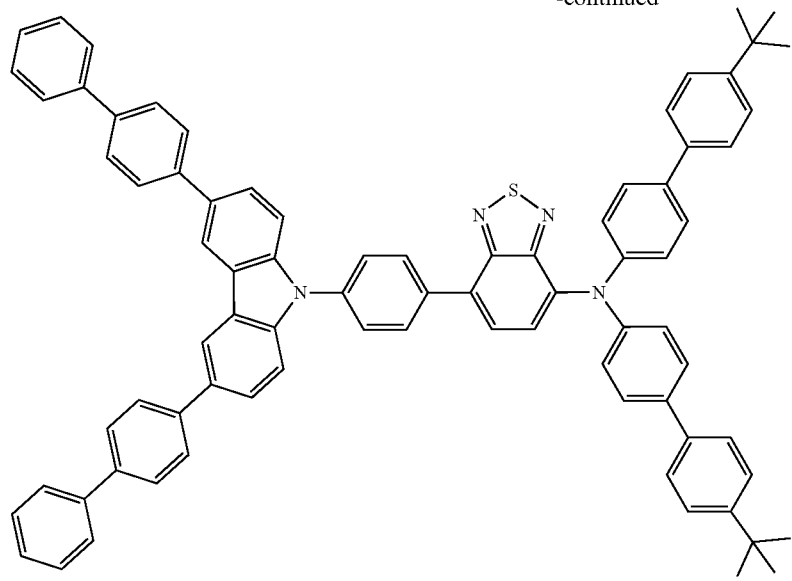
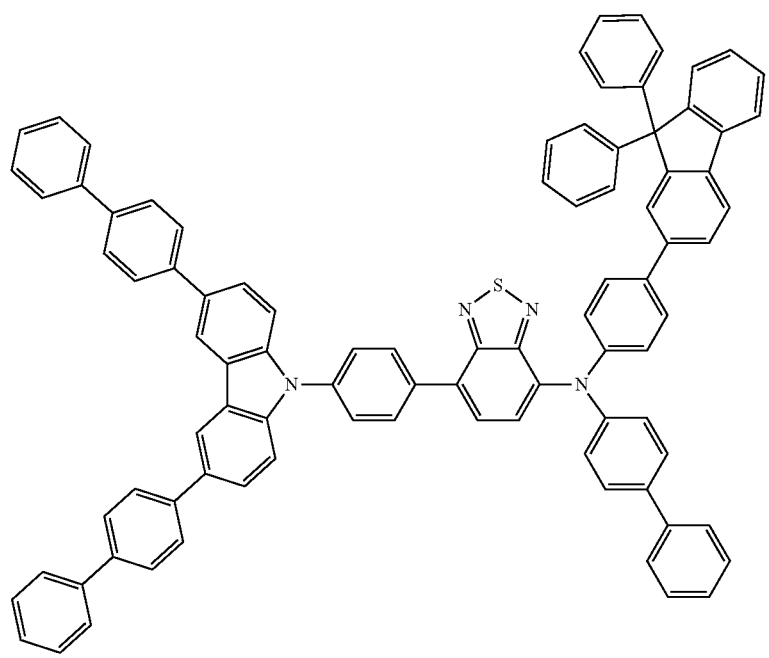

-continued
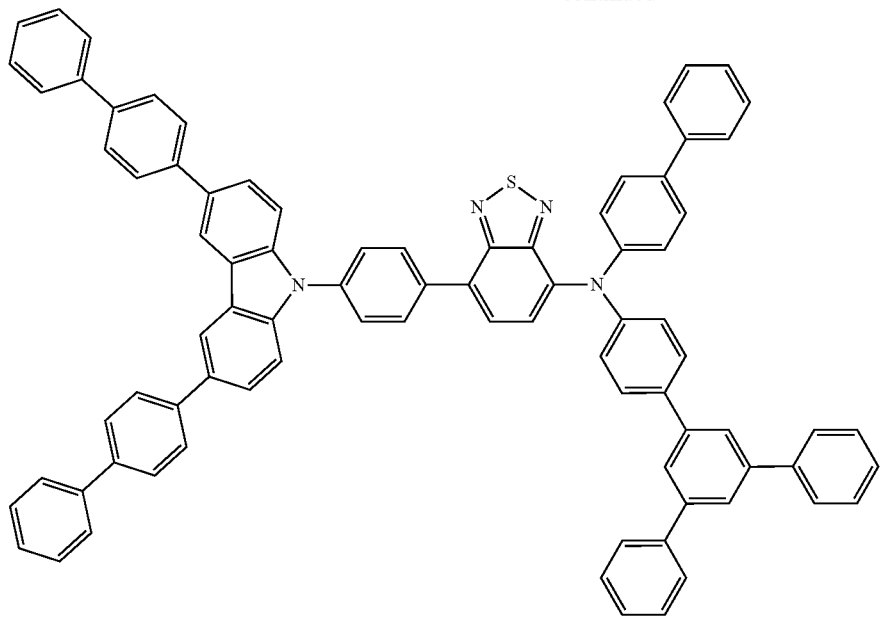
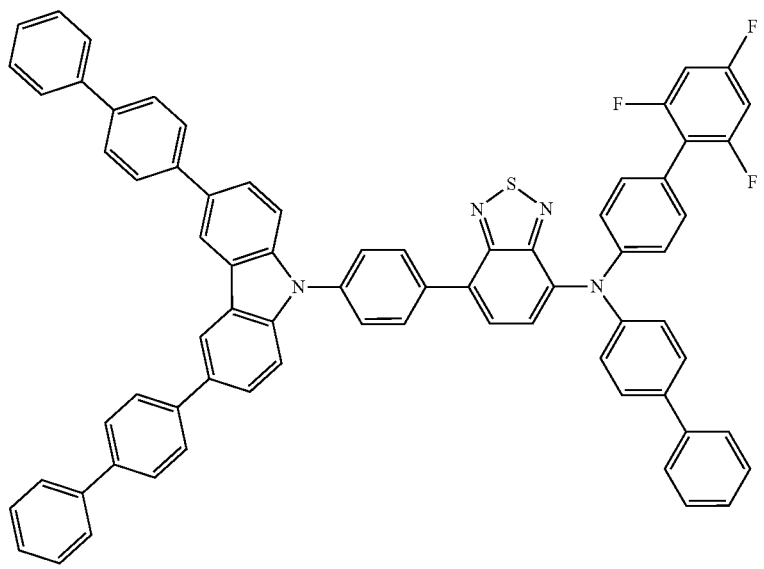

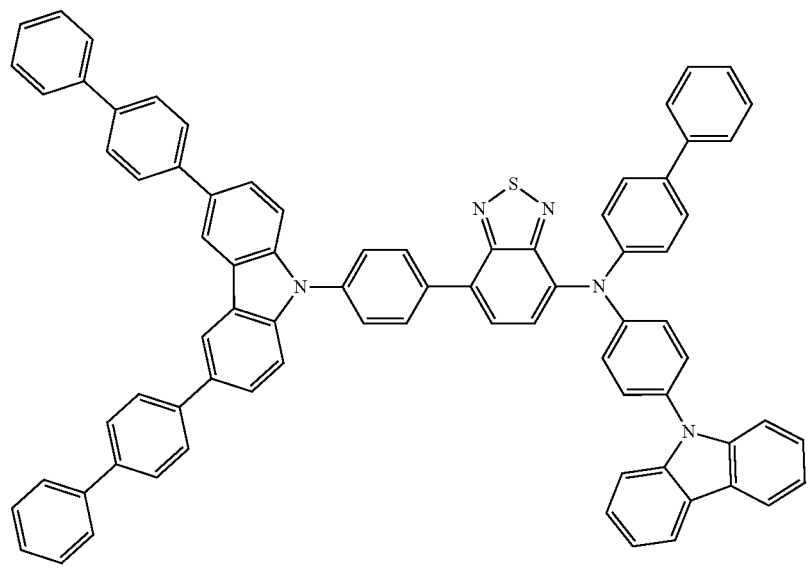
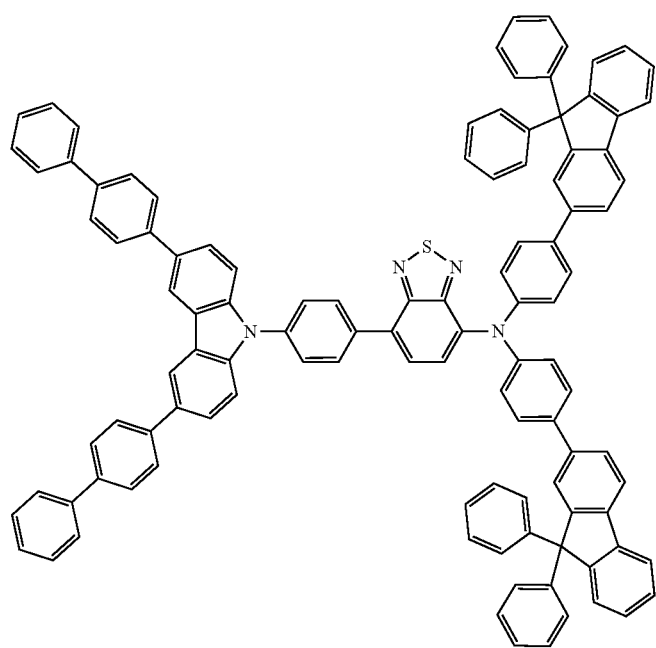

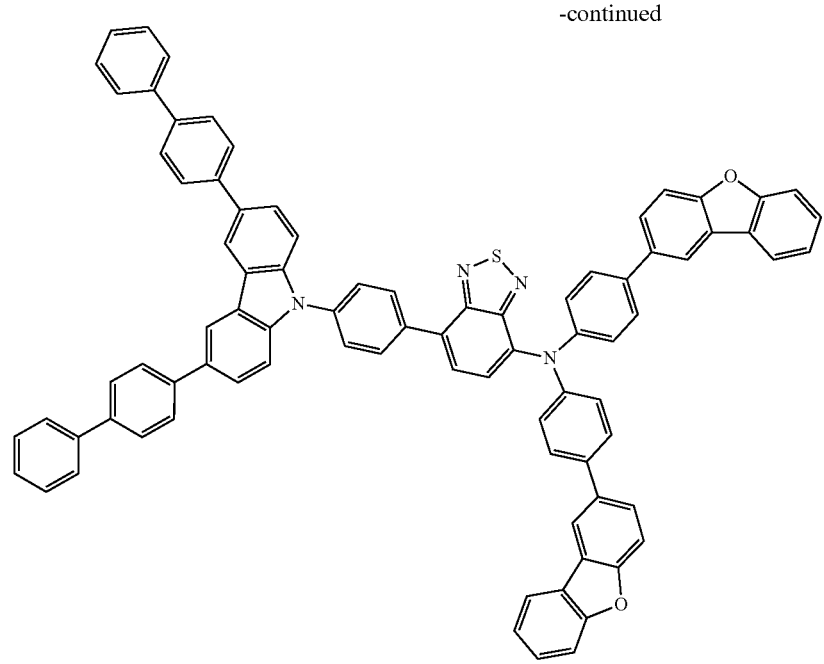
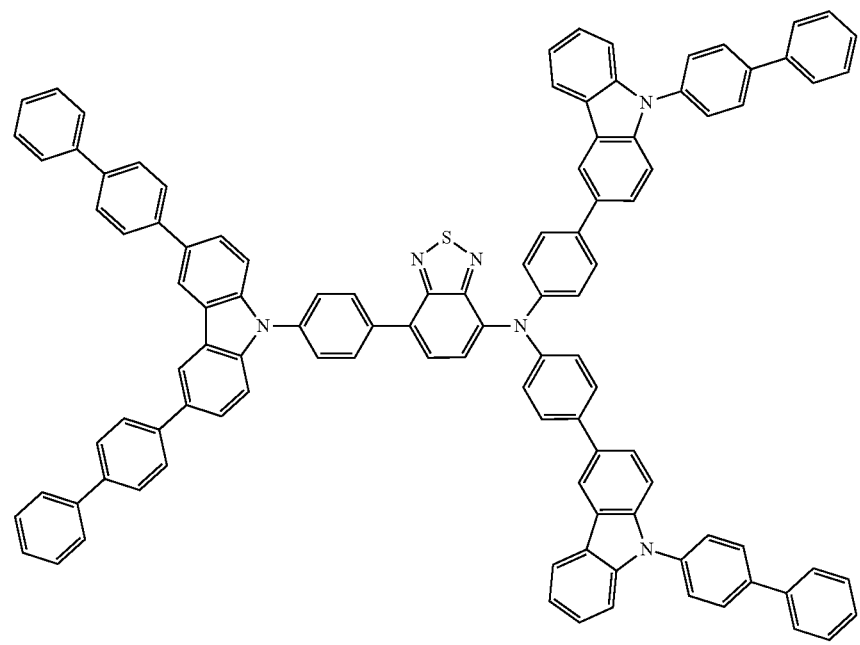

-continued
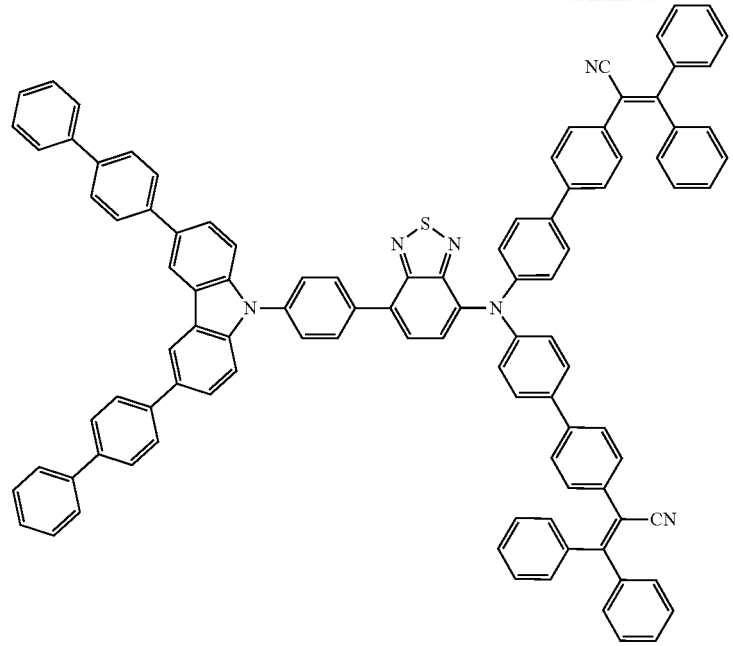
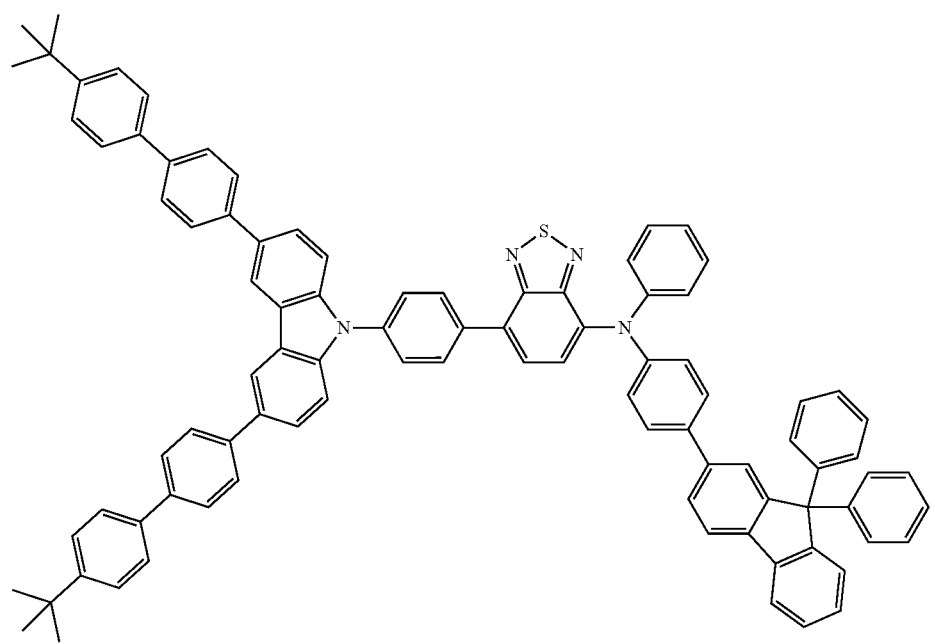

-continued
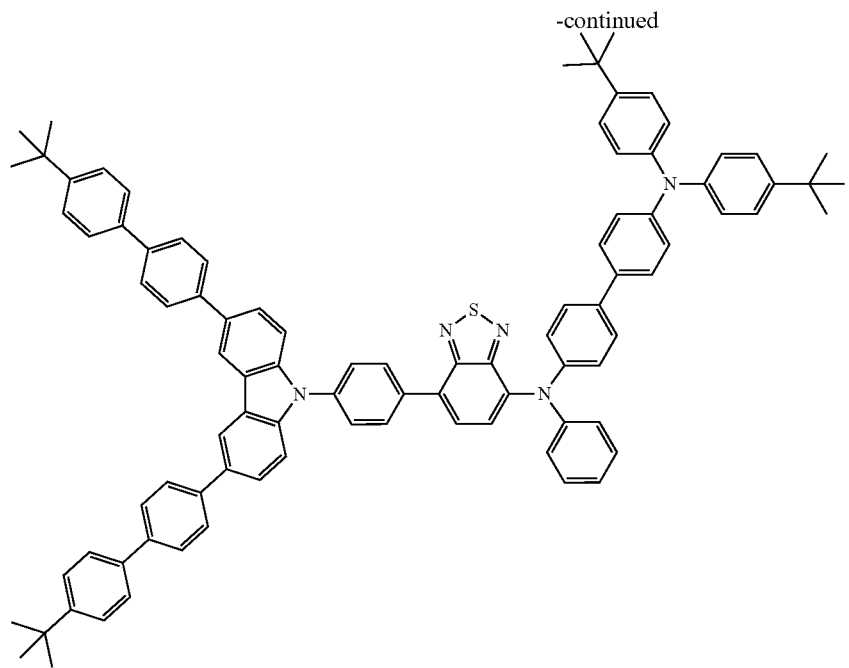
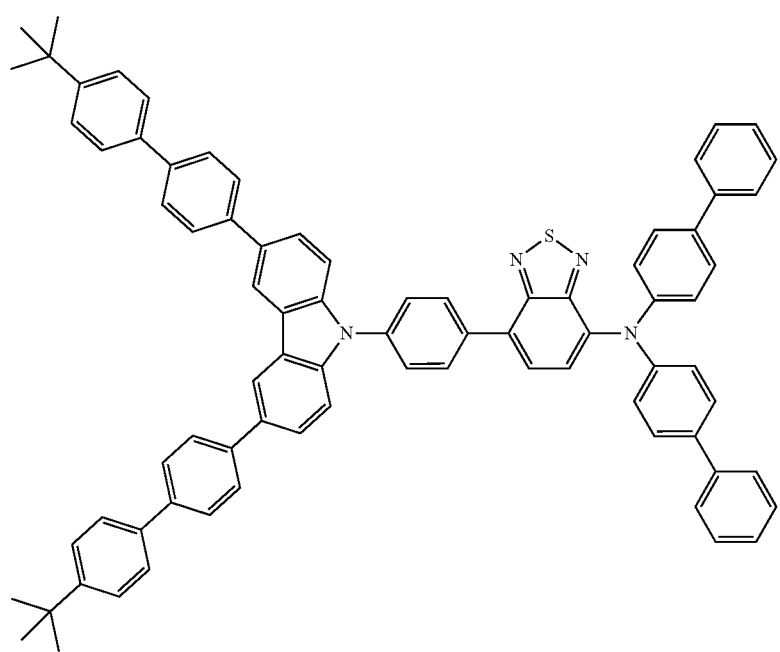

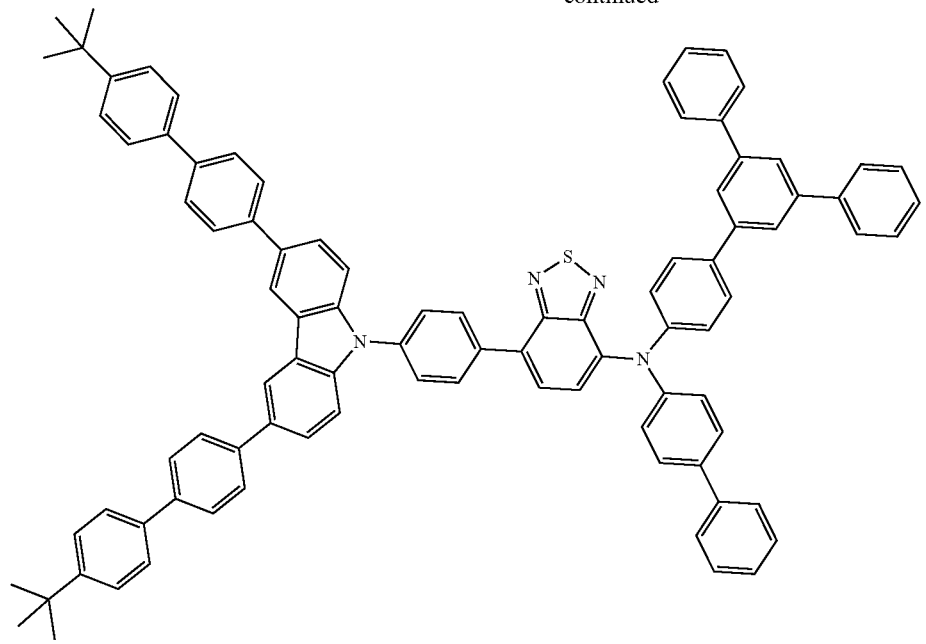
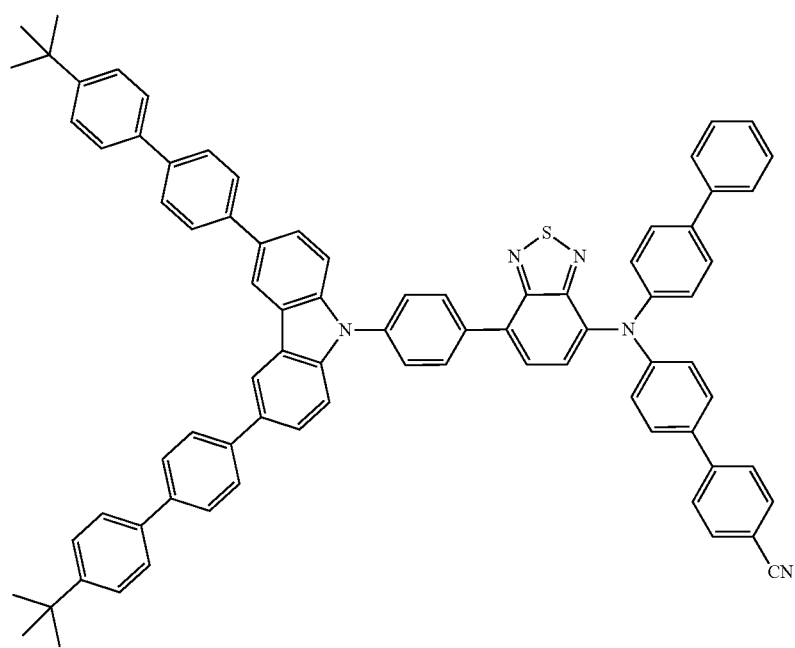

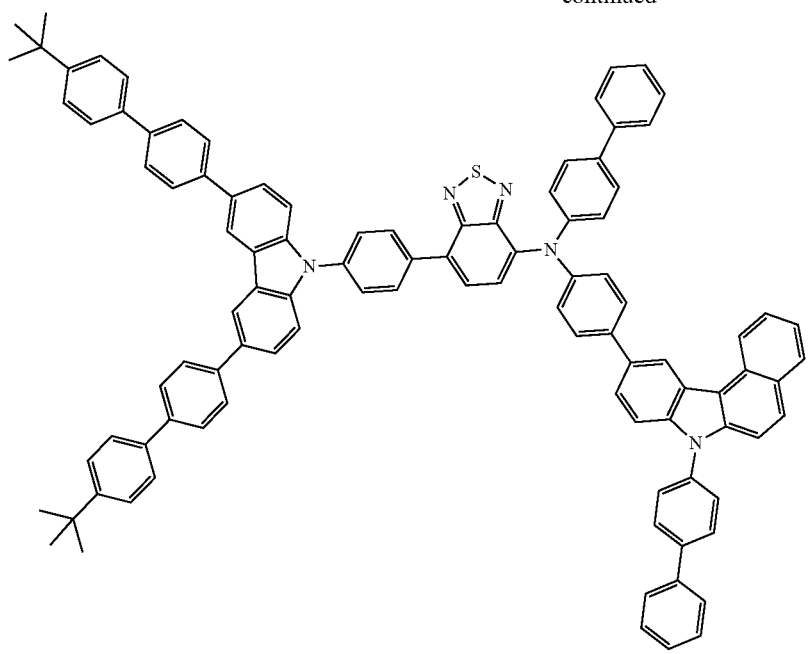
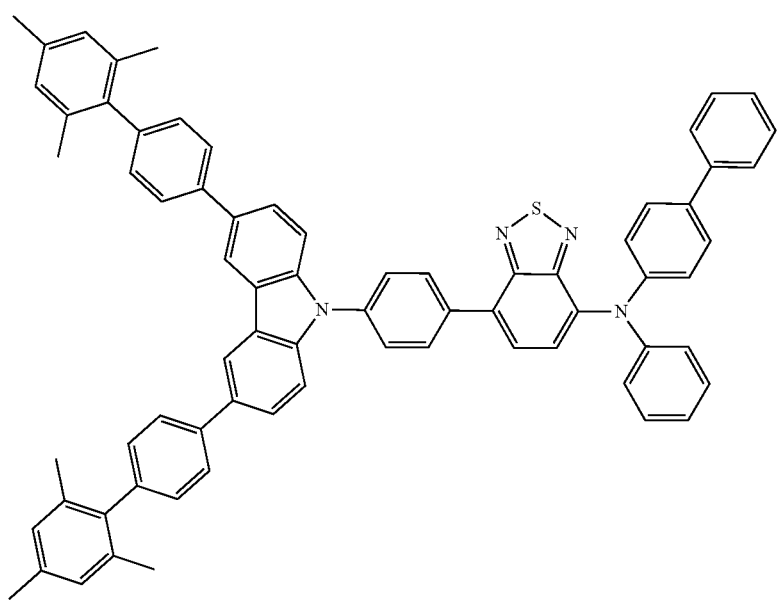

-continued
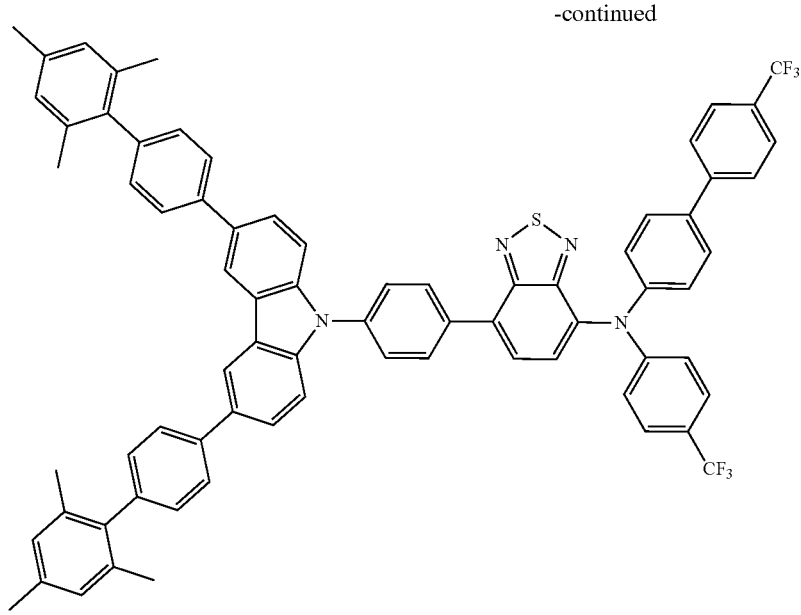
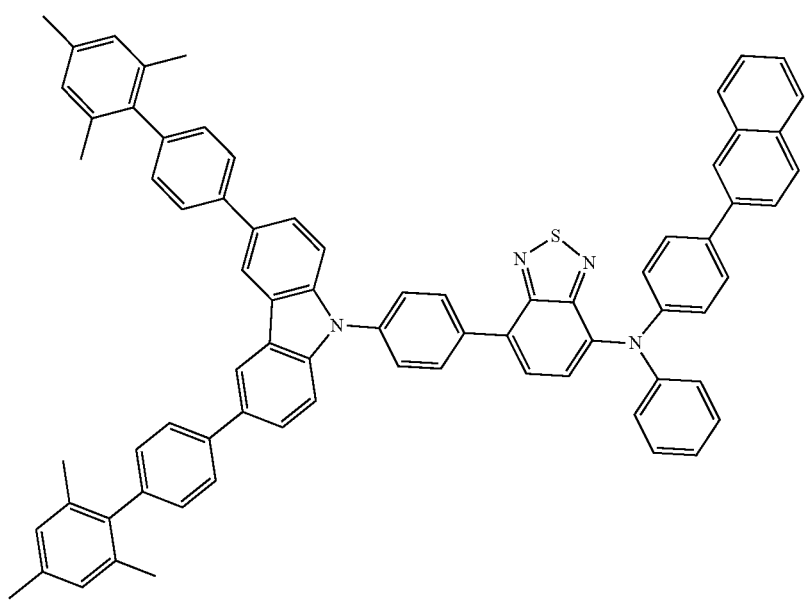

-continued
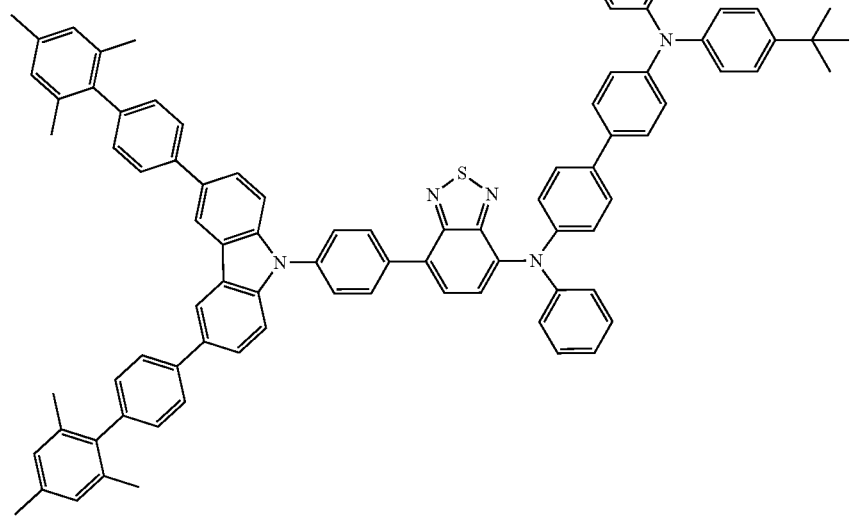
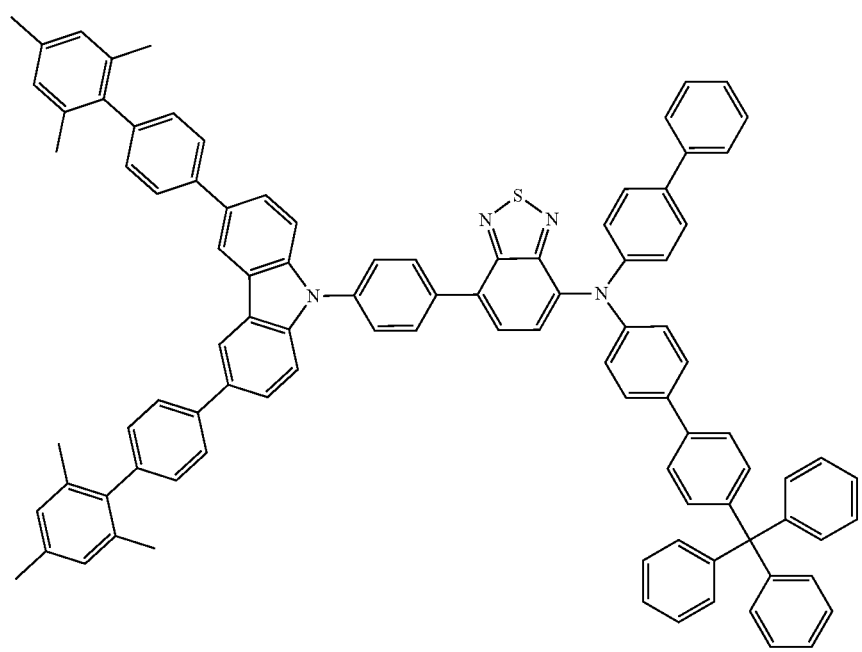

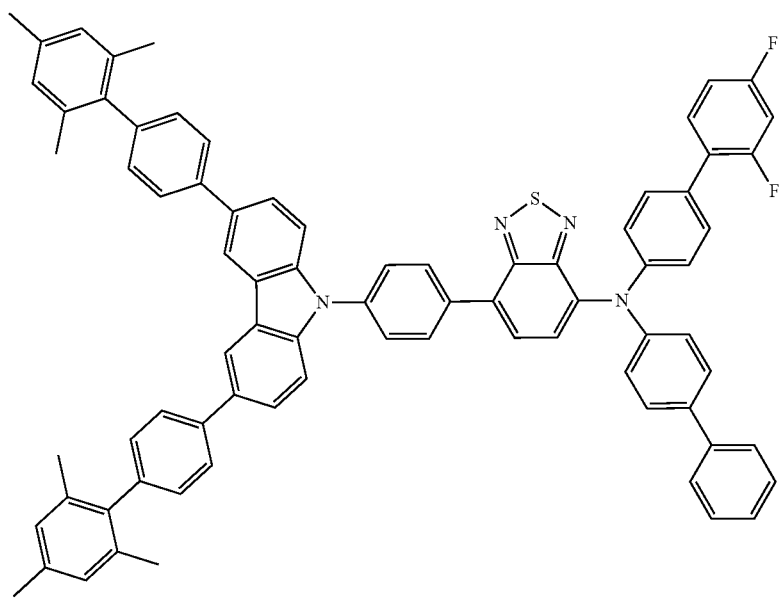
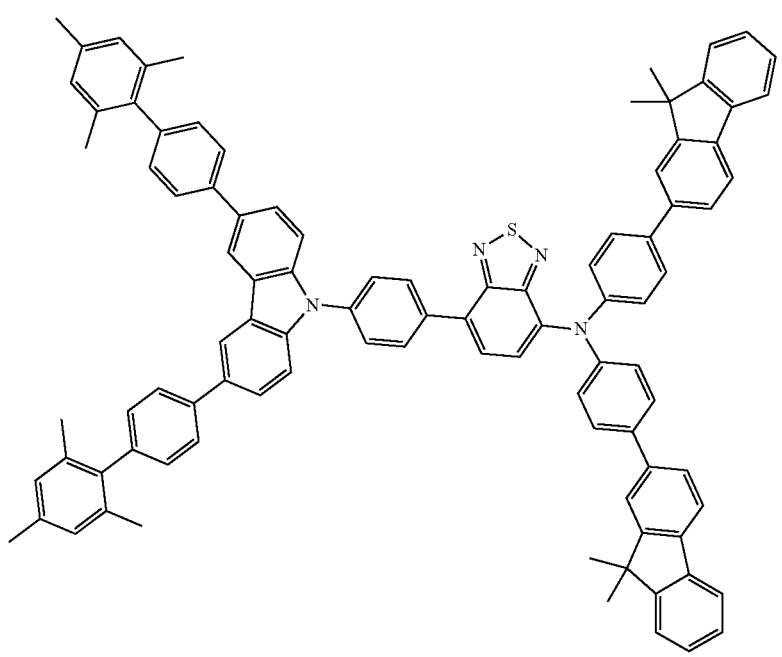

133 134
-continued
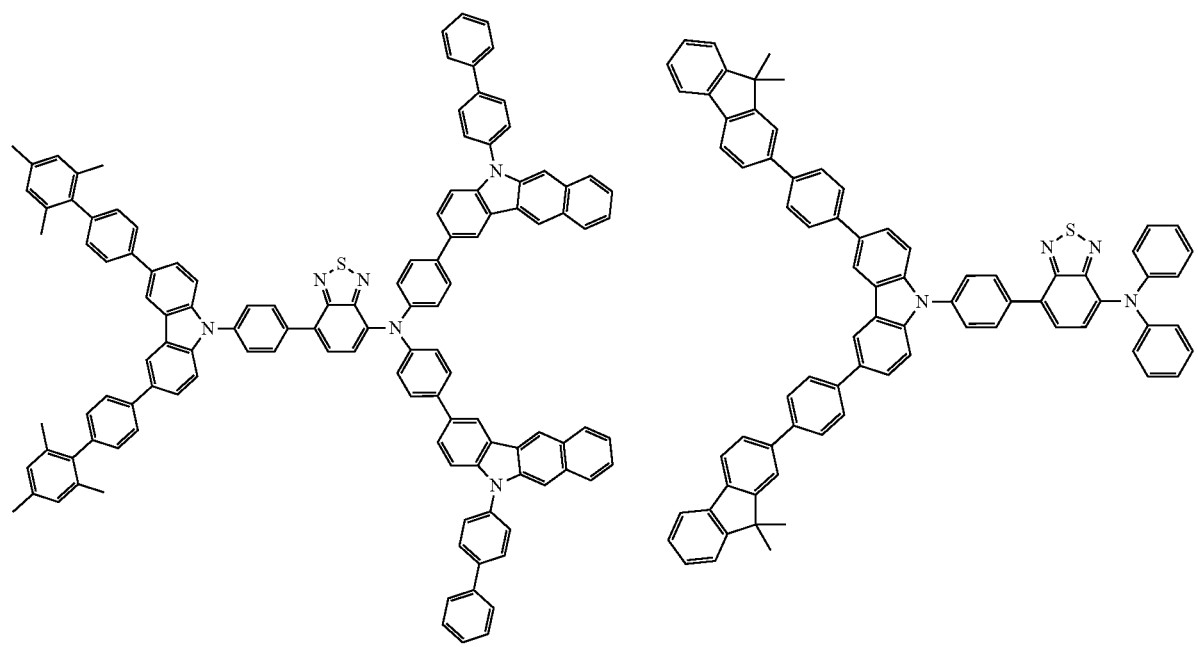
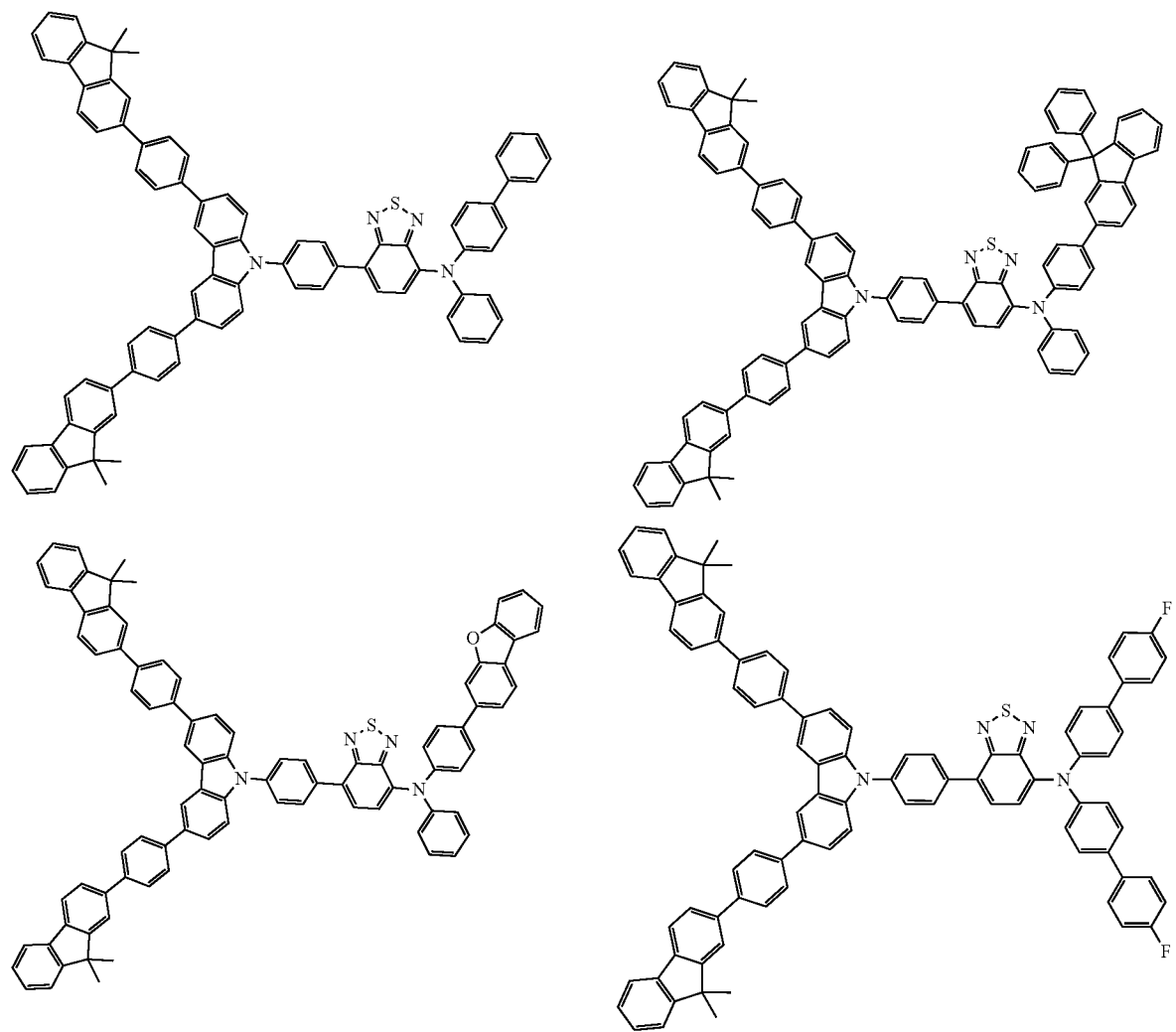

-continued
| 135 | 136 |
|---|---|
| 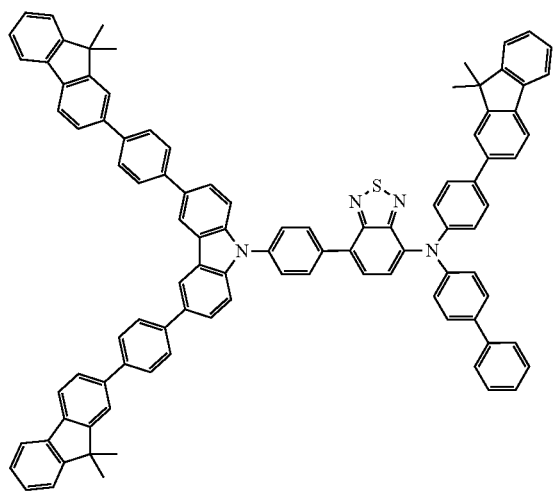 | 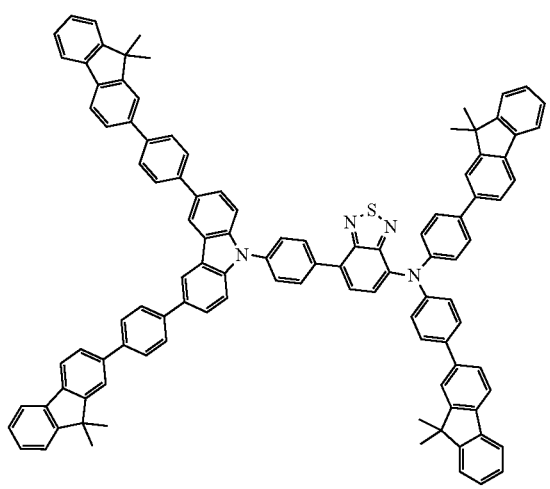 |
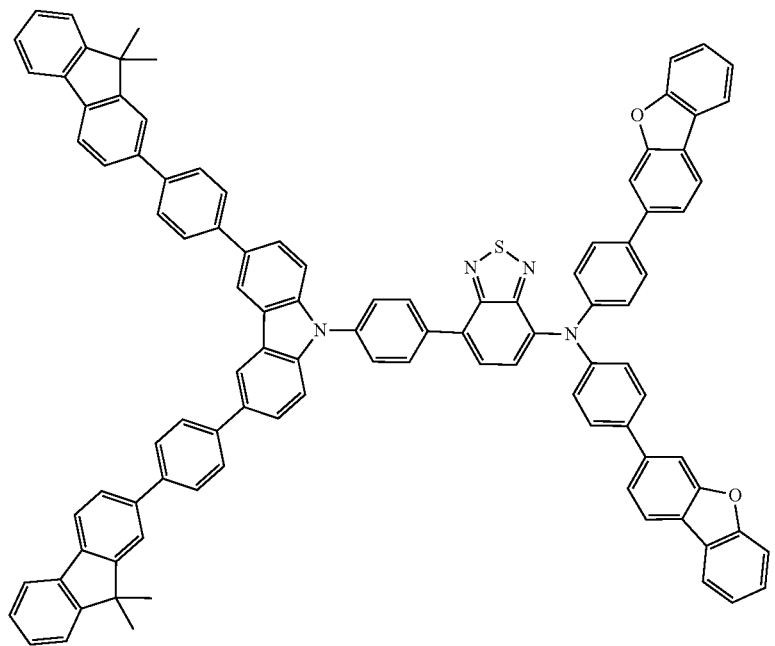

-continued
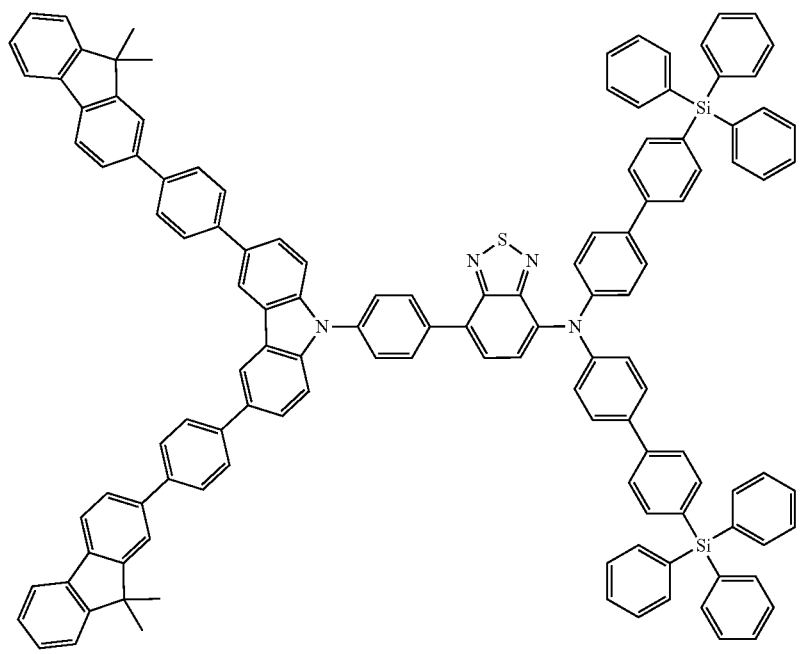
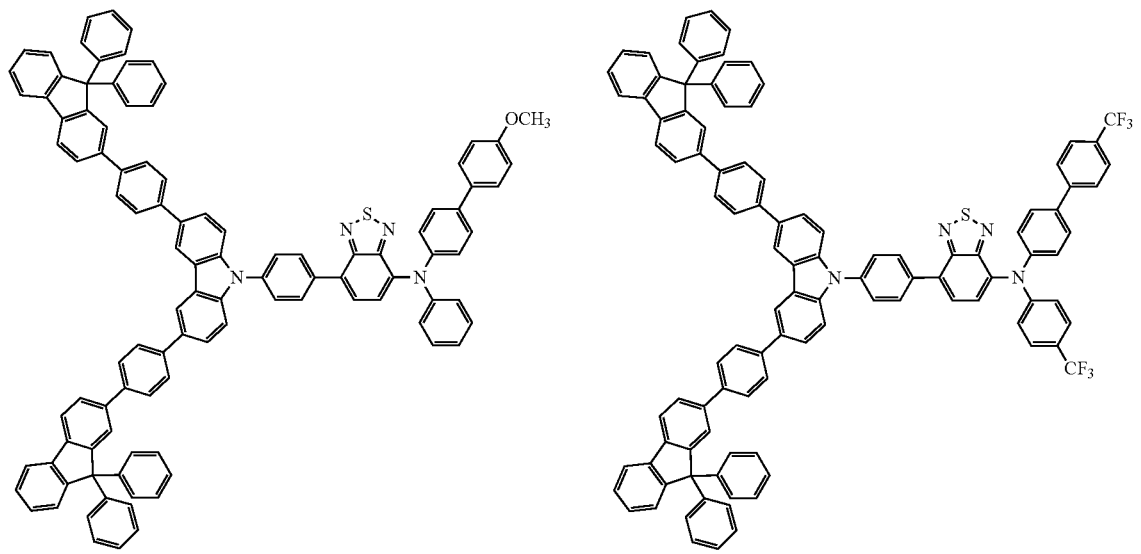

-continued
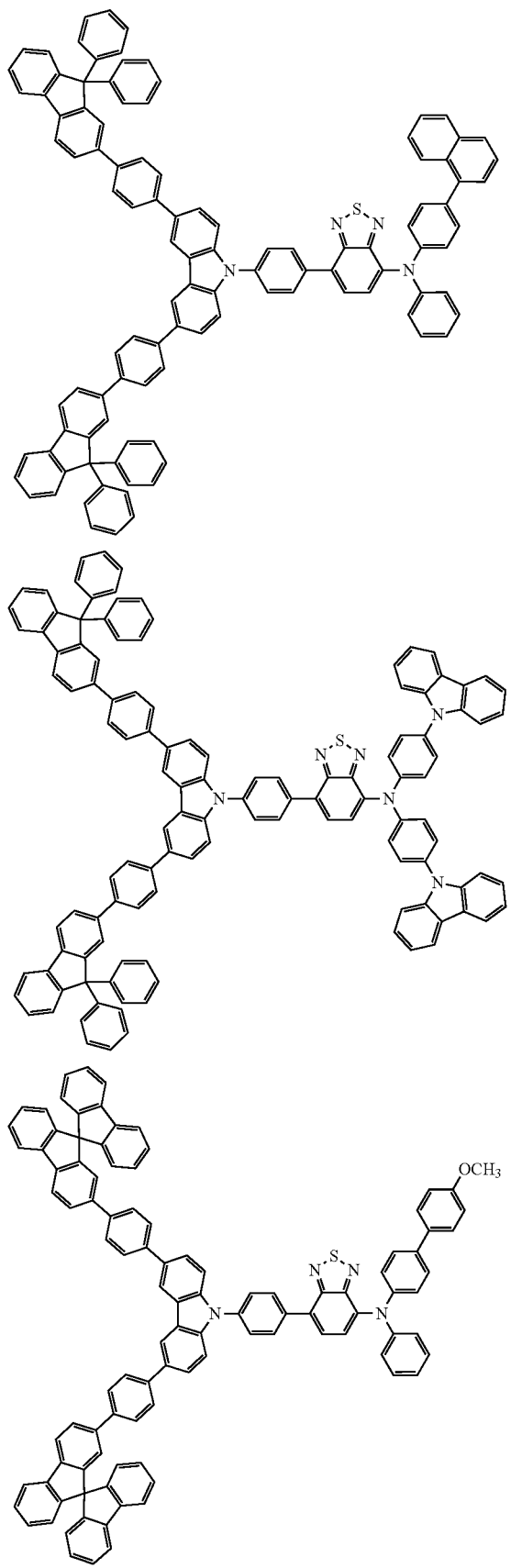
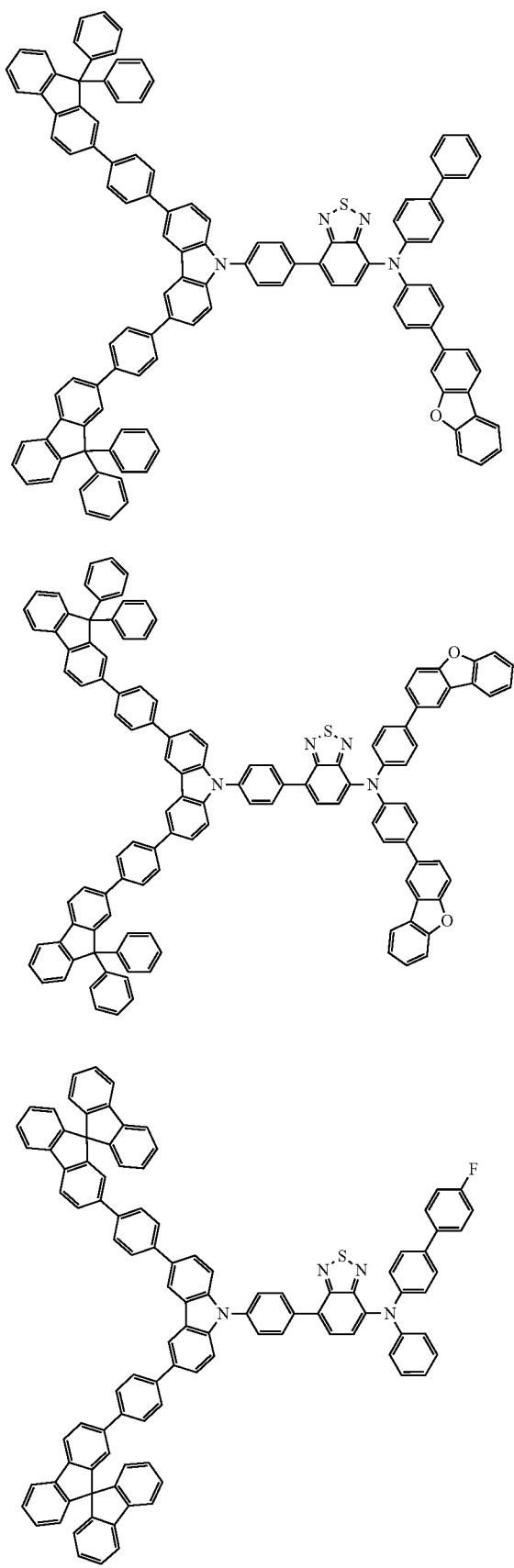

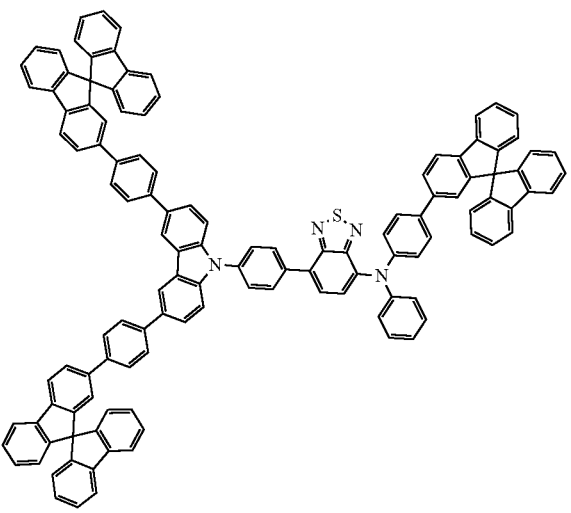
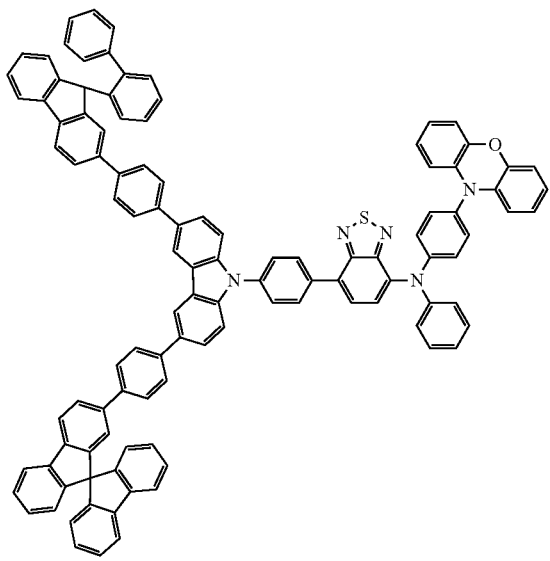
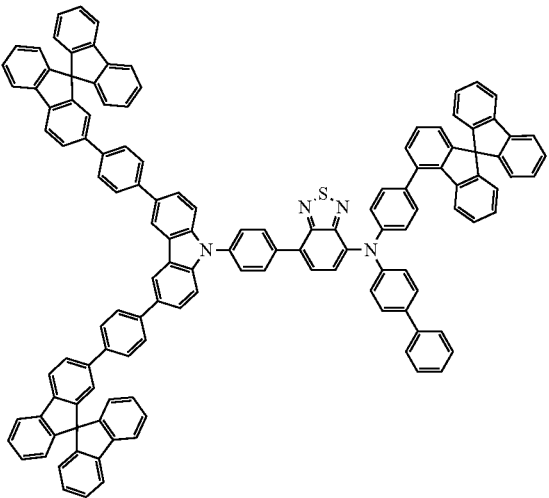
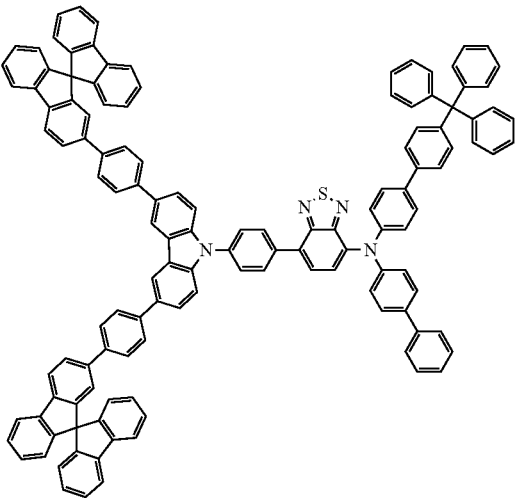
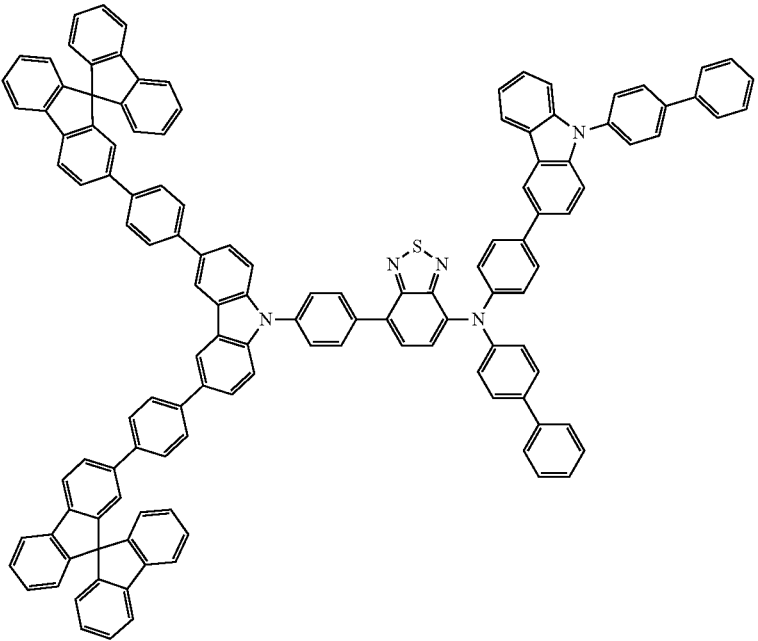

-continued
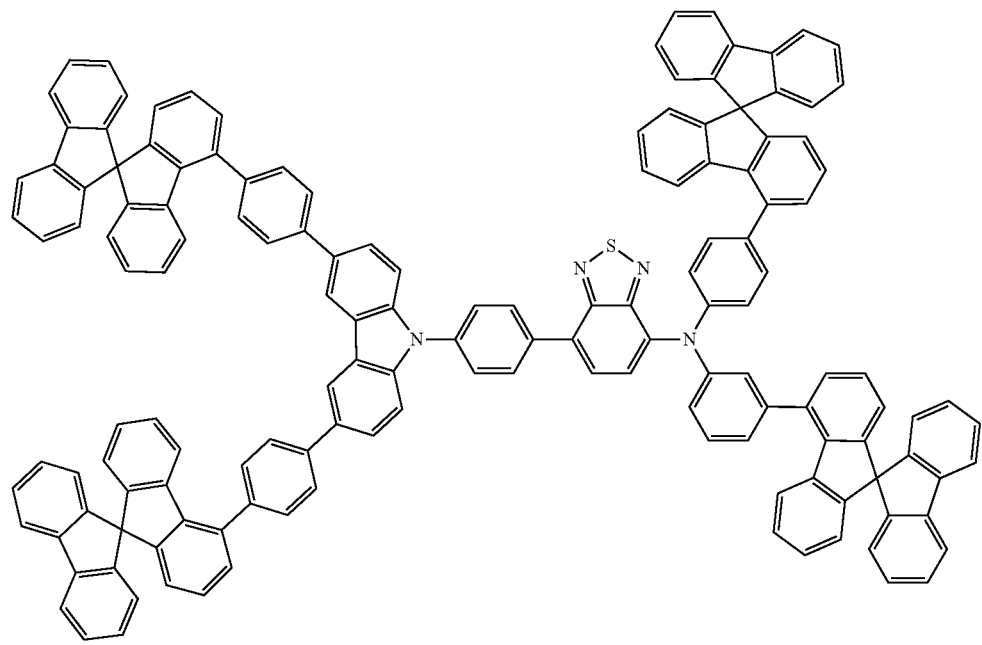
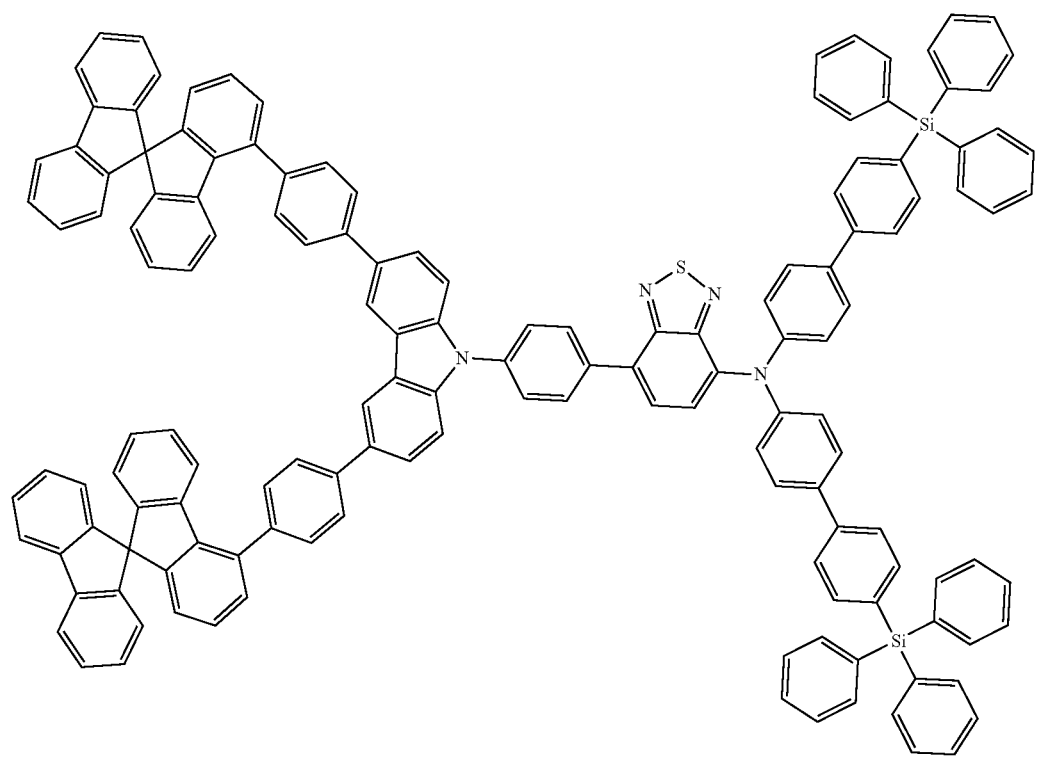

-continued
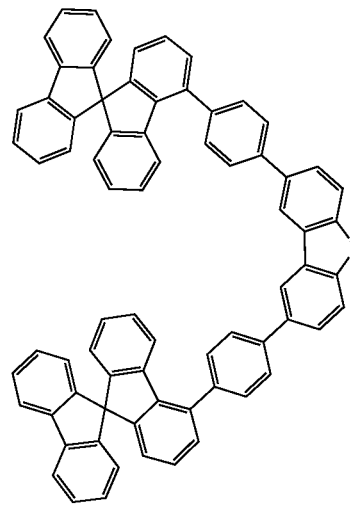
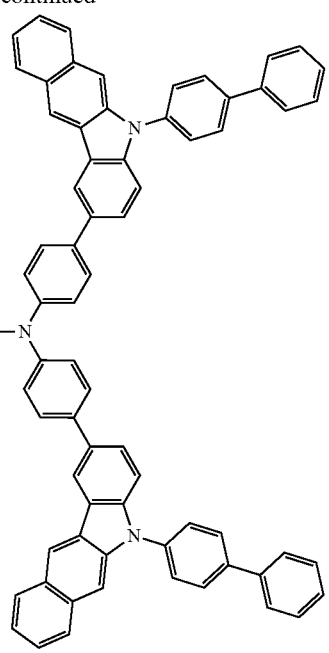
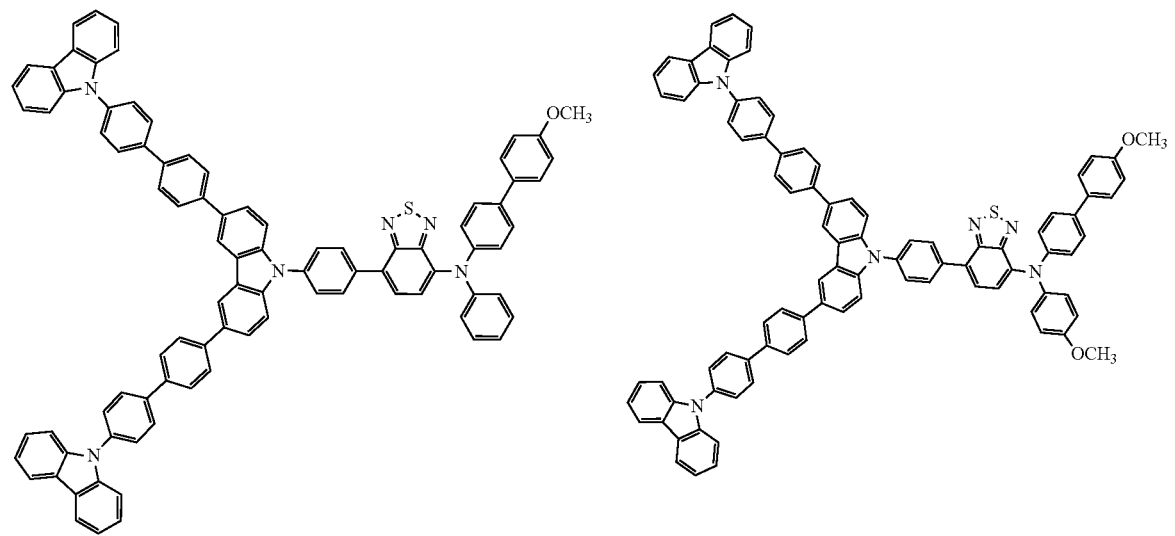

-continued
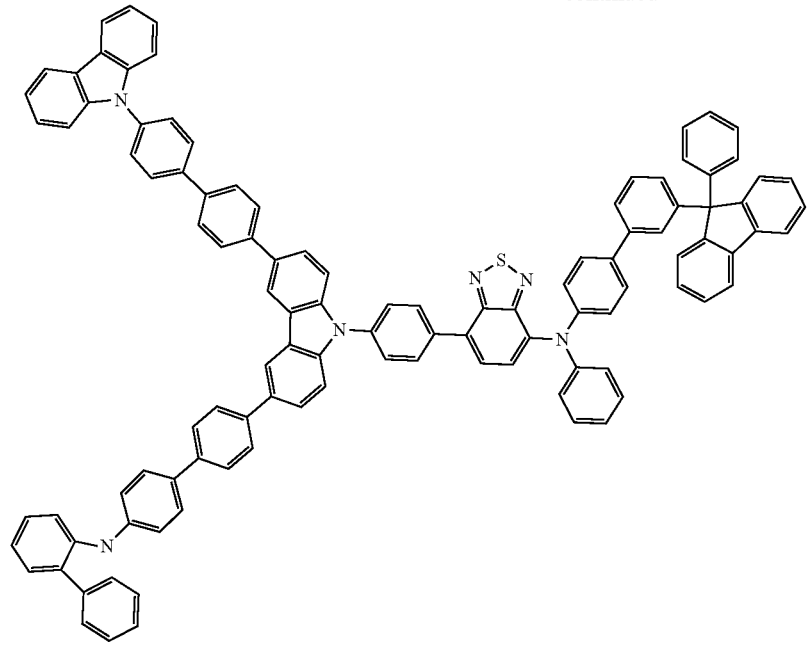
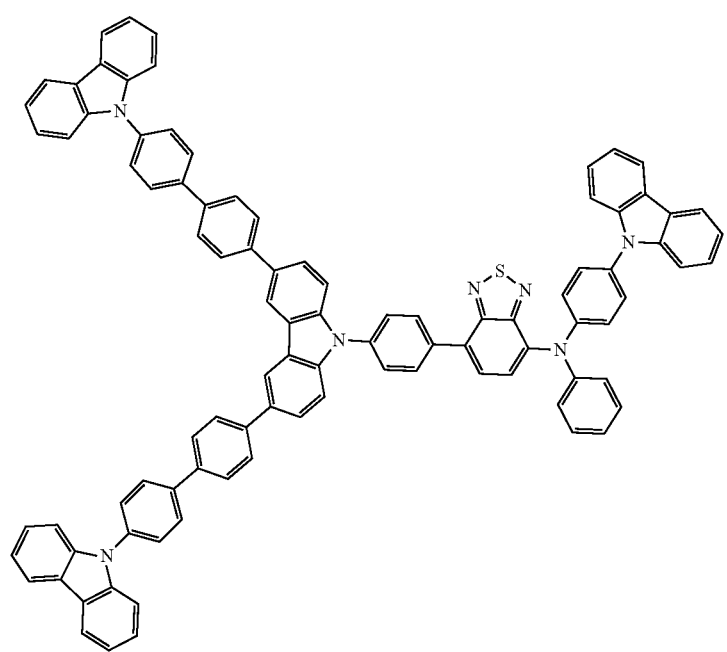

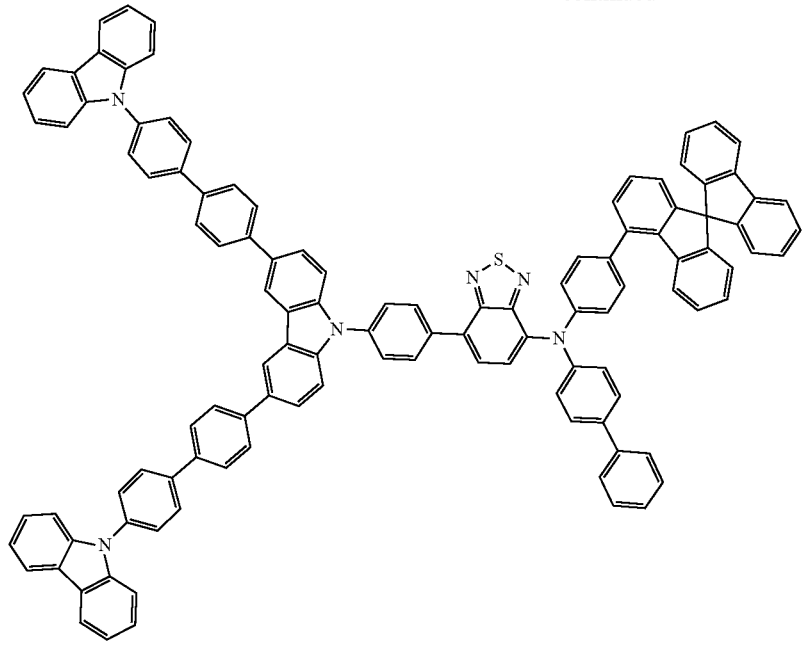
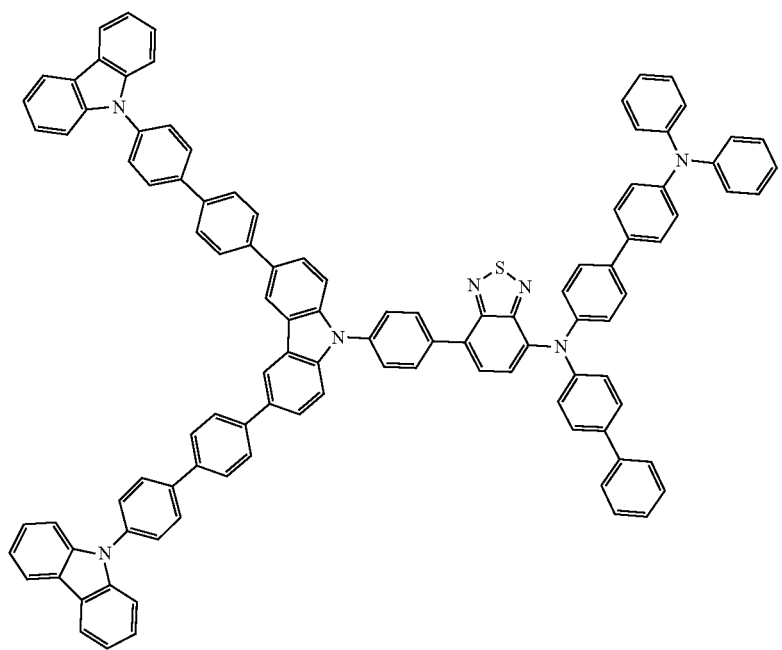

151
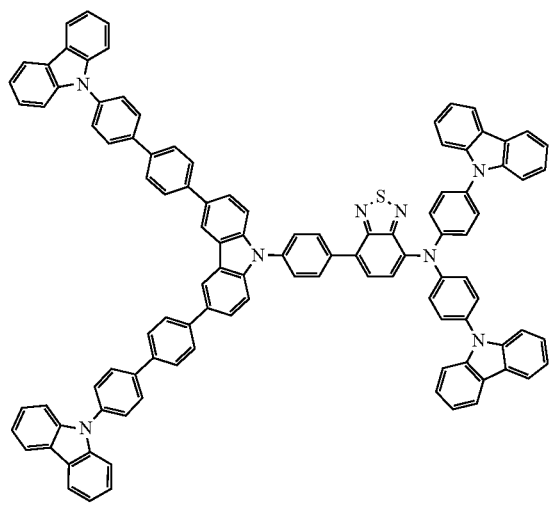
152
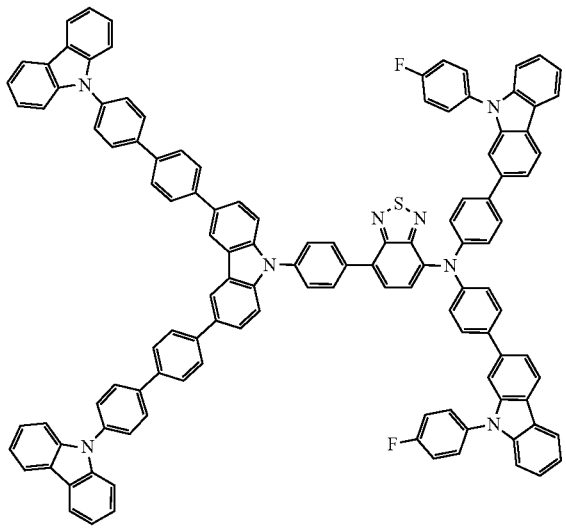
-continued
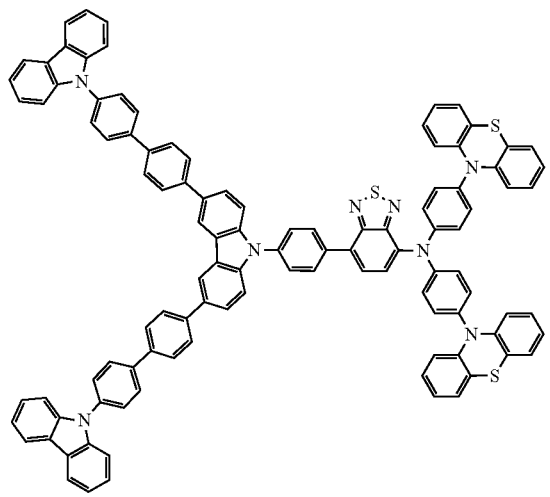
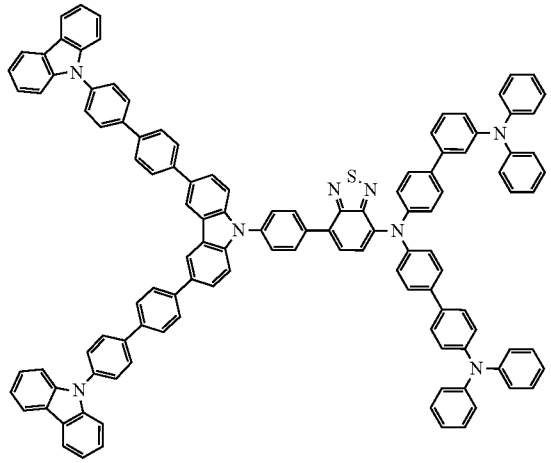
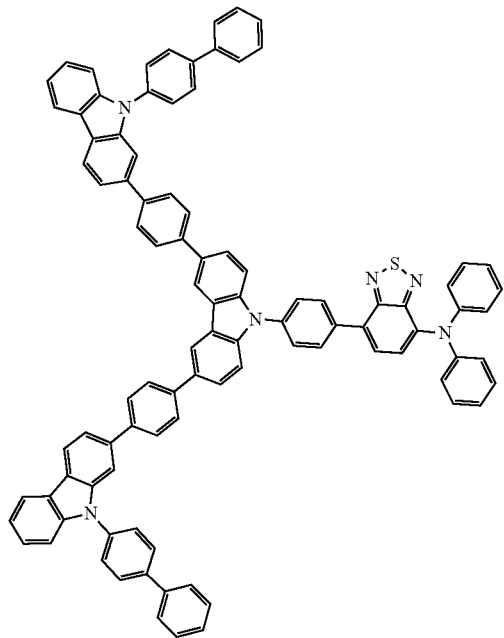
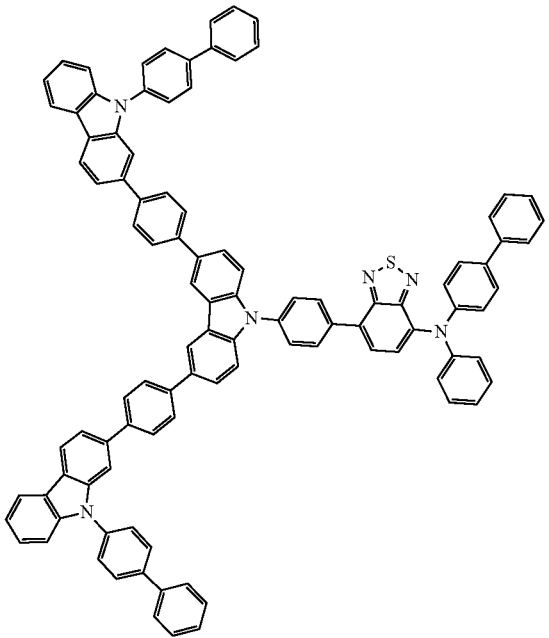

153
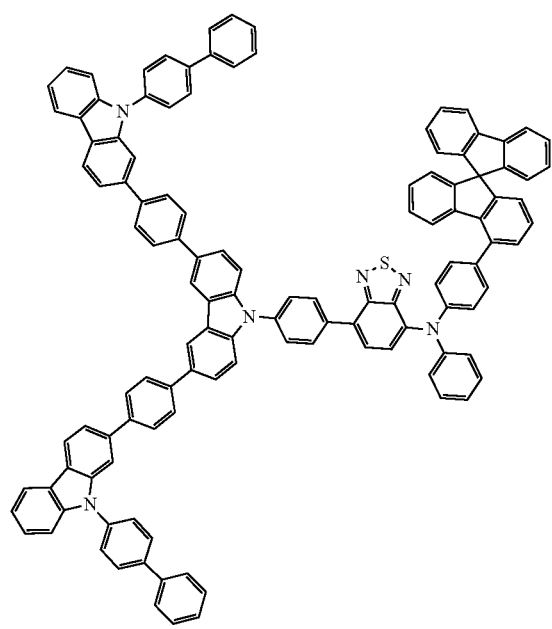
154
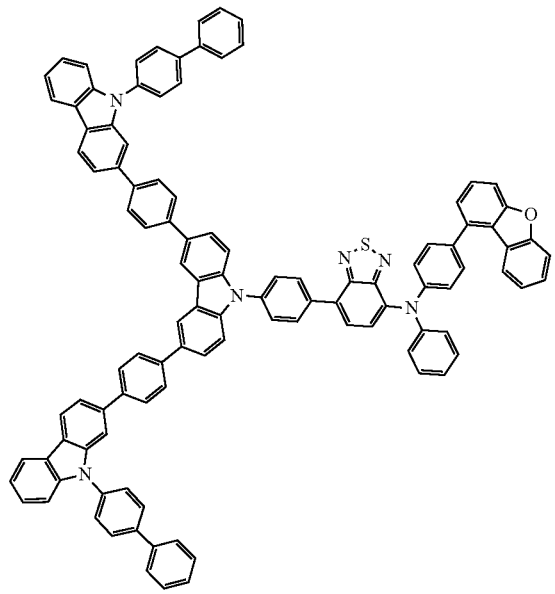
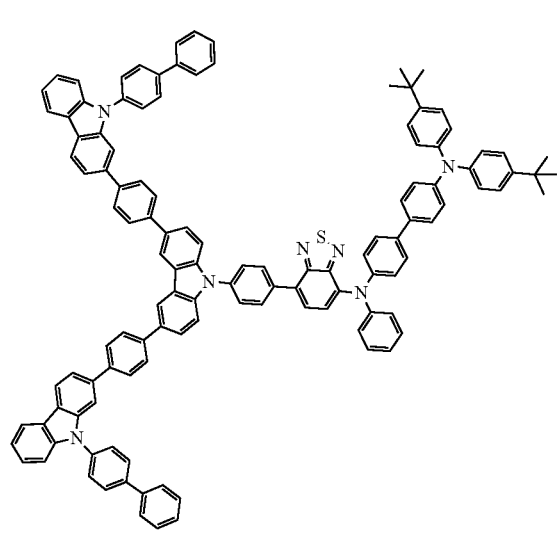
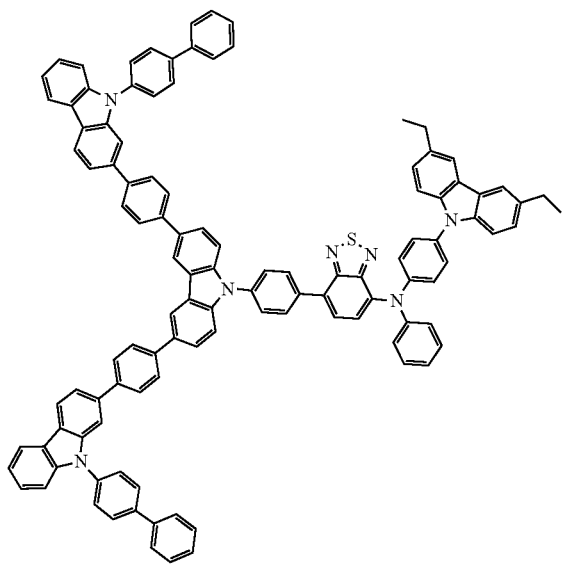

-continued
155
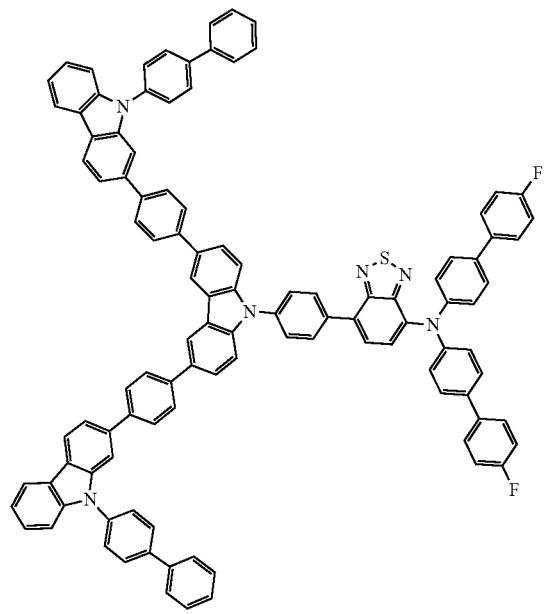
156
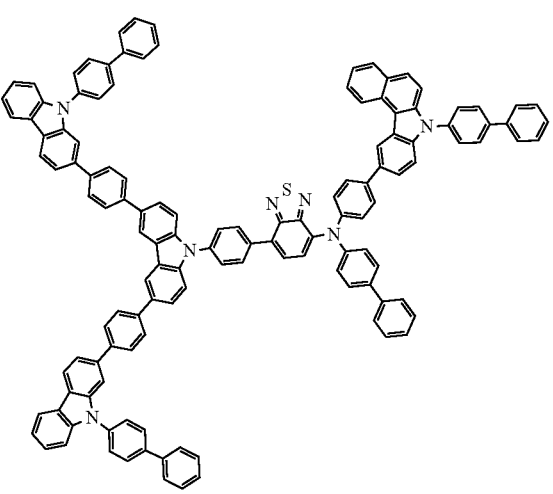
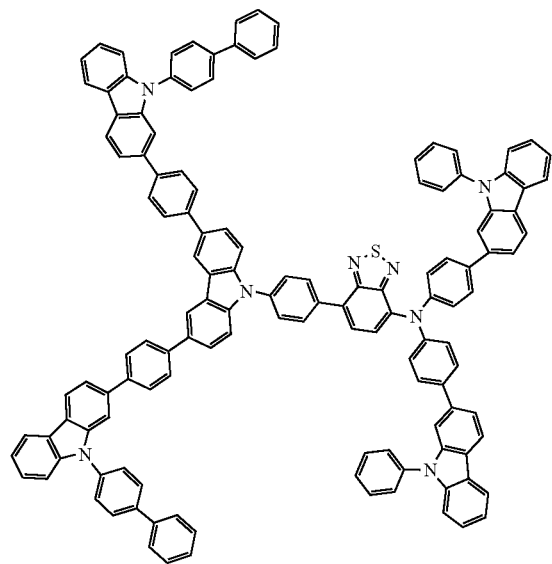
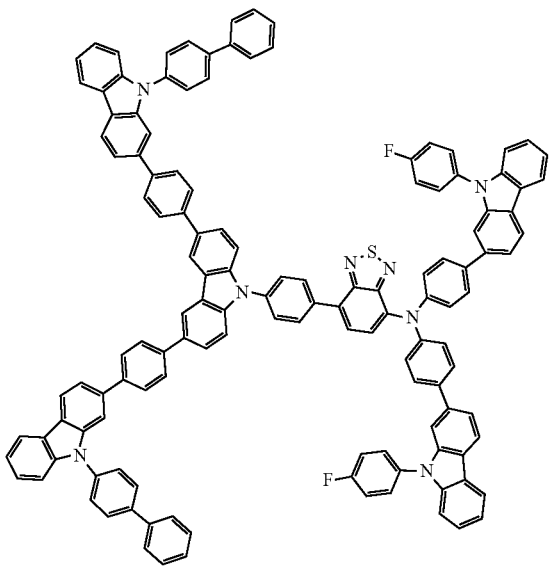

-continued
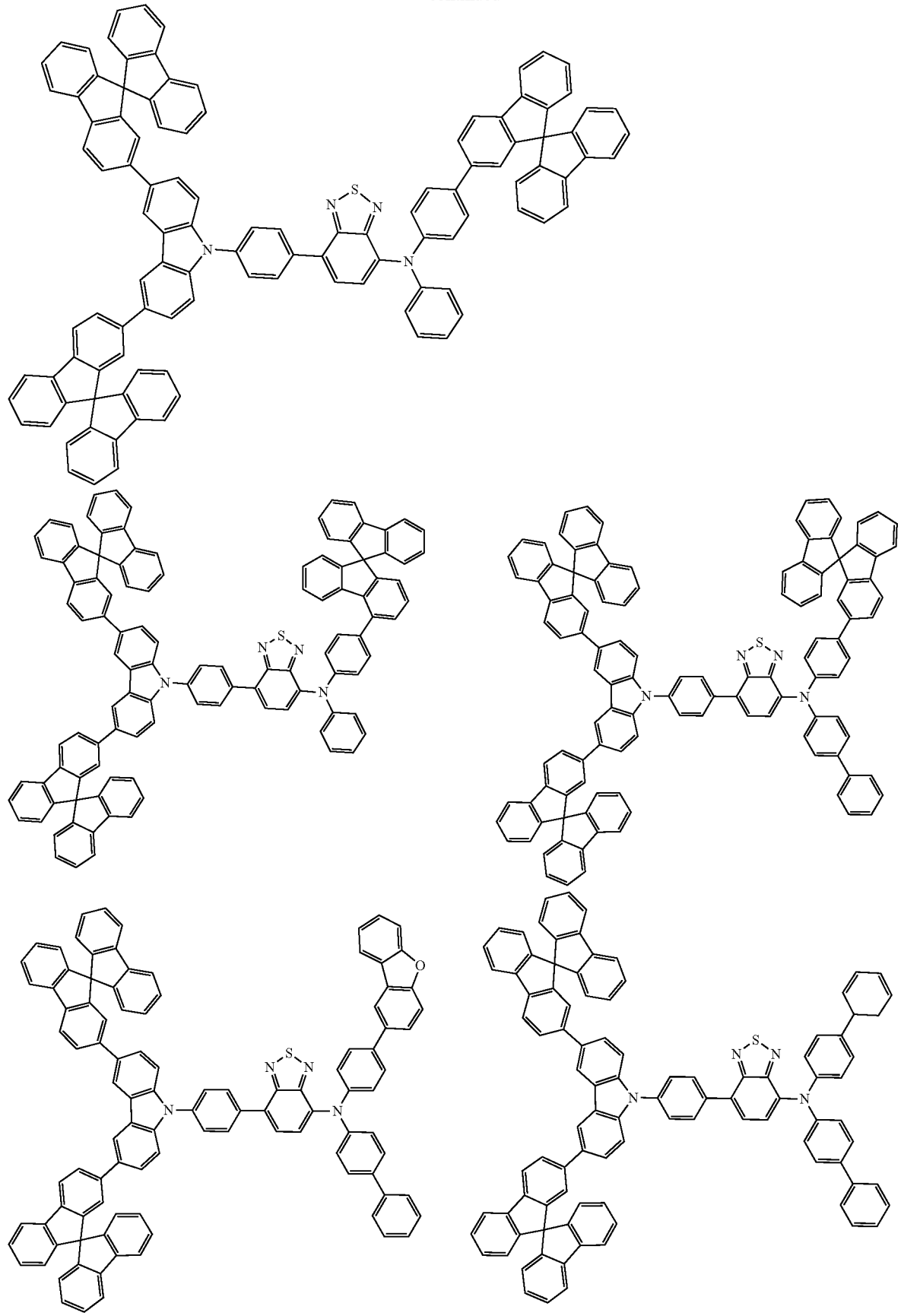

-continued
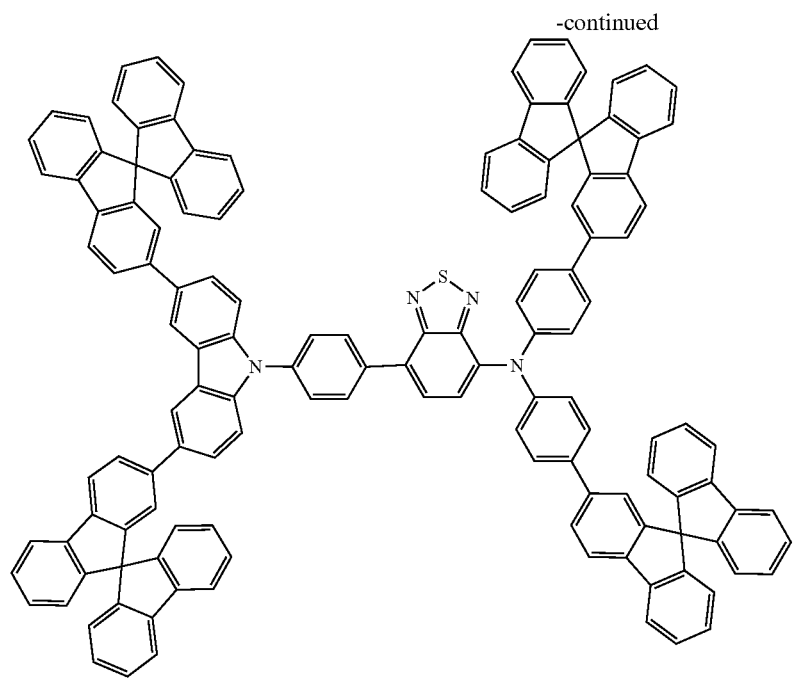
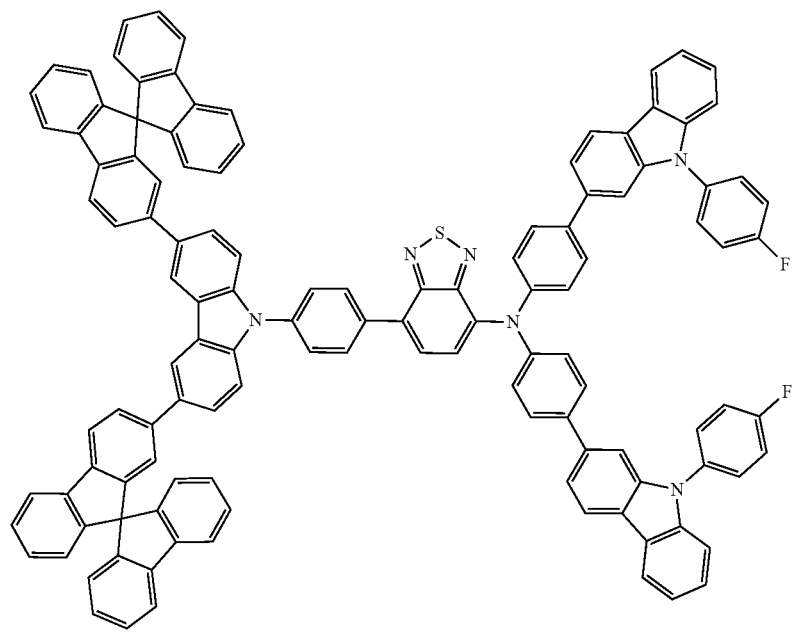

-continued
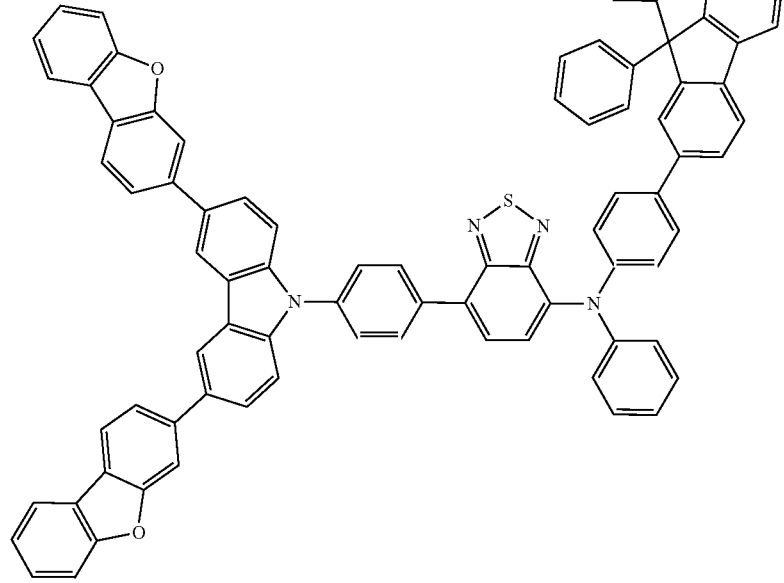

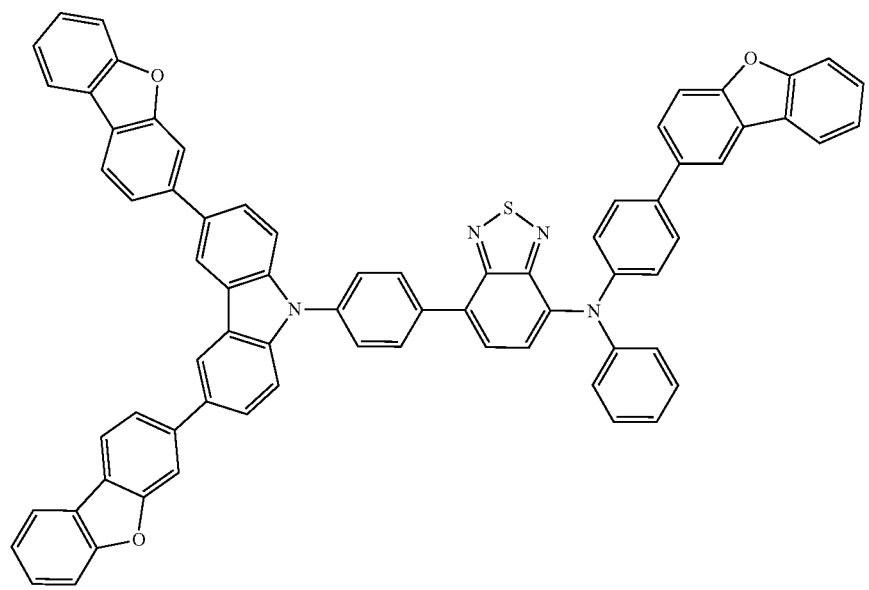
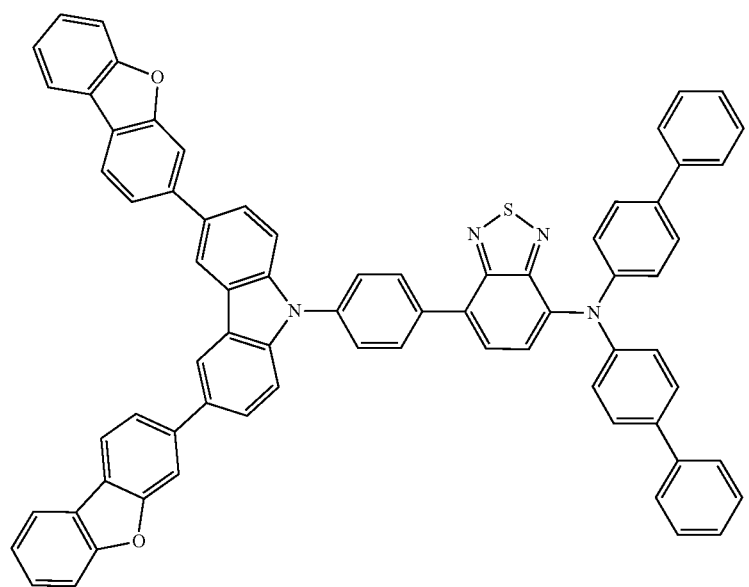

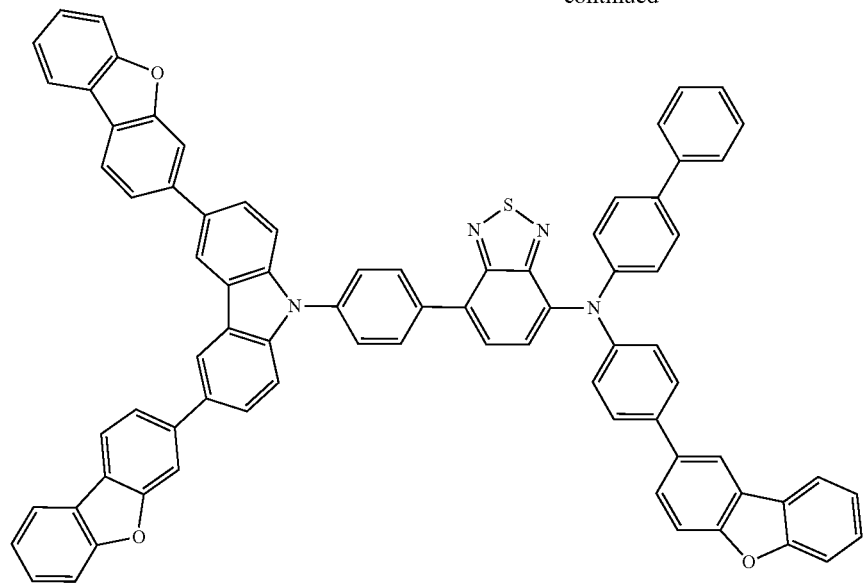
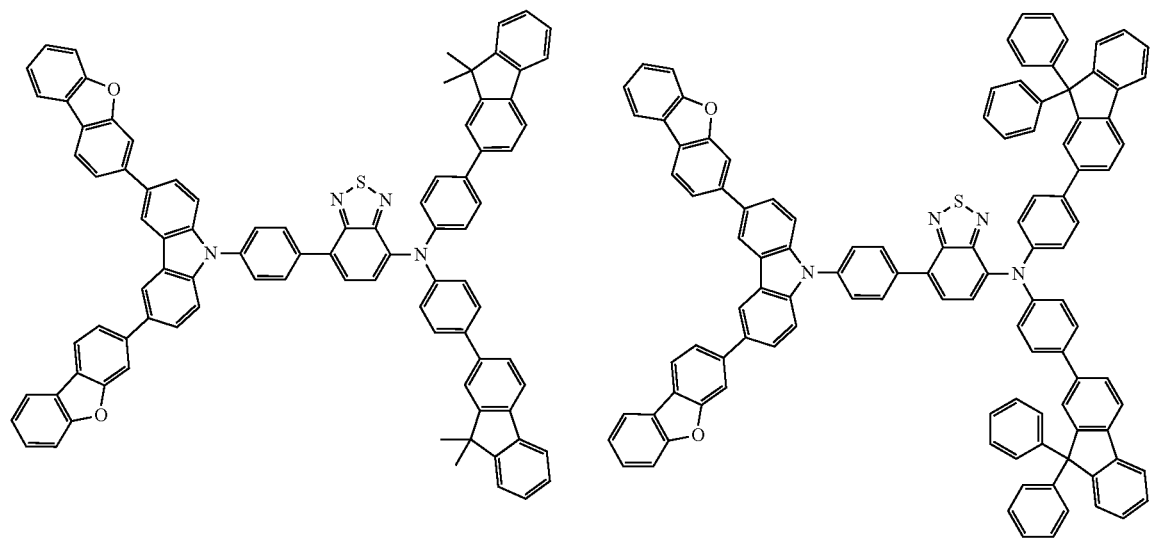

167
168
-continued
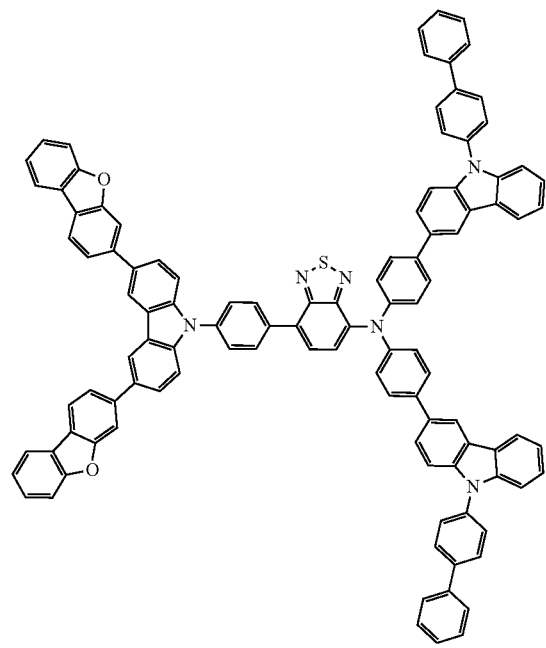
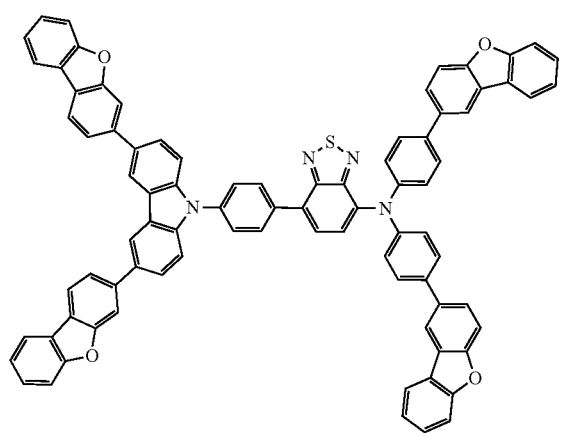
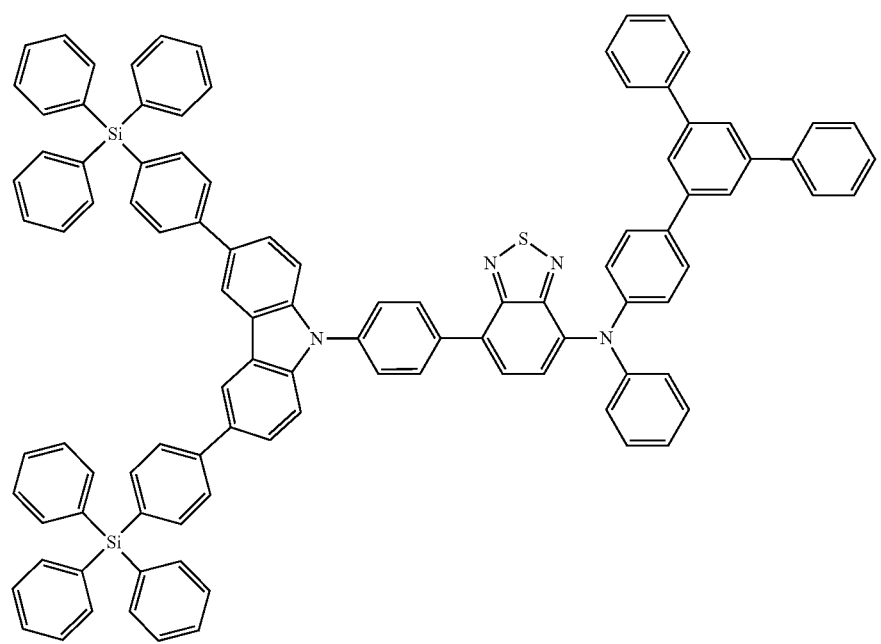

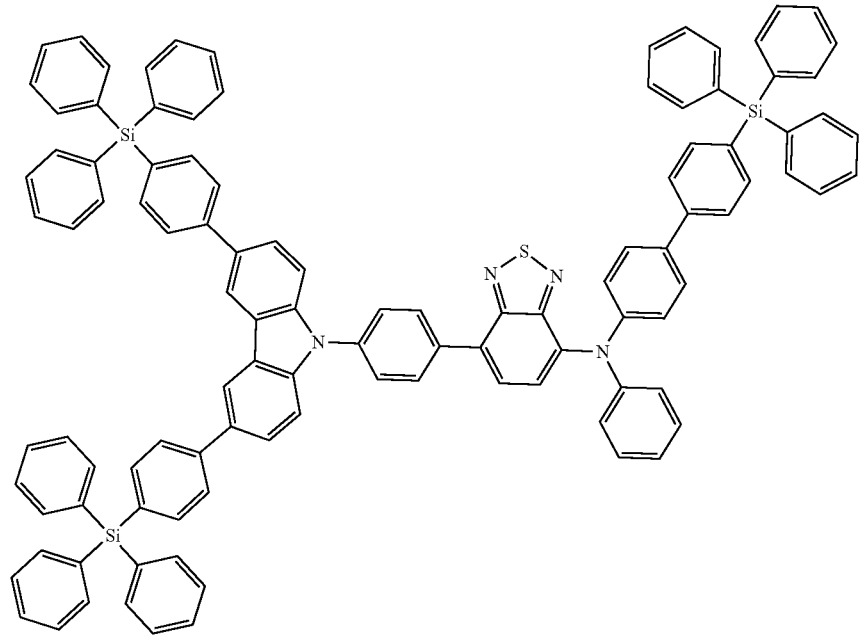
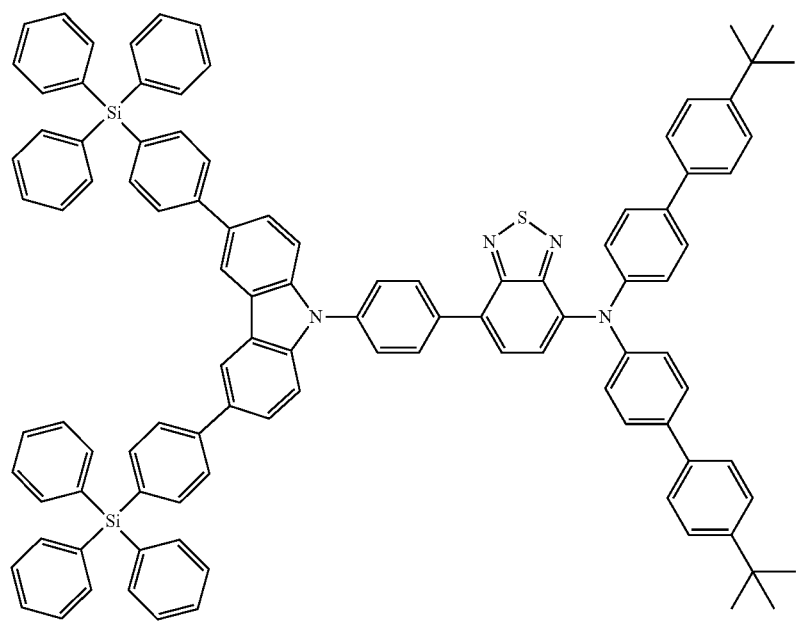

-continued
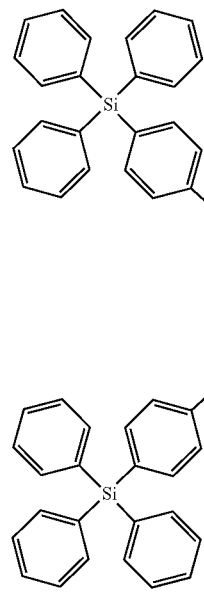
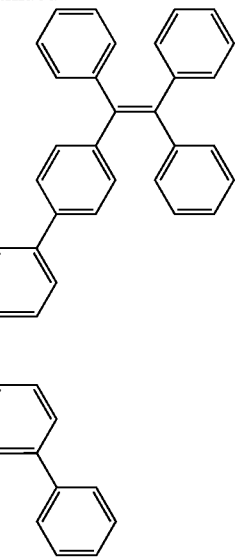
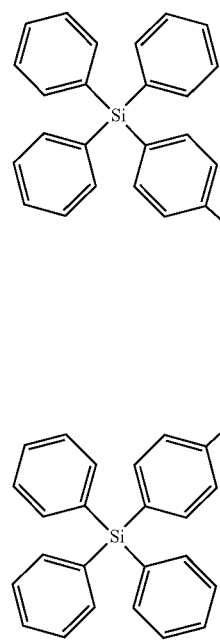
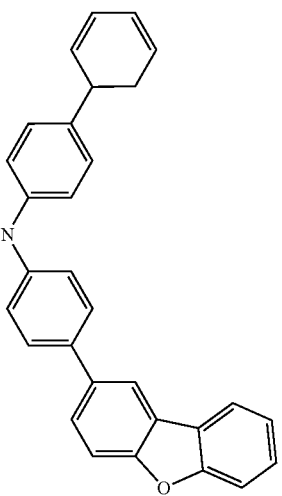

-continued
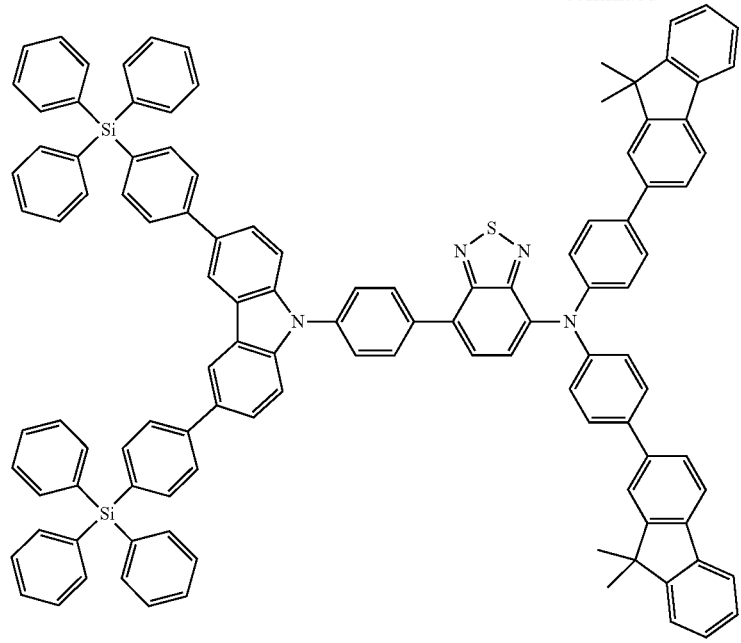
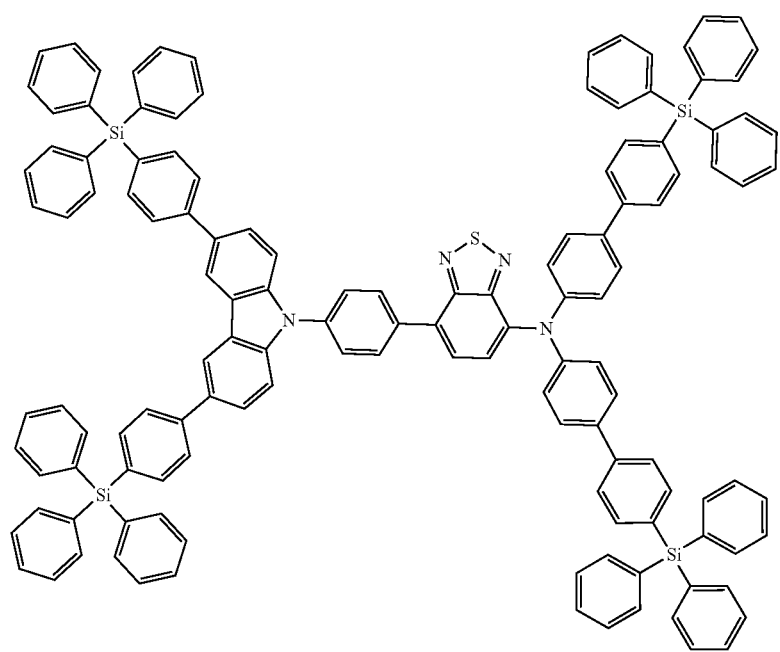

-continued
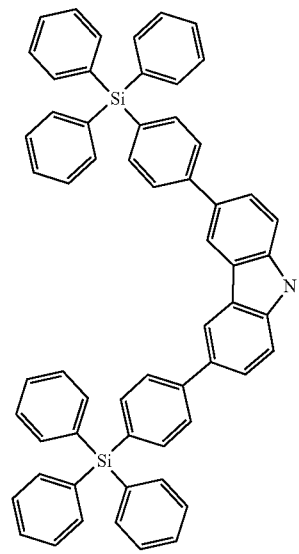 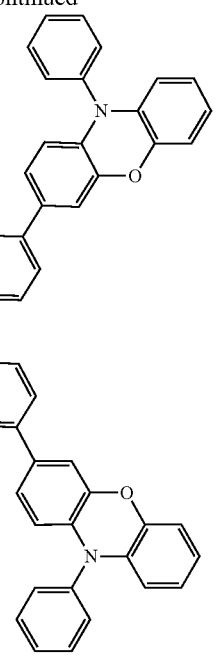
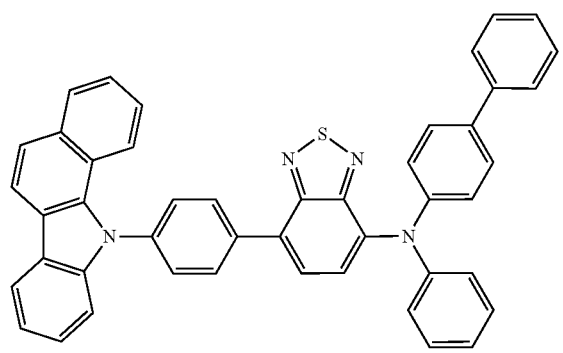 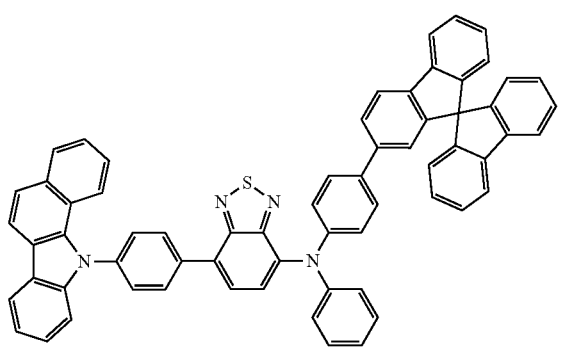
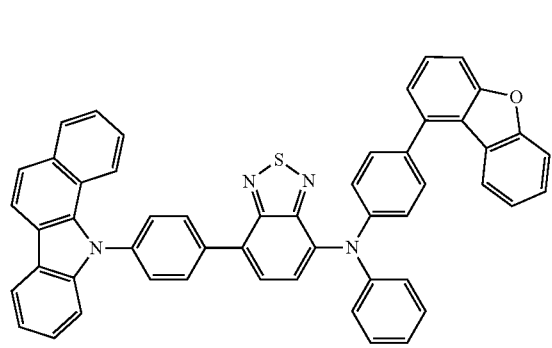 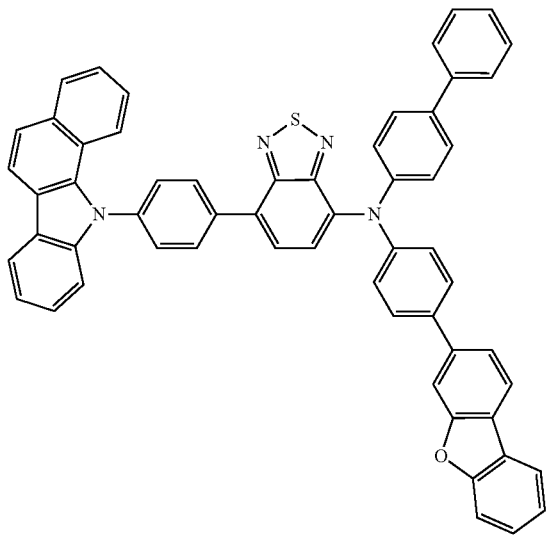

-continued
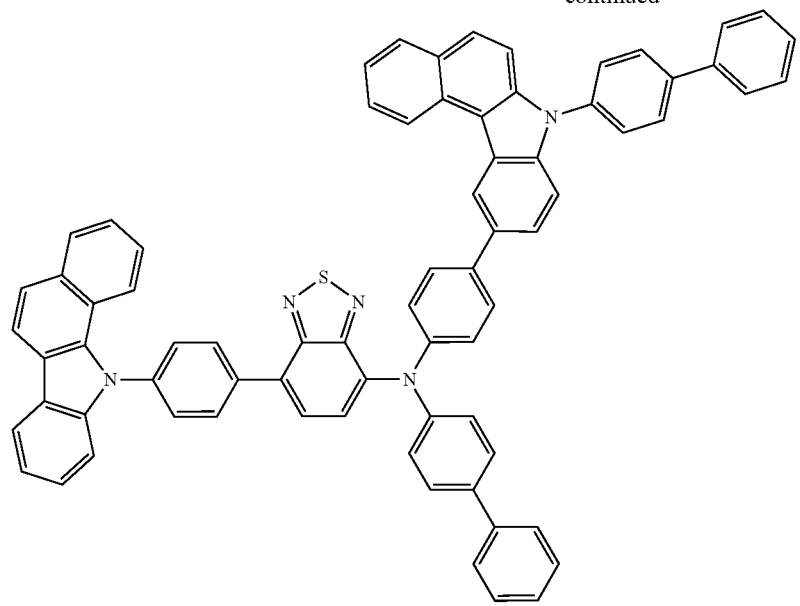
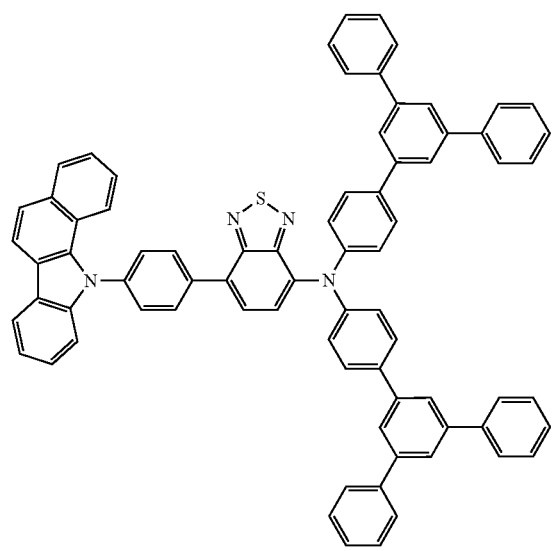
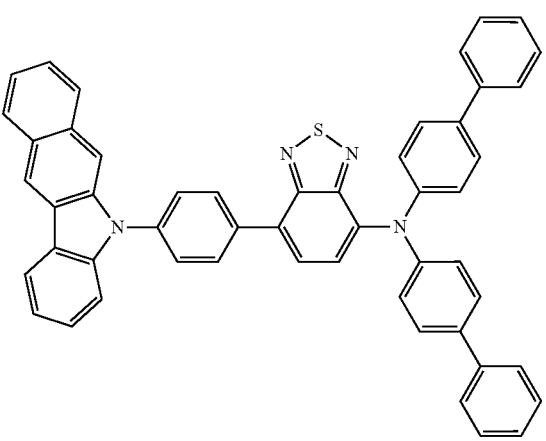
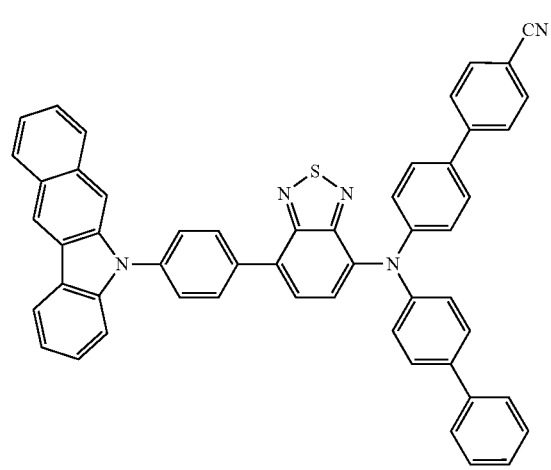

-continued
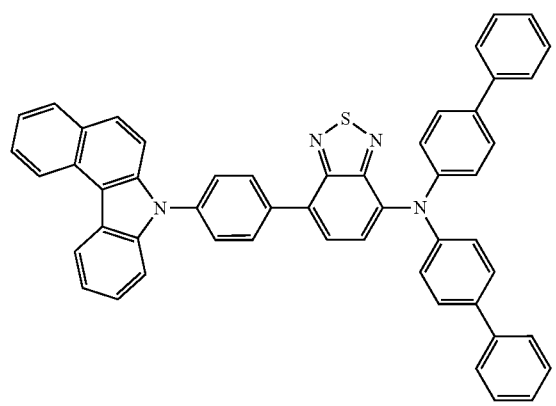
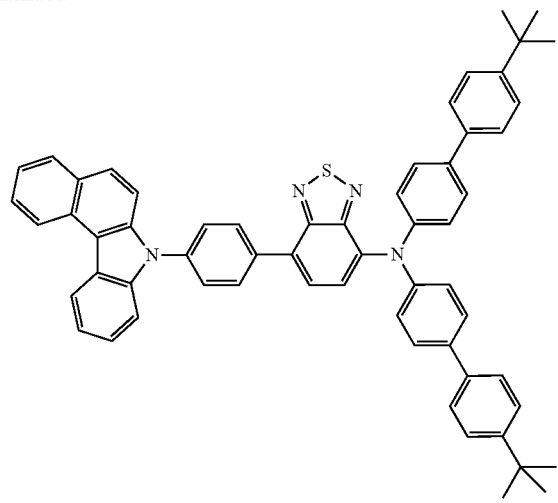
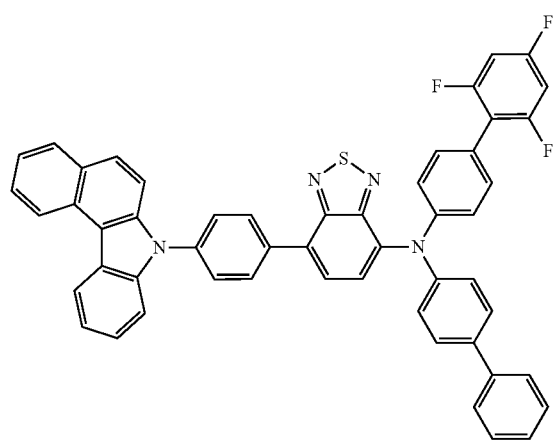
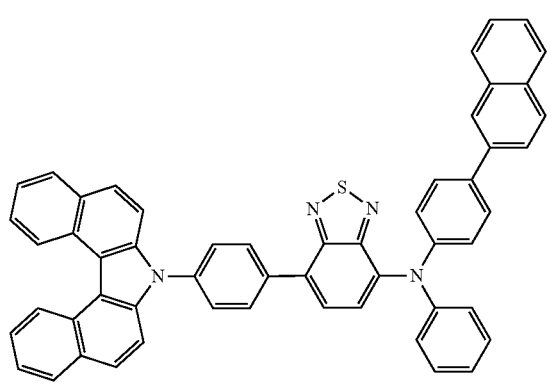
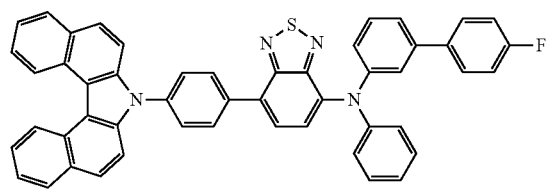
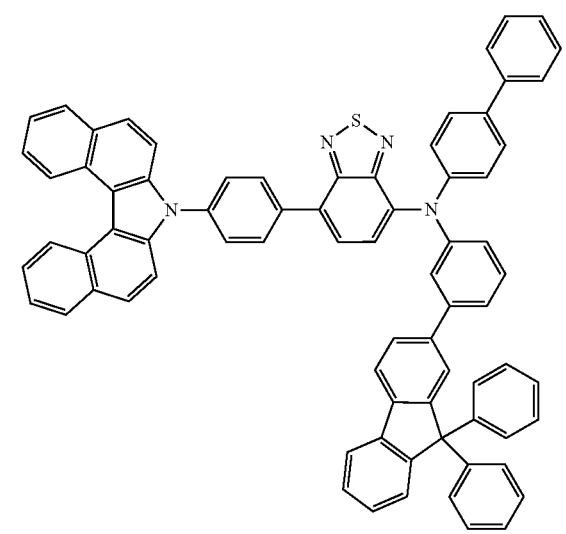

-continued
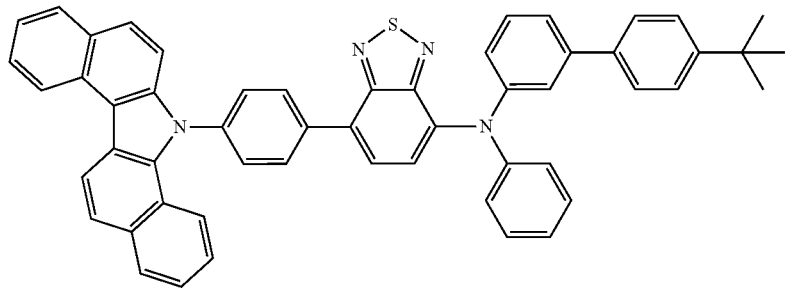
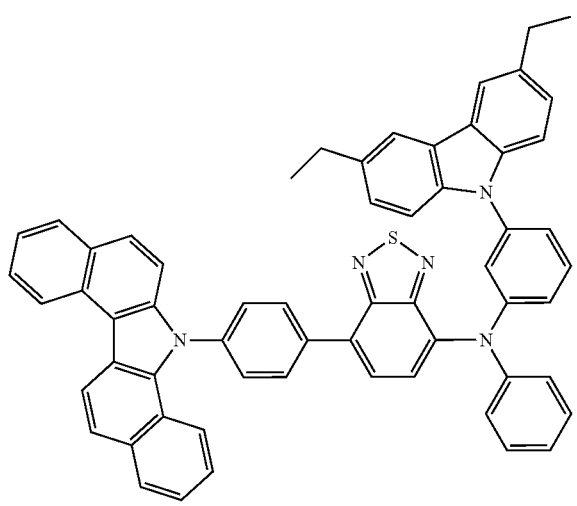
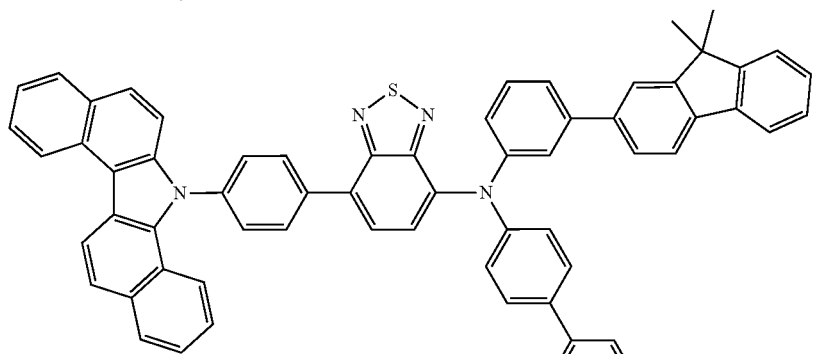
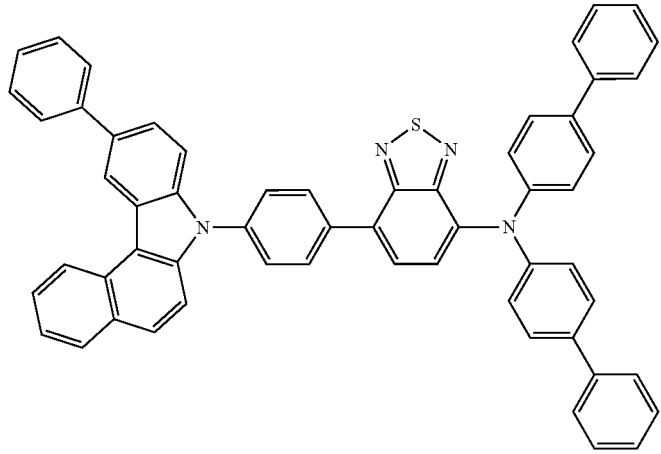

-continued
183
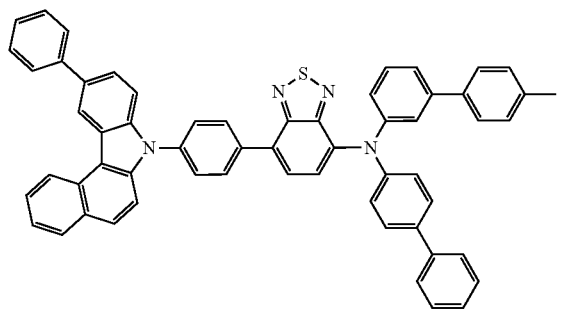
184
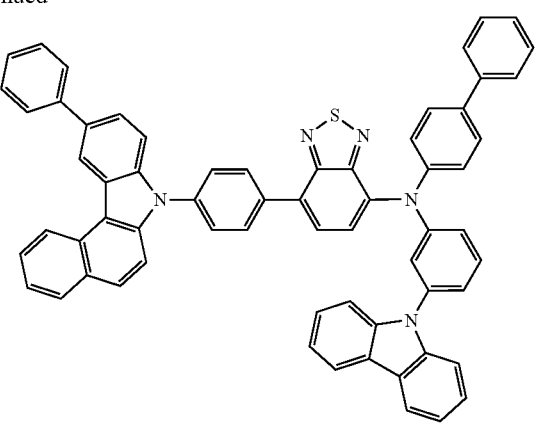
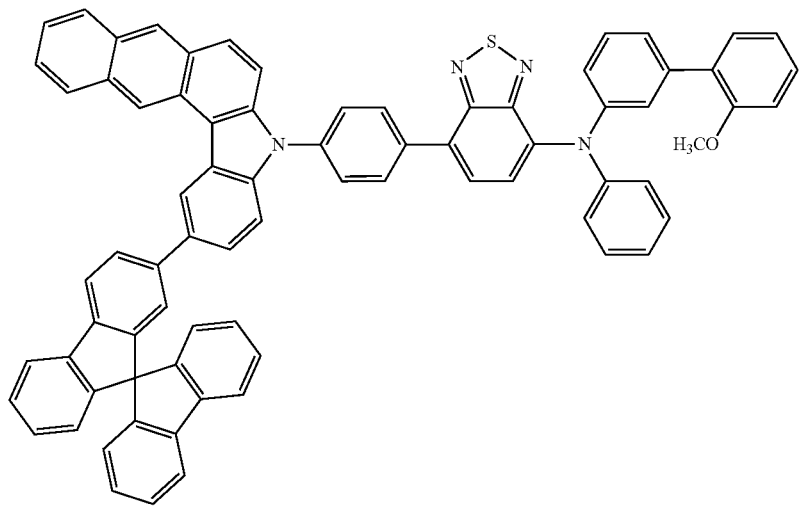
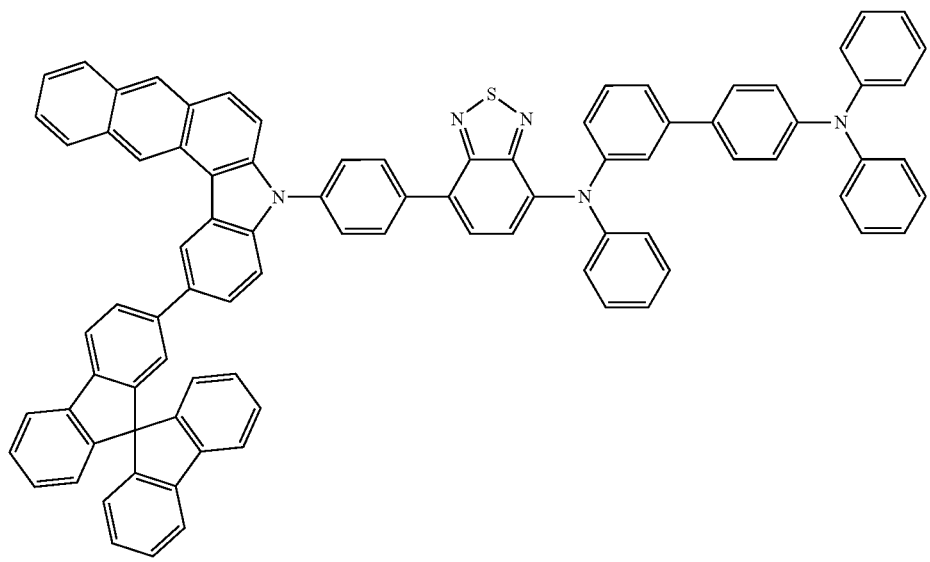

-continued
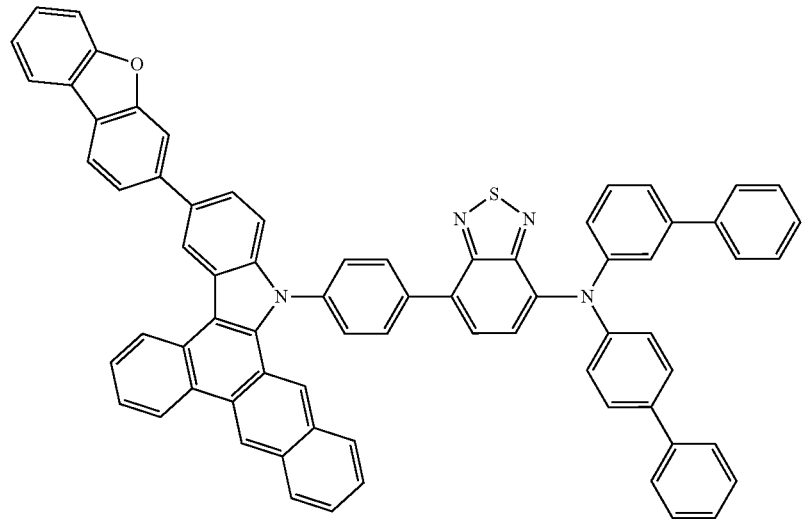
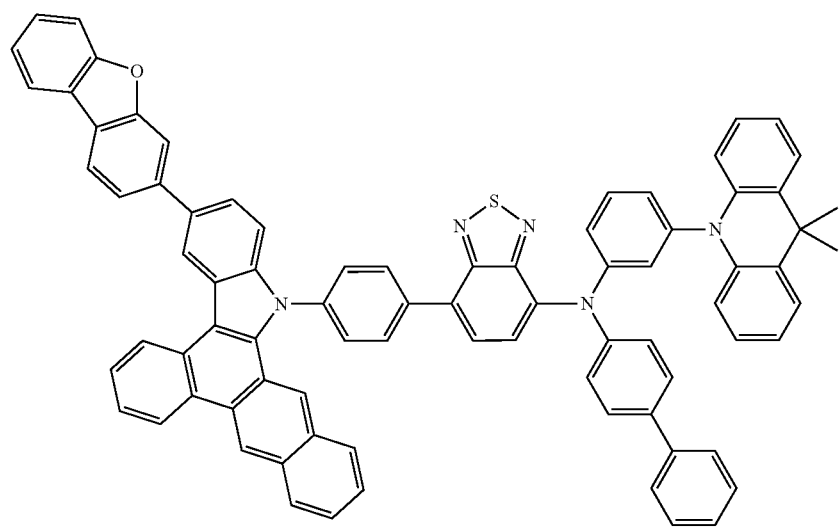
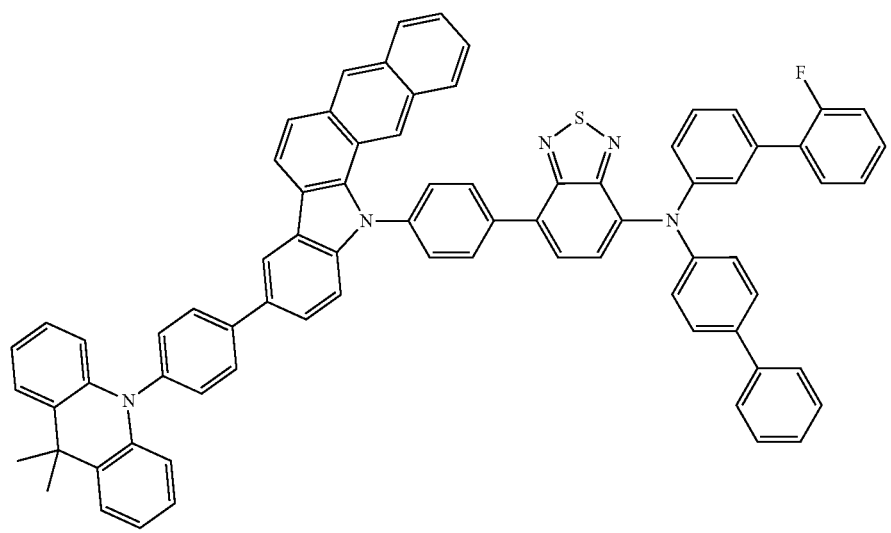

-continued
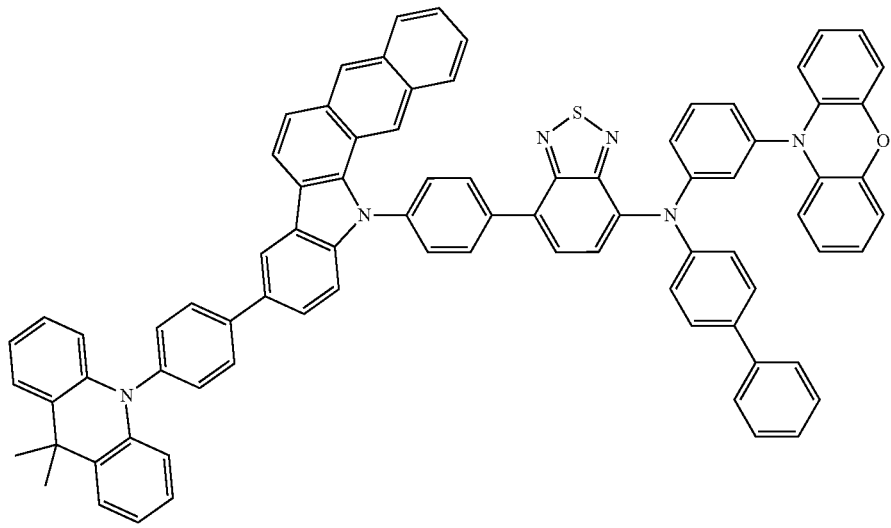
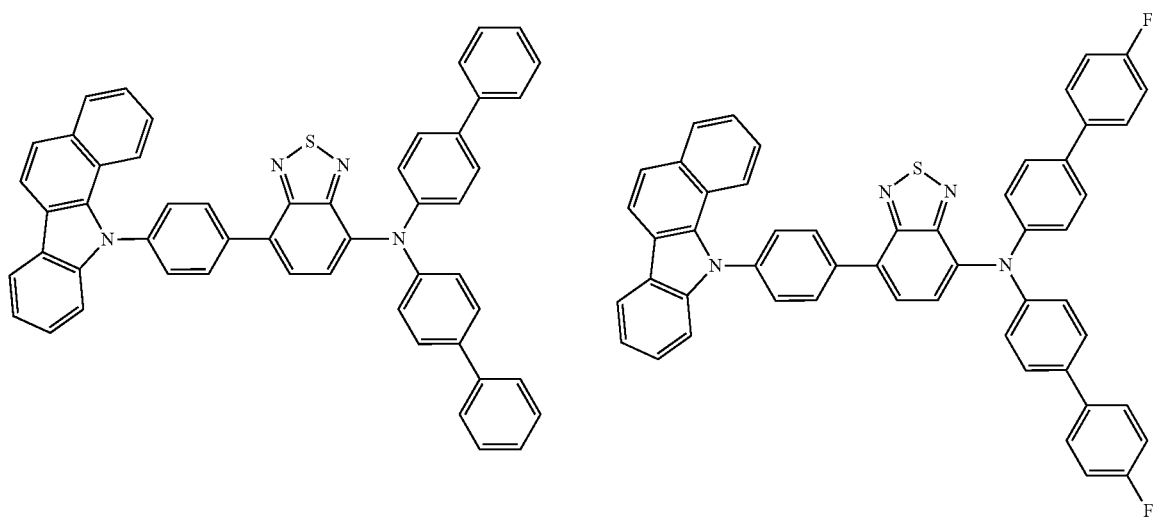
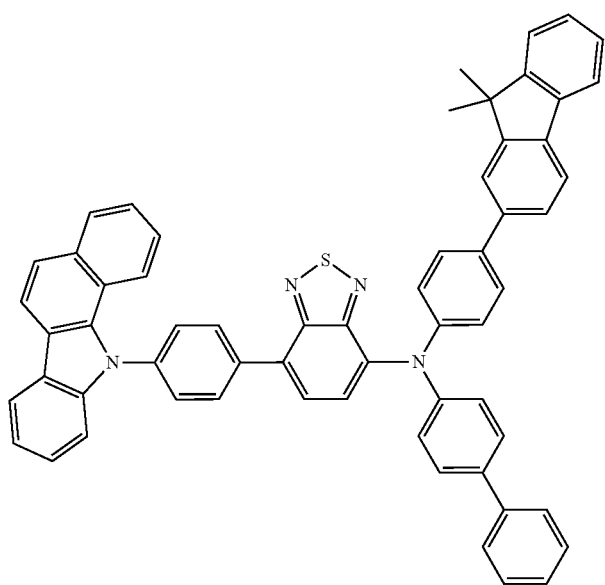

189
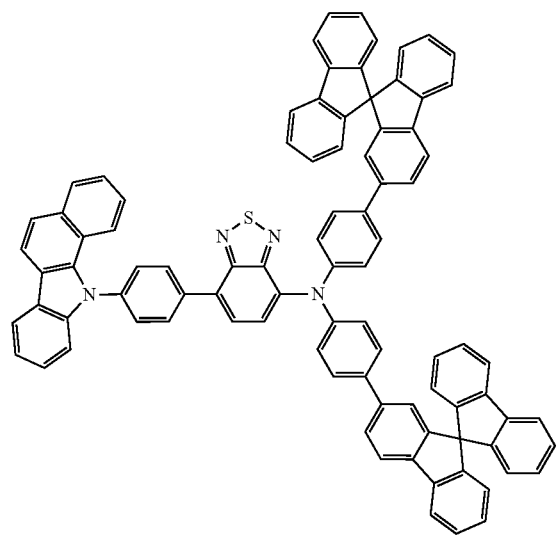
190
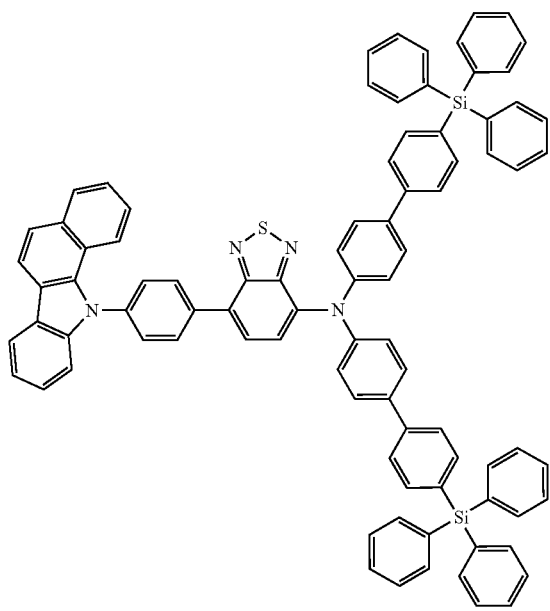
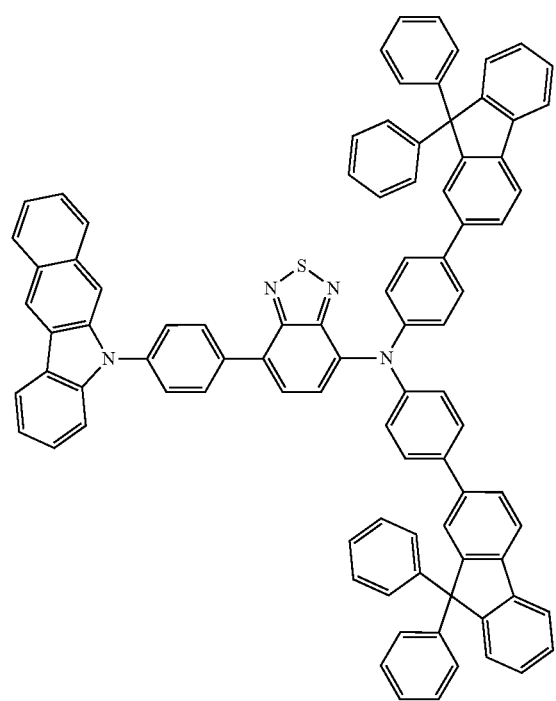
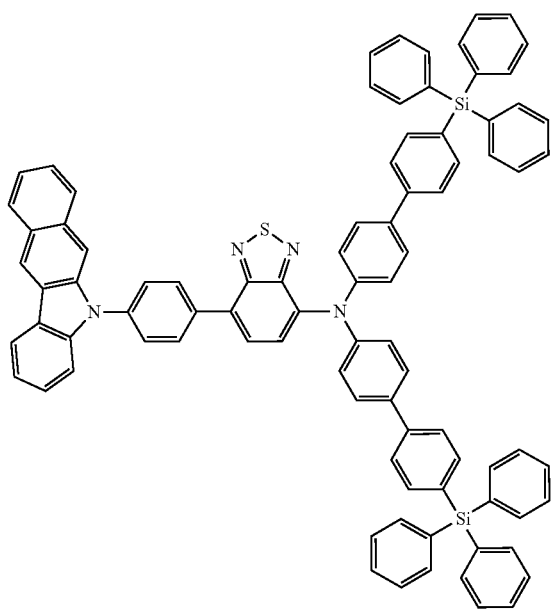

191 192
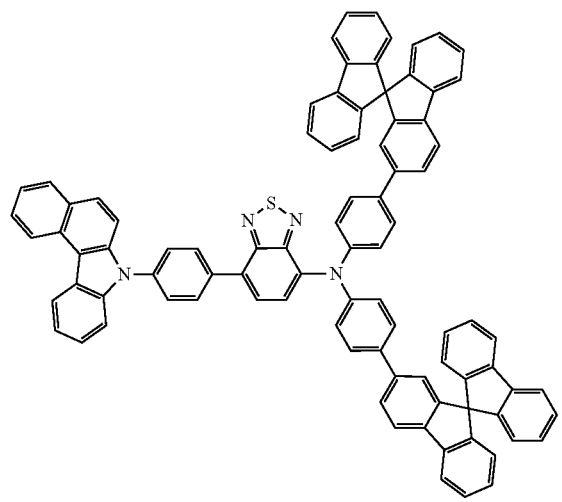 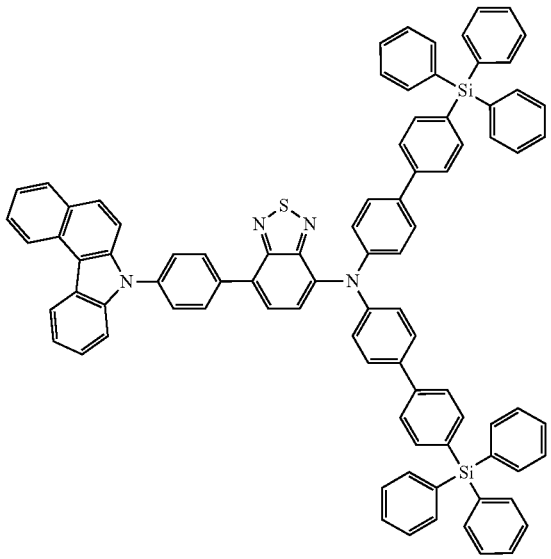
-continued
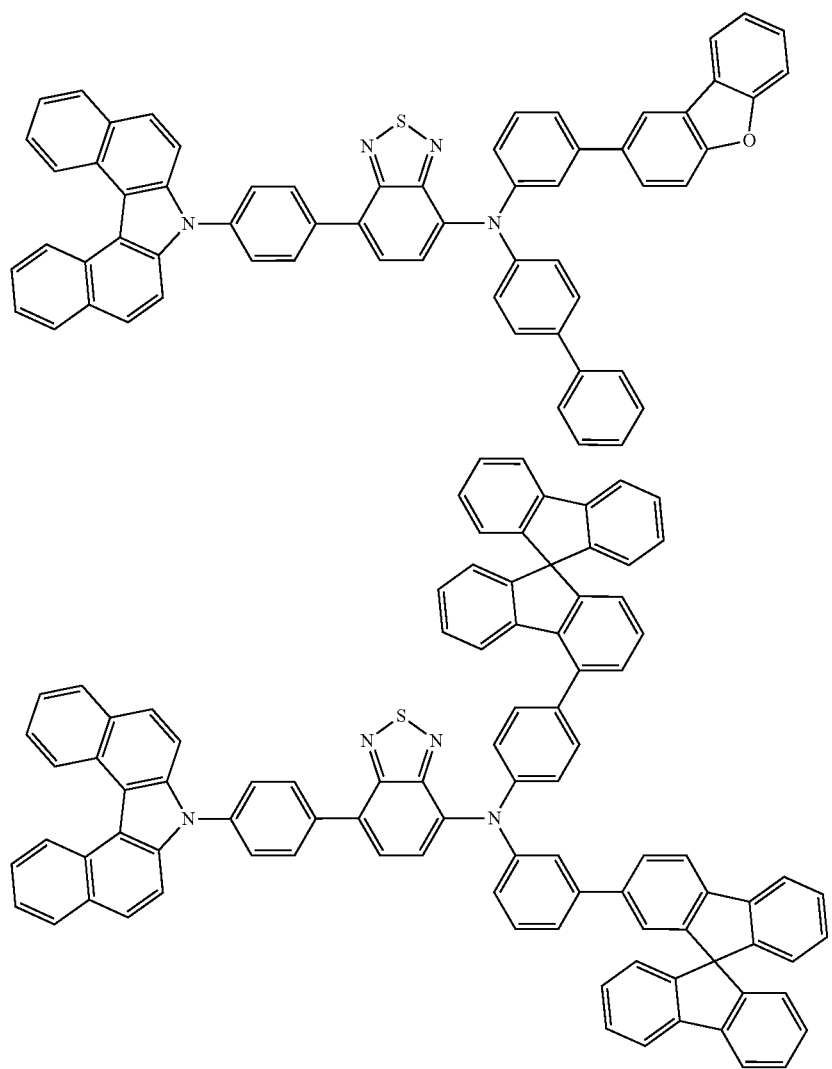

-continued
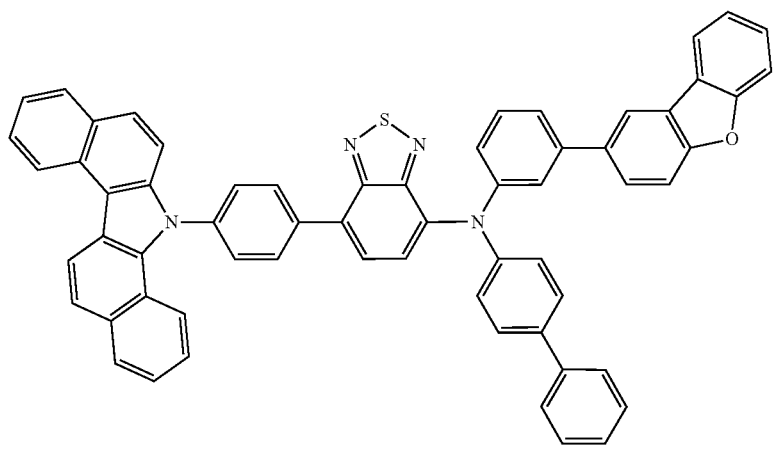
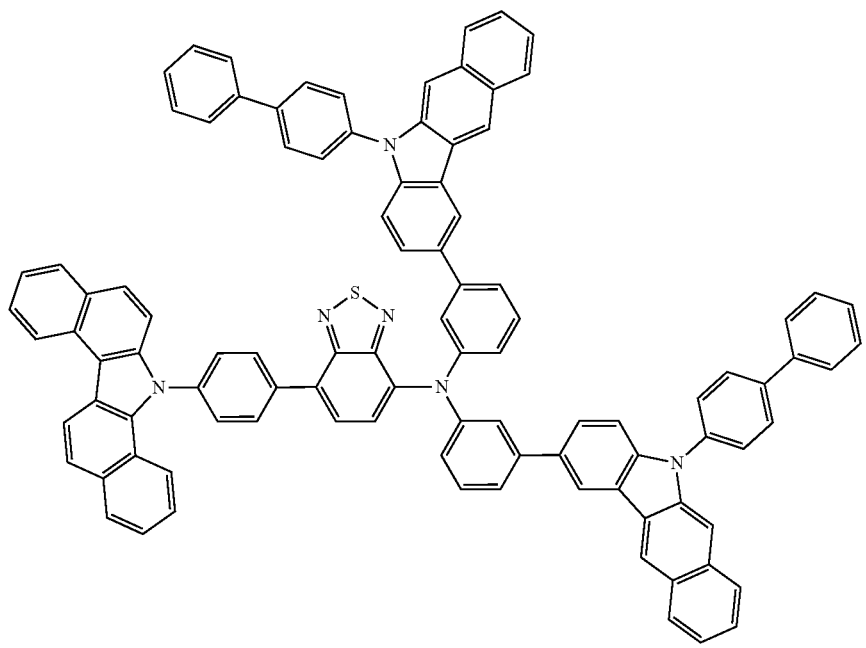
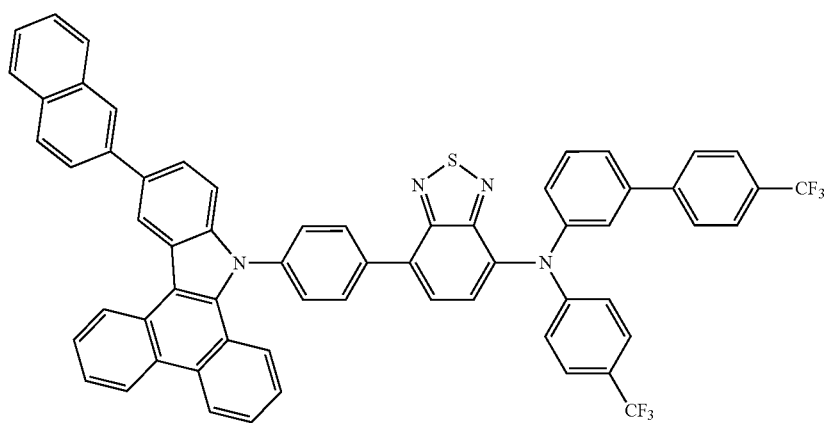

-continued
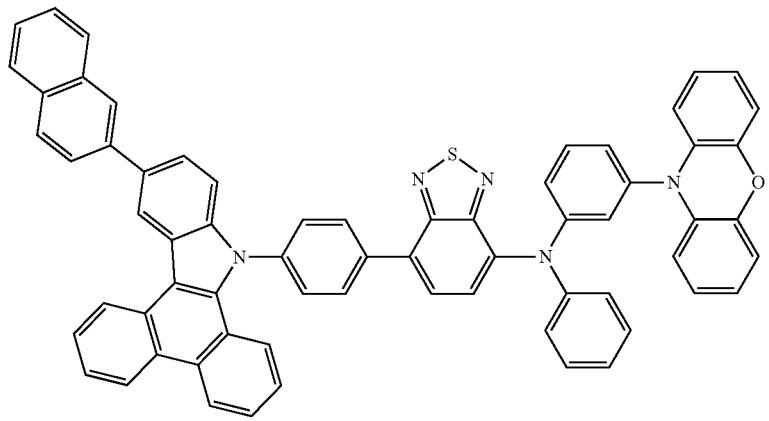
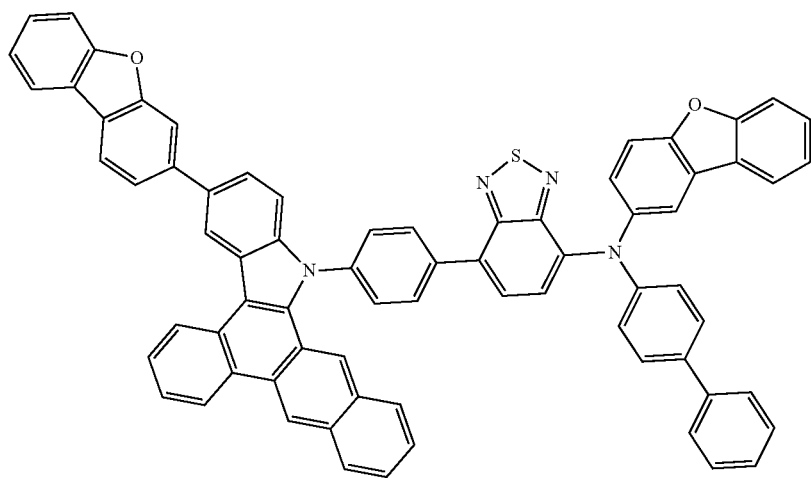
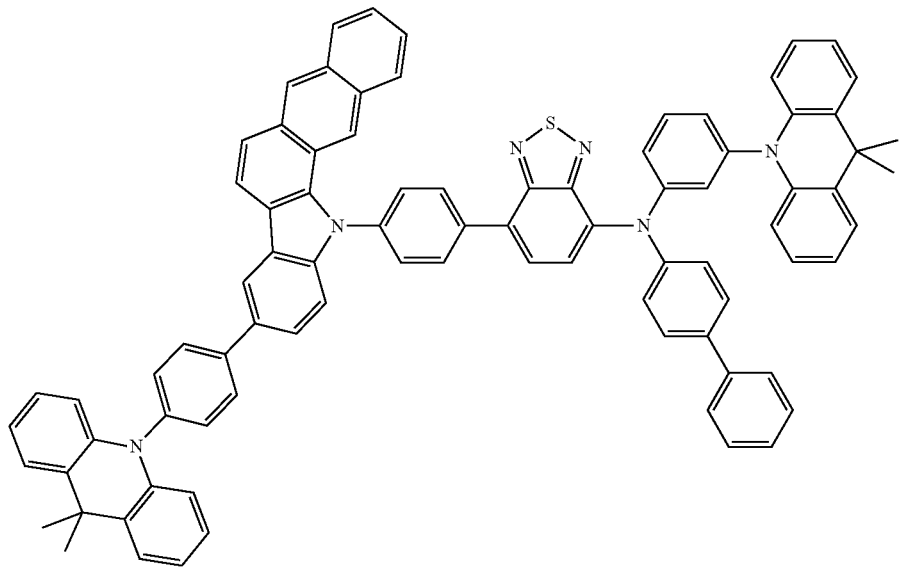 [SMILES: CC1(C)c2ccccc2N(c2ccc(-c3ccc4c(c3)c3ccc5cc6ccccc6cc5c3n4-c3ccc(-c4ccc(N(c5ccc(-c6ccccc6)cc5)c5cccc(N6c7ccccc7C(C)(C)c7ccccc76)c5)c5nsnc45)cc3)cc2)c2ccccc21]

The compound according to an exemplary embodiment of the present specification may be prepared by a preparation method to be described below.

For example, a core structure of the compound of Formula 1 may be prepared as in the following Reaction Formula 1. The substituent may be bonded by a method known in the art, and the kind and position of the substituent or the number of substituents may be changed according to the technology known in the art.

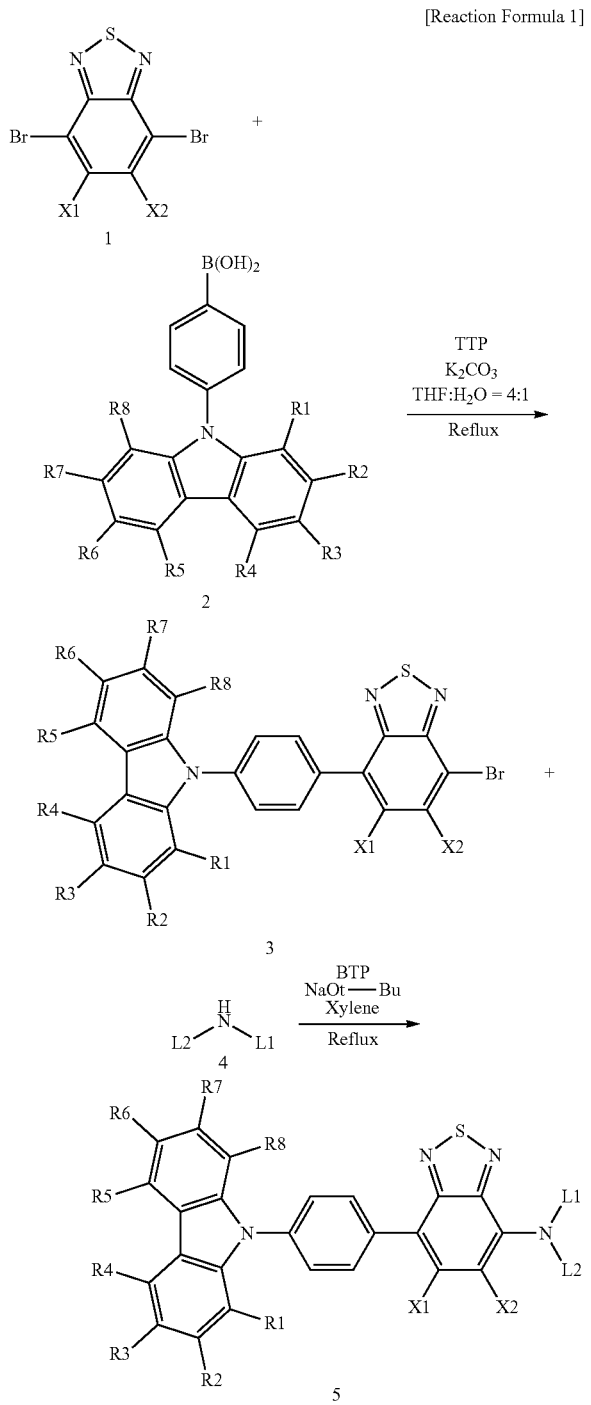

[Reaction Formula 1]

In Reaction Formula 1, definitions of X1, X2, R1 to R8, L1, and L2 are the same as those in Formula 1.

An exemplary embodiment of the present specification provides a color conversion film including: a resin matrix; and the compound represented by Formula 1, which is dispersed in the resin matrix.

The content of the compound represented by Formula 1 in the color conversion film may be within a range of 0.001 to 15 wt %.

The color conversion film may include one or two or more of the compounds represented by Formula 1. For example, the color conversion film may include one compound, which emits green light, among the compounds represented by Formula 1. As another example, the color conversion film may include one compound, which emits red light, among the compounds represented by Formula 1. As still another example, the color conversion film may include one compound, which emits green light, and two or more compounds, which emit red light, among the compounds represented by Formula 1.

The color conversion film may further include an additional fluorescent material in addition to the compound represented by Formula 1. When a light source which emits blue light is used, it is preferred that the color conversion film includes both a fluorescent material which emits green light and a fluorescent material which emits red light. Further, when a light source which emits blue light and green light is used, the color conversion film may include only a fluorescent material which emits red light. However, the color conversion film is not limited thereto, and even when a light source which emits blue light is used, the color conversion film may include only a compound, which emits red light, in the case where a separate film including a fluorescent material which emits green light is stacked. Conversely, even when a light source which emits blue light is used, the color conversion film may include only a compound, which emits green light, in the case where a separate film including a fluorescent material which emits red light is stacked.

The color conversion film may further include: a resin matrix; and an additional layer including a compound which is dispersed in the resin matrix and emits light having a wavelength different from that of the compound represented by Formula 1. The compound which emits light having a wavelength different from that of the compound represented by Formula 1 may also be the compound expressed as Formula 1, and may also be another publicly-known fluorescent material.

It is preferred that a material for the resin matrix is a thermoplastic polymer or a thermosetting polymer. Specifically, as the material for the resin matrix, it is possible to use a poly(meth)acrylic material such as polymethylmethacrylate (PMMA), a polycarbonate (PC)-based material, a polystyrene (PS)-based material, a polyarylene (PAR)-based material, a polyurethane (TPU)-based material, a styrene-acrylonitrile (SAN)-based material, a polyvinylidenefluoride (PVDF)-based material, a modified-polyvinylidenefluoride (modified-PVDF)-based material, and the like.

According to an exemplary embodiment of the present specification, the color conversion film according to the above-described exemplary embodiment additionally includes light diffusion particles. By dispersing light diffusion particles in the color conversion film instead of a light diffusion film used in the related art in order to improve brightness, an attachment process may be omitted, and higher brightness may be exhibited, as compared to the case where a separate light diffusion film is used.

As the light diffusion particle, a particle having a high refractive index thang a resin matrix may be used, and it is possible to use, for example, $TiO_2$, silica, borosilicate, alumina, sapphire, air or another gas, air- or gas-filled hollow beads or particles (for example, air/gas-filled glass or polymer); polymer particles including polystyrene, polycarbonate, polymethylmethacrylate, acryl, methyl methacrylate, styrene, a melamine resin, a formaldehyde resin, or a melamine and formaldehyde resin, or any suitable combination thereof.

The particle diameter of the light diffusion particles may be within a range of 0.1 μm to 5 μm, for example, within a range of 0.3 μm to 1 μm. The content of the light diffusion particles may be determined, if necessary, and may be, for example, within a range of about 1 part by weight to about 30 parts by weight based on 100 parts by weight of the resin matrix.

The color conversion film according to the above-described exemplary embodiment may have a thickness of 0.1 μm to 200 μm. In particular, the color conversion film may exhibit high brightness even in a small thickness of 0.1 μm to 20 μm. This is because the content of the fluorescent material molecules included in a unit volume is higher than that of a quantum dot.

A base material may be provided on one surface of the color conversion film according to the above-described exemplary embodiment. The base material may function as a support when manufacturing the color conversion film. The kind of base material is not particularly limited, and the material or thickness of the base material is not limited as long as the base material is transparent and may function as the support. Here, transparency means that the transmittance in visible light is 70% or more. For example, as the base material, a PET film may be used.

The above-described color conversion film may be prepared by coating a base material with a resin solution, in which the above-described compound represented by Formula 1 is dissolved, and drying the resin solution, or extruding the above-described compound represented by Formula 1 together with the resin to produce a film.

Since the above-described compound represented by Formula 1 is dissolved in the resin solution, the compound represented by Formula 1 is uniformly distributed in the solution. This is different from a process of producing a quantum dot film, which requires a separate dispersing process.

The preparation method of the resin solution in which the compound represented by Formula 1 is dissolved is not particularly limited as long as the above-described compound represented by Formula 1 is in a state where the resin is dissolved in the solution.

According to an example, the resin solution in which the compound represented by Formula 1 is dissolved may be prepared by a method of dissolving the compound represented by Formula 1 in a solvent to prepare a first solution, dissolving a resin in a solvent to prepare a second solution, and mixing the first solution with the second solution. When the first solution and the second solution are mixed, it is preferred to uniformly mix the solutions. However, the method is not limited thereto, and it is possible to use a method of simultaneously adding a compound represented by Formula 1 and a resin to a solvent to dissolve the compound and the resin, a method of dissolving the compound represented by Formula 1 in a solvent, and subsequently adding a resin thereto to dissolve the resin, a method of dissolving a resin in a solvent, and subsequently adding the compound represented by Formula 1 thereto to dissolve the compound, and the like.

As the resin included in the solution, it is possible to use the above-described resin matrix material, a monomer which is curable by the resin matrix material, or a mixture thereof. Examples of the monomer which is curable by the resin matrix material include a (meth)acrylic monomer, and the monomer may be formed of a resin matrix material by UV curing. When a curable monomer is used as described above, an initiator required for curing may be further added, if necessary.

The solvent is not particularly limited, and is not particularly limited as long as the solvent does not adversely affect the coating process and may be removed by a subsequent drying. As the non-limiting example of the solvent, it is possible to use acetone, toluene, chloroform, methyl ethyl ketone, methyl isobutyl ketone, methyl cellosolve, ethyl cellosolve, tetrahydrofuran, 1,4-dioxane, ethylene glycol dimethyl ether, ethylene glycol diethyl ether, propylene glycol dimethyl ether, propylene glycol methyl ether acetate, propylene glycol diethyl ether, diethylene glycol dimethyl ether, diethylene glycol diethyl ether, diethylene glycol methyl ethyl ether, chloroform, methylene chloride, 1,2-dichloroethane, 1,1,1-trichloroethane, 1,1,2-trichloroethane, 1,1,2-trichloroethene, hexane, heptane, octane, cyclohexane, benzene, toluene, xylene, methanol, ethanol, isopropanol, propanol, butanol, t-butanol, 2-ethoxy propanol, 2-methoxy propanol, 3-methoxy butanol, cyclohexanone, cyclopentanone, propylene glycol methyl ether acetate, propylene glycol ethyl ether acetate, 3-methoxybutyl acetate, ethyl 3-ethoxypropionate, ethyl cellosolve acetate, methyl cellosolve acetate, butyl acetate, dipropylene glycol monomethyl ether, and the like, and one or a mixture of two or more may be used. When the first solution and the second solution are used, the solvents included in the respective solutions may also be the same as or different from each other. Even when different solvents are used in the first solution and the second solution, it is preferred that these solvents have compatibility so as to be mixed with each other.

For the process of coating a base material with the resin solution, in which the compound represented by Formula 1 is dissolved, a roll-to-roll process may be used. For example, the roll-to-roll process may be performed by a process of unwinding a base material from a roll on which the base material is wound, coating one surface of the base material with a resin solution, in which the compound represented by Formula 1 is dissolved, drying the resin solution, and then winding the base material again on the roll. When the roll-to-roll process is used, it is preferred that the viscosity of the resin solution is determined within a range in which the process may be implemented, and the viscosity may be determined within a range of, for example, 200 to 2,000 cps.

As the coating method, various publicly-known methods may be used, and for example, a die coater may also be used, and various bar-coating methods such as a comma coater and a reverse comma coater may also be used.

After the coating, a drying process is performed. The drying process may be performed under conditions required for removing the solvent. For example, it is possible to obtain a color conversion film including a fluorescent material including the compound represented by Formula 1, which has a desired thickness and concentration, on a base material by carrying out the drying in an oven located close to a coater under a condition to sufficiently evaporate a solvent, in a direction in which the base material progresses during the coating process.

When the monomer which is curable by the resin matrix material is used as a resin included in the solution, curing, for example, UV curing may be performed before the drying or simultaneously with the drying.

When the compound represented by Formula 1 is extruded with a resin to produce a film, an extrusion method known in the art may be used, and for example, a color conversion film may be prepared by extruding the compound represented by Formula 1 with a resin such as a polycarbonate (PC)-based resin, a poly(meth)acrylic resin, and a styrene-acrylonitrile (SAN)-based resin.

According to an exemplary embodiment of the present specification, a protective film or a barrier film may be provided on at least one surface of the color conversion film. As the protective film and the barrier film, films known in the art may be used.

Another exemplary embodiment of the present specification provides a backlight unit including the above-described color conversion film. The backlight unit may have a backlight unit configuration known in the art, except that the backlight unit includes the color conversion film. For example, FIG. 1 illustrates an example thereof. According to FIG. 1, the color conversion film according to the above-described exemplary embodiments is provided on a surface opposite to a surface of a light guide plate facing a reflective plate. FIG. 1 exemplifies a configuration including a light source and a reflective plate surrounding the light source, but the configuration is not limited to such a structure, and may be modified depending on the structure of the backlight unit known in the art. Further, as a light source, a direct type as well as a side chain type may be used, and a reflective plate or a reflective layer may be omitted or replaced with other configurations, if necessary, and an additional film, for example, a light diffusion film, a light collecting film, a brightness enhancement film, and the like may be further provided, if necessary. Preferably, a light collecting film and a brightness enhancement film are further provided on a color conversion film.

In the configuration of the backlight unit illustrated in FIG. 1, a scattering pattern may be provided on an upper or lower surface of the light guide plate, if necessary. Light incident into the light guide plate has a non-uniform light distribution caused by repeated optical processes such as reflection, total reflection, refraction, and transmission, and the scattering pattern may be used for inducing the non-uniform light distribution to uniform luminance.

According to still another exemplary embodiment of the present application, a display device including the above-described backlight unit is applied. The display device is not particularly limited as long as the device includes the above-described backlight unit as a constituent element. For example, the display device includes a display module and a backlight unit. FIG. 2 illustrates a structure of a display device. However, the structure is not limited thereto, and an additional film, for example, a light diffusion film, a light collecting film, a brightness enhancement film, and the like may be further provided between the display module and the backlight unit, if necessary.

Hereinafter, the present specification will be described in detail with reference to Examples for specifically describing the present specification. However, the Examples according to the present specification may be modified in various forms, and it is not interpreted that the scope of the present application is limited to the Examples described in detail below. The Examples of the present application are provided for more completely explaining the present specification to the person with ordinary skill in the art.

PREPARATION EXAMPLES

The compound according to an exemplary embodiment of the present specification may be prepared by a preparation method to be described below.

For example, the core structure of the compound having the structure of Formula 1 may be prepared by the following Reaction Formula 1. The substituent may be bonded by a method known in the art, and the kind and position of the substituent or the number of substituents may be changed according to the technology known in the art.

[Reaction Formula 1]

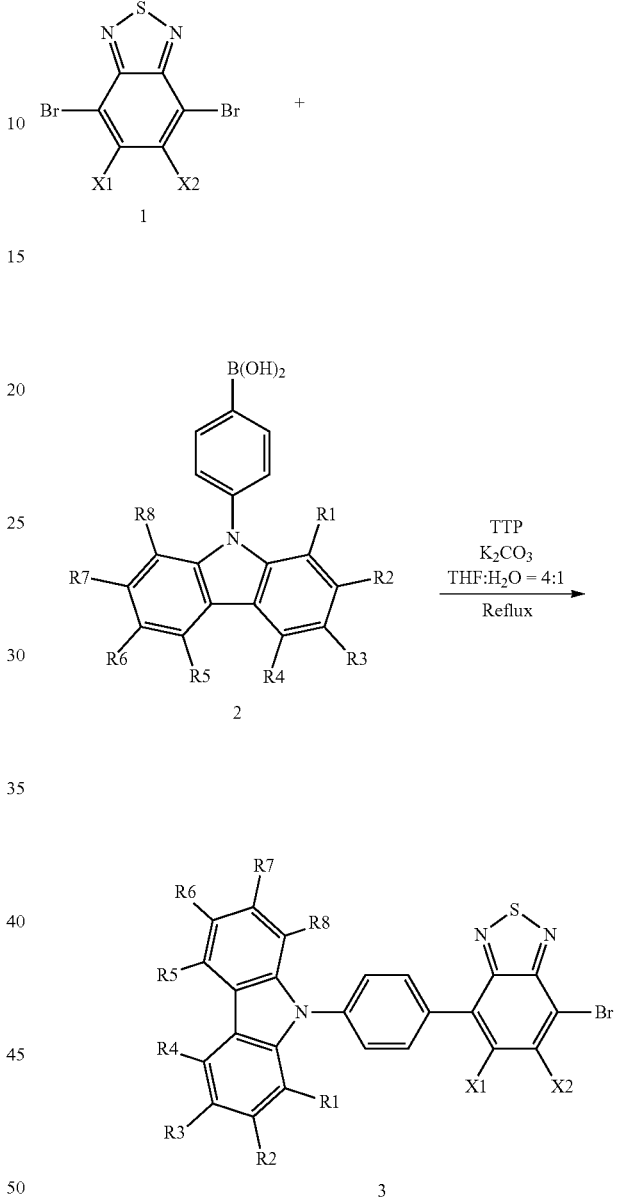

After 1 equivalent of Monomer 1 and 0.9 equivalent of Monomer 2 were dissolved in a tetrahydrofuran solvent in a reaction vessel, 2 equivalents of potassium carbonate were dissolved in water and the resulting solution was introduced thereto. After the temperature was stabilized by heating and stirring the resulting solution at 80° C. under nitrogen, the reaction was performed by adding 0.03 equivalent of a catalyst Pd(PPh$_3$)$_4$ thereto. When the reaction was completed, extraction was performed by using chloroform and water, and then water was removed from a separated organic layer by using anhydrous magnesium sulfate. After the organic layer from which water had been removed was concentrated through distillation under reduced pressure, Monomer 3 was secured through filtration under reduced pressure by using ethanol to secure crystals.

Preparation Example 1. Synthesis of Compound A1

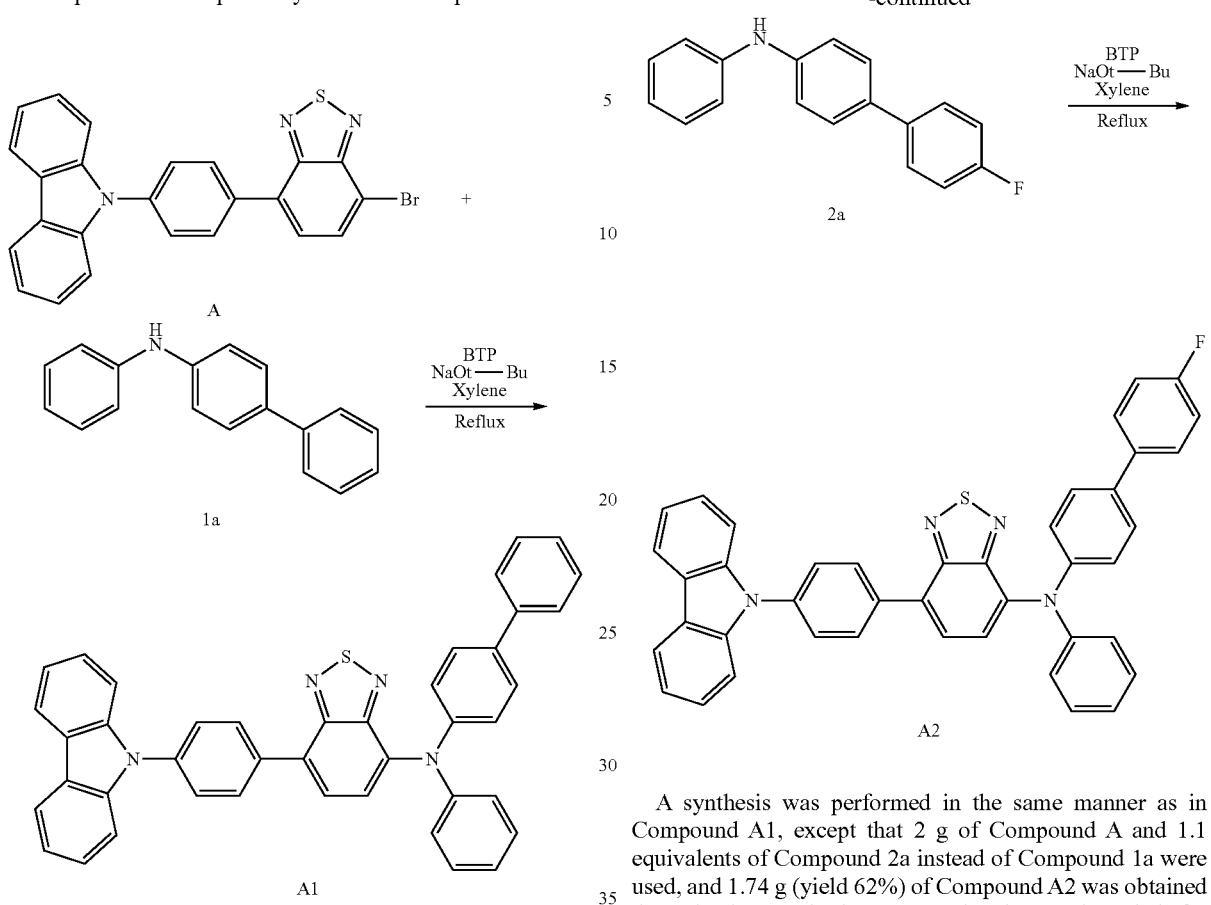

After 2 g of Compound A, 1.1 equivalents of Compound 1a, and 2 equivalents of sodium butoxide were diluted in 30 mL of xylene, the diluted mixture was heated and stirred at 90° C. under nitrogen. After the heating temperature was stabilized, the reaction was performed by adding 0.01 equivalent of a catalyst Pd[P(t-Bu)$_3$]$_2$ thereto. After the reaction was completed, extraction was performed by using water and chloroform, moisture was removed from the extracted organic layer by using anhydrous magnesium sulfate, and then the solvent was concentrated through distillation under reduced pressure. The concentrated product was recrystallized by using chloroform and ethanol, thereby obtaining 2.34 g (yield 86%) of Compound A1. HR LC/MS/MS m/z calcd for $C_{42}H_{28}N_4S$ (M+): 620.2035; found: 620.2034.

Preparation Example 2. Synthesis of Compound A2

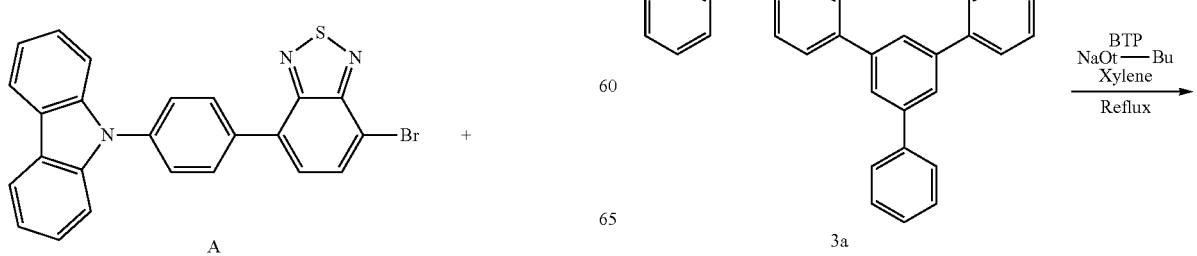

A synthesis was performed in the same manner as in Compound A1, except that 2 g of Compound A and 1.1 equivalents of Compound 2a instead of Compound 1a were used, and 1.74 g (yield 62%) of Compound A2 was obtained through the synthesis. HR LC/MS/MS m/z calcd for $C_{42}H_{27}FN_4S$ (M+): 638.1940; found: 638.1938.

Preparation Example 3. Synthesis of Compound A3

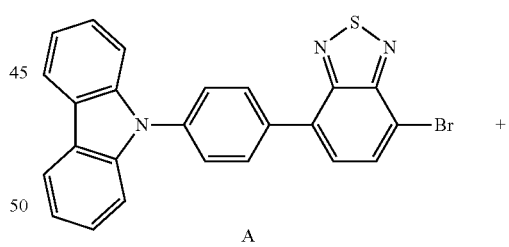

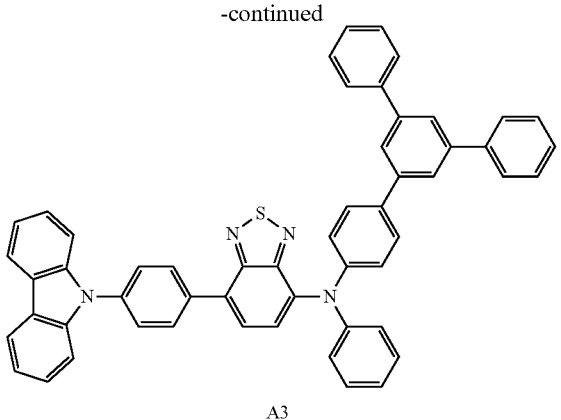

A3

A synthesis was performed in the same manner as in Compound A1, except that 3 g of Compound A and 1.1 equivalents of Compound 3a instead of Compound 1a were used, and 3.91 g (yield 77%) of Compound A3 was obtained through the synthesis. HR LC/MS/MS m/z calcd for $C_{54}H_{36}N_4S$ (M+): 772.2661; found: 772.2660.

Preparation Example 4. Synthesis of Compound A4

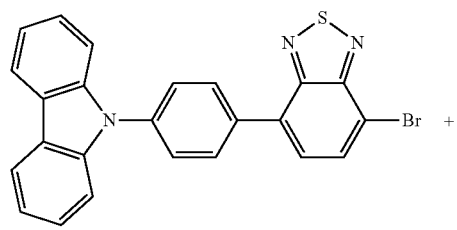

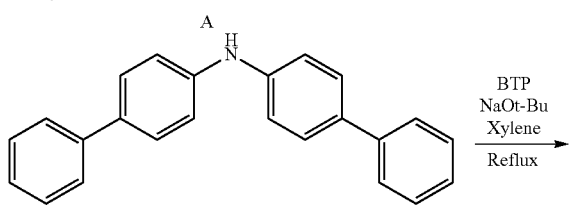

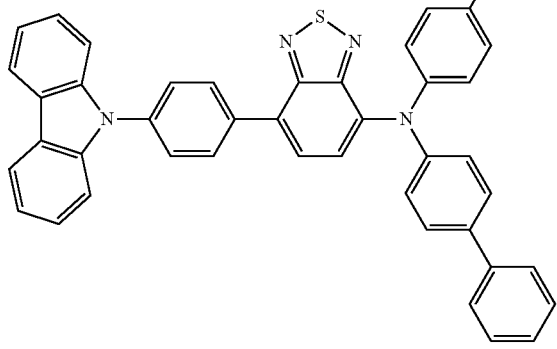

A4

A synthesis was performed in the same manner as in Compound A1, except that 3 g of Compound A and 1.1 equivalents of Compound 4a instead of Compound 1a were used, and 3.30 g (yield 72%) of Compound A4 was obtained through the synthesis. HR LC/MS/MS m/z calcd for $C_{48}H_{32}N_4S$ (M+): 696.2348; found: 696.2348.

Preparation Example 5. Synthesis of Compound A5

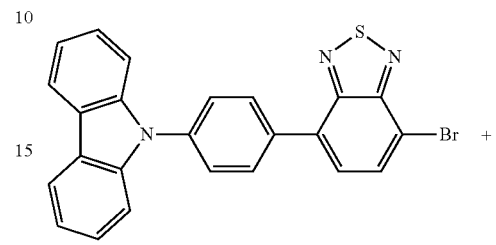

A

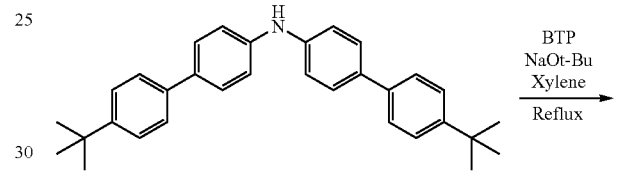

5a

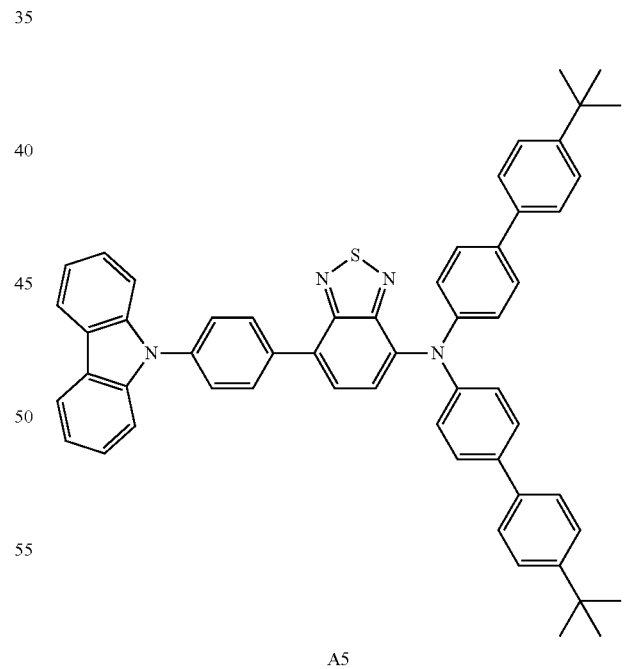

A5

A synthesis was performed in the same manner as in Compound A1, except that 3 g of Compound A and 1.1 equivalents of Compound 5a instead of Compound 1a were used, and 4.47 g (yield 84%) of Compound A5 was obtained through the synthesis. HR LC/MS/MS m/z calcd for $C_{56}H_{48}N_4S$ (M+): 808.3600; found: 808.3601.

Preparation Example 6. Synthesis of Compound A6
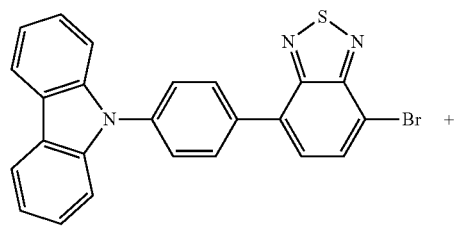
A
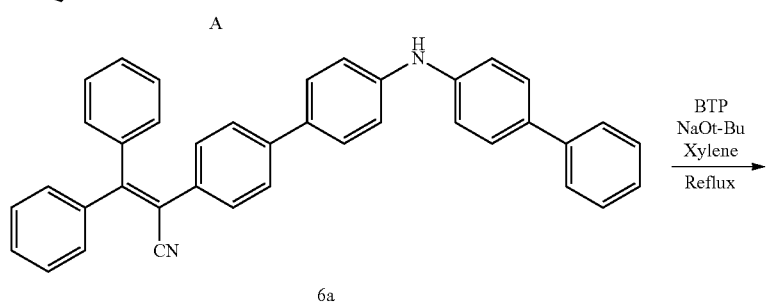
6a
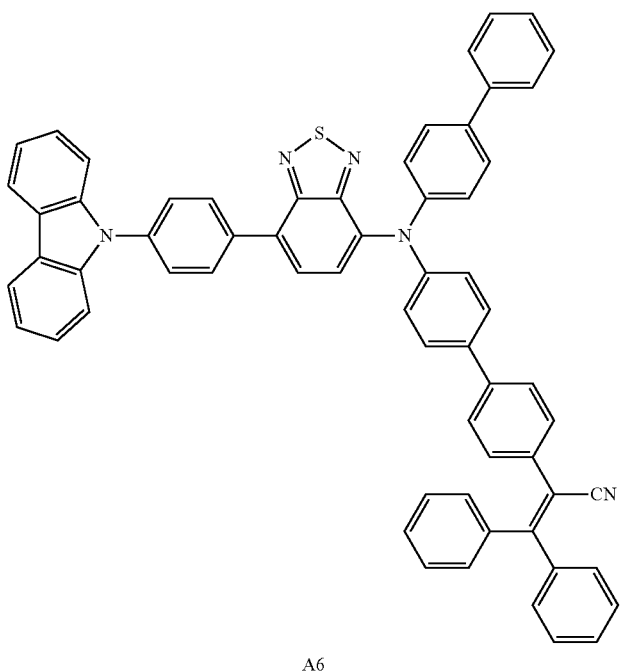
A6
A synthesis was performed in the same manner as in Compound A1, except that 3 g of Compound A and 1.1 equivalents of Compound 6a instead of Compound 1a were used, and 3.20 g (yield 54%) of Compound A6 was obtained through the synthesis. HR LC/MS/MS m/z calcd for $C_{63}H_{41}N_4S$ (M+): 899.3083; found: 899.3084.
Preparation Example 7. Synthesis of Compound A7
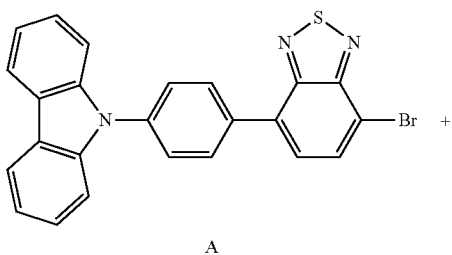
A -continued
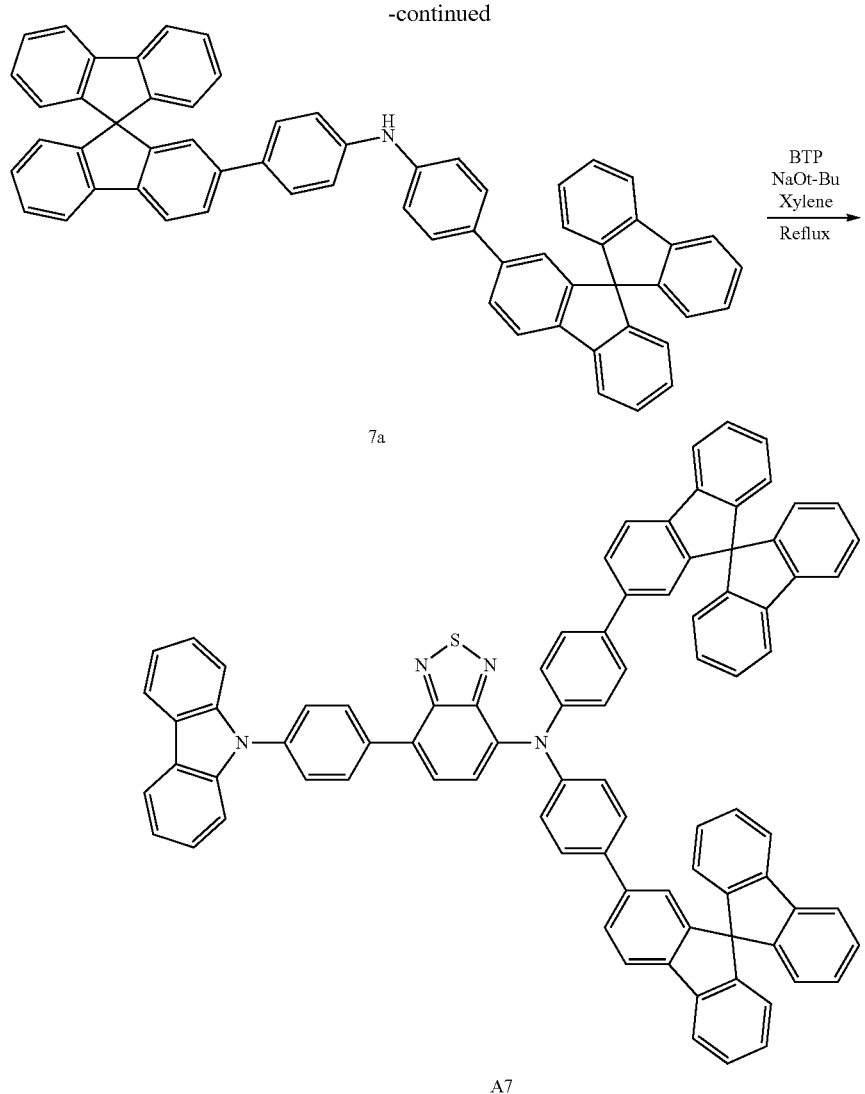
A synthesis was performed in the same manner as in Compound A1, except that 1 g of Compound A and 1.1 equivalents of Compound 7a instead of Compound 1a were used, and 1.83 g (yield 71%) of Compound A7 was obtained through the synthesis. HR LC/MS/MS m/z calcd for $C_{86}H_{52}N_4S$ (M+): 1172.3913; found: 1172.3912.
Preparation Example 8. Synthesis of Compound B1
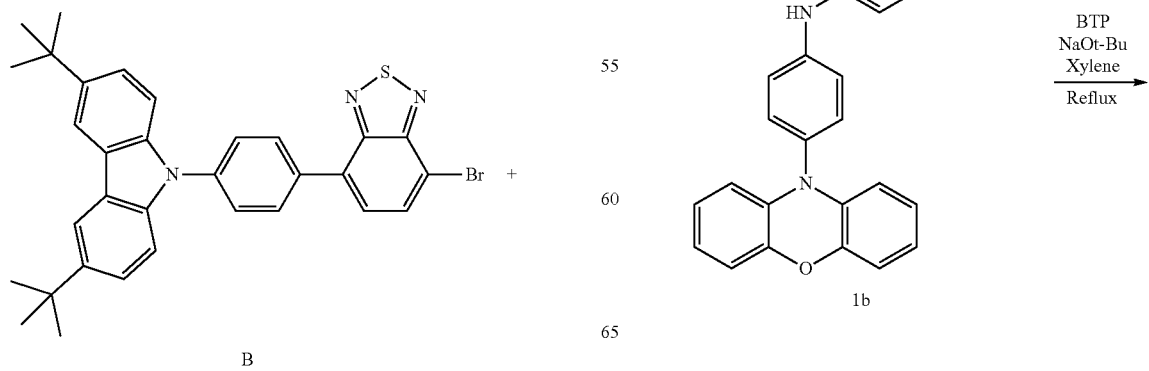

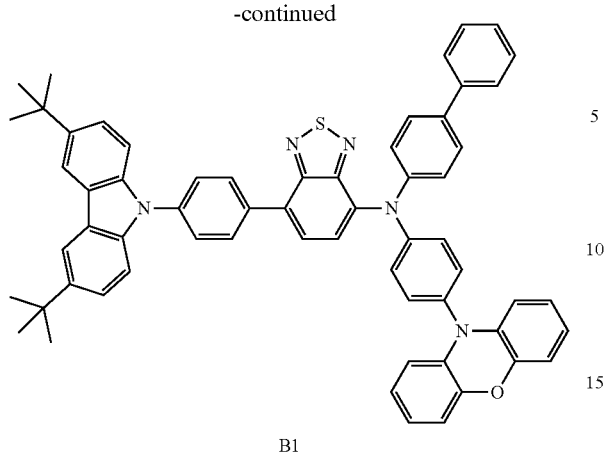

B1

A synthesis was performed in the same manner as in Compound A1, except that 2 g of Compound B and 1.1 equivalents of Compound 1b were used instead of Compound A and Compound 1a, respectively, and 1.74 g (yield 54%) of Compound B1 was obtained through the synthesis. HR LC/MS/MS m/z calcd for $C_{62}H_{51}N_5OS$ (M+): 913.3814; found: 913.3812.

Preparation Example 9. Synthesis of Compound B2

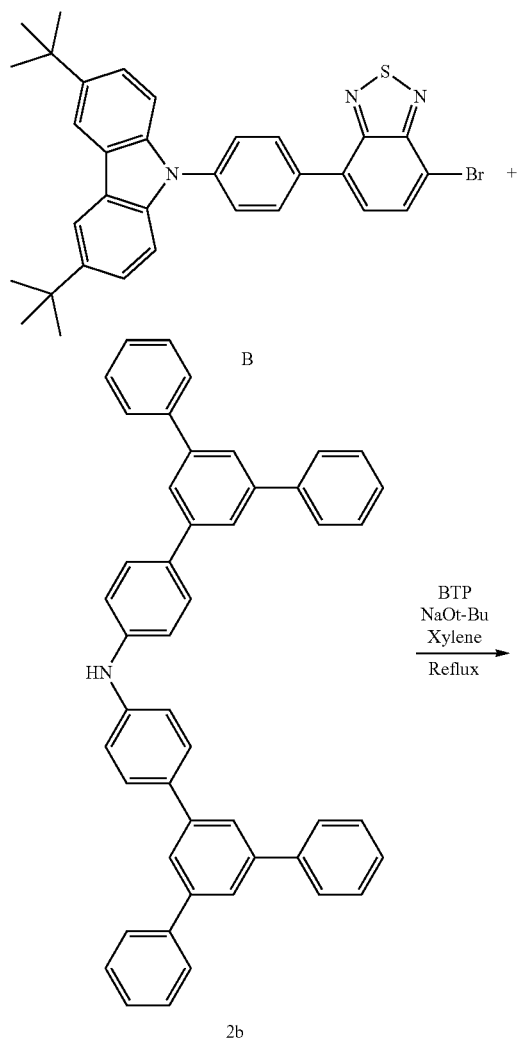

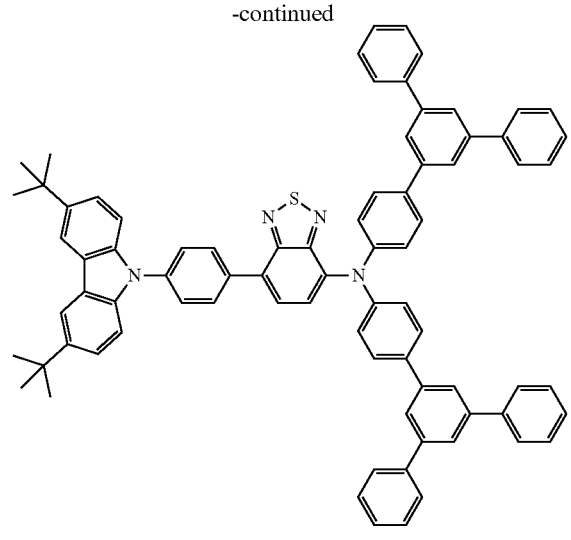

B2

A synthesis was performed in the same manner as in Compound A1, except that 2 g of Compound B and 1.1 equivalents of Compound 2b were used instead of Compound A and Compound 1a, respectively, and 2.66 g (yield 68%) of Compound B2 was obtained through the synthesis. HR LC/MS/MS m/z calcd for $C_{80}H_{64}N_4S$ (M+): 1112.4852; found: 1112.4853.

Preparation Example 10. Synthesis of Compound C1

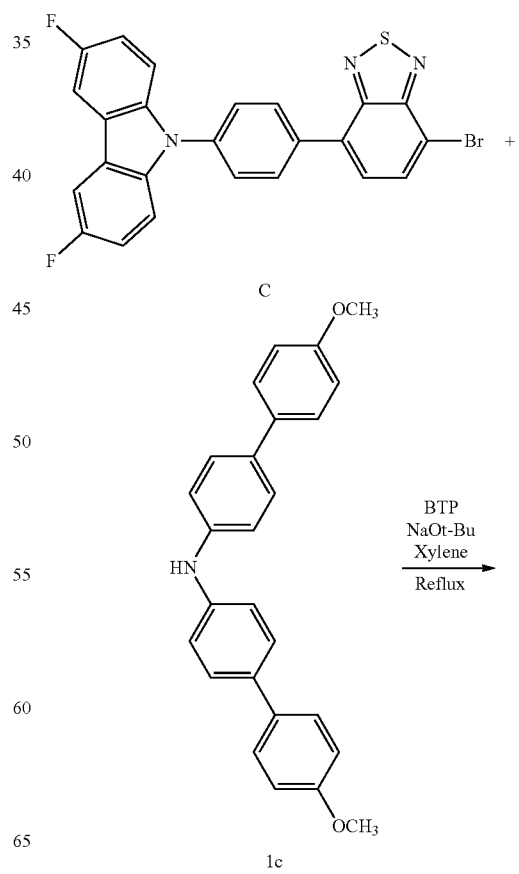

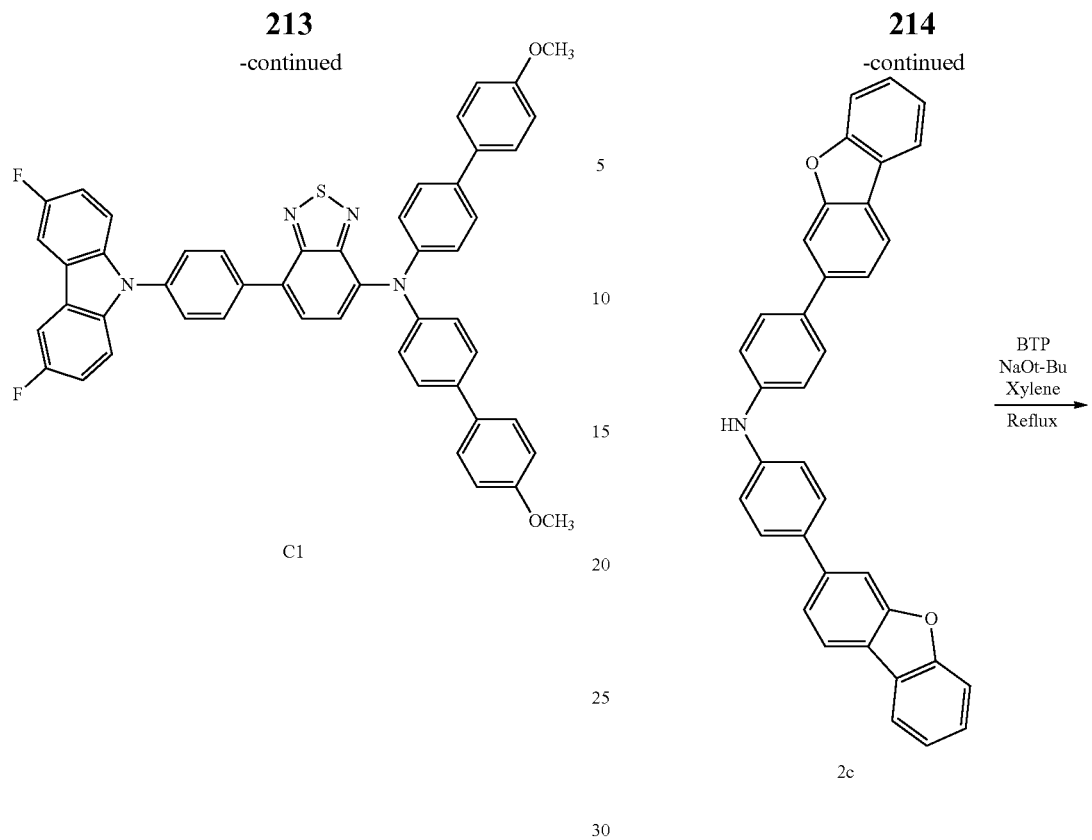

C1

A synthesis was performed in the same manner as in Compound A1, except that 2 g of Compound C and 1.1 equivalents of Compound 1c were used instead of Compound A and Compound 1a, respectively, and 1.84 g (yield 57%) of Compound C1 was obtained through the synthesis. HR LC/MS/MS m/z calcd for $C_{50}H_{34}F_2N_4O_2S$ (M+): 792.2362; found: 792.2362.

Preparation Example 11. Synthesis of Compound C2

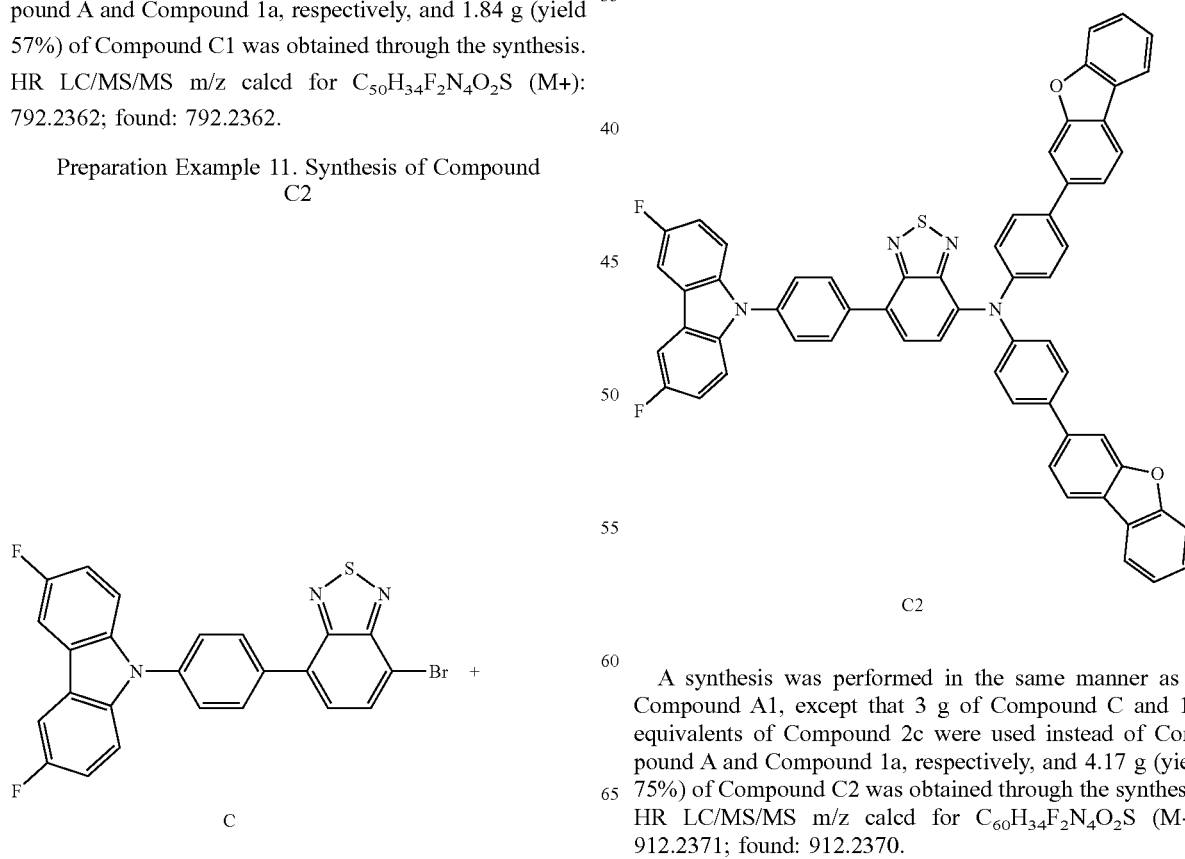

C2

A synthesis was performed in the same manner as in Compound A1, except that 3 g of Compound C and 1.1 equivalents of Compound 2c were used instead of Compound A and Compound 1a, respectively, and 4.17 g (yield 75%) of Compound C2 was obtained through the synthesis. HR LC/MS/MS m/z calcd for $C_{60}H_{34}F_2N_4O_2S$ (M+): 912.2371; found: 912.2370.

Preparation Example 12. Synthesis of Compound D1

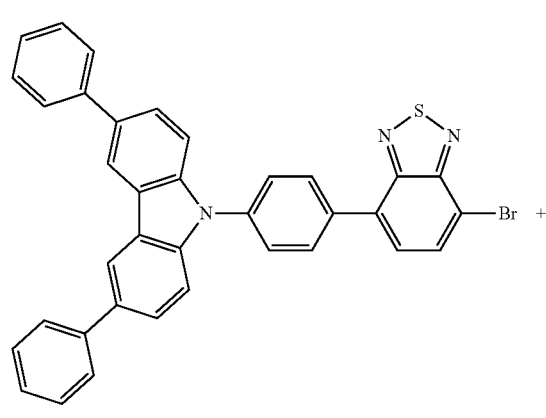

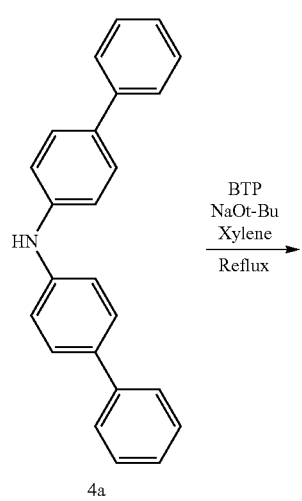

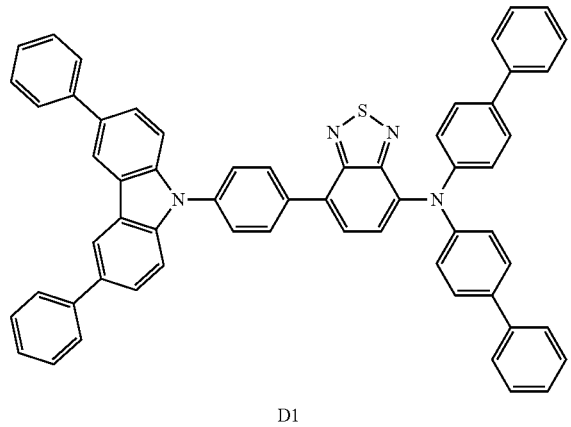

A synthesis was performed in the same manner as in Compound A1, except that 2 g of Compound D and 1.1 equivalents of Compound 4a were used instead of Compound A and Compound 1a, respectively, and 1.84 g (yield 66%) of Compound D1 was obtained through the synthesis. HR LC/MS/MS m/z calcd for $C_{60}H_{40}N_4S$ (M+): 848.2974; found: 848.2974.

Preparation Example 13. Synthesis of Compound D2

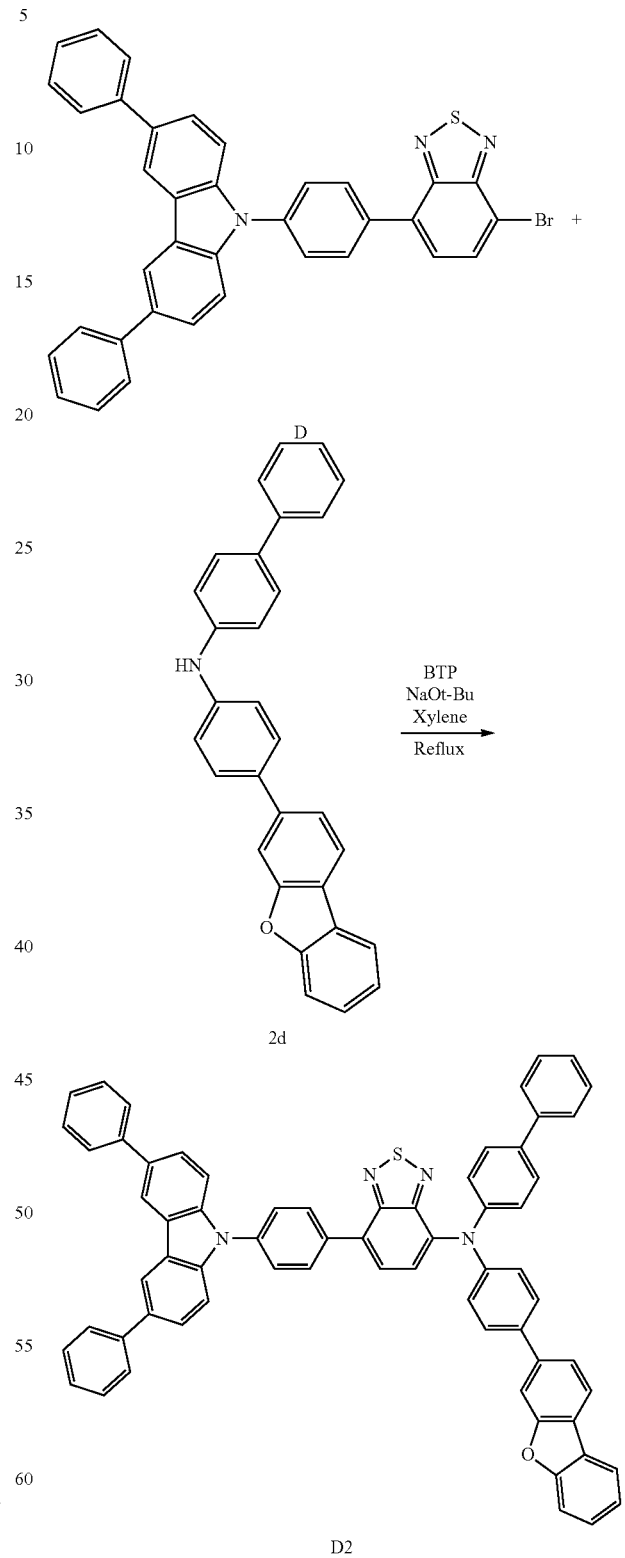

A synthesis was performed in the same manner as in Compound A1, except that 1.5 g of Compound D and 1.1 equivalents of Compound 2d were used instead of Compound A and Compound 1a, respectively, and 1.74 g (yield 75%) of Compound D2 was obtained through the synthesis. HR LC/MS/MS m/z calcd for $C_{66}H_{42}N_4OS$ (M+): 938.3079; found: 938.3077.

Preparation Example 14. Synthesis of Compound D3

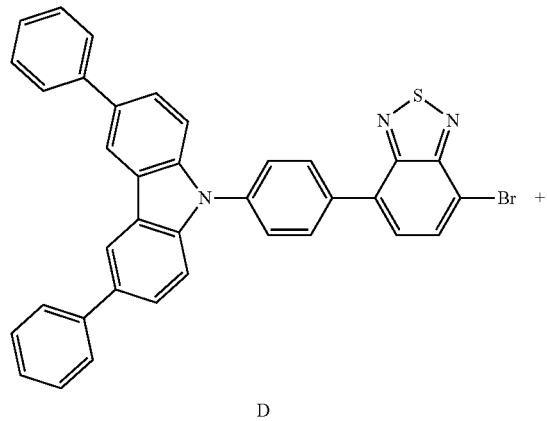

D

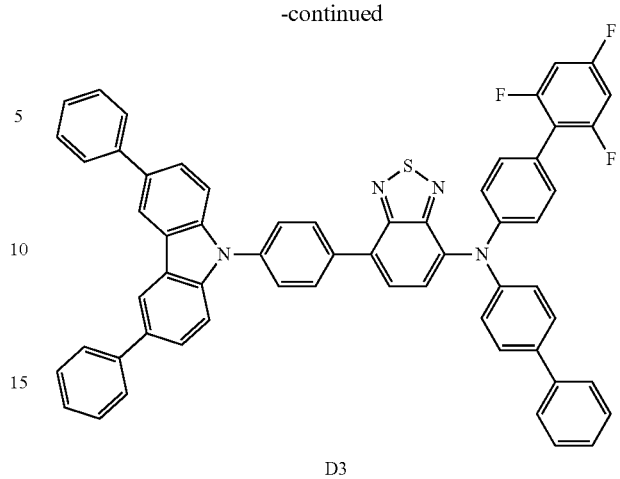

D3

A synthesis was performed in the same manner as in Compound A1, except that 3 g of Compound D and 1.1 equivalents of Compound 3d were used instead of Compound A and Compound 1a, respectively, and 2.27 g (yield 51%) of Compound D3 was obtained through the synthesis. HR LC/MS/MS m/z calcd for $C_{60}H_{37}F_3N_4S$ (M+): 902.2691; found: 902.2691.

Preparation Example 15. Synthesis of Compound D4

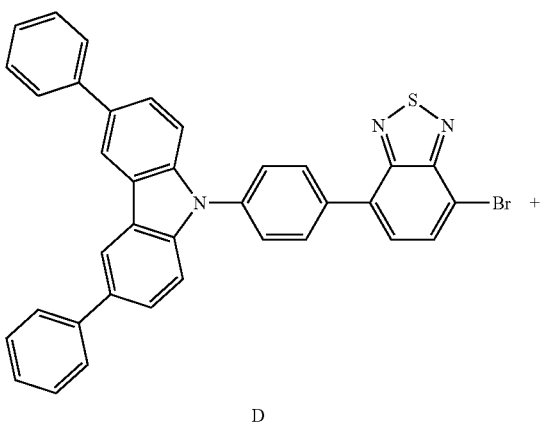

D

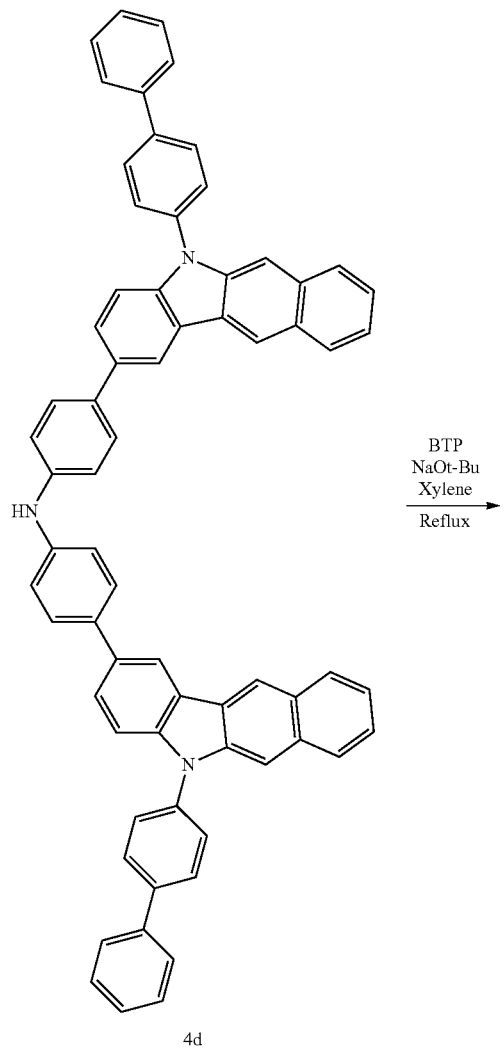

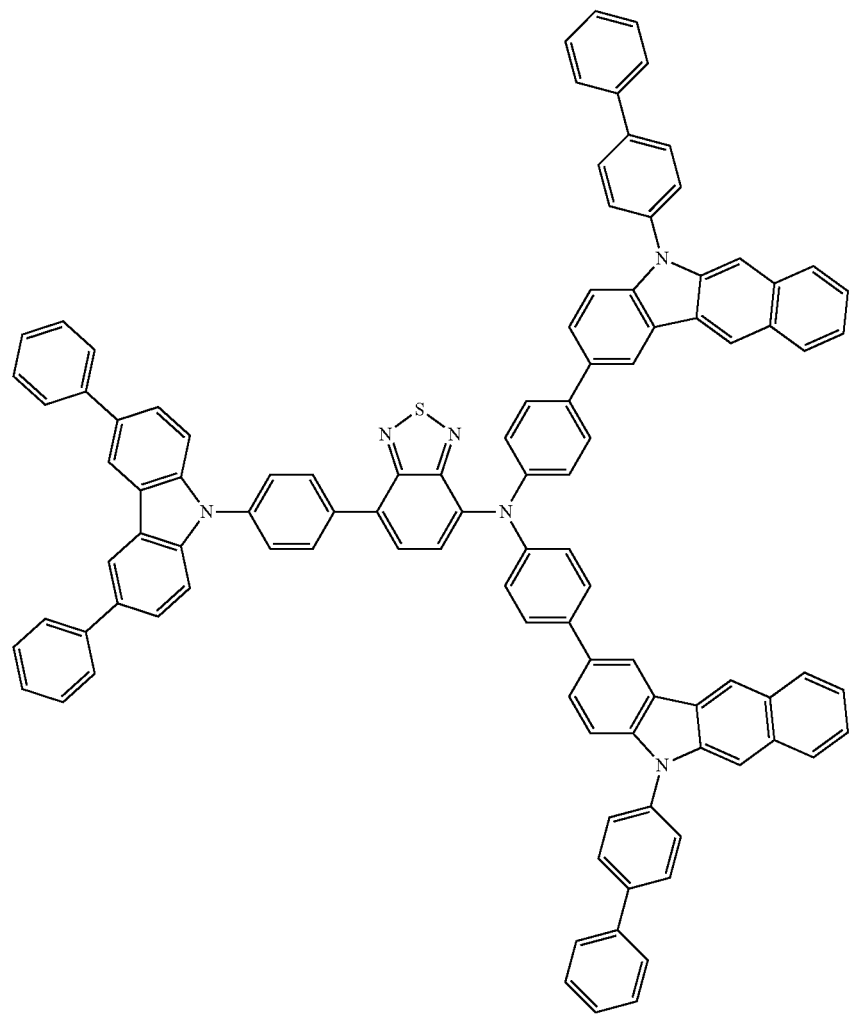
D4

A synthesis was performed in the same manner as in Compound A1, except that 2 g of Compound D and 1.1 equivalents of Compound 4d were used instead of Compound A and Compound 1a, respectively, and 2.73 g (yield 58%) of Compound D4 was obtained through the synthesis. HR LC/MS/MS m/z calcd for $C_{104}H_{66}N_6S$ (M+): 1431.5103; found: 1431.5103.

Preparation Example 16. Synthesis of Compound E1

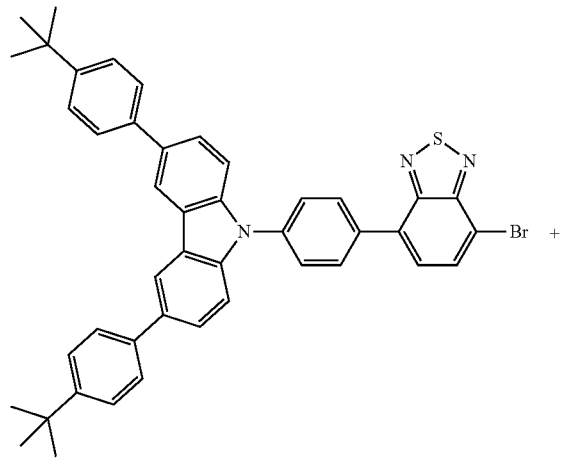

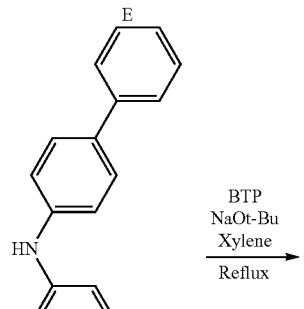

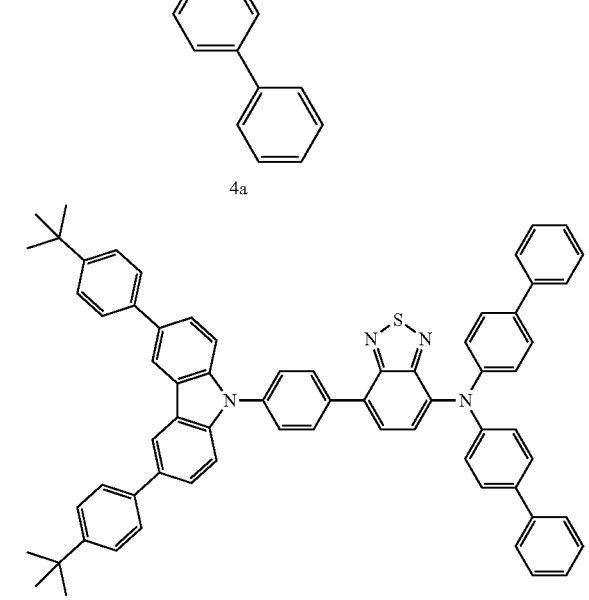

E1

A synthesis was performed in the same manner as in Compound A1, except that 3 g of Compound E and 1.1 equivalents of Compound 4a were used instead of Compound A and Compound 1a, respectively, and 1.92 g (yield 48%) of Compound E1 was obtained through the synthesis. HR LC/MS/MS m/z calcd for $C_{68}H_{56}N_4S$ (M+): 960.4226; found: 960.4225.

Preparation Example 17. Synthesis of Compound E2

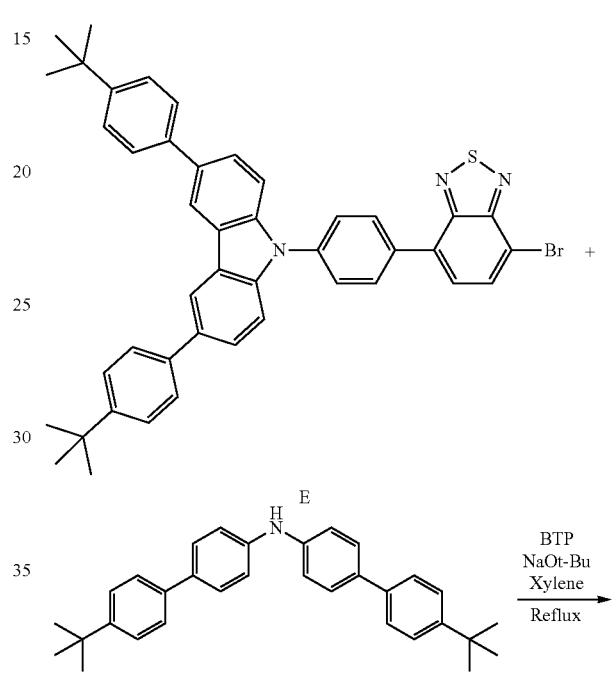

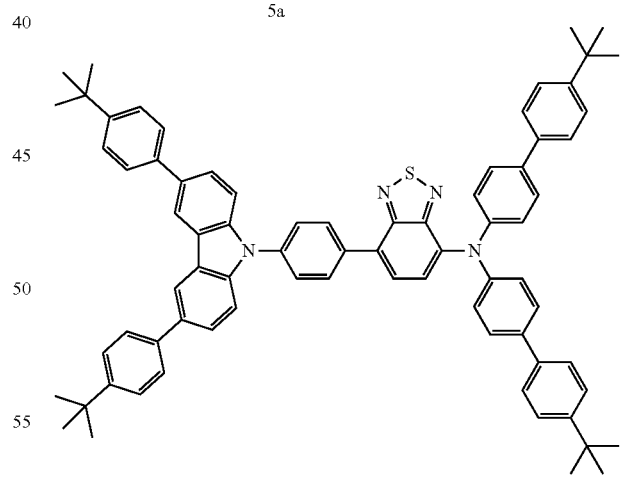

E2

A synthesis was performed in the same manner as in Compound A1, except that 3.5 g of Compound E and 1.1 equivalents of Compound 5a were used instead of Compound A and Compound 1a, respectively, and 2.76 g (yield 53%) of Compound E2 was obtained through the synthesis. HR LC/MS/MS m/z calcd for $C_{76}H_{72}N_4S$ (M+): 1072.5478; found: 1072.5477.

Preparation Example 18. Synthesis of Compound E3
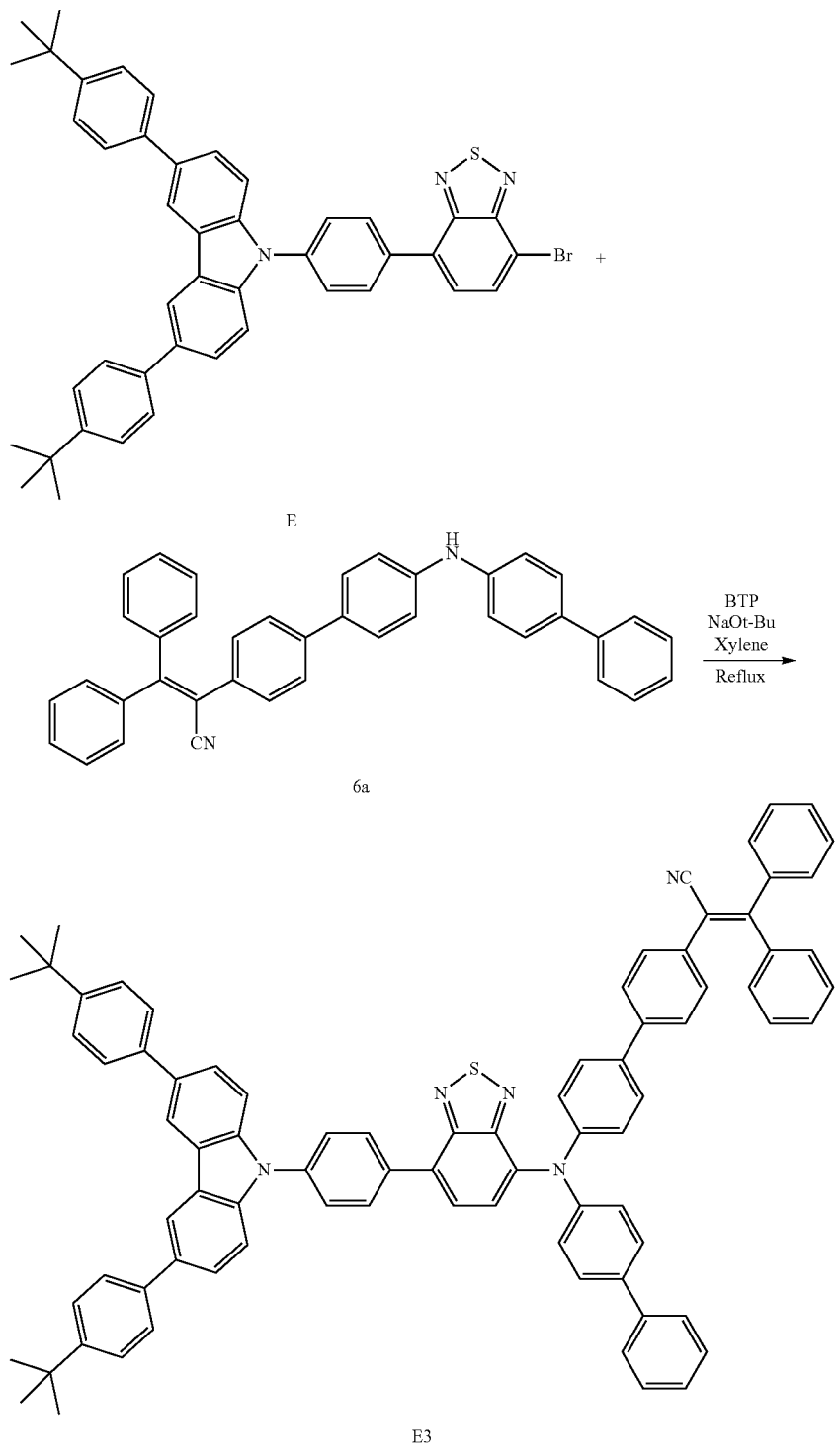
A synthesis was performed in the same manner as in Compound A1, except that 3 g of Compound E and 1.1 equivalents of Compound 6a were used instead of Compound A and Compound 1a, respectively, and 3.15 g (yield 65%) of Compound E3 was obtained through the synthesis. HR LC/MS/MS m/z calcd for $C_{83}H_{65}N_5S$ (M+): 1163.4961; found: 1163.4961.

Preparation Example 19. Synthesis of Compound E4
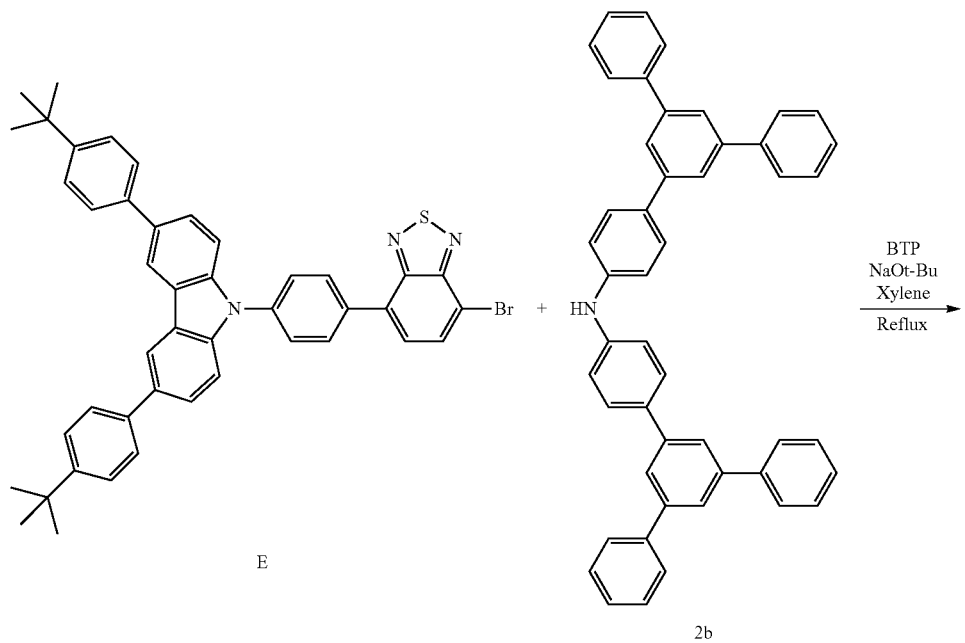
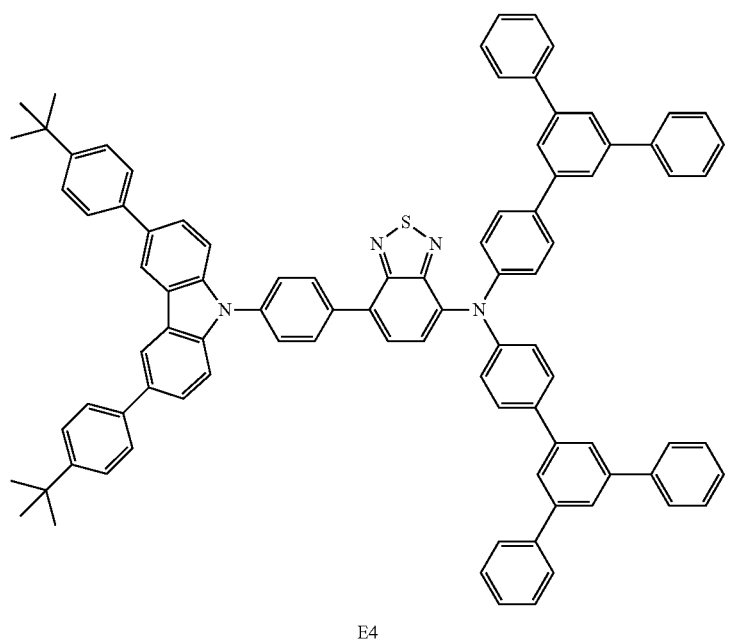
A synthesis was performed in the same manner as in Compound A1, except that 2 g of Compound E and 1.1 equivalents of Compound 2b were used instead of Compound A and Compound 1a, respectively, and 1.93 g (yield 55%) of Compound E4 was obtained through the synthesis. HR LC/MS/MS m/z calcd for $C_{92}H_{72}N_4S$ (M+): 1264.5478; found: 1264.5477.

Preparation Example 20. Synthesis of Compound F1
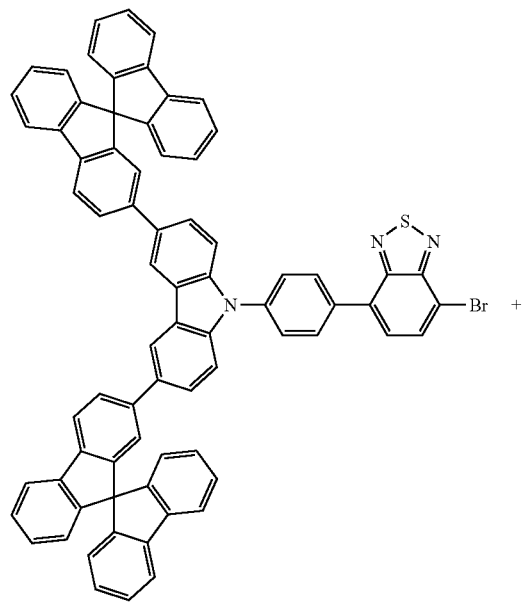
F
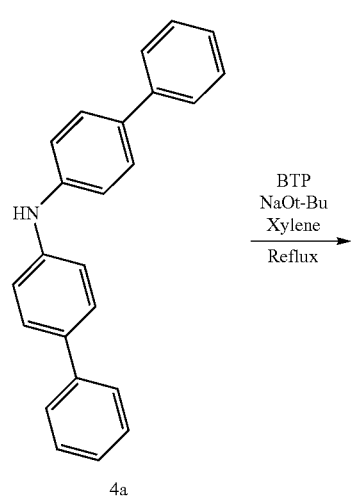
4a
BTP
NaOt-Bu
Xylene
Reflux
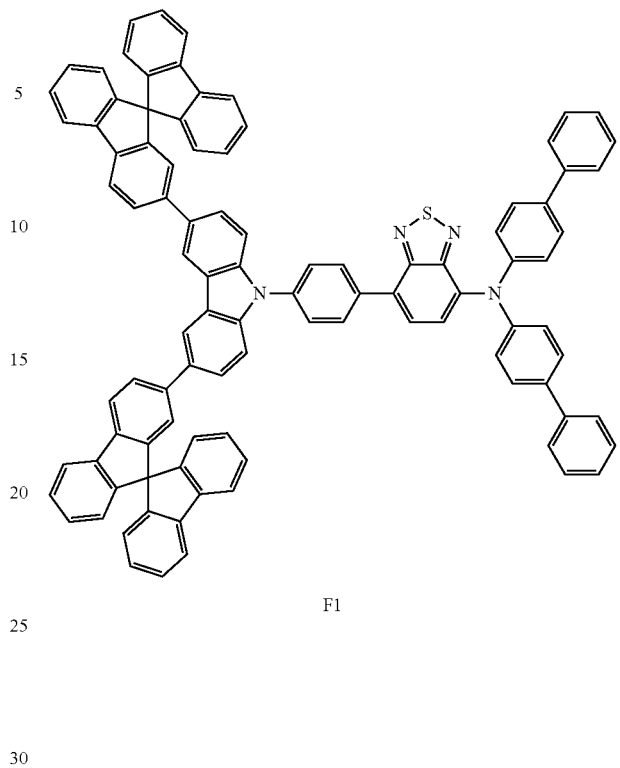
F1
A synthesis was performed in the same manner as in Compound A1, except that 1 g of Compound F and 1.1 equivalents of Compound 4a were used instead of Compound A and Compound 1a, respectively, and 0.79 g (yield 65%) of Compound F1 was obtained through the synthesis. HR LC/MS/MS m/z calcd for $C_{98}H_{60}N_4S$ (M+): 1325.4572; found: 1325.4572.

Preparation Example 21. Synthesis of Compound F2
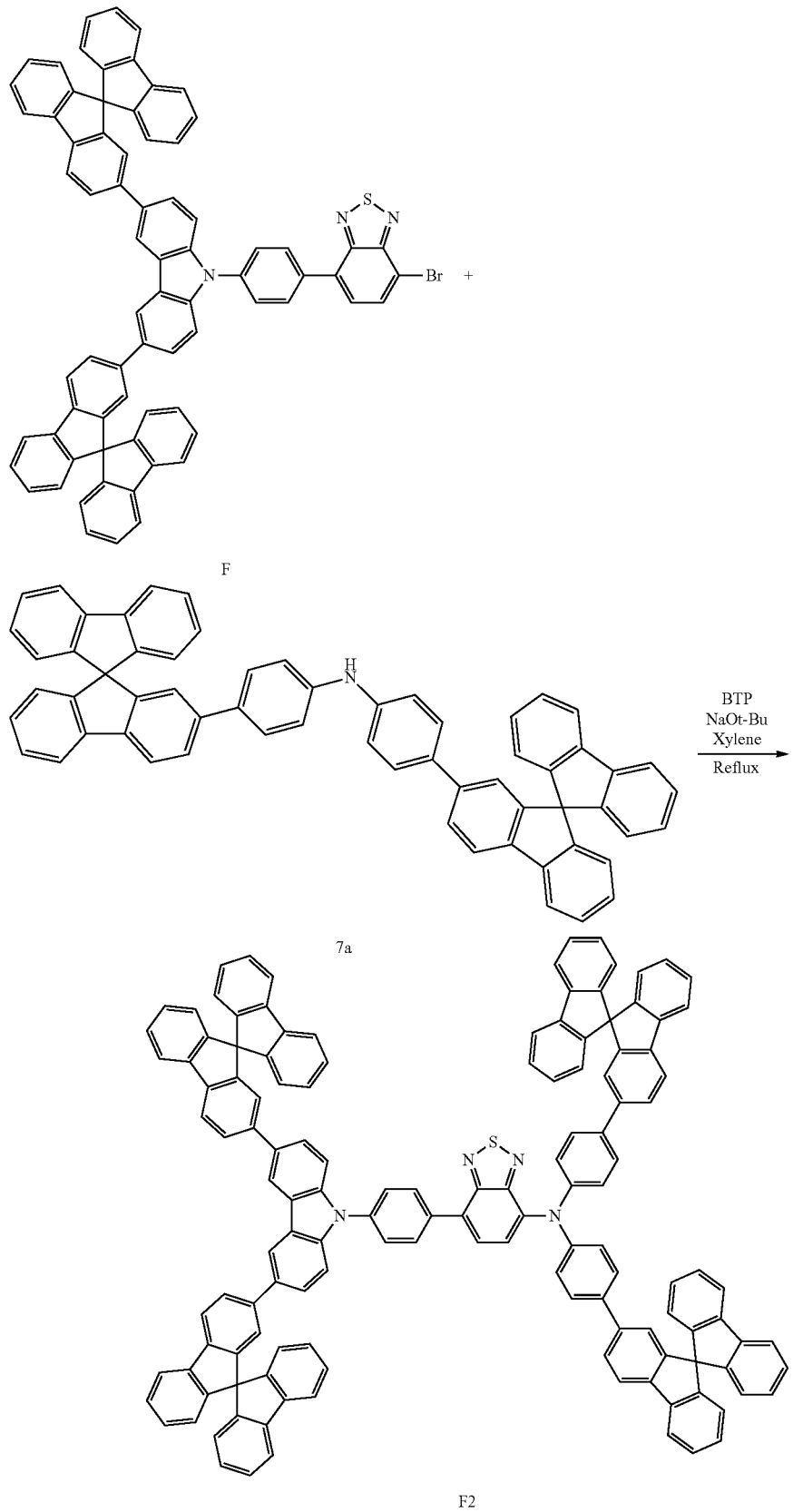

A synthesis was performed in the same manner as in Compound A1, except that 2 g of Compound F and 1.1 equivalents of Compound 7a were used instead of Compound A and Compound 1a, respectively, and 1.69 g (yield 51%) of Compound F2 was obtained through the synthesis. HR LC/MS/MS m/z calcd for $C_{136}H_{80}N_4S$ (M+): 1801.6137; found: 1801.6135.

Preparation Example 22. Synthesis of Compound G1

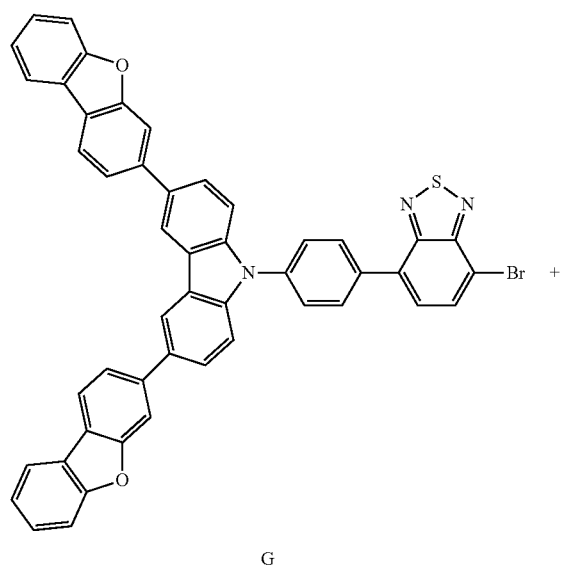

G

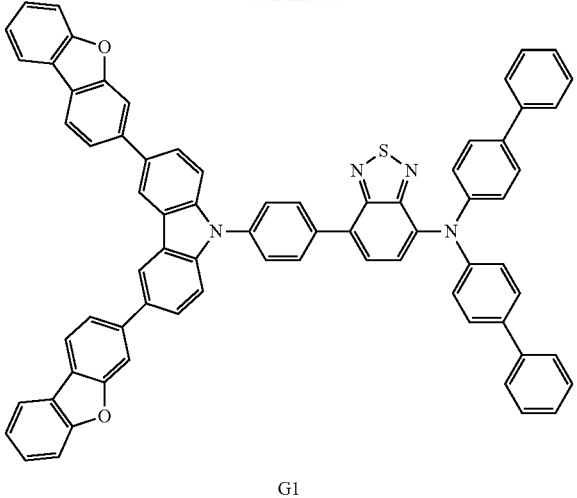

G1

A synthesis was performed in the same manner as in Compound A1, except that 2 g of Compound G and 1.1 equivalents of Compound 4a were used instead of Compound A and Compound 1a, respectively, and 1.64 g (yield 63%) of Compound G1 was obtained through the synthesis. HR LC/MS/MS m/z calcd for $C_{72}H_{44}N_4O_2S$ (M+): 1028.3185; found: 1028.3184.

Preparation Example 23. Synthesis of Compound G2

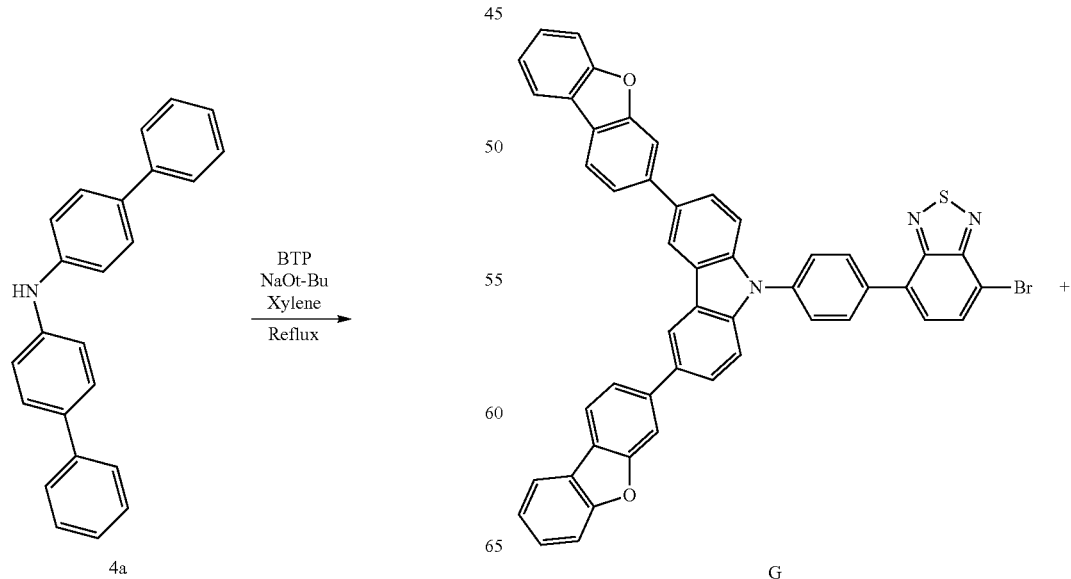

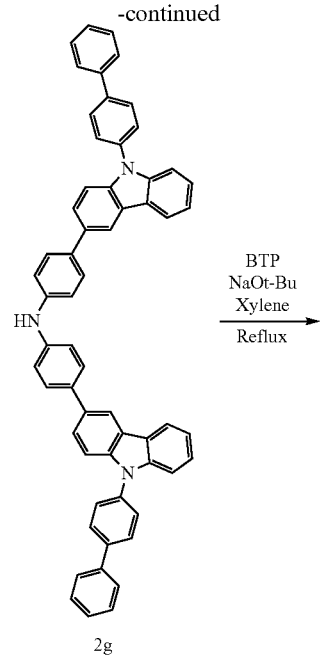
2g
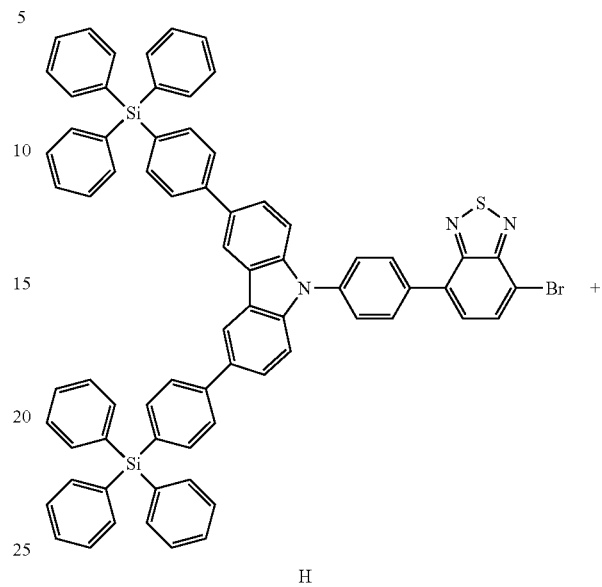
Preparation Example 24. Synthesis of Compound H1
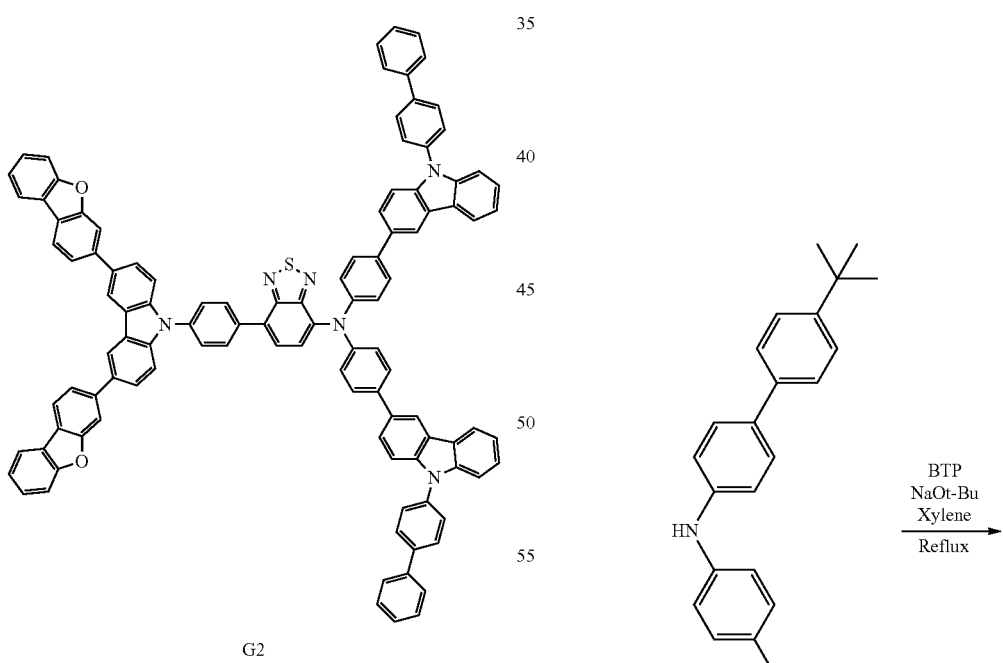
A synthesis was performed in the same manner as in Compound A1, except that 1.5 g of Compound G and 1.1 equivalents of Compound 2g were used instead of Compound A and Compound 1a, respectively, and 1.58 g (yield 55%) of Compound G2 was obtained through the synthesis. HR LC/MS/MS m/z calcd for $C_{108}H_{66}N_6O_2S$ (M+): 1511.5002; found: 1511.5002.

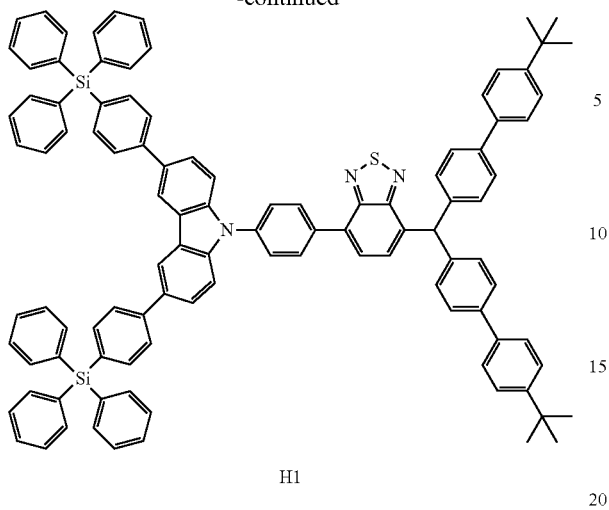
H1
A synthesis was performed in the same manner as in Compound A1, except that 3 g of Compound H and 1.1 equivalents of Compound 5a were used instead of Compound A and Compound 1a, respectively, and 1.77 g (yield 45%) of Compound H1 was obtained through the synthesis. HR LC/MS/MS m/z calcd for $C_{104}H_{84}N_4SSi_2$ (M+): 1477.5989; found: 1477.5988.
Preparation Example 25. Synthesis of Compound H2
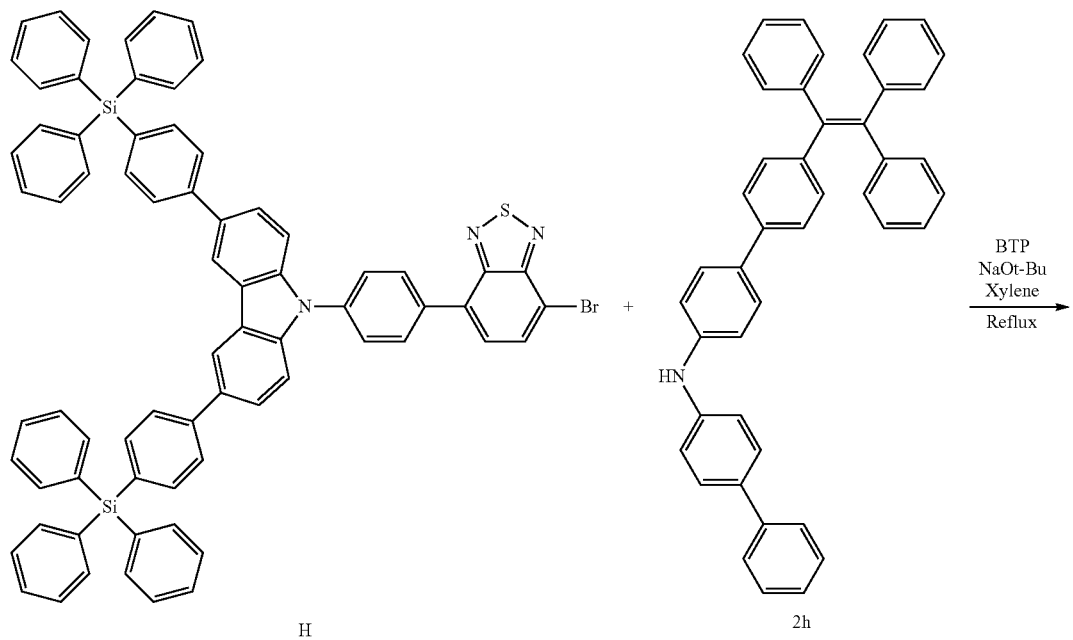

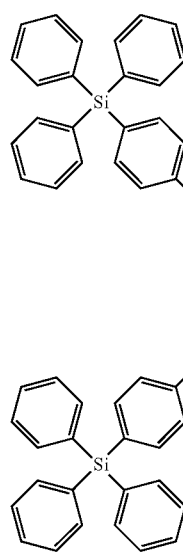
H2
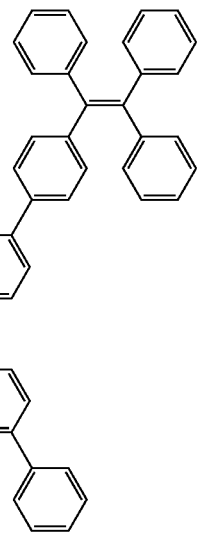
A synthesis was performed in the same manner as in Compound A1, except that 2 g of Compound H and 1.1 equivalents of Compound 2h were used instead of Compound A and Compound 1a, respectively, and 1.50 g (yield 52%) of Compound H2 was obtained through the synthesis. HR LC/MS/MS m/z calcd for $C_{116}H_{82}N_4SSi_2$ (M+): 1619.5832; found: 1619.5831.
Preparation Example 26. Synthesis of Compound I1
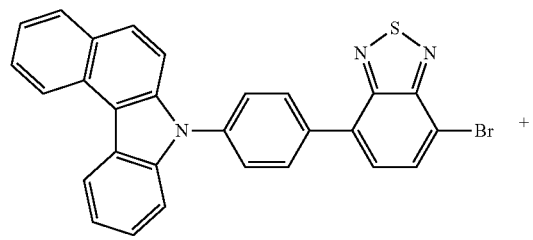
I
-continued
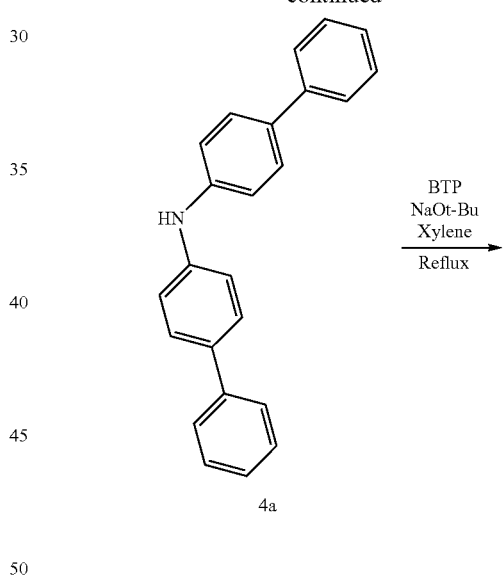
4a
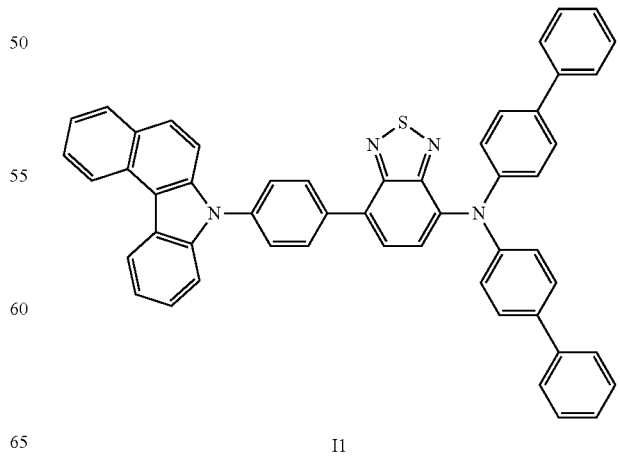
I1

A synthesis was performed in the same manner as in Compound A1, except that 2 g of Compound I and 1.1 equivalents of Compound 4a were used instead of Compound A and Compound 1a, respectively, and 2.01 g (yield 68%) of Compound I1 was obtained through the synthesis. HR LC/MS/MS m/z calcd for $C_{52}H_{34}N_4S$ (M+): 746.2504; found: 746.2504.

Preparation Example 27. Synthesis of Compound 12

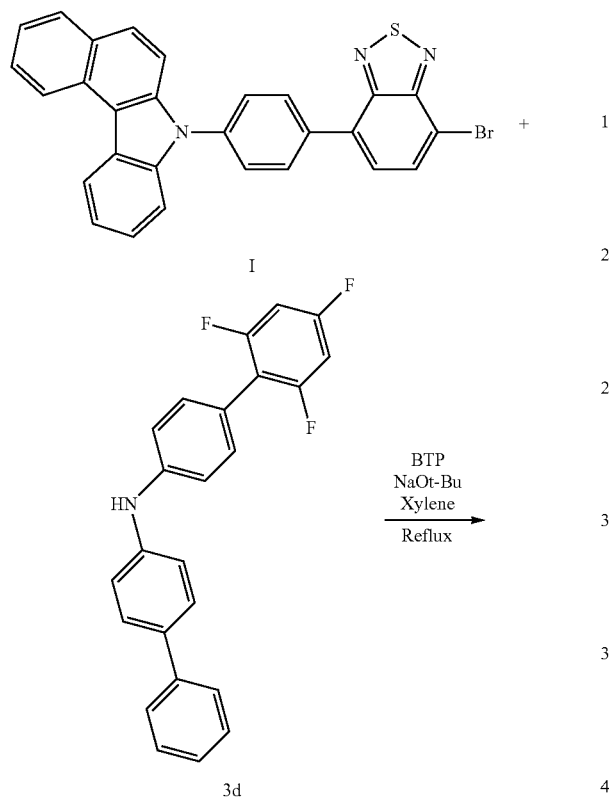

Preparation Example 28. Synthesis of Compound 13

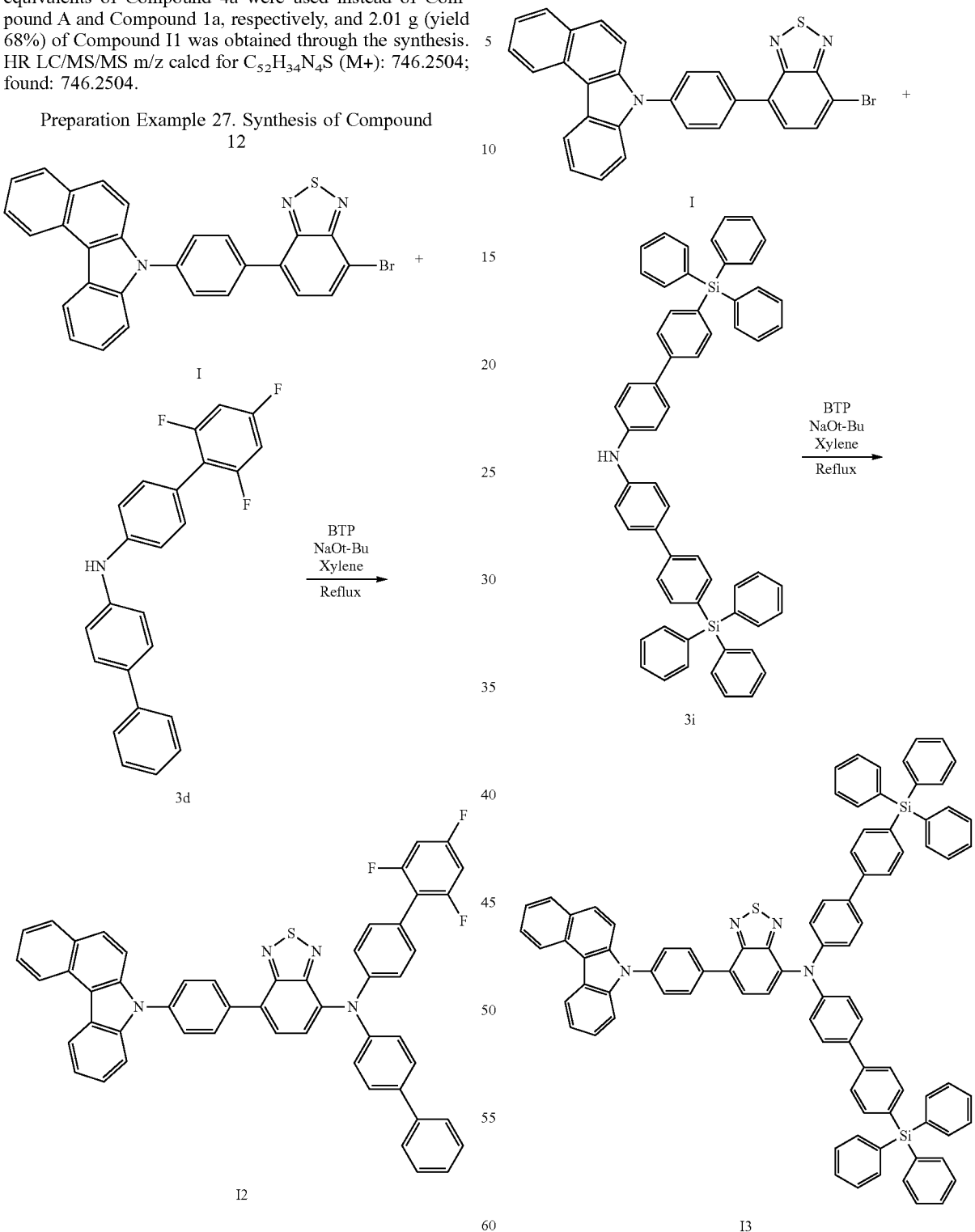

A synthesis was performed in the same manner as in Compound A1, except that 2 g of Compound I and 1.1 equivalents of Compound 3d were used instead of Compound A and Compound 1a, respectively, and 2.28 g (yield 72%) of Compound 12 was obtained through the synthesis. HR LC/MS/MS m/z calcd for $C_{52}H_{31}F_3N_4S$ (M+): 801.2300; found: 801.2301.

A synthesis was performed in the same manner as in Compound A1, except that 2 g of Compound I and 1.1 equivalents of Compound 3i were used instead of Compound A and Compound 1a, respectively, and 2.69 g (yield 54%) of Compound 13 was obtained through the synthesis.

HR LC/MS/MS m/z calcd for $C_{88}H_{62}N_4SSi_2$ (M+): 1262.4234; found: 1262.4234.

Preparation Example 29. Synthesis of Compound J1

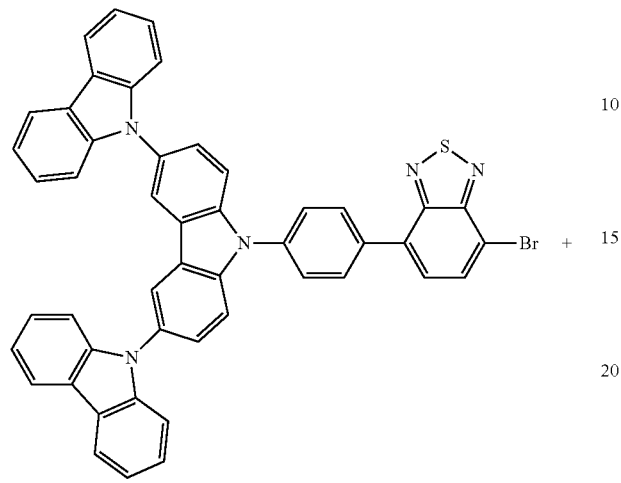

J

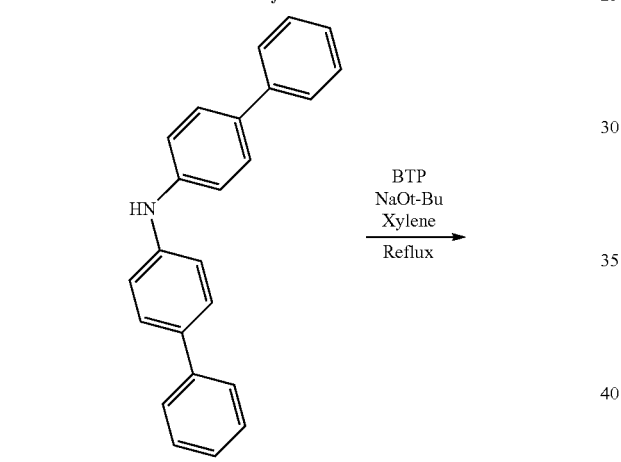

4a

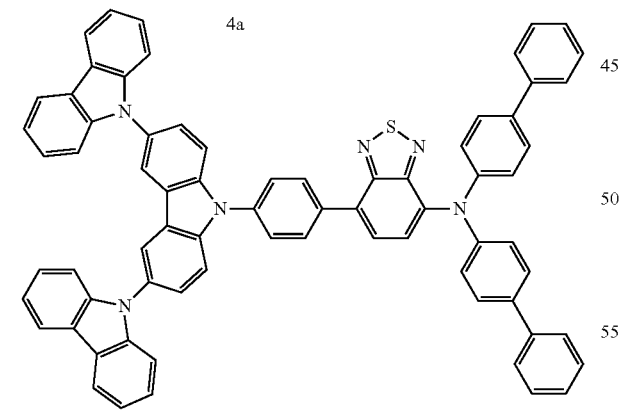

J1

A synthesis was performed in the same manner as in Compound A1, except that 2 g of Compound J and 1.1 equivalents of Compound 4a were used instead of Compound A and Compound 1a, respectively, and 1.49 g (yield 57%) of Compound J1 was obtained through the synthesis. HR LC/MS/MS m/z calcd for $C_{72}H_{46}N_6S$ (M+): 1026.3505; found: 1026.3506.

Preparation Example 30. Synthesis of Compound K1
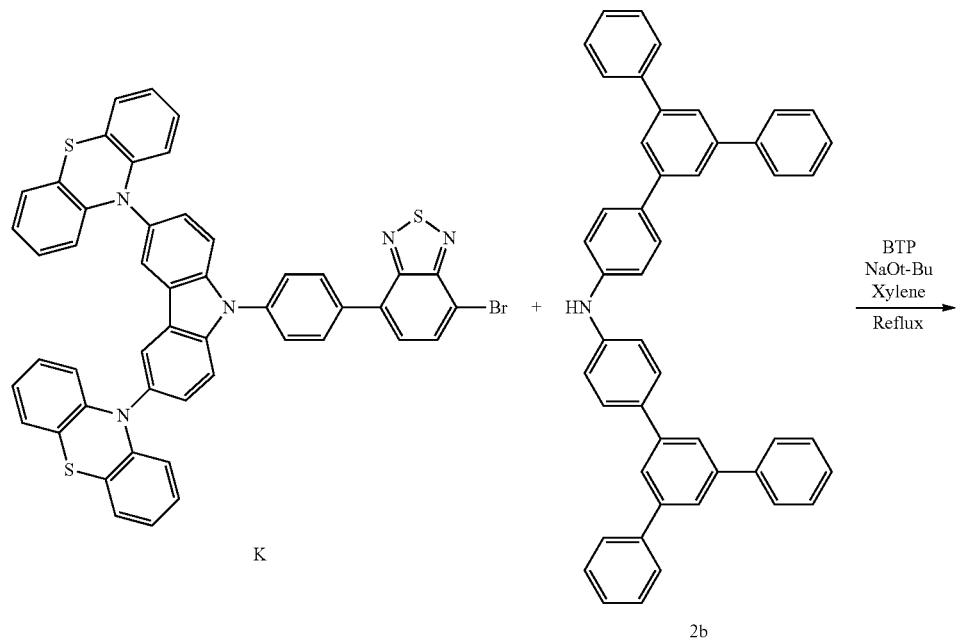
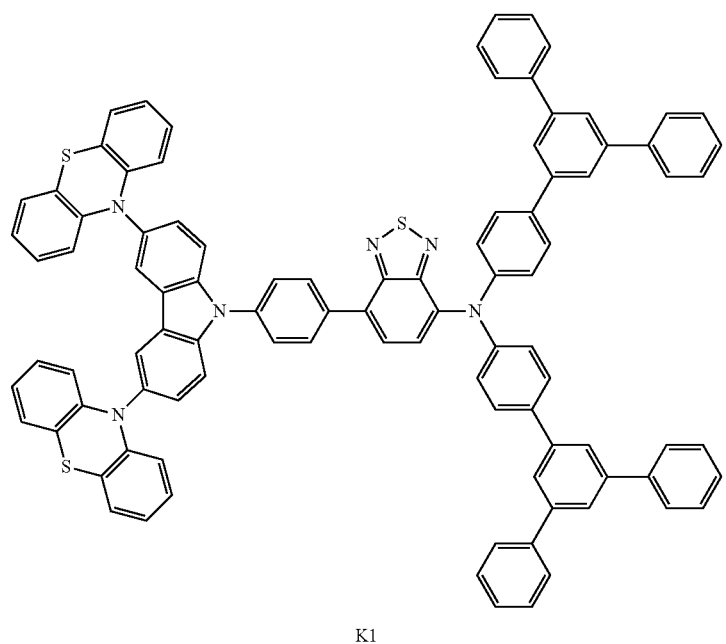
A synthesis was performed in the same manner as in Compound A1, except that 1.5 g of Compound K and 1.1 equivalents of Compound 2b were used instead of Compound A and Compound 1a, respectively, and 1.03 g (yield 42%) of Compound K1 was obtained through the synthesis. HR LC/MS/MS m/z calcd for $C_{96}H_{62}N_6S_3$ (M+): 1395.4232; found: 1395.4233.

Preparation Example 31. Synthesis of Compound L1

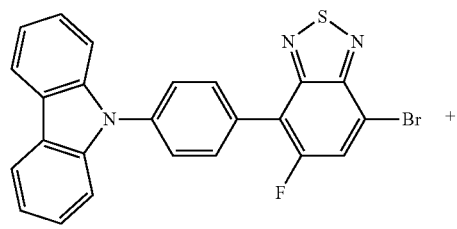

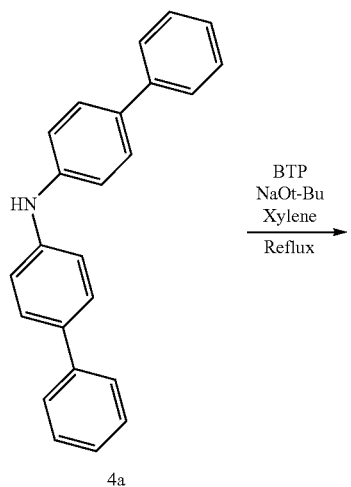

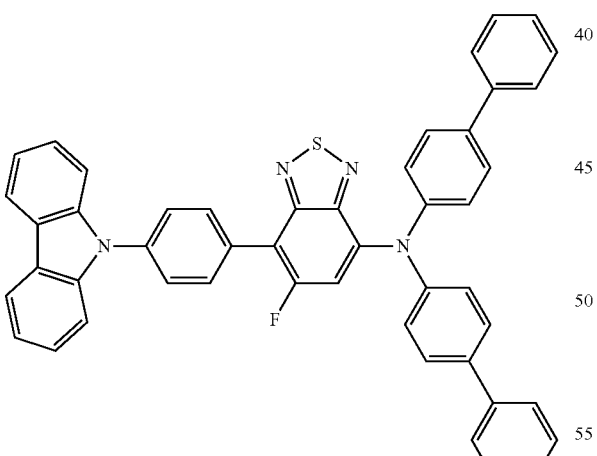

A synthesis was performed in the same manner as in Compound A1, except that 2 g of Compound L and 1.1 equivalents of Compound 4a were used instead of Compound A and Compound 1a, respectively, and 2.02 g (yield 67%) of Compound L1 was obtained through the synthesis. HR LC/MS/MS m/z calcd for $C_{48}H_{31}FN_4S$ (M+): 714.2253; found: 714.2253.

Preparation Example 32. Synthesis of Compound M1

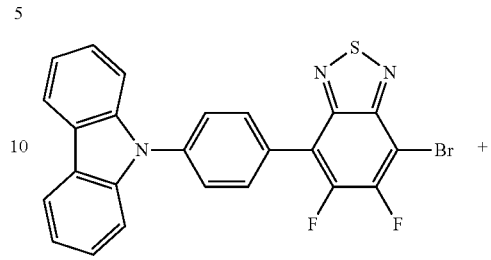

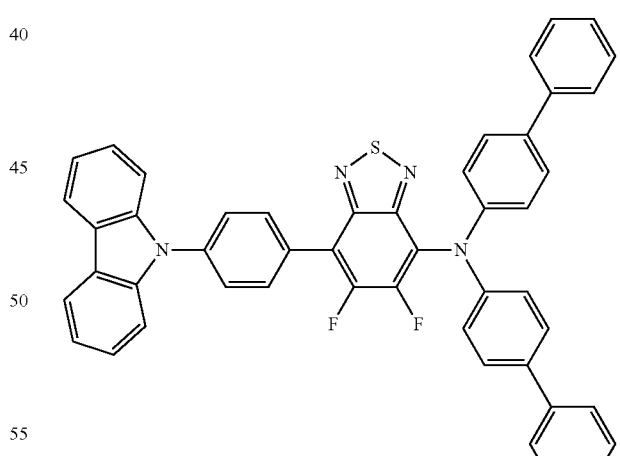

A synthesis was performed in the same manner as in Compound A1, except that 2 g of Compound M and 1.1 equivalents of Compound 4a were used instead of Compound A and Compound 1a, respectively, and 2.14 g (yield 72%) of Compound M1 was obtained through the synthesis. HR LC/MS/MS m/z calcd for $C_{48}H_{30}F_2N_4S$ (M+): 732.2193; found: 732.2193.

Preparation Example 33. Synthesis of Comparative Compound Z1

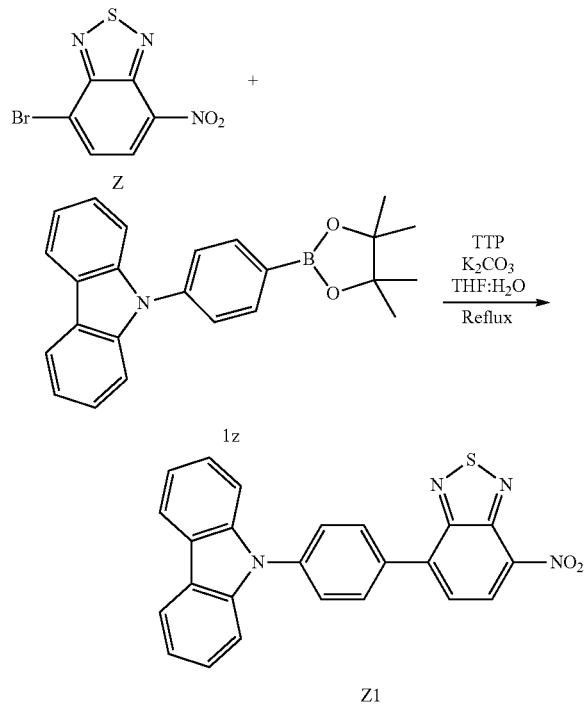

After 2 g of Compound Z and 1.1 equivalents of Compound 1z were dissolved in a THF solvent in a reaction vessel, 2 equivalents of potassium carbonate were dissolved in water and the resulting solution was introduced thereto. After the temperature was stabilized by heating and stirring the resulting solution at 80° C. under nitrogen, the reaction was performed by adding 0.03 equivalent of a catalyst Pd(PPh$_3$)$_4$ thereto. When the reaction was completed, extraction was performed by using chloroform and water, and then water was removed from a separated organic layer by using anhydrous magnesium sulfate. After the organic layer from which water had been removed was concentrated through distillation under reduced pressure, recrystallization was performed by using ethanol, thereby securing 1.46 g (yield 45%) of Comparative Compound Z1. HR LC/MS/MS m/z calcd for C$_{24}$H$_{14}$N$_4$O$_2$S (M+): 422.0837; found: 422.0836.

EXAMPLES

Example 1

1.5 parts by weight of Compound A1 (maximum absorption wavelength of 491 nm and maximum light emission wavelength of 610 nm in a toluene solution) prepared in Preparation Example 1 was dissolved in a solvent propylene glycol monomethyl ether acetate (PGMEA), such that 33.9 parts by weight of an acrylic binder, 59.3 parts by weight of a polyfunctional monomer (pentaerythritol triacrylate, Nippon Kayaku Co., Ltd.), 2.3 parts by weight of a bonding aid and a surfactant (KBM 503, Shinetsu), and 3.0 parts by weight of a photoinitiator (Tinuvin® 477, BASF) had a solid content of 21 wt %, thereby preparing a solution. After the mixed solution was sufficiently stirred, a glass substrate was coated with a thin film, and then the thin film was dried to prepare a color conversion film. The brightness spectrum of the prepared color conversion film was measured by a spectroradiometer (SR series manufactured by Topcon, Inc.). Specifically, the prepared color conversion film was stacked on one surface of a light guide plate of a backlight unit including an LED blue backlight (maximum light emission wavelength of 450 nm) and the light guide plate, a prism sheet and a DBEF film were stacked on the color conversion film, and then an initial value was set, such that the luminance of the blue LED light was 600 nit based on the film.

Example 2

A color conversion film was prepared in the same manner as in Example 1, except that in Example 1, Compound A2 (maximum absorption wavelength of 489 nm and maximum light emission wavelength of 608 nm in a toluene solution) was used instead of Compound A1.

Example 3

A color conversion film was prepared in the same manner as in Example 1, except that in Example 1, Compound A3 (maximum absorption wavelength of 488 nm and maximum light emission wavelength of 606 nm in a toluene solution) was used instead of Compound A1.

Example 4

A color conversion film was prepared in the same manner as in Example 1, except that in Example 1, Compound A4 (maximum absorption wavelength of 494 nm and maximum light emission wavelength of 613 nm in a toluene solution) was used instead of Compound A1.

Example 5

A color conversion film was prepared in the same manner as in Example 1, except that in Example 1, Compound A5 (maximum absorption wavelength of 497 nm and maximum light emission wavelength of 621 nm in a toluene solution) was used instead of Compound A1.

Example 6

A color conversion film was prepared in the same manner as in Example 1, except that in Example 1, Compound A6 (maximum absorption wavelength of 493 nm and maximum light emission wavelength of 618 nm in a toluene solution) was used instead of Compound A1.

Example 7

A color conversion film was prepared in the same manner as in Example 1, except that in Example 1, Compound A7 (maximum absorption wavelength of 498 nm and maximum light emission wavelength of 626 nm in a toluene solution) was used instead of Compound A1.

Example 8

A color conversion film was prepared in the same manner as in Example 1, except that in Example 1, Compound B2 (maximum absorption wavelength of 497 nm and maximum light emission wavelength of 628 nm in a toluene solution) was used instead of Compound A1.

Example 9

A color conversion film was prepared in the same manner as in Example 1, except that in Example 1, Compound D1 (maximum absorption wavelength of 491 nm and maximum light emission wavelength of 613 nm in a toluene solution) was used instead of Compound A1.

Example 10

A color conversion film was prepared in the same manner as in Example 1, except that in Example 1, Compound D3 (maximum absorption wavelength of 490 nm and maximum light emission wavelength of 618 nm in a toluene solution) was used instead of Compound A1.

Example 11

A color conversion film was prepared in the same manner as in Example 1, except that in Example 1, Compound E2 (maximum absorption wavelength of 494 nm and maximum light emission wavelength of 617 nm in a toluene solution) was used instead of Compound A1.

Example 12

A color conversion film was prepared in the same manner as in Example 1, except that in Example 1, Compound E3 (maximum absorption wavelength of 491 nm and maximum light emission wavelength of 612 nm in a toluene solution) was used instead of Compound A1.

Example 13

A color conversion film was prepared in the same manner as in Example 1, except that in Example 1, Compound E4 (maximum absorption wavelength of 487 nm and maximum light emission wavelength of 608 nm in a toluene solution) was used instead of Compound A1.

Example 14

A color conversion film was prepared in the same manner as in Example 1, except that in Example 1, Compound F1 (maximum absorption wavelength of 492 nm and maximum light emission wavelength of 614 nm in a toluene solution) was used instead of Compound A1.

Example 15

A color conversion film was prepared in the same manner as in Example 1, except that in Example 1, Compound H1 (maximum absorption wavelength of 495 nm and maximum light emission wavelength of 612 nm in a toluene solution) was used instead of Compound A1.

Example 16

A color conversion film was prepared in the same manner as in Example 1, except that in Example 1, Compound I1 (maximum absorption wavelength of 493 nm and maximum light emission wavelength of 611 nm in a toluene solution) was used instead of Compound A1.

Example 17

A color conversion film was prepared in the same manner as in Example 1, except that in Example 1, Compound I3 (maximum absorption wavelength of 491 nm and maximum light emission wavelength of 608 nm in a toluene solution) was used instead of Compound A1.

Example 18

A color conversion film was prepared in the same manner as in Example 1, except that in Example 1, Compound K1 (maximum absorption wavelength of 502 nm and maximum light emission wavelength of 623 nm in a toluene solution) was used instead of Compound A1.

Example 19

A color conversion film was prepared in the same manner as in Example 1, except that in Example 1, Compound L1 (maximum absorption wavelength of 492 nm and maximum light emission wavelength of 608 nm in a toluene solution) was used instead of Compound A1.

Comparative Example

An experiment was performed in the same manner as in Example 1, except that in Example 1, Compound Z1 (maximum absorption wavelength of 418 nm in a toluene solution) was used instead of Compound A1.

The physical properties of the compounds, used in Examples 1 to 19 and the Comparative Example, in a solution phase, and the thin film light emission wavelengths and thin film quantum efficiencies (PLQY (%)) when the compounds are applied to the color conversion films are as the following Table 1.

TABLE 1

| Example | Compound | Solution | | | Thin film | |
|---|---|---|---|---|---|---|
| | | $\lambda_{uv, max}$ (nm) | $\lambda_{PL, max}$ (nm) | PLQY (%) | $\lambda_{PL, max}$ (nm) | PLQY (%) |
| 1 | A1 | 491 | 610 | 58.9 | 627 | 35.1 |
| 2 | A2 | 489 | 608 | 56.8 | 624 | 31.3 |
| 3 | A3 | 488 | 606 | 66.2 | 616 | 42.5 |
| 4 | A4 | 494 | 613 | 59.1 | 633 | 38.4 |
| 5 | A5 | 497 | 621 | 42.2 | 642 | 23.1 |
| 6 | A6 | 493 | 618 | 23 | 630 | 51.2 |
| 7 | A7 | 498 | 626 | 28.7 | 643 | 17 |
| 8 | B2 | 497 | 628 | 48.2 | 636 | 39.5 |
| 9 | D1 | 491 | 613 | 51.9 | 634 | 25.8 |
| 10 | D3 | 490 | 618 | 39.5 | 646 | 24.9 |
| 11 | E2 | 494 | 617 | 66.3 | 642 | 42.1 |
| 12 | E3 | 491 | 612 | 34.2 | 641 | 45.4 |
| 13 | E4 | 487 | 608 | 61.3 | 633 | 48.9 |
| 14 | F1 | 492 | 614 | 58.1 | 630 | 21.1 |
| 15 | H1 | 495 | 612 | 62 | 626 | 47 |
| 16 | I1 | 493 | 611 | 42.1 | 627 | 28.4 |
| 17 | I3 | 491 | 603 | 62.1 | 613 | 42 |
| 18 | K1 | 502 | 623 | 60.2 | 652 | 47.8 |
| 19 | L1 | 492 | 608 | 60.5 | 632 | 47.8 |
| Comparative Example | Z1 | 418 | — | — | 605 | 8.2 |

The physical properties were measured after each of the compounds was prepared at a concentration of $10^{-5}$ M under a toluene solvent.

In Table 1, $\lambda_{uv,max}$ means the maximum absorption wavelength of the material in a solution state, $\lambda_{PL,max}$ means the maximum light emission wavelength of the material appearing in a solution and a thin film, and PLQY (%) means the fluorescence efficiency of the material appearing in a solution and thin film state.

The thin film light emission wavelength was measured by using FS-2 equipment manufactured by SCINCO Co., Ltd., and the quantum efficiency was measured by using Quantaurus-QY equipment manufactured by Hamamatsu Corp.

As confirmed in Table 1, it could be confirmed that the color conversion films manufactured in Examples 1 to 19 had better thin film quantum efficiencies than that of the color conversion film manufactured through the Comparative Example.

The invention claimed is:
1. A compound represented by the following Formula 1:

[Formula 1]

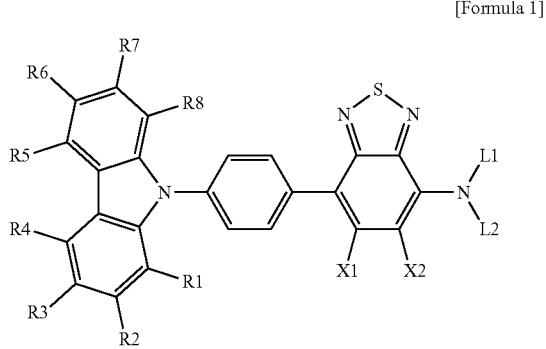

wherein R1 to R8 are the same as or different from each other, and are each independently hydrogen; deuterium; a halogen group; a substituted or unsubstituted alkyl group; a substituted or unsubstituted aryl group; a substituted or unsubstituted silyl group; or a substituted or unsubstituted heteroaryl group, or adjacent groups are optionally bonded to each other to form one or more rings, X1 and X2 are the same as or different from each other, and are each independently hydrogen; deuterium; a halogen group; a substituted or unsubstituted alkyl group; a substituted or unsubstituted aryl group; or a substituted or unsubstituted heteroaryl group, and L1 and L2 are the same as or different from each other, and are each independently a substituted or unsubstituted aryl group.

2. The compound of claim 1, wherein R1 to R8 are the same as or different from each other, and are each independently hydrogen; deuterium; a halogen group; a substituted or unsubstituted alkyl group having 1 to 30 carbon atoms; an aryl group having 6 to 30 carbon atoms, which is unsubstituted or substituted with one or more selected from the group consisting of a halogen group, a substituted or unsubstituted alkyl group having 1 to 30 carbon atoms, a substituted or unsubstituted alkoxy group having 1 to 30 atoms, a substituted or unsubstituted silyl group, a substituted or unsubstituted aryl group having 6 to 30 carbon atoms, and a substituted or unsubstituted heteroaryl group having 2 to 30 carbon atoms; a silyl group which is substituted with an alkyl group; a carbazolyl group; a substituted or unsubstituted dihydroacridine group; a phenothiazine group; a phenoxazine group; or a dibenzofuranyl group, or adjacent groups are bonded to each other to form one or more substituted or unsubstituted rings having 3 to 30 carbon atoms.

3. The compound of claim 1, wherein L1 and L2 are the same as or different from each other, and are each independently an aryl group having 6 to 30 carbon atoms, which is unsubstituted or substituted with one or more selected from the group consisting of a halogen group, a cyano group, a substituted or unsubstituted amine group having 1 to 30 carbon atoms, a substituted or unsubstituted alkyl group having 1 to 30 carbon atoms, a substituted or unsubstituted alkenyl group having 2 to 30 carbon atoms, a substituted or unsubstituted alkoxy group having 1 to 30 carbon atoms, a substituted or unsubstituted silyl group, a substituted or unsubstituted arylalkenyl group, a substituted or unsubstituted aryl group having 6 to 30 carbon atoms, and a substituted or unsubstituted heteroaryl group having 2 to 30 carbon atoms.

4. The compound of claim 1, wherein the compound of Formula 1 is represented by any one of the following structural formulae:

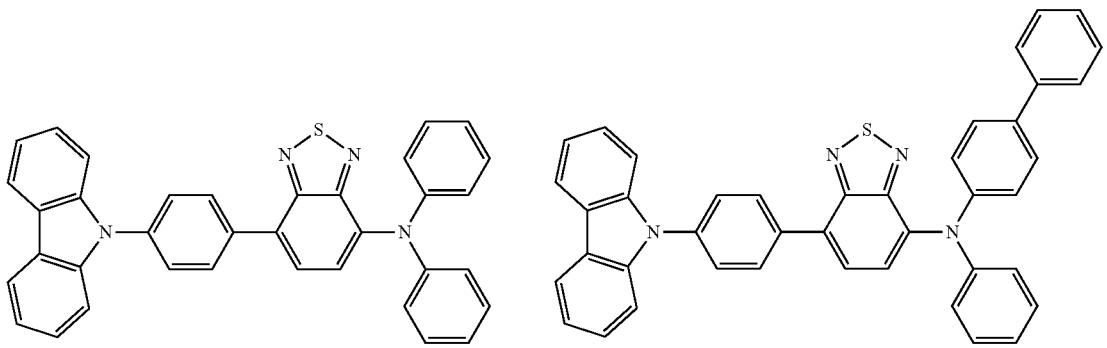

255 256
-continued
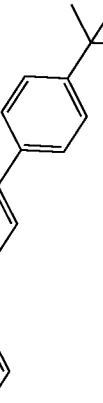
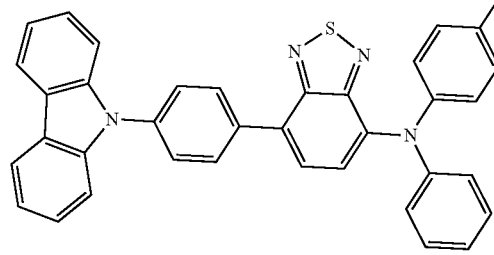
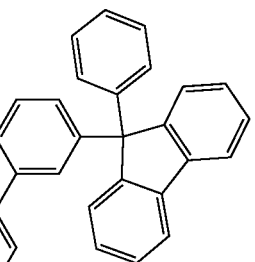
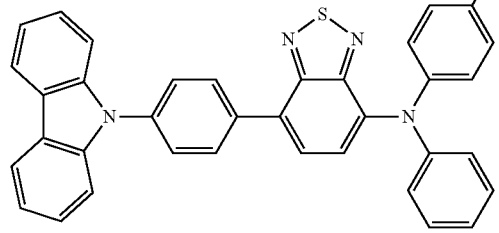
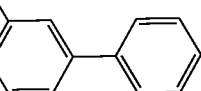
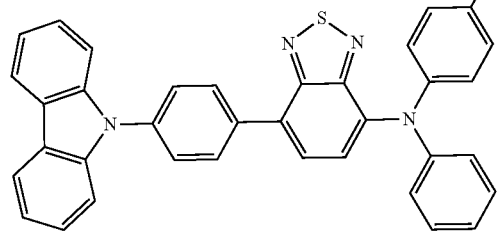
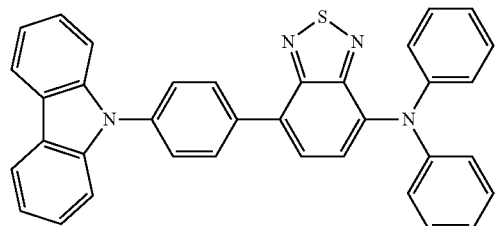
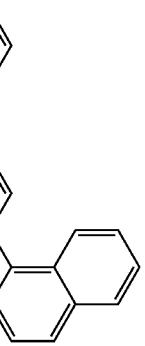
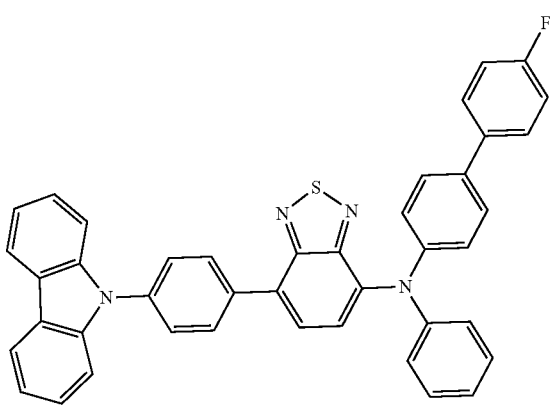

-continued
257 258
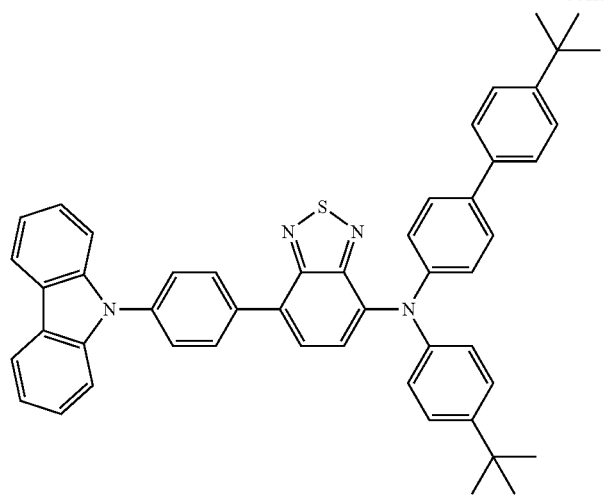
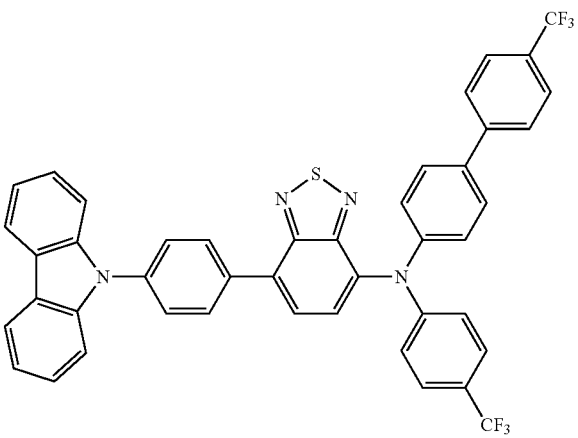
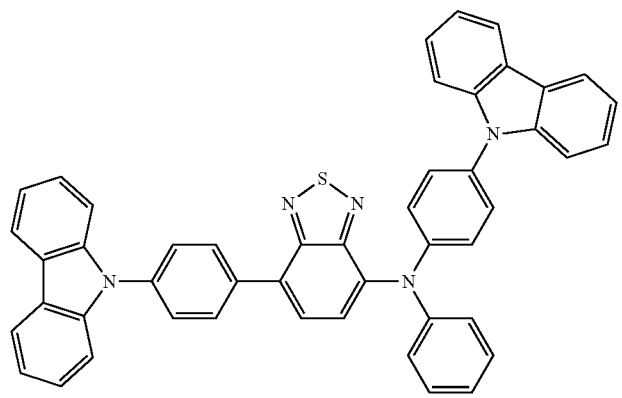
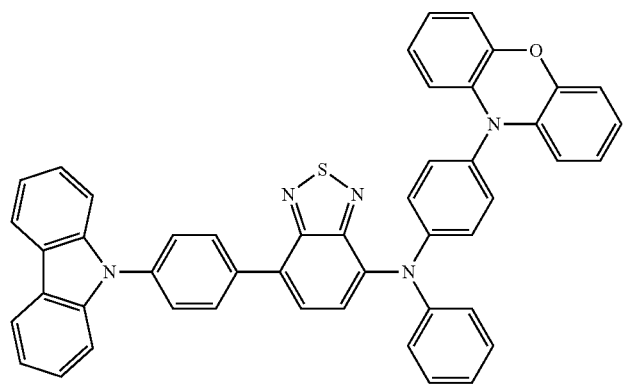

-continued
259
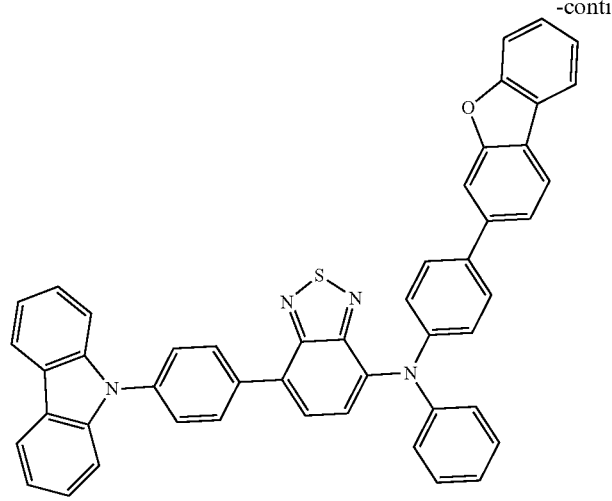
260
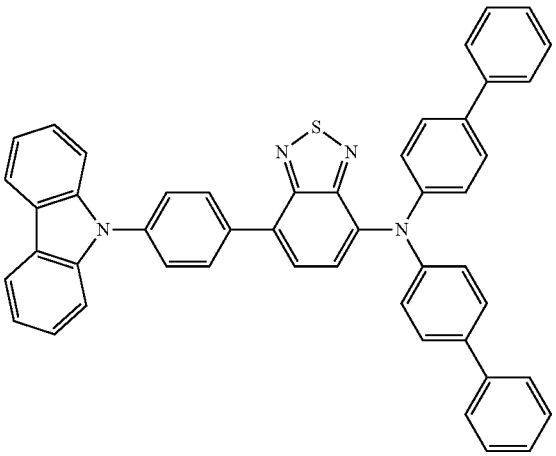
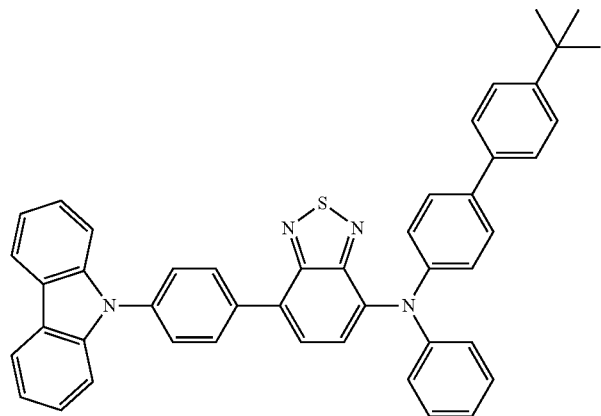
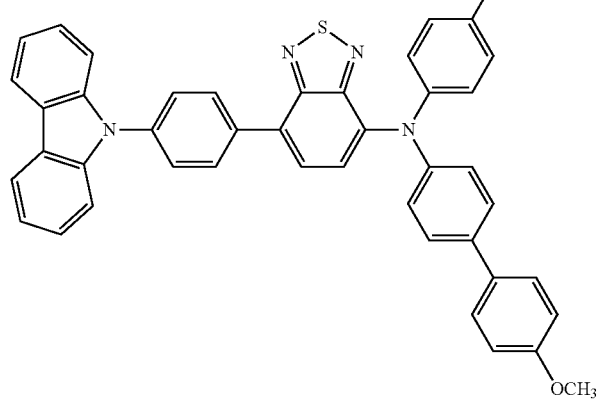

-continued
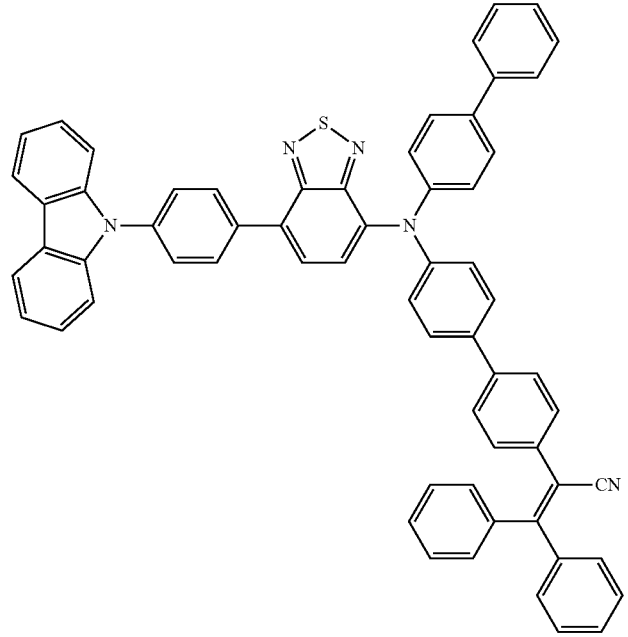
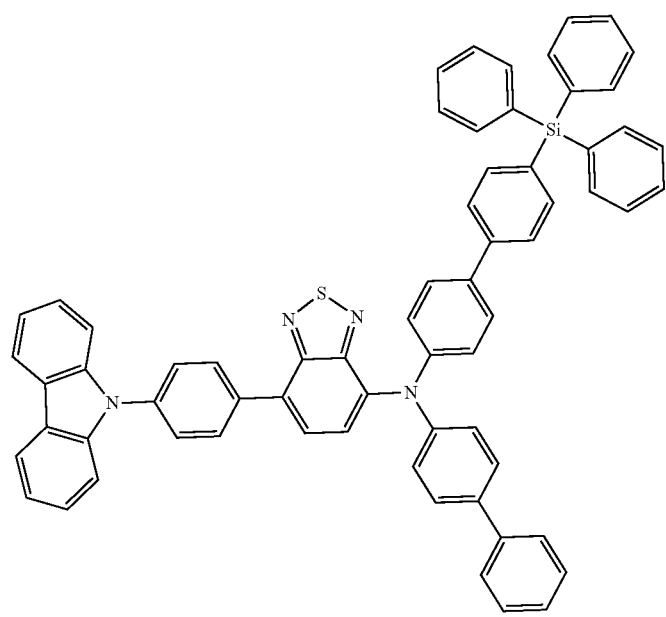

-continued
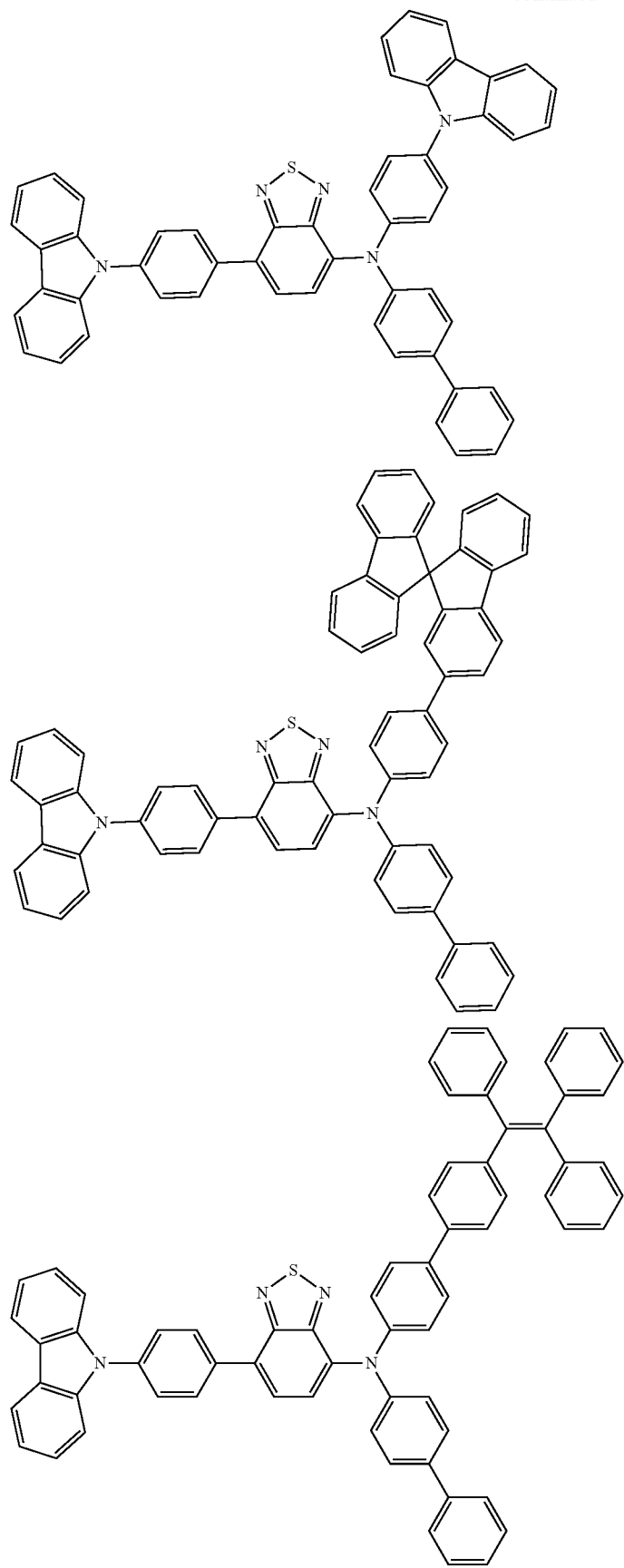

-continued
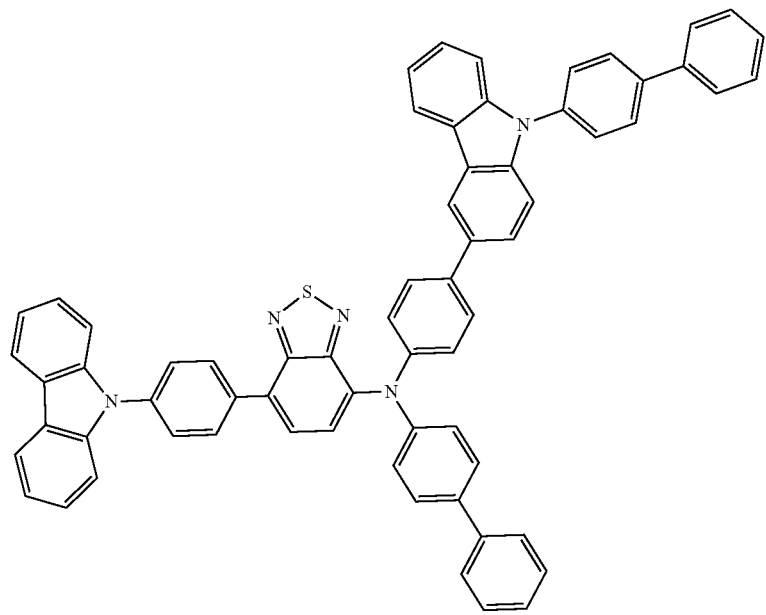
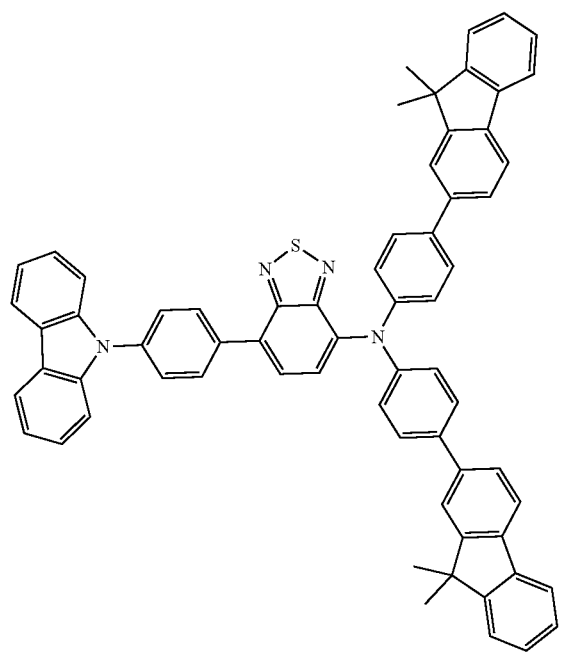

-continued
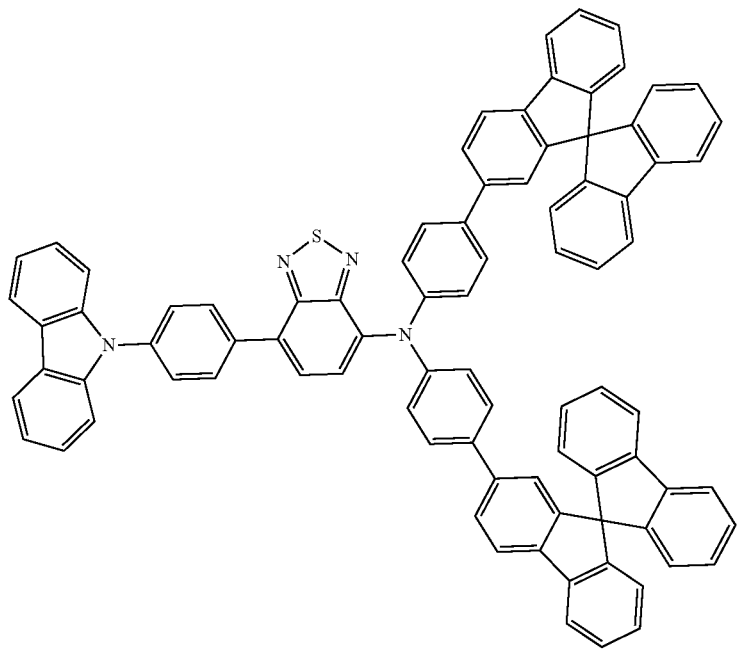
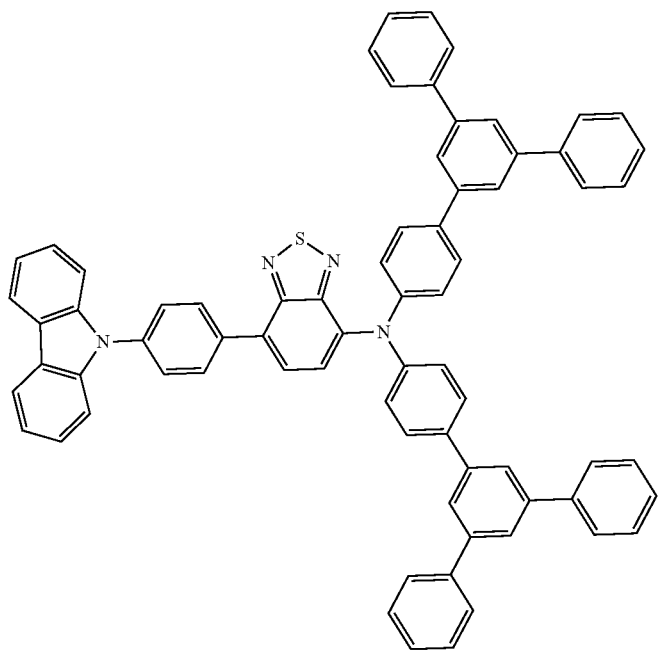

-continued
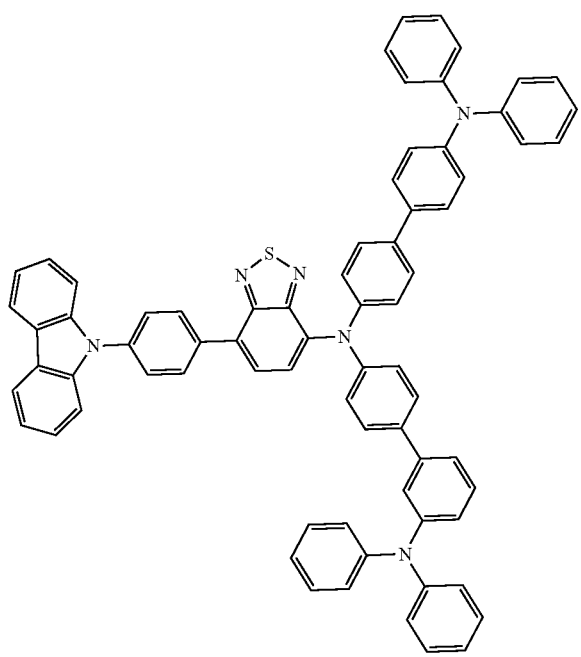 [SMILES: c1ccc(N(c2ccccc2)c2ccc(-c3ccc(N(c4ccc(-c5cccc(N(c6ccccc6)c6ccccc6)c5)cc4)c4ccc(-c5ccc(-n6c7ccccc7c7ccccc76)cc5)c5nsnc45)cc3)cc2)cc1]
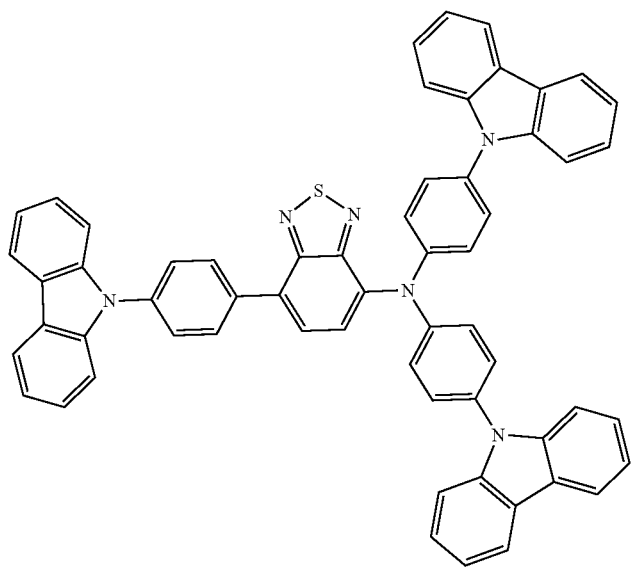

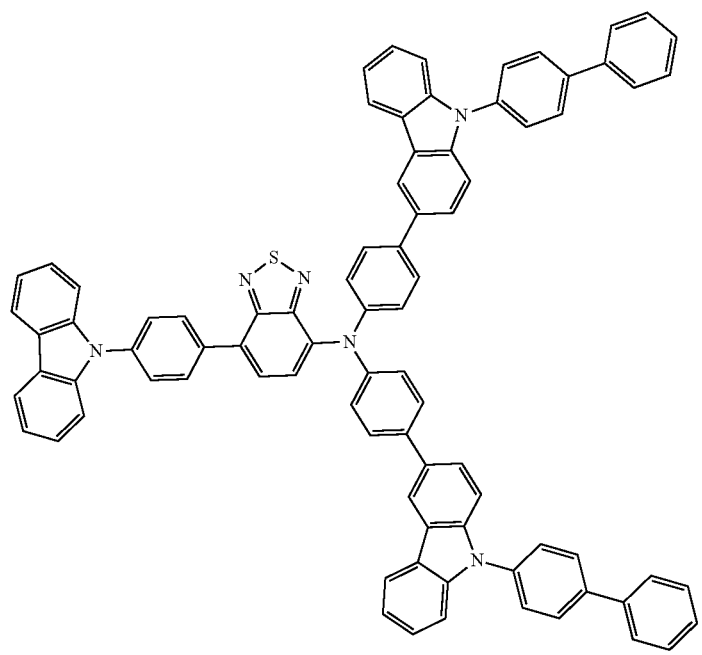
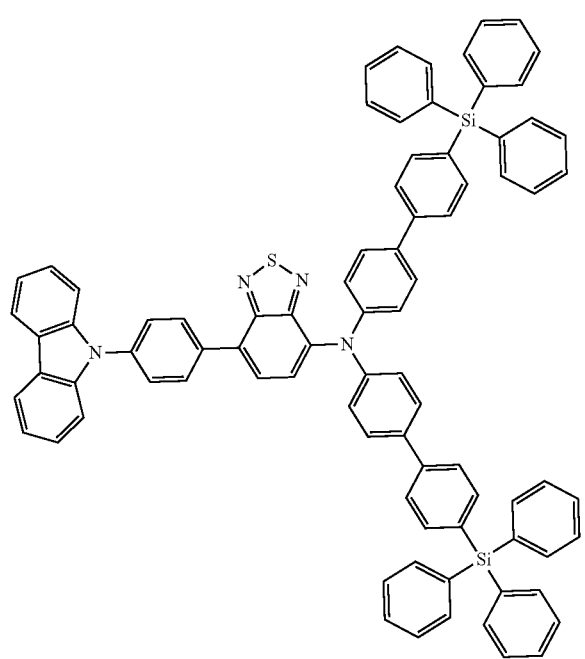

-continued
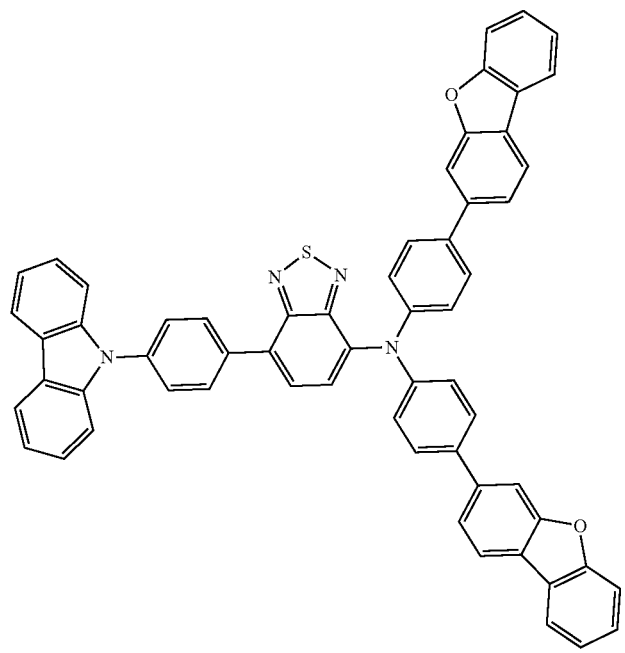
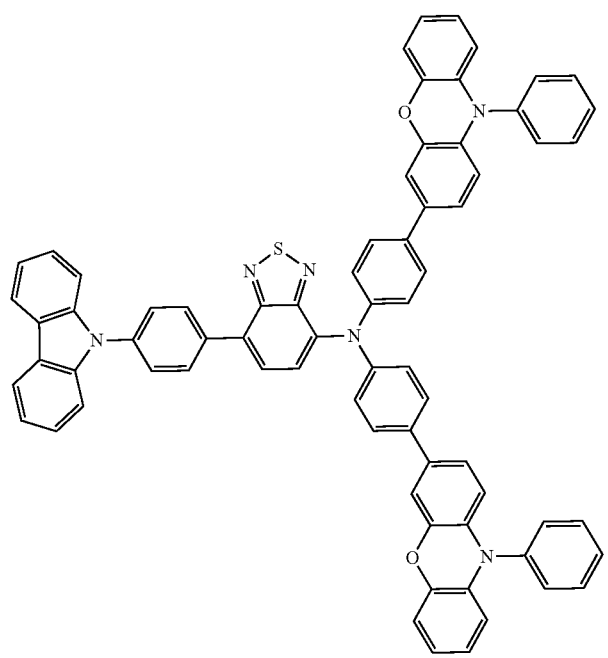

-continued
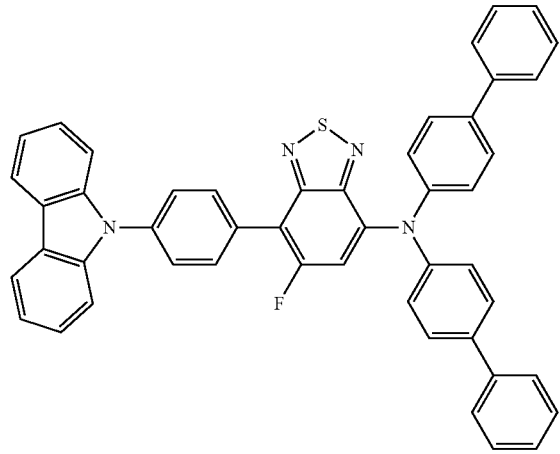
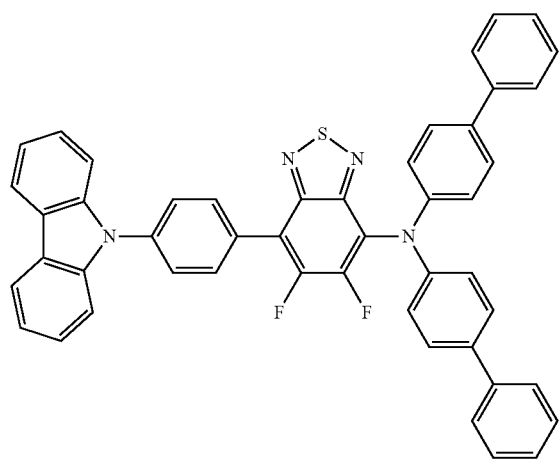
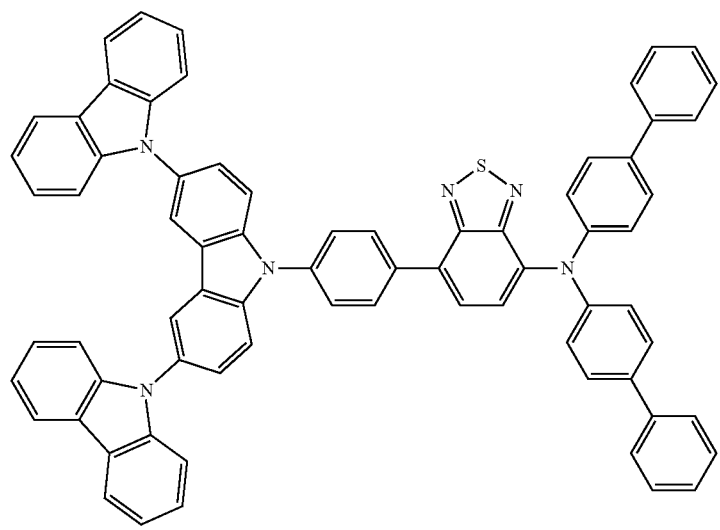

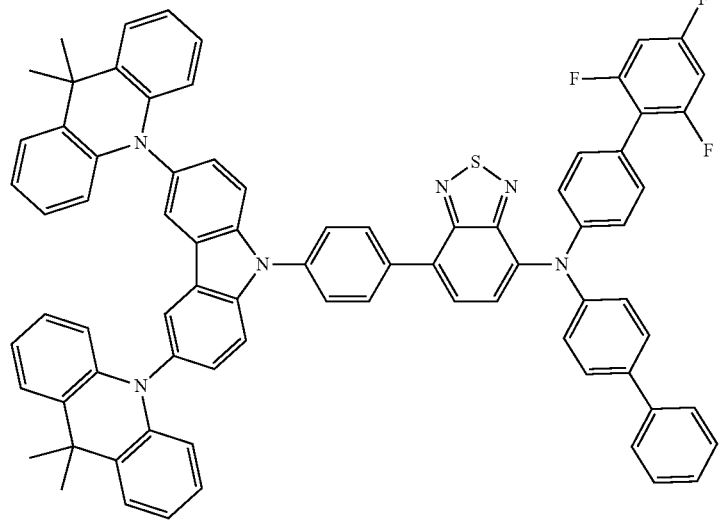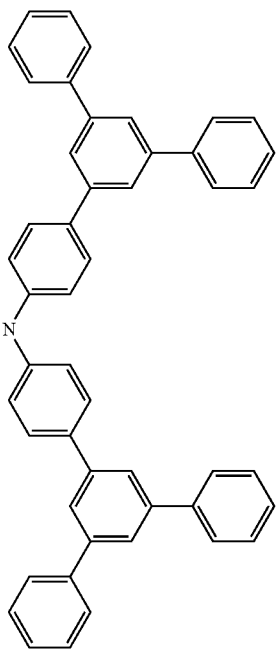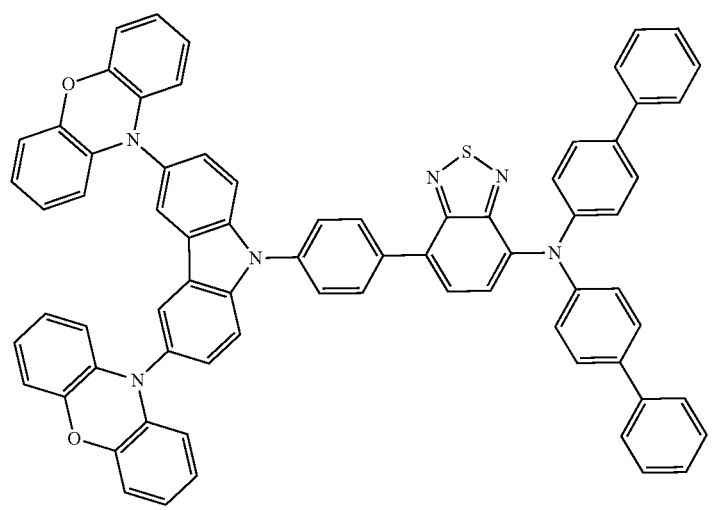

-continued
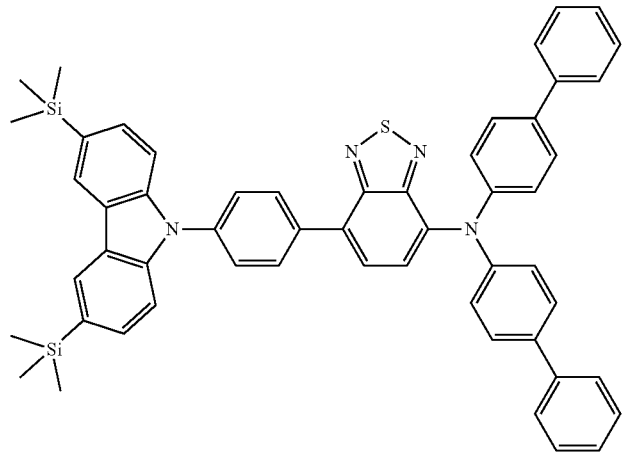
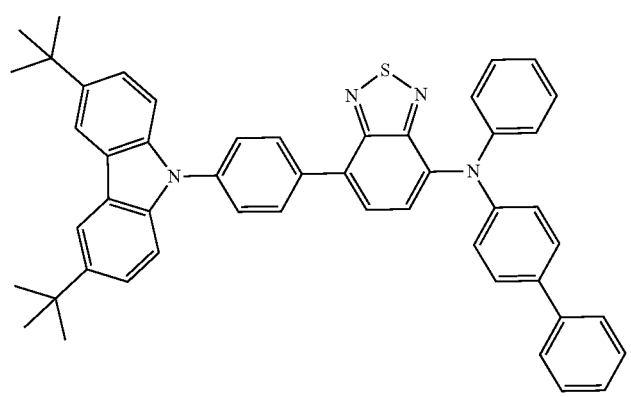
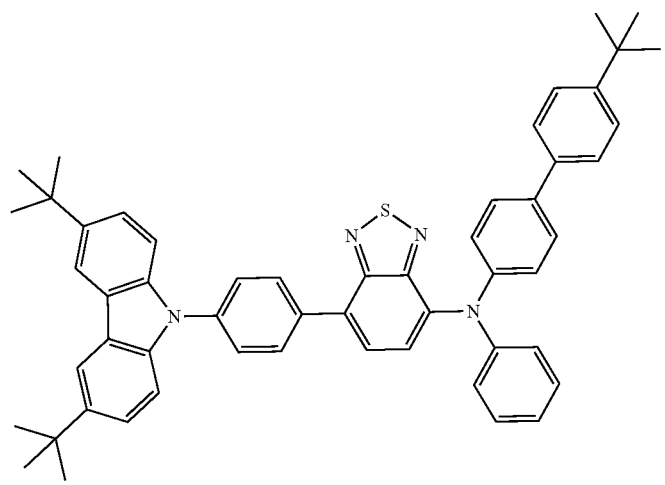

-continued
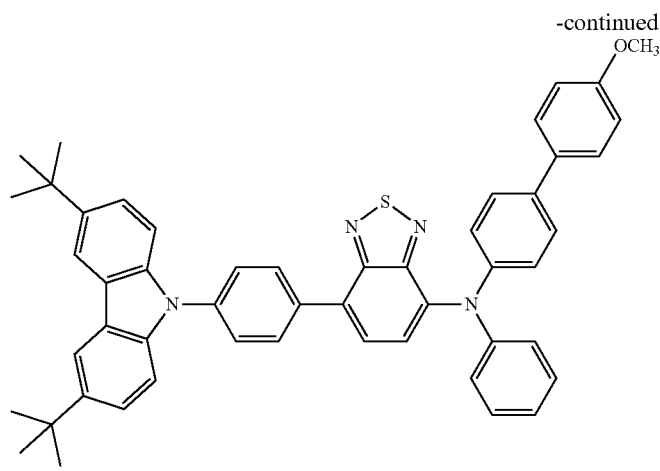
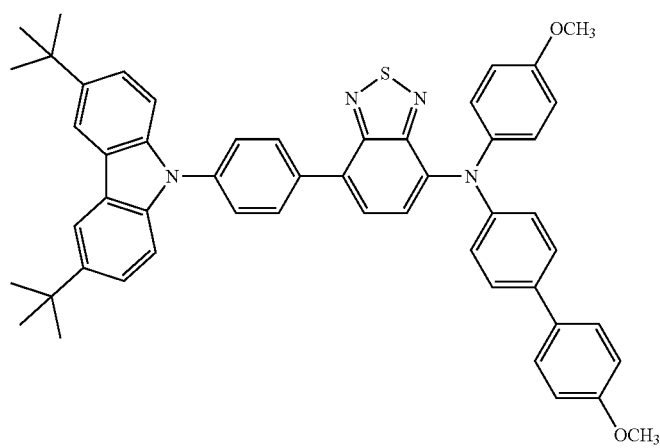
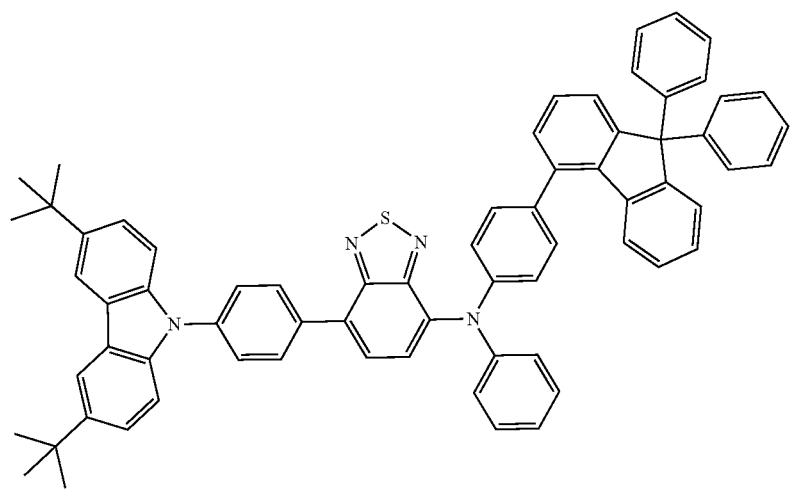

-continued
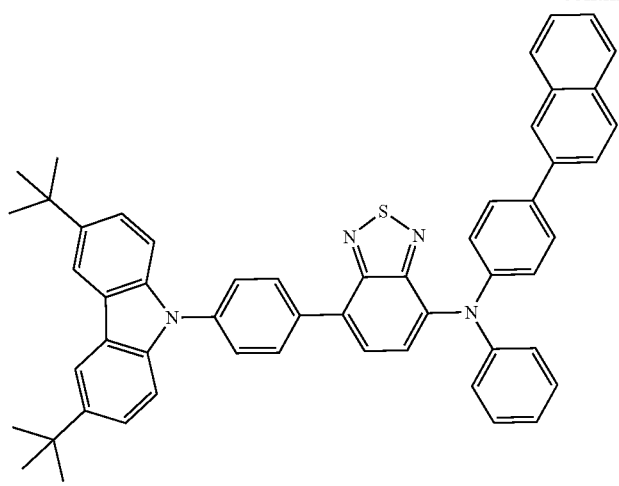
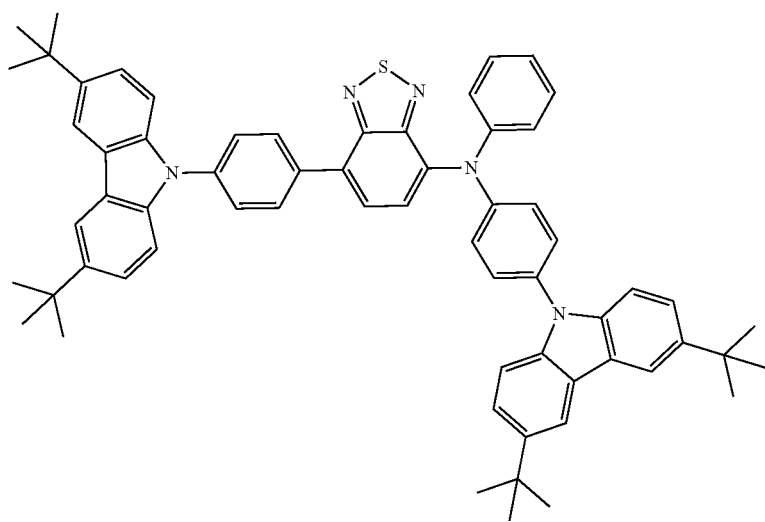
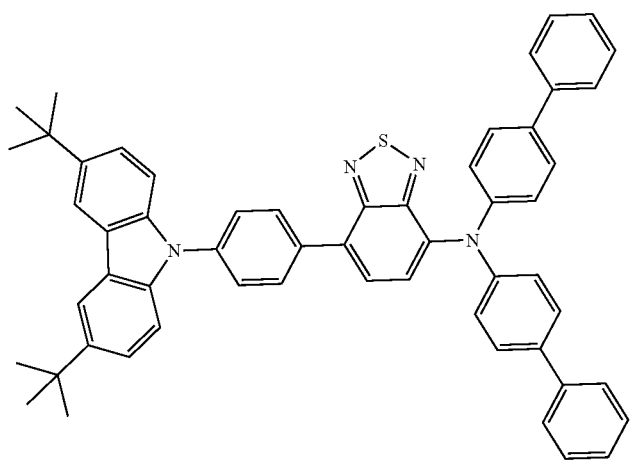

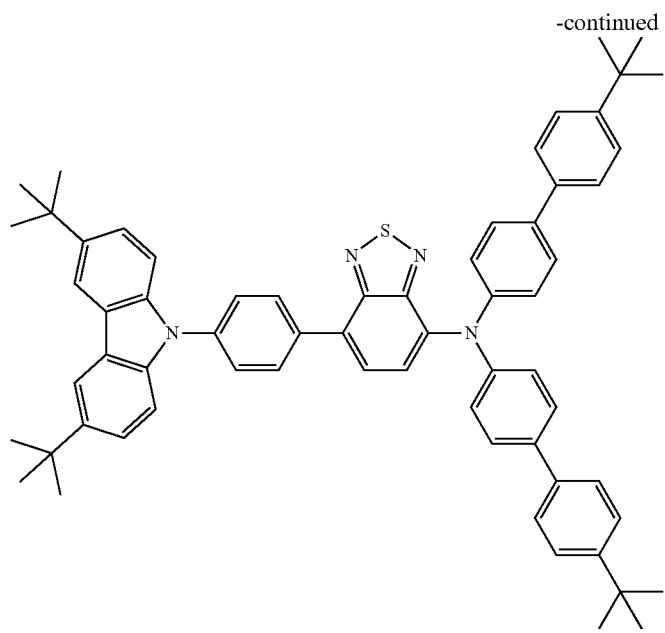
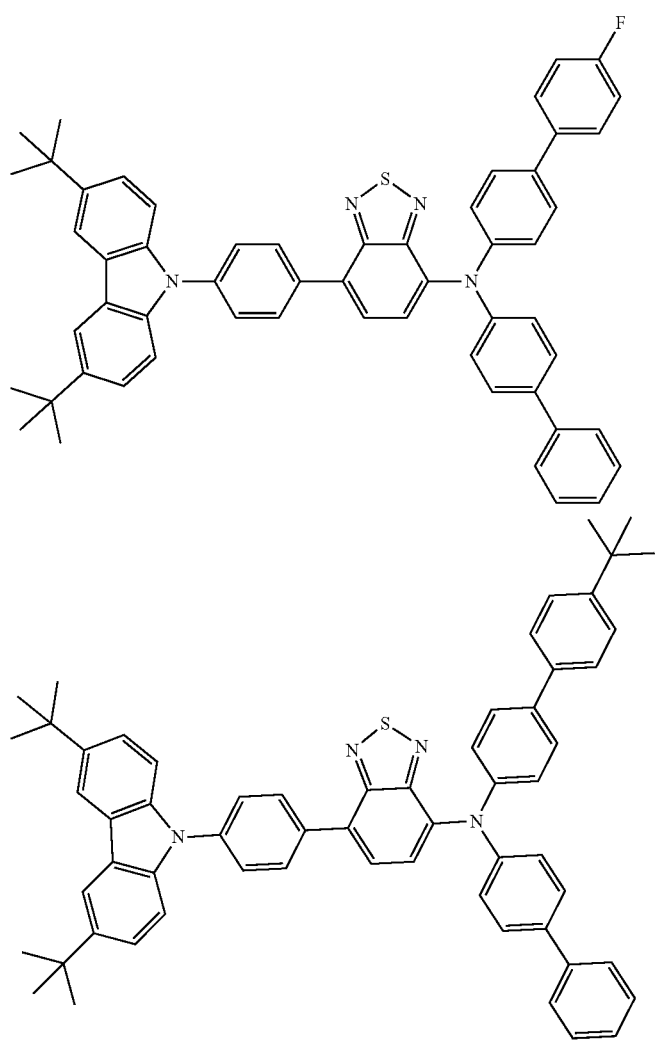

-continued
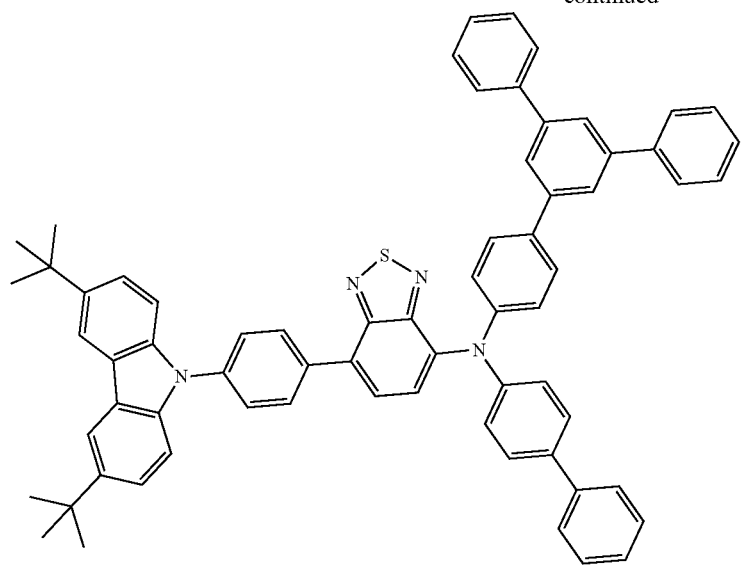
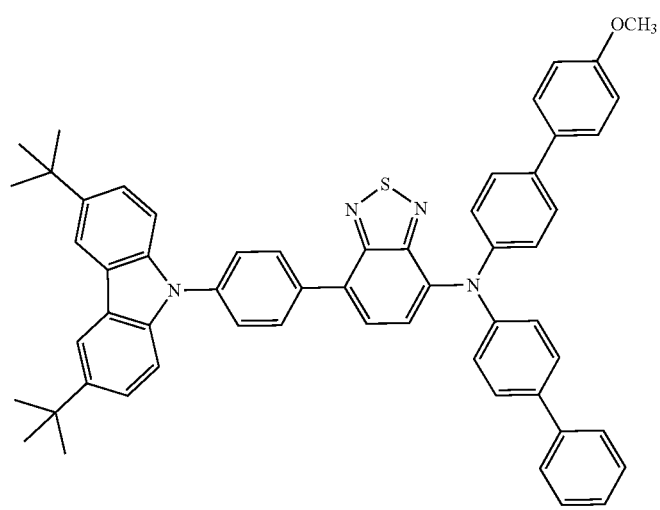
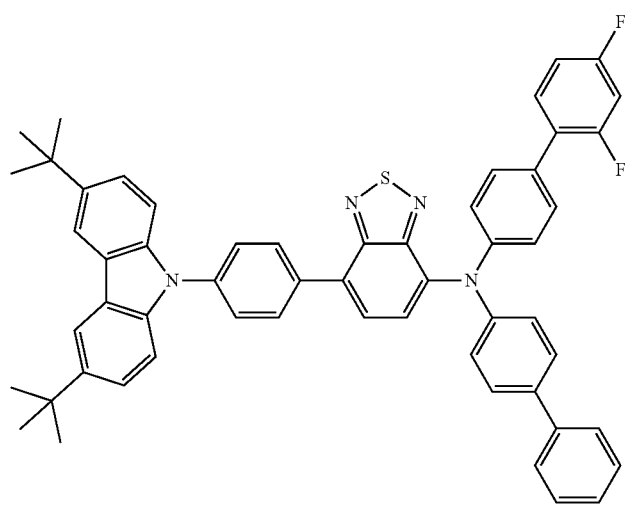 [SMILES: CC(C)(C)c1ccc2c(c1)c1cc(C(C)(C)C)ccc1n2-c1ccc(-c2ccc(N(c3ccc(-c4ccccc4)cc3)c3ccc(-c4ccc(F)cc4F)cc3)c3nsnc23)cc1]

-continued
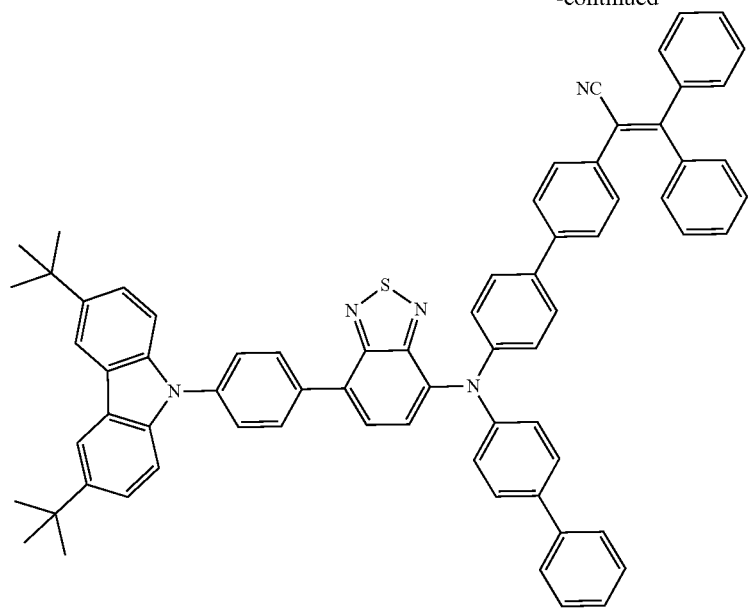
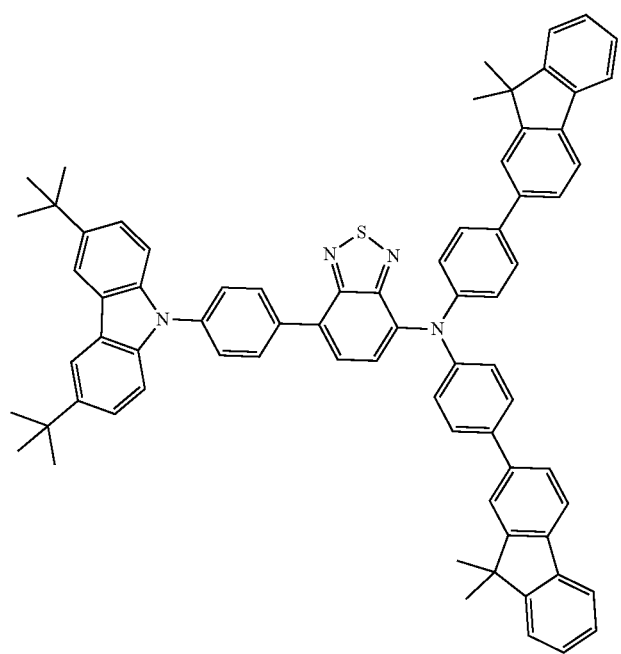

-continued
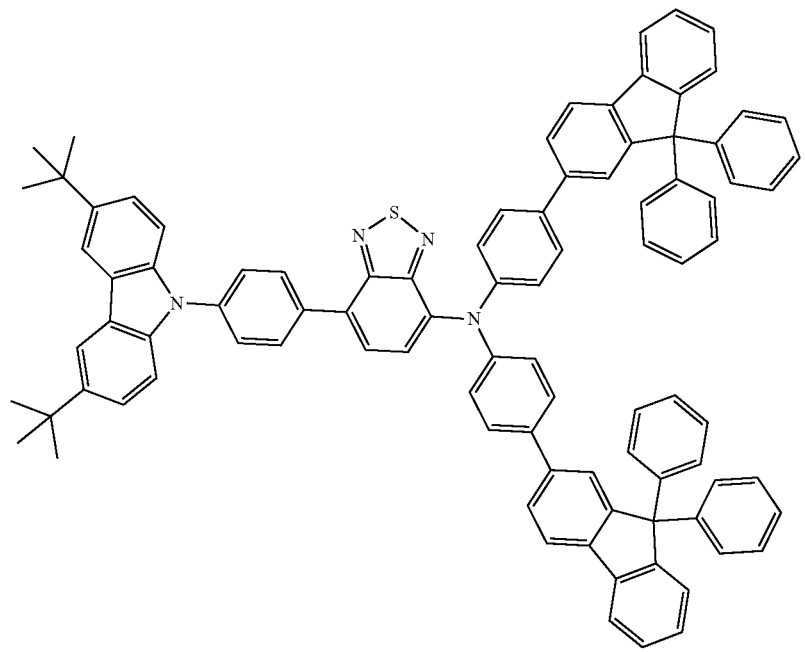
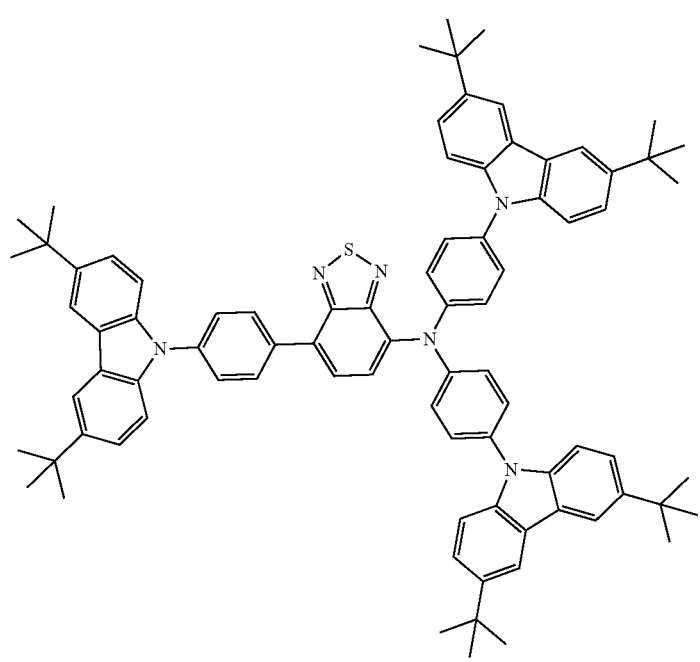

-continued
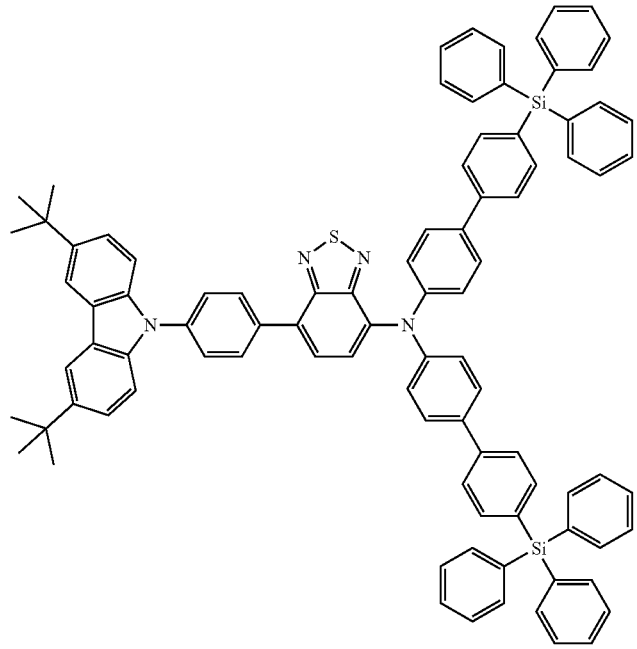
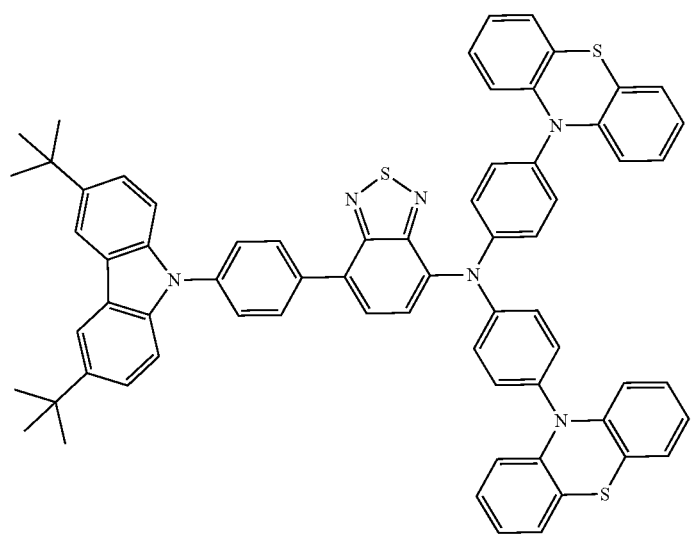

-continued
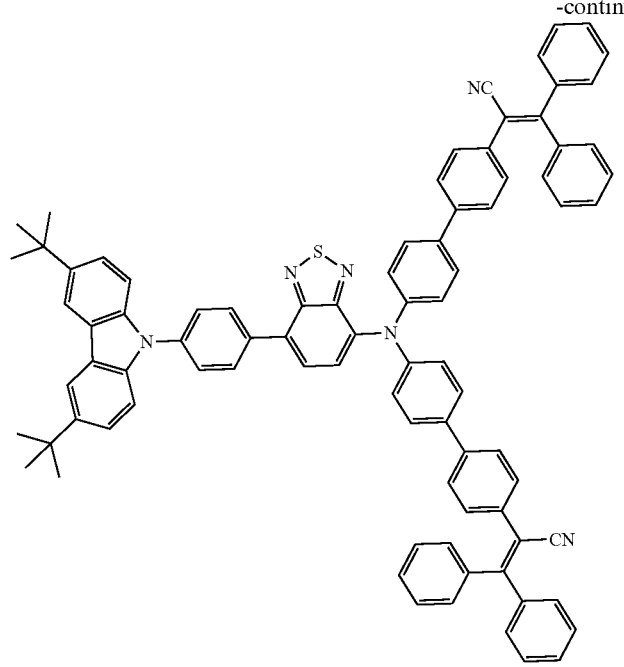
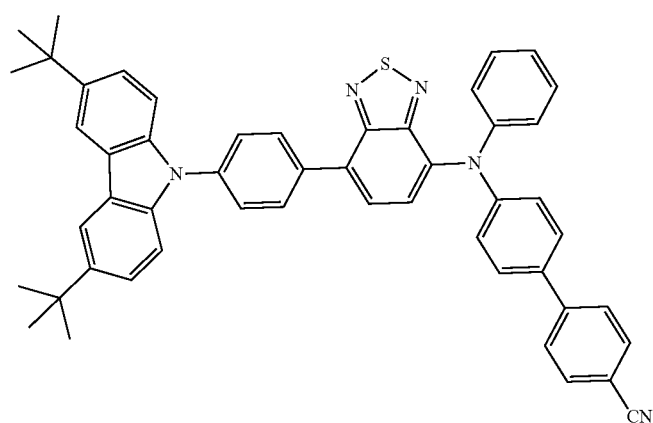
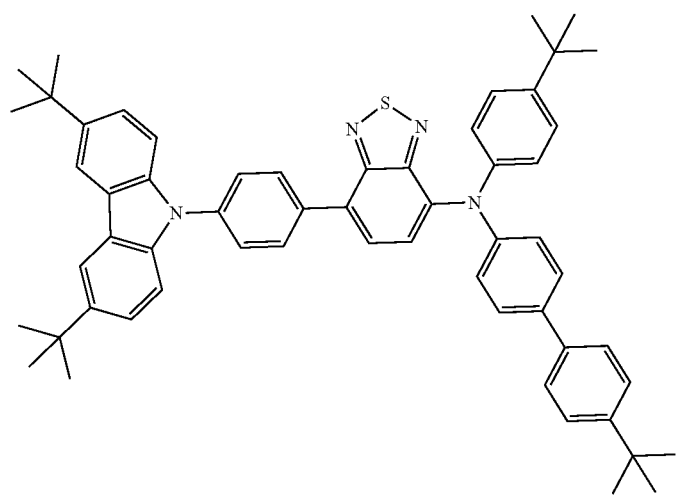

-continued
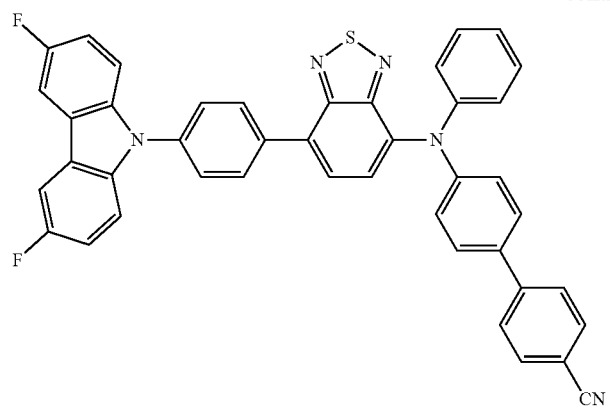
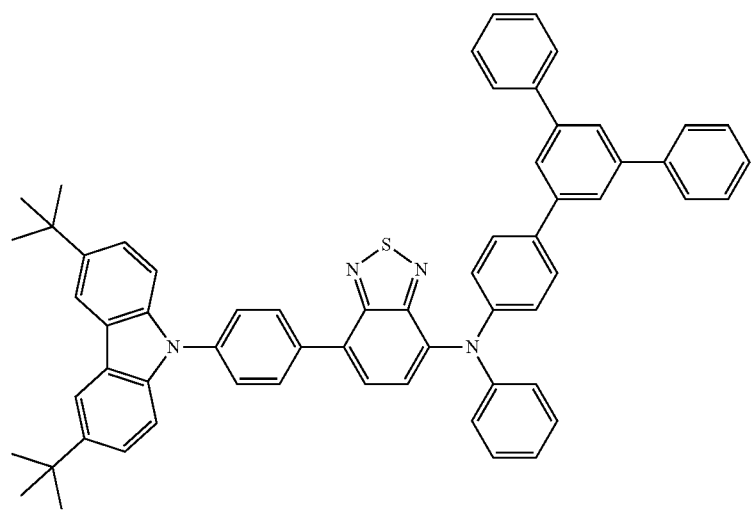
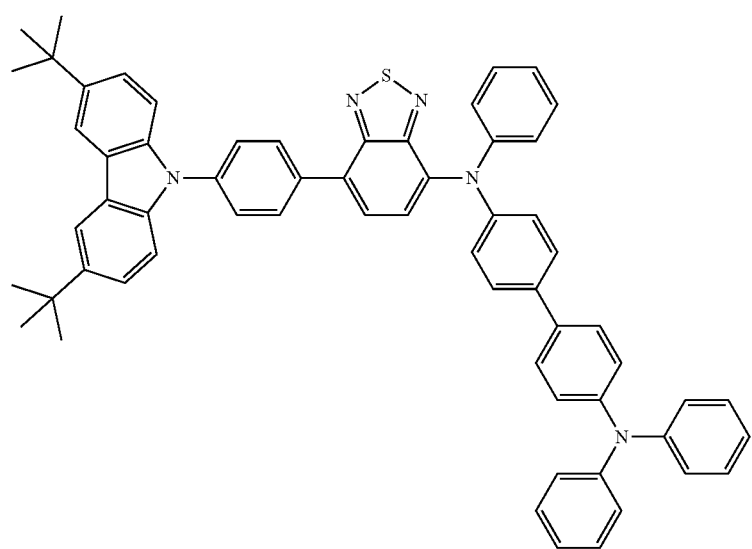

-continued
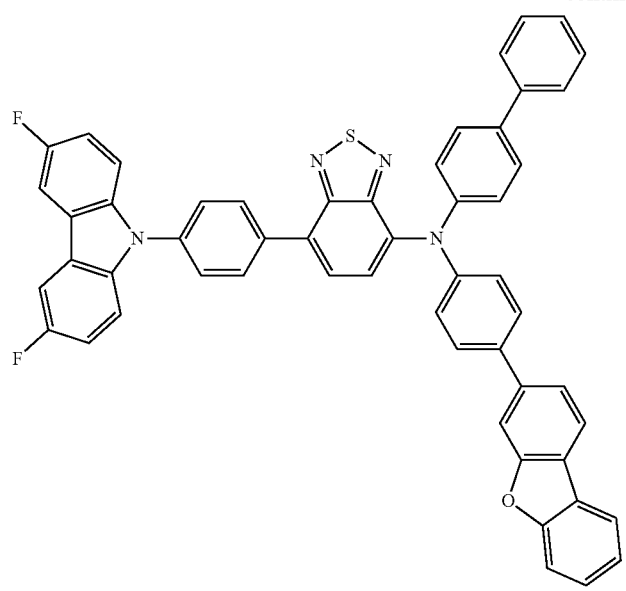
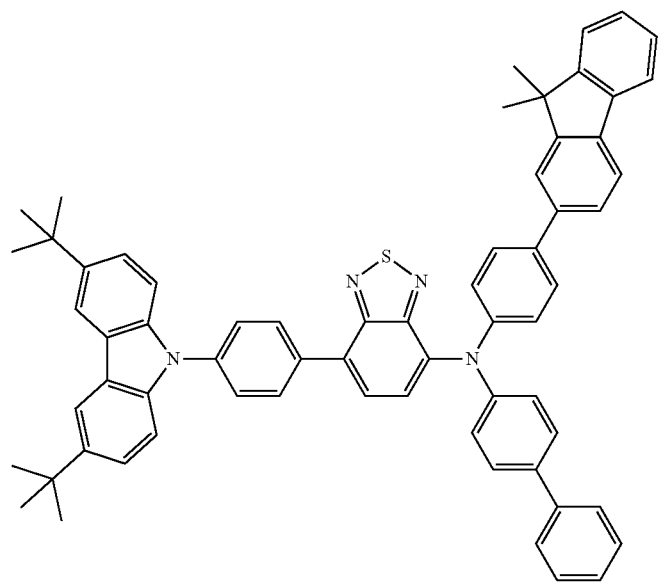

-continued
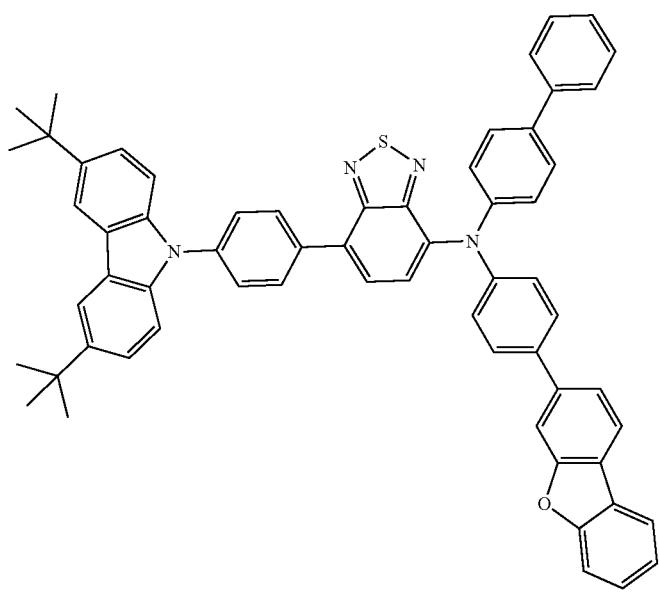
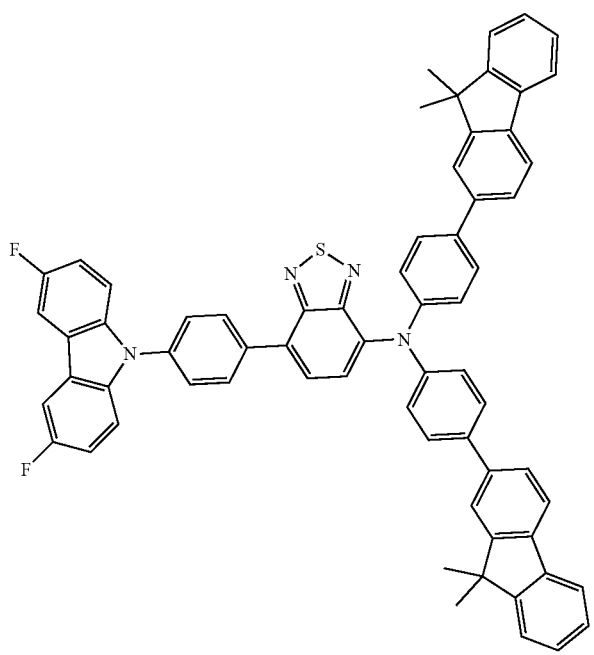

-continued
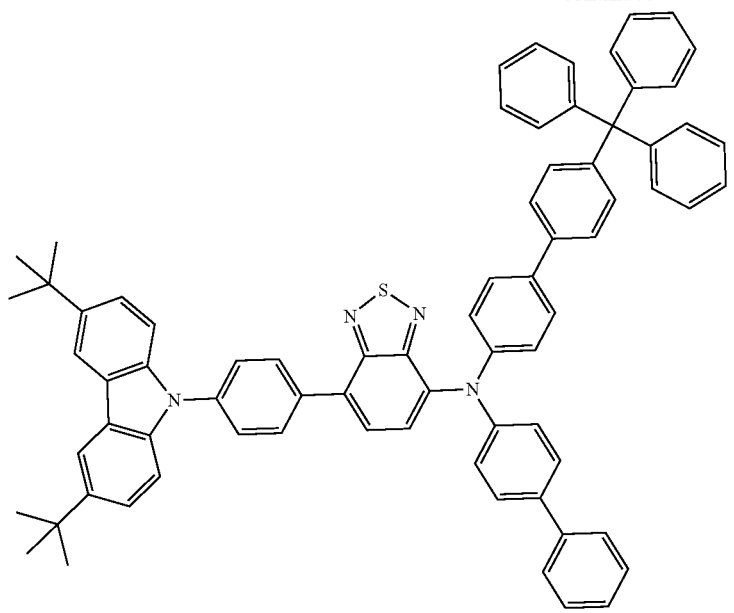
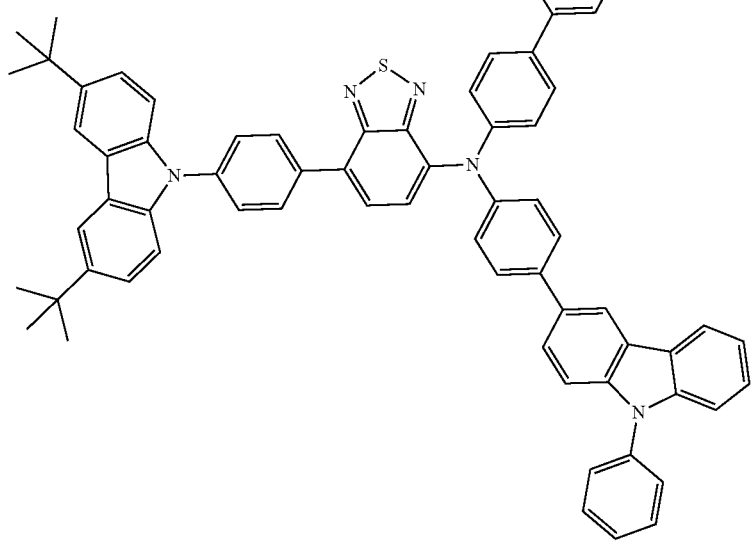
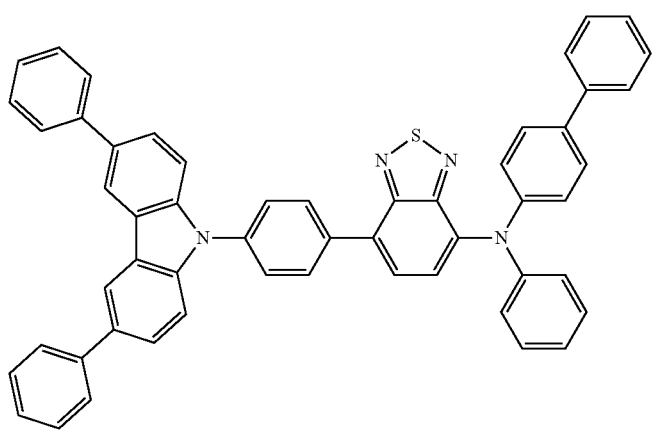

-continued
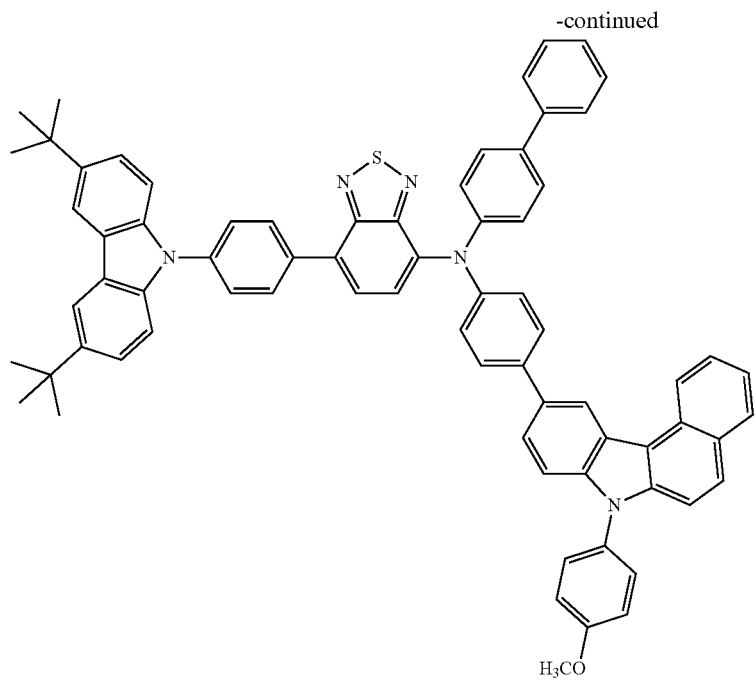
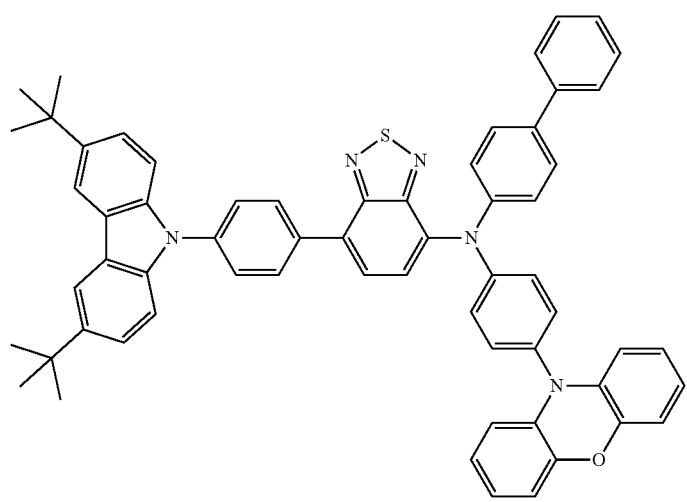
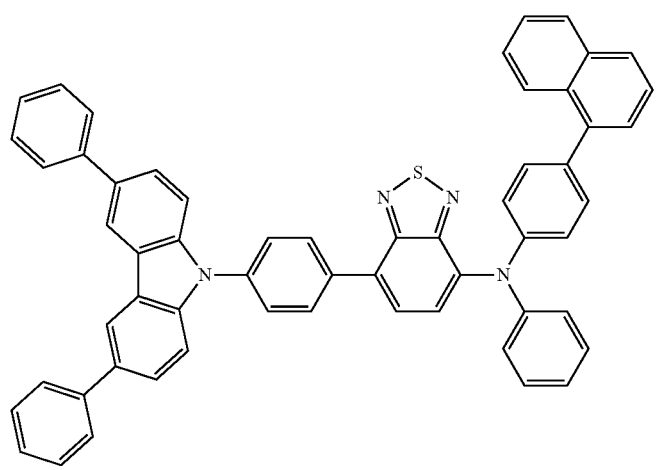

-continued
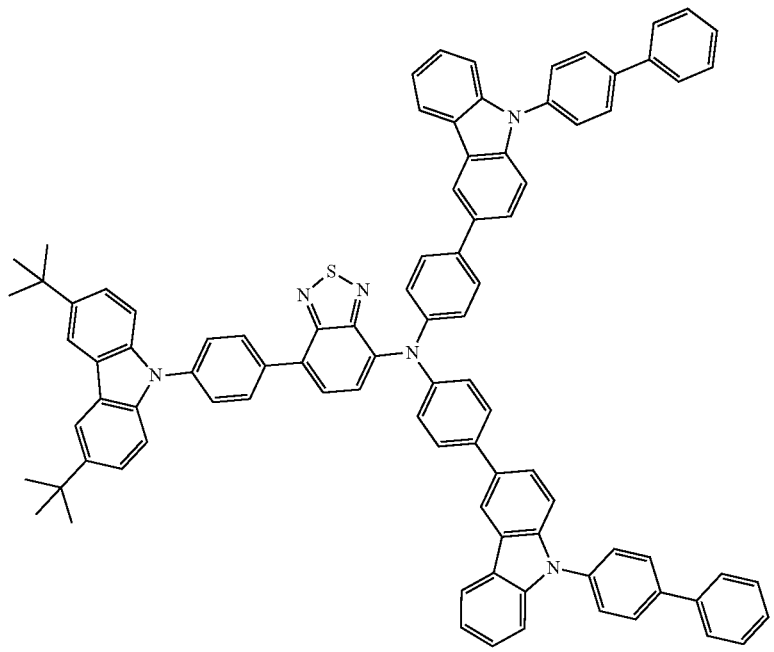
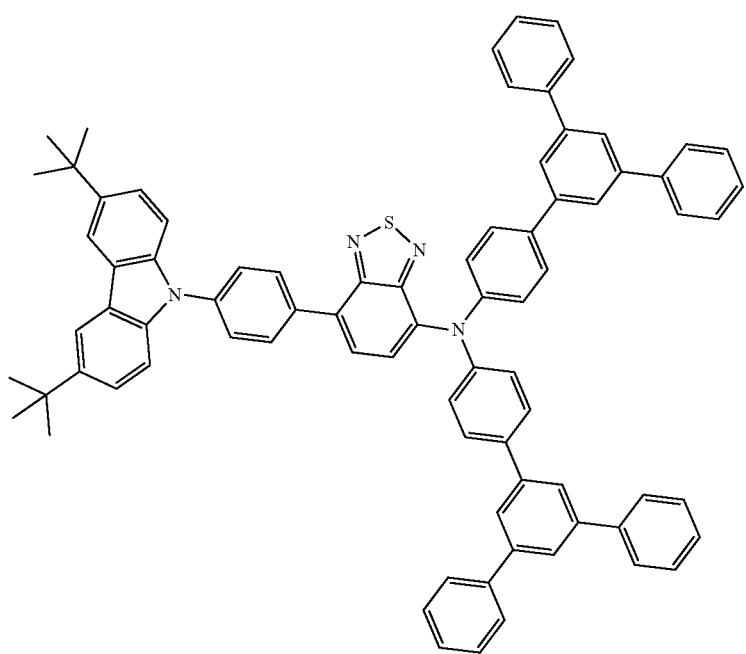

-continued
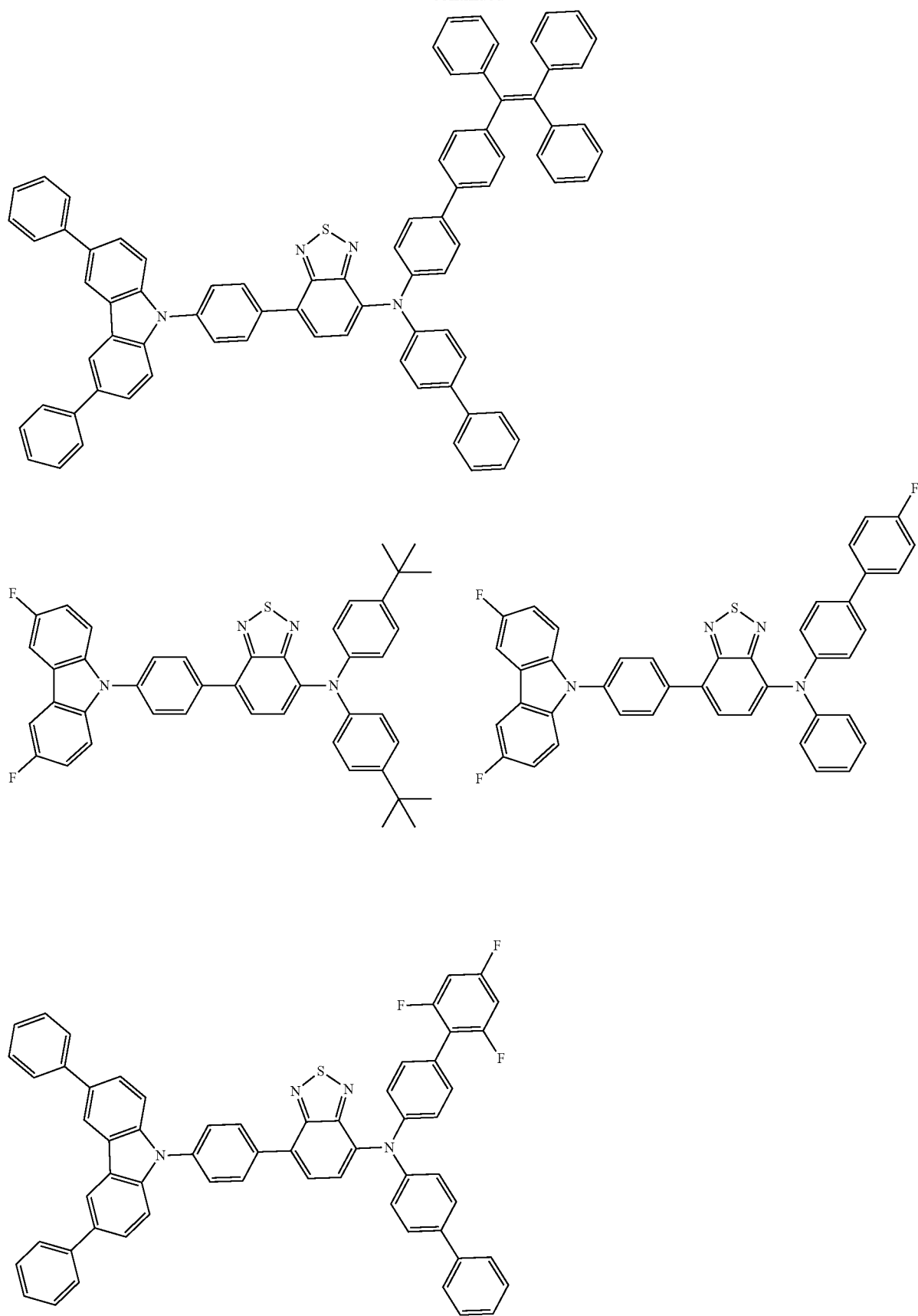

-continued
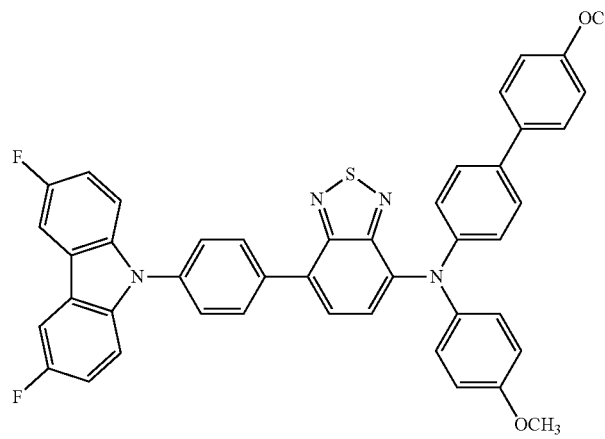
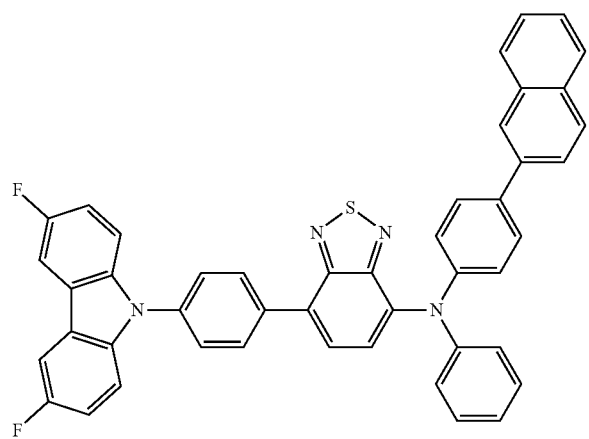
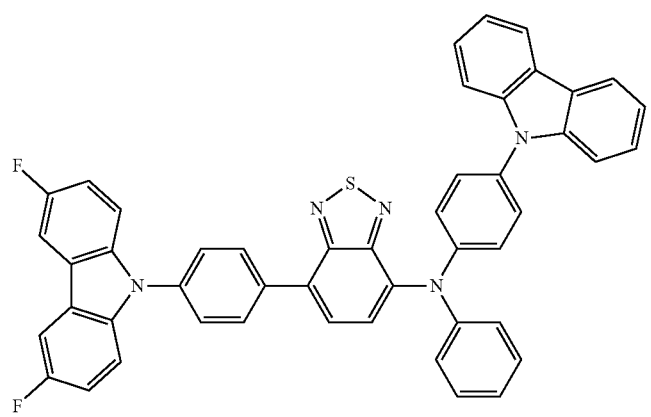

-continued
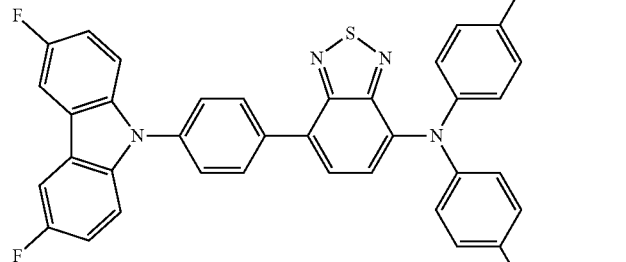
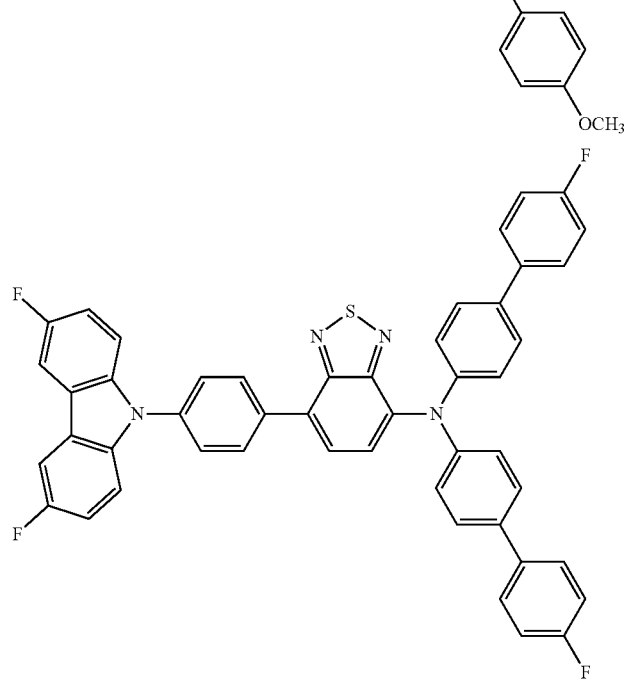
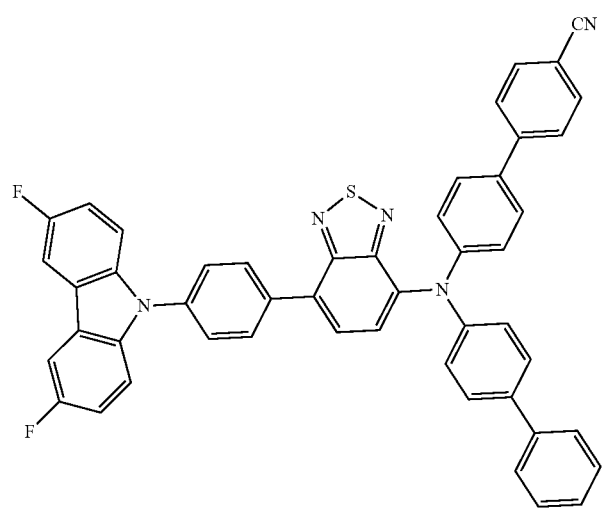

-continued
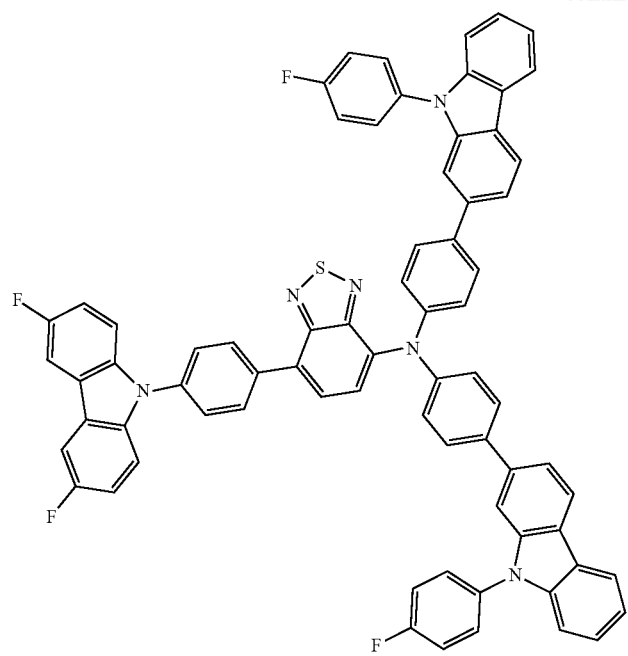
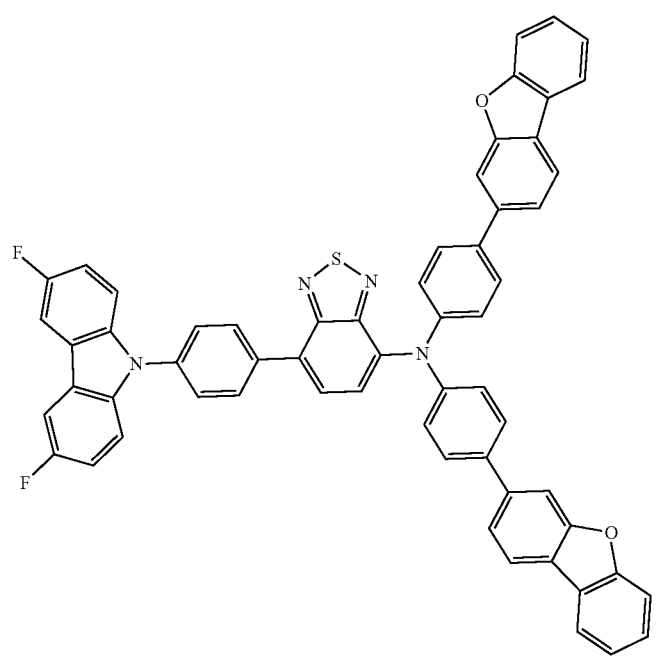

-continued
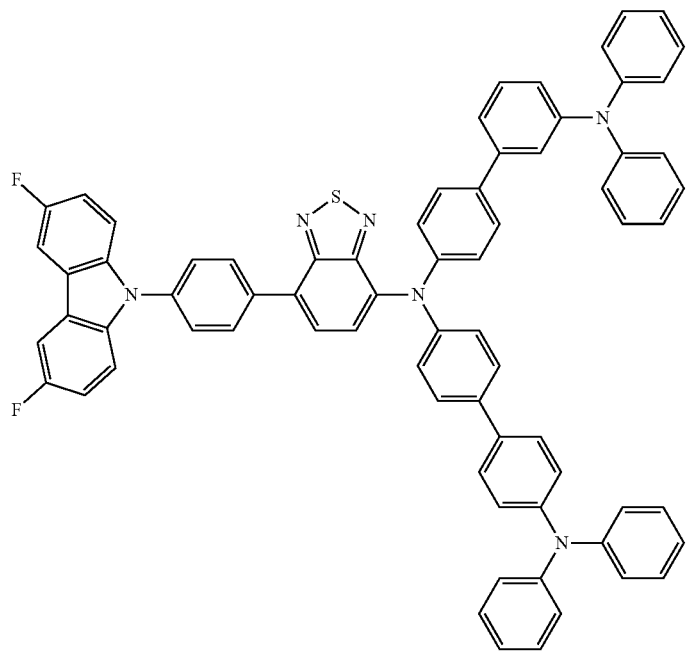
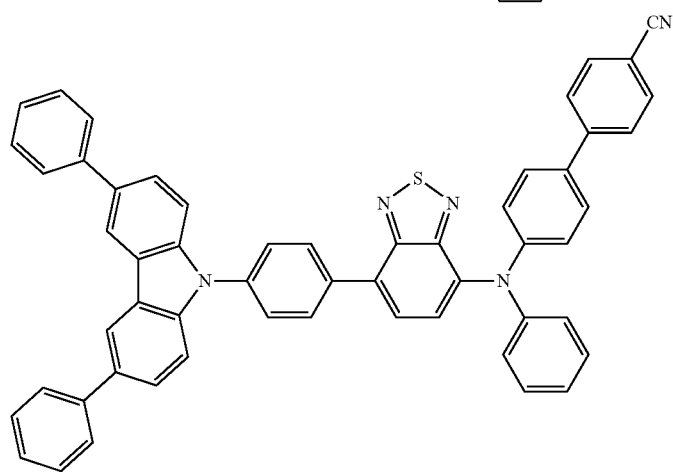
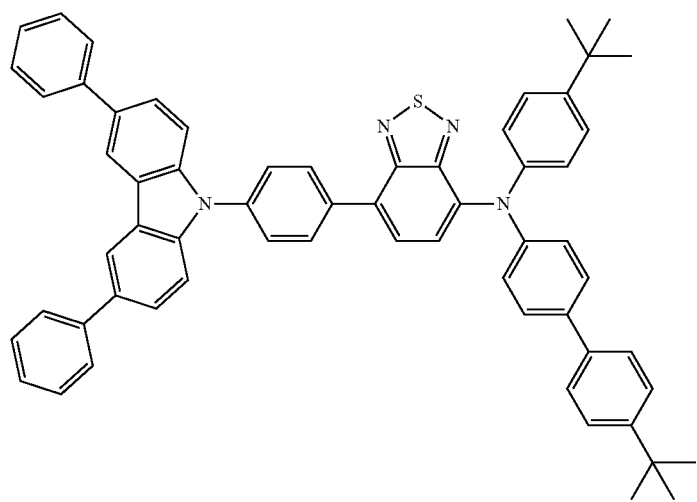

-continued
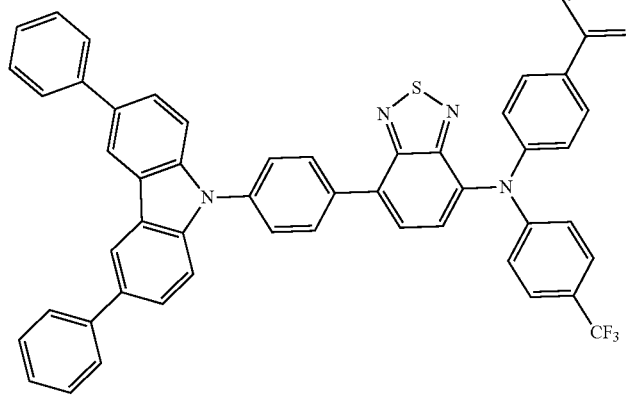
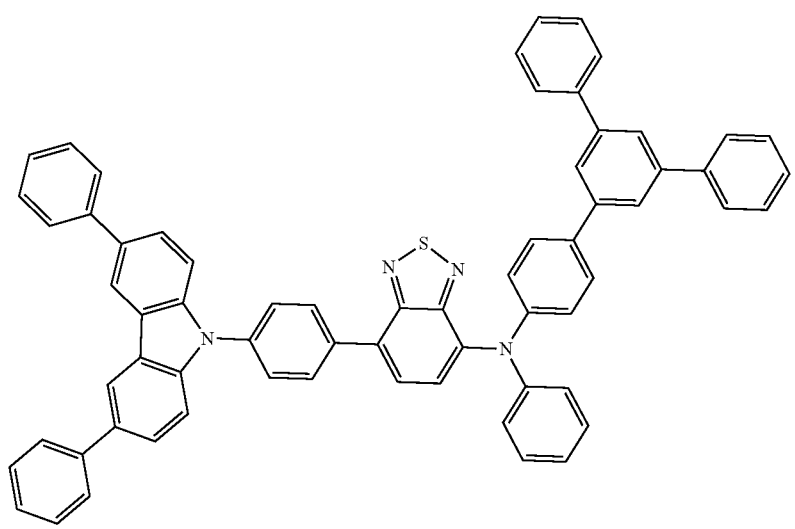
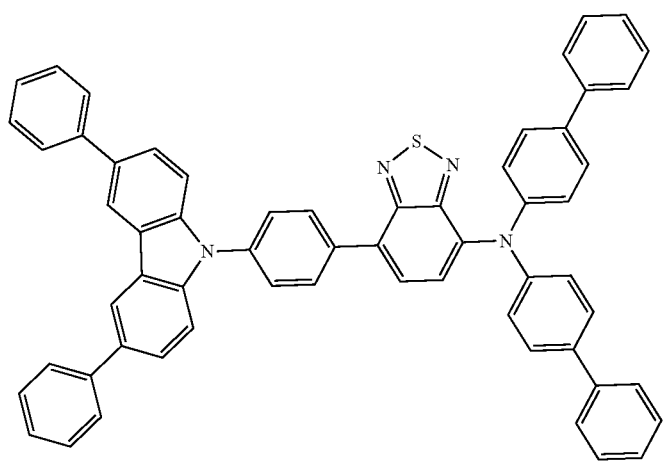

-continued
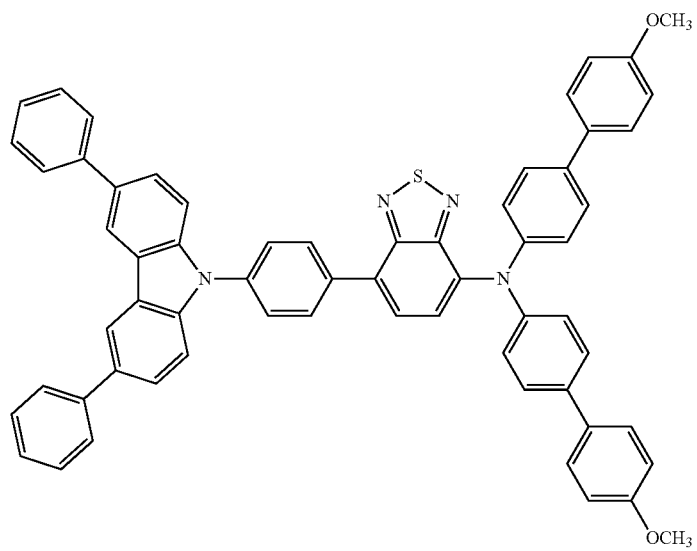
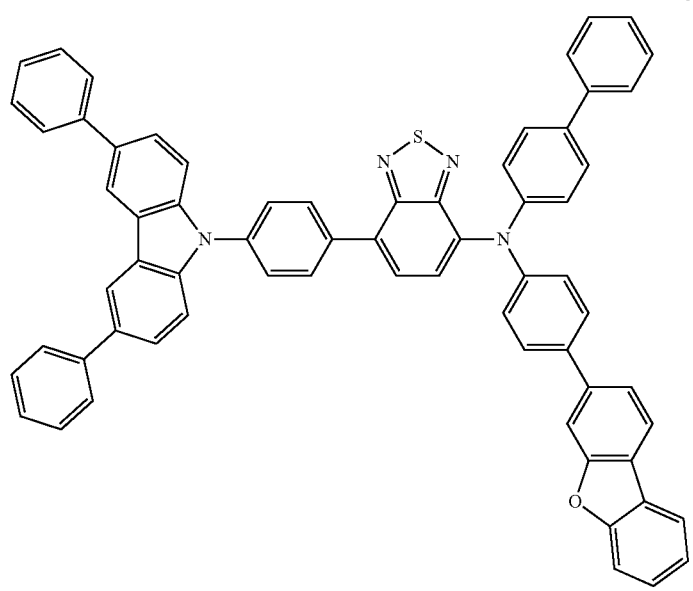
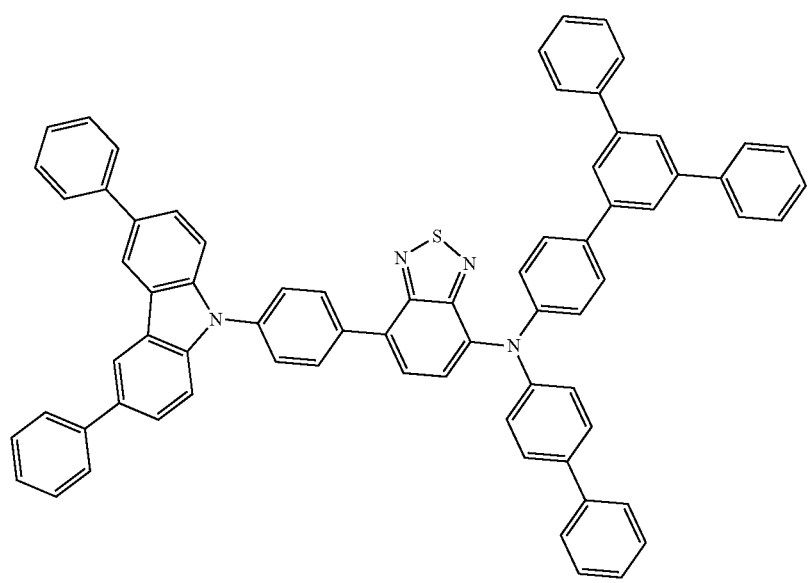

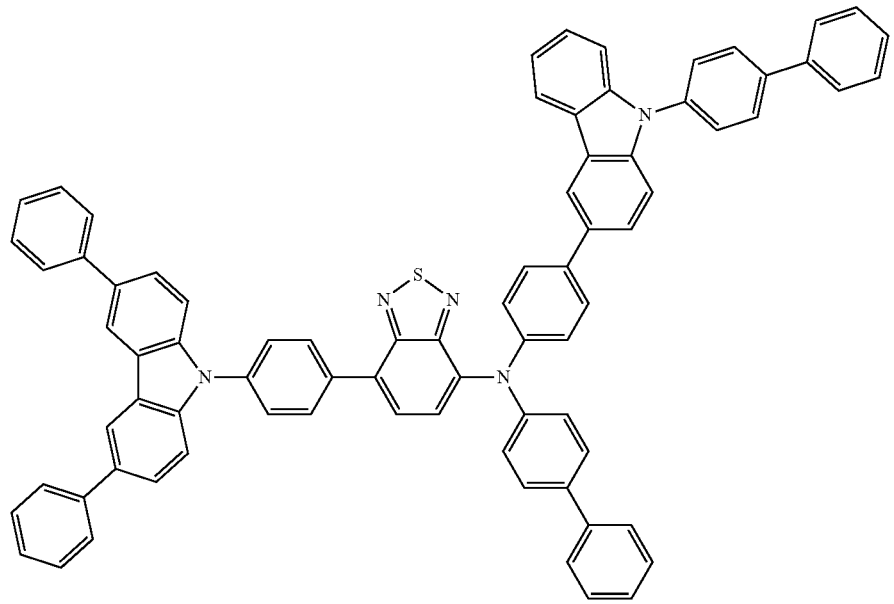
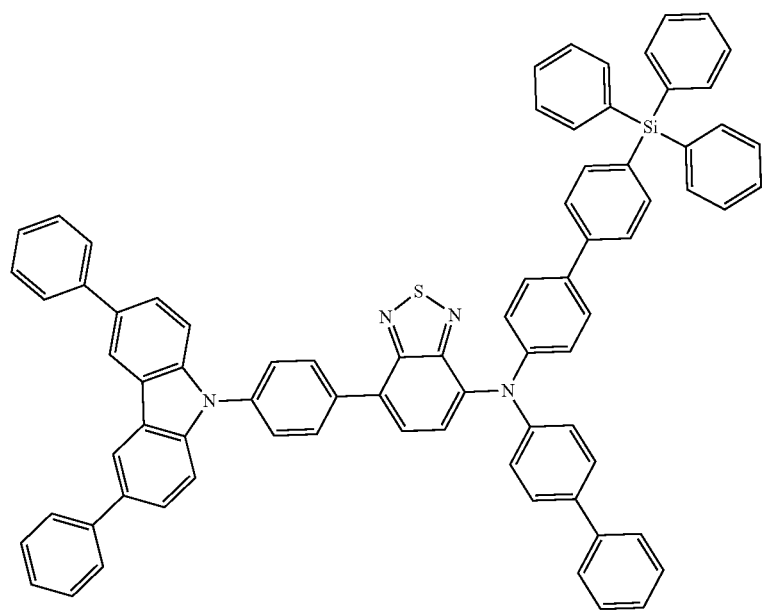

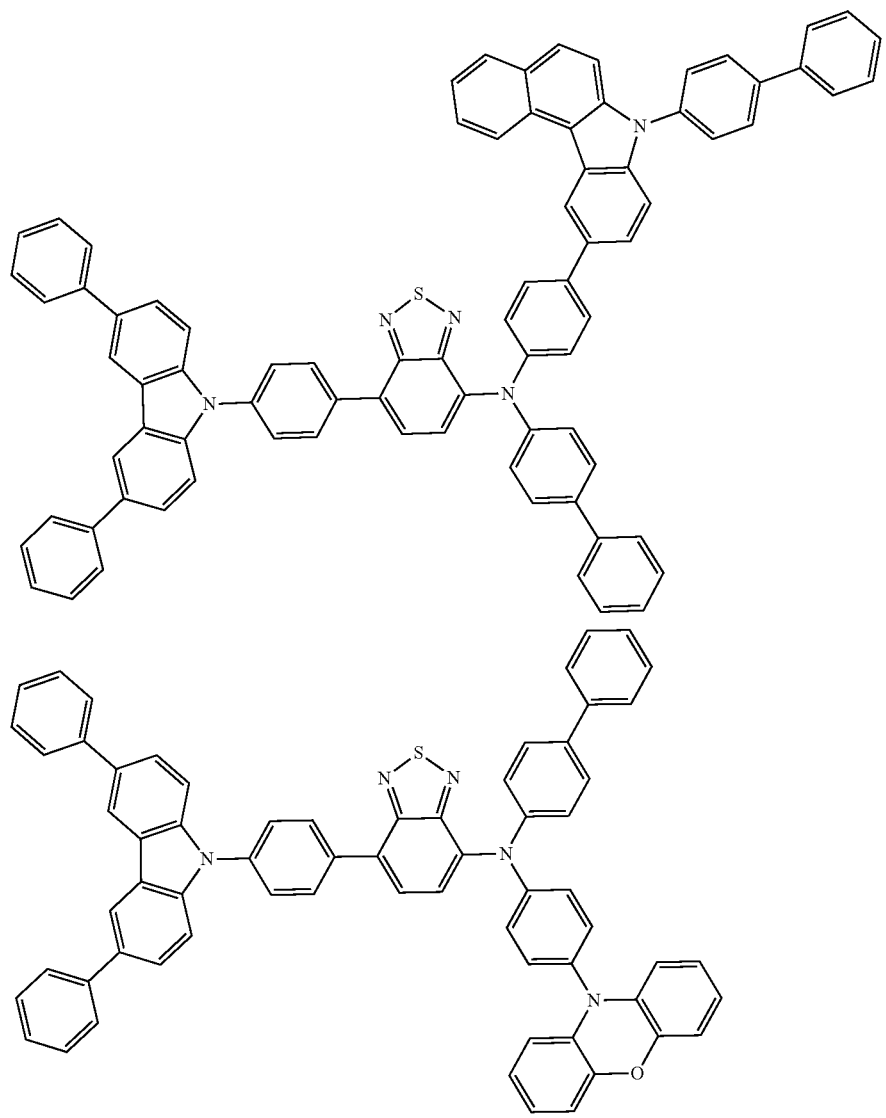
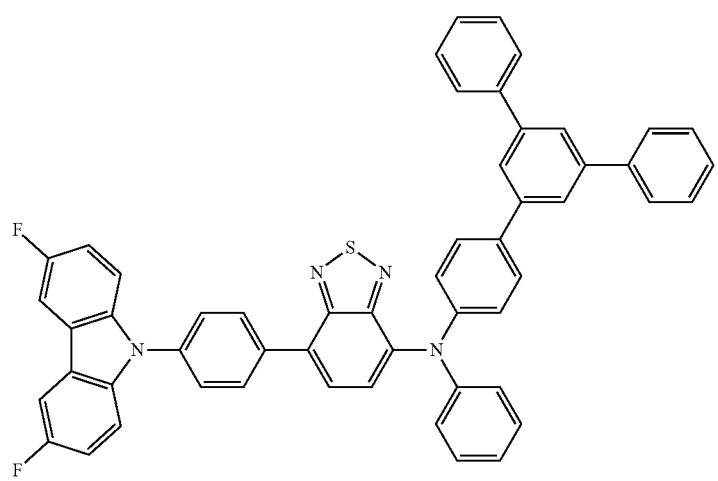

-continued
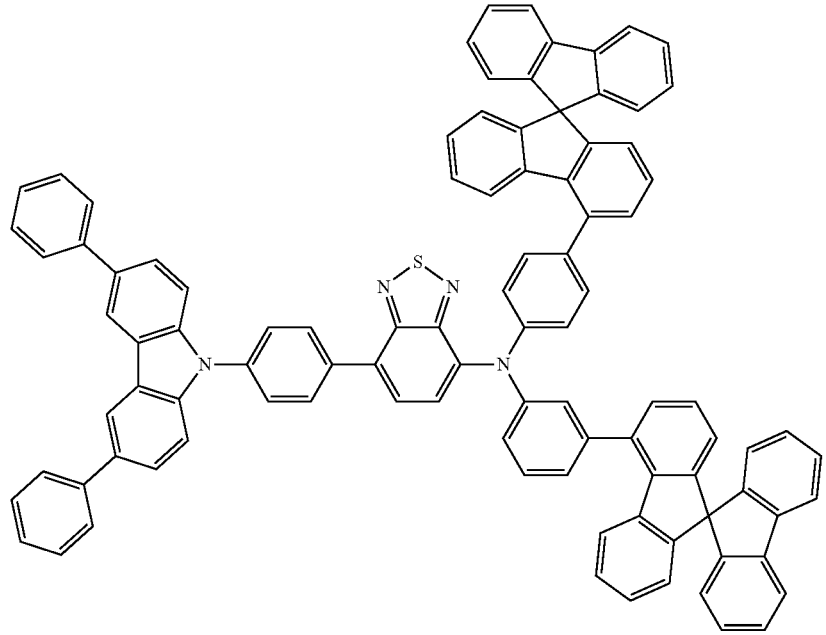
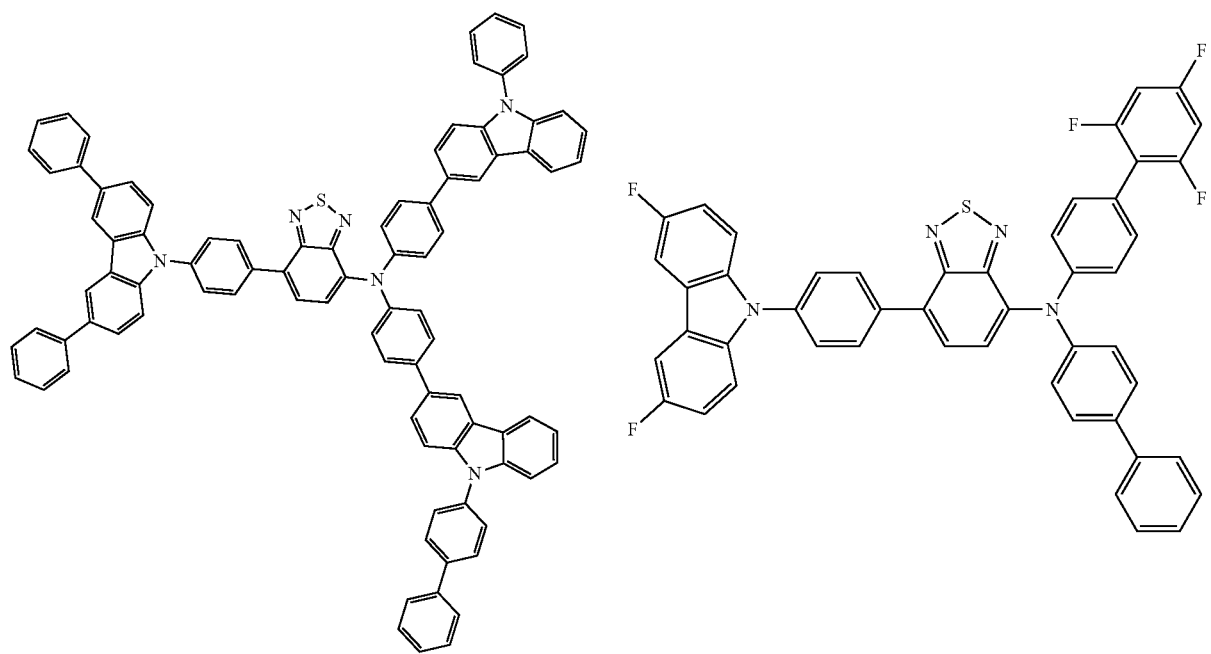

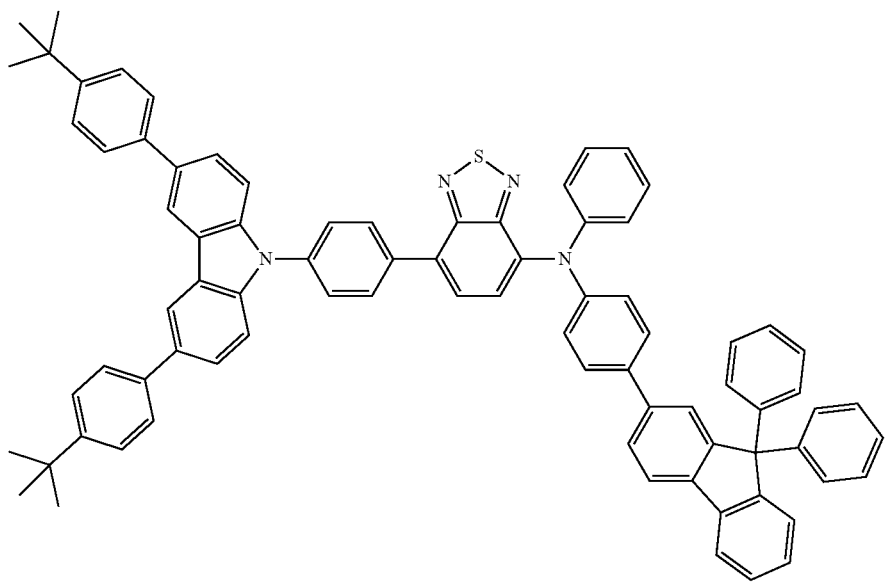

-continued
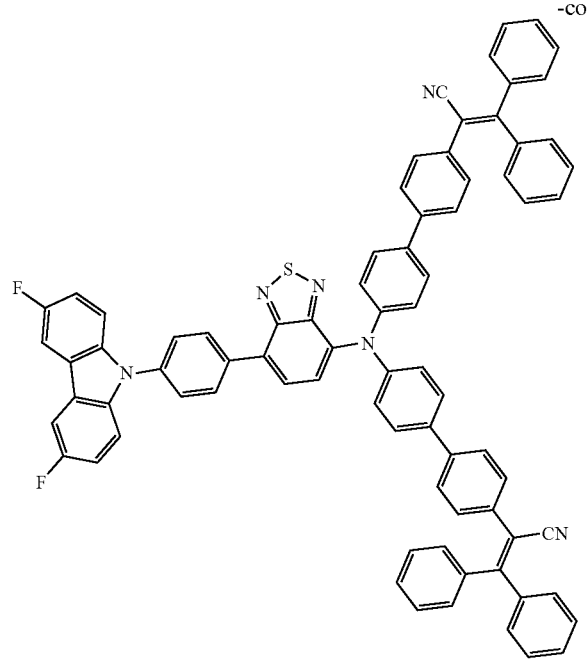
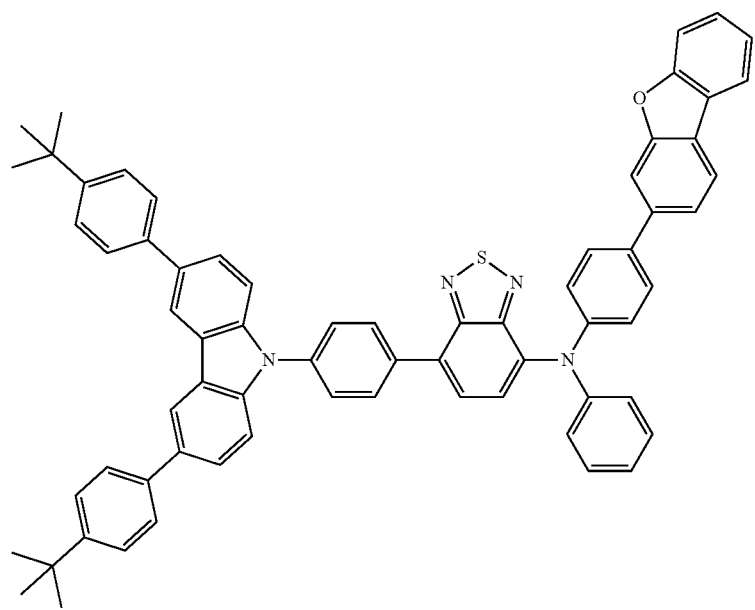

-continued
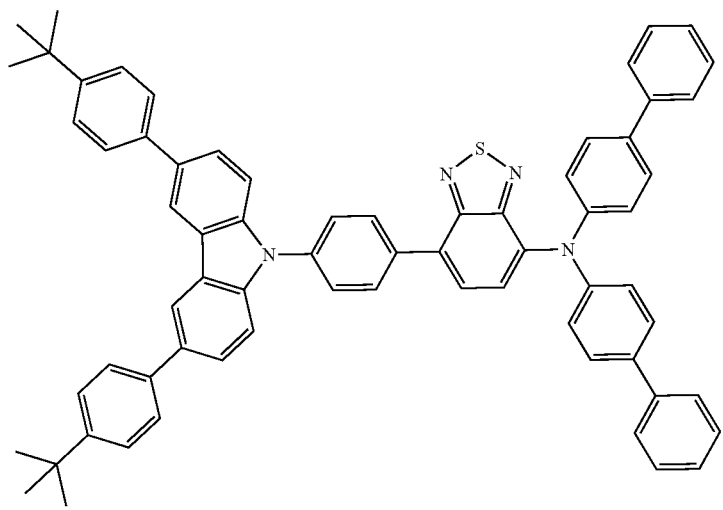
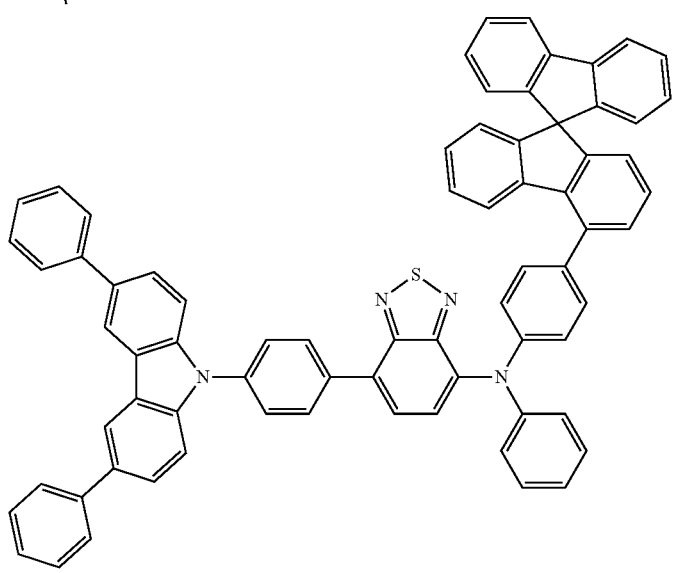
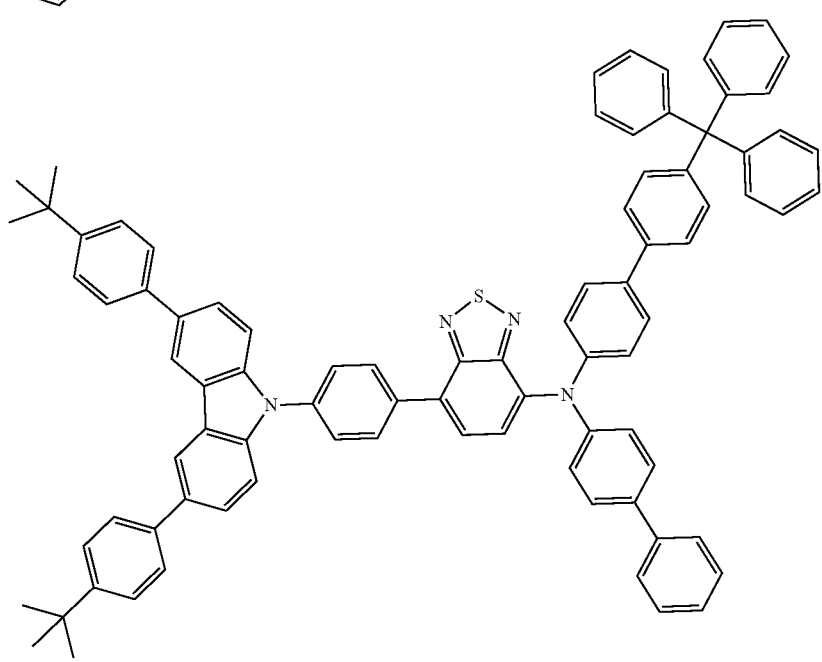

-continued
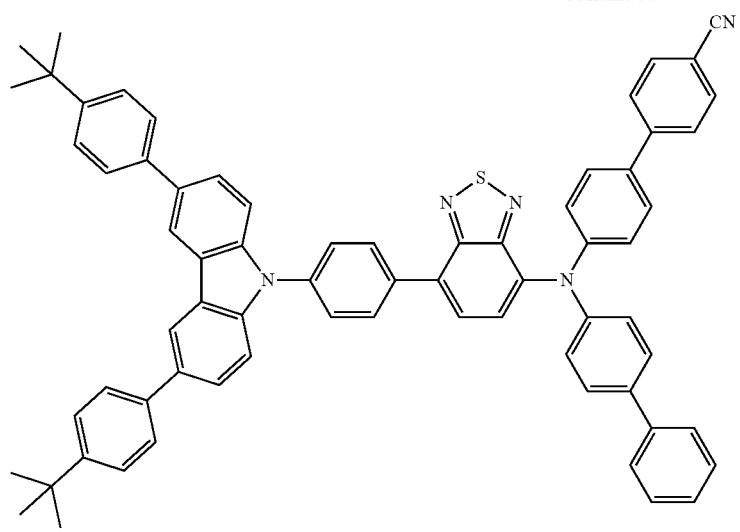
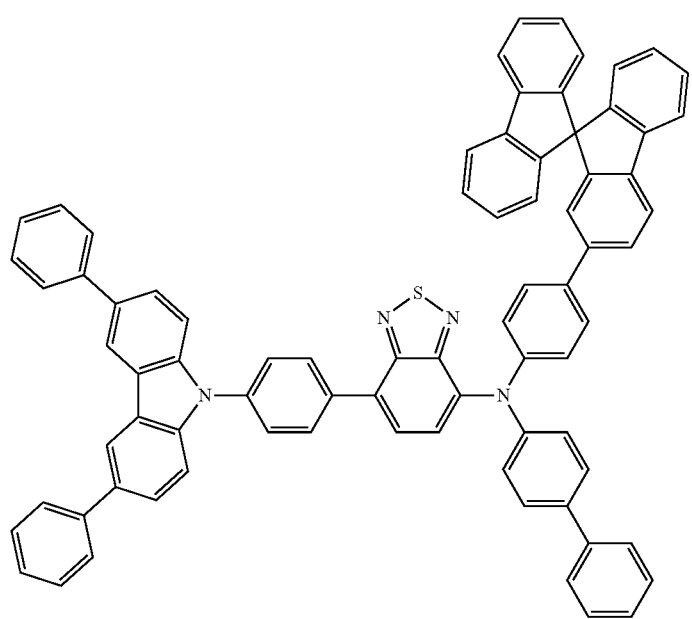

-continued
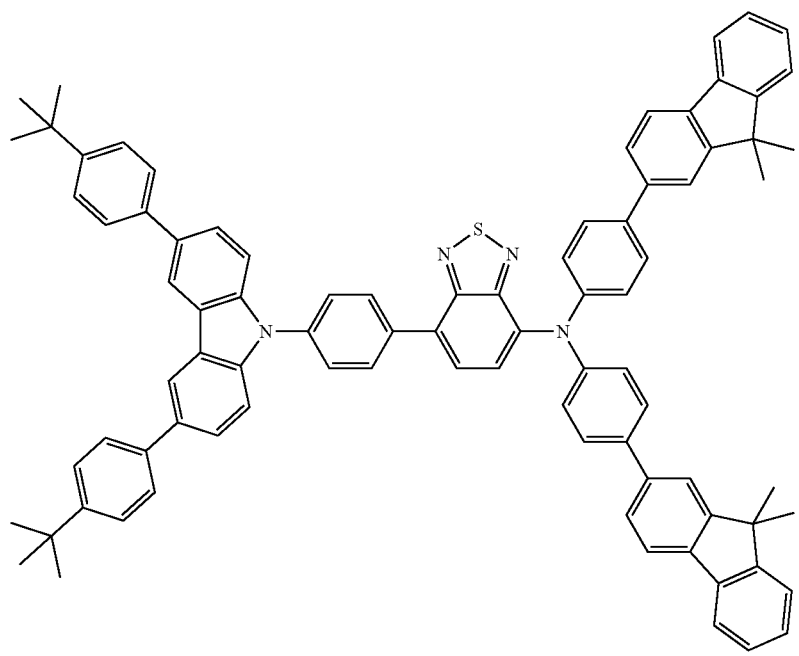
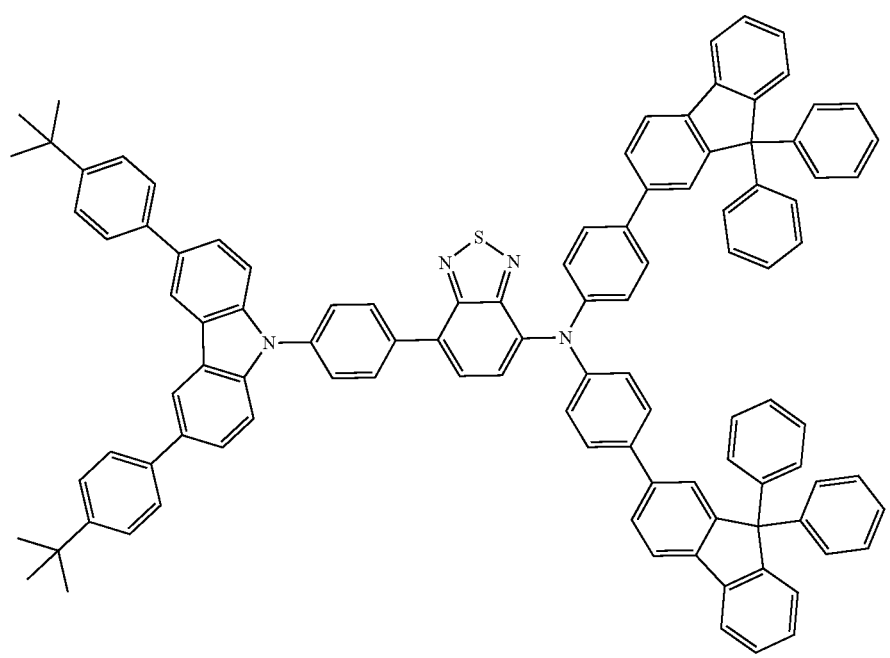

-continued
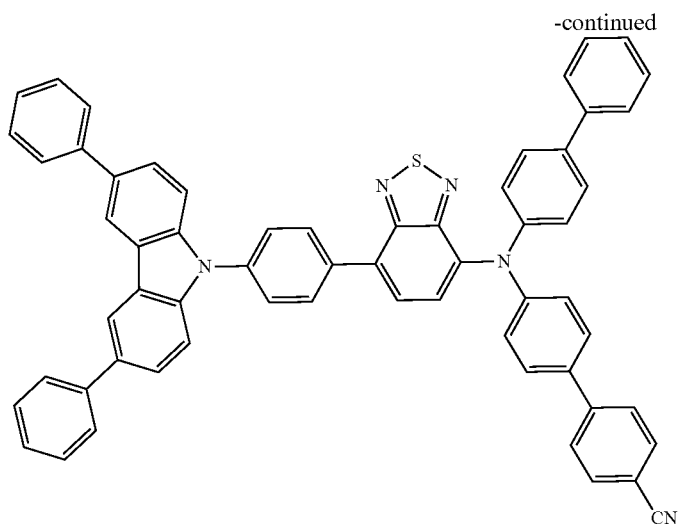
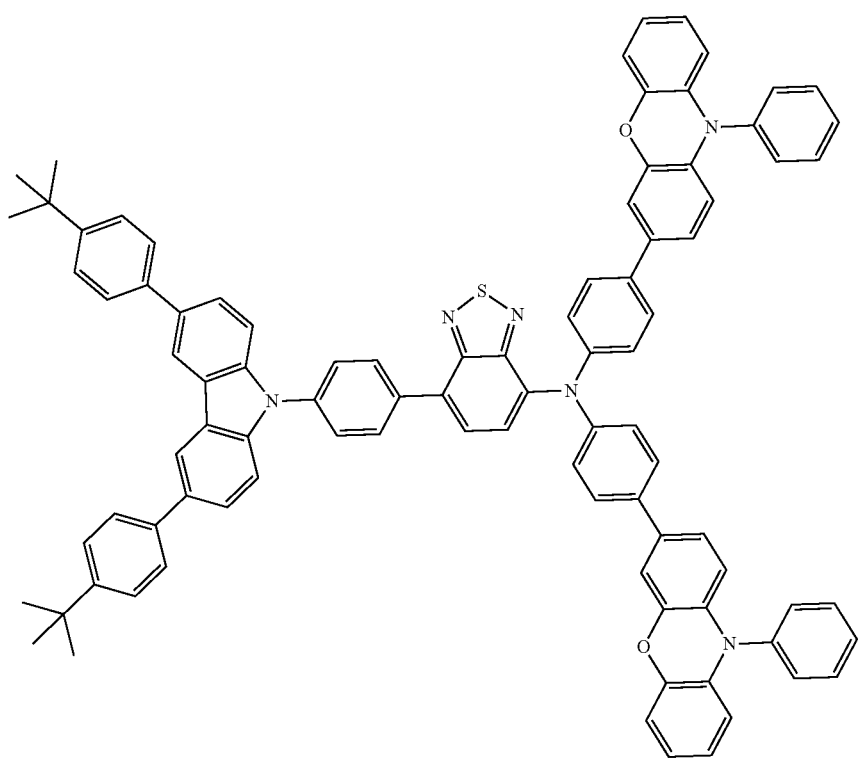

-continued
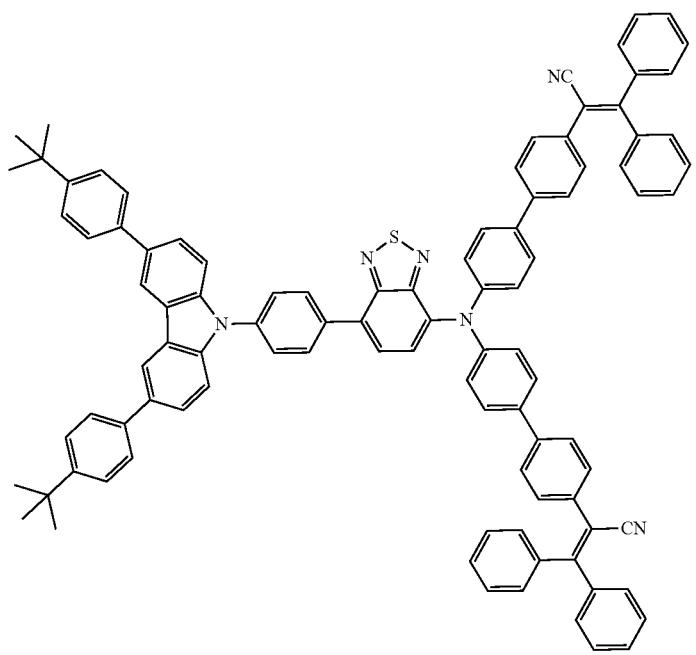
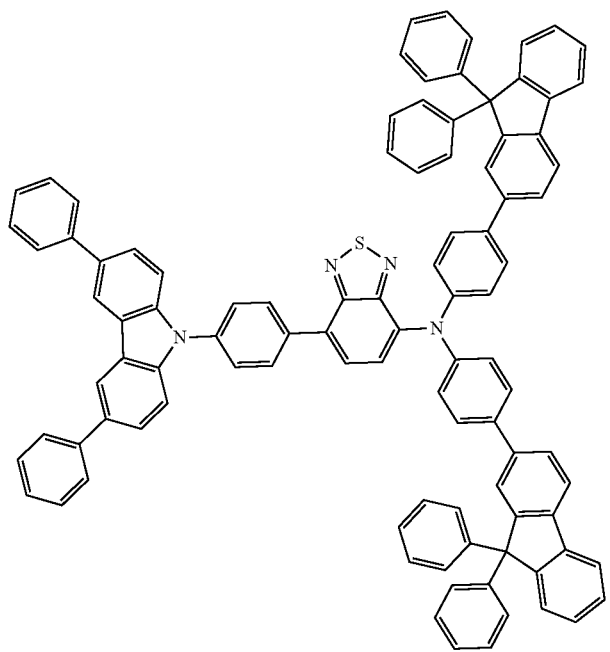

-continued
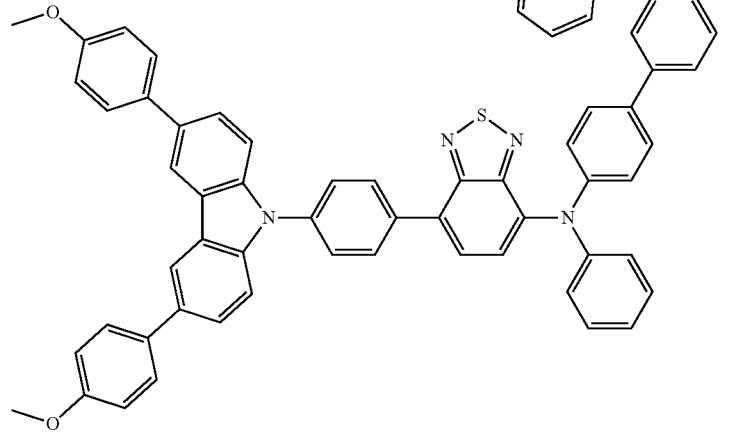
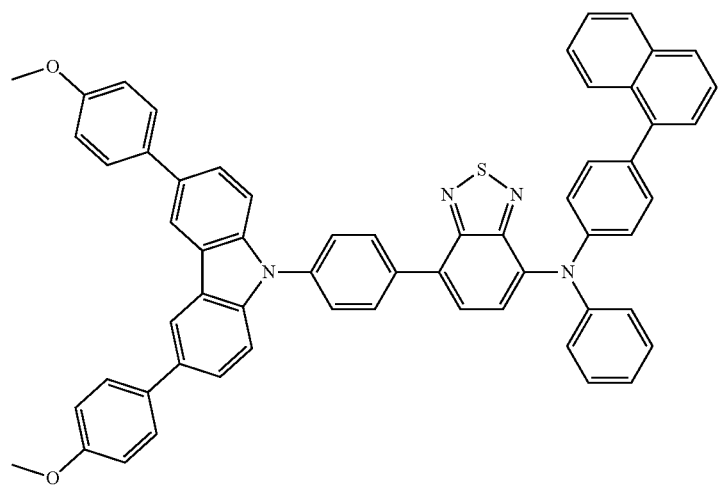
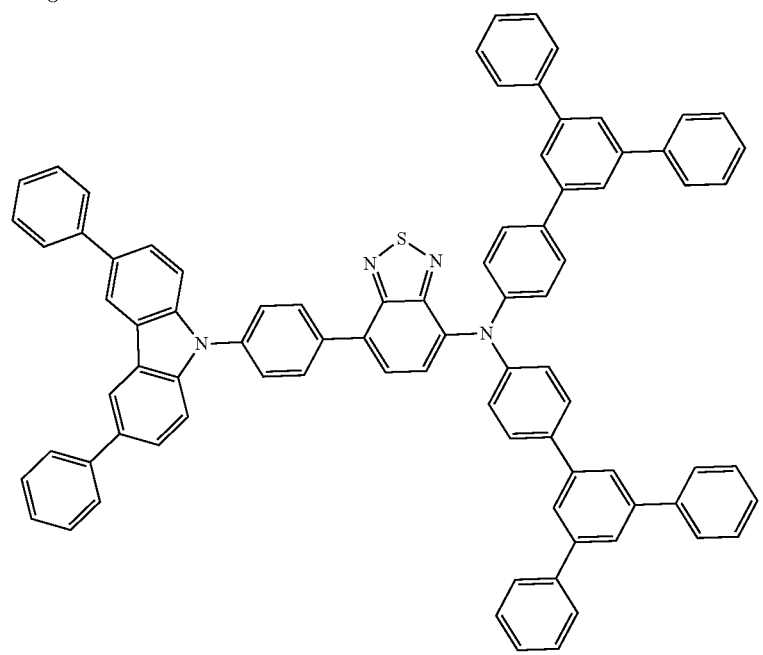

-continued
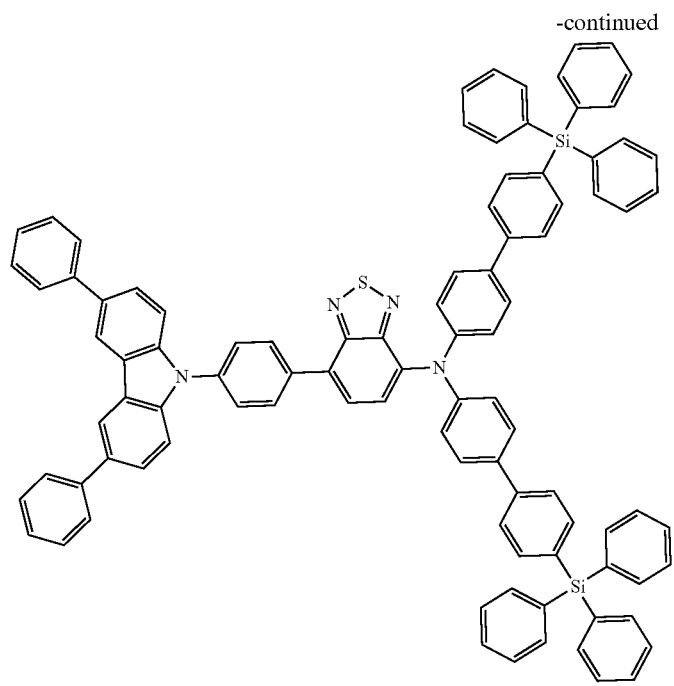
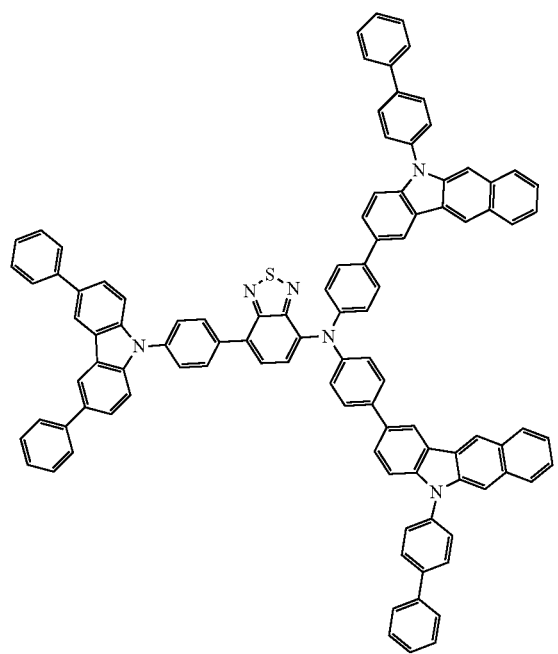

-continued
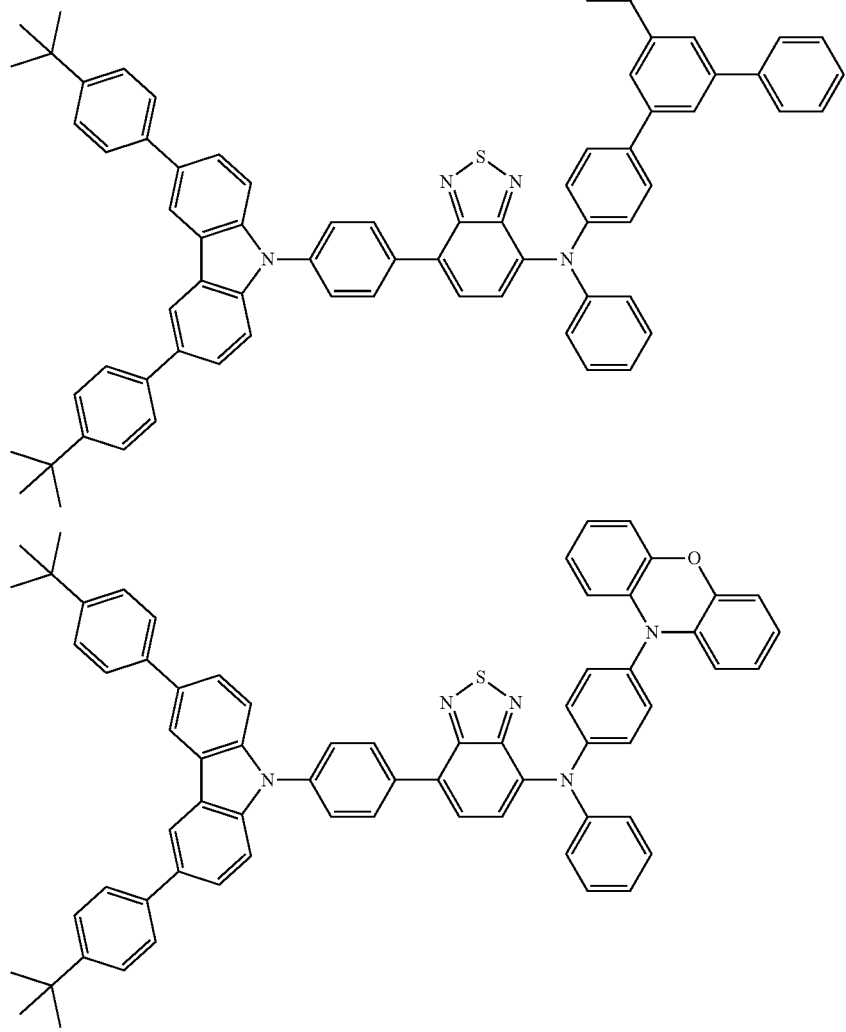
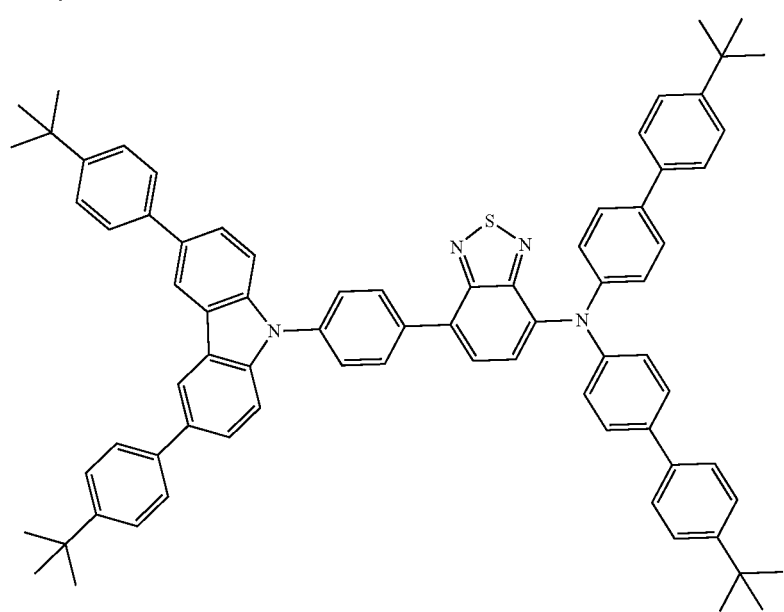

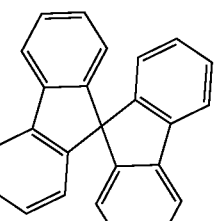
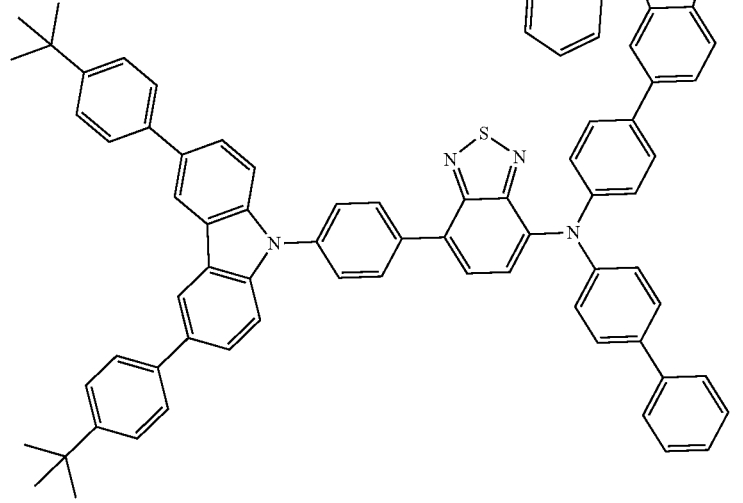
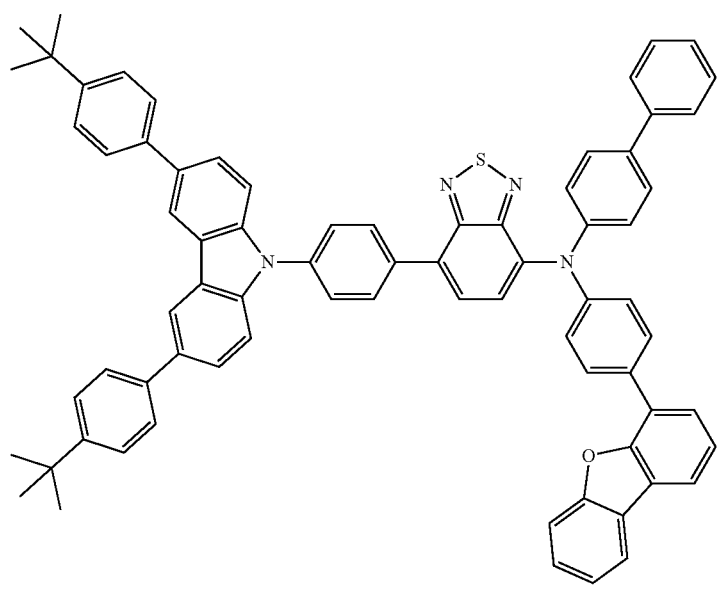

-continued
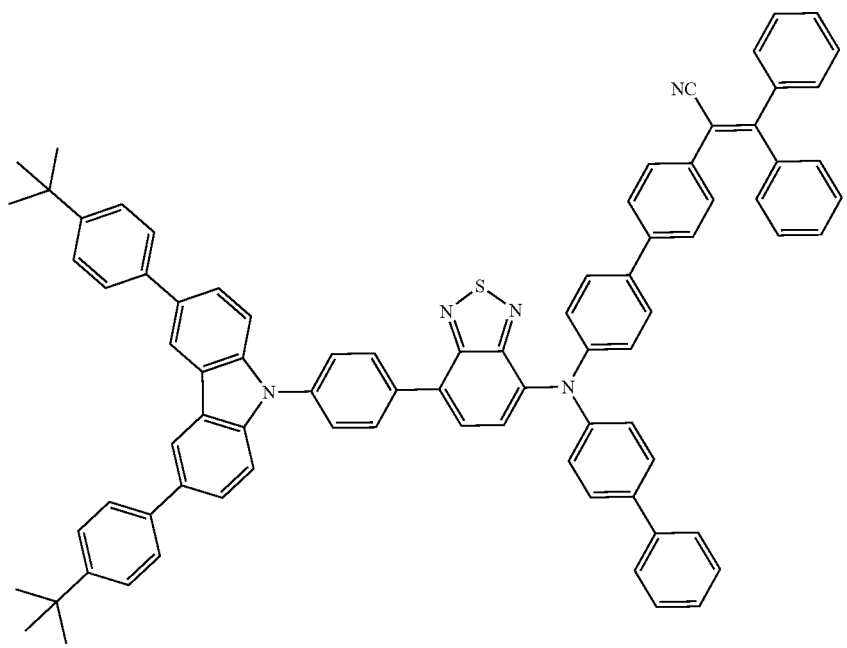
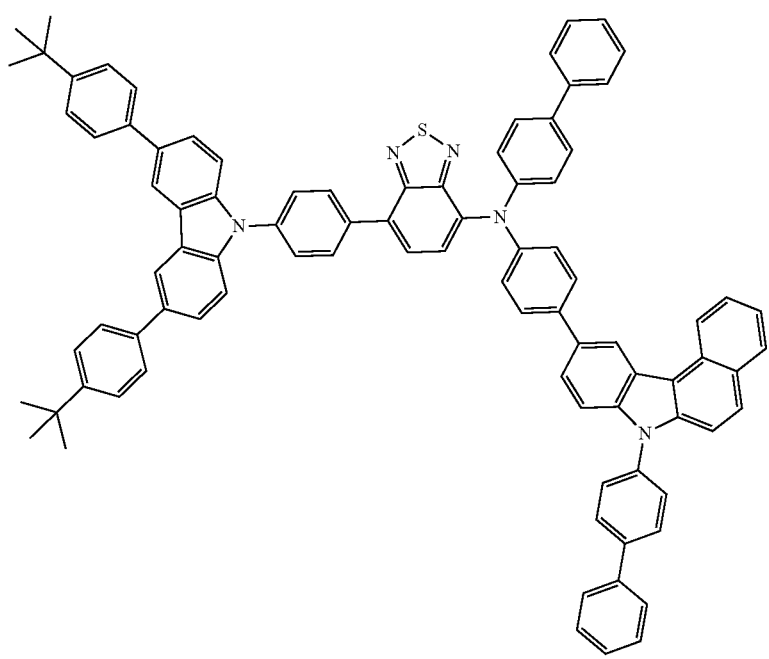

-continued
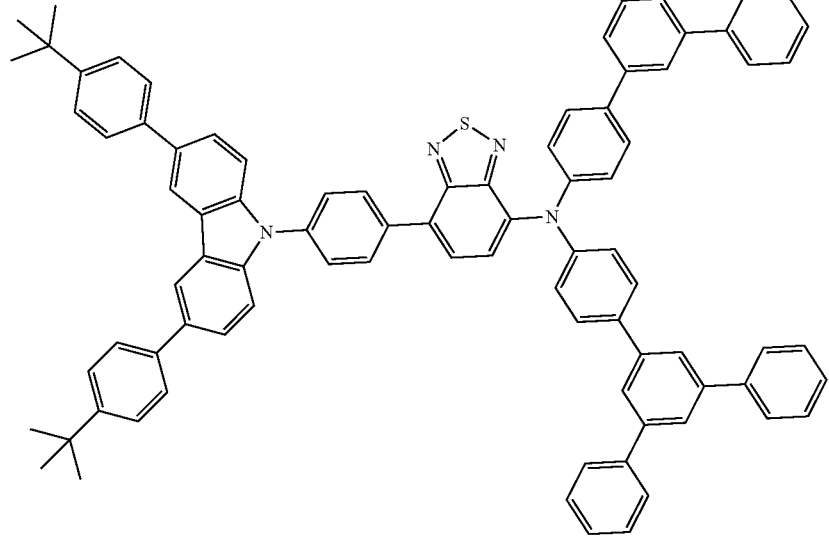
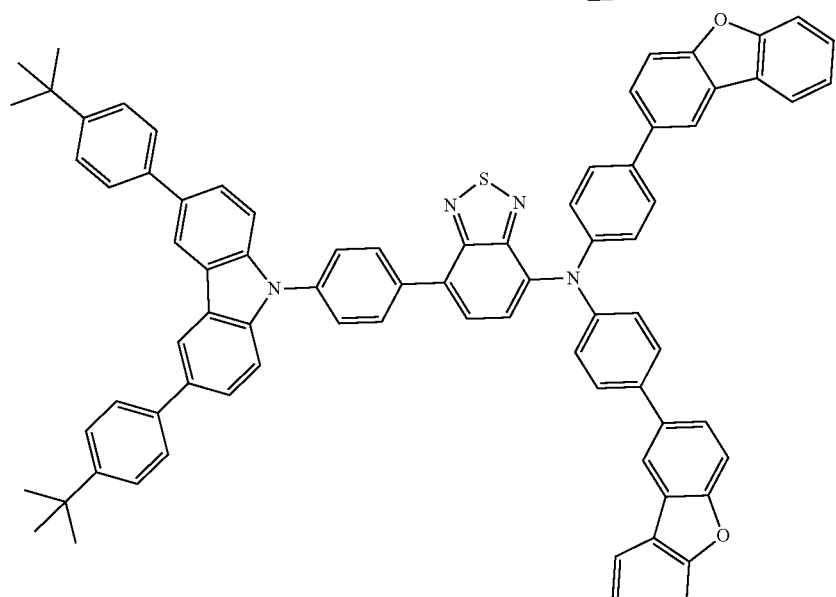
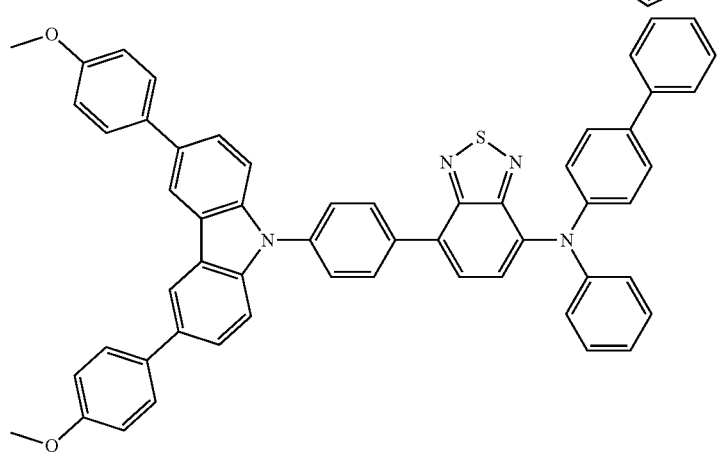

-continued
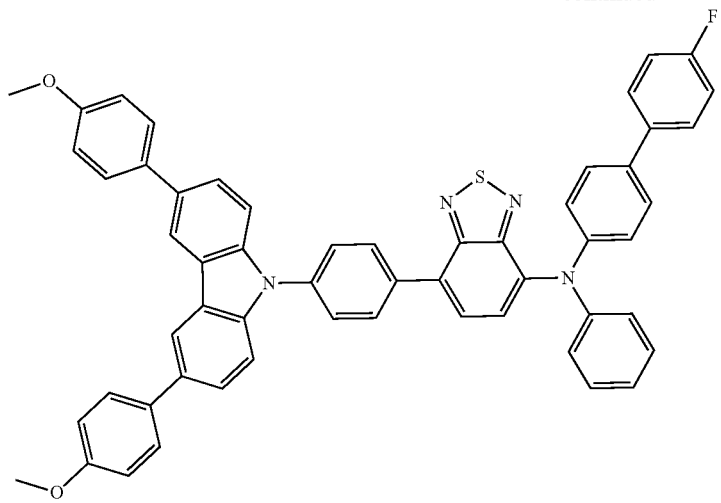
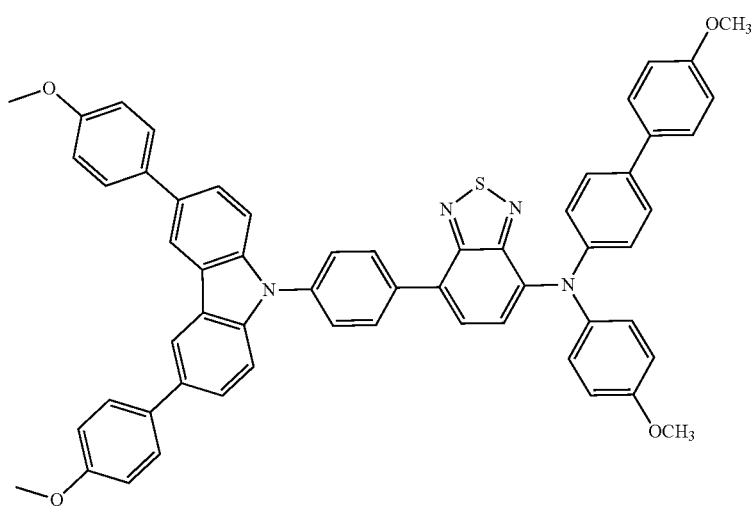
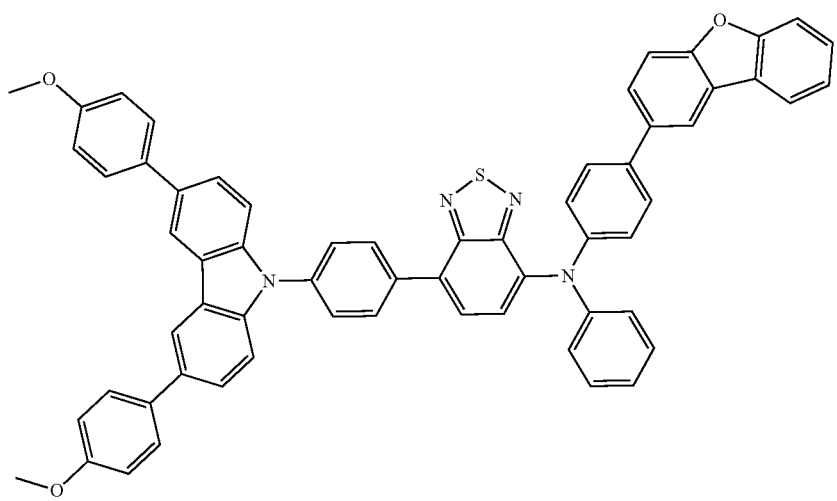

-continued
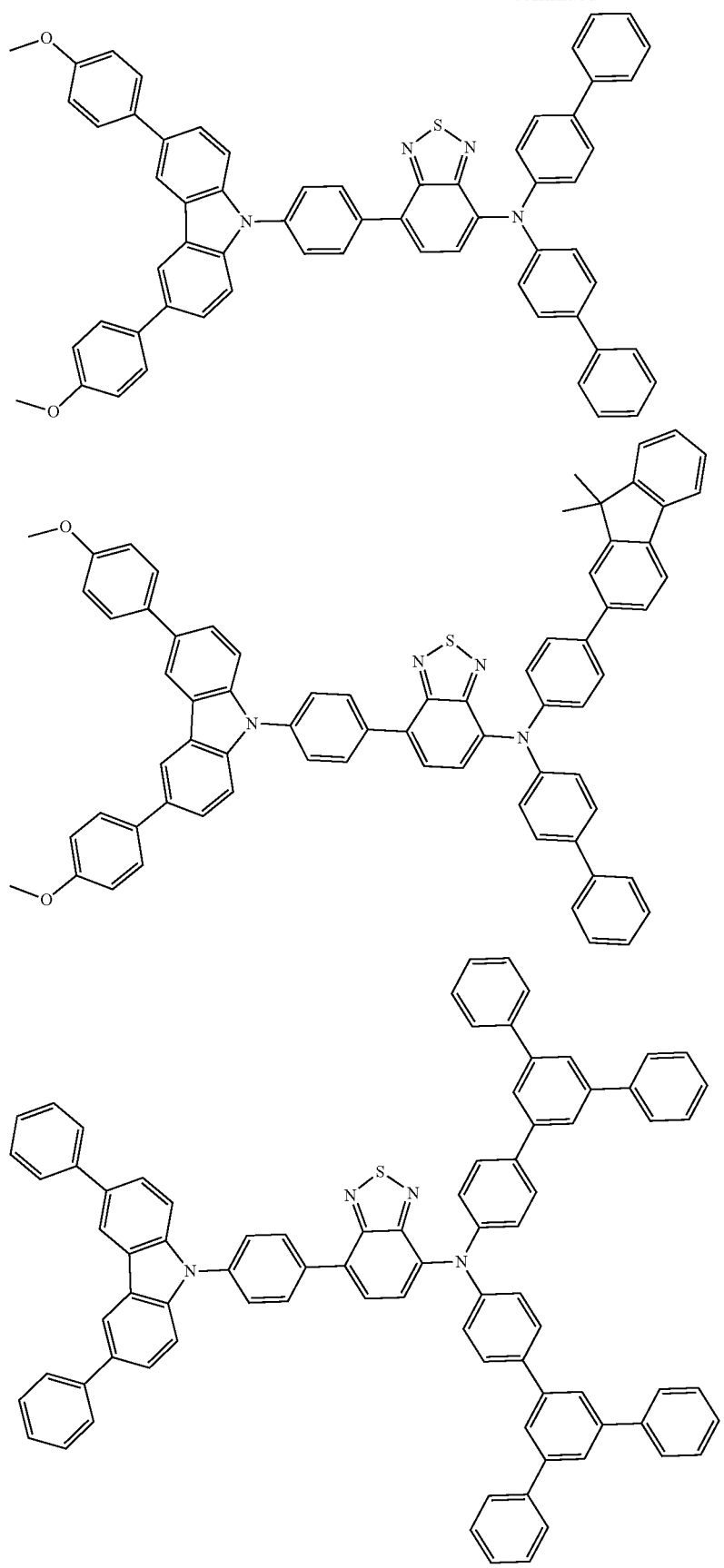

-continued
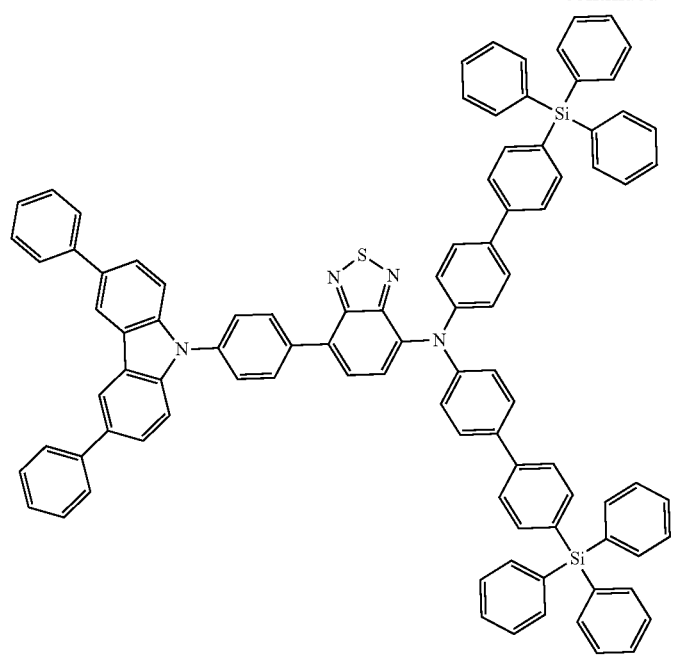
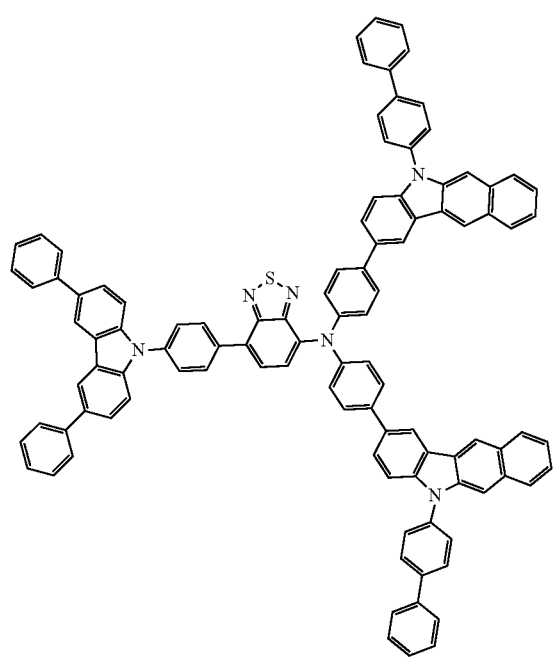

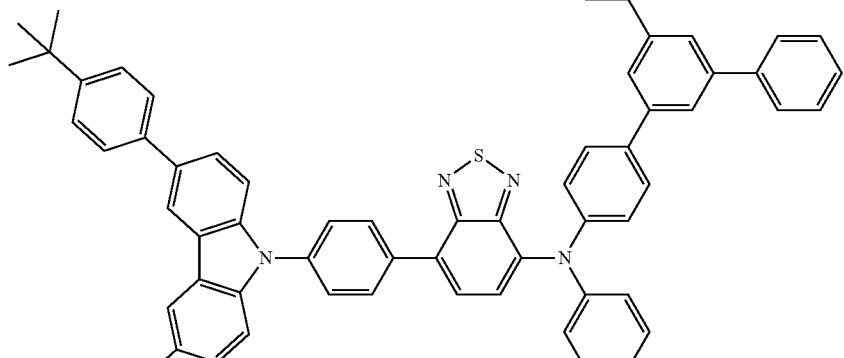
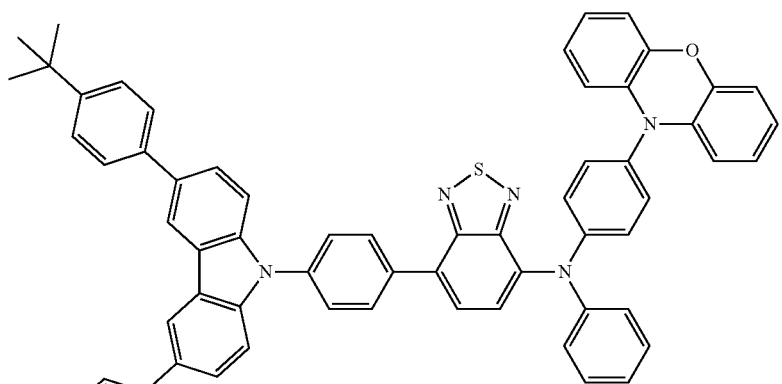
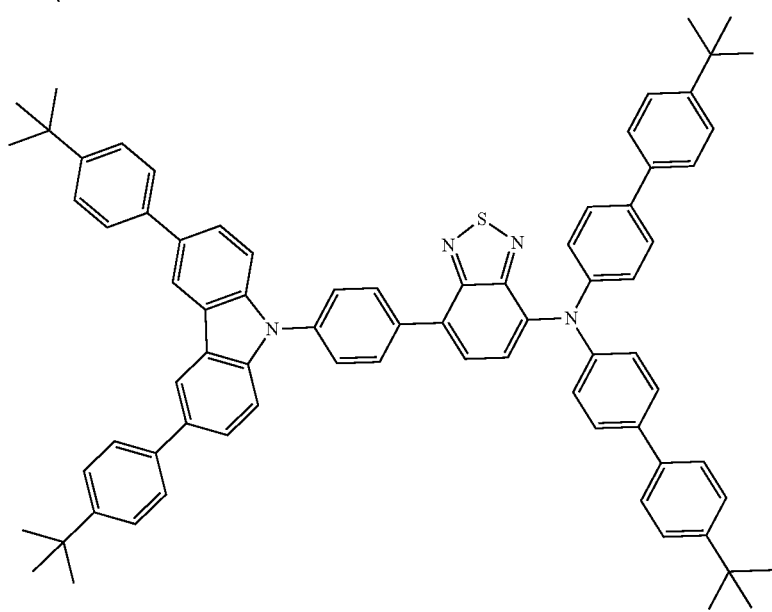

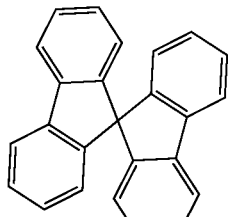
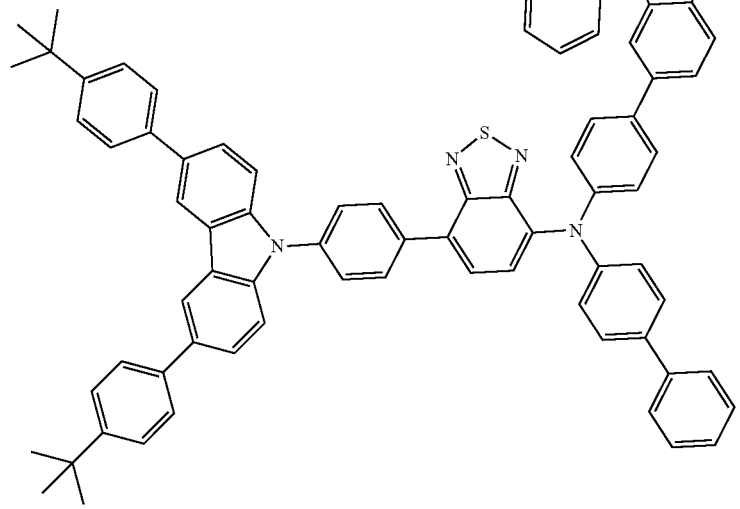
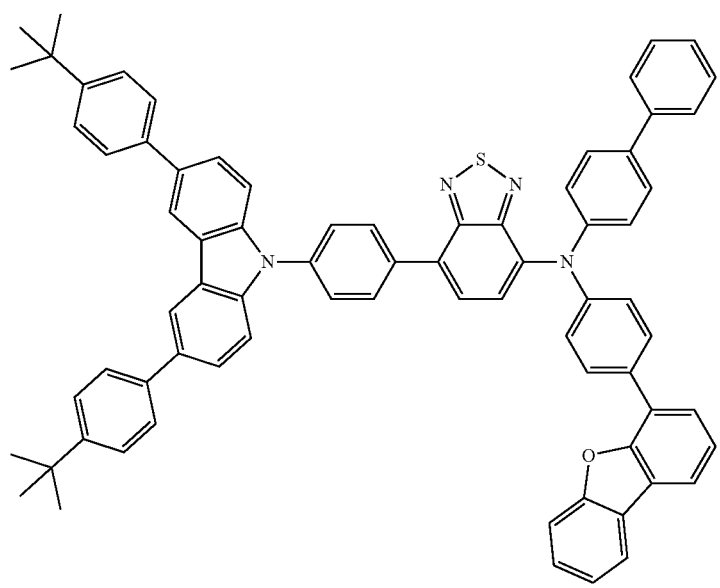
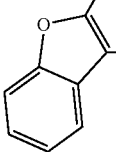

-continued
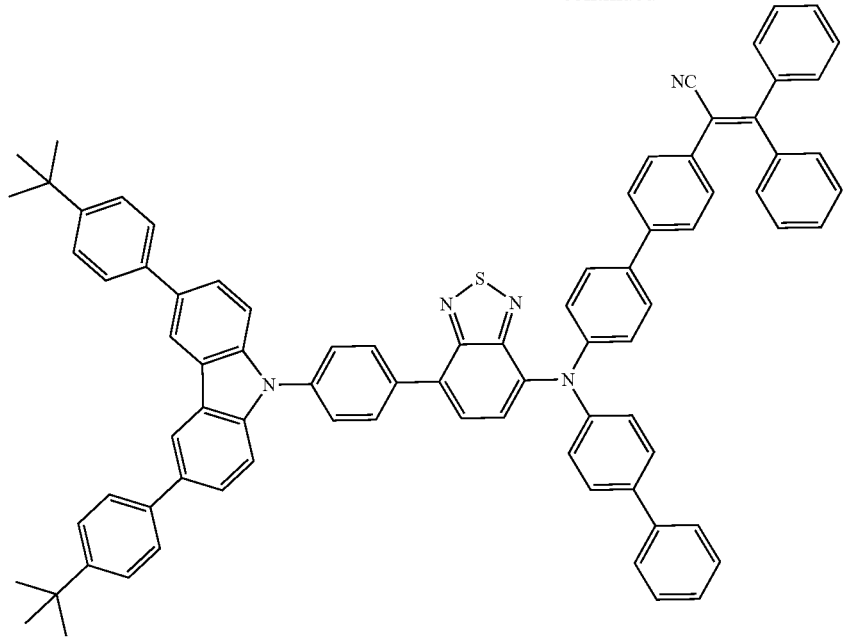
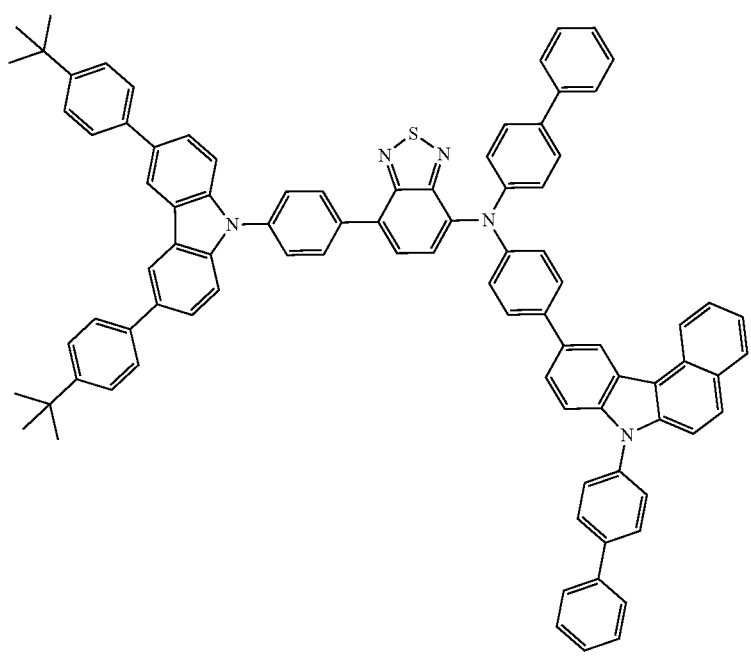

-continued
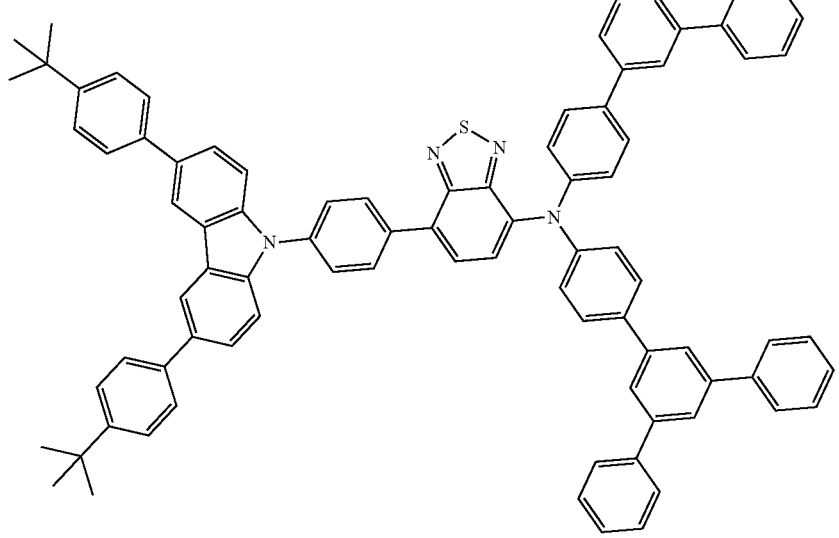
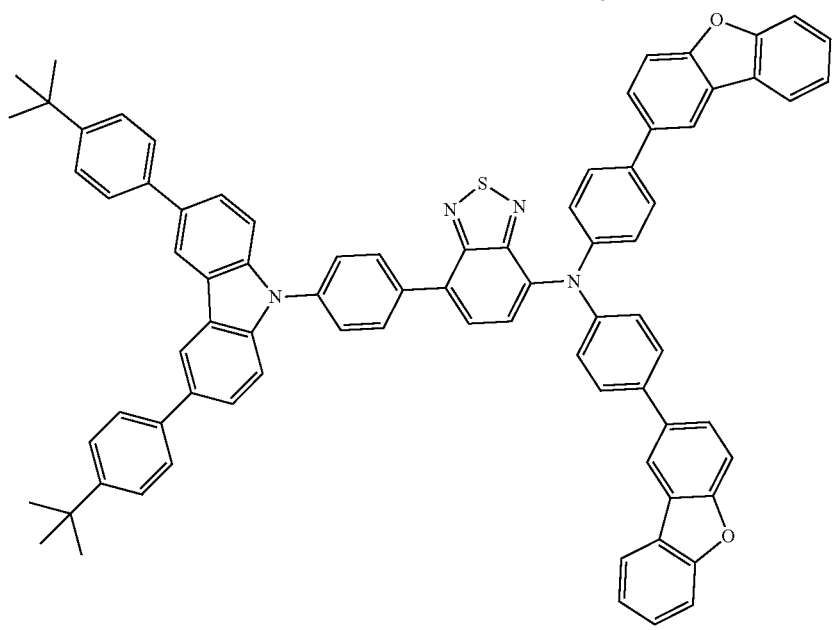
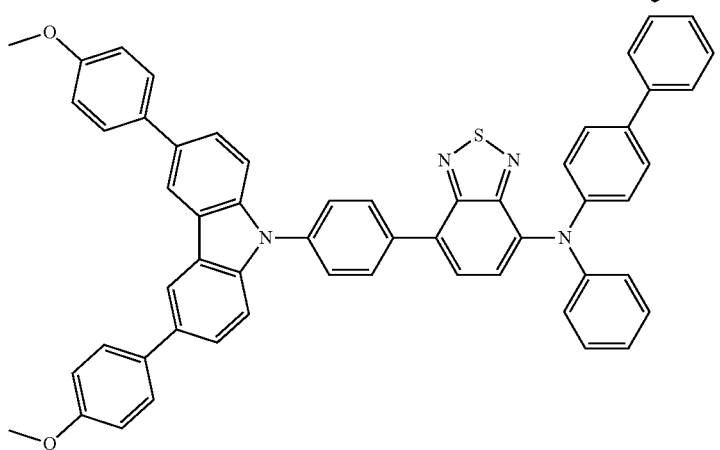

-continued
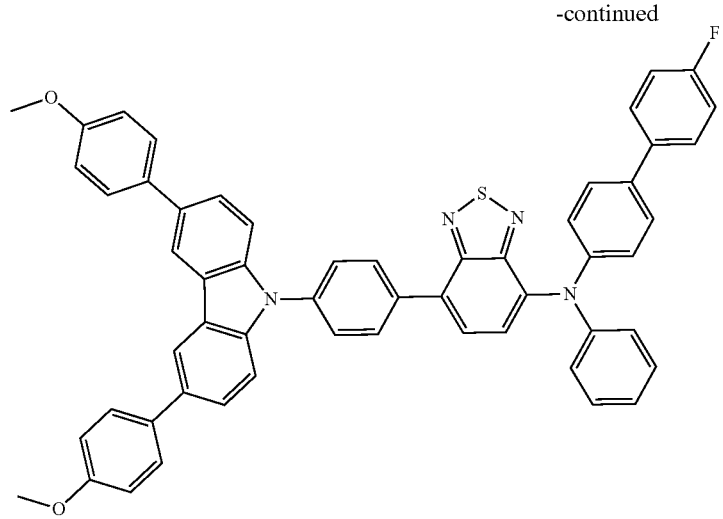
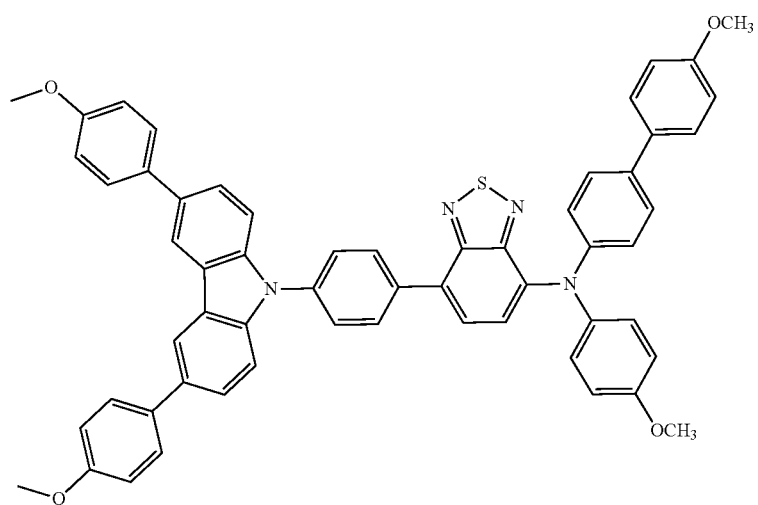
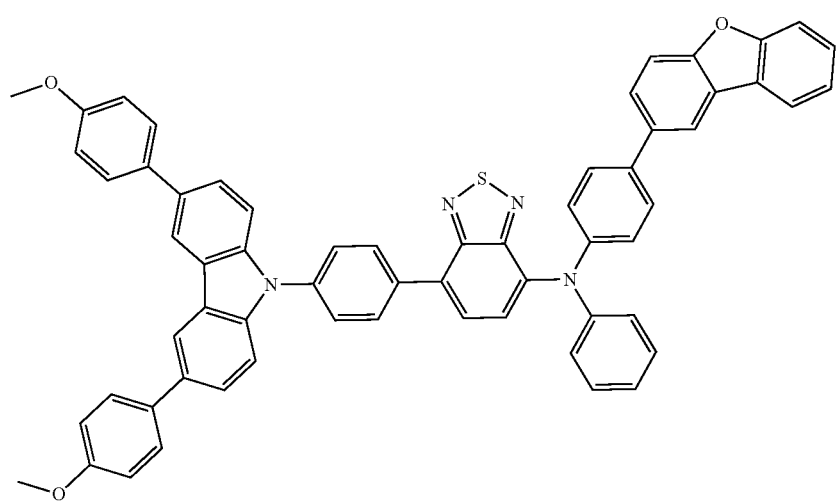

-continued
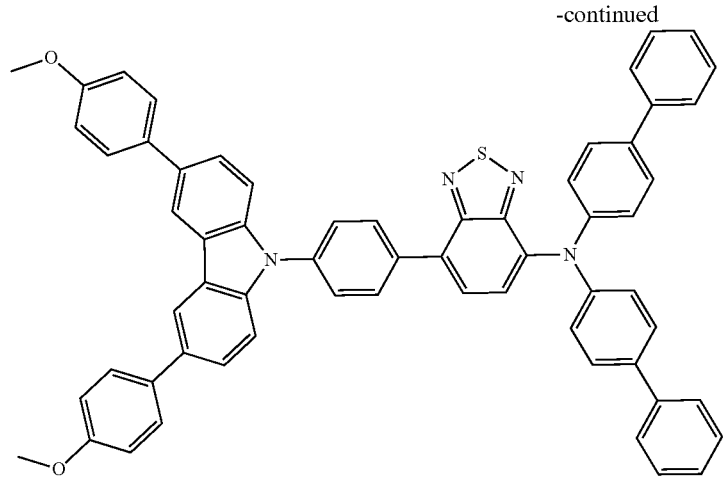
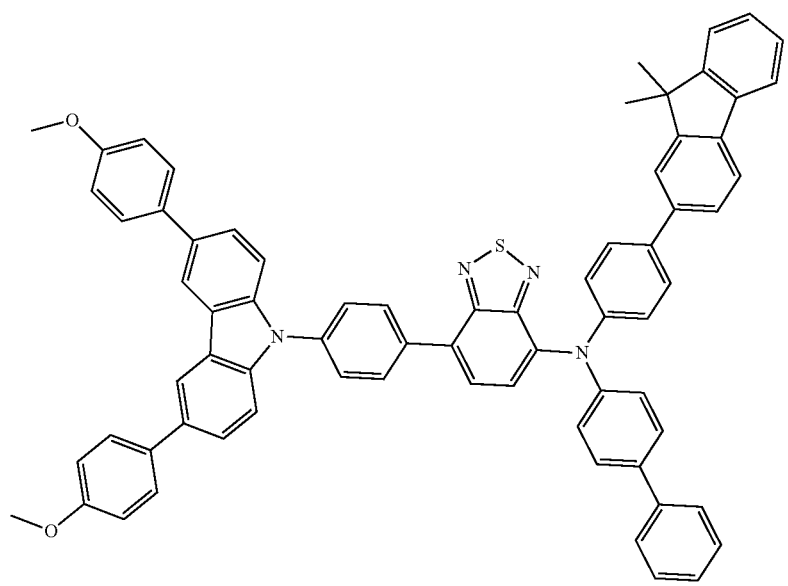
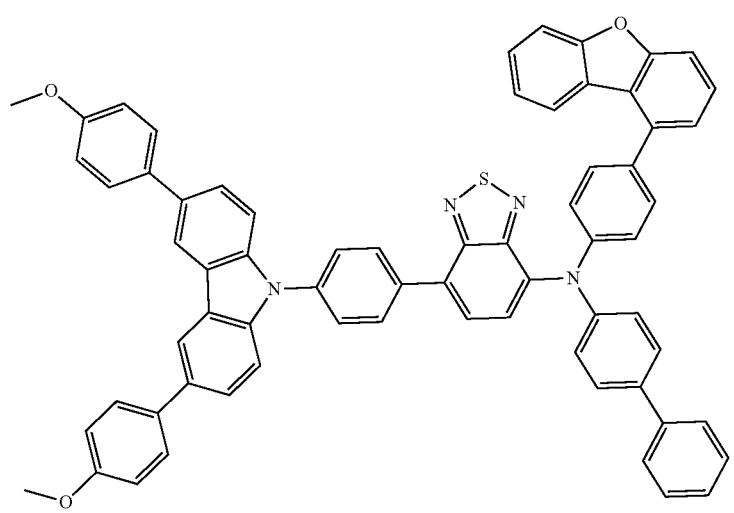

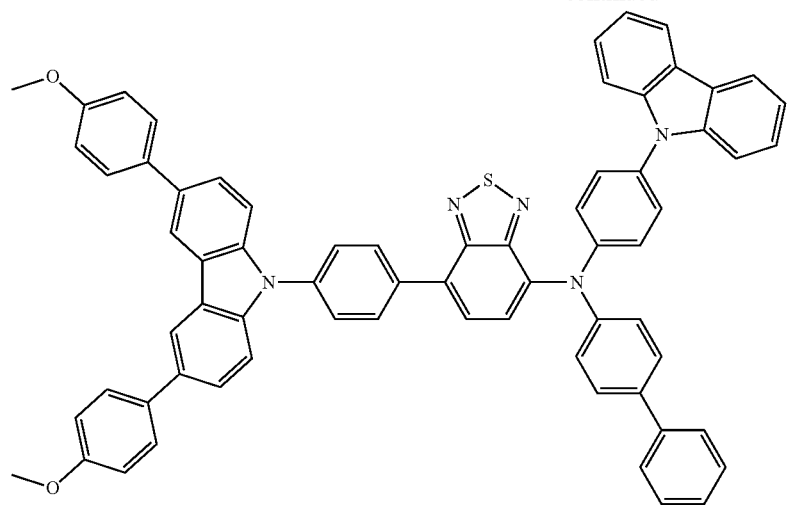
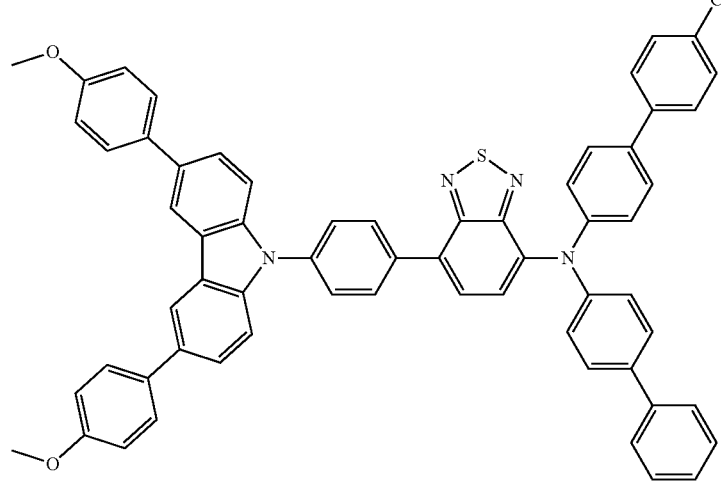
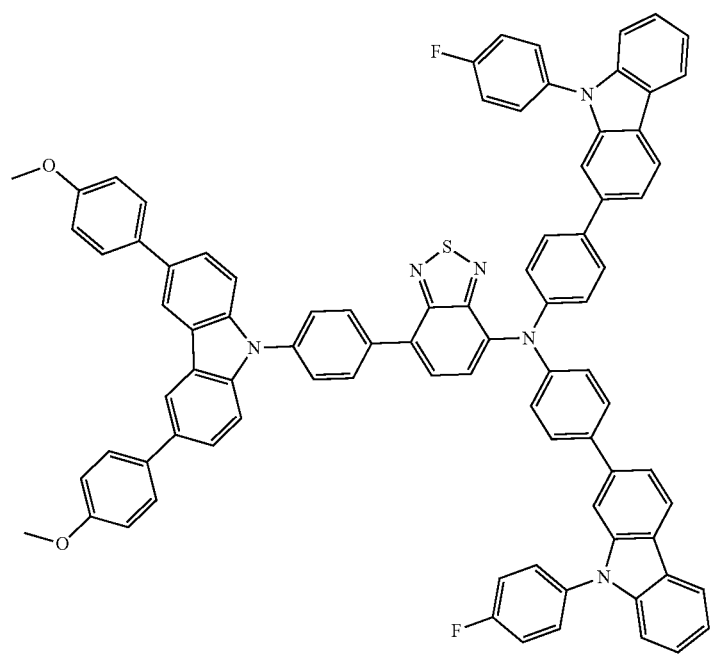

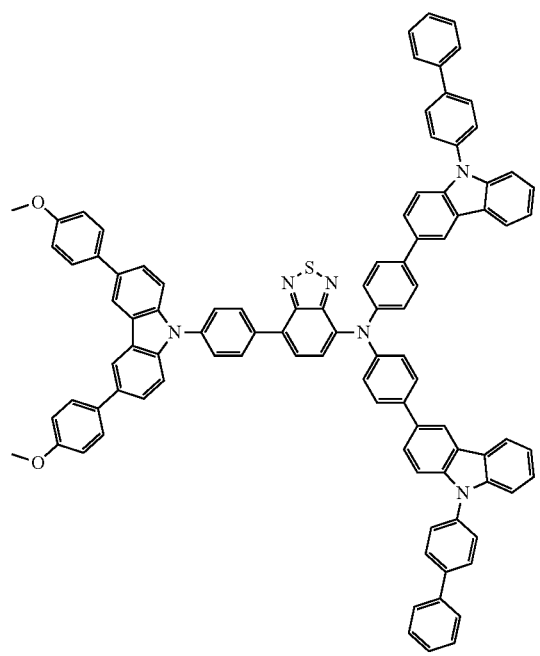
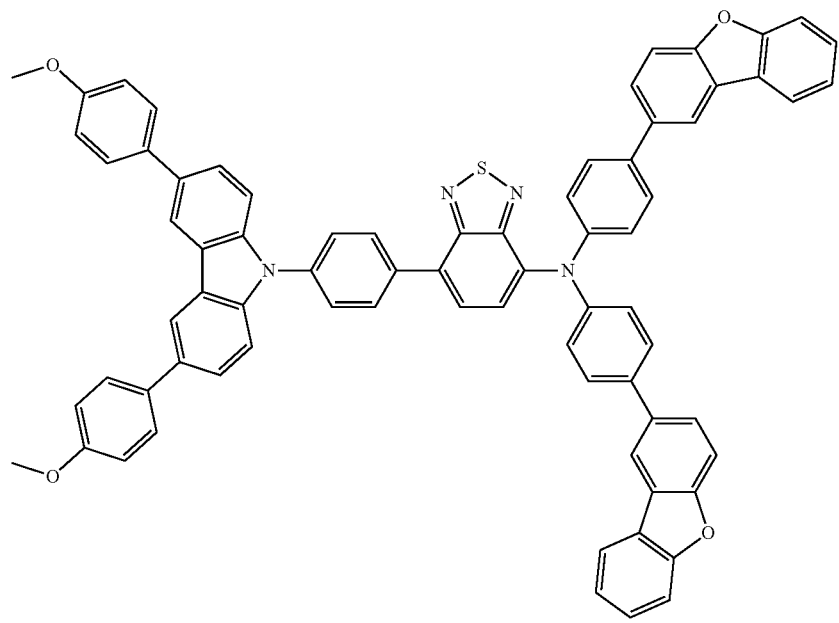
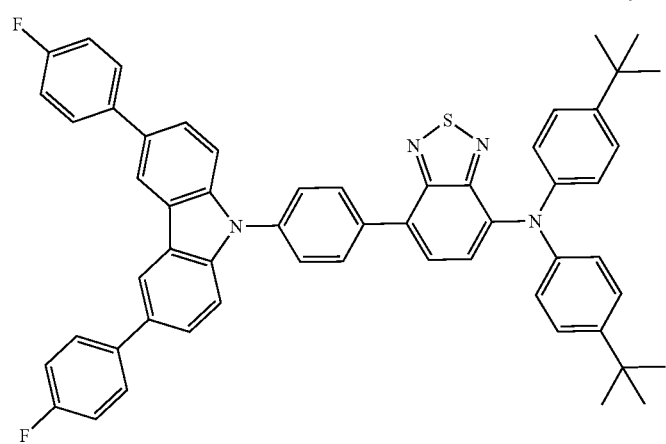

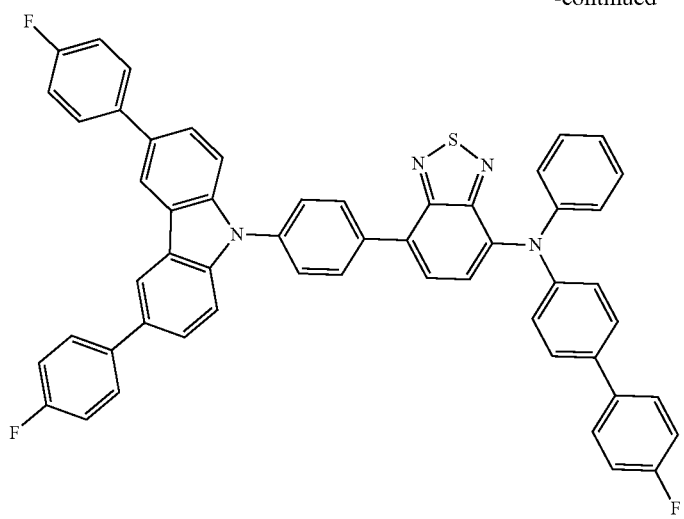
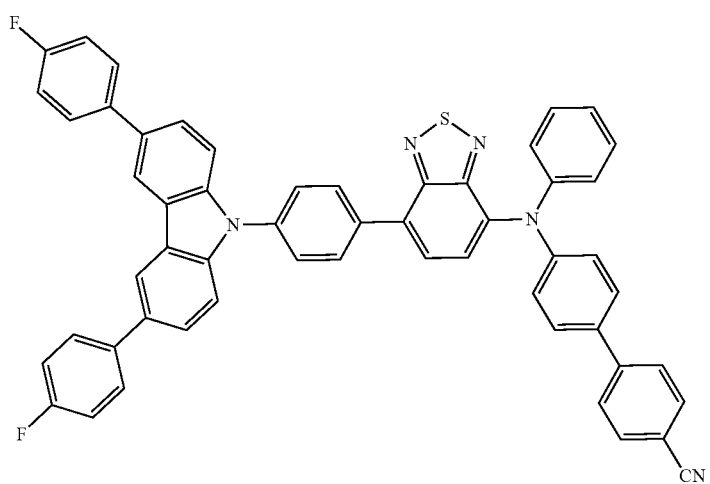
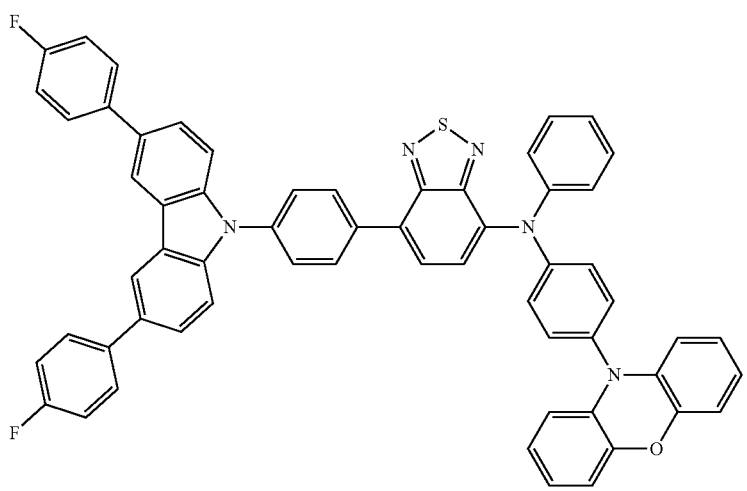

-continued
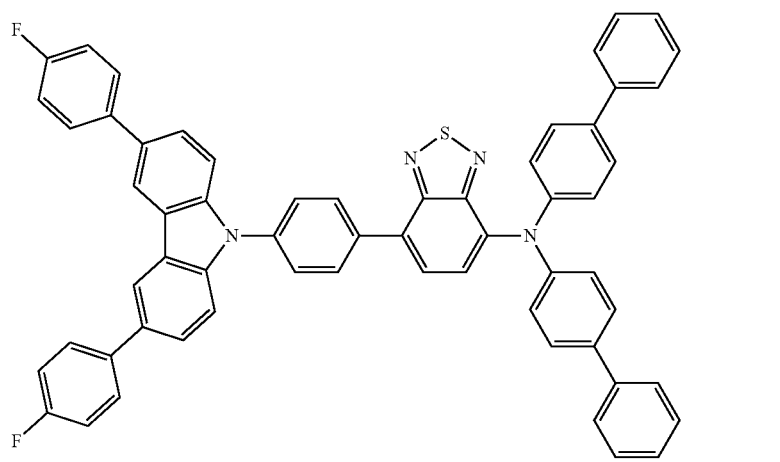 [SMILES: Fc1ccc(-c2ccc3c(c2)c2cc(-c4ccc(F)cc4)ccc2n3-c2ccc(-c3ccc(N(c4ccc(-c5ccccc5)cc4)c4ccc(-c5ccccc5)cc4)c4nsnc34)cc2)cc1]
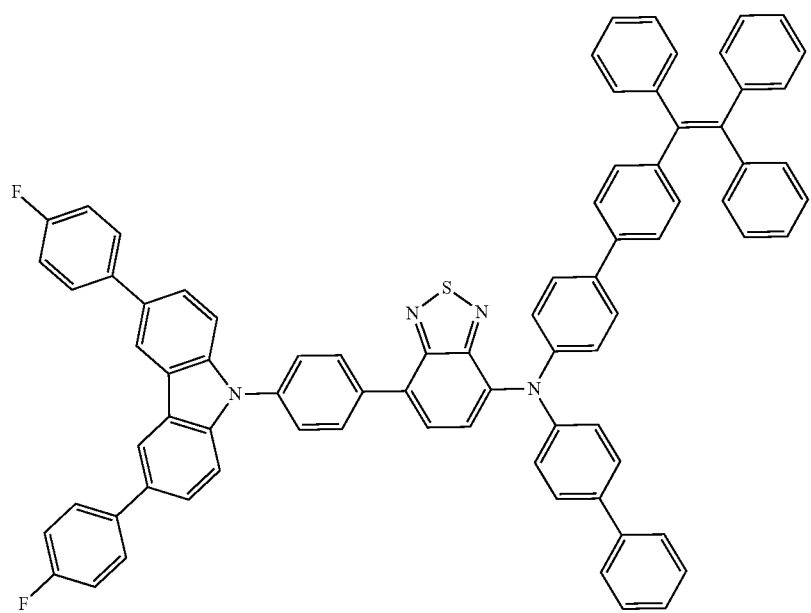
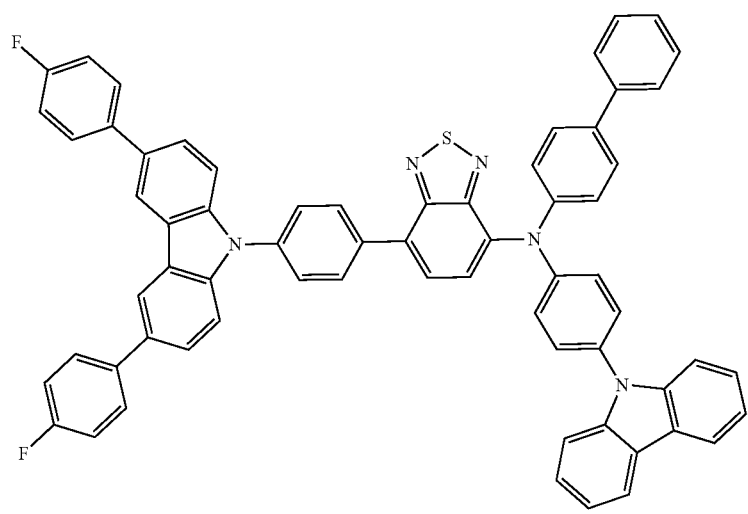

-continued
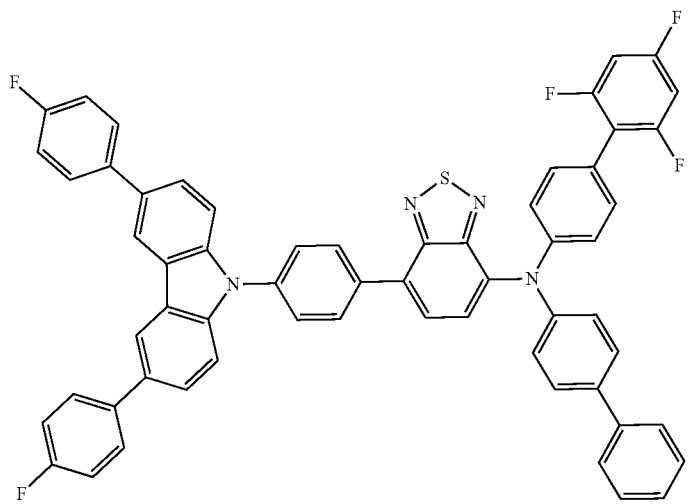
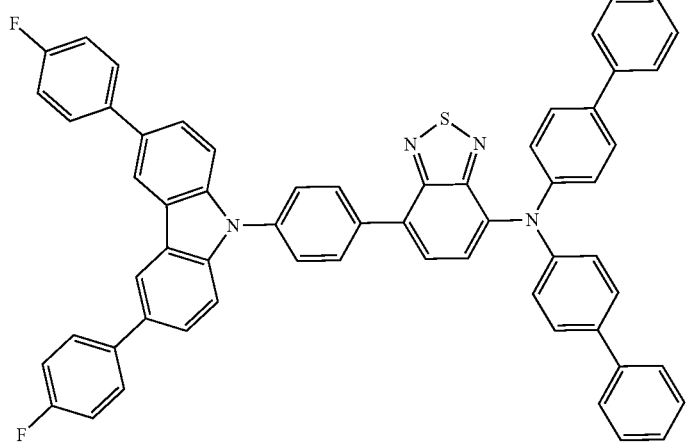
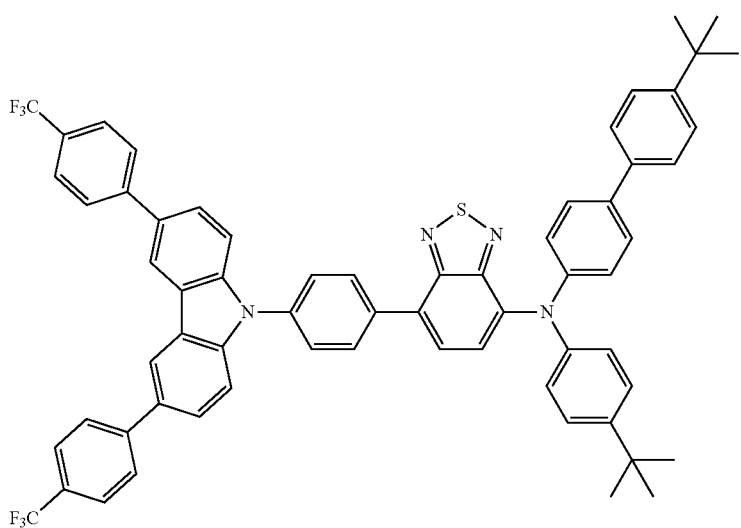

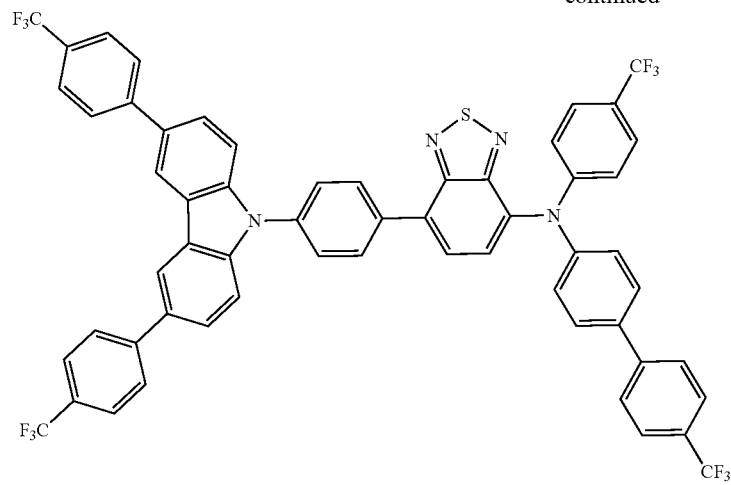
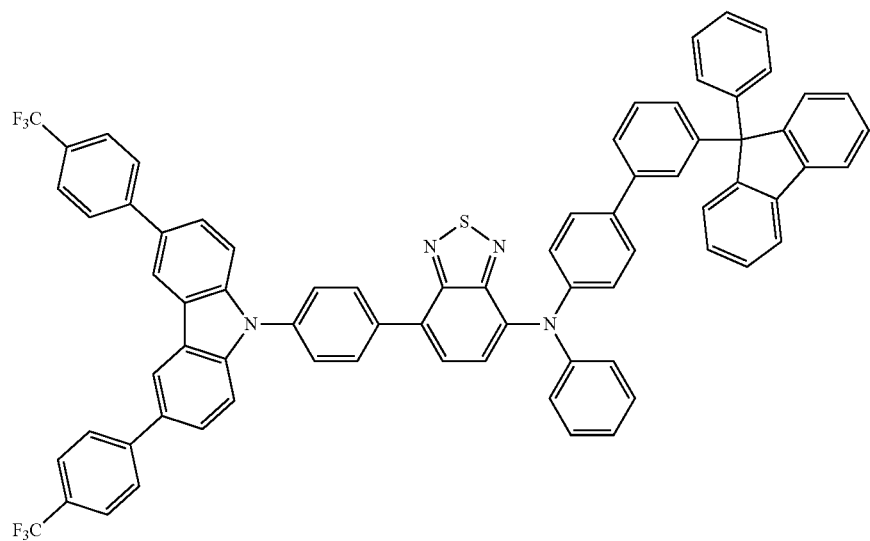
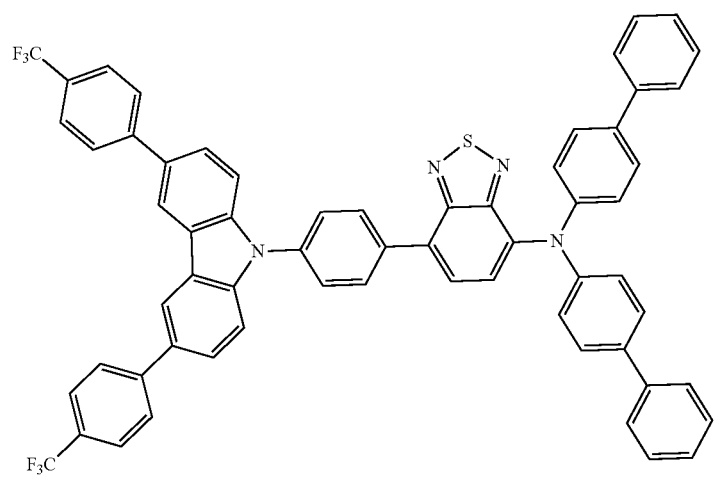

-continued
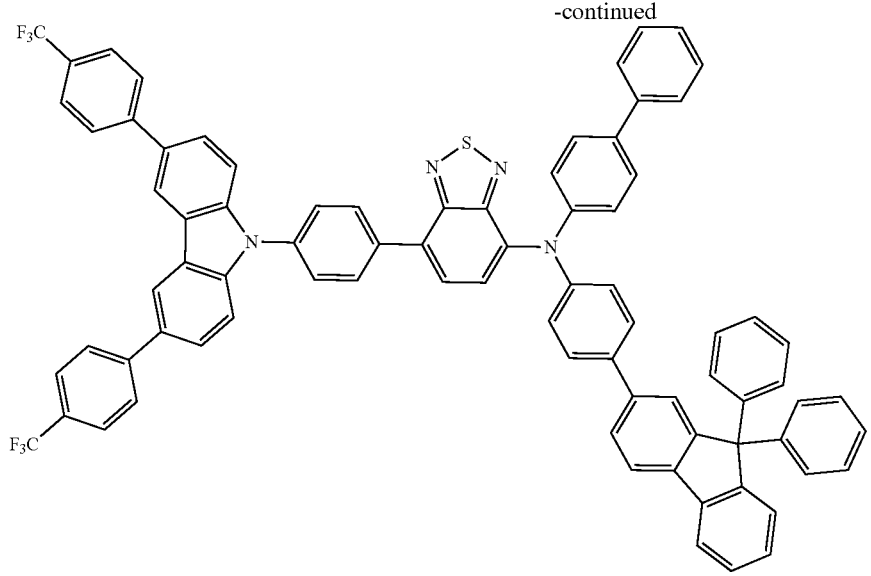
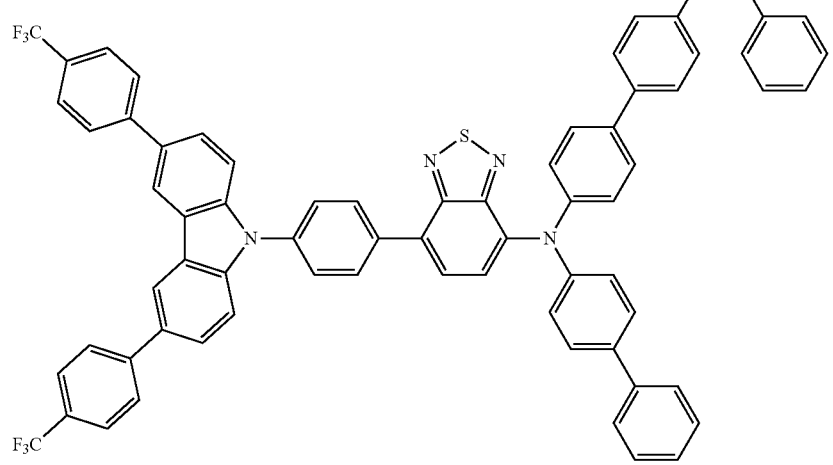
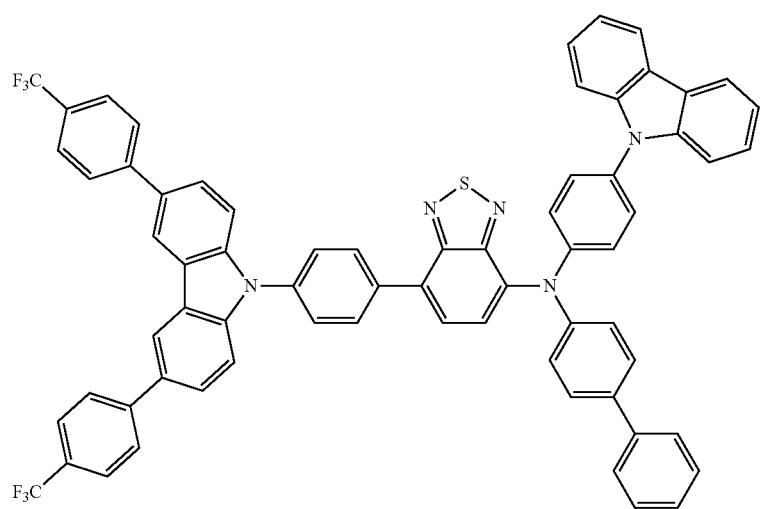

-continued
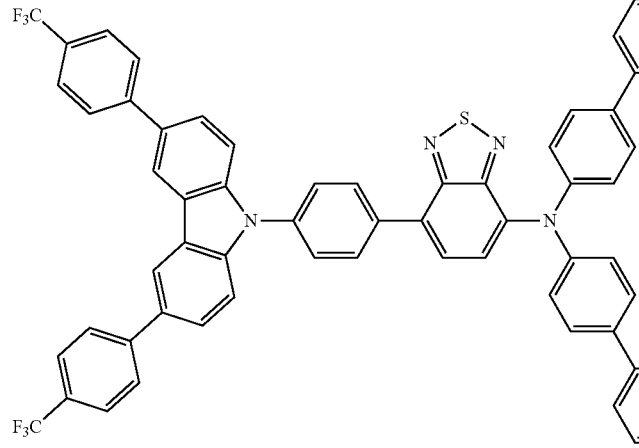
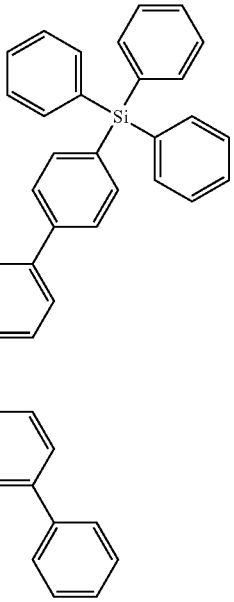
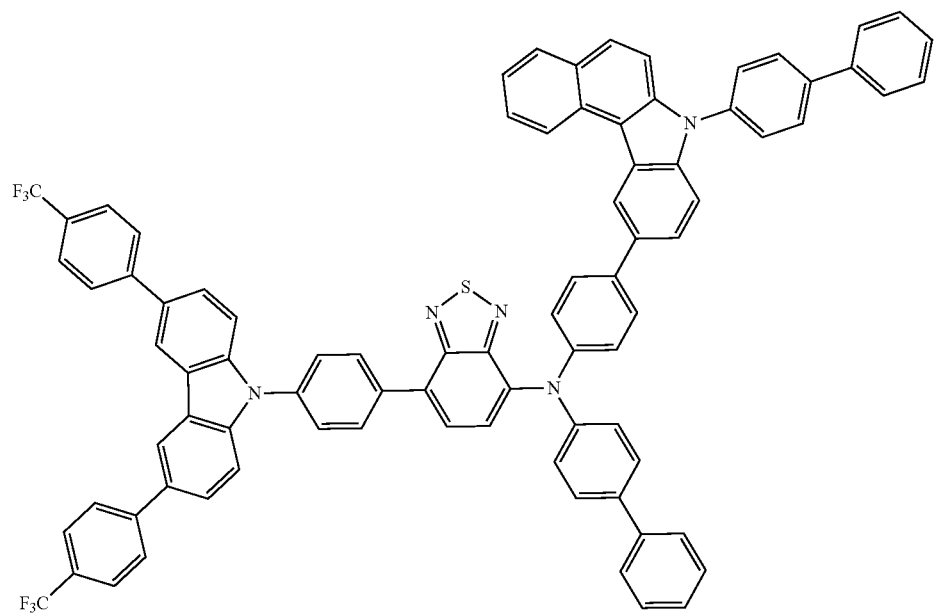

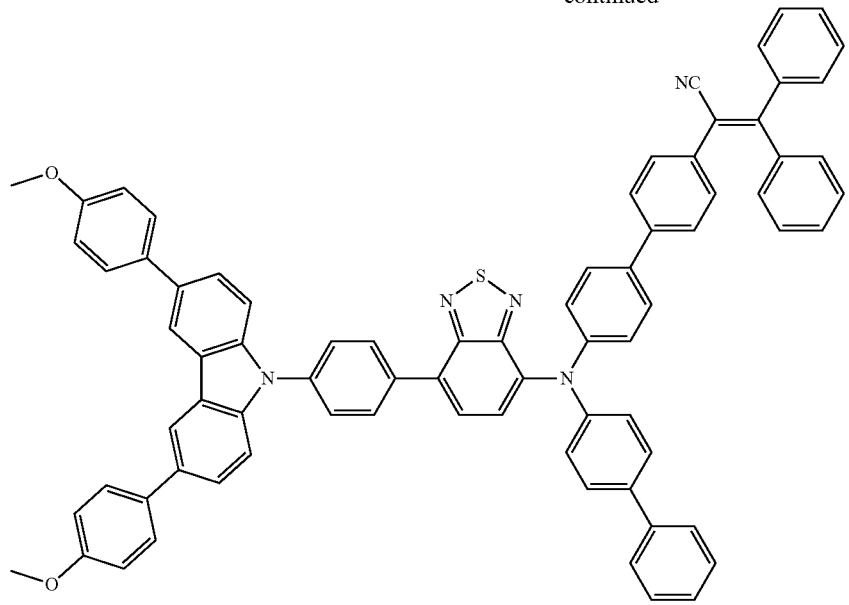
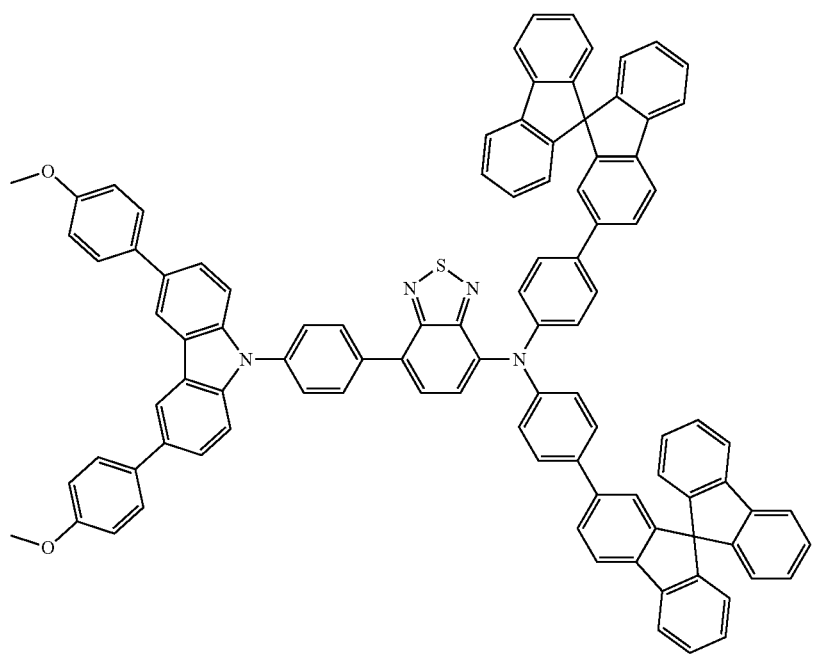

-continued
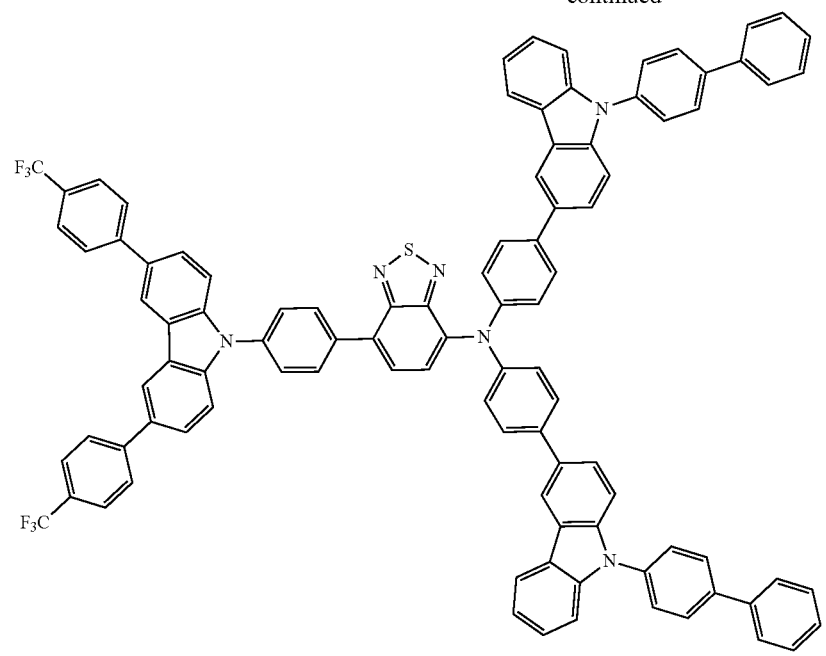
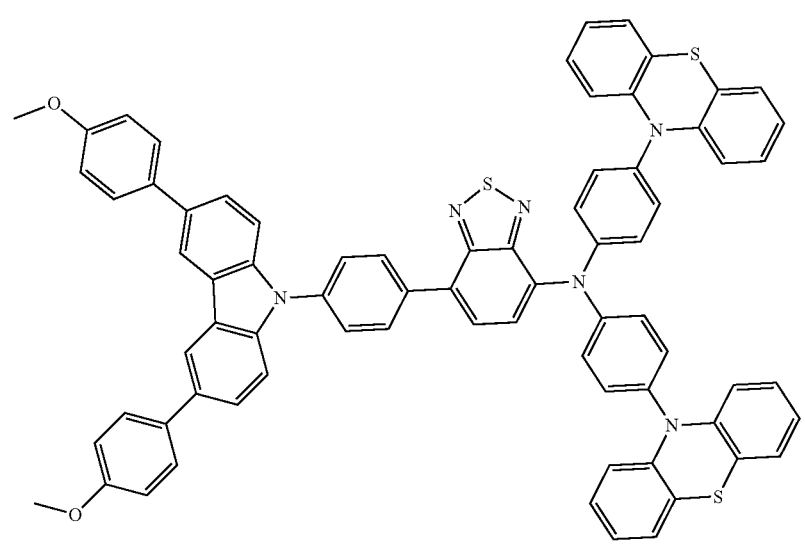

-continued
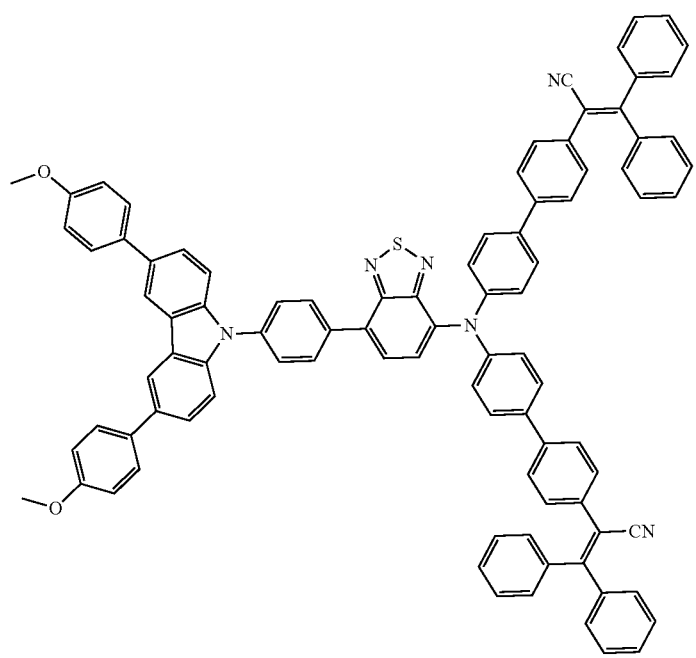
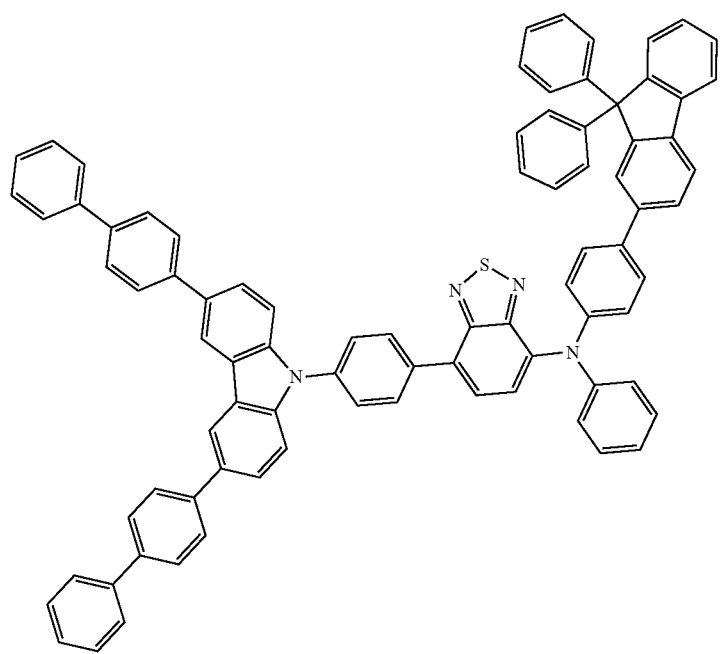

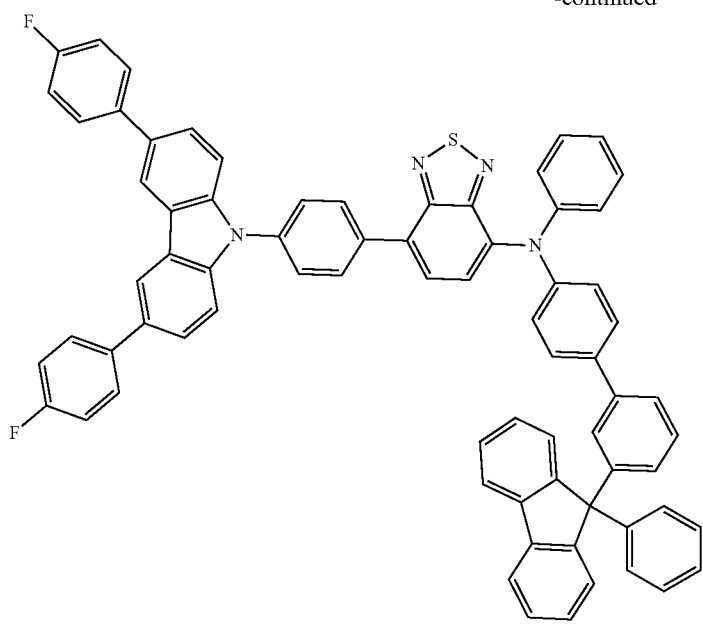
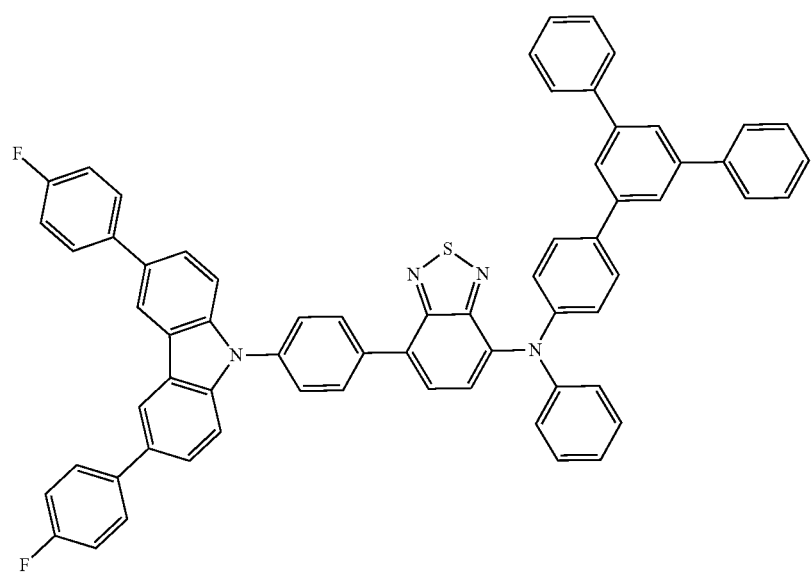

-continued
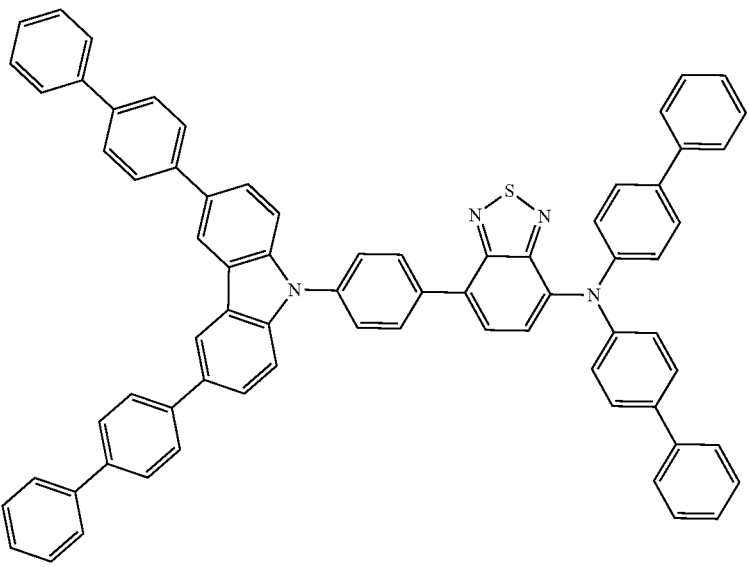
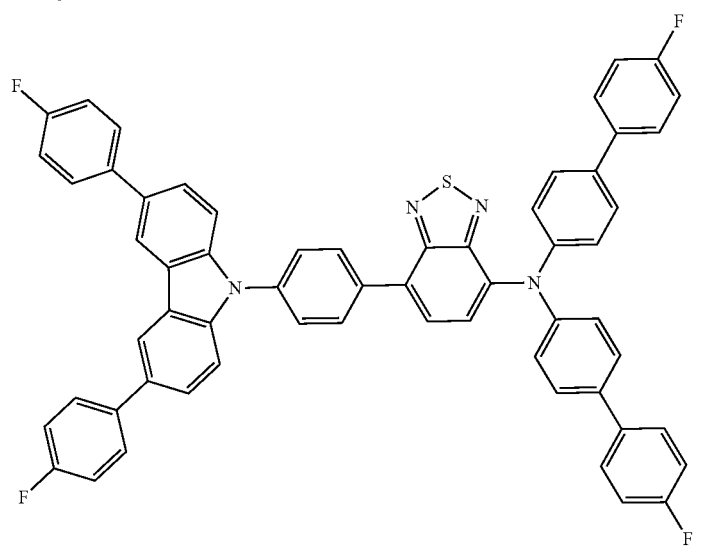
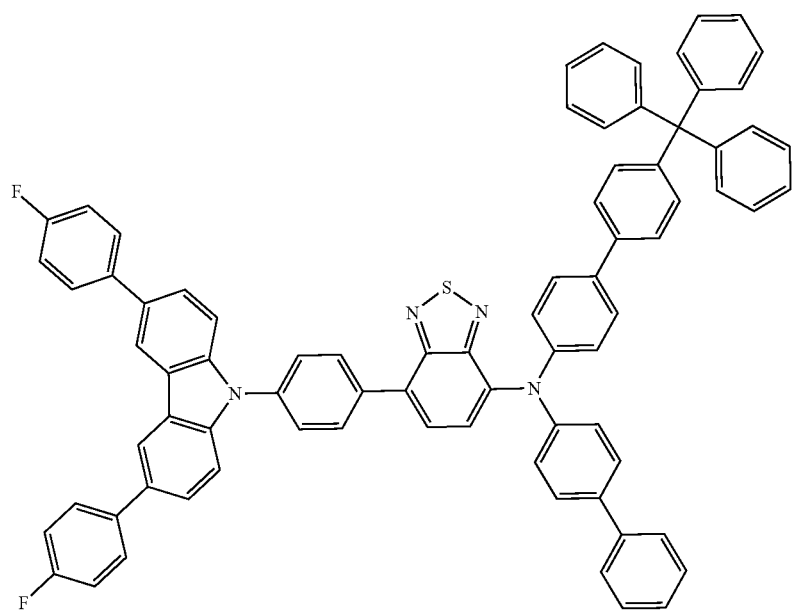

-continued
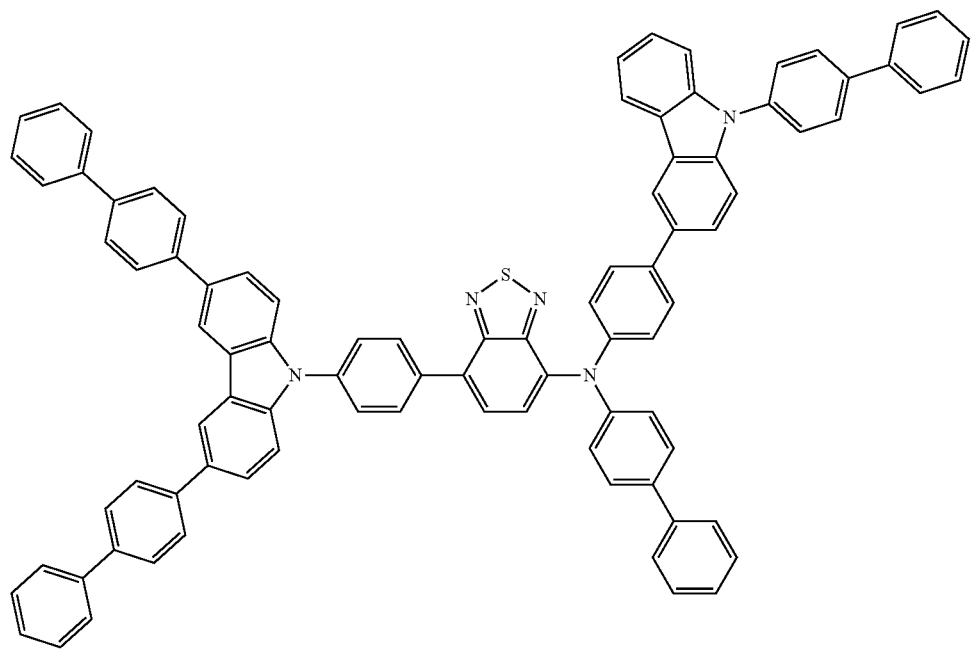
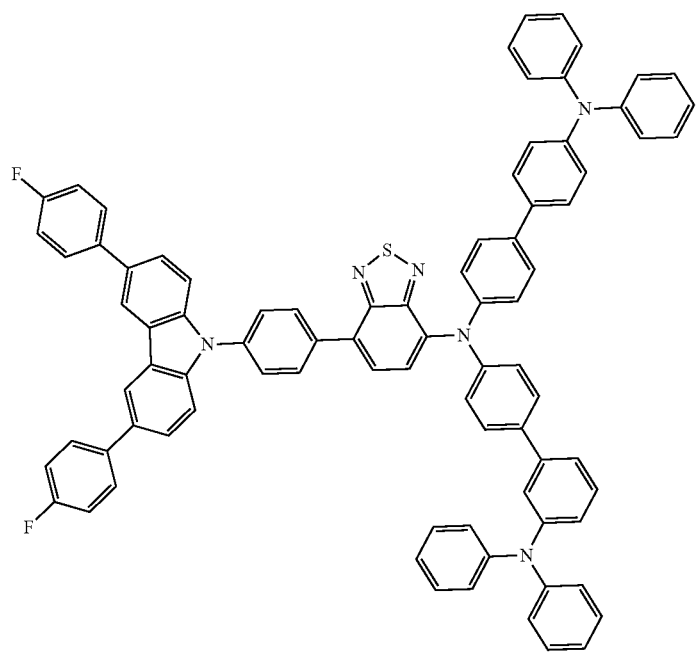

-continued
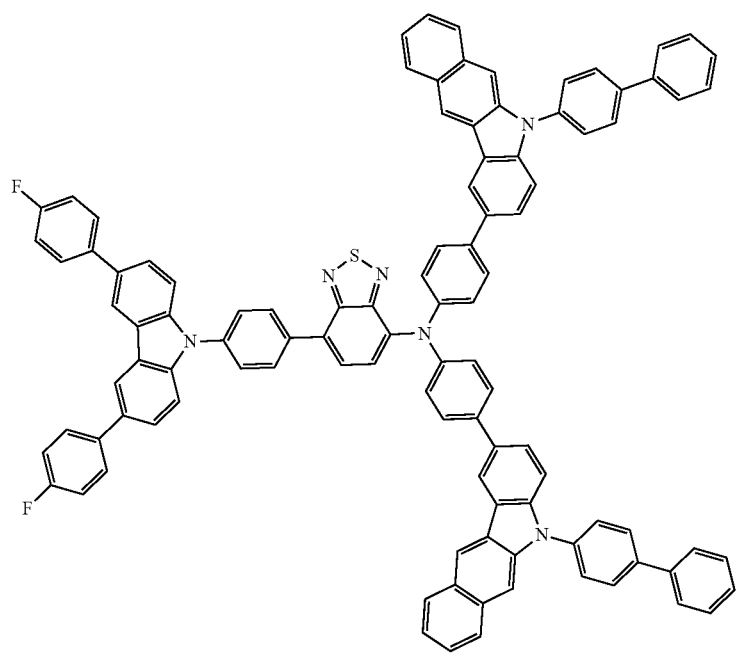
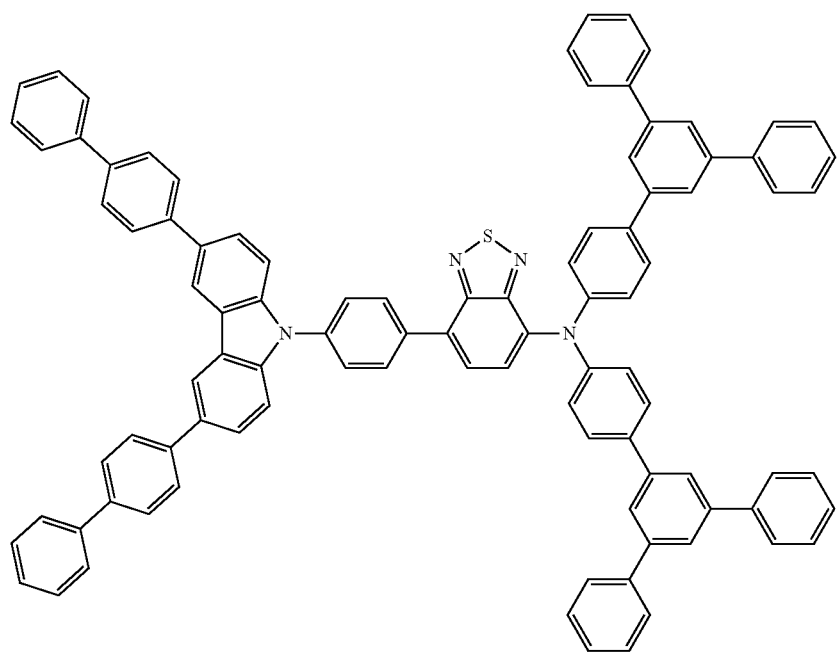

-continued
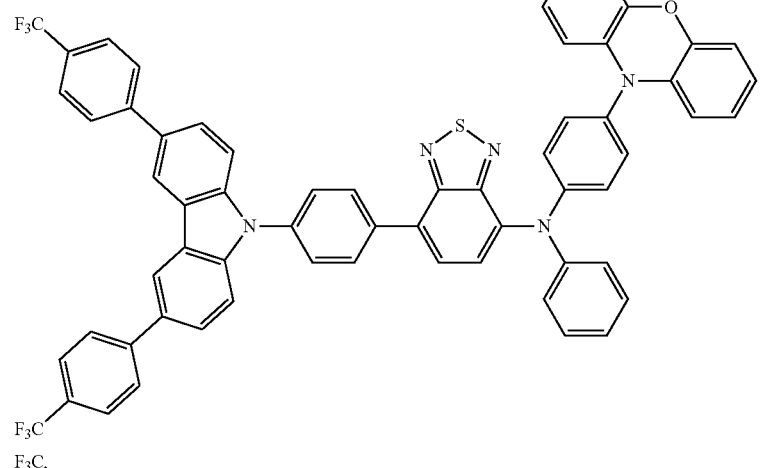
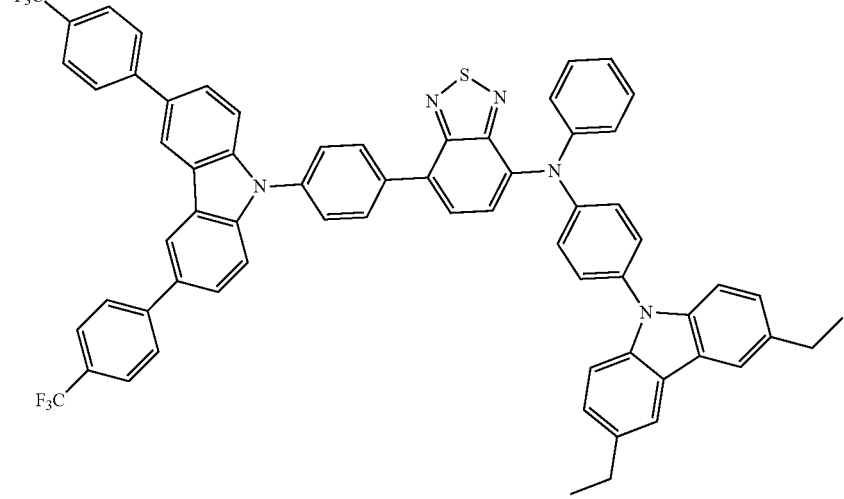
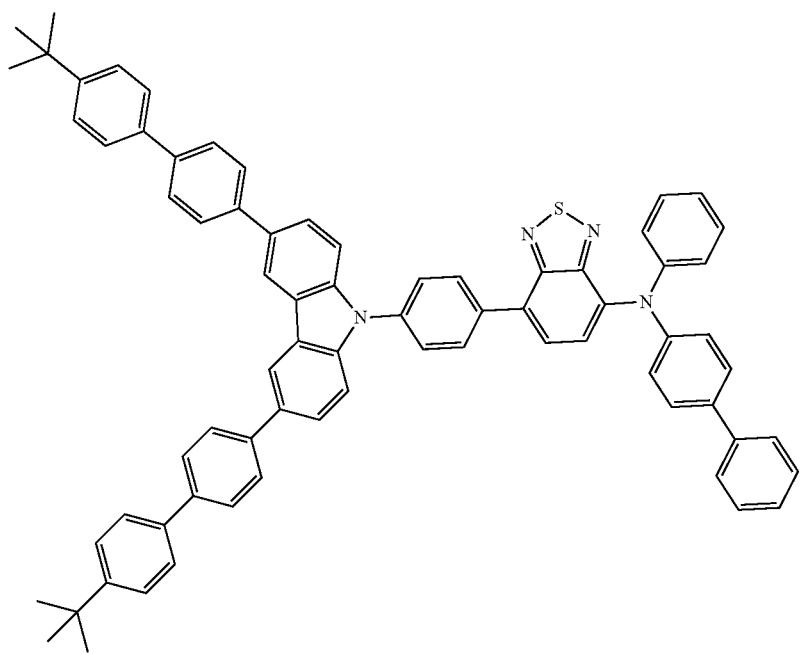

-continued
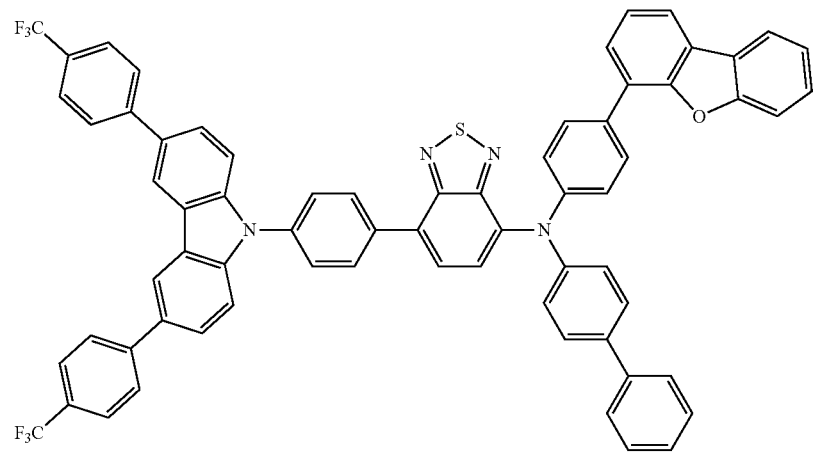
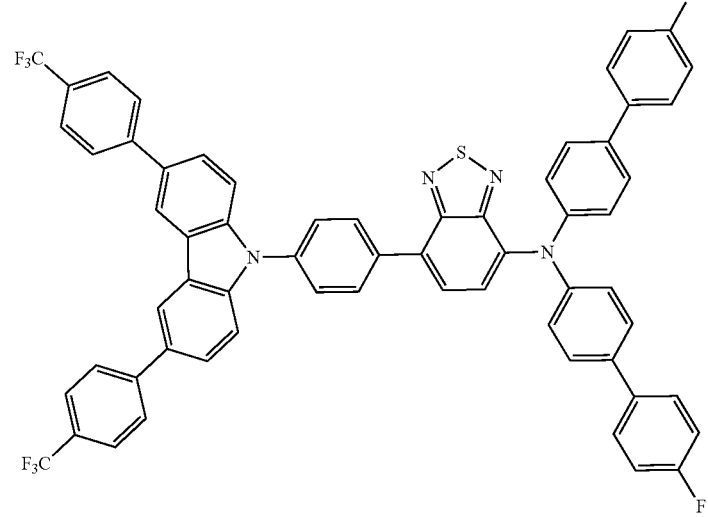
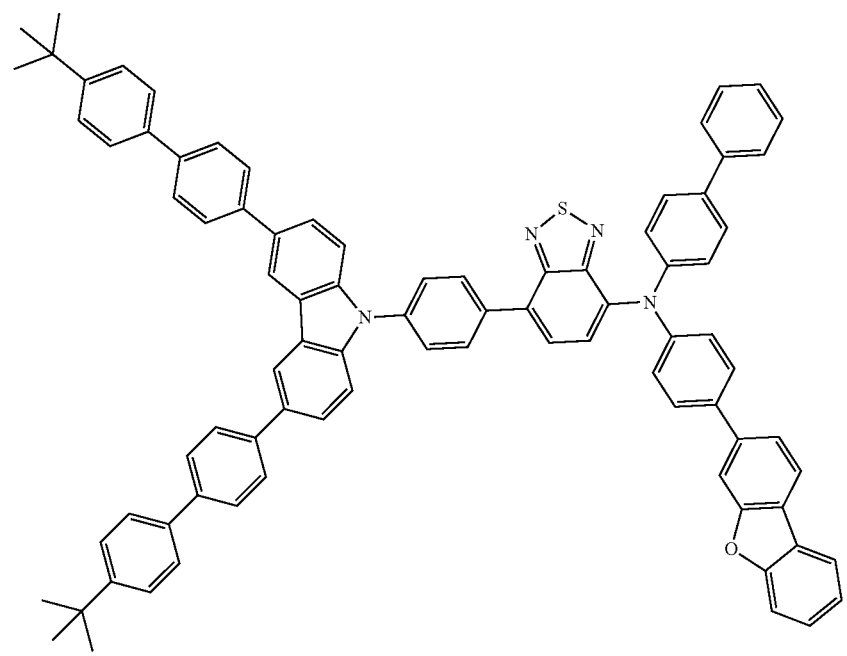

-continued
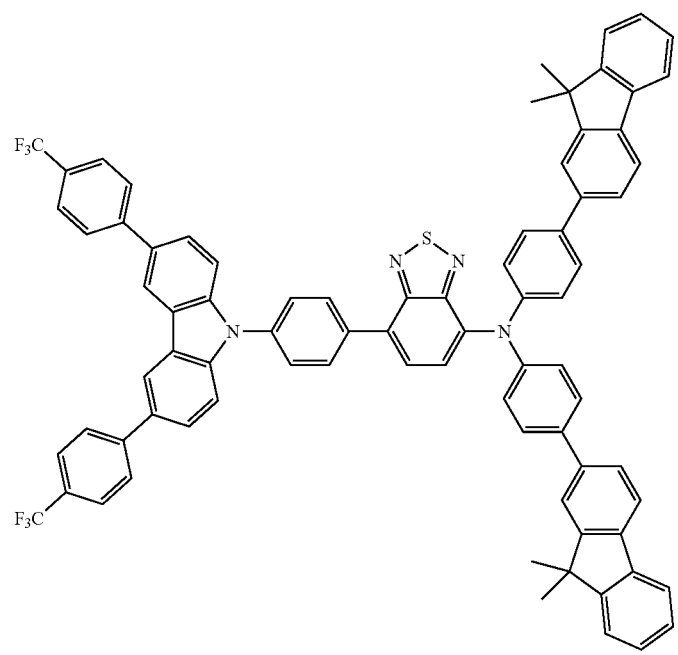
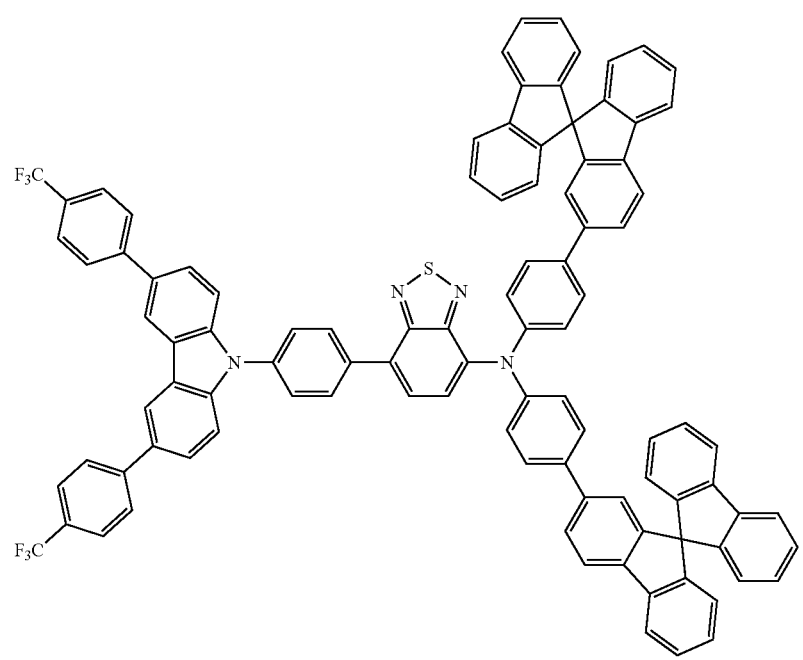

-continued
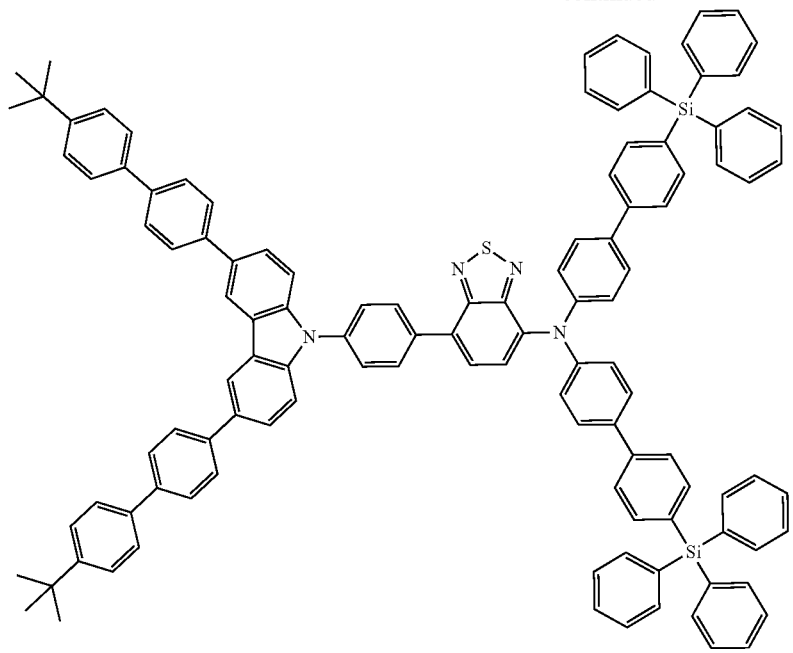
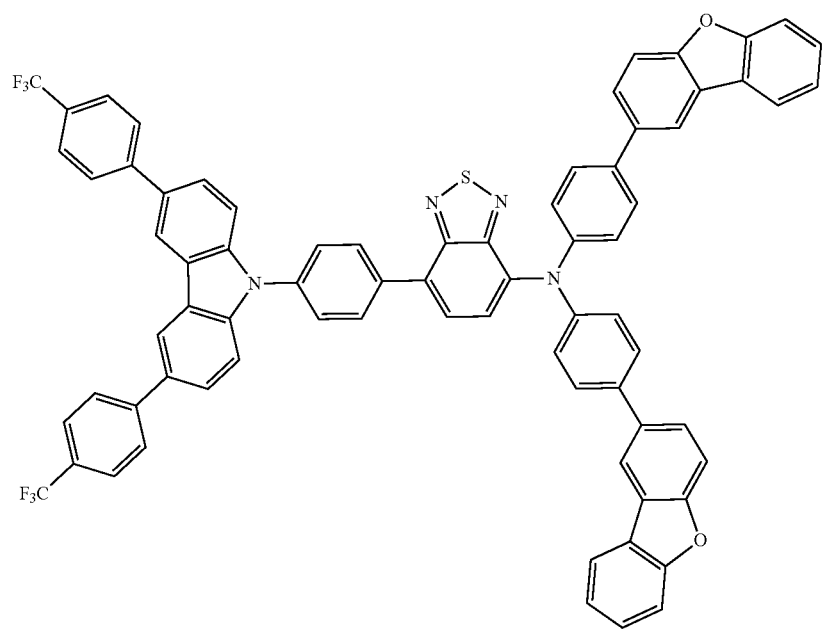

-continued
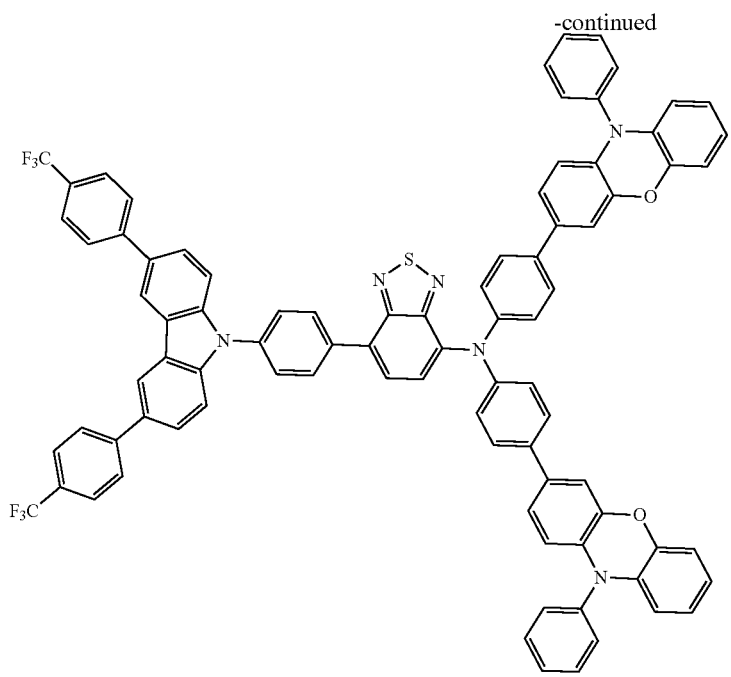
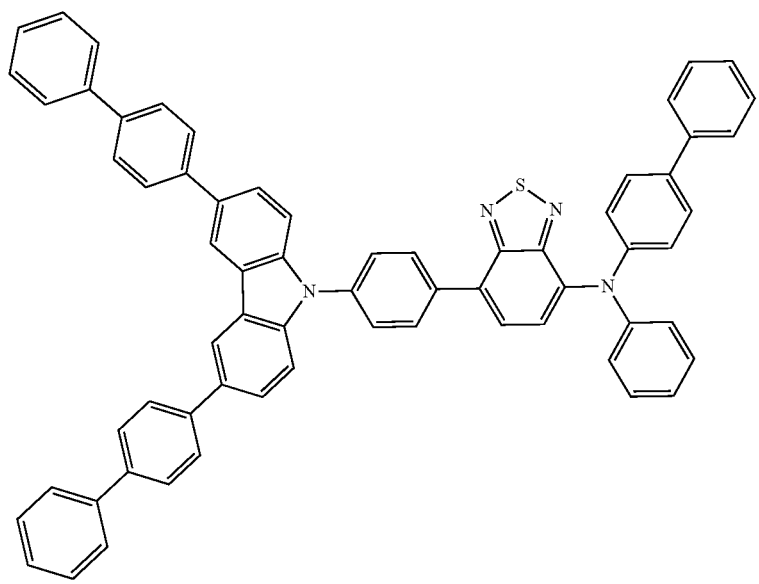

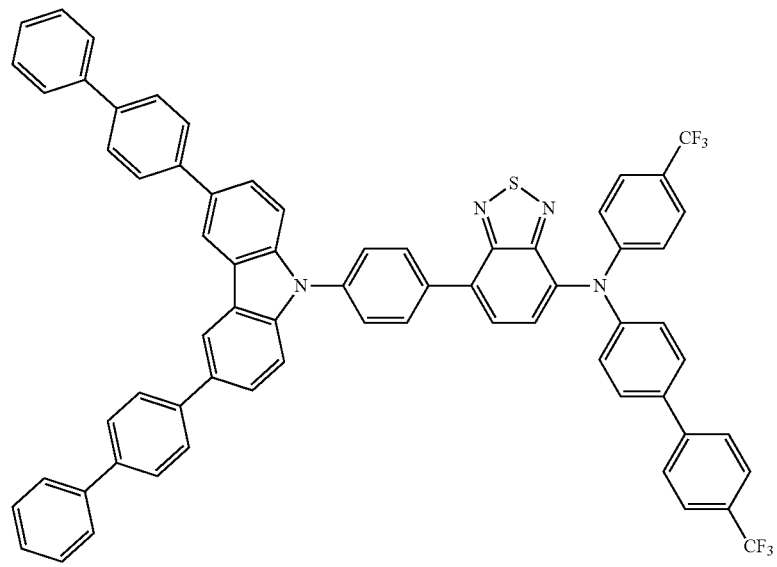
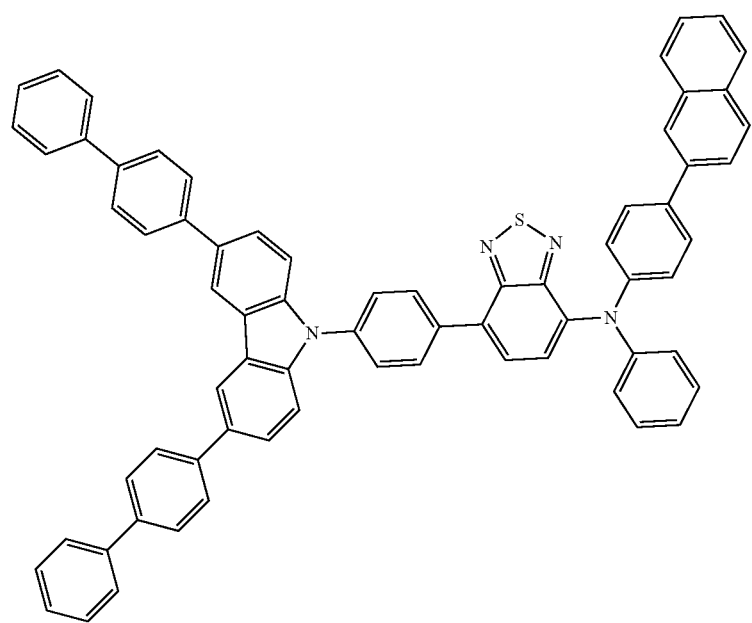

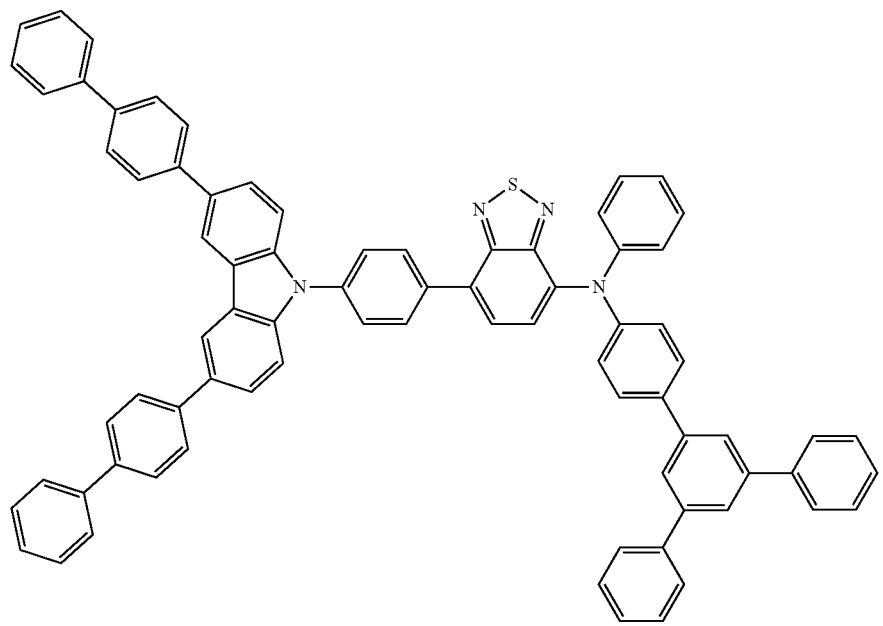
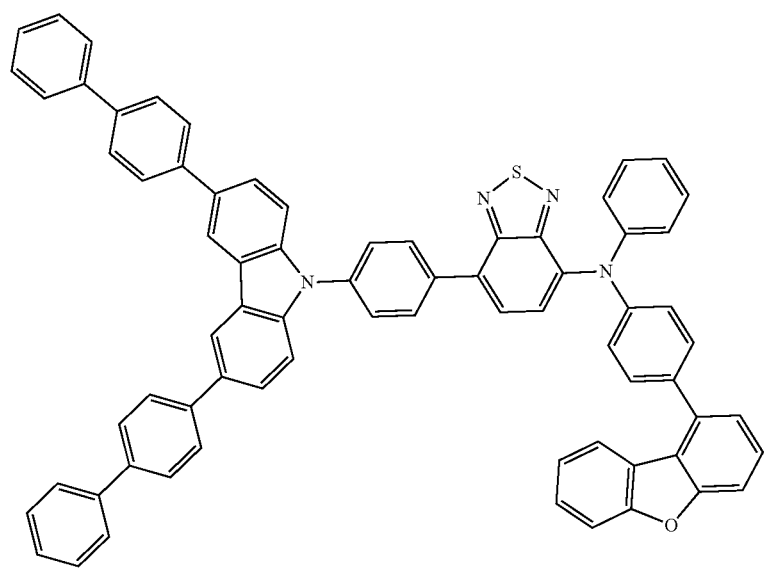

-continued
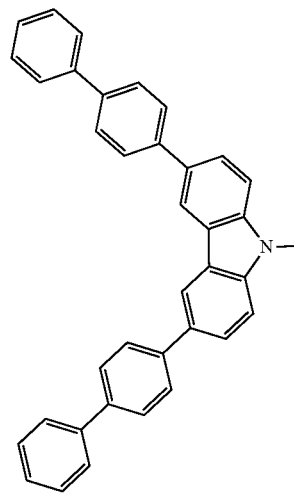
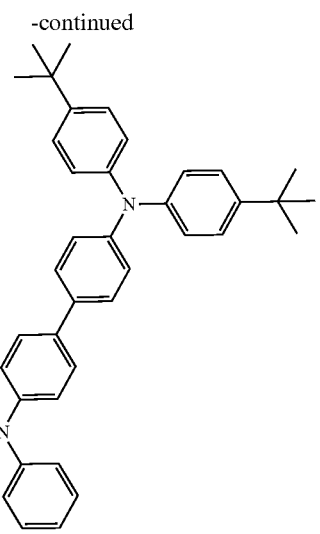
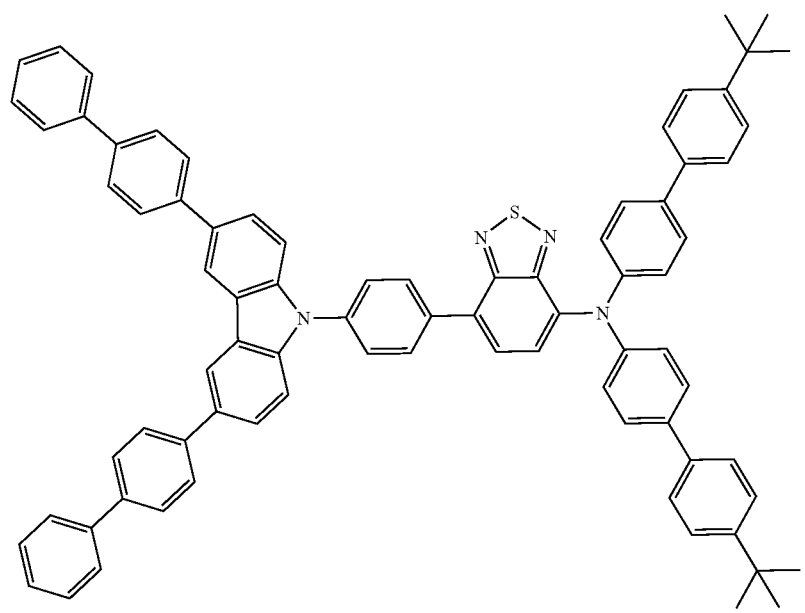

-continued
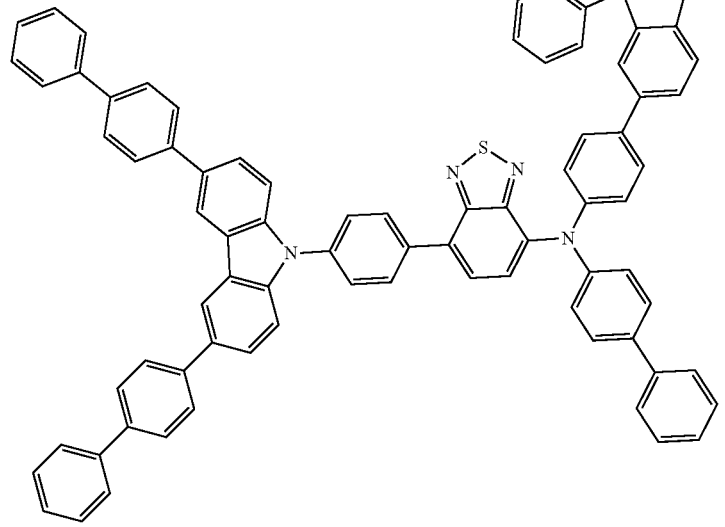
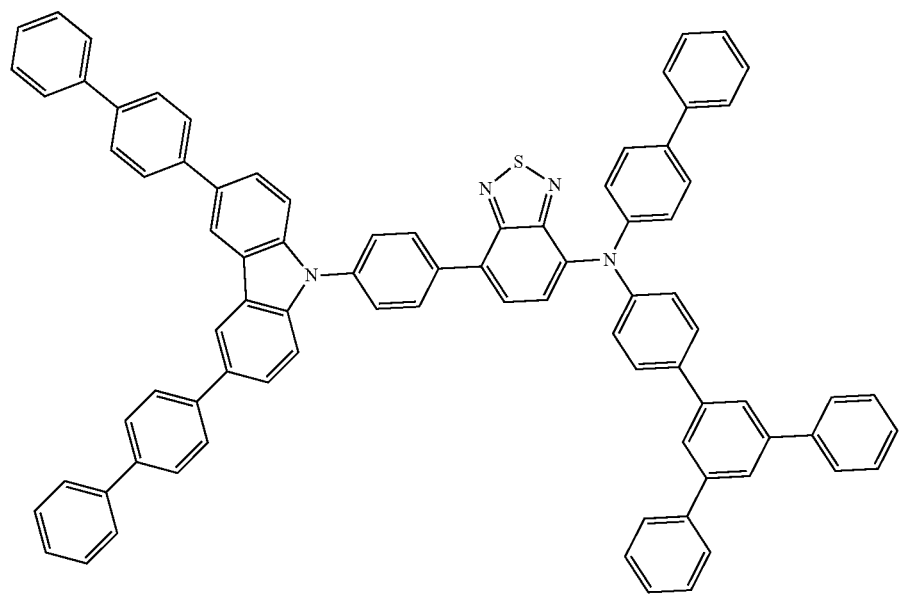

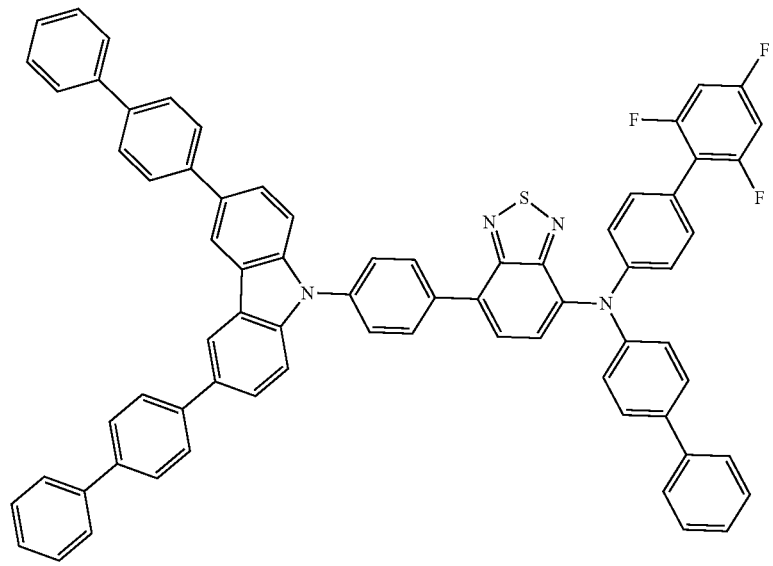
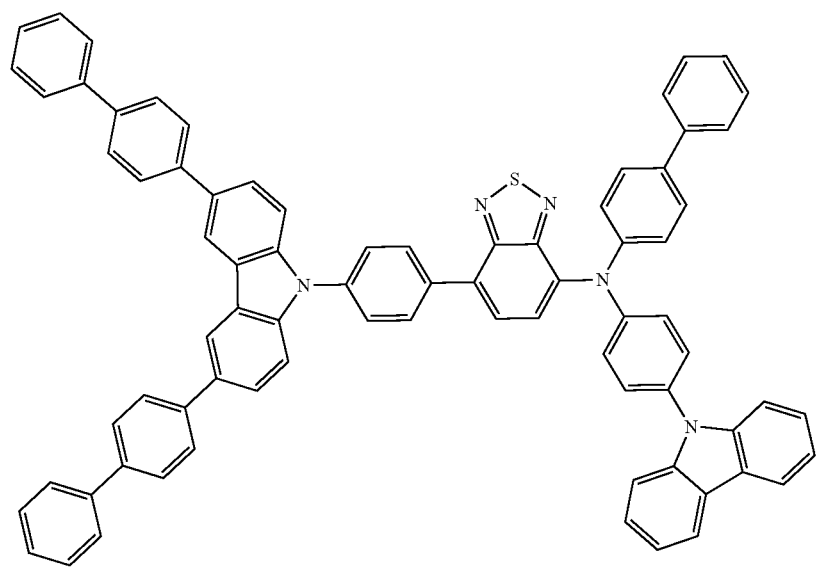

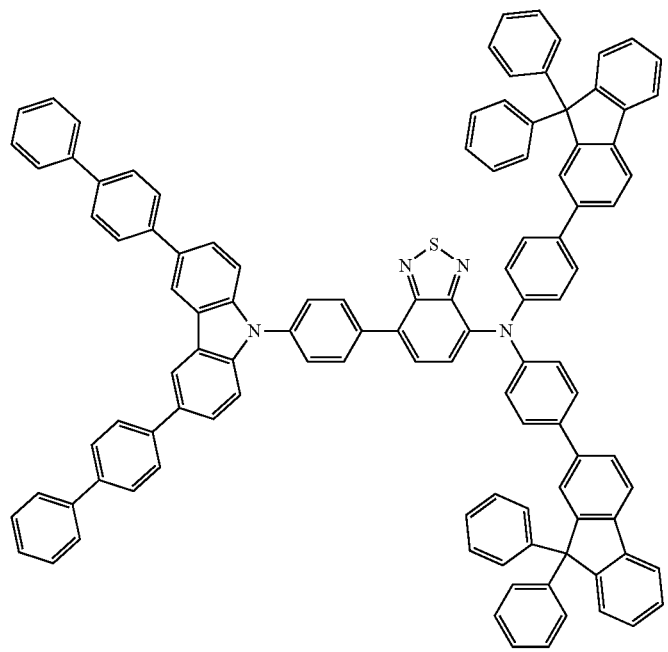
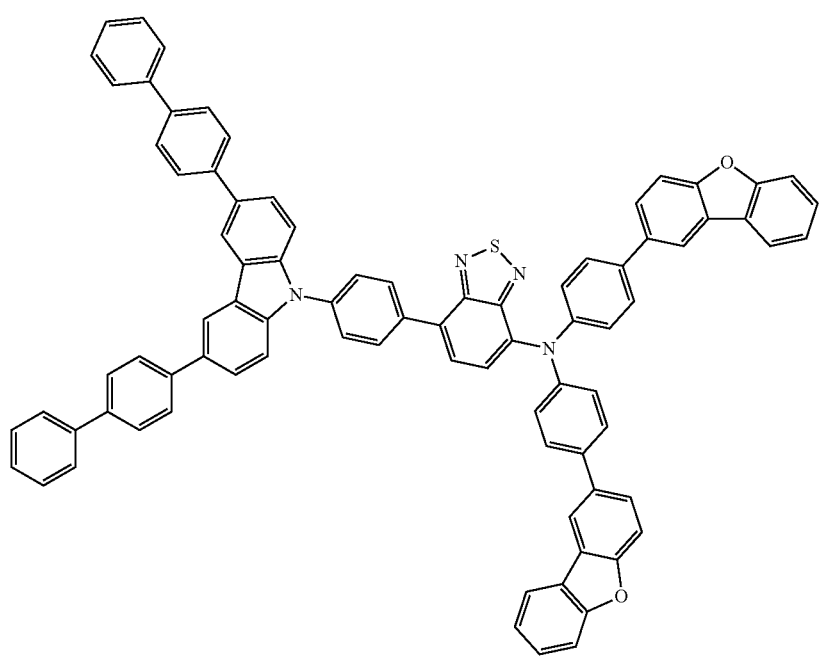

-continued
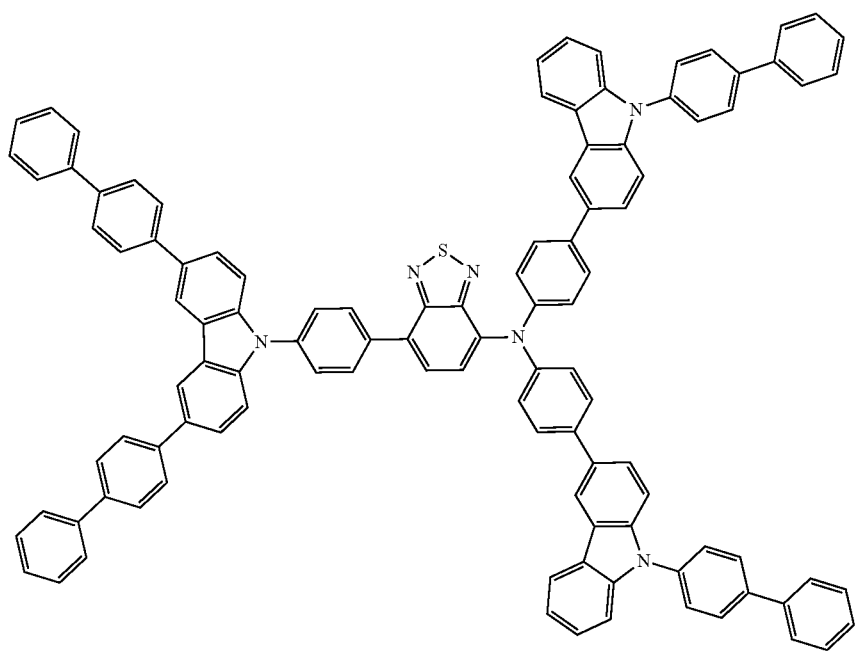
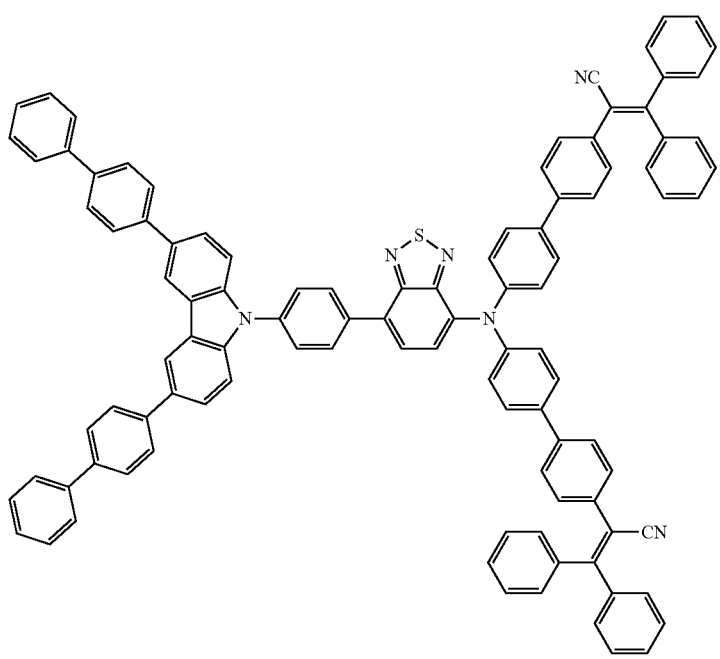

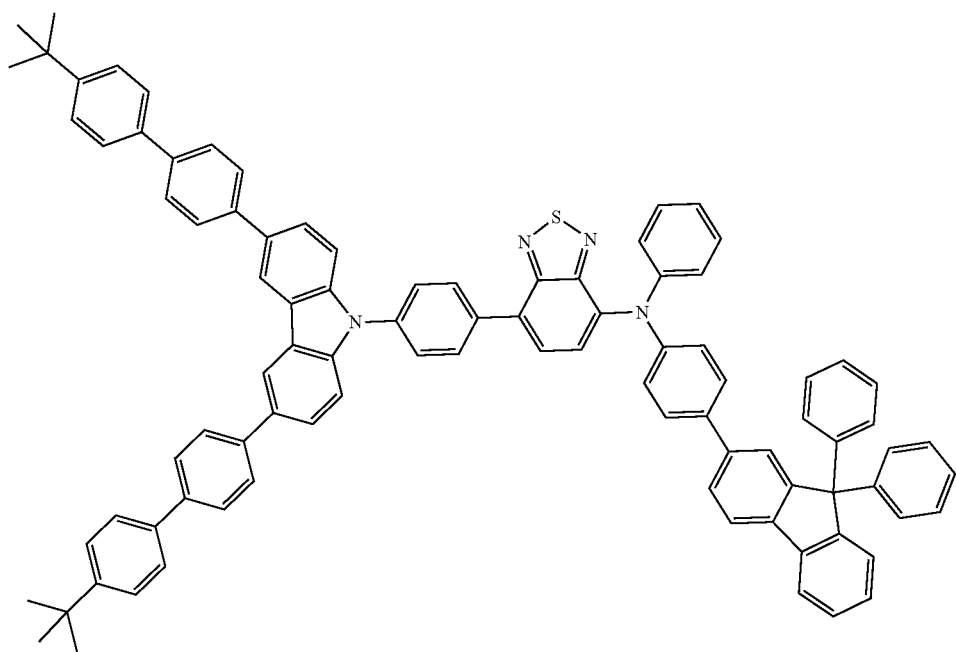
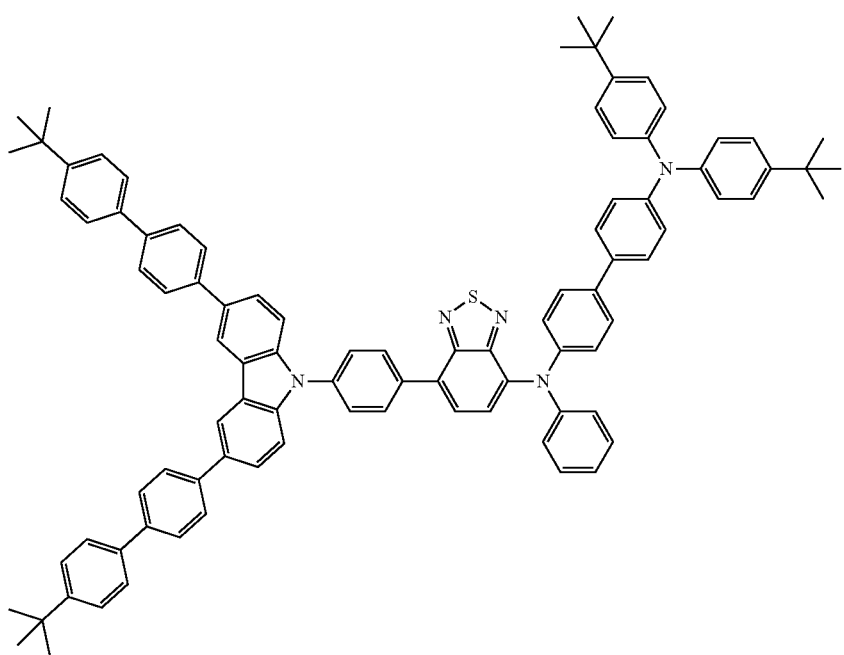

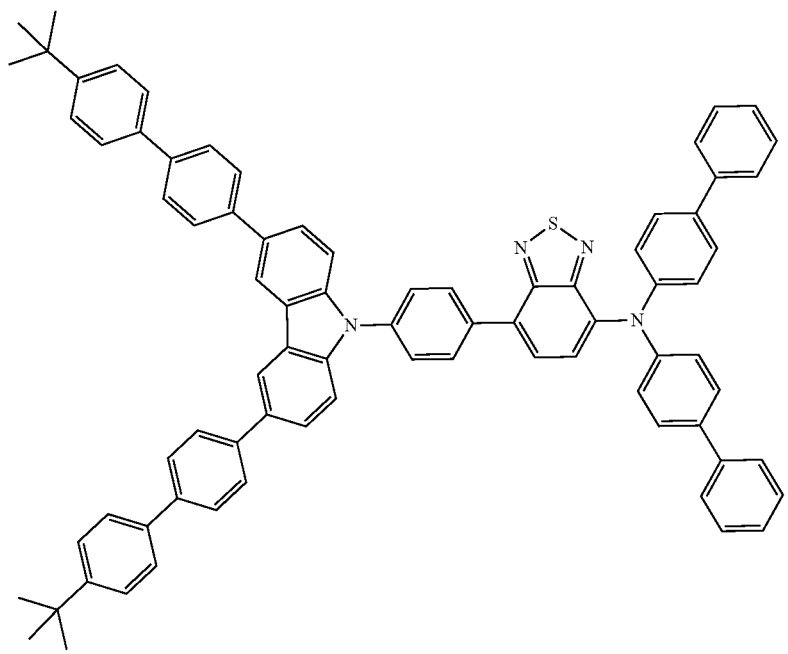
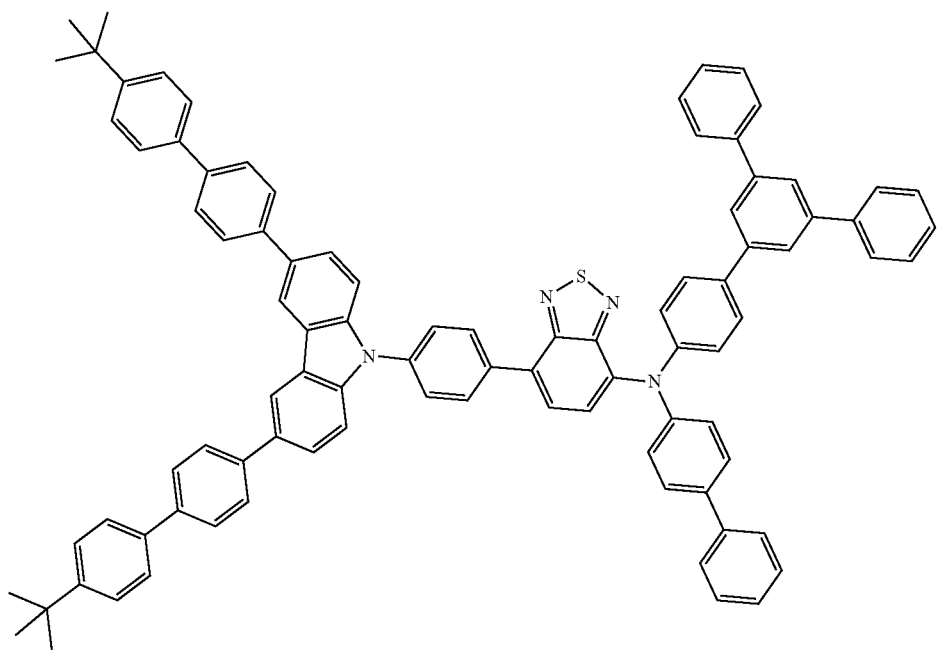

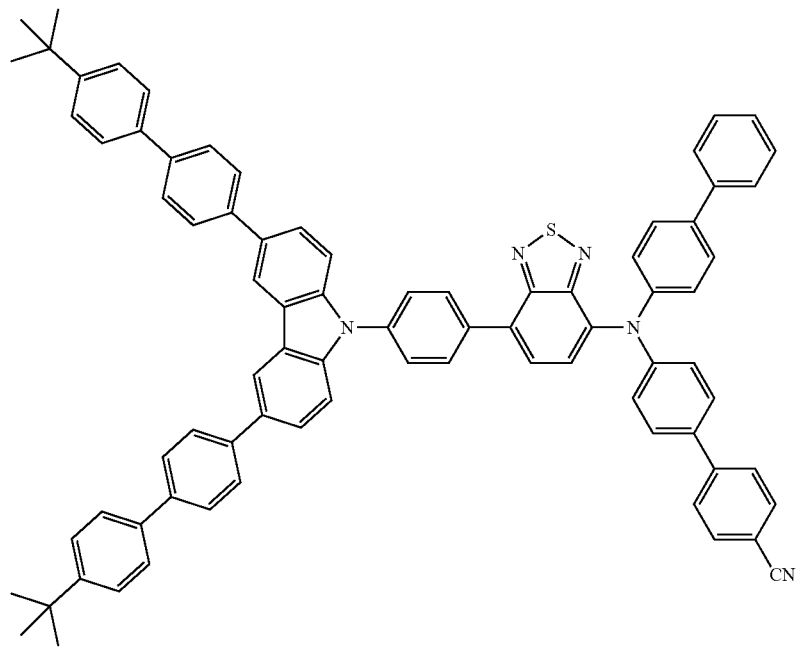
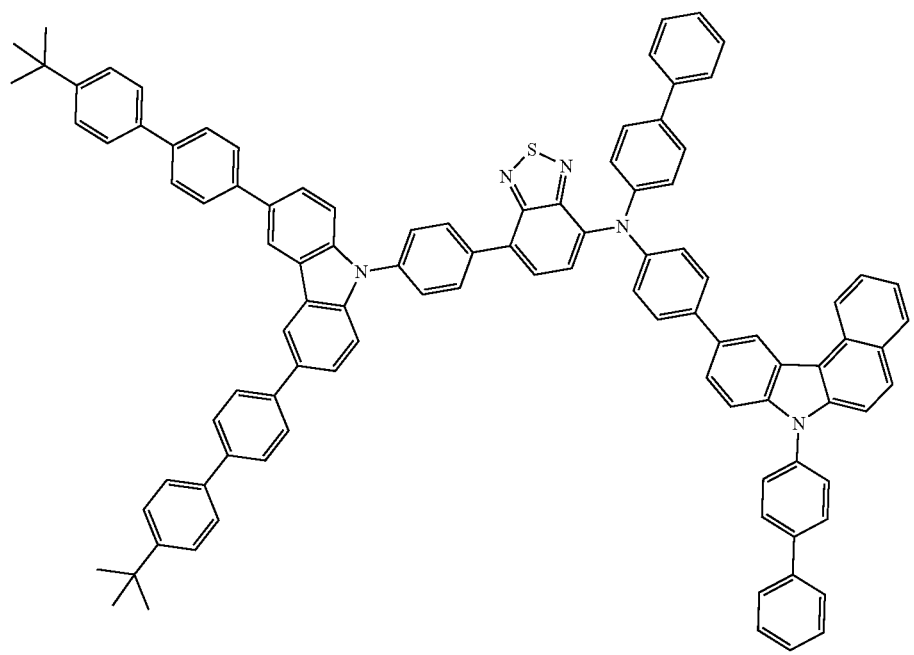

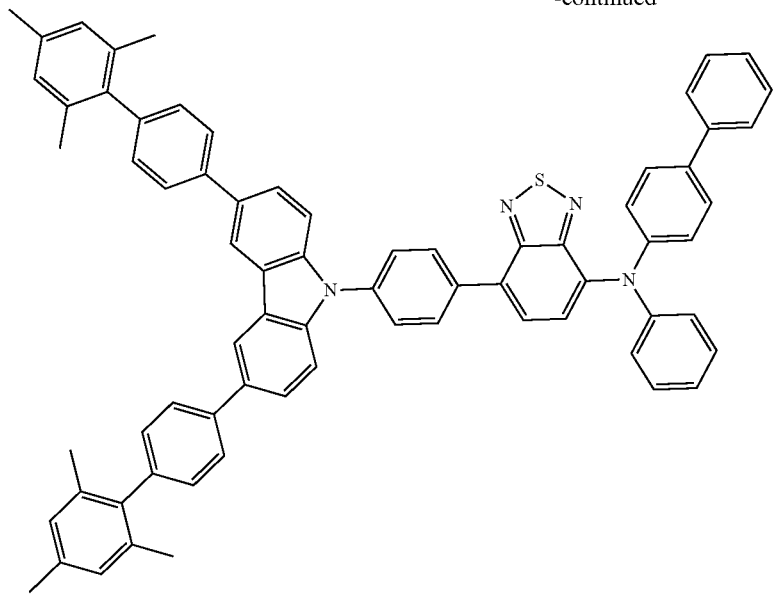
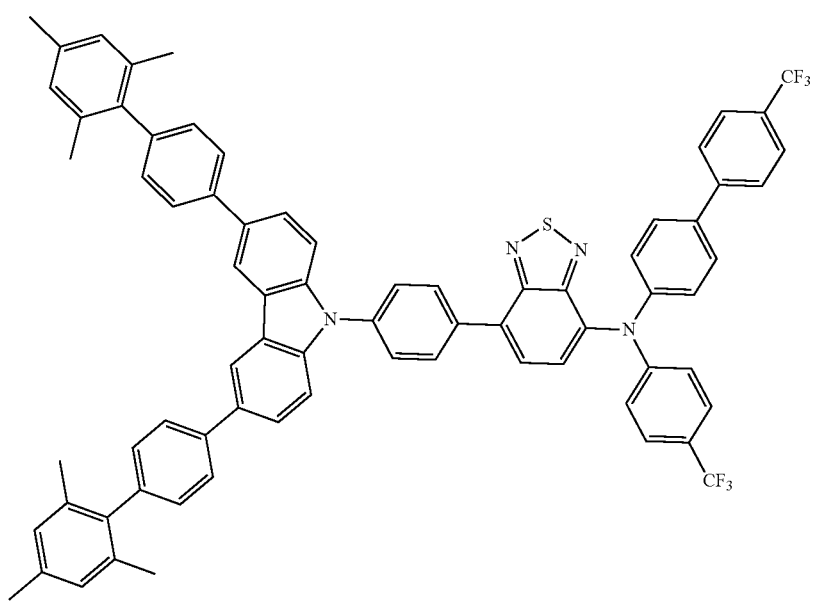

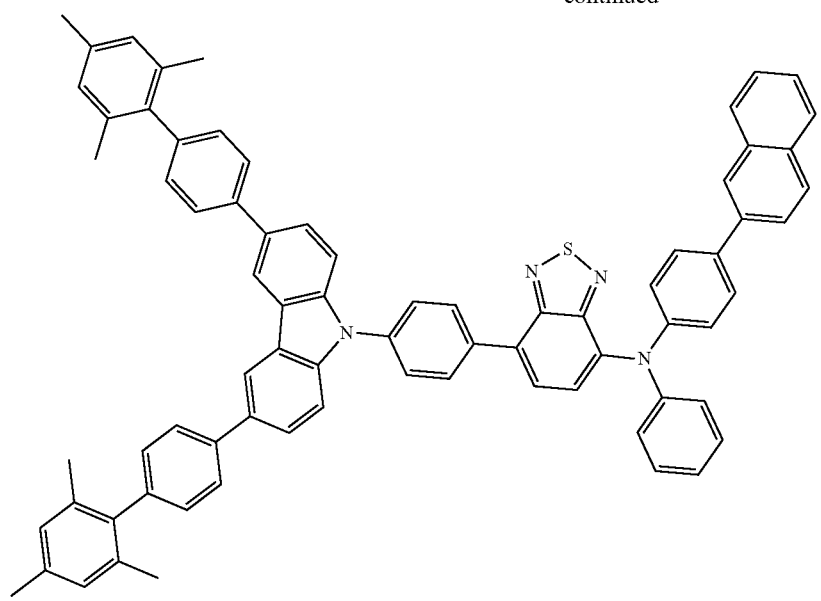
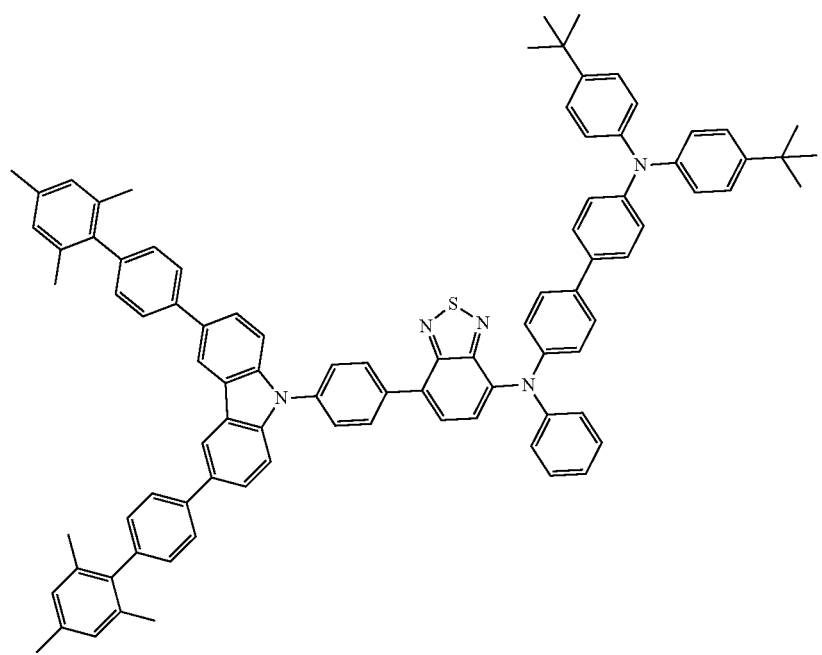

-continued
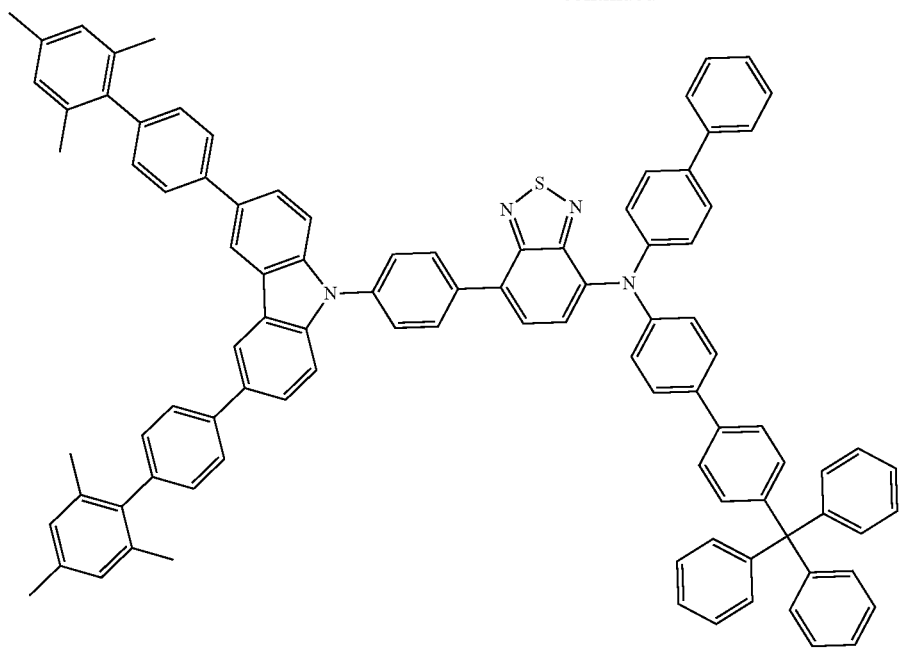
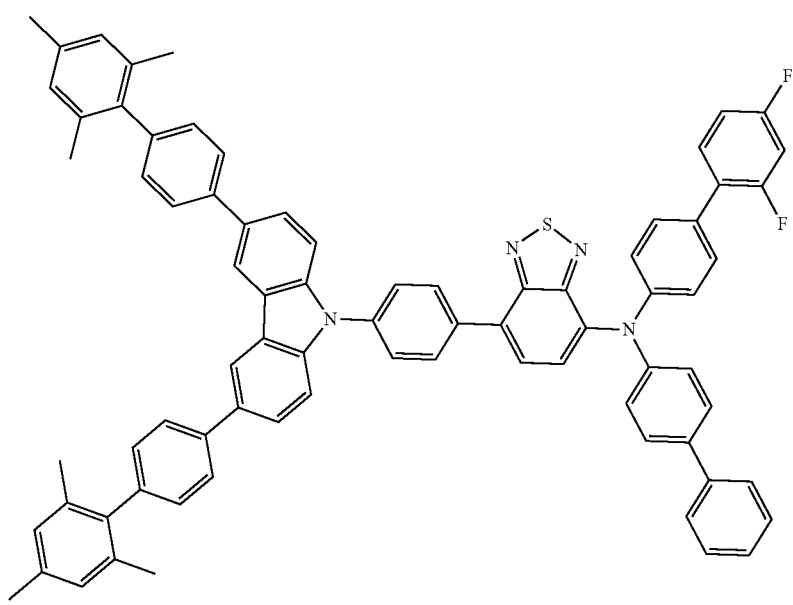

-continued
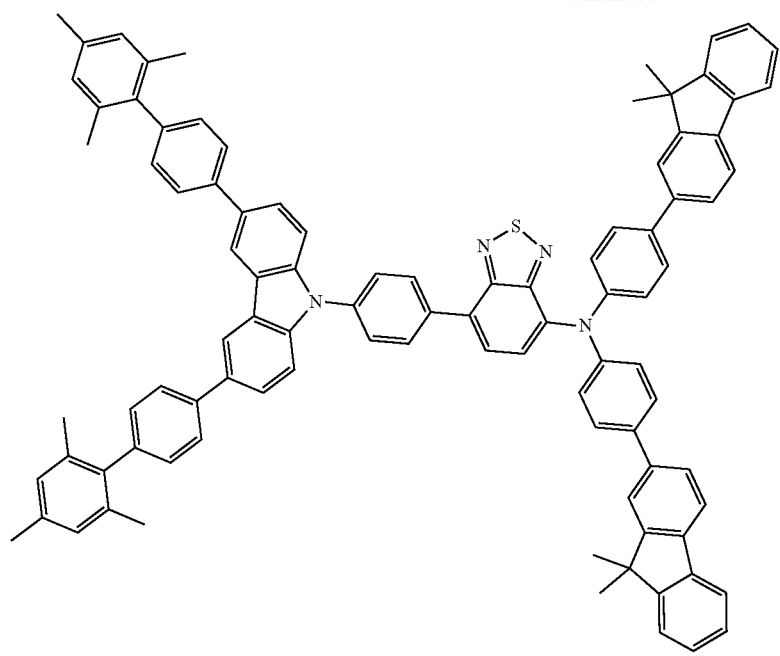
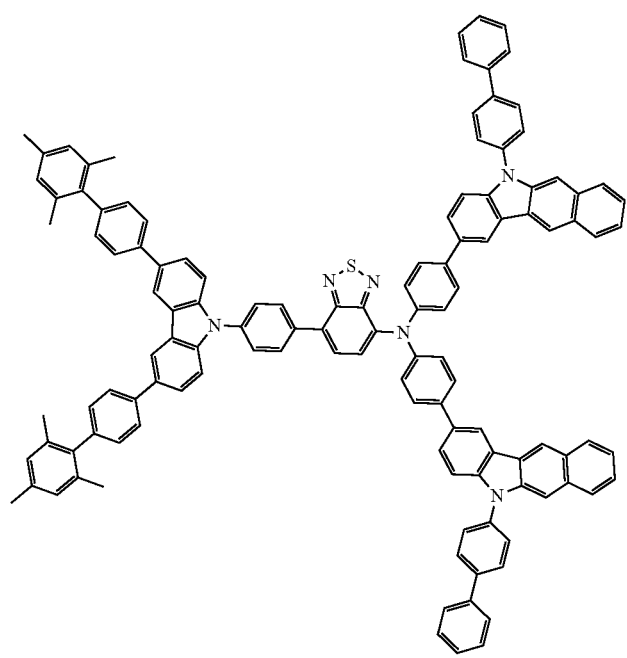

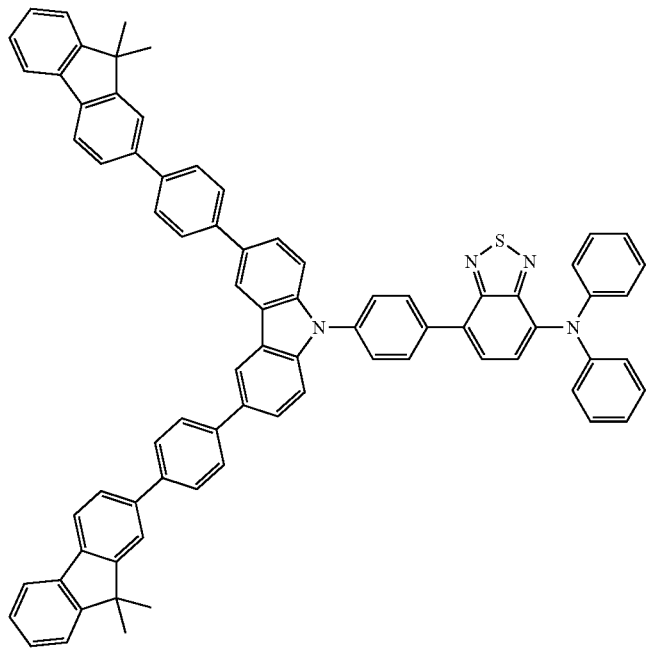
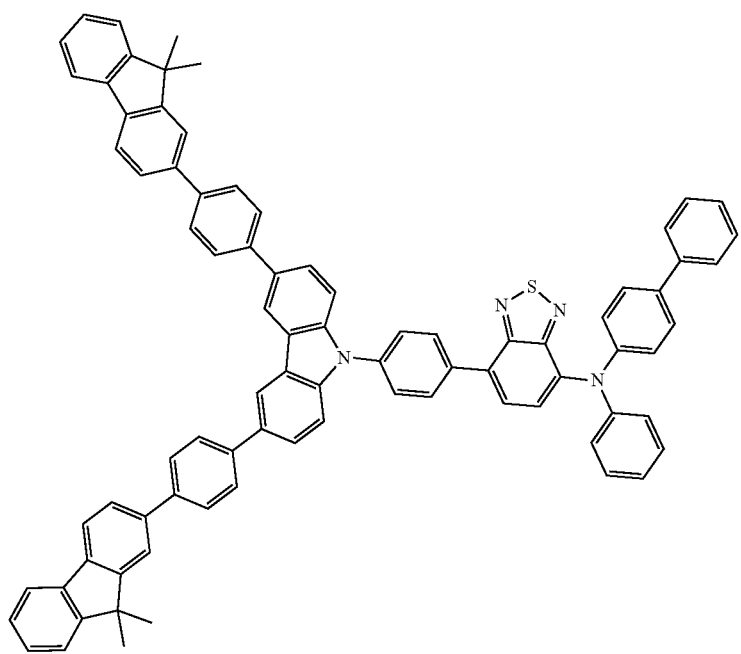

-continued
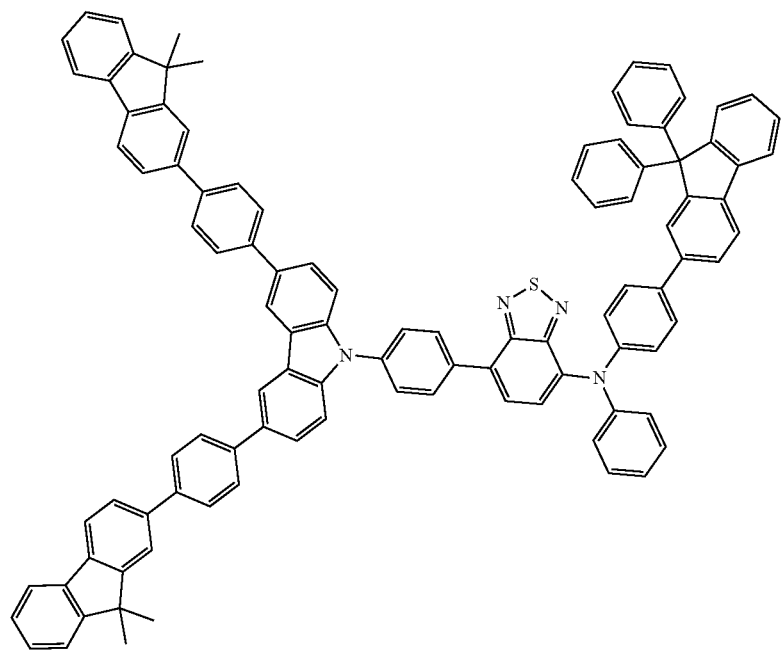
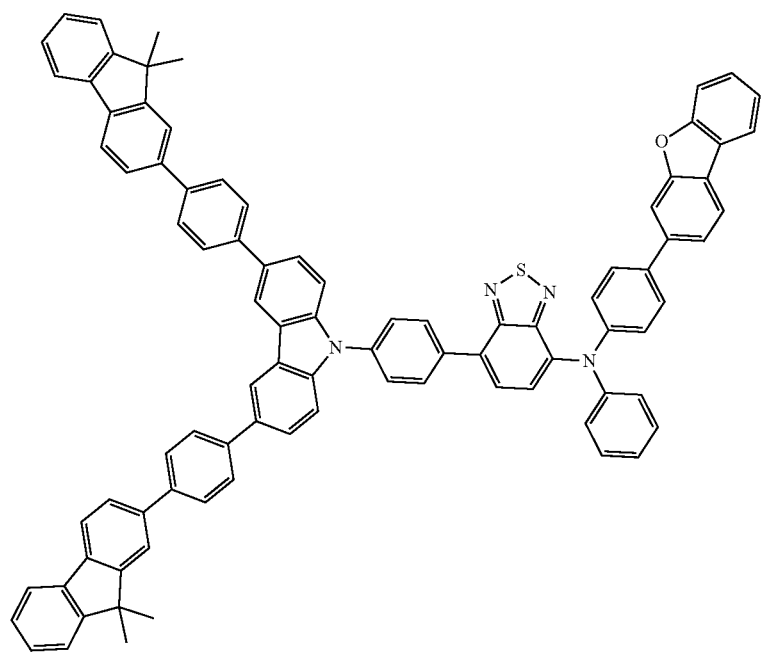

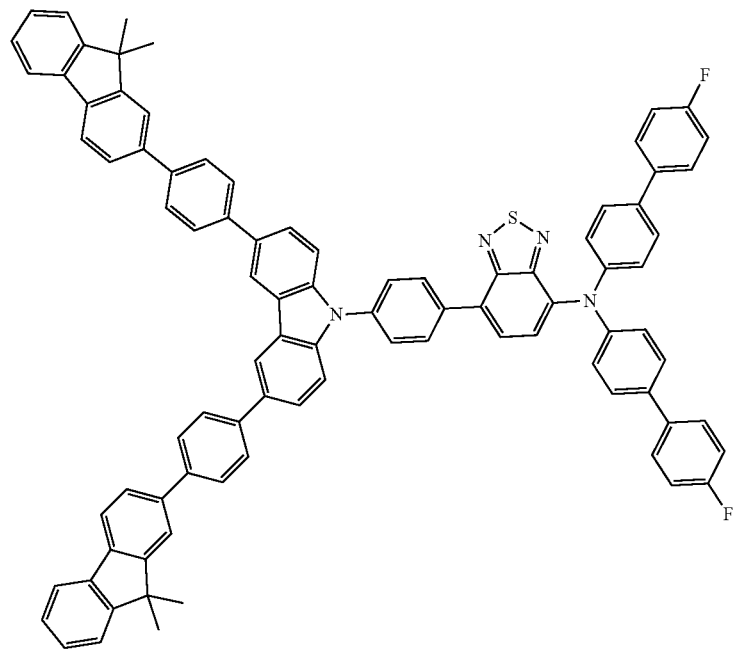
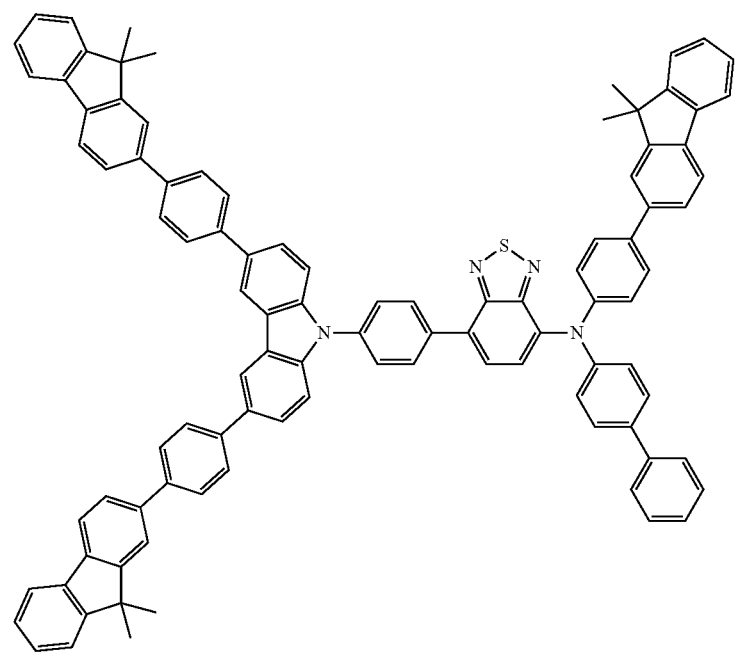

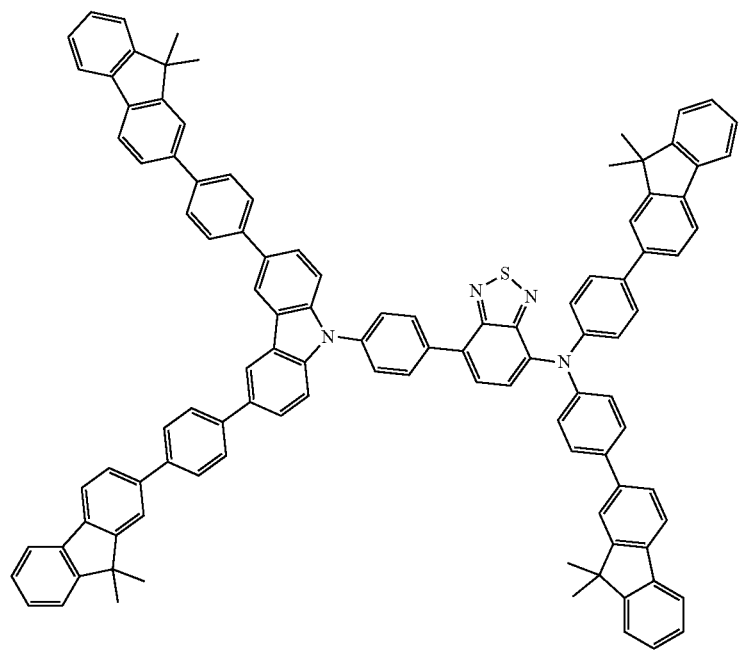
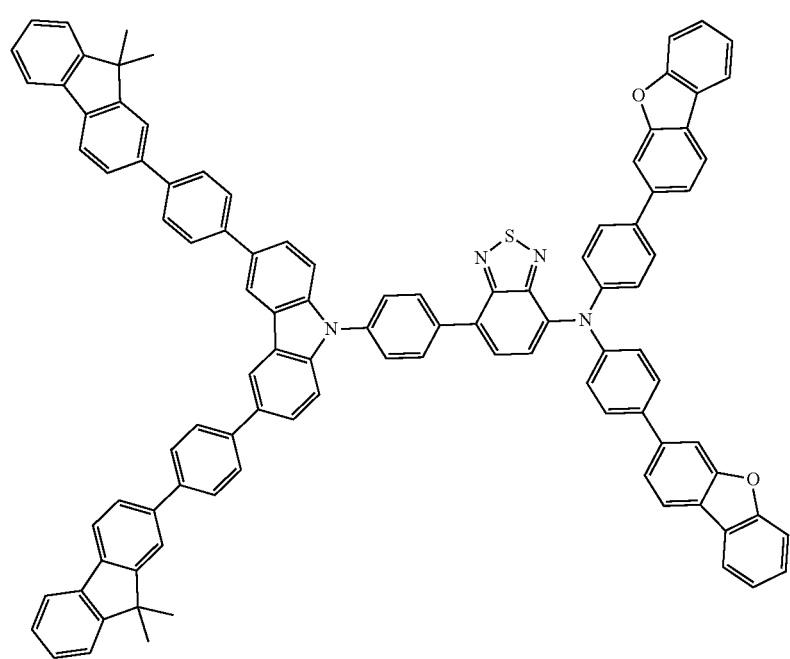

-continued
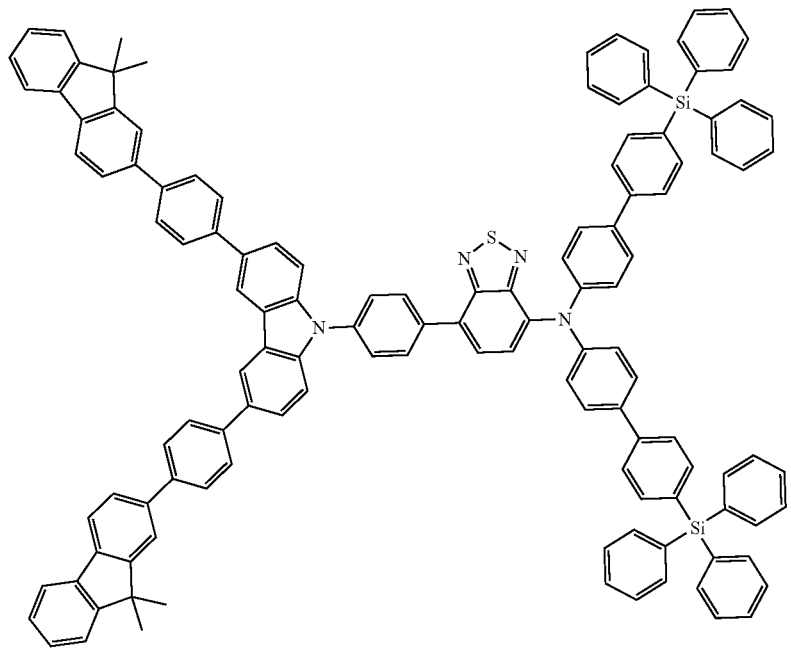
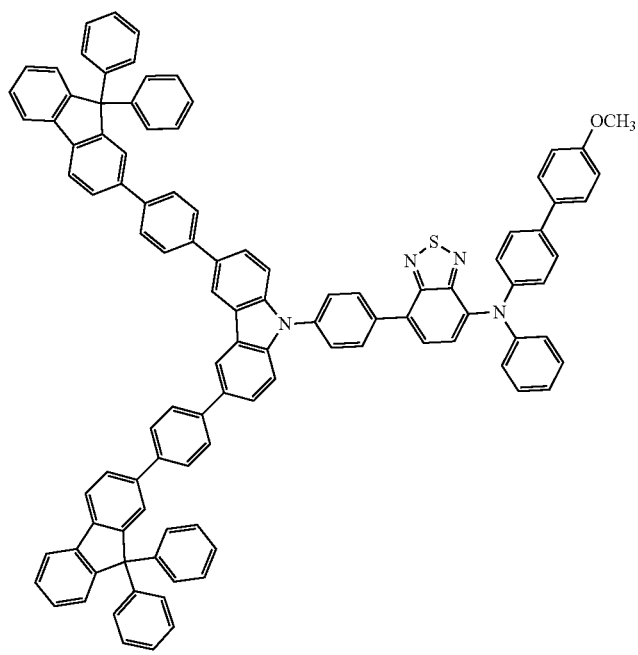

-continued
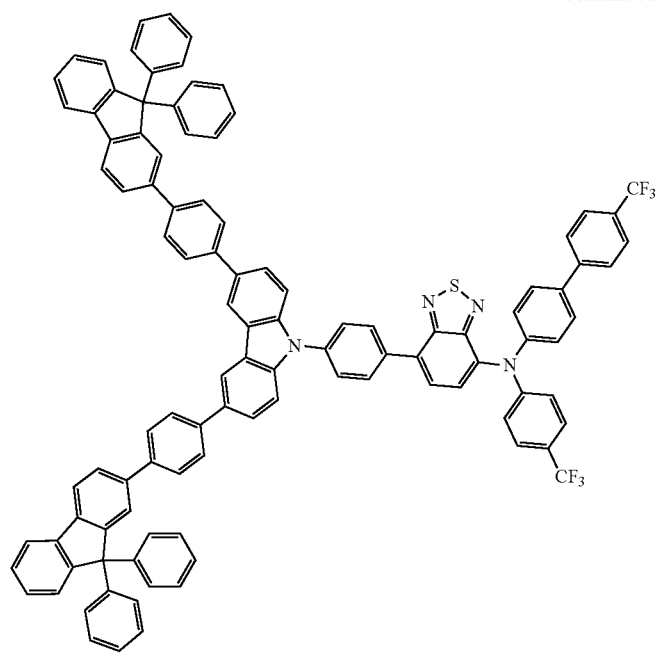
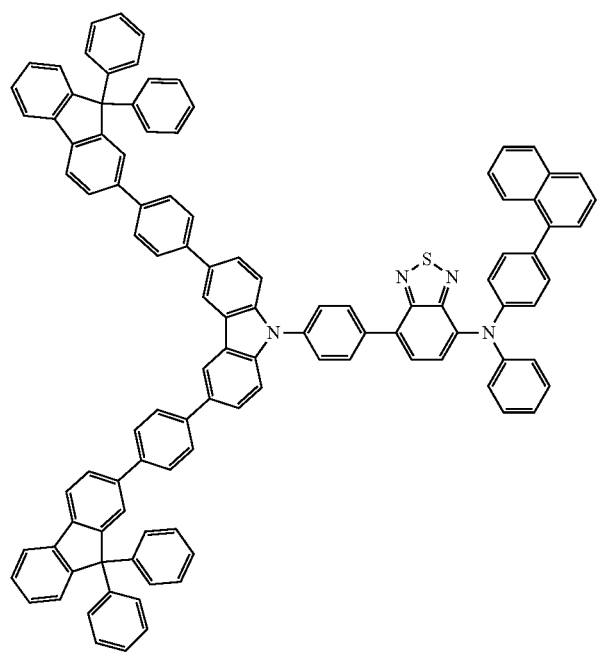

-continued
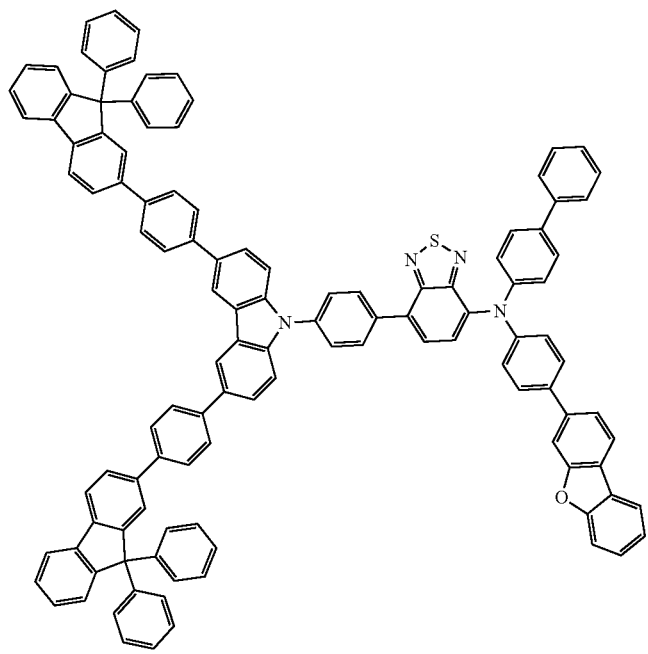
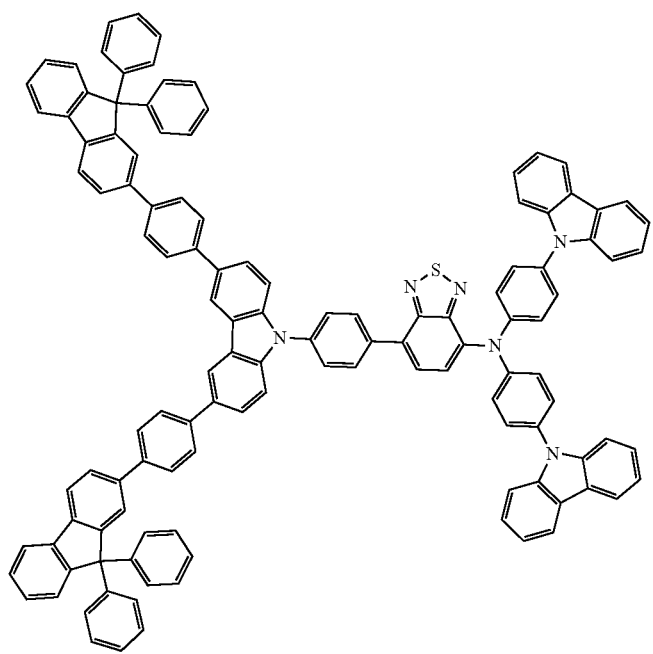

-continued
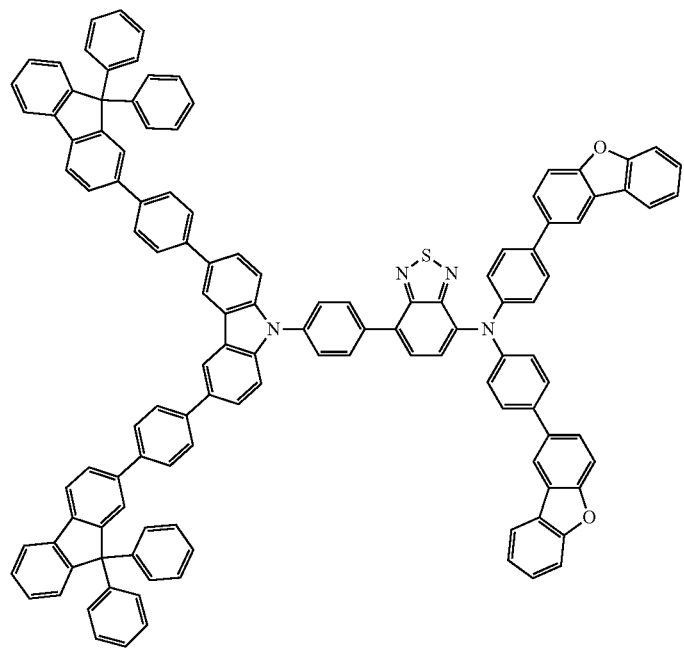
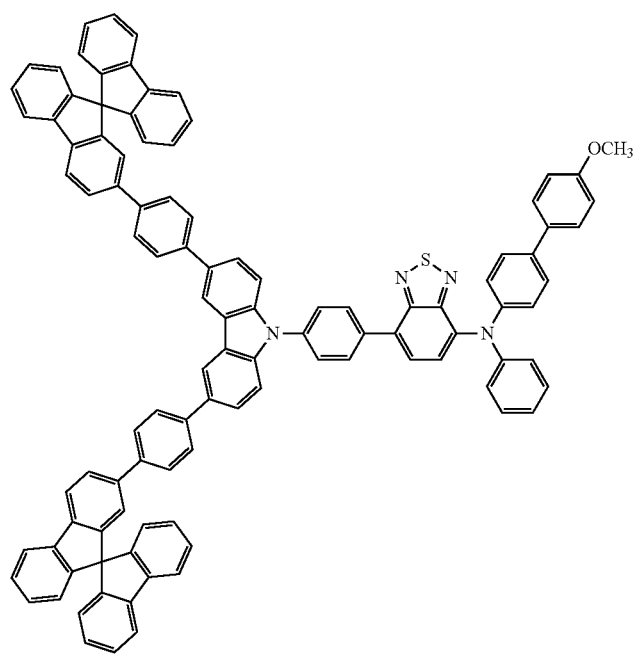

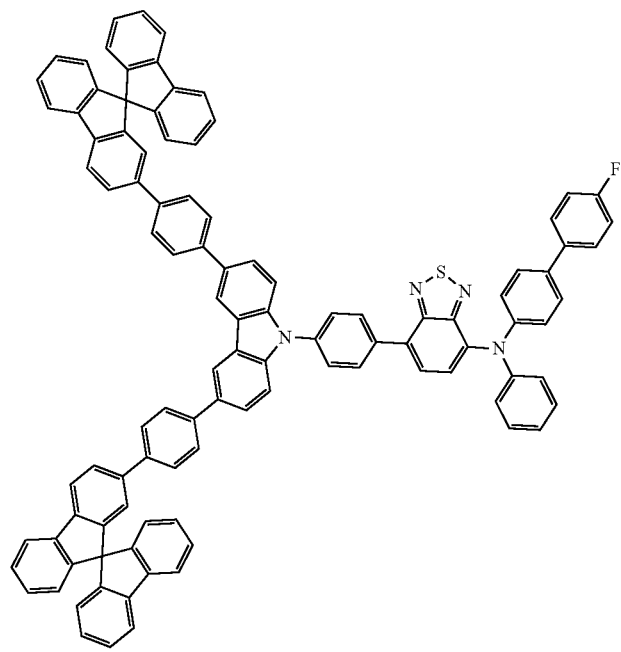
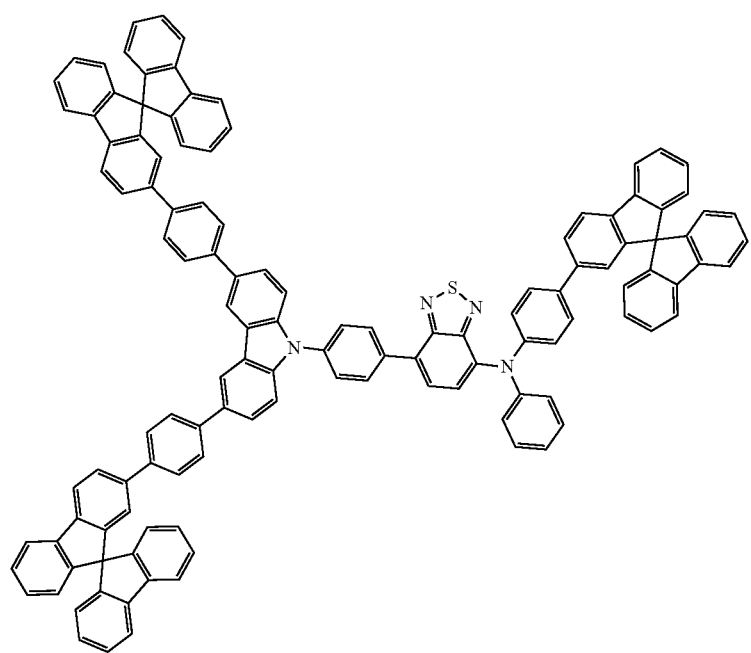

-continued
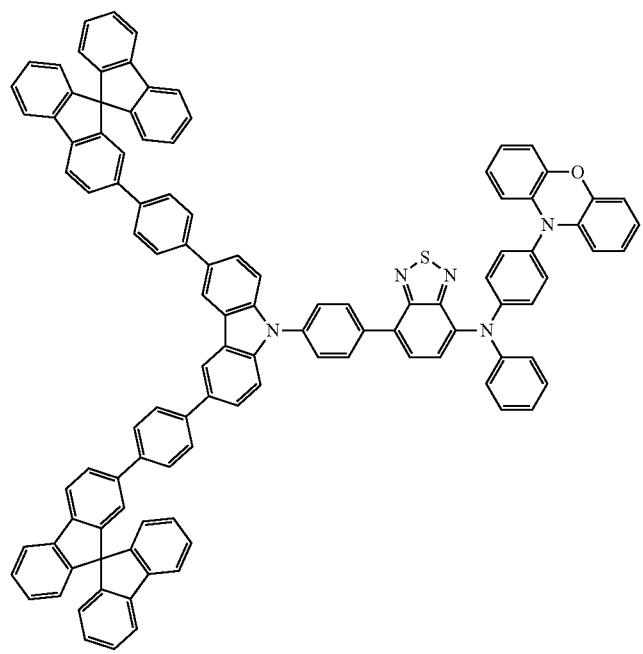
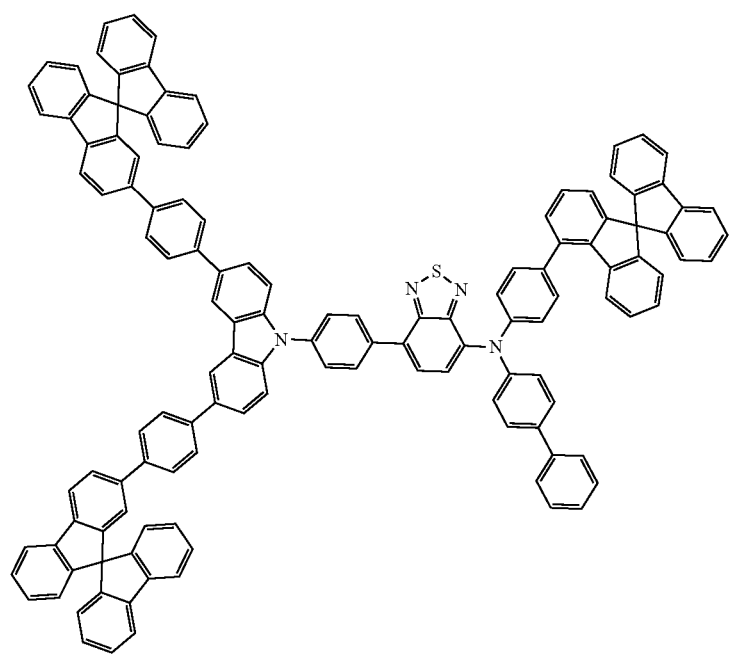

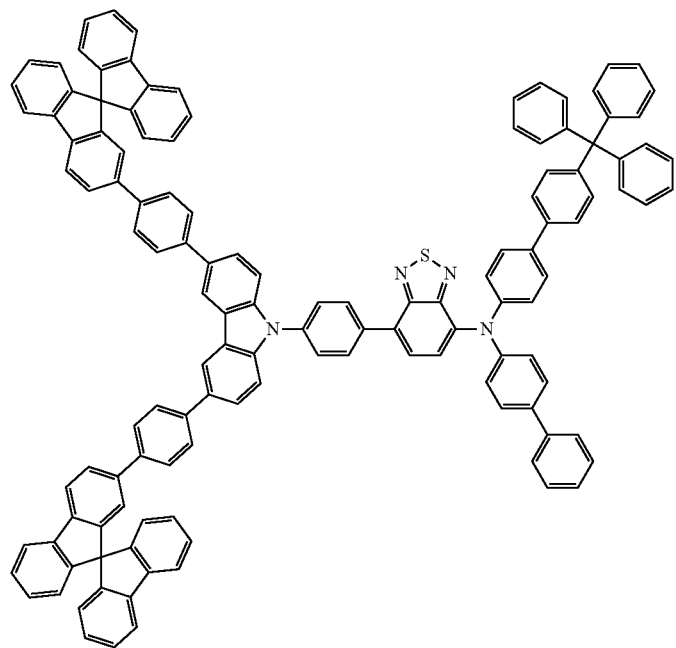
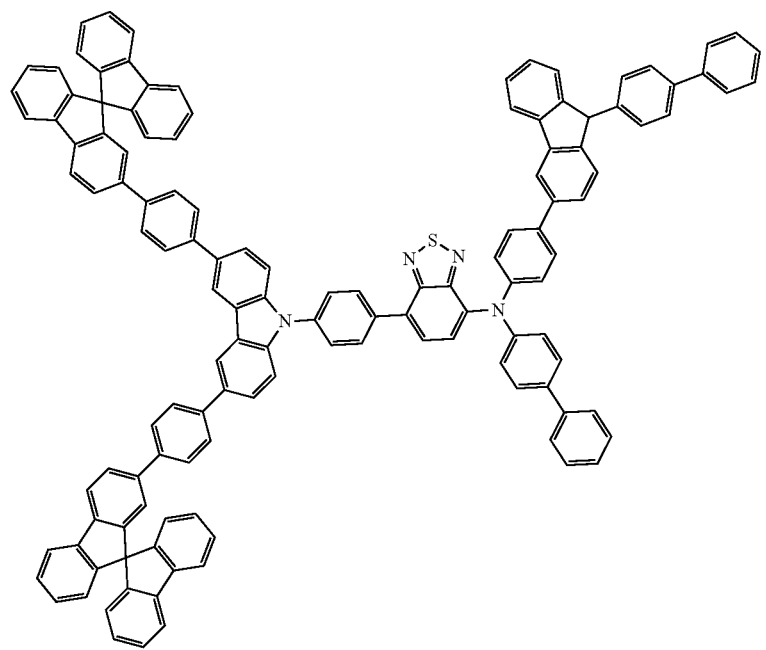

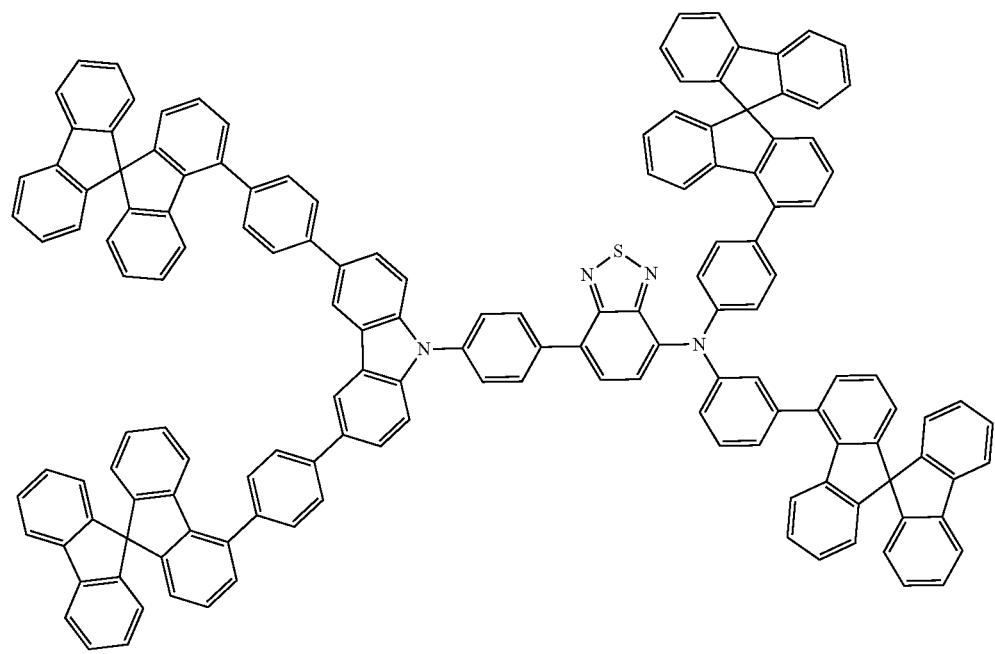
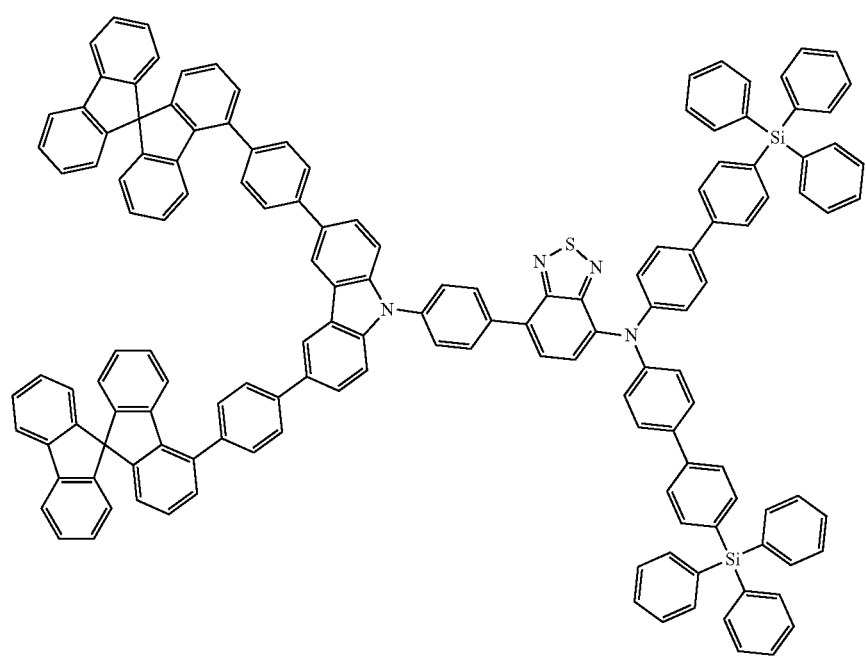

-continued
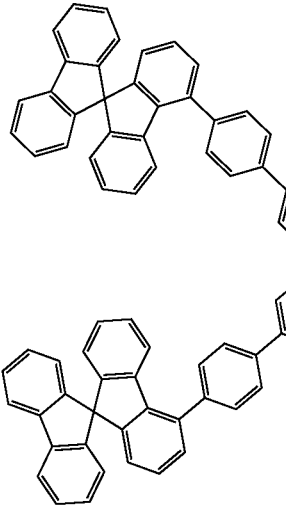 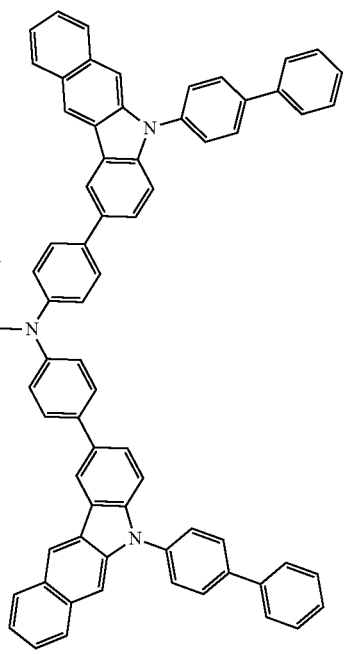
 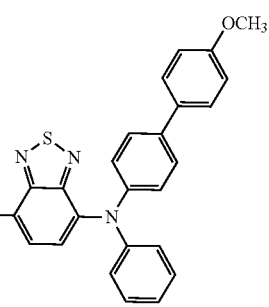

-continued
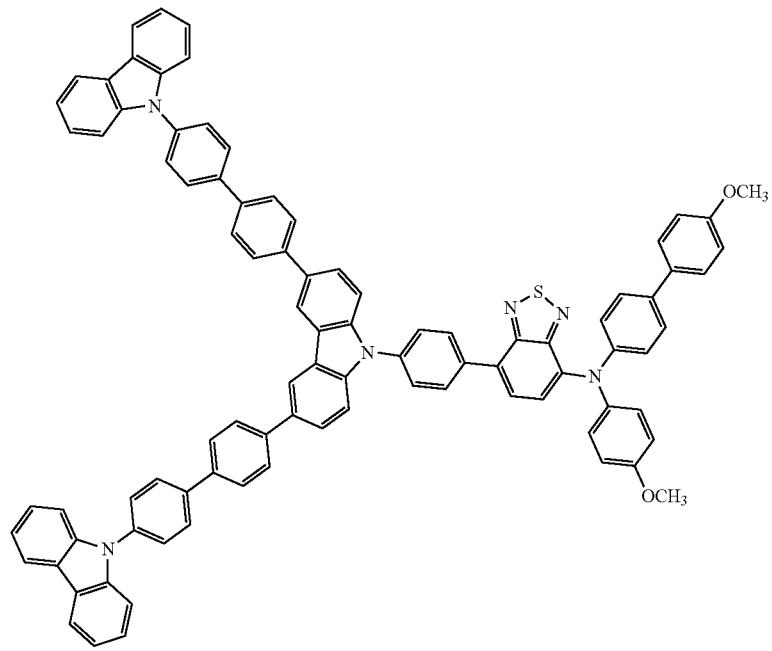
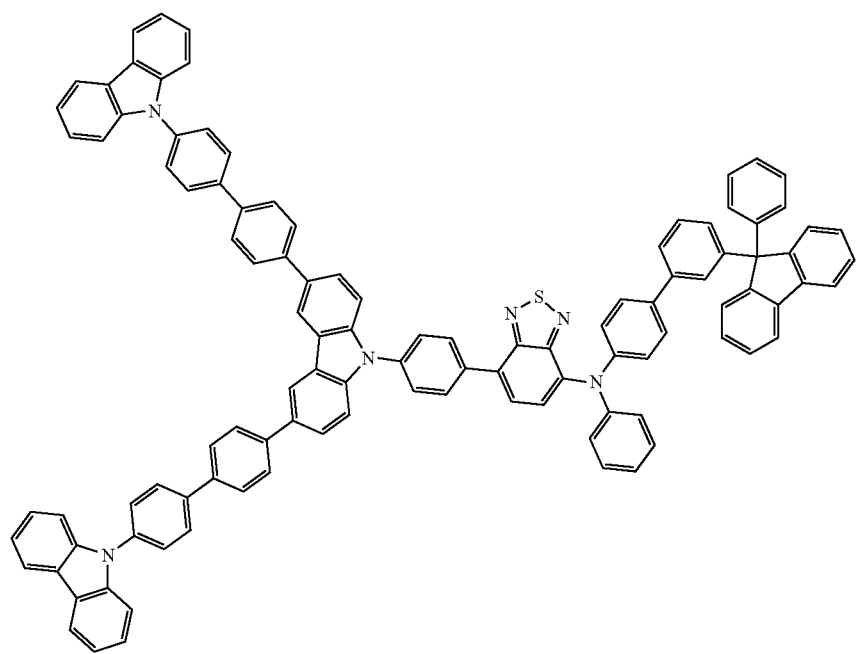

-continued
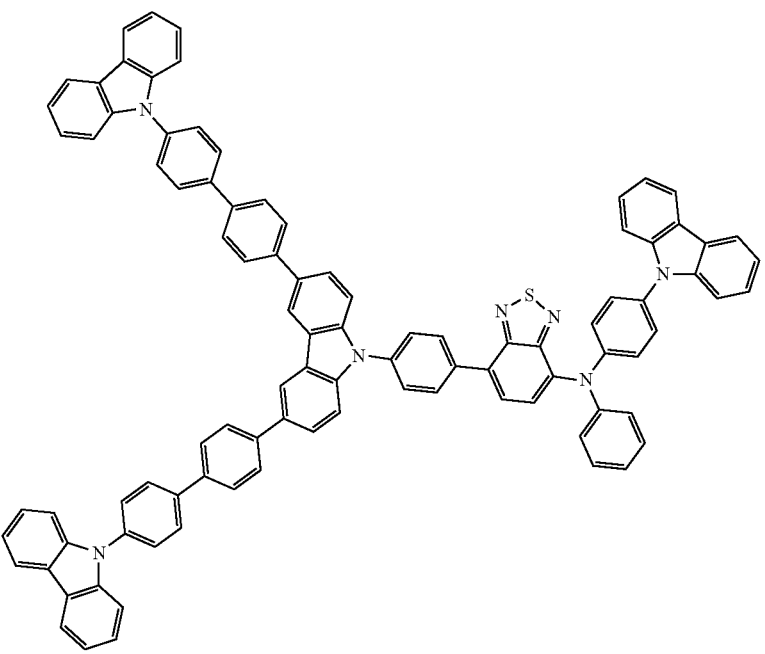
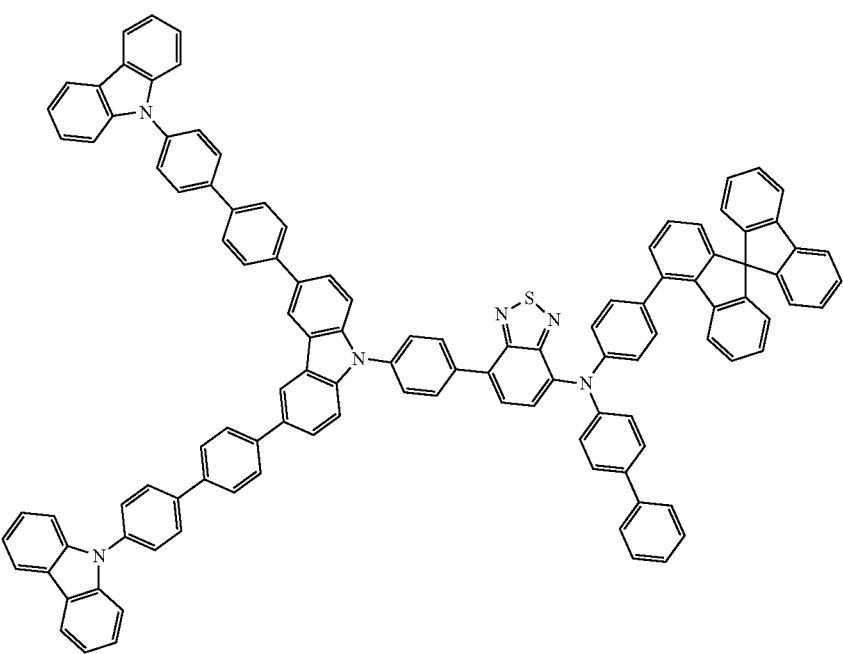

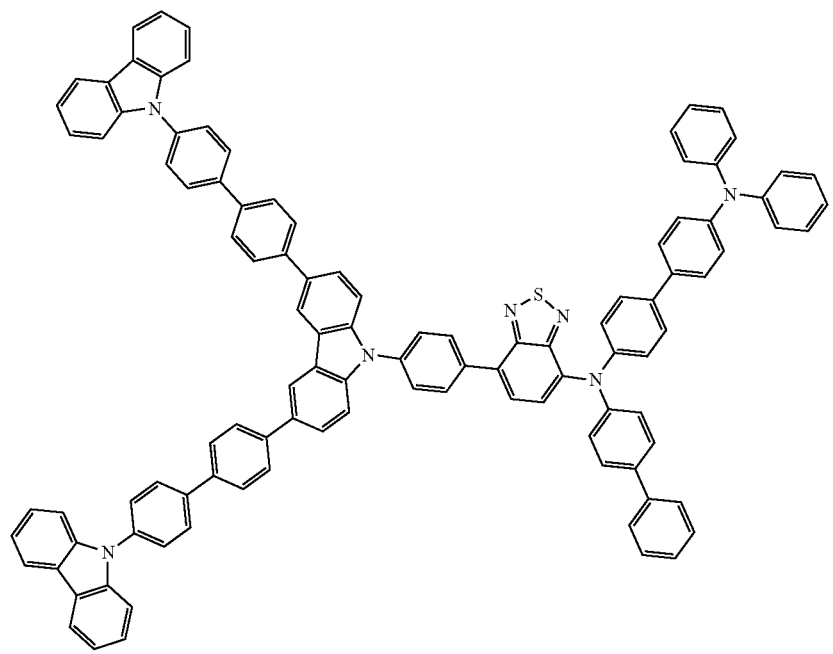
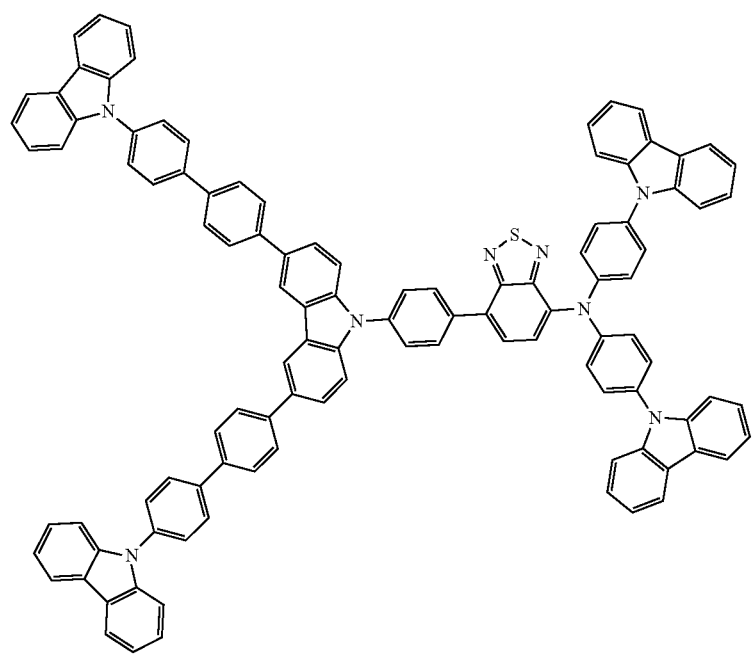

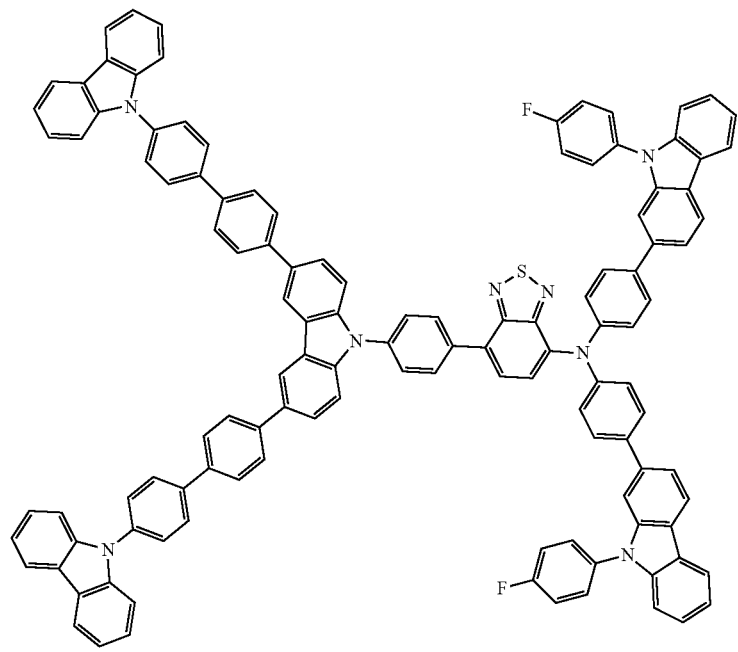
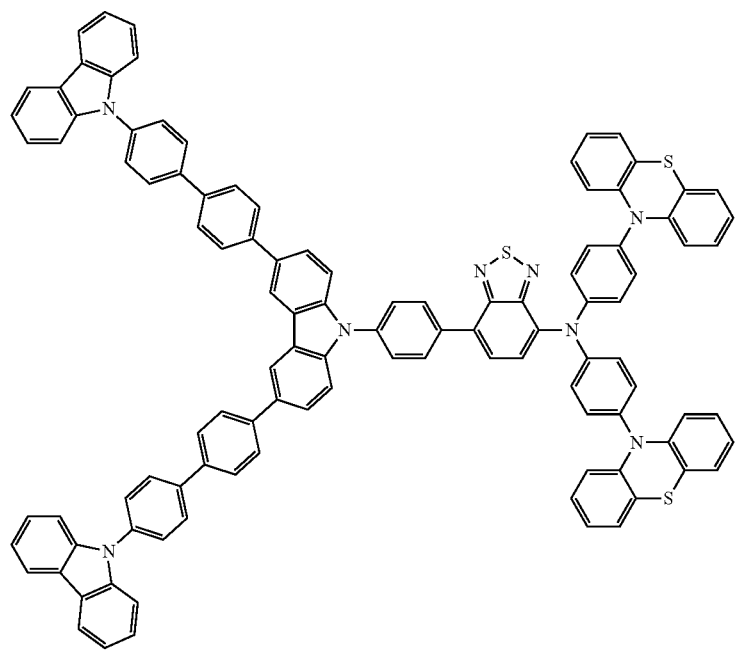

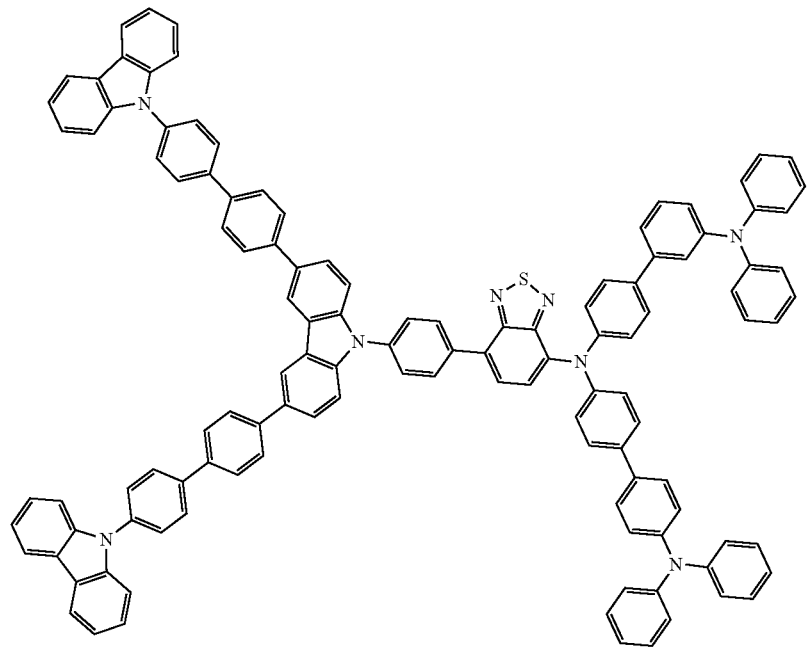
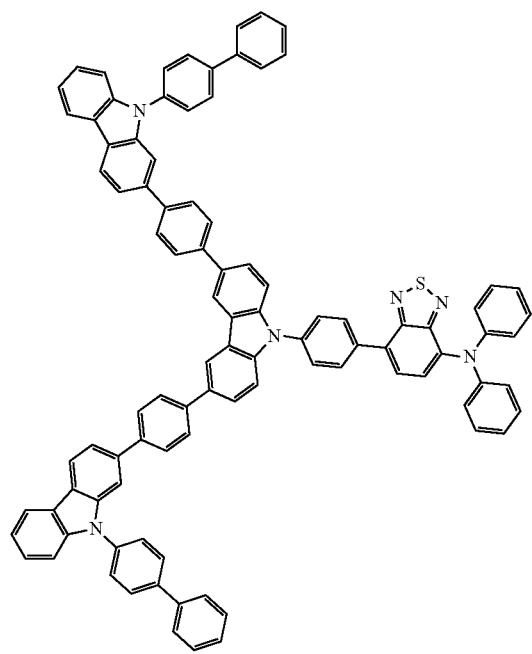

-continued
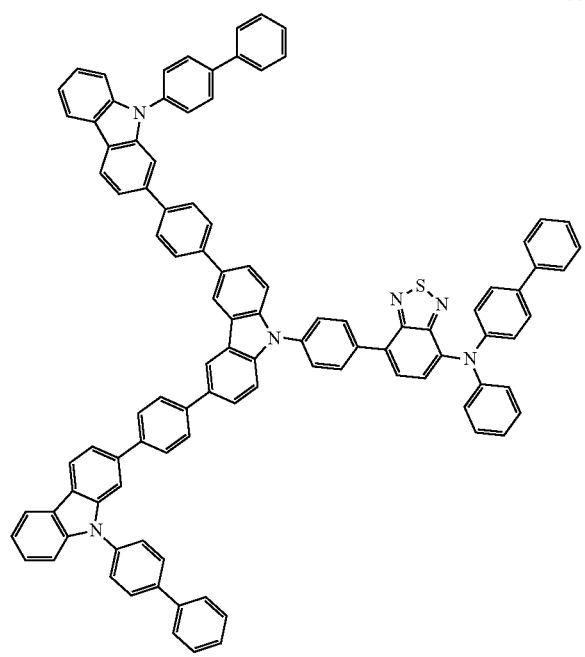
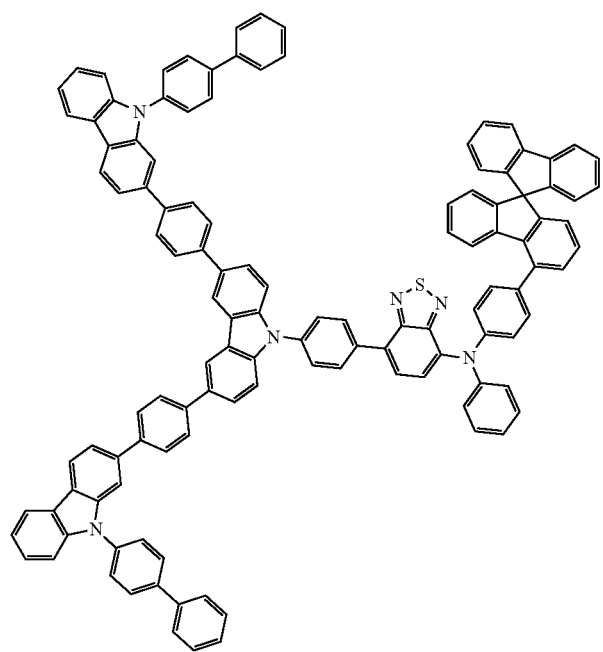

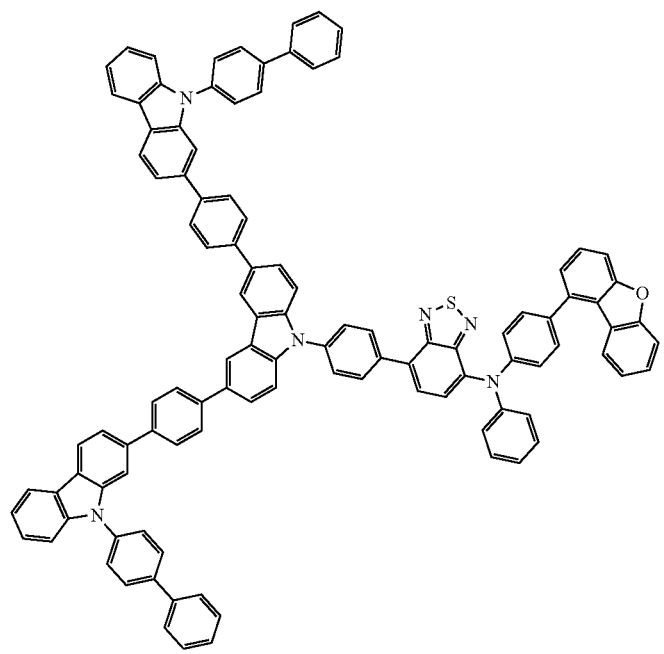
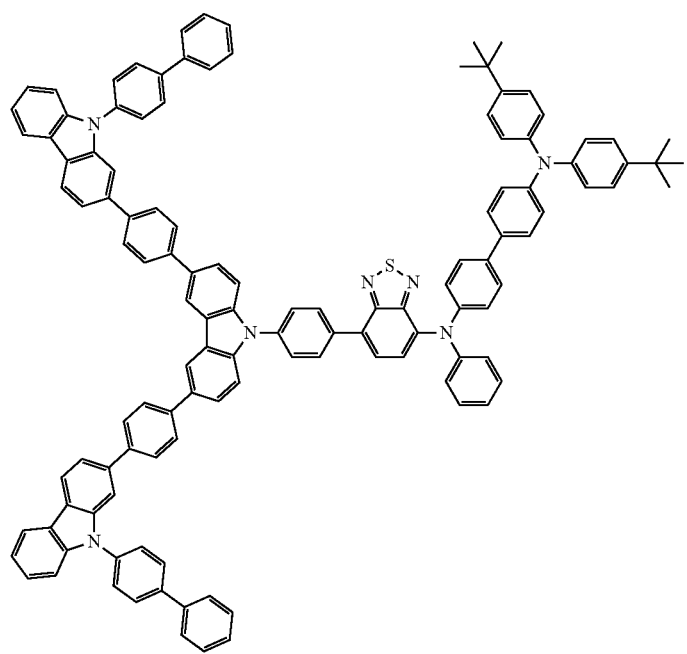

-continued
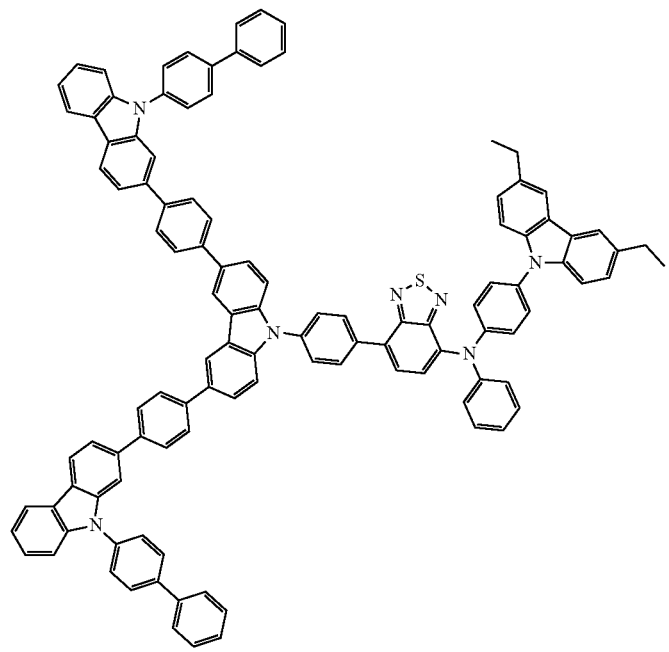
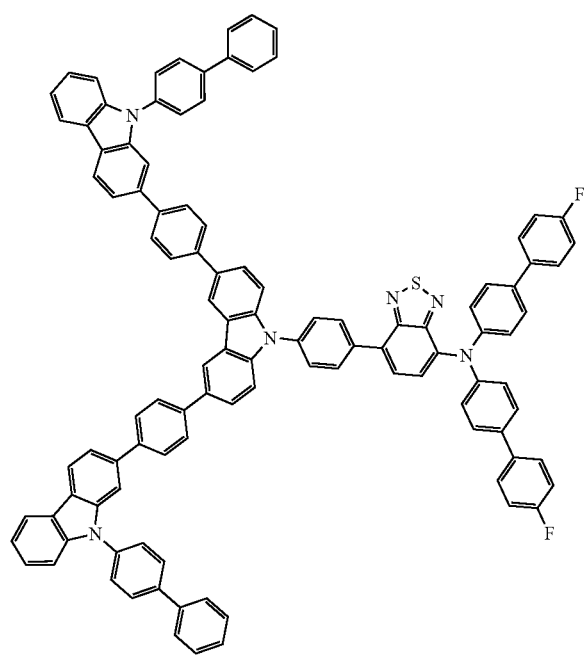

-continued
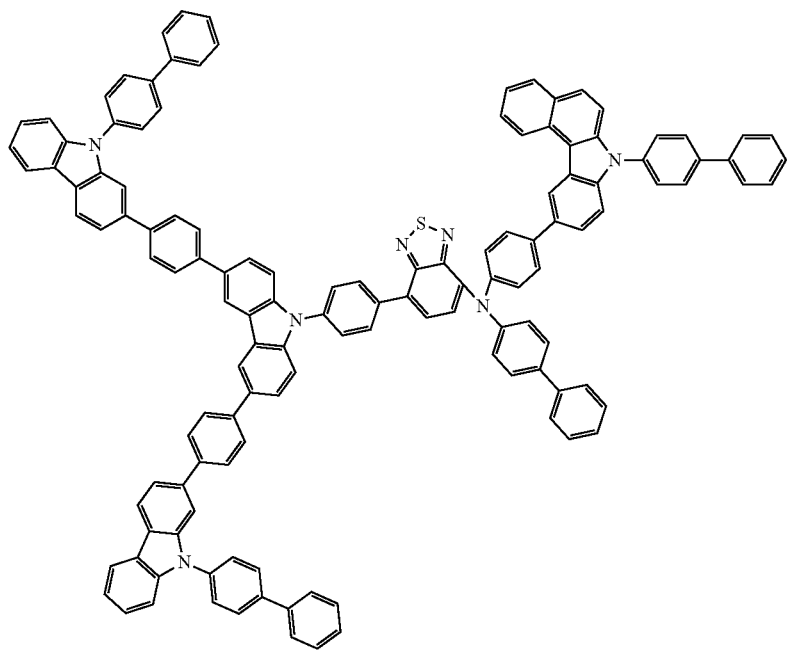
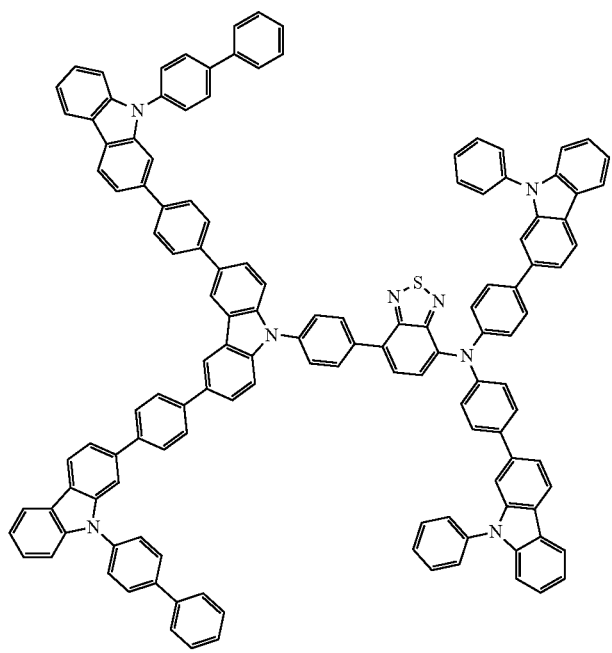

-continued
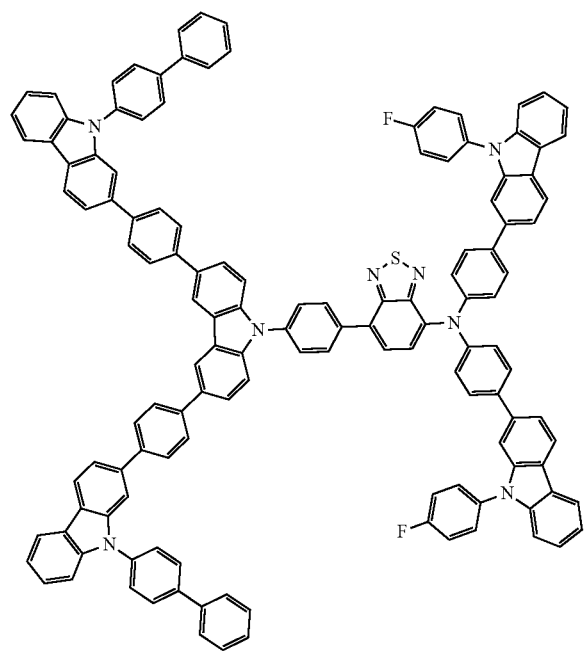
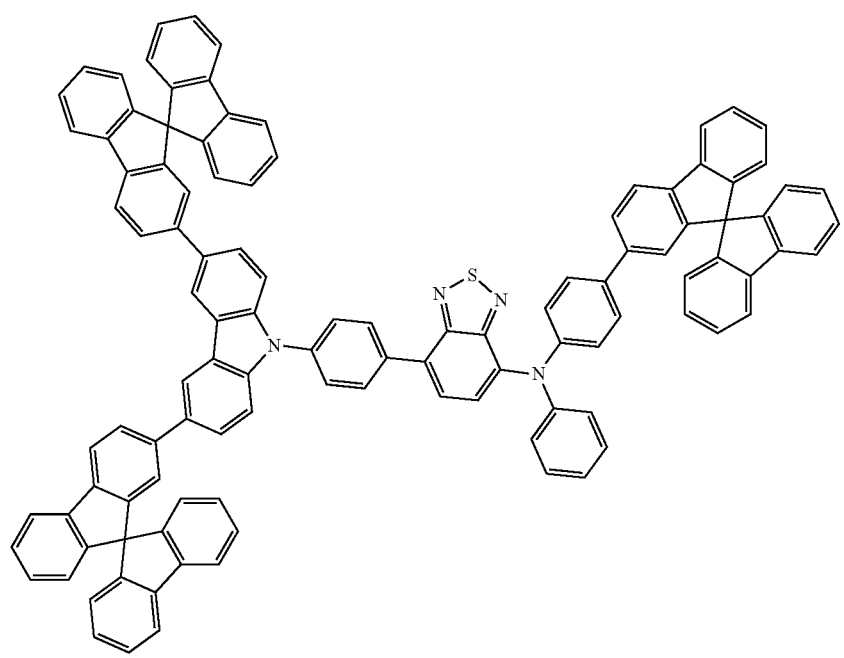

-continued
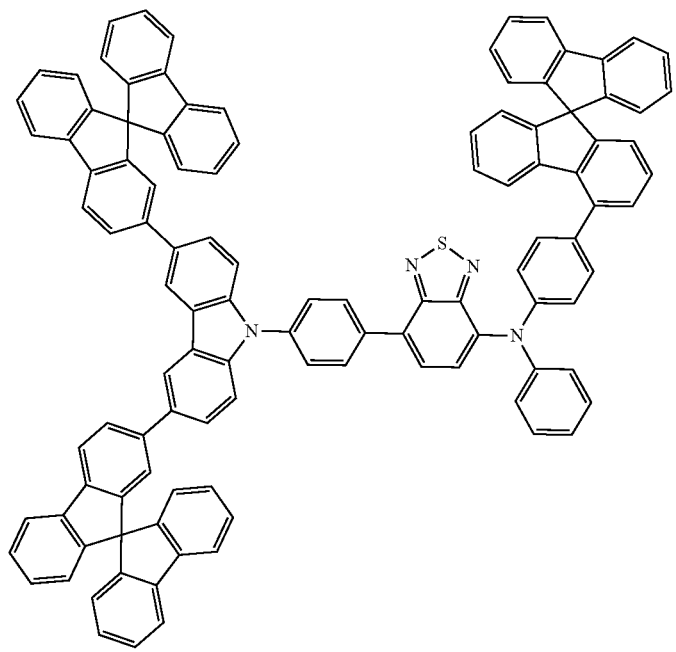
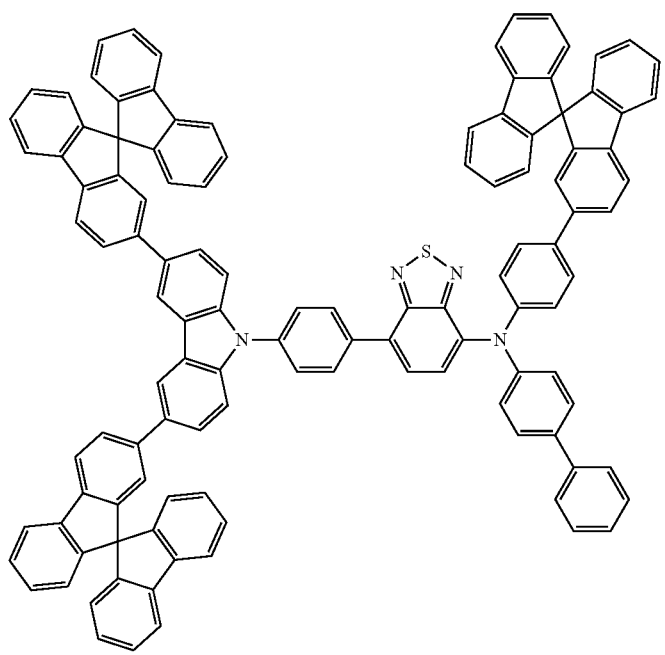

-continued
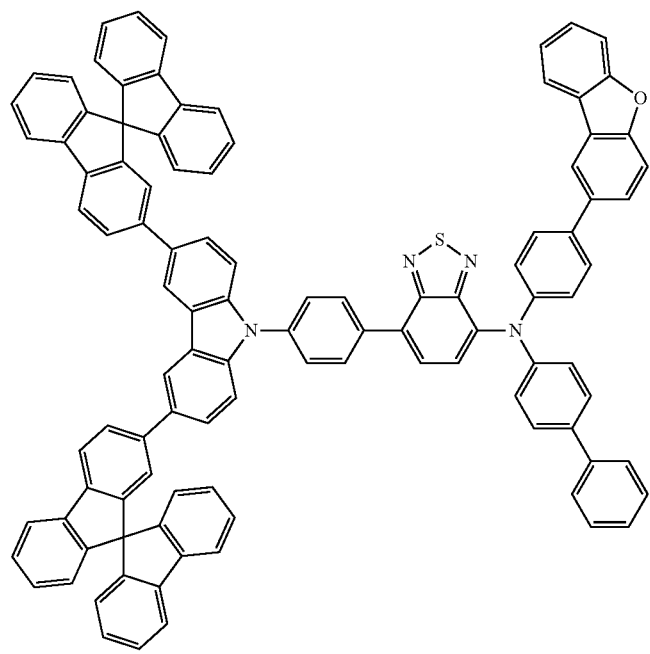
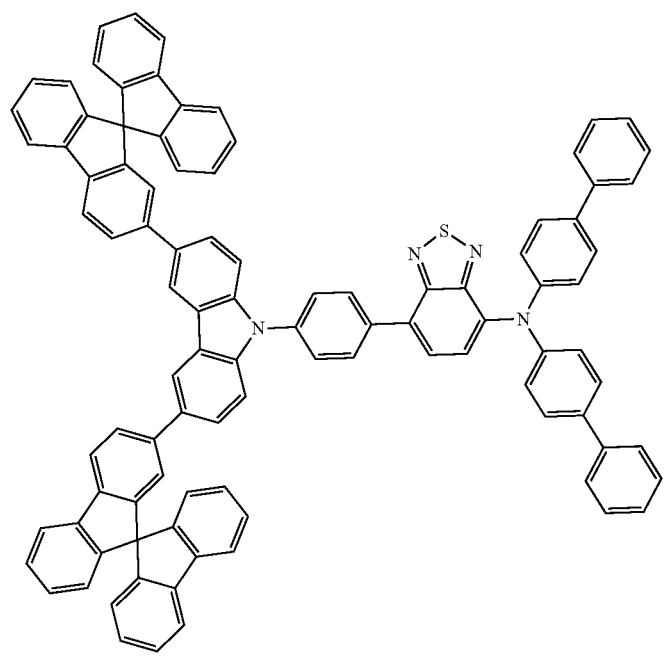

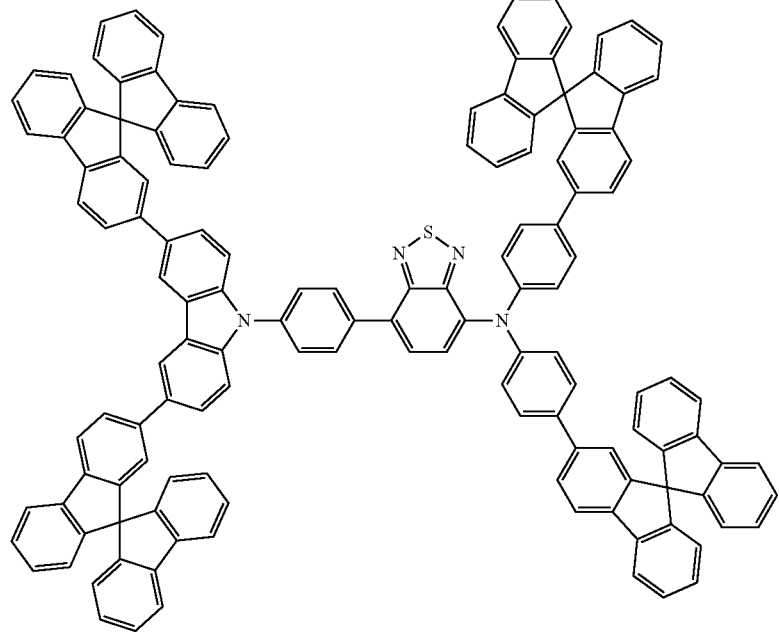
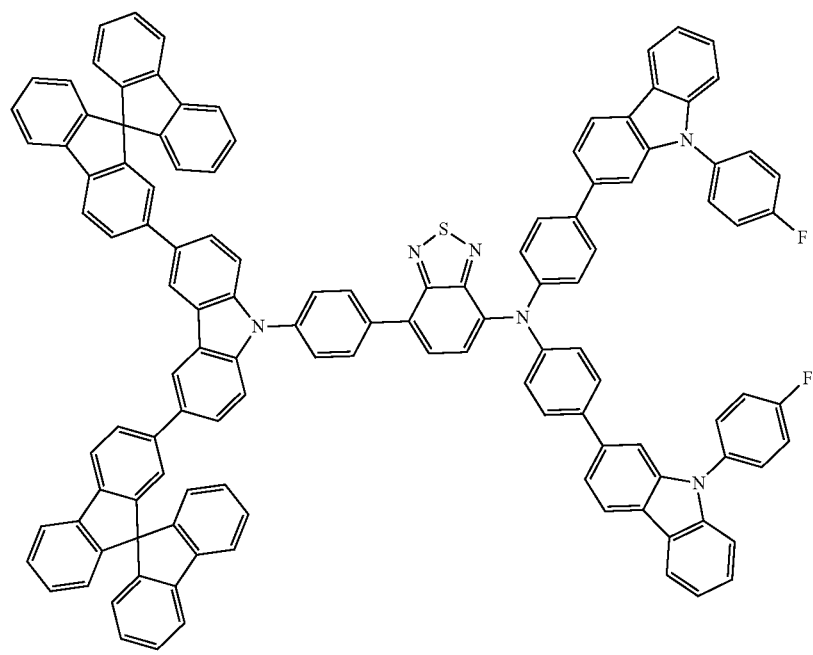

-continued
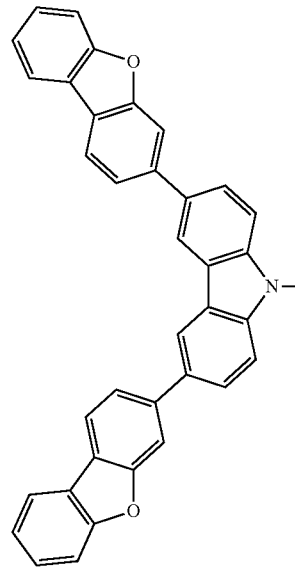

-continued
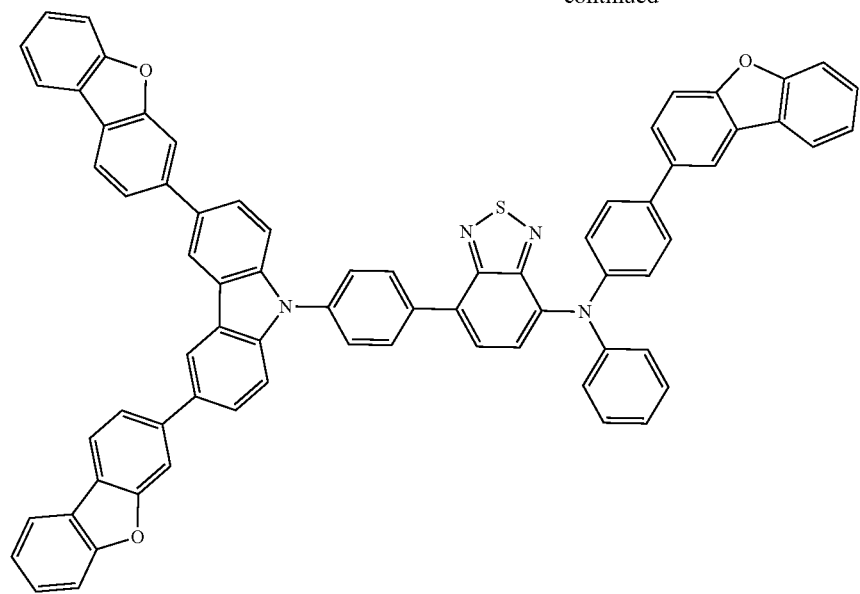
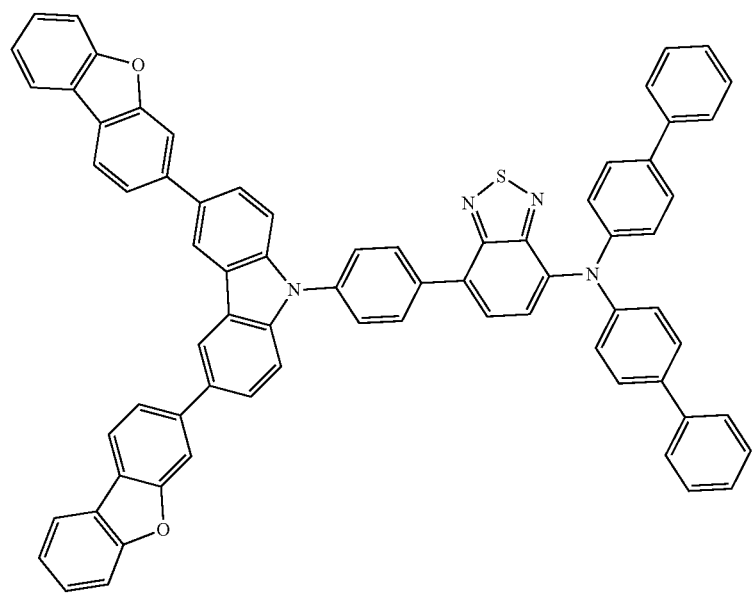

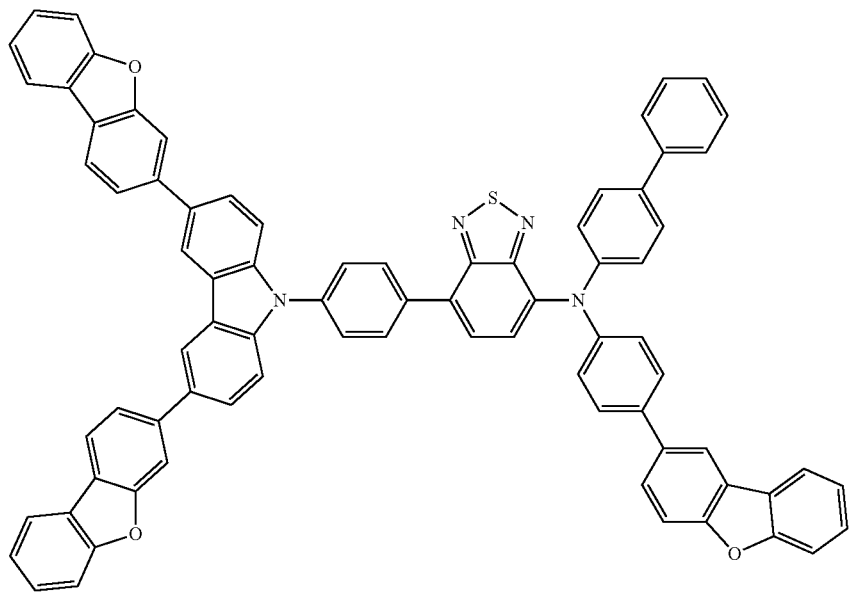
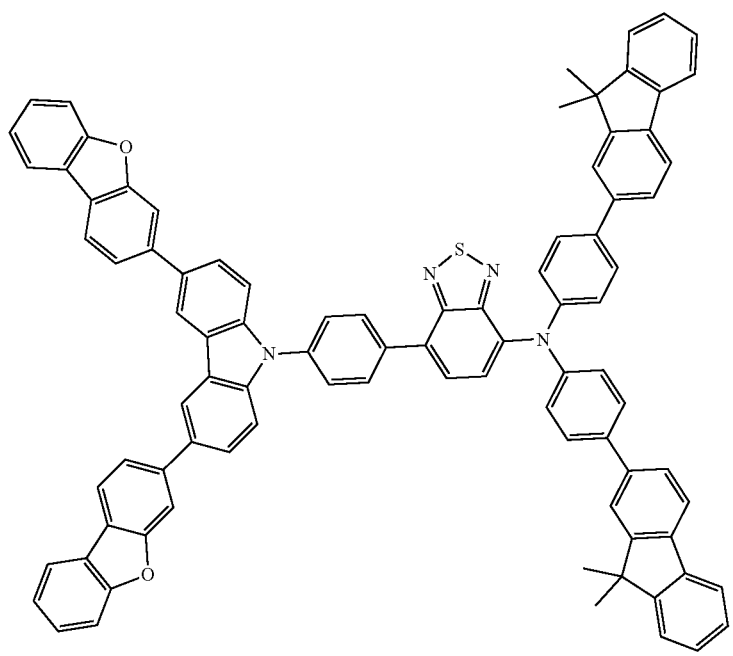

-continued
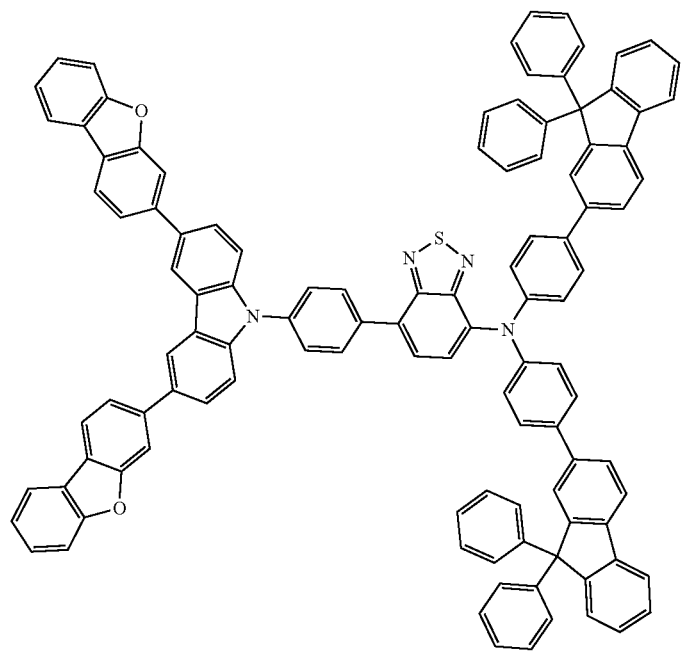
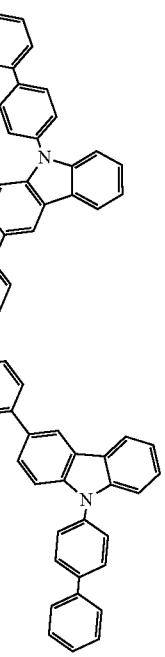

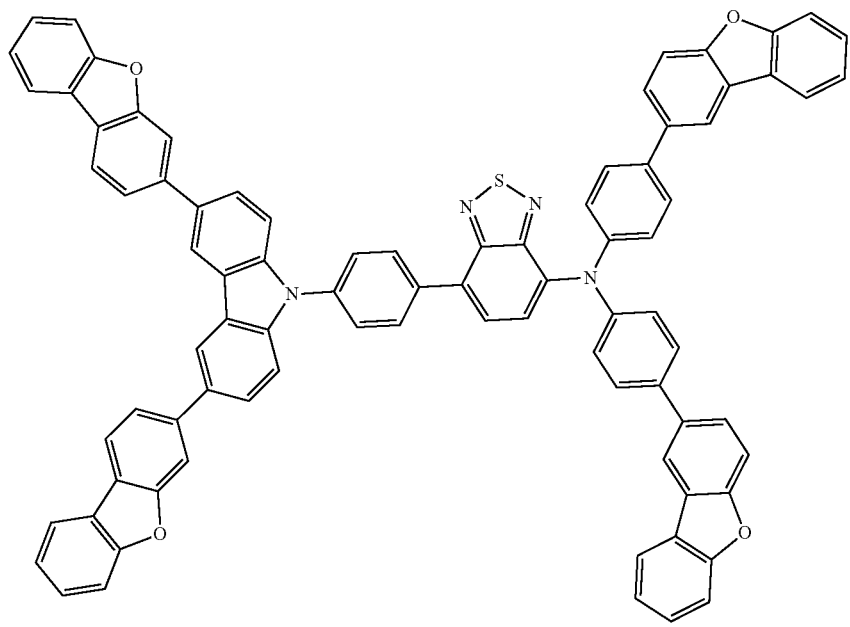
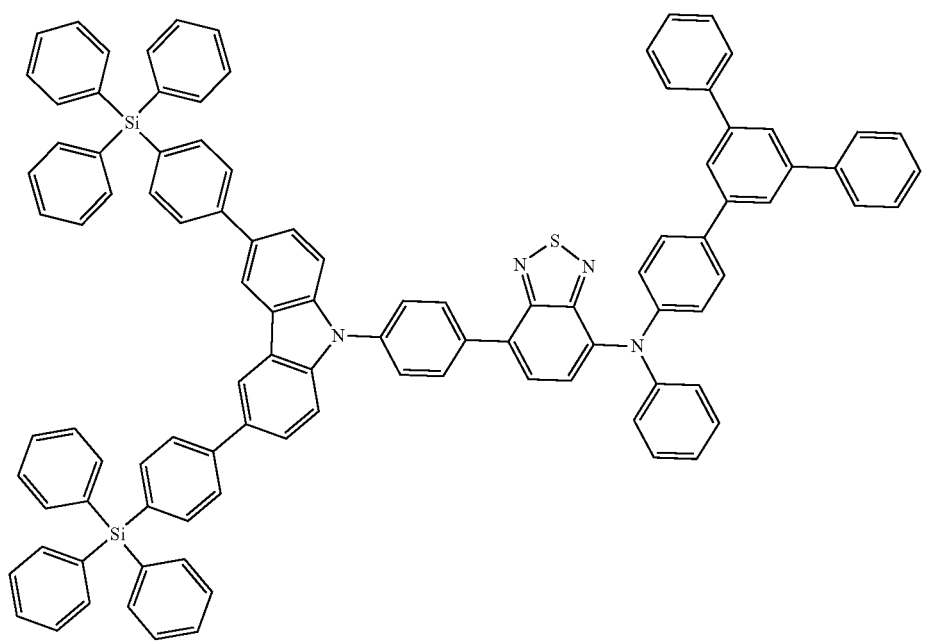

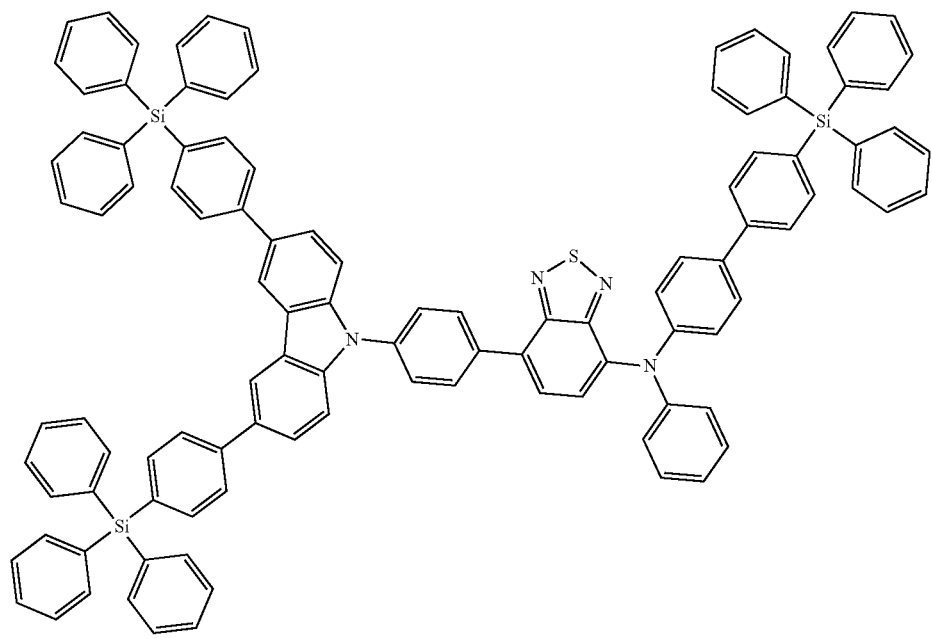
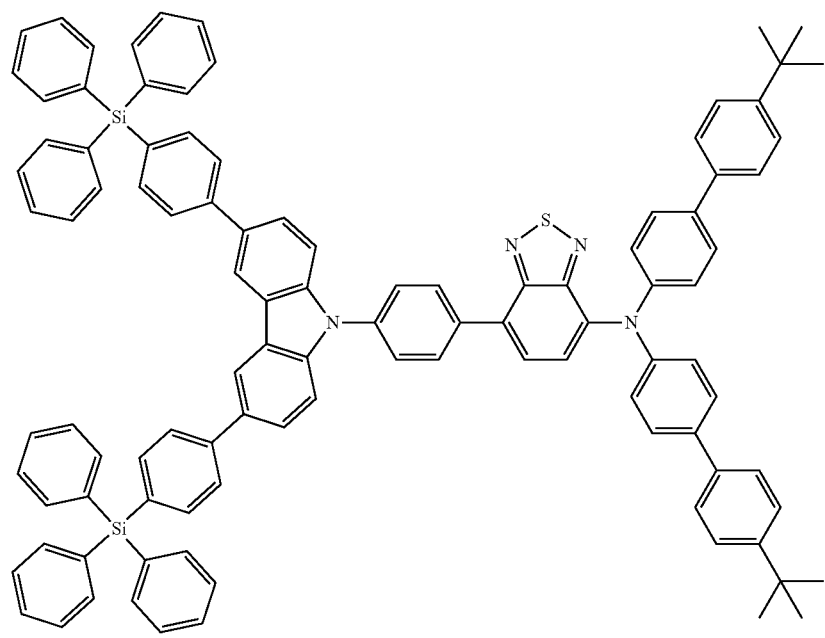

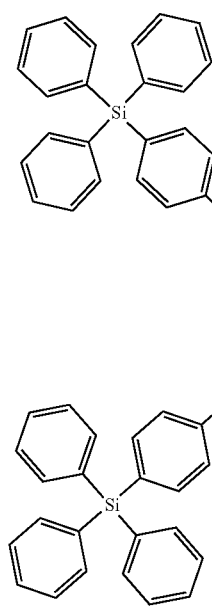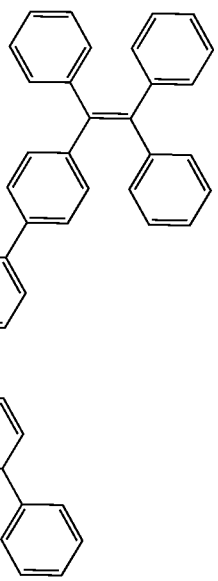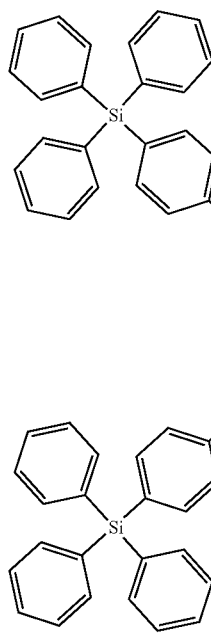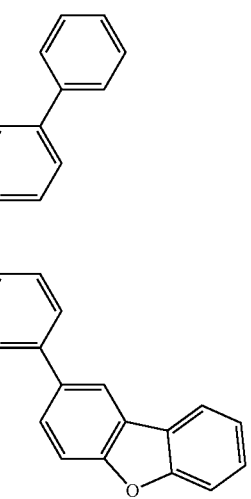

-continued
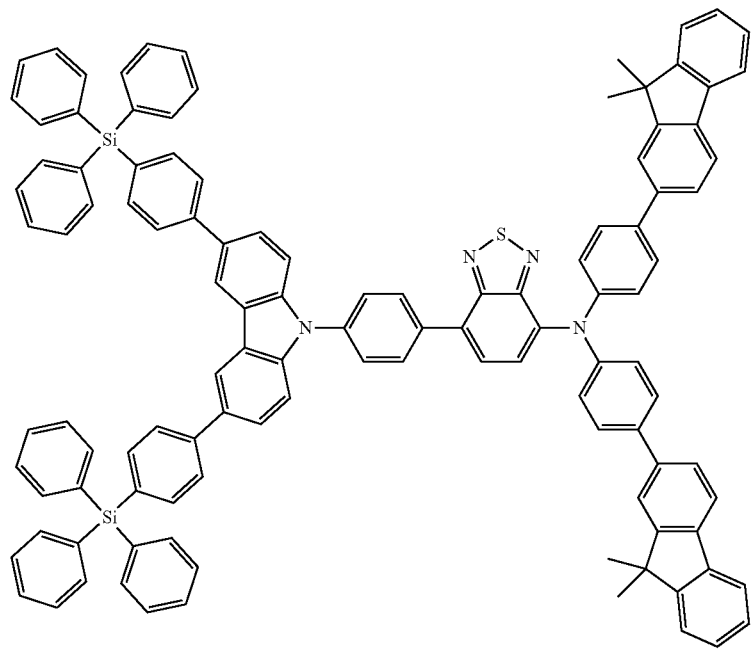
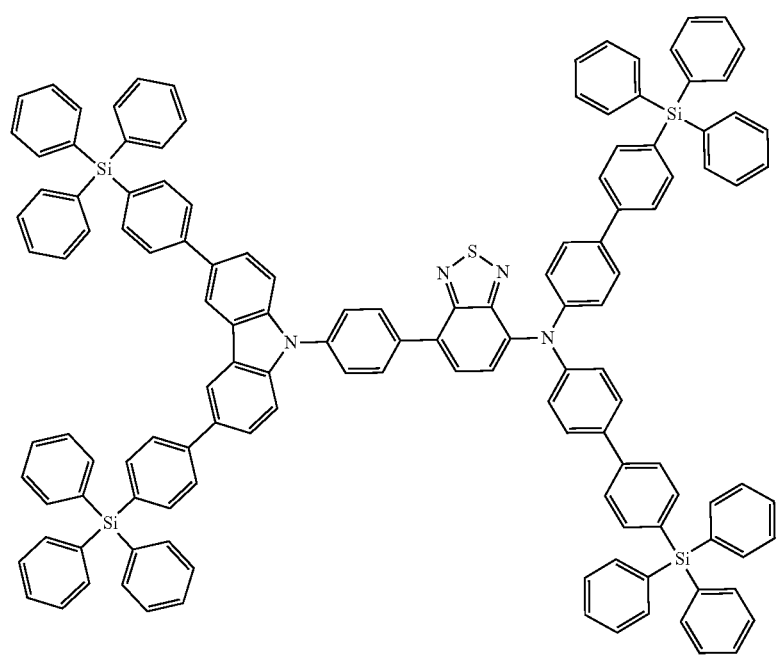

-continued
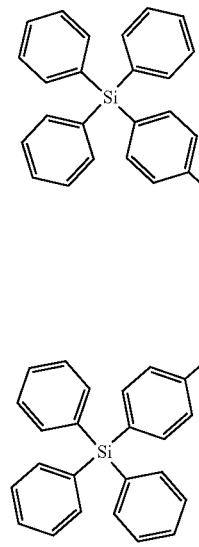
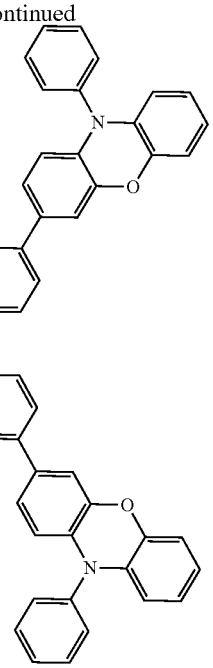
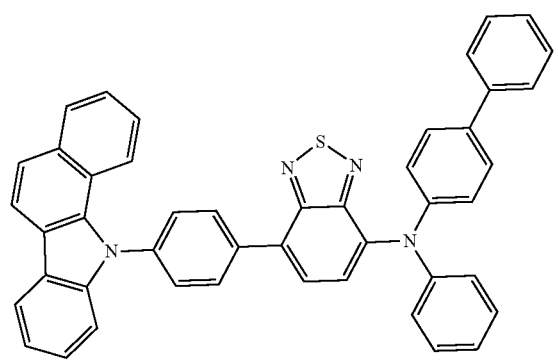
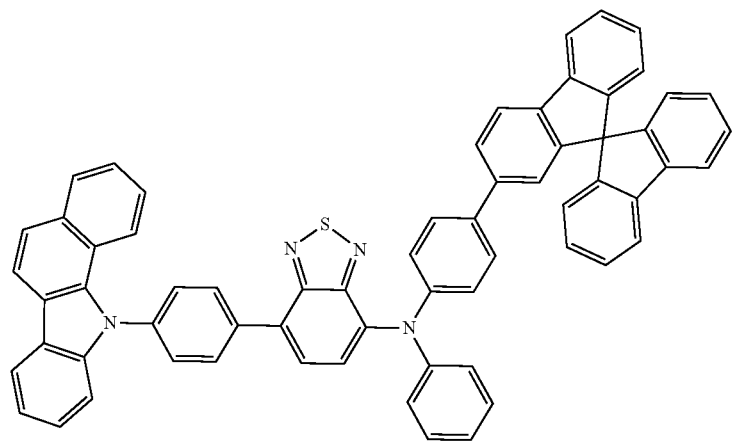

-continued
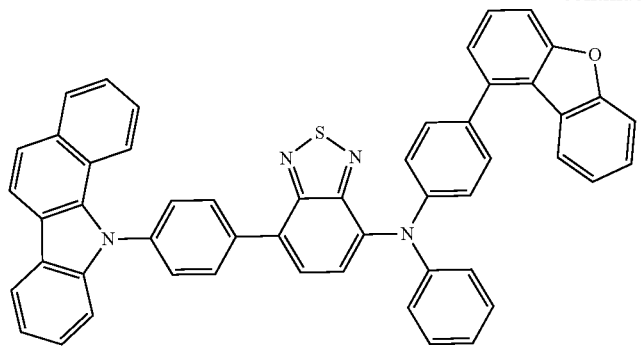
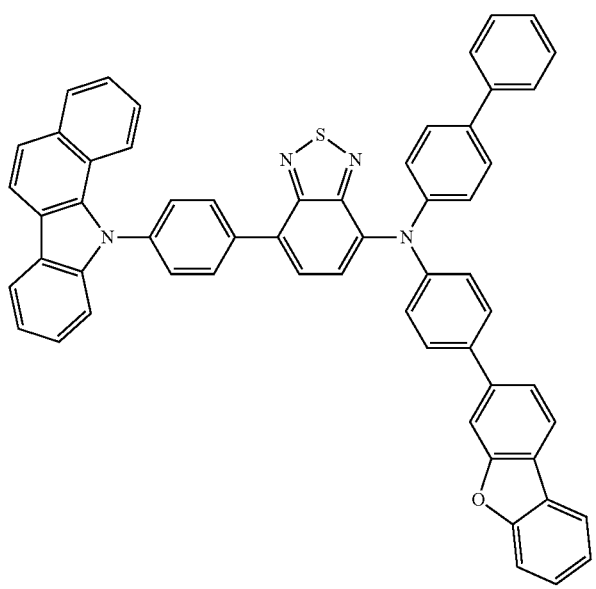
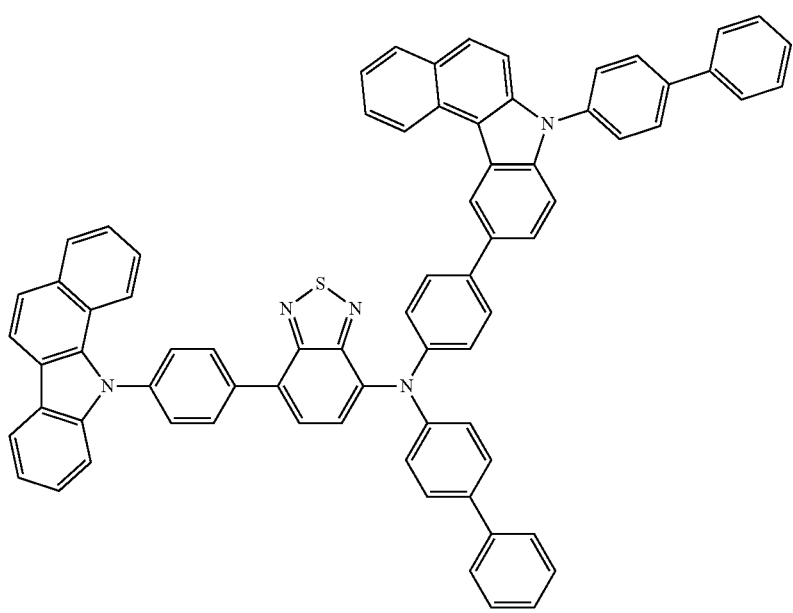

-continued
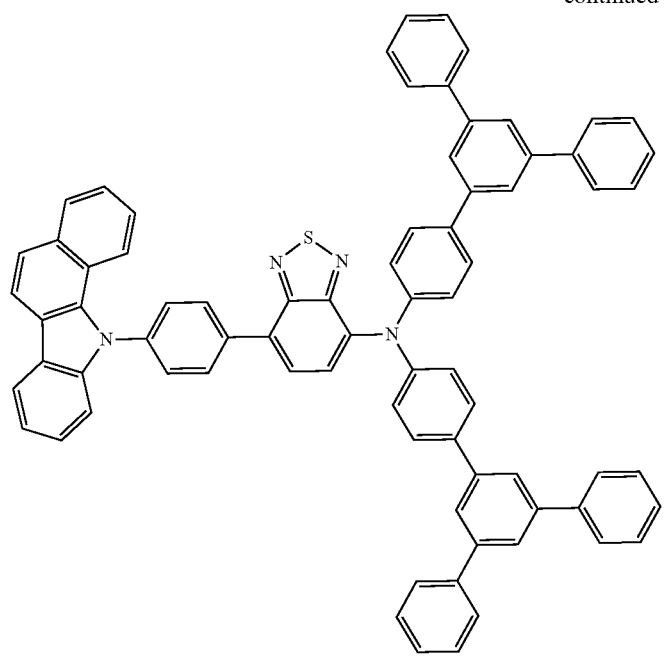
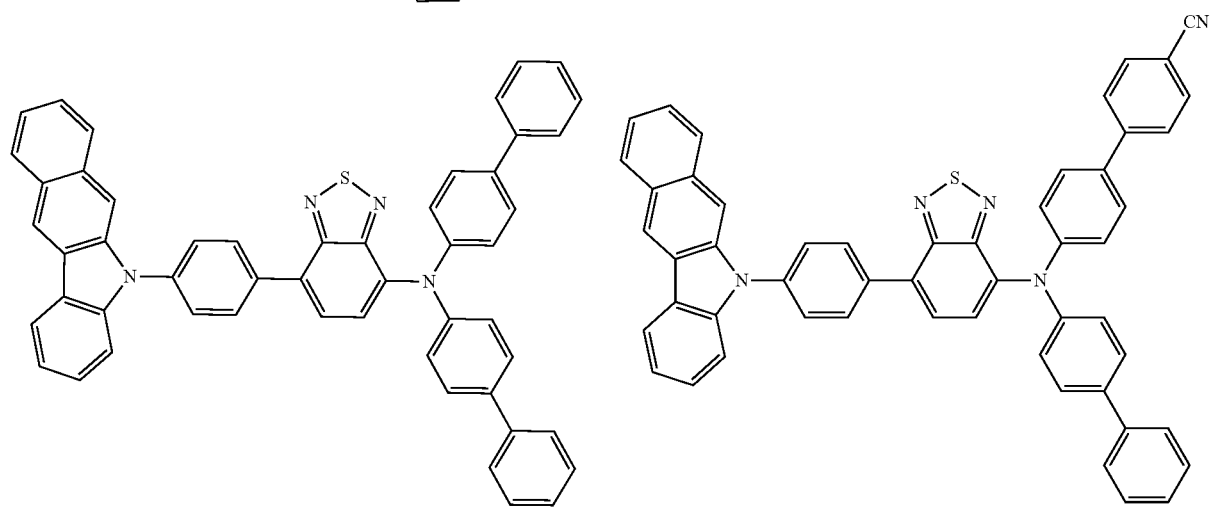
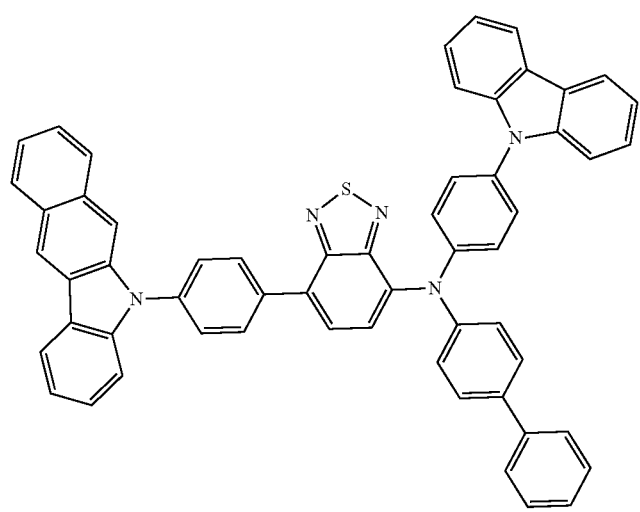

-continued
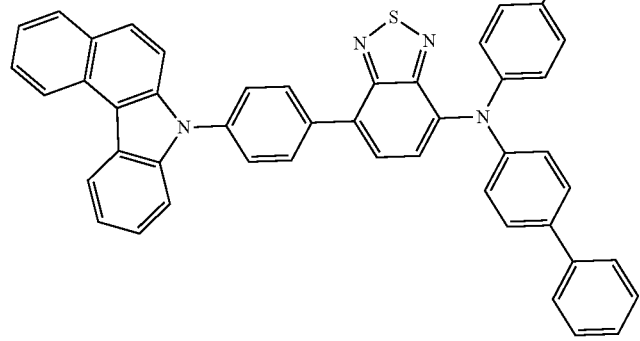
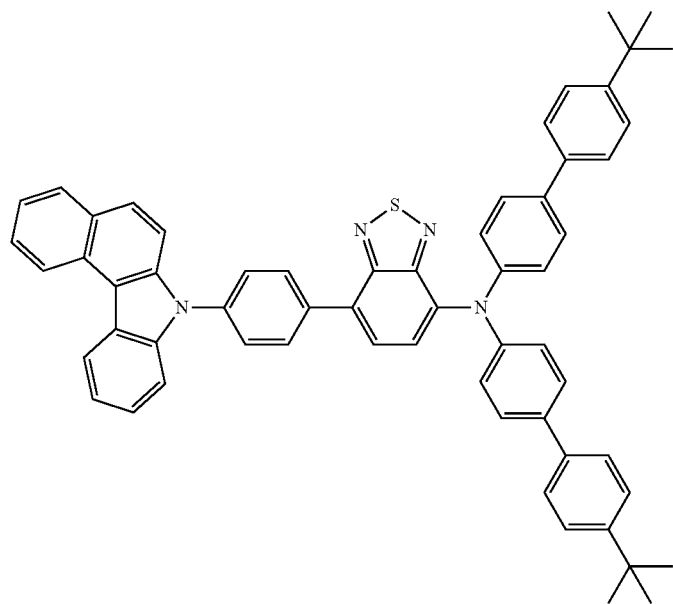
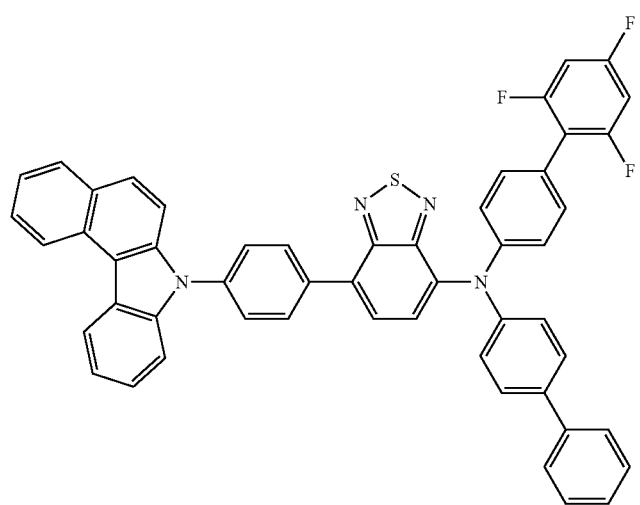

-continued
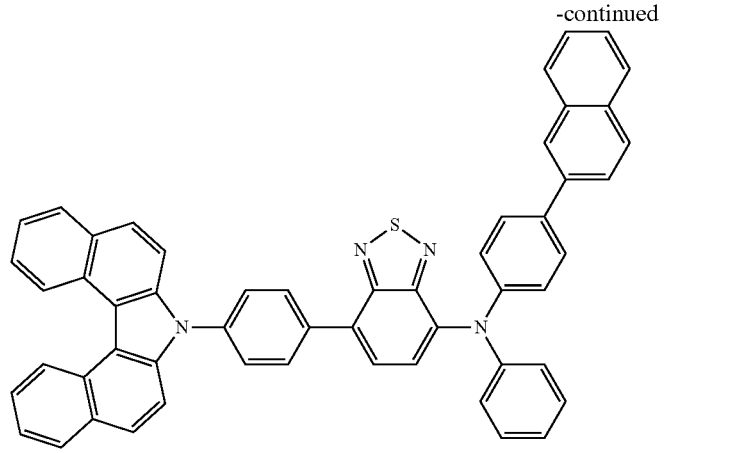
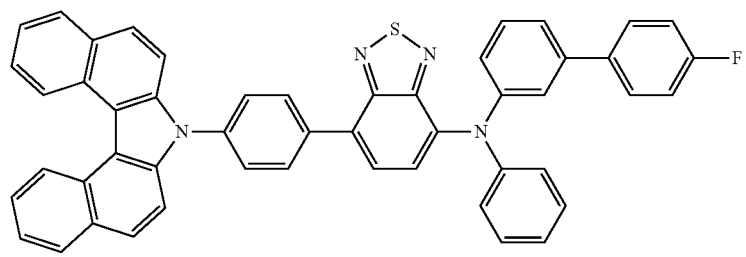
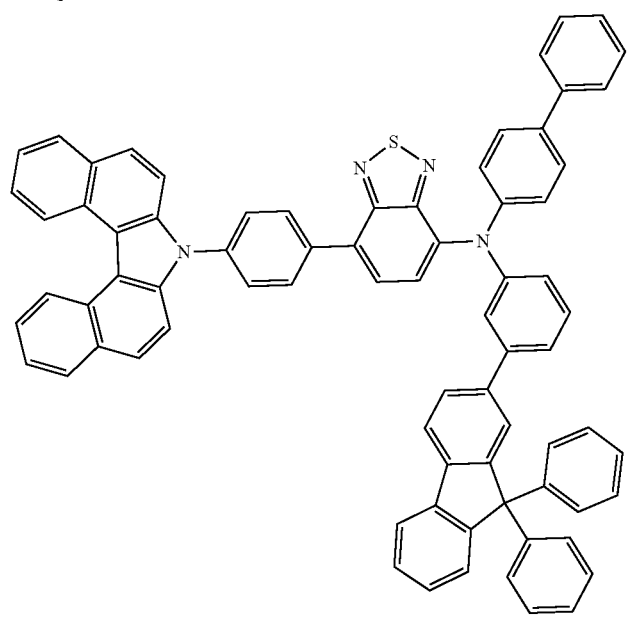
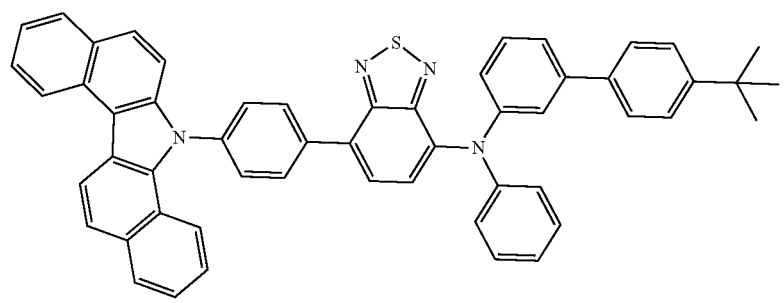

-continued
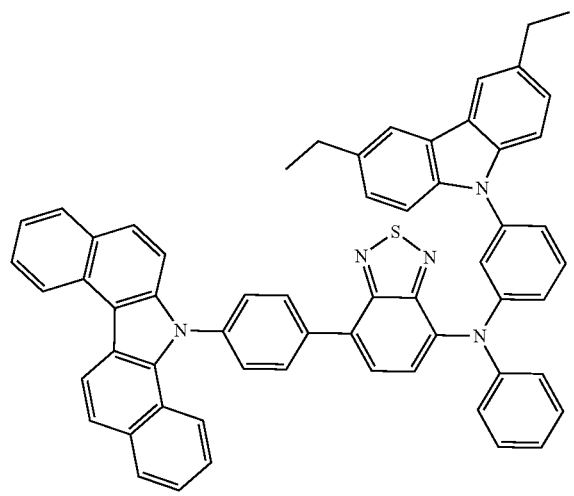
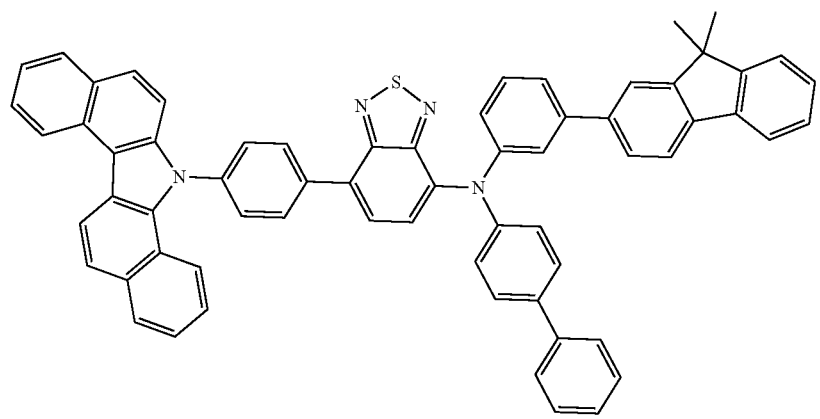
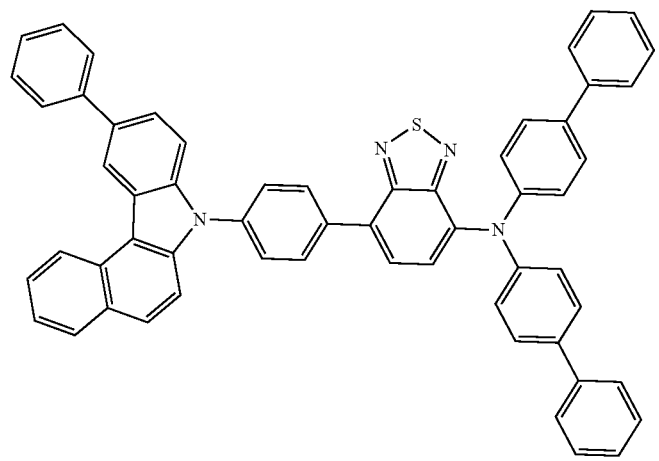

-continued
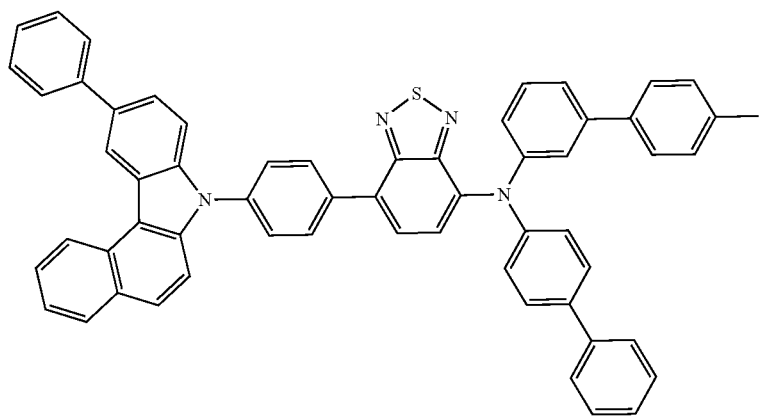
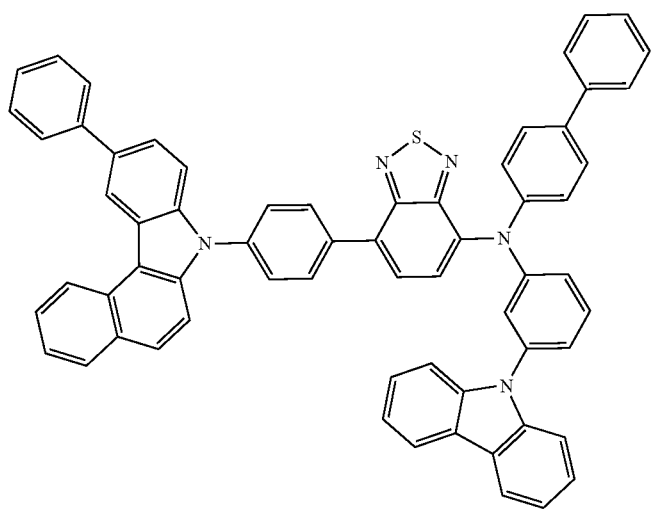
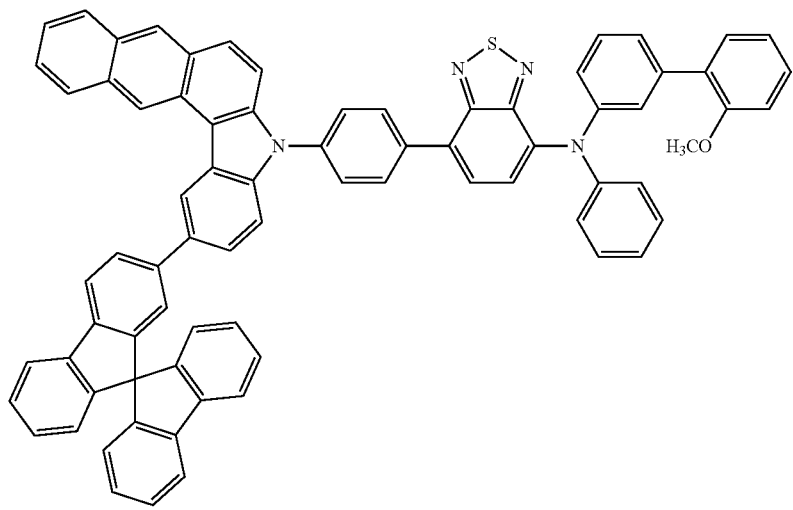

-continued
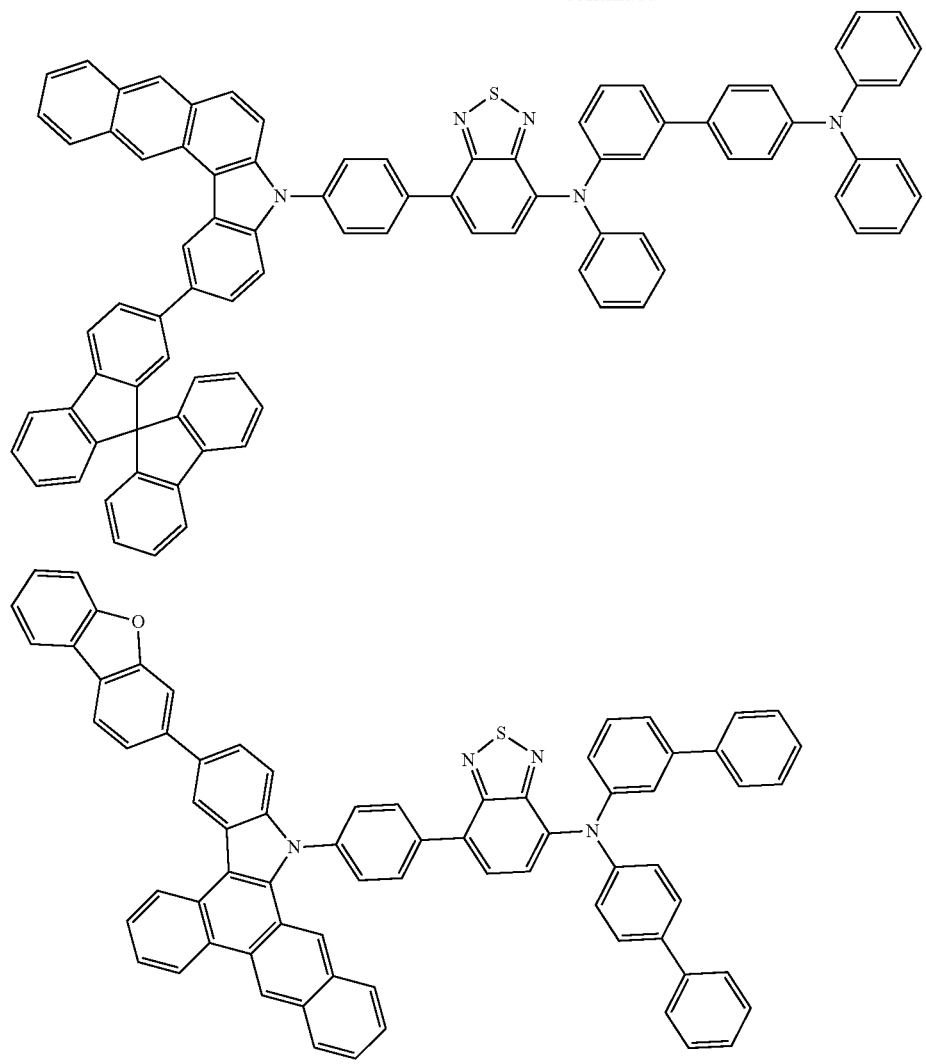
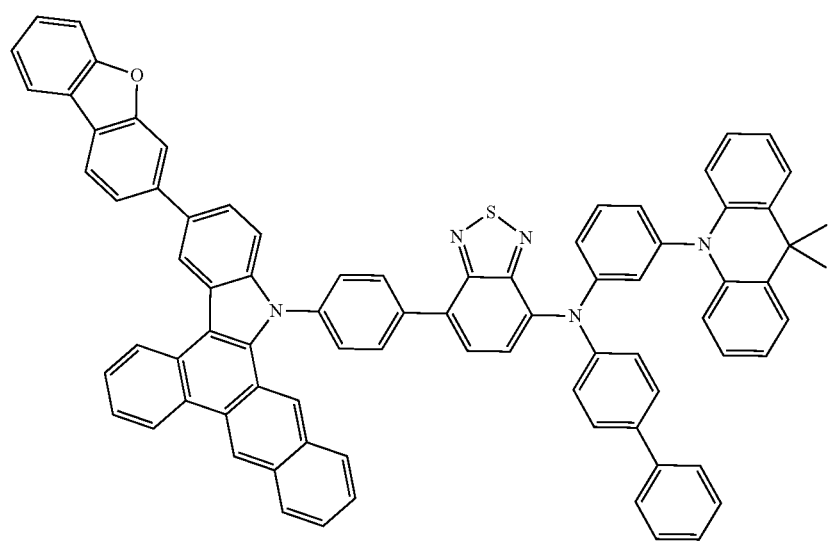

525
526
-continued
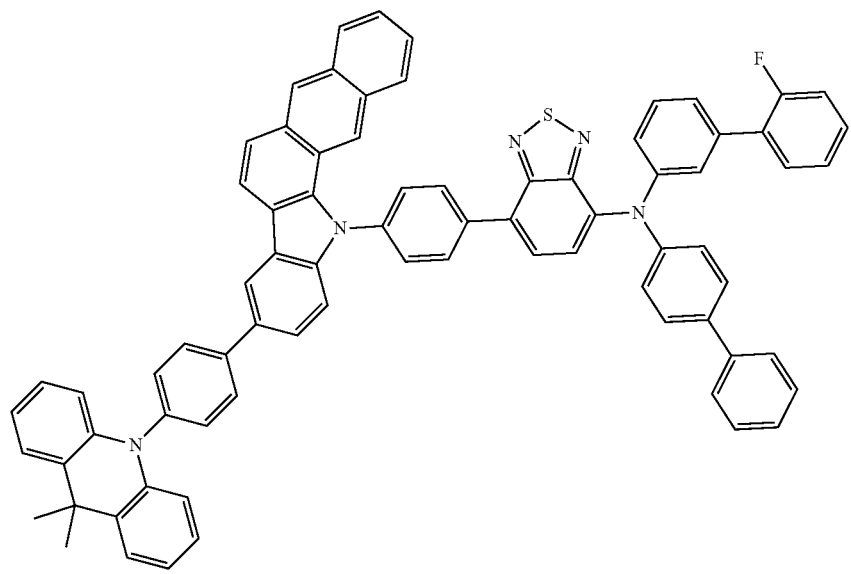
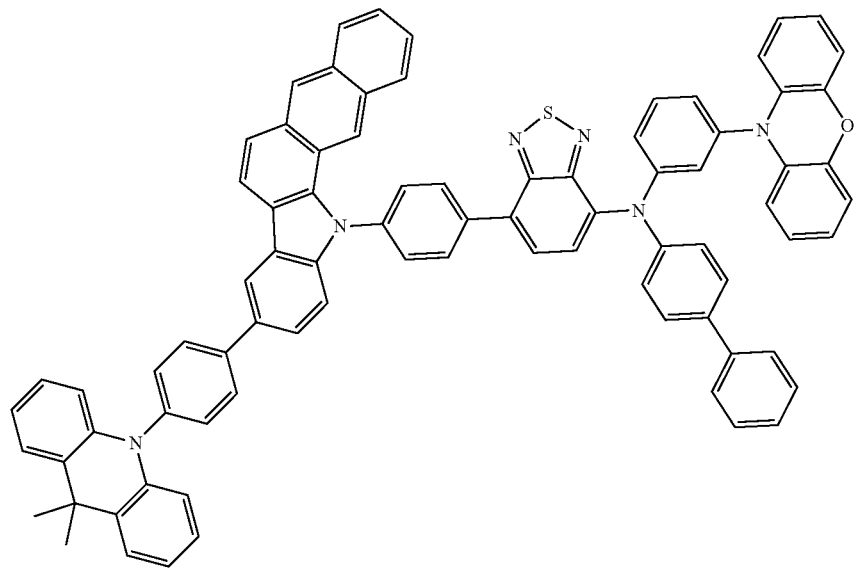
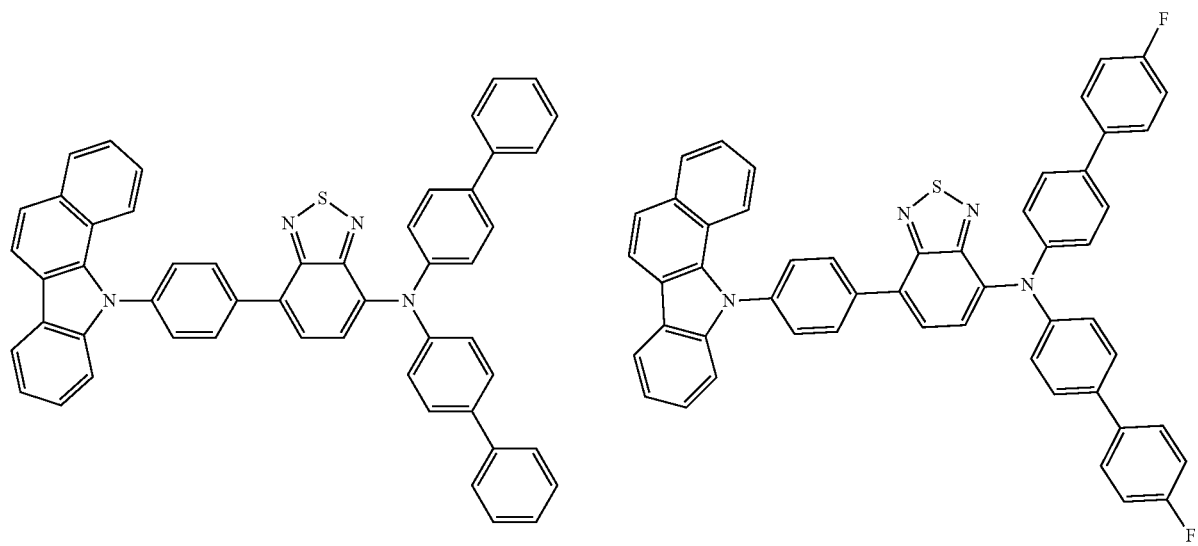

-continued
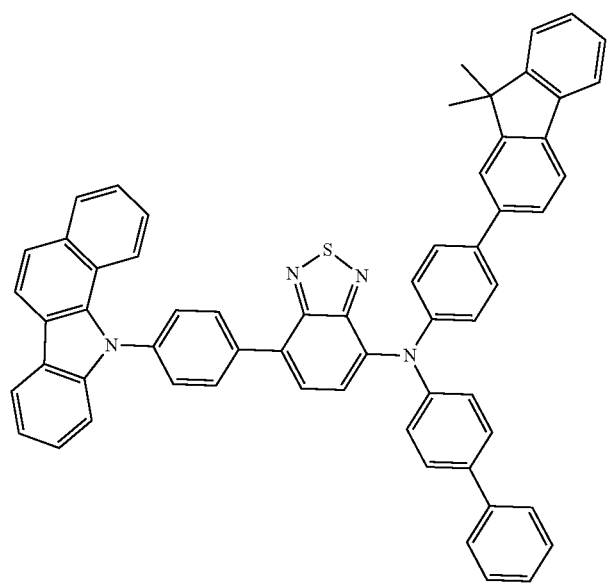
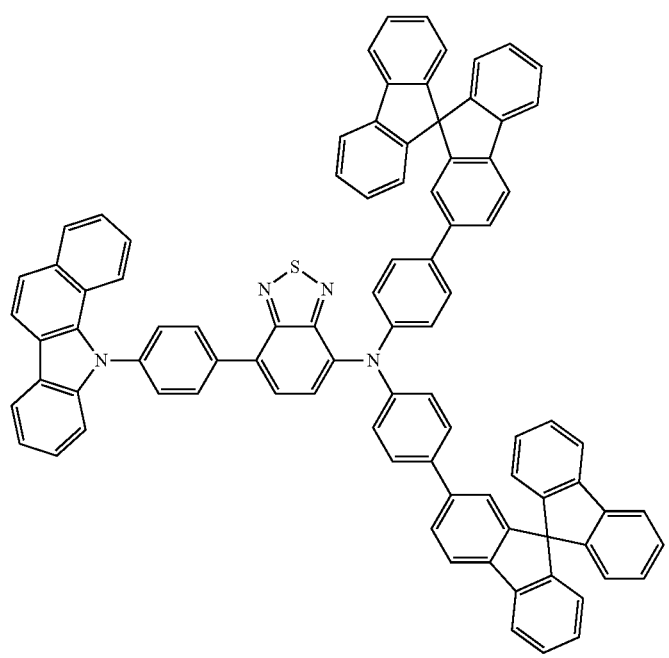

-continued
529
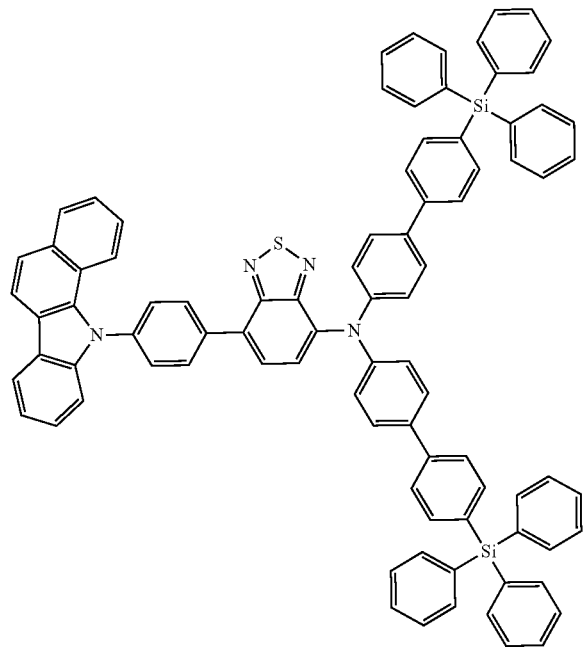
530
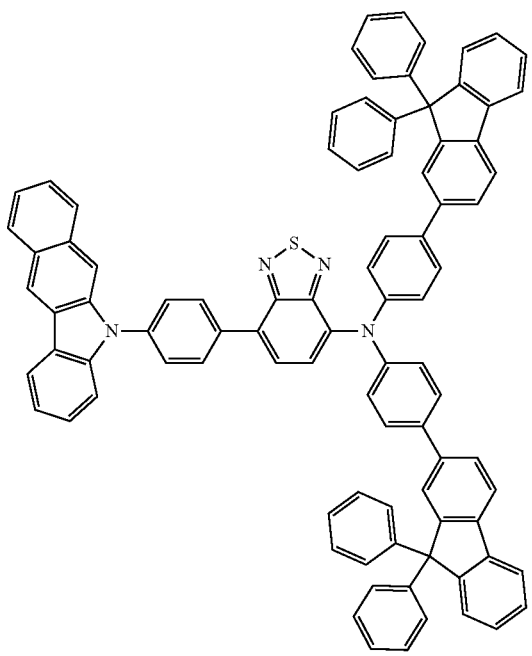
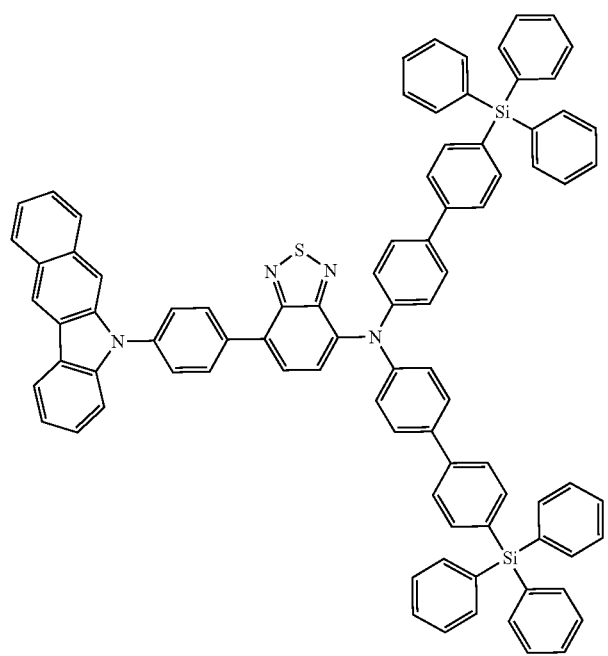

-continued
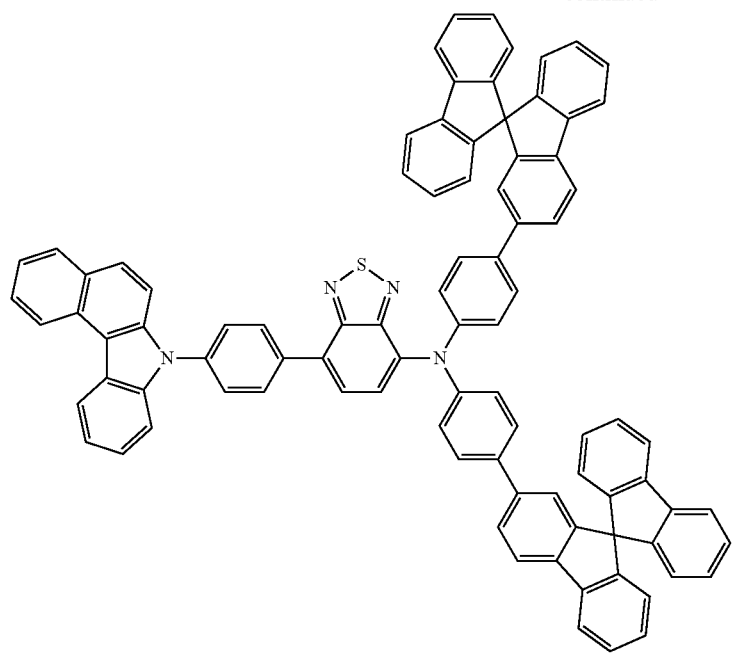
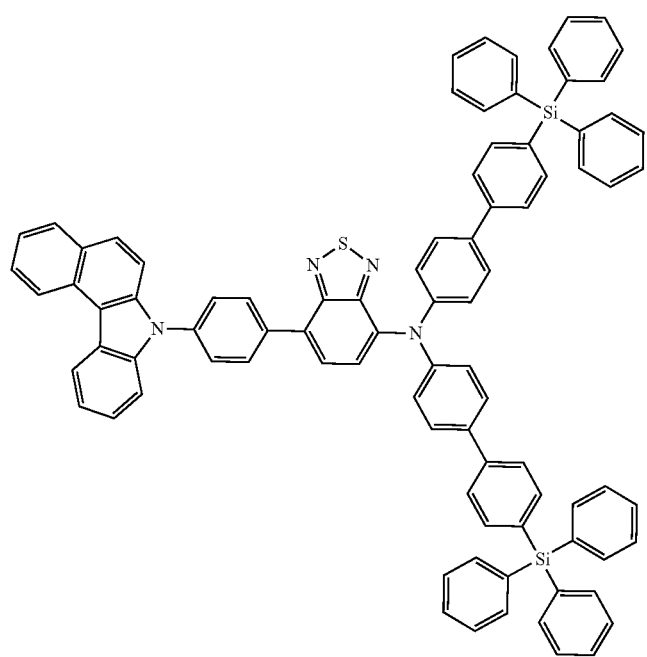

-continued
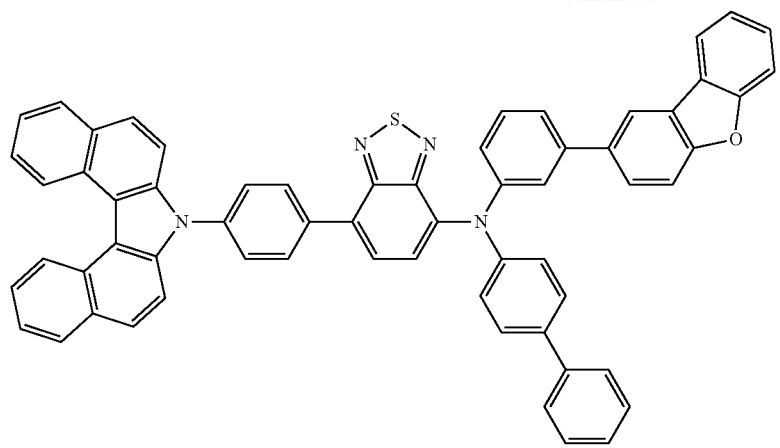
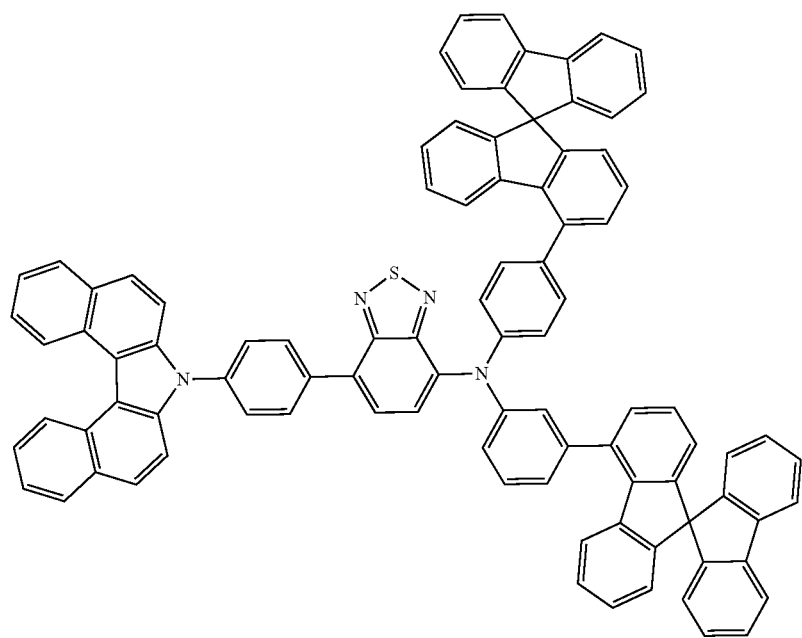
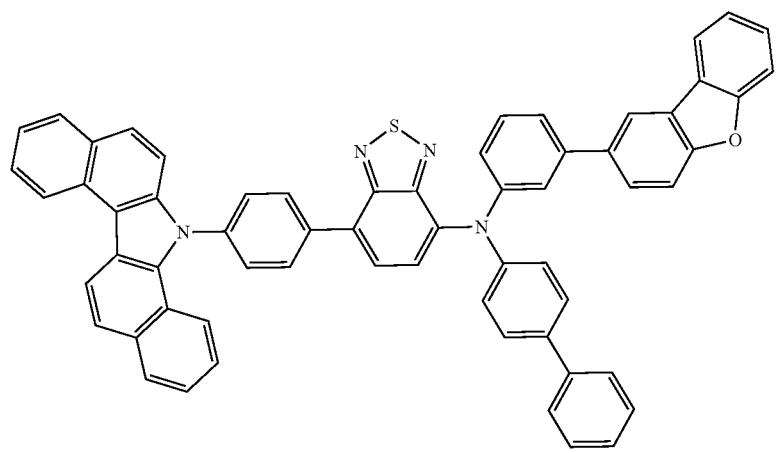

-continued
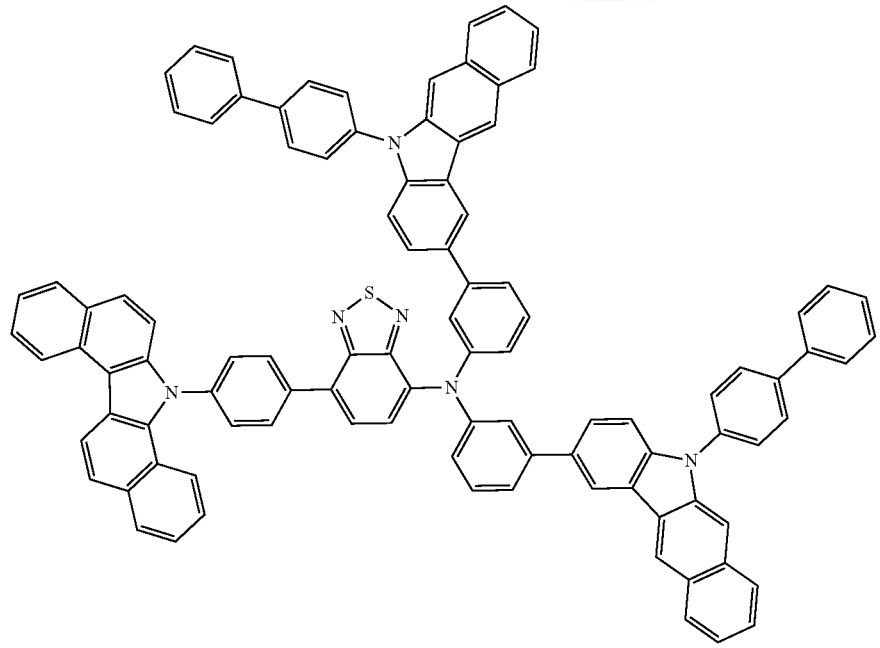
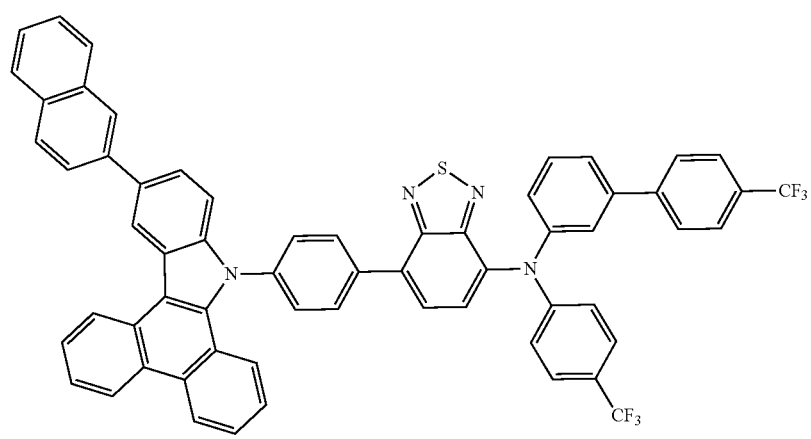
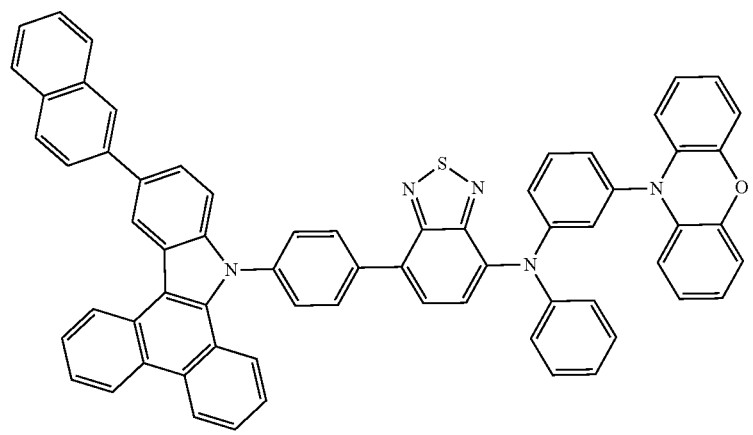

-continued

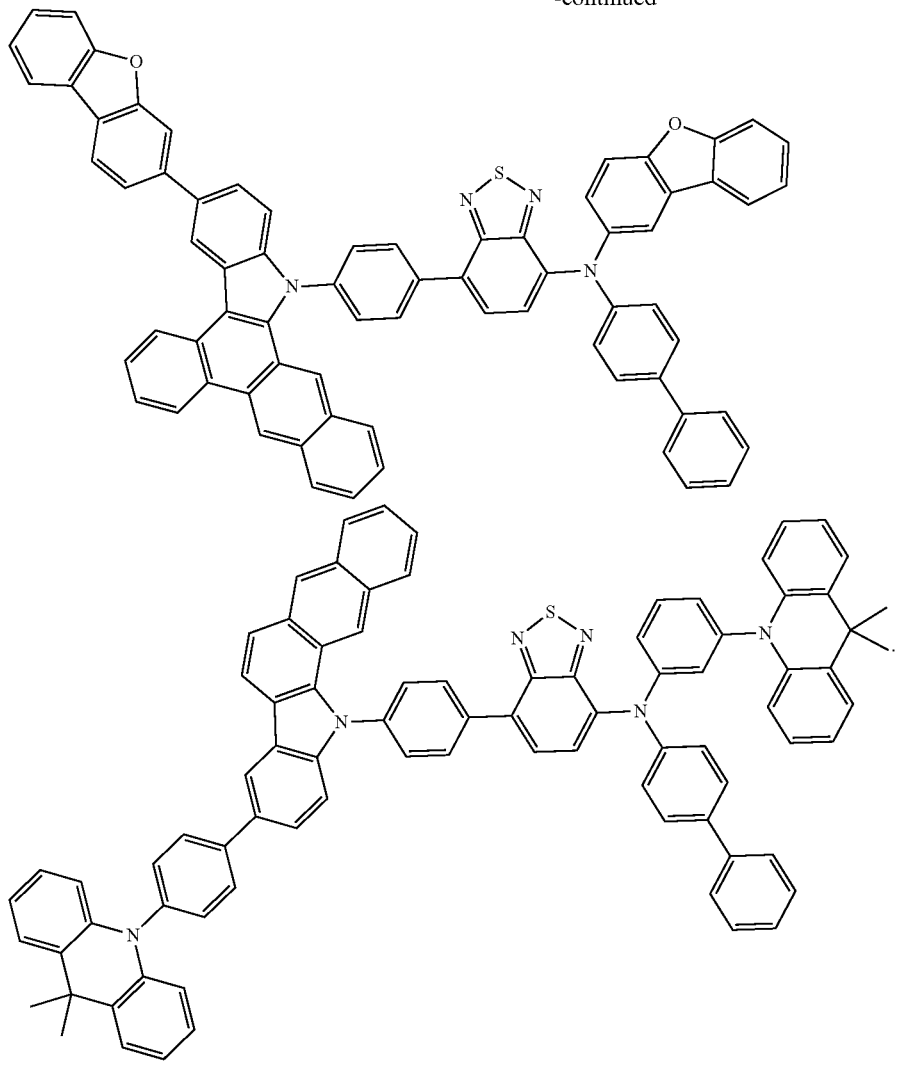

5. A color conversion film comprising:
a resin matrix; and
at least one of the compounds represented by Formula 1 of claim 1, which is dispersed in the resin matrix.

6. A backlight unit comprising the color conversion film according to claim 5.

7. A display device comprising the backlight unit according to claim 6.

8. The color conversion film of claim 6, further comprising light diffusion particles selected from the group consisting of TiO2, silica, borosilicate, alumina and sapphire.

9. The color conversion film of claim 5, comprising the at least one of the compounds of Formula 1 in a range of 0.001 wt % to 15 wt %.

10. The color conversion film of claim 5, wherein the at least one of compounds is at least one of the compounds of claim 4.

11. The color conversion film of claim 5, wherein the resin matrix is a thermoplastic polymer or a thermosetting polymer.

12. The compound of claim 1, wherein R1 to R8 are the same as or different from each other, and are each independently hydrogen; deuterium; fluorine; a methyl group; an ethyl group; a propyl group; a butyl group; an aryl group having 6 to 20 carbon atoms, which is unsubstituted or substituted with one or more selected from the group consisting of fluorine, a methyl group, an ethyl group, a propyl group, a butyl group, a trifluoromethyl group, a methoxy group, a triphenylsilyl group, a fluorenyl group, and a carbazole group which is unsubstituted or substituted with an aryl group; a silyl group which is substituted with a methyl group or an ethyl group; a carbazolyl group; a dihydroacridine group which is substituted with an alkyl group; a phenothiazine group; a phenoxazine group; or a dibenzofuranyl group, or adjacent groups may be bonded to each other to form one or more substituted or unsubstituted rings having 3 to 30 carbon atoms.

13. The compound of claim 1, wherein X1 and X2 are the same as or different from each other, and are each independently hydrogen; deuterium; or a halogen group.

14. The compound of claim 1, wherein L1 and L2 are the same as or different from each other, and are each independently an aryl group having 6 to 30 carbon atoms, which is unsubstituted or substituted with one or more selected from the group consisting of fluorine, a cyano group, an N-biphenylamine group which is substituted with an aryl group unsubstituted or substituted with an alkyl group, a methyl group, a propyl group, a butyl group, a neopentyl group which is substituted with an aryl group, a trifluoromethyl group, an ethenyl group which is substituted with a cyano group and an aryl group, an ethenyl group which is substituted with an aryl group, a methoxy group, a triphenylsilyl group, a fluorenyl group, a terphenyl group, a naphthyl group, a phenoxazine group which is unsubstituted or substituted with an aryl group, a phenothiazine group, a dibenzofuranyl group, a dihydroacridine group which is substituted with an alkyl group, and a carbazole group which is unsubstituted or substituted with an aryl group unsubstituted or substituted with an alkyl group or a halogen group.

* * * * *